United States Patent
Barrangou et al.

(10) Patent No.: US 10,787,654 B2
(45) Date of Patent: Sep. 29, 2020

(54) METHODS AND COMPOSITIONS FOR SEQUENCE GUIDING CAS9 TARGETING

(71) Applicant: North Carolina State University, Raleigh, NC (US)

(72) Inventors: Rodolphe Barrangou, Raleigh, NC (US); Kurt M. Selle, Raleigh, NC (US); Alexandra E. Briner, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 15/113,656

(22) PCT Filed: Jan. 23, 2015

(86) PCT No.: PCT/US2015/012747
§ 371 (c)(1),
(2) Date: Jul. 22, 2016

(87) PCT Pub. No.: WO2015/112896
PCT Pub. Date: Jul. 30, 2015

(65) Prior Publication Data
US 2017/0002339 A1   Jan. 5, 2017

Related U.S. Application Data

(60) Provisional application No. 61/931,515, filed on Jan. 24, 2014, provisional application No. 61/986,427, filed on Apr. 30, 2014.

(51) Int. Cl.
*C12N 9/22* (2006.01)
*C12N 15/85* (2006.01)

(52) U.S. Cl.
CPC ............... *C12N 9/22* (2013.01); *C12N 15/85* (2013.01); *C12Y 301/00* (2013.01)

(58) Field of Classification Search
None
See application file for complete search history.

(56) References Cited

U.S. PATENT DOCUMENTS

| | | | |
|---|---|---|---|
| 9,023,649 B2 | 5/2015 | Mali et al. | |
| 9,260,723 B2 | 2/2016 | Mali et al. | |
| 2006/0199190 A1 | 9/2006 | Russell et al. | |
| 2009/0007301 A1 | 1/2009 | Wintz et al. | |
| 2013/0288251 A1 | 10/2013 | Horvath et al. | |
| 2014/0068797 A1 | 3/2014 | Doudna et al. | |
| 2014/0113376 A1 | 4/2014 | Sorek et al. | |
| 2014/0186958 A1 | 7/2014 | Zhang et al. | |
| 2014/0273233 A1 | 9/2014 | Chen et al. | |
| 2014/0356867 A1 | 12/2014 | Peter et al. | |
| 2014/0356956 A1 | 12/2014 | Church et al. | |
| 2015/0050699 A1 | 2/2015 | Siksnys et al. | |
| 2015/0056628 A1 | 2/2015 | Russell et al. | |
| 2015/0064138 A1 | 3/2015 | Lu et al. | |
| 2015/0098954 A1 | 4/2015 | Hyde et al. | |
| 2015/0132263 A1 | 5/2015 | Liu et al. | |
| 2015/0291961 A1 | 10/2015 | Siksnys et al. | |
| 2015/0315576 A1 | 11/2015 | Caliando et al. | |
| 2015/0353901 A1 | 12/2015 | Liu et al. | |
| 2016/0017366 A1* | 1/2016 | Chen .................... | C12N 15/102 |
| | | | 435/462 |
| 2016/0024510 A1 | 1/2016 | Bikard et al. | |
| 2016/0186152 A1 | 6/2016 | Brouns et al. | |
| 2016/0186213 A1 | 6/2016 | Zhang et al. | |
| 2016/0298096 A1* | 10/2016 | Charpentier ............. | C12N 9/22 |
| 2016/0333348 A1 | 11/2016 | Clube et al. | |
| 2016/0345578 A1 | 12/2016 | Barrangou et al. | |
| 2017/0196225 A1 | 7/2017 | Clube et al. | |
| 2017/0246221 A1 | 8/2017 | Clube et al. | |
| 2018/0064114 A1 | 3/2018 | Clube | |
| 2018/0064115 A1 | 3/2018 | Clube et al. | |
| 2018/0070594 A1 | 3/2018 | Clube et al. | |
| 2018/0084785 A1 | 3/2018 | Clube | |
| 2018/0084786 A1 | 3/2018 | Clube | |
| 2018/0146681 A1 | 5/2018 | Clube | |
| 2018/0200387 A1 | 7/2018 | Porteus | |

FOREIGN PATENT DOCUMENTS

| | | |
|---|---|---|
| EP | 2860267 | 4/2015 |
| WO | 2006/113709 | 10/2006 |
| WO | 2010/054154 | 5/2010 |
| WO | WO 2010/075424 | 7/2010 |
| WO | 2013/098244 | 7/2013 |
| WO | 2013/141680 | 9/2013 |
| WO | WO 2013176772 | 11/2013 |
| WO | WO 2013/188638 | 12/2013 |
| WO | WO 2013188522 | 12/2013 |
| WO | 2014/022702 | 2/2014 |
| WO | WO 2014/071235 | 5/2014 |

(Continued)

OTHER PUBLICATIONS

Heinl et al., Insights into the completely annotated genome of Lactobacillus buchneri CD034, a strain isolated from stable grass silage; Journal of Biotechnology, vol. 161, pp. 153-166, 2012.*
Crawley et al., Characterizing the activity of abundant, diverse and active CRISPR-Cas systems in lactobacilli; Scientific Reports, vol. 8, 11544, pp. 1-12, 2018 (Year: 2018).*
Barrangou R. "CRISPR-Cas systems and RNA-guided interference", *Wiley interdisciplinary reviews, RNA* (2013) 4: pp. 267-278.
Barrangou R., et al. "CRISPR: new horizons in phage resistance and strain identification" *Annu Rev Food Sci Technol* (2012) 3, pp. 143-162.
Barrangou R., et al. "CRISPR-Cas systems: prokaryotes upgrade to adaptive immunity", *Mol Cell* (2014) 54(2): pp. 234-244.
Barrangou, R. "Diversity of CRISPR-Cas immune systems and molecular machines", *Genome Biology* (2015) 16:247, 11 pages.

(Continued)

*Primary Examiner* — Mindy G Brown
(74) *Attorney, Agent, or Firm* — Myers Bigel, P.A.

(57) ABSTRACT

The present invention is directed to methods and compositions for genome editing and DNA targeting of proteins.

21 Claims, 33 Drawing Sheets
Specification includes a Sequence Listing.

(56) References Cited

FOREIGN PATENT DOCUMENTS

| WO | WO 2014065596 | 5/2014 |
|---|---|---|
| WO | WO 2014110006 | 7/2014 |
| WO | WO 2014113493 | 7/2014 |
| WO | WO 2014/124226 | 8/2014 |
| WO | WO 2014144155 | 9/2014 |
| WO | WO 2014144592 | 9/2014 |
| WO | WO 2014150624 | 9/2014 |
| WO | WO 2014186686 | 11/2014 |
| WO | 2014/204727 | 12/2014 |
| WO | WO 2014191128 | 12/2014 |
| WO | WO 2014191518 | 12/2014 |
| WO | WO 2014201015 | 12/2014 |
| WO | WO 20142014727 | 12/2014 |
| WO | WO 2015021353 | 2/2015 |
| WO | WO 2015026886 | 2/2015 |
| WO | WO 2015/034872 | 3/2015 |
| WO | WO 2015035139 | 3/2015 |
| WO | WO 2015040402 | 3/2015 |
| WO | WO 2015/053995 | 4/2015 |
| WO | WO 2015/070193 | 5/2015 |
| WO | WO 2015077290 | 5/2015 |
| WO | 2015/089486 | 6/2015 |
| WO | WO 2015089277 | 6/2015 |
| WO | WO 2015089406 | 6/2015 |
| WO | WO 2015116686 | 6/2015 |
| WO | WO 2015119941 | 8/2015 |
| WO | WO 2015139139 | 9/2015 |
| WO | 2015/155686 | 10/2015 |
| WO | 2015/159068 | 10/2015 |
| WO | WO 2015/148680 | 10/2015 |
| WO | WO 2015/159086 | 10/2015 |
| WO | WO 2015/159087 | 10/2015 |
| WO | WO 2015150683 | 10/2015 |
| WO | WO 2015153791 | 10/2015 |
| WO | WO 2015153889 | 10/2015 |
| WO | WO 2015153940 | 10/2015 |
| WO | WO 2015155686 | 10/2015 |
| WO | WO 2015189693 | 12/2015 |
| WO | WO 2015200555 | 12/2015 |
| WO | WO 2016/084088 | 6/2016 |
| WO | 2016/196361 | 12/2016 |
| WO | 2017/027423 | 2/2017 |
| WO | 2017/066497 | 4/2017 |
| WO | 2017/0147507 | 8/2017 |

OTHER PUBLICATIONS

Barrangou, R., et al. "CRISPR provides acquired resistance against viruses in prokaryotes" *Science* (2007) 315(5819): pp. 1709-1712.
Bhaya et al. "CRISPR-Cas Systems in Bacteria and Archaea: Versatile Small RNAs for Adaptive Defense and Regulation", *Annu. Rev. Genet.* (2011) 45: pp. 273-297.
Bikard D. et al "Programmable repression and activation of bacterial gene expression using an engineered CRISPR-Cas system" *Nucleic Acids Res* (2013) 41(15): pp. 7429-7437.
Bikard D., et al. "CRISPR interference can prevent natural transformation and virulent acquisition during in vivo bacterial infection", *Cell Host & Microbe* (2012), 10 pages.
Bikard D., at al. "Exploiting CRISPR-Cas nucleases to produce sequence-specific antimicrobial", *Nature Biotechnology* 2014, 6 pages.
Briner et al. "Guide RNA Functional Modules Direct Cas9 Activity and Orthogonality" *Molecular Cell.* (2014) 56(2): pp. 333-339.
Briner AE, Barrangou R. "*Lactobacillus buchneri* Genotyping on the Basis of Clustered Regularly Interspaced Short Palindromic Repeat (CRISPR) Locus Diversity", *Appl Environ Microbiol.* 80;994-1001, (2014).
Brouns SJJ, et al. "Small CRISPR RNAs guide antiviral defense in prokaryotes", *Science* (2008) 321:5891, pp. 960-964.
Carte et al, "The three major types of CRISPR-Cas systems function Independently in CRISPR RNA biogenesis in *Streptococcus thermophilus*", *Molecular Microbiology*, 93(1), pp. 98-112 (2014).

Chylinski et al. "The tracrRNA and Cas9 families of type II CRISPR-Cas immunity systems", *RNA Biology*, 10:5 (2013) pp. 726-737.
Chylinski et al. "Classification and evolution of type II CRISPR-Cas Systems", *Nucleic Acids Research*, (2014) 15 pages.
Citorik R., et al. "Sequence-specific antimicrobials using efficiently delivered RNA-guided nucleases", *Nature Biotechnology* 2014, 7 pages.
Cong et al. "Multiplex Genome Engineering Using CRISPR/Cas Systems" *Science* (2013) vol. 339 (6121): pp. 819-823.
Darmon E, Leach DF "Bacterial Genome Instability", *Microbiol. Mol. Biol. Rev.* (2014) vol. 78, pp, 1-39.
Deltcheva, E. et al. "CRISPR RNA maturation by trans-encoded small RNA and host factor RNase III", *Nature*, vol. 471, (Mar. 2011) pp. 602-607.
Doench et al. "Rational design of highly active sgRNAs for CRISPR-Cas9-mediated gene inactivation", *Nature Biotechnology*, 32:12 (2014) 8 pages.
Edgar R., et al. "The *Escherichla coli* CRISPR System Protects from Lysagenization, Lysogens, and Prophage Induction", *Journal of Bacteriology* (2010), vol. 192, No. 23, pp. 6292-6294.
Estvelt et al. "Orthogonal Cas9 proteins for RNA-guided gene regulation and editing", *Nature Methods*, 10:11 (2013) pp. 1116-1121.
Fonfara, I. et al. "Phylogeny of Cas9 determines functional exchangeability of dual-RNA and Cas9 among orthologous type II CRISPR-Cas systems", *Nucleic Acids Res* (2013) 14 pages.
Fu et al. "Improving CRISPR-Cas nuclease specificity using truncated guide RNAs", *Nature Biotechnology*, 32:3 (2013) 9 pages.
Garneau JE, et al. "The CRISPR/Cas bacterial immune system cleaves bacteriophage and plasmid DNA" *Nature* (2010) 468(7320): pp. 67-71.
Gasiunas et al. "Cas9-crRNA ribonucleoprotein complex mediates specific DNA cleavage for adaptive immunity in bacteria", *Proc. Natl. Acad. Sci.* (2012), 109:E2579-E2586.
Gilbert, L. A. et al. "CRiSPR-Mediated Modular RNA-Guided Regulation of Transcription in Eukaryotes", *Cell 154.* (2013) pp. 442-451.
Gilbert et al. "Genome-Scale CRISPR-Mediated Control of Gene Repression and Activation", *Cell*, 159 (2014) pp. 647-661.
Gomaa AA, et al. "Programmable Removal of Bacterial Strains by Use of Genome-Targeting CRISPR-Cas Systems", *mBio* (2014), 5(1):e00928-13.
Haurwitz et al. "Sequence- and Structure-Specific RNA Processing by a CRISPR Endonuclease", *Science* (2010) 329: pp. 1355-1358.
Horvath and Barrangou "CRISPR/Cas, the Immune System of Bacteria and Archaea", *Science* (2010) 327, pp. 167-170.
Horvath, P. et al. "Diversity, Activity, anti Evolution of CRISPR Loci in *Streptococcus thermophilus*", *J. Bacteriol.* 190 (2008) pp. 1401-1412.
Hsu et al. "DNA targeting specificity of RNA-guided Cas9 nucleases", *Nature Biotechnology*, 31:9 (2013) pp. 827-834.
Jiang, W. et al. "Dealing with the Evolutionary Downside of CRISPR Immunity: Bacteria and Beneficial Plasmids", *PLOS Genetics* (2013) vol. 9, issue 9, 13 pages.
Jiang, W. et al. "RNA-guided editing of bacterial genomes using CRISPR-Cas systems", *Nat. Biotechnol.* (2013) vol. 31, pp. 233-239.
Jinek et al. "A Programmable Dual-RNA-Guided DNA Enclonuclease in Adaptive Bacterial Immunity", *Science* (2012) vol. 337, pp. 816-821.
Jinek, M. et al., "Structures of Cas9 endonucleases reveal RNA-mediated conformational activation", *Science* (2014) vol. 343, 6176, 28 pages.
Karvelis et al. "crRNA and tracrRNA guide Cas9-mediated DNA interference in *Streptococcus thermophilus*", *RNA Biol.* (2013) vol. 10: pp. 841-851.
Kobayashi K. et al. "Essential *Bacillus subtilis* genes", *Proc. Natl. Acad. Sci. U.S.A.* (2003) vol. 100, pp. 4678-4683.
Labrie SJ et al. "Bacteriophage resistance mechanisms" *Nat. Rev. Microbiol* (2010) vol. 8, pp. 317-327.

(56) References Cited

OTHER PUBLICATIONS

Luo, M. et al., "Reourposing endogenous type I CRiSPR-Cas systems for programmable gene repression", *Nucleic Acid Research* (2014) 8 pages.
Magadan et al. "Cleavage of Phage DNA by the *Streptococcus thermophilus* CRIBPR3-Cas System", *PLoS One* (2012) 7:e40913 8 pages.
Mahilion J. et al. "Insertion sequences", *Microbiol Mol Biol Rev* (1998) vol. 62(3): pp. 725-774.
Makarova and Koonin "Annotation and Classification of CRISPR-Cas Systems", *Methods Mol Biol.* (2015), 1311: pp. 47-75.
Makarova et al. "An updated evolutionary classification of CRISPR-Cas systems", *Nat Rev Microbiol.* 13:722-736 (2015), 15 pages.
Makarova et al. "Unification of Cas protein families and a simple scenario for the origin and evolution of CRISPRCas systems", *Biol Direct.* (2011) vol. 6:38, 27 pages.
Makarova, K S. et al. "Evolution and classification of the CRISPR-Cas systems", *Nat Rev Microbiol.* (2011) vol. 9; pp. 467-477.
Marraffini and Sontheimer "CRISPR interference Limits Horizontal Gene Transfer in Staphyiococci by Targeting DNA", *Science* (2008) vol. 322: pp. 1843-1845.
Mojica, F. et al. "Short motif sequences determine the targets of the prokaryotic CRISPR defence system", *Microbiology* (2009) vol. 155, 8 pages.
Nishimasu, H., et al. "Crystal Structure of Cas9 in Complex with Guide RNA and Target DNA", *Cell* (2014) vol. 156; pp. 935-949.
Oh JH and van Pijkeren JP "CRISPR-Cas9-assisted recornbireering in *Lactobacillus reuteri*", *Nucleic Acids Res* (2014) vol. 10.1093/nar/gku623.
Qi, L. S. et al. "Repurposing CRISPR as an RNA-Guided Platform for Sequence-Specific Control of Gene Expression", *Cell* 152, 1173-1183 (2013) 11 pages.
Sander JD, and Joung JK. "CRISPR-Cas systems for editing, regulating and targeting genomes", *Nat. Biotechol.* (2014) vol. 32, pp. 347-355.
Sapranauskas et al. "The *Streptococcus thermophilus* CRISPR/Cas system provides immunity in *Escherichia coli*", *Nucleic Acid Res.* (2011) vol. 39: pp. 9275-9282.
Salle K. Barrangou R. "Harnessing CRISPR-Cas systems for bacterial genome editing", *Cell Press: Trends Microbiol.* (2015) vol. 23(4): pp. 225-232.
Selle, K. et al. "CRISPR-based screening of genomic island excision events in bacteria", *Proc Natl Acad Sci USA*, (2015); 112(26): pp. 8076-8081.
Salle, K. et al., "CRISPR-Based Technologies and the Future of Food Science", *Journal of Food Science* (2015) vol. 80, 6 pages.
Semenova et al. "Interference by clustered regularly interspaced short palindromic repeat (CRISPR) RNA is governed by a seed sequence", *PNAS*, 108:25 (2011) 6 pages.
Sinkuna, T. et al. "In vitro reconstitution of Cascade-mediated CRISPR immunity in *Streptococcus thermophilus*", *The EMBO Journal* (2013) vol. 32, pp. 385-394.
Stern, A. et al., "Self targeting by CRISPR: gene regulation or autoimmunity" *Cell Press: Trends in Genetics*, (2010) vol. 26, No. 8, 6 pages.
Sternberg et al. "DNA interrogation by the CRISPR RNA-guided endonuclease Cas9", *Nature*, vol. 507, (2014) 17 pages.
Terns and Terns "CRISPR-based adaptive immune systems". *Curr. Opin. Microbiol.* (2011) vol. 14: pp. 321-327.
Vercoe RB, et al. "Cytotoxic chromosomat targeting by CRISPR/Cas systems can reshape bacterial genomes and expel or remodel pathogenicity istands", *PLoS Genet* (2013) vol. 9(4):e1003454.
Westra et al. "The CRISPRs, They Are A-Changin': How Prokaryotes Generate Adaptive Immunity", *Annu. Rev. Genet.* (2012) vol. 46; pp. 311-339.
Wiedenheft et al. "RNA-guided complex from abacterial immune system enhances target recognition through seed sequence interactions", *PNAS*, 108:36 (2011) 7 pages.

Notification of Transmittal of the International Search Report and the Written Opinion of the International Searching Authority, or the Declaration, PCT/US2016/034812, dated Sep. 15, 2016, 9 pages.
Ajdic et al. "hypotnetioal protein SMU_L1405c (*Streptococcus mutans* UA159", Proc. Natl. Acad. Sci. U.S.A. 99 (22), 14434-14439 (2002) URL: https://www.ncbi.nlm.nih.gov/protein/NP_721764.1/, retrieved Jul. 20, 2018.
Cochrane Kyla et al., "Complete genome sequences and analysis of the Fusobacterium nucleatum subspecies *animalis* 7-1 bacteriophage PHIFunu1 and PHIFunu2", Anaerobe, 38:125-129 (2016).
Heinl, Stefan et al. "Insights into the completely annotated genome of Lactobacillus buchneri CCD034, a strain isolated from stable grass silage", Journal of Biotechnoiogy, 161:153-166 (2012).
International Search Report and Written Opinion for PCT/US2015/047136 dated Nov. 26. 2015, 10 pages.
Karvelis, Tautvydas et al., "crRNA and tracerRNK guide Cas9-mediated DNA interference in *Streptococcus thermophilus*:" RNA Biology, 2013, vol. 10, Issue 5, pp. 841-851.
Karvelis, Tautvydas et al., "Programmable DNA cleavage in vitro by Cas9," Biochem. Soc. Trans. 2013, vol. 41, part 6, pp. 1401-1406.
Marcotte, H. et al. "Proteomes—Lactobacillus gasseri DSM 14869", NCBI Reference Sequence CP006803: (2013) URL: https://www.uniprot.org/proteomes/UP000217220, retrieved Jul. 20, 2018.
Nale Janet Y. et al., "Diverse temperate bacteriophage carriage in Clostridium difficile 027 strains", PLoS One, 7(5) 1-9 (2012).
Notification and Transmittal of International Search Report and Written Opinion of the International Searching Authority for International Application No. PCT/IB2015/052515; dated Oct. 10, 2015; 12 pages.
Notification of International Preliminary Report on Patentability corresponding to International Application No. PCT/IB2015/052515; dated Oct. 12, 2016, 7 pages.
Novagen "pCDF-1b Vector" Sep. 10, 2003. Retrieved from the Internet on Sep. 1, 2015, at http://www.helmholtz-muenchen.de/fieadmin/PEPF/pCDF_vectors/pCDF-1b_map.pdf, 2 pages.
Ramakrishna Suresh et al. "Gene disruption by cell-penetrating peptide-mediated delivery of Cas9 protein and guide RNA", Genome Research, 24:1020-1027 (2014).
Seed Kimberley D. et al., "A bacteriophage encodes its own CRISPR/Cas adaptive response to evade host innate immunity", Nature, 494:7438, pp. 489-491 (2013).
Uchiyama Jumpei et al., "Characterization of Helicobacter pylori bacteriophage KHP30", Applied and environmental microbiology, 79(10):3176-3184 (2013).
Written Opinion and international Search Report corresponding to International Application No. PCT/US2016/037493, dated Sep. 15, 2016, 8 pages.
Written Opinion of the International Search Report regarding international Application No. PCT/US2016/067657, dated Mar. 6, 2017, 9 pages.
Final Office Action, U.S. Appl. No. 15/302,655, dated Nov. 2, 2018, 21 pp.
Office Action, U.S. Appl. No. 15/032,985, dated Feb. 5, 2019, 11 pages.
Rath D et al. The CRISPR-Cas immune system: Biology, mechanisms and applications. Biochimie. 2015;117: 119-128.
Spath K et al. Lactobacillus plantarum and Lactobacillus buchneri as expression systems: Evaluation of different origins of replication for the design of suitable shuttle vectors. Mol. Biotechnol. 2012; 52: 40-48.
Grissa I et al. The CRISPRdb database and tools to display CRISPRs and to generate dictionaries of spacers and repeats. BMC Bioinformatics. 2007; 8(172): pp. 1-10.
Final Office Action, U.S. Appl. No. 16/153,052, dated Dec. 26, 2018, 14 pages.
Final Office Action, U.S. Appl. No. 15/507,176, dated Jan. 16, 2019, 19 pages.
Claesson MJ et al. NCBI reference sequence NC_007929, direct submission Dec. 16, 2005, p. 1 (2005).
Milani C et al. Genomic encyclopedia of type strains of the genus *Bifidobacterium*, Applied and Environmental Microbiology. Oct. 2014; 80(20): 6290-6302.

(56) References Cited

OTHER PUBLICATIONS

Database GenBank [online]. NBI, U.S. National Library of Medicine. Aug. 5, 2014, "CRISPER-associated protein, Csn1 family [Bifidobacterium bombi DSM 19703]." XP002785852, retrieved from NCBI accession No. GenBank: KFF31259, Database accession No. KFF31259, 1 page.
Cong et al. Supplementary Materials for "Multiplex Genome Engineering Using CRISPR/Cas Systems" Science, 339 (6121):819-823 (2013).
Yosef et al. "High-temperature protein G is essential for activity of the *Escherichia coli* clustered regularly interspaced short palindromic repeats (CRISPR)/Cas system" Proc Natl Acad Sci, 108(50):20136-20141 (2011.
Sanozky-Dawes et al. "Occurrence and activity of a type II CRISPR-Cas, system in Lactobacillus gasseri" Microbiology, 161:1752-1761 2015.
Anderson et al. "Lactobacillus gasseri CRISPR-Cas9 characterization In Vitro reveals a flexible mode of protospacer-adjacent motif recognition" PLOS ONE, 13(2) 14 pages 2018.
Crawley AB et al. Characterizing the activity of abundant, diverse and active CRISPR-Cas systems in lactobacilli. Scientific Reports. 2018; 8: 111544, 1-12.
Beisel CL et al. A CRISPR design for next-generation antimicrobials. Genome Biology. 2014; 15: 516, 4 pages.
Citorik RJ et al. "Sequence-specific antimicrobials using efficiently delivered RNA-guiding nucleases Supplemental Material," Nature Biotechnology. Sep. 21, 2014: 32(11): 1141-1145, DOI:10.1038/nbt.3011, 14 pages.
International Search Report and Written Opinion, PCT/US2018/934322, dated Sep. 13, 2018, 7 pages.

Liu S et al. Complete genome sequence of Lactobacillus buchneri NRRL B-30929, a novel rain from a commercial ethanol plant Journal of Bacteriology, Aug. 2011; 193(15): 4019-4020.
Liu S et al. NCBI (2011) CRISPR-associated protein, Csn1 family [Lactobacillus buchneri], pp. 1-3.
International Preliminary Report on Patentability Notification, PCT/US2018/034322 dated Dec. 5, 2019, 7 pages.
International Search Report and Written Opinion corresponding to PCT/US2019/52683, dated Dec. 23, 2019, 9 pages.
International Search Report and Written Opinion corresponding to PCT/US2019/52878, dated Dec. 27, 2019, 14 pages.
International Search Report and Written Opinion corresponding to PCT/US2019/52864, dated Dec. 17, 2019, 15 pages.
GenBank Accession No. FN692037.1, "Lactobacillus crispatus ST1 complete genome, strain ST1" Feb. 27, 2015.
Ojala et al. "Comparative genomics of Lactobacillus crispatus suggests novel mechanism for the competitive exciusion of Garnerella vaginalis" BNC Genomics. 15:1070 (2014).
Yosef et al. "High-tempefature protein G is essential for activity of the *Escherichia coli* ciustered regularly interspaced short palindromic repeats (CRISPR)/Cas system" Proc Natl Acad Sci, 108(50):20136-20141 (2011).
International Search Report and Written Opinion corresponding to PCT/US2019/52861, dated Feb. 12, 2020, 18 pages.
Westra et al. "CRISPR Immunity Relies on the Consecutive Binding and Degradation Negatively Supercoiled Invader DNA by Cascade and Cas3" Molecular Cell, 46:595-605 (2012).
Hidalgo-Cantabrana et al. "Genome editing using the endogenous type I CRISPR-Cas system in Lactobacillus crispatus" PNAS, 116)32):15774-15783 (2019).
Gasiijnas et al. "Molecular mechanisms of CRISPR-mediated microbial immunity" Cellular and Molecular Life Sciences. 71 449-465 (2014).

\* cited by examiner

Fig. 1

```
CLUSTAL 2.1 multiple sequence alignment

St_henryi_DSM_19005                 GATAAGGCTT 10
St_infantarius_subsp_infantari      GATAAGGCTT 10
St_orisratti_DSM_15617              GATAAGGCTT 10
St_parasanguinis_F0449              GATAAGGCTT 10
St_gordonii_str_Challis_substr      GATAAGGCTT 10
St_anginosus_1_2_62CV               GATAAGGCTT 10
St_intermedius_B196                 GATAAGGCTT 10
St_mutans_NLML5                     GATAAGGCTT 10
St_vestibularis_ATCC_49124          GATAAGGCTT 10
St_thermophilus_CRISPR1             GATAAGGCTT 10
St_lutetiensis_033                  --TAAGGC-- 6
St_gallolyticus_ATCC_BAA-2069       --TAAGGC-- 6
St_intermedius_SK54                 --TAAGGC-- 6
St_mutans_UA159                     --TAAGGC-- 6
St_anginosis_DSM20563               --TAAGGC-- 6
St_equi_subsp_zooepidemicus         --TAAGGC-- 6
St_dysagalactiae_subsp_equisim      --TAAGGC-- 6
St_pyogenes_M1_GAS                  --TAAGGC-- 6
St_agalactiae_GB00300               --TAAGGC-- 6
St_oralis_SK304                     --TAAGGC-- 6
St_mitis_SK321                      --TAAGGC-- 6
St_sanguinis_SK330                  --TAAGGC-- 6
St_salivarius_K12                   --TAAGGC-- 6
St_thermophilus_LMD-9_CRISPR3       --TAAGGC-- 6
Lb_brevis_subsp_gravesensis_AT      --TCAAACAA 8
Lb_buchneri_ATCC_11577              --TCAAACAA 8
Lb_casei                            --TCAAACAA 8
Lb_coryniformis_subsp_corynifo      --TCAAACAA 8
Lb_curvatus_CRL_705                 --TCAAACAA 8
Lb_mucosae_LM1_177_17               --TCAAACAA 8
Lb_paracasei_subsp_Paracasei_8      --TCAAACAA 8
Lb_paracasei_subsp_Tolerans_Lp      --TCAAACAA 8
Lb_pentosus_IG1                     --TCAAACAA 8
Lb_pentosus_KCA1                    --TCAAACAA 8
Lb_plantarum_EGD-AQ4                --TCAAACAA 8
Lb_reuteri_mlc3                     --TCAAACAA 8
Lb_rhamnosus_GG                     --TCAAACAA 8
Lb_salivarius_UCC118                --TCAAACAA 8
Lb_sanfranciscensis_TMW_1.1304      --TCAAACAA 8
Lb_fermentum_28-3-CHN               --TCAAACGA 8
Lb_buchneri_CD034                   --TCAAGCAA 8
Lb_crispatus_FB049-03               --TCAAGCAA 8
Lb_delbrueckii_subsp_Lactis_CR      --TCAAGCAA 8
Lb_gasseri_K7                       --TCAAGCAA 8
Lb_hominis_CRBIP                    --TCAAGCAA 8
Lb_jensenii_115-3-CHN               --TCAAGCAA 8
Lb_johnsonii_DPC_6026               --TCAAGCAA 8
Lb_otakiensis_JCM_15040             --TCAAGCAA 8
Lb_rossiae_DSM_15814                --TCAAGCAA 8
Lb_ruminis_ATCC_25644               --TCAAGCAA 8
                                      *  *  *
```

St CRISPR 1 nexus

St CRISPR 3 nexus

Lrh nexus

Lbu nexus

Fig. 5

CLUSTAL 2.1 multiple sequence alignment

```
Lb_fermentum_28-3-CHN                 CAAGA- 5
Lb_pentosus_KCA1                      CAAGA- 5
Lb_plantarum_EGD-AQ4                  CAAGA- 5
Lb_otakiensis_JCM_15040               TAAAA- 5
Lb_rossiae_DSM_15814                  TAAAA- 5
Lb_johnsonii_DPC_6026                 TAAAA- 5
Lb_jensenii_115-3-CHN                 TAAAA- 5
Lb_hominis_CRBIP                      TAAAA- 5
Lb_gasseri_K7                         TAAAA- 5
Lb_delbrueckii_subsp_Lactis_CR        TAAAA- 5
Lb_crispatus_FB049-03                 TAAAA- 5
Lb_buchneri_CD034                     TAAAA- 5
Lb_sanfranciscensis_TMW_1.1304        TAAAA- 5
Lb_reuteri_mlc3                       TAAAA- 5
Lb_curvatus_CRL_705                   TAAAA- 5
Lb_coryniformis_subsp_corynifo        TAAAA- 5
St_lutetiensis_033                    TAAAA- 5
St_gallolyticus_ATCC_BAA-2069         TAAAA- 5
St_intermedius_SK54                   TAAAA- 5
St_mutans_UA159                       TAAAA- 5
St_anginosis_DSM20563                 TAAAA- 5
St_equi_subsp_zooepidemicus           TAAAA- 5
St_dysagalactiae_subsp_equisim        TAAAA- 5
St_pyogenes_M1_GAS                    TAAAA- 5
St_agalactiae_GB00300                 TAAAA- 5
St_oralis_SK304                       TAAAA- 5
St_mitis_SK321                        TAAAA- 5
St_sanguinis_SK330                    TAAAA- 5
St_salivarius_K12                     TAAAA- 5
St_thermophilus_LMD-9_CRISPR3         TAAAA- 5
St_infantarius_subsp_infantari        TACAAA 6
St_henryi_DSM_19005                   TACAAA 6
St_orisratti_DSM_15617                TACAAA 6
St_parasanguinis_F0449                TACAAA 6
St_gordonii_str_Challis_substr        TACAAA 6
St_anginosus_1_2_62CV                 TACAAA 6
St_intermedius_B196                   TACAAA 6
St_mutans_NLML5                       TACAAA 6
St_vestibularis_ATCC_49124            TACAAA 6
St_thermophilus_CRISPR1               TACAAA 6
Lb_brevis_subsp_gravesensis_AT        TAAAG- 5
Lb_buchneri_ATCC_11577                TAAAG- 5
Lb_mucosae_IM1_177_17                 TAAAG- 5
Lb_casei                              TGAGA- 5
Lb_paracasei_subsp_Paracasei_8        TGAGA- 5
Lb_paracasei_subsp_Tolerans_Lp        TGAGA- 5
Lb_rhamnosus_GG                       TGAGA- 5
Lb_pentosus_IG1                       TGAAA- 5
Lb_salivarius_UCC118                  TGAAA- 5
Lb_ruminis_ATCC_25644                 TGAAA- 5
```

St CRISPR 1 anti-stitches

St CRISPR 3 anti-stitches

Lrh anti-stitches

Lbu anti-stitches

Fig. 7

| | | |
|---|---|---|
| St_thermophilus_LMD-9_CRISPR3 | GAGT-- | 4 |
| St_gallolyticus_ATCC_BAA-2069 | GAGT-- | 4 |
| St_lutetiensis_033 | GAGT-- | 4 |
| Lb_coryniformis_subsp_corynifo | GAGT-- | 4 |
| Lb_curvatus_CRL_705 | GAGT-- | 4 |
| Lb_mucosae_LM1_177_17 | GAGT-- | 4 |
| Lb_reuteri_mlc3 | GAGT-- | 4 |
| Lb_rhamnosus_GG | GAGT-- | 4 |
| Lb_salivarius_UCC118 | GAGT-- | 4 |
| Lb_sanfranciscensis_TMW_1.1304 | GAGT-- | 4 |
| Lb_fermentum_28-3-CHN | TAGT-- | 4 |
| St_intermedius_SK54 | AAGT-- | 4 |
| Lb_ruminis_ATCC_25644 | AAGT-- | 4 |
| St_mutans_UA159 | AAGT-- | 4 |
| St_anginosis_DSM20563 | AAGT-- | 4 |
| St_equi_subsp_zooepidemicus | AAGT-- | 4 |
| St_dysagalactiae_subsp_equisim | AAGT-- | 4 |
| St_pyogenes_M1_GAS | AAGT-- | 4 |
| St_oralis_SK304 | AAGT-- | 4 |
| St_mitis_SK321 | AAGT-- | 4 |
| St_sanguinis_SK330 | AAGT-- | 4 |
| St_salivarius_K12 | AAGT-- | 4 |
| St_thermophilus_CRISPR1 | AAGC-- | 4 |
| St_vestibularis_ATCC_49124 | AAGC-- | 4 |
| St_mutans_NLML5 | AAGC-- | 4 |
| St_intermedius_B196 | AAGC-- | 4 |
| St_anginosus_1_2_62CV | AAGC-- | 4 |
| St_gordonii_str_Challis_substr | AAGC-- | 4 |
| St_parasanguinis_F0449 | AAGC-- | 4 |
| St_orisratti_DSM_15617 | -AGCC- | 4 |
| St_henryi_DSM_19005 | -AGCC- | 4 |
| St_infantarius_subsp_infantari | -AGCC- | 4 |
| Lb_brevis_subsp_gravesensis_AT | -GGTT- | 4 |
| Lb_buchneri_ATCC_11577 | -GGTT- | 4 |
| Lb_pentosus_IG1 | -TATT- | 4 |
| Lb_jensenii_115-3-CHN | --ATTT | 4 |
| Lb_delbrueckii_subsp_Lactis_CR | -GATT- | 4 |
| Lb_gasseri_K7 | -GATT- | 4 |
| Lb_hominis_CRBIP | -GATT- | 4 |
| Lb_johnsonii_DPC_6026 | -GATT- | 4 |
| Lb_crispatus_FB049-03 | -AATT- | 4 |
| St_agalactiae_GB00300 | GCGT-- | 4 |
| Lb_pentosus_KCA1 | GCGT-- | 4 |
| Lb_plantarum_EGD-AQ4 | GCGT-- | 4 |
| Lb_rossiae_DSM_15814 | GCGT-- | 4 |
| Lb_buchneri_CD034 | GTGT-- | 4 |
| Lb_otakiensis_JCM_15040 | GTGT-- | 4 |
| Lb_casei | ACGT-- | 4 |
| Lb_paracasei_subsp_Paracasei_8 | ACGT-- | 4 |
| Lb_paracasei_subsp_Tolerans_Lp | ACGT-- | 4 |

St CRISPR 1 bulge

St CRISPR 3 bulge

Lrh bulge

Lbu bulge

Fig. 9

CLUSTAL 2.1 multiple sequence alignment

```
St_thermophilus_CRISPR1              GTTTT-----TGTACTCTCAAGATTAAGTAACTGTACAAC- 36
St_vestibularis_ATCC_49124           GTTTT-----TGTACTCTCAAGATTAAGTAACTGTACAAC- 36
St_mutans_NLML5                      GTTTT-----TGTACTCTCAAGATTAAGTAACTGTACAAC- 36
St_gordonii_str_Challis_substr       GTTTT-----TGTACTCTCAAGATTAAGTAACTGTACAAC- 36
St_anginosus_1_2_62CV                GTTTT-----TGTACTCTCAAGATTAAGTAACTGTAAAAC- 36
St_orisratti_DSM_15617               GTTTT-----TGTACTCTCAAGATTAAGTAACTGTAAAAC- 36
St_henryi_DSM_19005                  GTTTT-----TGTACTCTCAAGATTAAGTAACTGTAAAAC- 36
St_infantarius_subsp_infantari       GTTTT-----TGTACTCTCAAGATTAAGTAACCGTAAAAC- 36
St_intermedius_B196                  GTTTT-----TGTACTCTCAAGATTAAGTAACTGCAAAAC- 36
St_parasanguinis_F0449               GTTTT-----TGTACTCTCAAGATTAAGTAACTGCAAAAC- 36
Lb_rossiae_DSM_15814                 GTTTAGA--TGTA-TGTCA-GATCAATAGGGTTA-AGAAC- 36
St_mutans_UA159                      GTTTAGAGCTGTGTTGT-----TTCGAATGGTTCCAAAAC- 36
St_lutetiensis_033                   GTTTAGAGCTGTGTTGT-----TTCGAATGGTTCCAAAAC- 36
St_oralis_SK304                      GTTTAGAGCTGTGTTGT-----TTCGAATGGTTCCAAAAC- 36
St_mitis_SK321                       GTTTAGAGCTGTGTTGT-----TTCGAATGGTTCCAAAAC- 36
St_sanguinis_SK330                   GTTTAGAGCTGTGTTGT-----TTCGAATGGTTCCAAAAC- 36
St_salivarius_K12                    GTTTAGAGCTGTGTTGT-----TTCGAATGGTTCCAAAAC- 36
St_thermophilus_LMD-9_CRISPR3        GTTTAGAGCTGTGTTGT-----TTCGAATGGTTCCAAAAC- 36
St_agalactiae_GB00300                GTTTAGAGCTGTGCTGT-----TTCGAATGGTTCCAAAAC- 36
St_anginosus_DSM20563                GTTTAGAGCTGTGCTGT-----TTCGAATGGTTCCAAAAC- 36
St_gallolyticus_ATCC_BAA-2069        GTTTAGAGCTGTGCTGT-----TTCGAATGGTTCCAAAAC- 36
St_pyogenes_M1_GAS                   GTTTAGAGCTATGCTGT-----TTGAATGGTCCCAAAAC- 36
St_dysagalactiae_subsp_equisim       GTTTAGAGCTATGTTGT-----TTGAATGGTCCCAAAAC- 36
St_equi_subsp_zooepidemicus          GTTTAGAGTTATGCTGT-----ATTGAATGGTTCCAAAAC- 36
Lb_buchneri_ATCC_11577               GCTTTAGTAGTAGTTCAA----AACAATGATGTTTTATCC- 36
Lb_mucosae_LM1_177_17                GCTTTAGATGGATGTTAA----ATCAATGATGTAATTCTC- 36
Lb_brevis_subsp_gravesensis_AT       GCTTTAGTAGGATGTTAA----ATCAATGATGTTAAACCC- 36
Lb_casei                             GTCTCAGGTAGATGTCGA----ATCAATCAG-TTCAAGAGC- 36
Lb_paracasei_subsp_Paracasei_8       GTCTCAGGTAGATGTCGA----ATCAATCAG-TTCAAGAGC- 36
Lb_paracasei_subsp_Tolerans_Lp       GTCTCAGGTAGATGTCGA----ATCAATCAG-TTCAAGAGC- 36
Lb_rhamnosus_GG                      GTCTCAGGTAGATGTCAG----ATCAATCAG-TTCAAGAGC- 36
Lb_pentosus_KCA1                     GTCTTGAATAGTAGTCAT----ATCAAACAGGTTT-AGAAC- 36
Lb_plantarum_EGD-AQ4                 GTCTTGAATAGTAGTCAT----ATCAAACAGGTTT-AGAAC- 36
Lb_fermentum_28-3-CHN                GTCTTGGATGAGTGTCAG----ATCAG-TAGTTCCGAGTAC- 36
Lb_reuteri_mlc3                      GTTTAGATGTACTTCAA----ATCAATAATGTTT-AGAAC- 36
Lb_sanfranciscensis_TMW_1.1304       GTTTAGAAGTACGTCAT----TCTAATGAGATTA-AGAG-- 35
Lb_ruminis_ATCC_25644                GTTTCAGCTGGATGTCAT----ATCAATGATGTTA-TGAAC- 36
Lb_coryniformis_subsp_corynifo       GTTTAGAAGAGTGTTAA----ATCAATGAG-TT-TAGAACC 36
Lb_curvatus_CRL_705                  GTTTAGAAGAGTATCAA----ATCAATGAG-TAGTTCAAC- 36
Lb_gasseri_K7                        GTTTAGATGGTTGTTAG----ATCAATAAGGCTT-AGATC- 36
Lb_johnsonii_DPC_6026                GTTTAGATGGTTGTTAG----ATCAATAAGGTTT-AGATC- 36
Lb_hominis_CRBIP                     GTTTAGTTAGTTGTTAG----ATCAATAAGGTTT-AGATC- 36
Lb_crispatus_FB049-03                GTTTAGATGATTGTTAG----ATCAATGAGGTTT-AGATC- 36
Lb_buchneri_NRRLB-30929              GTTTAGAAGGATGTTAA----ATCAATAAGGTTA-AACCC- 36
Lb_otakiensis_JCM_15040              GTTTAGAAGGATGTTAA----ATCAATAAGGTTA-AACCC- 36
Lb_pentosus_IG1                      GTTTCAGAAGGACATTAA----ATCAATAAGGTCA-AGACC- 36
Lb_salivarius_UCC118                 GTTTCAGAAGTATGTTAA----ATCAATAAGGTTA-AGACC- 36
Lb_delbrueckii_subsp_Lactis_CR       GTTTAGAAGGTTGTCTA----TTCAATAAGGTTT-AACCC- 36
                                     *  *
```

Fig. 11

| | | |
|---|---|---|
| St_thermophilus_CRISPR1 | -AAGCTACAAAGATAAGGCTT | 20 |
| St_vestibularis_ATCC_49124 | -AAGCTACAAAGATAAGGCTT | 20 |
| St_mutans_NLML5 | -AAGCTACAAAGATAAGGCTT | 20 |
| St_intermedius_B196 | -AAGCTACAAAGATAAGGCTT | 20 |
| St_anginosus_1_2_62CV | -AAGCTACAAAGATAAGGCTT | 20 |
| St_gordonii_str_Challis_substr | -AAGCTACAAAGATAAGGCTT | 20 |
| St_parasanguinis_F0449 | -AAGCTACAAAGATAAGGCTT | 20 |
| St_orisratti_DSM_15617 | -AGCCTACAAAGATAAGGCTT | 20 |
| St_henryi_DSM_19005 | -AGCCTACAAAGATAAGGCTT | 20 |
| St_infantarius_subsp_infantari | -AGCCTACAAAGATAAGGCTT | 20 |
| Lb_animalis_KCTC_3501 | -AAGTTA-AAA--TAAGGTTT | 17 |
| St_intermedius_SK54 | -AAGTTA-AAA--TAAGGC-- | 15 |
| St_mutans_UA159 | -AAGTTA-AAA--TAAGGC-- | 15 |
| St_anginosis_DSM20563 | -AAGTTA-AAA--TAAGGC-- | 15 |
| St_equi_subsp_zooepidemicus | -AAGTTA-AAA--TAAGGC-- | 15 |
| St_dysagalactiae_subsp_equisim | -AAGTTA-AAA--TAAGGC-- | 15 |
| St_pyogenes_M1_GAS | -AAGTTA-AAA--TAAGGC-- | 15 |
| St_oralis_SK304 | -AAGTTA-AAA--TAAGGC-- | 15 |
| St_mitis_SK321 | -AAGTTA-AAA--TAAGGC-- | 15 |
| St_sanguinis_SK330 | -AAGTTA-AAA--TAAGGC-- | 15 |
| St_salivarius_K12 | -AAGTTA-AAA--TAAGGC-- | 15 |
| St_thermophilus_LMD-9_CRISPR3 | -GAGTTA-AAA--TAAGGC-- | 15 |
| St_agalactiae_GB00300 | -GCGTTA-AAA--TAAGGC-- | 15 |
| St_gallolyticus_ATCC_BAA-2069 | -GAGTTA-AAA--TAAGGC-- | 15 |
| St_lutetiensis_033 | -GAGTTA-AAA--TAAGGC-- | 15 |
| Lb_brevis_subsp_gravesensis_AT | -GGTTTA-AAG--TCAAACAA | 17 |
| Lb_buchneri_ATCC_11577 | -GGTTTA-AAG--TCAAACAA | 17 |
| Lb_farciminis_KCTC_3681 | -AGATTA-AAA--T-AAACAA | 16 |
| Lb_casei | -ACGTTG-AGA--TCAAACAA | 17 |
| Lb_paracasei_subsp_Paracasei_8 | -ACGTTG-AGA--TCAAACAA | 17 |
| Lb_paracasei_subsp_Tolerans_Lp | -ACGTTG-AGA--TCAAACAA | 17 |
| Lb_rhamnosus_GG | -GAGTTG-AGA--TCAAACAA | 17 |
| Lb_salivarius_UCC118 | -GAGTTG-AAA--TCAAACAA | 17 |
| Lb_pentosus_IG1 | -TATTTG-AAA--TCAAACAA | 17 |
| Lb_coryniformis_subsp_corynifo | -GAGTTA-AAA--TCAAACAA | 17 |
| Lb_curvatus_CRL_705 | -GAGTTA-AAA--TCAAACAA | 17 |
| Lb_reuteri_mlc3 | -GAGTTA-AAA--TCAAACAA | 17 |
| Lb_sanfranciscensis_TMW_1.1304 | -GAGTTA-AAA--TCAAACAA | 17 |
| Lb_mucosae_LM1_177_17 | -GAGTTA-AAG--TCAAACAA | 17 |
| Lb_pentosus_KCA1 | -GCGTCA-AGA--TCAAACAA | 17 |
| Lb_plantarum_EGD-AQ4 | -GCGTCA-AGA--TCAAACAA | 17 |
| Lb_fermentum_28-3-CHN | -TAGTCA-AGA--TCAAACGA | 17 |
| Lb_buchneri_CD034 | -GTGTTA-AAA--TCAAGCAA | 17 |
| Lb_otakiensis_JCM_15040 | -GTGTTA-AAA--TCAAGCAA | 17 |
| Lb_rossiae_DSM_15814 | -GCGTTA-AAA--TCAAGCAA | 17 |
| Lb_delbrueckii_subsp_Lactis_CR | -GATTTA-AAA--TCAAGCAA | 17 |
| Lb_gasseri_K7 | -GATTTA-AAA--TCAAGCAA | 17 |
| Lb_hominis_CRBIP | -GATTTA-AAA--TCAAGCAA | 17 |
| Lb_johnsonii_DPC_6026 | -GATTTA-AAA--TCAAGCAA | 17 |
| Lb_jensenii_115-3-CHN | ATTTTTA-AAA--TCAAGCAA | 18 |
| Lb_crispatus_FB049-03 | -AATTTA-AAA--TCAAGCAA | 17 |
| Lb_ruminis_ATCC_25644 | -AAGTTG-AAA--TCAAGCAA | 17 |

| Species | Sequence |
|---|---|
| S. pyogenes | AAGGC---------UA-------GUCCGU |
| S. dysagalactiae | AAGGC---------UA-------GUCCGU |
| S. equi | AAGGCU--------UU-------GUCCGU |
| S. thermophilus CRISPR3 | AAGGCU--------UA-------GUCCGU |
| S. salivarius | AAGGCU--------UA-------GUCCGU |
| S. gallolyticus | AAGGCU--------UU-------GUCCGU |
| S. lutetiensis | AAGGCU--------UU-------GUCCGU |
| S. anginosis A | AAGGCU--------UU-------GUCCGU |
| S. mitis | AAGGCU--------UU-------GUCCGU |
| S. sanguinis | AAGGCU--------UU-------GUCCGU |
| S. oralis | AAGGCU--------UU-------GUCCGU |
| S. mutans | AAGGCU--------UC-------AUGCCG |
| S. intermedius | AAGGCU--------UC-------AUGCCG |
| S. anginosus B | AAGGCU--------UC-------AUGCCG |
| S. thermophilus CRISPR1 | AAGGCU--------UC-------AUGCCG |
| S. vestibularis | AAGGCU--------UC-------AUGCCG |
| S. gordonii | AAGGCU--------UC-------AUGCCG |
| S. parasanguinis | AAGGCU--------UC-------AUGCCG |
| S. orisratti | AAGGCU--------UC-------AUGCCG |
| S. henryi | AAGGCU--------UC-------AUGCCG |
| S. infantarius | AAGGCU--------UC-------AUGCCG |
| L. brevis | CAAACAAGGCA------GUAA------UGCCAAGUUC |
| L. buchneri A | CAAACAAGGUA------GCAA------UACCAAGUUC |
| L. mucosae | CAAACAAUGCA------UUC------UGCAAAGUUA |
| L. curvatus | CAAACAAGGUC------UUCG------GACCAAGUUU |
| L. fermentum | CAAACGAGUGG------UUUU------CCACGAGUUA |
| L. reuteri | CAAACAAGUGC------UUCA------GCACAAGUUU |
| L. plantarum | CAAACAAGGCA------UUU------UGCCGAGUUU |
| L. pentosus | CAAACAAGGCA------UUU------UGCCGAGUUU |
| L. coryniformis | CAAACAAGGC------GUAA------GCCAAGUUU |
| L. buchneri B | CAAGCAAAGCGC----UUU----GCGCGGAGUUU |
| L. otakiensis | CAAGCAAUGCGC----UUU----GCGCGGAGUUU |
| L. paracasei | CAAACAAAGCC------UC------GGCUGAGUUU |
| L. casei | CAAACAAAGCC------UC------GGCUGAGUUU |
| L. rhamnosus | CAAACAAAGCU------UC------AGCUGAGUUU |
| L. gasseri | CAAGCAAUGCAUCUUUUGAUGCAAAGUUU |
| L. hominis | CAAGCAAUGCAUCUUUUGAUGCAAAGUUU |
| L. johnsonii | CAAGCAAUGCAUCUUUUGAUGCAAAGUUU |
| L. jensenii | CAAGCAAGGCU------UUCG------GGCCGAGUUU |
| L. delbrueckii | CAAGCAAAGCUC------UUCG------GAGCGGAGUUU |
| L. rossiae | CAAGCAAGGCU------UUCG------AGCCAAGUUU |

| | |
|---|---|
| S. thermophilus CRISPR3 | GTTTTAGAGCTGTGTTGTTTCGAATGGTTCCAAAAC |
| S. salivarius | GTTTTAGAGCTGTGTTGTTTCGAATGGTTCCAAAAC |
| S. sanguinis | GTTTTAGAGCTGTGTTGTTTCGAATGGTTCCAAAAC |
| S. mitis | GTTTTAGAGCTGTGTTGTTTCGAATGGTTCCAAAAC |
| S. oralis | GTTTTAGAGCTGTGTTGTTTCGAATGGTTCCAAAAC |
| S. lutetiensis | GTTTTAGAGCTGTGTTGTTTCGAATGGTTCCAAAAC |
| S. gallolyticus | GTTTTAGAGCTGTGCTGTTTCGAATGGTTCCAAAAC |
| S. equi | GTTTTAGAGTTATGCTGTATTGAATGGTTCCAAAAC |
| S. pyogenes | GTTTTAGAGCTATGCTGTTTTGAATGGTCCCAAAAC |
| S. dysagalactiae | GTTTTAGAGCTATGTTGTTTTGAATGGTCCCAAAAC |
| S. anginosus B | GTTTTAGAGCTGTGCTGTTTCGAATGGTTCCAAAAC |
| | ********y*ry*w*y*****y***** |

| | |
|---|---|
| S. infantarius | GTTTTTGTACTCTCAAGATTTAAGTAACCGTAAAAC |
| S. intermedius | GTTTTTGTACTCTCAAGATTTAAGTAACTGCAAAAC |
| S. parasanguinis | GTTTTTGTACTCTCAAGATTTAAGTAACTGCAAAAC |
| S. thermophilus CRISPR1 | GTTTTTGTACTCTCAAGATTTAAGTAACTGTACAAC |
| S. vestibularis | GTTTTTGTACTCTCAAGATTTAAGTAACTGTACAAC |
| S. mutans | GTTTTTGTACTCTCAAGATTTAAGTAACTGTACAAC |
| S. gordonii | GTTTTTGTACTCTCAAGATTTAAGTAACTGTACAAC |
| S. anginosus A | GTTTTTGTACTCTCAAGATTTAAGTAACTGTAAAAC |
| S. orisratti | GTTTTTGTACTCTCAAGATTTAAGTAACTGTAAAAC |
| S. henryi | GTTTTTGTACTCTCAAGATTTAAGTAACTGTAAAAC |
| | ***************************y*y*m*** |

| | |
|---|---|
| L. fermentum | GTCTTGGATGAGTGTCAGATCAGTAGTTCCGAGTAC |
| L. rhamnosus | GTCTCAGGTAGATGTCAGATCAATCAGTTCAAGAGC |
| L. casei | GTCTCAGGTAGATGTCGAATCAATCAGTTCAAGAGC |
| L. paracasei | GTCTCAGGTAGATGTCGAATCAATCAGTTCAAGAGC |
| L. pentosus | GTCTTGAATAGTAGTCATATCAAACAGGTTTAGAAC |
| L. plantarum | GTCTTGAATAGTAGTCATATCAAACAGGTTTAGAAC |
| L. reuteri | GTTTTAGATGTACTTCAAATCAATAATGTTTAGAAC |
| L. curvatus | GTTTTAGAAGAGTATCAAATCAATGAGTAGTTCAAC |
| L. buchneri A | GCTTTAGTAGTAGTTCAAAACAATGATGTTTTATCC |
| L. coryniformis | GTTTTAGAAGAGTGTTAAATCAATGAGTTTAGAACC |
| L. brevis | GCTTTAGTAGGATGTTAAATCAATGATGTTAAACCC |
| L. mucosae | GCTTTAGATGGATGTTAAATCAATGATGTAATTCTC |
| L. rossiae | GTTTTAGATGTATGTCAGATCAATAGGGTTAAGAAC |
| L. hominis | GTTTTAGTTAGTTGTTAGATCAATAAGGTTTAGATC |
| L. gasseri | GTTTTAGATGGTTGTTAGATCAATAAGGCTTAGATC |
| L. johnsonii | GTTTTAGATGGTTGTTAGATCAATAAGGTTTAGATC |
| L. jensenii | GTTTTAGAAGGTTGTTAAATCAGTAAGTTGAAAAAC |
| L. buchneri B | GTTTTAGAAGGATGTTAAATCAATAAGGTTAAACCC |
| L. otakiensis | GTTTTAGAAGGATGTTAAATCAATAAGGTTAAACCC |
| L. delbrueckii | GTTTTAGAAGGTTGTCTATTCAATAAGGTTTAACCC |
| | *yyy*rrrwr....*y..ww**rw.rkk.......* |

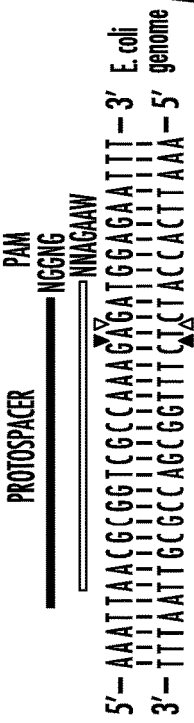
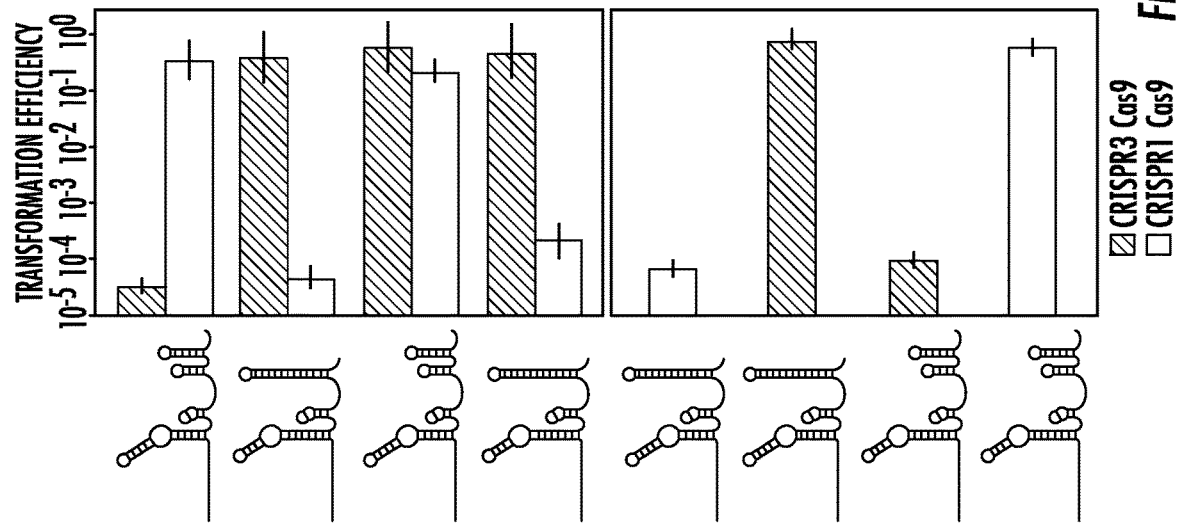
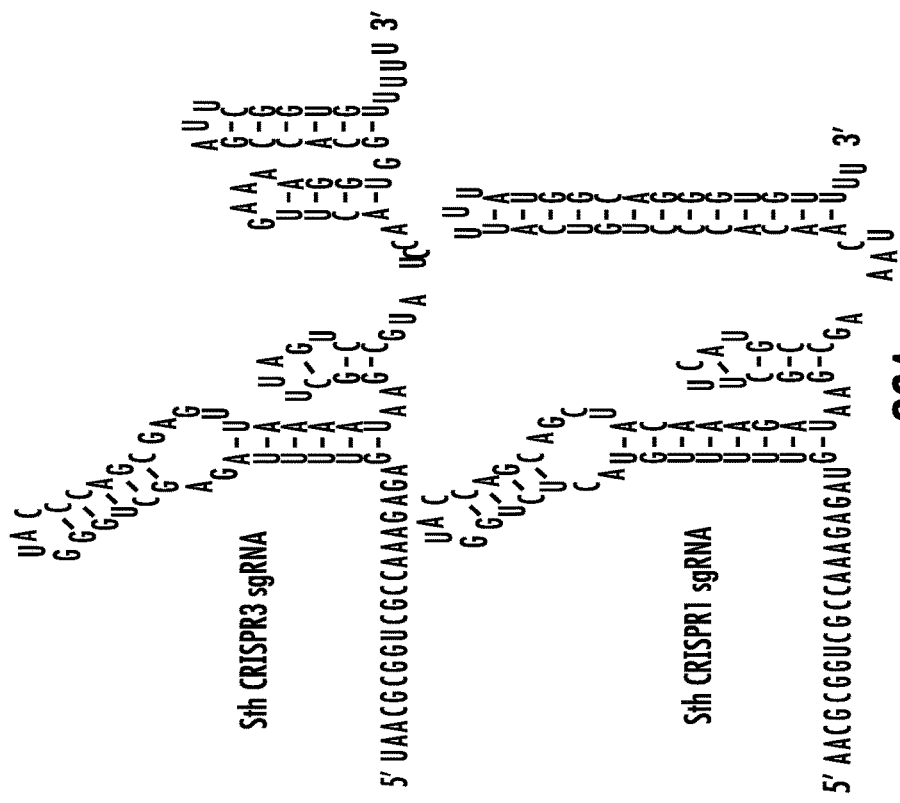

METHODS AND COMPOSITIONS FOR SEQUENCE GUIDING CAS9 TARGETING

STATEMENT OF PRIORITY

This application is a 35 U.S.C. § 371 national phase application of International Application Serial No. PCT/US2015/012747, filed Jan. 23, 2015, which claims the benefit, under 35 U.S.C. § 119(e), of U.S. Provisional Application No. 61/931,515, filed Jan. 24, 2014, the entire contents of each of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 5051-847_ST25.txt, 608,022 bytes bytes in size, generated on Jun. 6, 2018 and filed via EFS-Web, is provided in lieu of a paper copy. This Sequence Listing is hereby incorporated by reference into the specification for its disclosures.

FIELD OF THE INVENTION

The invention relates to a synthetic CRISPR-cas system and methods of use thereof for genome editing.

BACKGROUND OF THE INVENTION

Clustered Regularly Interspaced Short Palindromic Repeats (CRISPR), in combination with associated sequences (cas) constitute the CRISPR-Cas system, which confers adaptive immunity in many bacteria. CRISPR-mediated immunization occurs through the uptake of DNA from invasive genetic elements such as plasmids and phages, as novel "spacers."

CRISPR-Cas systems consist of arrays of short DNA repeats interspaced by hypervariable sequences, flanked by cas genes, that provide adaptive immunity against invasive genetic elements such as phage and plasmids, through sequence-specific targeting and interference (Barrangou et al. 2007. *Science.* 315:1709-1712; Brouns et al. 2008. *Science* 321:960-4; Horvath and Barrangou. 2010. *Science.* 327:167-70; Marraffini and Sontheimer. 2008. *Science.* 322: 1843-1845: Bhaya et al. 2011. *Annu. Rev. Genet.* 45:273-297; Tems and Terns. 2011. *Curr. Opin. Microbiol.* 14:321-327; Westra et al. 2012. *Annu. Rev. Genet.* 46:311-339: Barrangou R. 2013. *RNA.* 4:267-278). Typically, invasive DNA sequences are acquired as novel "spacers" (Barrangou et al. 2007. *Science.* 315:1709-1712), each paired with a CRISPR repeat and inserted as a novel repeat-spacer unit in the CRISPR locus. Subsequently, the repeat-spacer array is transcribed as a long pre-CRISPR RNA (pre-crRNA) (Brouns et al. 2008. *Science* 321:960-4), which is processed into small interfering CRISPR RNAs (crRNAs) that drive sequence-specific recognition. Specifically, crRNAs guide nucleases towards complementary targets for sequence-specific nucleic acid cleavage mediated by Cas endonucleases (Gameau et al. 2010. *Nature.* 468:67-71; Haurwitz et al. 2010. *Science.* 329:1355-1358; Sapranauskas et al. 2011. *Nucleic Acid Res.* 39:9275-9282; Jinek et al. 2012. *Science.* 337:816-821; Gasiunas et al. 2012. *Proc. Natl. Acad. Sci.* 109:E2579-E2586; Magadan et al. 2012. *PLoS One.* 7:e40913; Karvelis et al. 2013. *RNA Biol.* 10:841-851). These widespread systems occur in nearly half of bacteria (~46%) and the large majority of archaea (~90%). They are classified into three main CRISPR-Cas systems types (Makarova et al. 2011. *Nature Rev. Microbiol.* 9:467-477; Makarova et al. 2013. *Nucleic Acid Res.* 41:4360-4377) based on the cas gene content, organization and variation in the biochemical processes that drive crRNA biogenesis, and Cas protein complexes that mediate target recognition and cleavage. In types I and III, the specialized Cas endonucleases process the pre-crRNAs, which then assemble into a large multi-Cas protein complex capable of recognizing and cleaving nucleic acids complementary to the crRNA. A different process is involved in Type II CRISPR-Cas systems. Here, the pre-CRNAs are processed by a mechanism in which a trans-activating crRNA (tracrRNA) hybridizes to repeat regions of the crRNA. The hybridized crRNA-tracrRNA are cleaved by RNase III and following a second event that removes the 5' end of each spacer, mature crRNAs are produced that remain associated with the both the tracrRNA and Cas9. The mature complex then locates a target dsDNA sequence ('protospacer' sequence) that is complementary to the spacer sequence in the complex and cuts both strands. Target recognition and cleavage by the complex in the type II system not only requires a sequence that is complementary between the spacer sequence on the crRNA-tracrRNA complex and the target 'protospacer' sequence but also requires a protospacer adjacent motif (PAM) sequence located at the 3' end of the protospacer sequence. The exact PAM sequence that is required can vary between different type II systems.

The present disclosure provides methods and compositions for increasing the efficiency and specificity of synthetic type II CRISPR-Cas systems that improve efficiency and specificity for genome editing and other uses.

SUMMARY OF THE INVENTION

One aspect of the invention provides a synthetic trans-encoded CRISPR(tracr) nucleic acid (e.g., tracrRNA, tracrDNA) construct comprising from 5' to 3', an anti-zipper sequence comprising at least about three-nucleotides: a bulge sequence comprising at least about three nucleotides; an anti-stitch sequence comprising a nucleotide sequence of NNANN; a nexus sequence comprising a nucleotide sequence of T(A/C)A(A/G)(G/A)C (or U(A/C)A(A/G)(G/A)C)), TCAAAC, (or UCAAAC), TAAGGC (or UAAGGC), GATAAGG (or GAUAAGG). GATAAGGCTT (or GAUAAGGCUU) (SEQ ID NO:74), TCAAG (or UCAAG), TCAAGCAA (or UCAAGCAA), T(C/A)AA(A/C)(C/A)(A/G)(A/T) (or U(C/A)AA(A/C)(C/A)(A/G)(A/U)), GATAAGGCCATGCC (SEQ ID NO:75), TAAGGCTAGTCC (SEQ ID NO:76), TCAAGCAAAGC (SEQ ID NO:77), or TCAAACAAAGCTTCAGC (SEQ ID NO:78); and a hairpin sequence comprising a nucleotide sequence having at least one hairpin, said hairpin comprising at least three matched base pairs, wherein the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence.

A second aspect of the invention provides a synthetic CRISPR nucleic acid (e.g., crRNA, crDNA) construct comprising, from 3' to 5', a zipper sequence comprising at least about three-nucleotides that hybridizes to the anti-zipper of a tracrRNA, a bulge sequence comprising at least two nucleotides (e.g., the nucleotide sequence of (—NN—)), a stitch sequence comprising a nucleotide sequence of NNTNN (or NNUNN) that hybridizes to the anti-stitch of a tracrRNA, a $G_{R1}$ comprising a nucleotide G or GTT, and a spacer sequence having a 5' end and a 3' end and comprising at least seven nucleotides at its 3' end having 100% identity to a target DNA, and the zipper sequence is located immediately upstream of the bulge sequence, the bulge sequence is located immediately upstream of the stitch sequence, the stitch sequence is located immediately upstream of the $G_{R1}$, and the $G_{R1}$ is located immediately upstream of the spacer sequence.

A third aspect of the invention provides a synthetic CRISPR nucleic acid array comprising, a nucleotide sequence encoding two or more CRISPR nucleic acid constructs of this invention, wherein the two or more CRISPR nucleic acid constructs are located immediately adjacent to one another on said nucleotide sequence and the zipper sequences of said two or more CRISPR nucleic acid constructs are identical, the stitch sequences of said two or more CRISPR nucleic acid constructs are identical, and the spacer sequences of said two or more CRISPR nucleic acid constructs are identical or non-identical.

A fourth aspect of the invention provides a chimeric nucleic acid construct comprising the synthetic tracr nucleic acid construct of the invention and the synthetic CRISPR nucleic acid construct of the invention, wherein the zipper sequence of the synthetic CRISPR nucleic acid construct is at least about 70% complementary to and is hybridized to the anti-zipper sequence of said synthetic tracr nucleic acid construct, the stitch sequence of the synthetic CRISPR nucleic acid construct is 100% complementary to and hybridizes to the anti-stitch sequence of said synthetic tracr nucleic acid construct and the bulge sequence of the synthetic CRISPR nucleic acid construct and the bulge sequence of the synthetic CRISPR nucleic acid construct are non-complementary.

A fifth aspect of the invention provides a method for site-specific cleavage of a double stranded target DNA, comprising: contacting a chimeric nucleic acid construct of this disclosure or an expression cassette comprising said chimeric nucleic acid construct with the target DNA in the presence of a Cas9 nuclease, thereby producing a site-specific cleavage of the target DNA in a region defined by hybridization of the spacer sequence to the target DNA.

A sixth aspect of the invention provides a method for site-specific cleavage of a double stranded target DNA, comprising:

contacting a trans-encoded CRISPR (tracr) nucleic acid molecule and a CRISPR nucleic acid molecule with the target DNA in the presence of a Cas9 nuclease, wherein (a) the tracr nucleic acid molecule is encoded by a nucleotide sequence comprising from 5' to 3', an anti-zipper sequence comprising at least about three-nucleotides: a bulge sequence comprising at least about three nucleotides; an anti-stitch sequence comprising a nucleotide sequence of NNANN; a nexus sequence comprising a nucleotide sequence of TNANNC, T(A/C)A(A/G)(G/A)C. TCAAAC, TAAGGC, GATAAGG, GATAAGGCTT (SEQ ID NO:74), TCAAG, TCAAGCAA, T(C/A)AA(A/C)(C/A)(A/G)(A/T), GATAAGGCCATGCC (SEQ ID NO:75), TAAGGCTAGTCC (SEQ ID NO:76), TCAAGCAAAGC (SEQ ID NO:77), or TCAAACAAAGCTTCAGC (SEQ ID NO:78); and a hairpin sequence comprising a nucleotide sequence having at least two hairpins, each hairpin comprising at least three matched base pairs, and the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence; and (b) the CRISPR nucleic acid molecule is encoded by a nucleotide sequence comprising from 3' to 5', a zipper sequence comprising at least about three nucleotides, a bulge sequence comprising a nucleotide sequence having at least two nucleotides (e.g., the nucleotide sequence of (—NN—)), a stitch sequence comprising a nucleotide sequence of NNTNN (or NNUNN), a $G_{R1}$ comprising a nucleotide G or GTT, and a spacer sequence having a 5' end and a 3' end and comprising at least seven nucleotides at its 3' end having 100% identity to a target DNA, and the zipper sequence is located immediately upstream of the bulge sequence, the bulge sequence is located immediately upstream of the stitch sequence, the stitch sequence is located immediately upstream of the $G_{R1}$, and the $G_{R1}$ is located immediately upstream of the spacer sequence, and further wherein, when the anti-zipper sequence and the zipper sequence are present, they hybridize to one another, and the anti-stitch sequence and the stitch sequence hybridize to one another, and the spacer sequence of the CRISPR nucleic acid molecule is at least about 80% complementary to and hybridizes to at least a portion of the target DNA (e.g., at least about 7 consecutive nucleotides of said target DNA (e.g., about 7, 8, 9, 10, 11, 12, 13, 14, 15, 16, 17, 18, 19, 20, and the like, and any range or variation therein) and adjacent to a protospacer adjacent motif (PAM) on the target DNA, thereby resulting in a site-specific cleavage of the target DNA in a region defined by the complementary binding of the spacer sequence of the CRISPR nucleic acid molecule to the target DNA. Thus, in representative embodiments, the spacer sequence of the CRISPR nucleic acid molecule hybridizes to a portion of a target DNA sequence that is adjacent to a PAM, wherein the target sequence can comprise, consist essentially of, or consist of about 7 to about 20 consecutive nucleotides of the target DNA sequence.

A seventh aspect of the invention provides a method for site-specific cleavage of a double stranded target DNA, comprising:

contacting the double stranded target DNA with a chimeric nucleic acid comprising, (a) a first nucleotide sequence comprising from 5' to 3', an anti-zipper sequence comprising at least about three nucleotides: a bulge sequence comprising at least about three nucleotides; an anti-stitch sequence comprising a nucleotide sequence of NNANN: a nexus sequence comprising a nucleotide sequence of TNANNC, T(A/C)A(A/G)(G/A)C, TCAAAC, TAAGGC, GATAAGG, GATAAGGCTT (SEQ ID NO:74), TCAAG, TCAAGCAA, T(C/A)AA(A/C)(C/A)(A/G)(A/T), GATAAGGCCATGCC (SEQ ID NO:75), TAAGGCTAGTCC (SEQ ID NO:76), TCAAGCAAAGC (SEQ ID NO:77), or TCAAACAAAGCTTCAGC (SEQ ID NO:78); and a hairpin sequence comprising a nucleotide sequence having at least one hairpin, said hairpin comprising at least three matched base pairs, and the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence;

(b) a second nucleotide sequence comprising from 3' to 5', a zipper sequence comprising at least about three nucleotides, which hybridizes to the anti-zipper sequence of the first nucleotide sequence, a bulge sequence comprising a nucleotide sequence having at least two nucleotides (e.g., the nucleotide sequence of (—NN—)), a stitch sequence comprising a nucleotide sequence of NNTNN (or NNUNN), a $G_{R1}$ comprising a nucleotide G or GTT, and a spacer sequence having a 5' end and a 3' end and comprising at least seven nucleotides at its 3' end that have 100% complementarity to a target DNA, and the zipper sequence is located immediately upstream of the bulge sequence, the bulge sequence is located immediately upstream of the stitch sequence, the stitch sequence is located immediately upstream of the $G_{R1}$, and the $G_{R1}$ is located immediately upstream of the spacer sequence, and (c) a third nucleotide sequence encoding an amino acid sequence having at least 80% identity to an amino acid sequence encoding a Cas9 nuclease, wherein, when the anti-zipper sequence and zipper sequence are present, they hybridize to one another, the anti-stitch sequence hybridizes to the stitch sequence and the spacer sequence of the second nucleotide sequence hybridizes to at least a portion of the target DNA (e.g., at least about 7 consecutive nucleotides of said target DNA, preferably up to about 20 consecutive nucleotides) and adjacent to a protospacer adjacent motif (PAM) on the target DNA, thereby resulting in a site-specific cleavage of the target DNA in a region defined by the complementary binding of the spacer sequence of the second nucleotide sequence to the target DNA An eighth aspect of the invention comprises a method of site-specific targeting of a polypeptide of interest to a double stranded (ds) target DNA, comprising contacting the chimeric nucleic acid construct of this disclosure or an expression cassette comprising said chimeric nucleic acid construct with the target DNA, thereby targeting the polypeptide of interest fused to the Cas9 to a specific site on the target DNA, said site defined by hybridization of the spacer sequence to the target DNA.

A ninth aspect of the invention comprises a method of site-specific targeting of a polypeptide of interest to a double stranded (ds) target DNA, comprising contacting a trans-encoded CRISPR (tracr) nucleic acid molecule and a CRISPR nucleic acid molecule with the target DNA in the presence of a Cas9 nuclease, wherein (a) the tracr nucleic acid molecule is encoded by a nucleotide sequence comprising from 5' to 3', an anti-zipper sequence comprising at least about three nucleotides; a bulge sequence comprising at least about three nucleotides; an anti-stitch sequence comprising a nucleotide sequence of NNANN; a nexus sequence comprising a nucleotide sequence of T(A/C)A(A/G)(G/A)C, TCAAAC. TAAGGC, GATAAGG, GATAAGGCTT (SEQ ID NO:74), TCAAG, TCAAGCAA, T(C/A)AA(A/C)(C/A)(A/G)(A/T), GATAAGGCCATGCC (SEQ ID NO:75), TAAGGCTAGTCC (SEQ ID NO:76), TCAAGCAAAGC (SEQ ID NO:77), or TCAAACAAAGCTTCAGC (SEQ ID NO:78); and a hairpin sequence comprising a nucleotide sequence having at least one hairpin, said hairpin comprising at least three matched base pairs, and the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence; and (b) the CRISPR nucleic acid molecule is encoded by a nucleotide sequence comprising from 3' to 5', a zipper sequence comprising at least about three nucleotides that hybridize to the anti-zipper sequence, a bulge sequence comprising a nucleotide sequence having at least two nucleotides (e.g., the nucleotide sequence of (—NN—)), a stitch sequence comprising a nucleotide sequence of NNTNN, a $G_{R1}$ comprising a nucleotide G or GTT, and a spacer sequence having a 5' end and a 3' end and comprising at least seven nucleotides at its 3' end having 100% identity to a target DNA, and the zipper sequence is located immediately upstream of the bulge sequence, the bulge sequence is located immediately upstream of the stitch sequence, the stitch sequence is located immediately upstream of the $G_{R1}$, and the $G_{R1}$ is located immediately upstream of the spacer sequence, and further wherein the Cas9 nuclease comprises a mutation in a HNH active site motif, a mutation in a RuvC active site motif, and is fused to a polypeptide of interest, the anti-zipper sequence and the zipper sequence hybridize to one another, the anti-stitch sequence hybridizes to the stitch sequence, and the spacer sequence hybridizes to at least a portion of the target DNA adjacent to a protospacer adjacent motif (PAM) on the target DNA, thereby resulting in a site-specific targeting of the polypeptide of interest to the target DNA in a region defined by the hybridization of the spacer sequence of the CRISPR nucleic acid molecule to the target DNA.

Further provided herein are expression cassettes, cells and kits comprising the nucleic acid constructs, nucleic acid arrays, nucleic acid molecules and/or nucleotide sequences of the invention.

These and other aspects of the invention are set forth in more detail in the description of the invention below.

BRIEF DESCRIPTION OF THE DRAWINGS

FIG. 1 shows a multiple sequence alignment for the nexus module.

FIG. 3A shows the consensus sequence for the Sth Cr1 group. FIG. 3B shows the consensus sequence for the Sth Cr3 group. FIG. 3C shows the consensus sequence for the Lrh group and FIG. 3D shows the consensus sequence for the Lbu group.

FIG. 5 shows a multiple sequence alignment for the anti-stitch module.

FIG. 6A shows the consensus sequence for the Sth Cr1 group. FIG. 6B shows the consensus sequence for the Sth Cr3 group. FIG. 6C shows the consensus sequence for the Lrh group and FIG. 6D shows the consensus sequence for the Lbu group.

FIG. 7 shows a multiple sequence alignment for the bulge module.

FIG. 8A shows the consensus sequence for the Sth Cr1 group. FIG. 8B shows the consensus sequence for the Sth Cr3 group. FIG. 8C shows the consensus sequence for the Lrh group and FIG. 8D shows the consensus sequence for the Lbu group.

FIG. 9 shows a multiple sequence alignment for the zipper module.

FIG. 11 shows a multiple sequence alignment for the bulge, anti-stitch and nexus modules.

FIG. 24A shows a phylogenetic tree based on Cas9 protein sequences from various *Streptococcus* and *Lactobacillus* species. The sequences clustered into three families in blue, orange and green. FIG. 24B shows a consensus sequence and secondary structure of the predicted guide RNA for each family. Each consensus RNA is composed of the crRNA (left) base-paired with the tracrRNA. Fully conserved bases are in color, variable bases are in black (2 possible bases) or represented by black dots (at least 3 possible bases), and base positions not always present are circled. Circles between positions indicate base pairing present in only some family members.

FIG. 25 shows CRISPR repeats sequence alignment. For each cluster, CRISPR repeat sequence alignments are shown, with conserved and consensus nucleotides specified at the bottom of each family, with Sth3 (top), Sth1 (middle) and Lb (bottom) families.

FIG. 26 shows tracrRNA sequence alignment. For each cluster, the experimentally determined, or computationally predicted tracrRNA sequence alignments are shown, with conserved and consensus nucleotides specified at the bottom of each family, with Sth3 (top), Sth1 (middle) and Lb (bottom) families.

FIG. 27 shows sgRNA nexus sequence alignment. Universally conserved residues are colored in red. Complementary nucleotides that constitute the nexus stem as summarized in FIG. 24B are underlined. Nucleotides that constitute the nexus loop are centered in the gap.

FIG. 29A-C shows sgRNA orthogonality. FIG. 29A shows sgRNA sequences for the *Streptococcus thermophilus* CRISPR3-Cas9 (top, blue) and the *S. thermophilus* CRISPR1-Cas9 (bottom, orange). FIG. 29B shows protospacer-targeting scheme. The predicted PAM for each sgRNA is shown. Triangles designate the putative cut sites for each Cas9. FIG. 29C Cas9:chimeric-sgRNA orthogonality in *E. coli*. Chimeric sgRNAs. Each sgRNA (left) was subjected to the transformation assay (right) in *E. coli* expressing the SthCRISPR3 Cas9 (blue) and/or the SthCRISPR1 Cas9 (orange). Low transformation efficiencies indicate functional Cas9:sgRNA pairs through lethal self-targeting of the *E. coli* genome. Values reflect the geometric mean and S.E.M. of three independent experiments.

DETAILED DESCRIPTION

Figure 2:
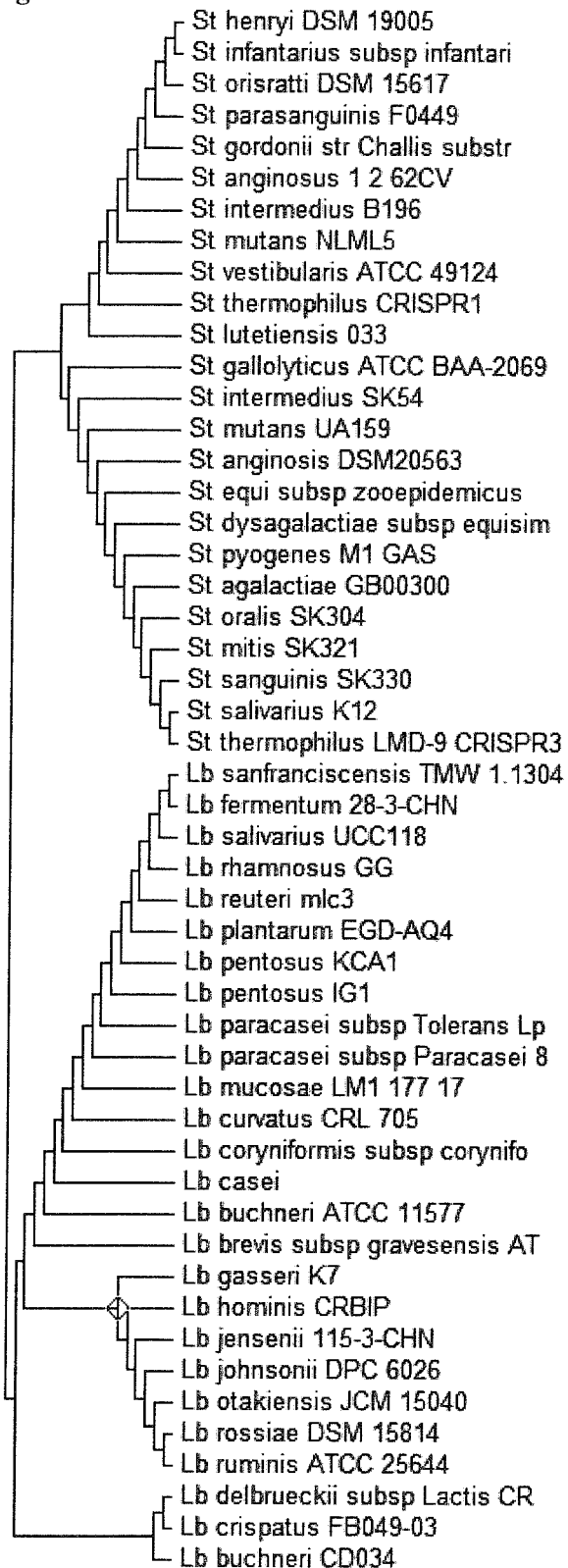
FIG. 2 shows a maximum likelihood tree for the nexus module.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A. B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The "bulge sequence" as used herein refers to non-complementary (non-hybridizing) nucleotide sequences comprised in a synthetic tracr nucleic acid construct and a synthetic CRISPR nucleic acid construct/CRISPR nucleic acid array. In the synthetic tracr nucleic acid construct, the bulge sequence is located between the anti-zipper and the anti-stitch sequences is comprised of about three nucleotides to about six nucleotides (e.g., about 3, 4, 5, 6 nucleotides; e.g., about 3 to about 6 nucleotides, about 3 to about 5 nucleotides, about 3 to about 4 nucleotides, and the like) that are non-complementary (100% non-identity) to a corresponding bulge sequence in the synthetic CRISPR nucleic acid construct/CRISPR nucleic acid array. The bulge sequence of the synthetic CRISPR nucleic acid construct/CRISPR nucleic acid array is located between the zipper and the stitch sequences and between the zipper and the stitch sequences and comprises, consists essentially of, or consists of at least two nucleotides (e.g., the nucleotide sequence of (—NN—)) (e.g., about 2, 3, 4, 5, 6 nucleotides; e.g., about 2 to about 6 nucleotides, about 2 to about 5 nucleotides, about 2 to about 4 nucleotides; about 3 to about 6 nucleotides, about 3 to about 5 nucleotides, and the like). The nucleotide composition of the bulge sequences can be any series of at least two (synthetic CRISPR nucleic acid construct/CRISPR nucleic acid array) or three or more (synthetic tracr nucleic acid construct) nucleotides as long as they are not complementary (e.g., 100% non-identity) and therefore do not hybridize to one another. As a result of the non-complementarity of the bulge sequences on the synthetic tracr nucleic acid construct and the synthetic CRISPR nucleic acid construct/CRISPR nucleic acid array, when the anti-zipper and zipper sequences and the anti-stitch and stitch sequences align and hybridize (as in the chimeric nucleic acid construct), a protrusion or bulge is formed on the synthetic tracr nucleic acid construct side of the chimeric nucleic acid construct (See, e.g., FIGS. 12-16). While not wishing to be bound by any particular theory, it is believed that the bulge structure may be involved in the functioning of the CRISPR-Cas system.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

"Cas9 nuclease" refers to a large group of endonucleases that catalyze the double stranded DNA cleavage in the CRISPR Cas system. These polypeptides are well known in the art and many of their structures (sequences) are characterized (See, e.g., WO2013/176772: WO/2013/188638). The domains for catalyzing the cleavage of the ds DNA are the RuvC domain and the HNH domain. The RuvC domain is responsible for nicking the (−) strand and the HNH domain is responsible for nicking the (+) strand (See, e.g., Gasiunas et al. *PNAS* 109(36):E2579-E2586 (Sep. 4, 2012)).

As used herein, "chimeric" refers to a nucleic acid molecule or a polypeptide in which at least two components are derived from different sources (e.g., different organisms, different coding regions).

"Complement" as used herein can mean 100% complementarity or identity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, "contact", contacting", "contacted," and grammatical variations thereof, refers to placing the components of a desired reaction together under conditions suitable for carrying out the desired reaction (e.g., integration, transformation, site-specific cleavage (nicking, cleaving), amplifying, site specific targeting of a polypeptide of interest and the like). The methods and conditions for carrying out such reactions are well known in the art (See, e.g., Gasiunas et al, (2012) *Proc. Natl. Acad Sci.* 109:E2579-E2586; M. R. Green and J. Sambrook (2012) Molecular Cloning: A Laboratory Manual. 4th Ed., Cold Spring Harbor Laboratory Press. Cold Spring Harbor, N.Y.).

A "fragment" or "portion" of a nucleotide sequence of the invention will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 990/identical) to the reference nucleic acid or nucleotide sequence. Such a nucleic acid fragment or portion according to the invention may be, where appropriate, included in a larger polynucleotide of which it is a constituent. Thus, hybridizing to (or hybridizes to, and other grammatical variations thereof), for example, at least a portion of a target DNA, refers to hybridization to a nucleotide sequence that is identical or substantially identical to a length of contiguous nucleotides of the target DNA.

As used herein a "$G_{R1}$" is single nucleotide, G, or a short three nucleotide sequence, GTT, comprised on the repeat portion of crRNA or a synthetic CRISPR nucleic acid construct. The $G_{R1}$ does not hybridize with the anti-repeat of the tracrRNA or the synthetic tracr nucleic acid construct of this disclosure. In a non-canonical Watson-crick base-pairing scheme, the $G_{R1}$ may, however, form a wobble base-pair with a U at the end of the anti-CRISPR repeat portion of the tracrRNA.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A "hairpin sequence" as used herein, is a nucleotide sequence comprising hairpins. A hairpin (e.g., stem-loop, fold-back) refers to a nucleic acid molecule having a secondary structure that includes a region of nucleotides that form a double strand that are further flanked on either side by single stranded-regions. Such structures are well known in the art. As known in the art, the double stranded region can comprise some mismatches in base pairing or can be perfectly complementary. In some embodiments of the present disclosure, a hairpin sequence of the nucleic acid constructs is located at the 3' end of a synthetic tracr nucleic acid construct and immediately downstream of a "nexus sequence". Without being bound by any particular theory, it is believed that hairpins may be involved in Cas9 binding to a crRNA-tracrRNA complex (e.g., the synthetic CRISPR nucleic acid construct-synthetic A "heterologous" or a "recombinant" nucleotide sequence is a nucleotide sequence not naturally associated with a host cell into which it is introduced, including non-naturally occurring multiple copies of a naturally occurring nucleotide sequence.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention. Thus, for example, a homologue of a Cas9 polypeptide useful with this invention can be about 70% homologous or more to any one of the Cas9 sequences provided herein.

As used herein, hybridization, hybridize, hybridizing, and grammatical variations thereof, refer to the binding of two fully complementary nucleotide sequences or substantially complementary sequences in which some mismatched base pairs may be present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al, (2012) *Proc. Natl. Acad. Sci.* 109:E2579-E2586: M. R. Green and J. Sambrook (2012) Molecular Cloning: A Laboratory Manual. 4th Ed., Cold Spring Harbor Laboratory Press, Cold Spring Harbor, N.Y.).

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

The terms, "invasive foreign genetic element," "invasive foreign nucleic acid" or "invasive foreign DNA" mean DNA that is foreign to the bacteria (e.g., genetic elements from, for example, pathogens including, but not limited to, viruses, bacteriophages, and/or plasmids).

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

"Nexus sequence" as used herein refers to a nucleotide sequence located immediately downstream of the "anti-stitch sequence" in a synthetic tracr nucleic acid construct. The nexus is about six to ten nucleotides in length comprising a highly conserved sequence: TNANNC. In some embodiments, the nexus can be a nucleotide sequence of T(A/C)A(A/G)(G/A)C (or U(A/C)A(A/G)(G/A)C)), GATAAGGCTT (or GAUAAGGCUU) (SEQ ID NO:74). TCAAGCAA (or UCAAGCAA), or T(C/A)AA(A/C)(C/A)(A/G)(A/T) (or U(C/A)AA(A/C)(C/A)(A/G)(A/U). Without being bound by any particular theory, based on the sequence conservation, it is believed that the nexus may be important in Cas9 orthogonality and recognition.

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The nucleic acid constructs of the present disclosure can be DNA or RNA, but are preferably DNA. Thus, although the nucleic acid constructs of this invention may be described and used in the form of DNA, depending on the intended use, they may also be described and used in the form of RNA.

A "synthetic" nucleic acid or nucleotide sequence, as used herein, refers to a nucleic acid or nucleotide sequence that is not found in nature but is constructed by the hand of man and as a consequence is not a product of nature.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Except as otherwise indicated, nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end. Thus, for example, an element in the 3' region of a polynucleotide can be located anywhere from the first nucleotide located at the 3' end of the polynucleotide to the nucleotide located halfway through the polynucleotide.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

A "protospacer sequence" refers to the target double stranded DNA and specifically to the portion of the target DNA that is fully or substantially complementary (and hybridizes) to the spacer sequence of the synthetic CRISPR nucleic acid construct.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%. 97%, 98%, 99%, or 100% as compared to a control. In particular embodiments, the reduction can result in no or essentially no (i.e., an insignificant amount, e.g., less than about 10% or even 5%) detectable activity or amount. Thus, in some embodiments, a mutation in a Cas9 nuclease can reduce the nuclease activity of the Cas9 by at least about 5%, 10%, 15%, 20%, 25%, 35%, 50%, 75%, 80%, 85%, 90%, 95%, 97%, 98%, 990%, or 100% as compared to a control (e.g., a wild-type Cas9).

A "repeat sequence" as used herein refers, for example, to the repeat sequences of wild-type CRISPR loci or of the synthetic CRISPR nucleic acid constructs that are separated by "spacer sequences." A repeat sequence can complementary (e.g., a 100% base pair match) to or substantially complementary, e.g., at least 70% complementary (e.g., 70%, 71%, 72%, 73%, 74%, 75%/0, 76%, 77%, 78%, 79%, 80%, 81%, 82%/0, 83%, 84%, 85%, 86%, 87%, 88%, 89%, 90%, 91%, 92%, 93%, 94%, 95%, 96%, 97%, 98%, 999%, or more), to a corresponding anti-repeat sequence.

A "repeat sequence" of a synthetic CRISPR nucleic acid construct of this disclosure comprises a "zipper sequence," a "bulge sequence," a "stitch sequence," and a "spacer sequence." In some embodiments, a synthetic CRISPR nucleic acid construct can comprise a $G_{R1}$ that in other embodiments is comprised in the stitch sequence.

A "zipper sequence." as used herein, refers to a portion of the repeat sequence that is located 3' or immediately upstream (3' to 5') of the bulge sequence in a synthetic CRISPR nucleic acid construct and comprises, consists of, or consists essentially of at least about three nucleotides (e.g., 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides, or any range or value therein). In some embodiments, a zipper sequence can be referred to as the "upper stem." A "zipper sequence" shares sufficient complementarity with a corresponding "anti-zipper sequence" located on a synthetic tracr nucleic acid construct such that upon contact the zipper sequence and the anti-zipper sequence and can hybridize to one another, thereby binding the two nucleic acid constructs together. In some embodiments, the zipper/anti-zipper sequence can be referred to as an "upper stem." A zipper sequence can be fully complementary (e.g., a 100% base pair match) to or substantially complementary, e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more) to the corresponding anti-zipper sequence. Accordingly, an anti-zipper sequence of a synthetic tracr nucleic acid construct of this invention comprises, consists of, or consists essentially of at least about three nucleotides (e.g., about 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides, or any range or value therein) that are fully complementary to or substantially complementary to the corresponding zipper sequence in a synthetic CRISPR nucleic acid construct or a synthetic CRISPR nucleic acid array. The anti-zipper sequence is the site of RNase III binding and as such comprises the nucleotide sequences that are well known in the art to be involved in RNase III binding (See, e.g., Pertzev and Nicholson, *Nucleic Acids Res.* 34(13):3708-3721(2006)).

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press. New York (1988): *Biocomputing: Informatics and Genome Projects* (Smith, D. W., ed.) Academic Press, New York (1993): *Computer Analysis of Sequence Data. Part I* (Griffin, A. M., and Griffin, H. G., eds.) Humana Press, New Jersey (1994); *Sequence Analysis in Molecular Biology* (von Heinje. G., ed.) Academic Press (1987); and *Sequence Analysis Primer* (Gribskov, M. and Devereux, J., eds.) Stockton Press, New York (1991).

A "spacer sequence" as used herein is a nucleotide sequence that is complementary to a target DNA (e.g., the "protospacer sequence"). The spacer sequence can be fully complementary or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target DNA. In representative embodiments, the spacer sequence has 100% complementarity to the target DNA. In additional embodiments, the complementarity of the 3' region of the spacer sequence to the target DNA is 100% but is less than 100% in the 5' region of the spacer and therefore the overall complementarity of the spacer sequence to the target DNA is less than 100%. Thus, for example, the first 7, 8, 9, 10, 11, 12, 13, 14, 15, 16, and the like, nucleotides in the 3' region of a 20 nucleotide spacer sequence (seed sequence) can be 100% complementary to the target DNA, while the remaining nucleotides in the 5' region of the spacer sequence are substantially complementary (e.g., at least about 70% complementary) to the target DNA. In some embodiments, the first 7 to 12 nucleotides of the spacer sequence can be 100% complementary to the target DNA, while the remaining nucleotides in the 5' region of the spacer sequence are substantially complementary (e.g., at least about 70% complementary) to the target DNA. In other embodiments, the first 7 to 10 nucleotides of the spacer sequence can be 100% complementary to the target DNA, while the remaining nucleotides in the 5' region of the spacer sequence are substantially complementary (e.g., at least about 70% complementary) to the target DNA. In representative embodiments, the first 7 nucleotides of the spacer sequence can be 100% complementary to the target DNA, while the remaining nucleotides in the 5' region of the spacer sequence are substantially complementary (e.g., at least about 70% complementary) to the target DNA.

A "stitch sequence" as used herein refers to a nucleotide sequence comprising, consisting essentially of, or consisting of about 5 nucleotides in length and having the consensus nucleotide sequence of NNTNN. The "stitch sequence" is located (5' to 3') on a synthetic CRISPR nucleic acid construct immediately upstream of the "bulge sequence" and downstream of the "$G_{R1}$". The "stitch sequence" tends to have a high AT content and hybridizes to the "anti-stitch sequence" located in the synthetic tracr nucleic acid construct. In some particular embodiments, the stitch sequence comprises, consists essentially of, or consists of the nucleotide sequence of (5' to 3') NNTNN, TTTGT, TTTTA, (T/C)(T/C)T(T/C)(T/G), TTTTTA, TTTCA.

An "anti-stitch sequence" as used herein, refers to a nucleotide sequence that is fully complementary to and hybridizes to the stitch sequence (e.g., NNANN, ACAAA, TAAAA, (T/C)(A/G)T(A/G)(A/G), TAAAA, TGAAA). The anti-stitch sequence is located on a synthetic tracr nucleic acid construct immediately downstream (5' to 3') of the bulge sequence and immediately upstream of the "nexus sequence." Without wishing to be bound by any particular theory, it is believed that the hybridization of the stitch sequence of the synthetic crRNA construct with the anti-stitch sequence of synthetic tracrRNA construct is involved in re-establishing base-pairing after the "bulge sequence." In some embodiments, the stitch/anti-stitch can be referred to as the "lower stem."

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%., 82%, 83%, 84%, 85%, 86%, 87%, 88%., 89%, 90° %, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of the invention, the substantial identity exists over a region of the sequences that is at least about 3 to about 15 (e.g., 3, 4, 5, 6, 7, 8, 9, 10, 11, 12, 13, 14, 15 residues in length and the like or any value or any range therein), at least about 5 to about 30, at least about 10 to about 30, at least about 16 to about 30, at least about 18 to at least about 25, at least about 18, at least about 22, at least about 25, at least about 30, at least about 40, at least about 50, about 60, about 70, about 80, about 90, about 100, about 110, about 120, about 130, about 140, about 150, or more residues in length, and any range therein. In representative embodiments, the sequences can be substantially identical over at least about 22 nucleotides. In some particular embodiments, the sequences are substantially identical over at least about 150 residues. In some embodiments, sequences of the invention can be about 70° % to about 100% identical over at least about 16 nucleotides to about 25 nucleotides. In some embodiments, sequences of the invention can be about 75% to about 100% identical over at least about 16 nucleotides to about 25 nucleotides. In further embodiments, sequences of the invention can be about 80% to about 100% identical over at least about 16 nucleotides to about 25 nucleotides. In further embodiments, sequences of the invention can be about 80% to about 100% identical over at least about 7 nucleotides to about 25 nucleotides. In some embodiments, sequences of the invention can be about 70% identical over at least about 18 nucleotides. In other embodiments, the sequences can be about 85% identical over about 22 nucleotides. In still other embodiments, the sequences can be 100% homologous over about 16 nucleotides. In a further embodiment, the sequences are substantially identical over the entire length of the coding regions. Furthermore, in representative embodiments, substantially identical nucleotide or protein sequences perform substantially the same function (e.g., Cas9 HNH and/or RuvC nickase activities).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues: always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see. Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M NaPO$_4$, 1 mM EDTA at 50° C. with washing in IX SSC, 0.1% SDS at 50° C. or in 7% sodium dodecyl sulfate (SDS), 0.5 M NaPO$_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0. IX SSC, 0.1% SDS at 50° C., or in 7% sodium dodecyl sulfate (SDS). 0.5 M NaPO$_4$, 1 mM EDTA at 50° C. with washing in 0.1×SSC, 0.1% SDS at 65° C.

Any nucleotide sequence and/or recombinant nucleic acid molecule of this invention can be codon optimized for expression in any species of interest. Codon optimization is well known in the art and involves modification of a nucleotide sequence for codon usage bias using species specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species specific codon usage table with the codons present in the native polynucleotide sequences. As is understood in the art, codon optimization of a nucleotide sequence results in a nucleotide sequence having less than 100% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original, native nucleotide sequence. Thus, in representative embodiments of the invention, the nucleotide sequence and/or recombinant nucleic acid molecule of this invention can be codon optimized for expression in the particular species of interest.

In some embodiments, the recombinant nucleic acids molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell.

In any of the embodiments described herein, the nucleotide sequences and/or recombinant nucleic acid molecules of the invention can be operatively associated with a variety of promoters and other regulatory elements for expression in various organisms cells. Thus, in representative embodiments, a recombinant nucleic acid of this invention can further comprise one or more promoters operably linked to one or more nucleotide sequences.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence, means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants. T. Kosuge, C. Meredith and A. Hollaender (eds.), Plenum Press, pp. 211-227).

Promoters can include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." These various types of promoters are known in the art.

The choice of promoter will vary depending on the temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a nucleic acid construct of the invention can be an "expression cassette" or can be comprised within an expression cassette. As used herein, "expression cassette" means a recombinant nucleic acid molecule comprising a nucleotide sequence of interest (e.g., the nucleic acid constructs of the invention (e.g., a synthetic tracr nucleic acid construct, a synthetic CRISPR nucleic acid construct, a synthetic CRISPR array, a chimeric nucleic acid construct; a nucleotide sequence encoding a polypeptide of interest, a nucleotide sequence encoding a cas9 nuclease)), therein said nucleotide sequence is operably associated with at least a control sequence (e.g., a promoter). Thus, some aspects of the invention provide expression cassettes designed to express the nucleotides sequences of the invention.

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression.

An expression cassette also can optionally include a transcriptional and/or translational termination region (i.e., termination region) that is functional in the selected host cell. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the host cell, or may be derived from another source (i.e., foreign or heterologous to the promoter, to the nucleotide sequence of interest, to the host, or any combination thereof).

An expression cassette also can include a nucleotide sequence for a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Of course, many examples of suitable selectable markers are known in the art and can be used in the expression cassettes described herein.

In addition to expression cassettes, the nucleic acid molecules and nucleotide sequences described herein can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an *Agrobacterium* binary vector in double or single stranded linear or circular form which may or may not be self transmissible or mobilizable. A vector as defined herein can transform prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukarvotic (e.g. higher plant, mammalian, yeast or fungal cells). In some representative embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, the nucleic acid molecules of this invention and/or expression cassettes can be comprised in vectors as described herein and as known in the art.

"Introducing," "introduce," "introduced" (and grammatical variations thereof) in the context of a polynucleotide of interest means presenting the nucleotide sequence of interest to the host organism or cell of said organism (e.g., host cell) in such a manner that the nucleotide sequence gains access to the interior of a cell. Where more than one nucleotide sequence is to be introduced these nucleotide sequences can be assembled as part of a single polynucleotide or nucleic acid construct, or as separate polynucleotide or nucleic acid constructs, and can be located on the same or different expression constructs or transformation vectors. Accordingly, these polynucleotides can be introduced into cells in a single transformation event, in separate transformation/transfection events, or, for example, they can be incorporated into an organism by conventional breeding protocols. Thus, in some aspects of the present invention one or more nucleic acid constructs of this invention (e.g., a synthetic tracr nucleic acid construct, a synthetic CRISPR nucleic acid construct, a synthetic CRISPR array, a chimeric nucleic acid construct; a nucleotide sequence encoding a polypeptide of interest, a nucleotide sequence encoding a cas9 nuclease, and the like) can be introduced into a host organism or a cell of said host organism.

The term "transformation" or "transfection" as used herein refers to the introduction of a heterologous nucleic acid into a cell. Transformation of a cell may be stable or transient. Thus, in some embodiments, a host cell or host organism is stably transformed with a nucleic acid molecule of the invention. In other embodiments, a host cell or host organism is transiently transformed with a recombinant nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant, a mammal, an insect, an archaea, a bacterium, and the like). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, the nucleotide sequences, constructs, expression cassettes can be expressed transiently and/or they can be stably incorporated into the genome of the host organism.

A recombinant nucleic acid molecule/polynucleotide of the invention can be introduced into a cell by any method known to those of skill in the art. In some embodiments of the invention, transformation of a cell comprises nuclear transformation. In other embodiments, transformation of a cell comprises plastid transformation (e.g., chloroplast transformation). In still further embodiments, the recombinant nucleic acid molecule/polynucleotide of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239: Ran et al. *Nature Protocols* 8:2281-2308 (2013))

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, or in separate transformation events, or, alternatively, where relevant, a nucleotide sequence can be incorporated into a plant, as part of a breeding protocol.

The present invention is directed to compositions and methods having increased efficiency and increased specificity for site-specific nicking, cleaving and/or modification of target DNA and for site-specific targeting of polypeptides of interest to target DNA.

Figure 20:
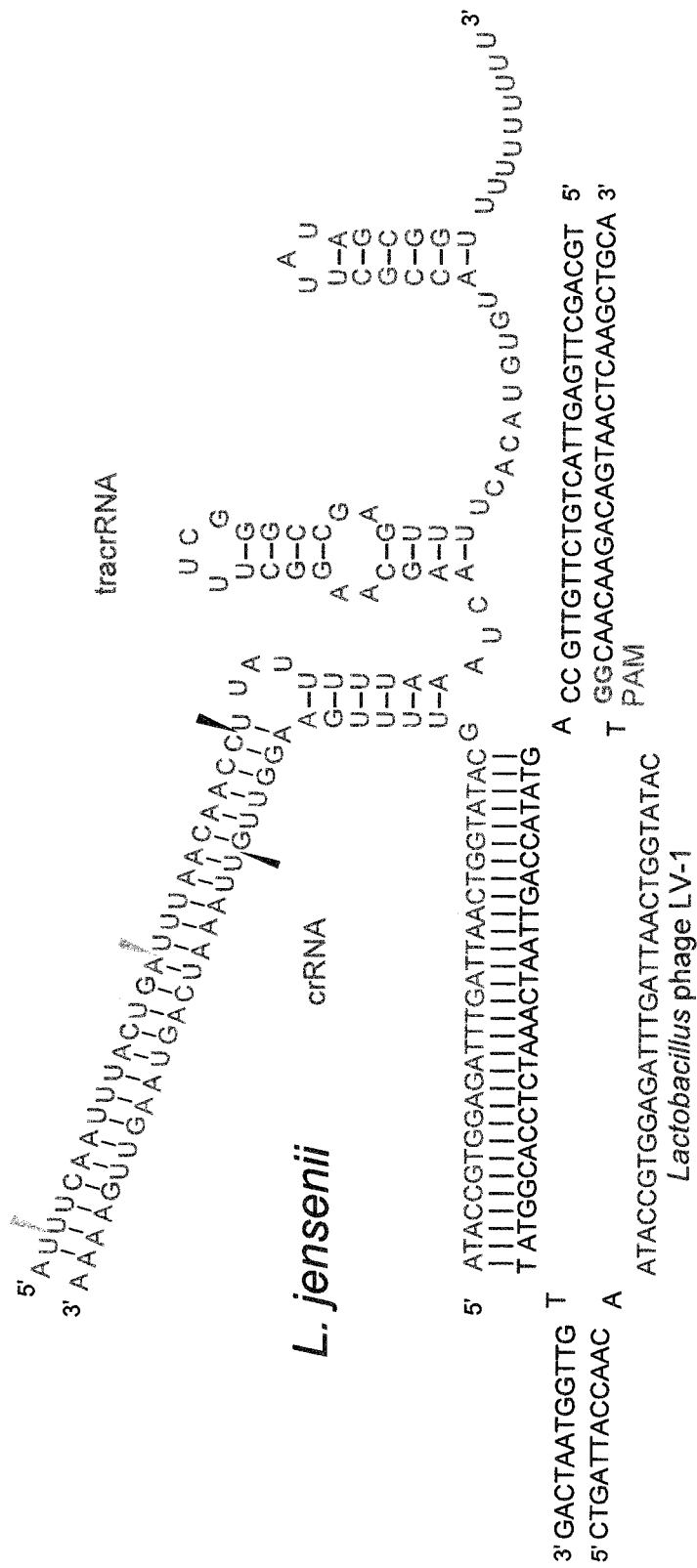
FIG. 20 shows sequence and structural details for CRISPR-Cas system elements for the *Lactobacillus jensenii*, representing the Lje group.
Figure 22:
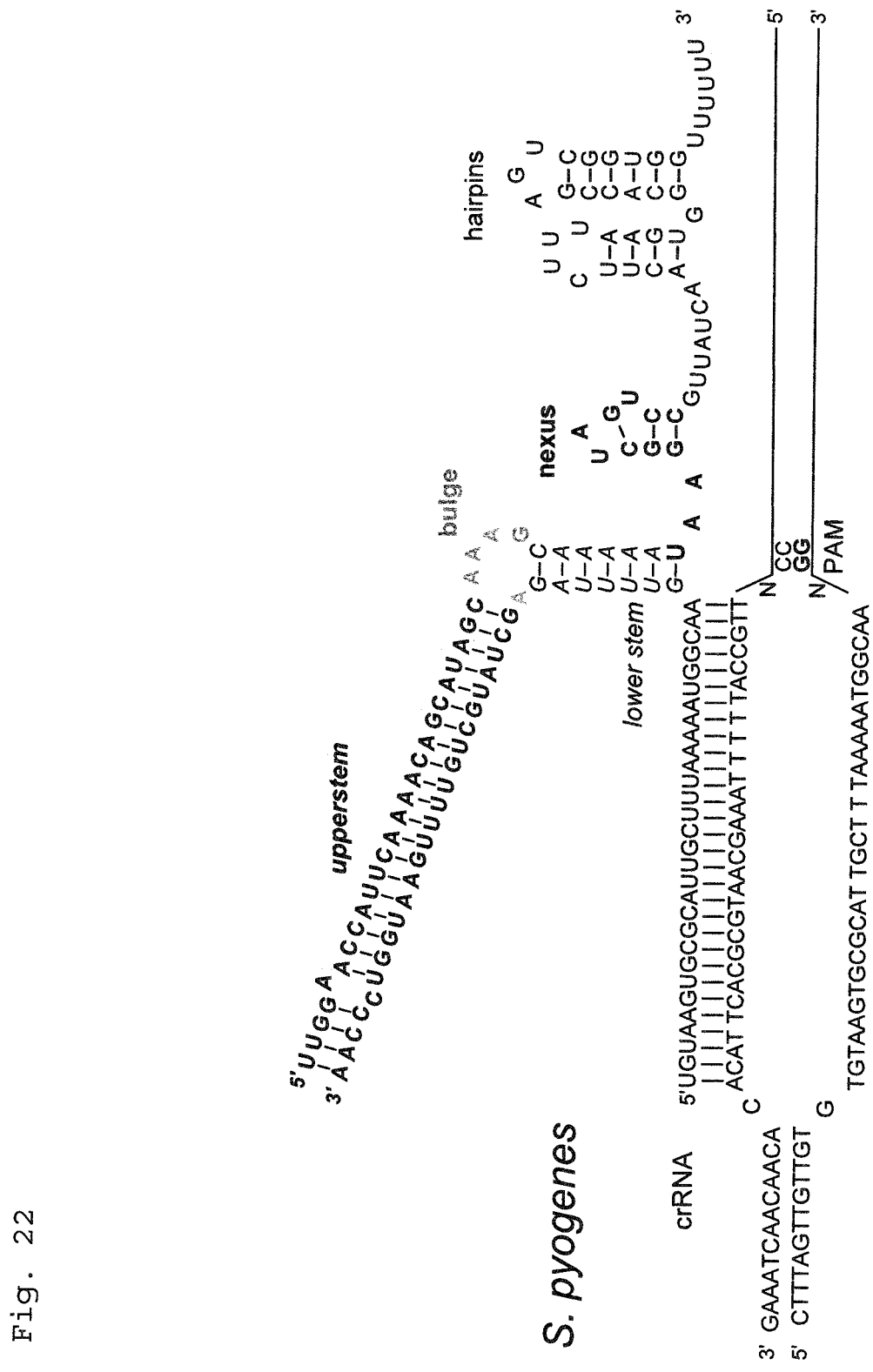
FIG. 22 shows sequence and structural details for CRISPR-Cas system elements for *Streptococcus pyogenes* M1 GAS.

The nucleic acid constructs and nucleotide sequences of the invention can be described in alternative ways that do not impact the overall structure or function of the constructs or sequences. Thus, for example, in some instances the synthetic CRISPR nucleic acid (crRNA) can comprise a wobble base $G_{R1}$ sequence (G/U) and a stitch sequence or alternatively, the crRNA can comprise a stitch sequence that comprises the (G/U) wobble base and therefore does not further describe a $G_{R1}$ sequence. In some cases, the $G_{R1}$ does not pair (i.e. G/A mismatch with Lje, FIG. 20). Further equivalencies include those as shown in the equivalency table (Table 1) provided below (see also, FIG. 22).

TABLE 1

Equivalencies for sequences as described herein.

| Original Nomenclature | Alternative Nomenclature |
|---|---|
| $G_{R1}$ | Comprised at the 5' end of the stitch. |
| Nexus comprises a "T" at the 5' end | The anti-stitch comprises what was the 5' "T" of the nexus and is extended to encompass at least an additional 6 nucleotides (e.g., AAGGCTAGTCC(GU); stitch and anti-stitch alternatively referred to as the "lower stem" |
| Bulge | Same (bulge) |
| Zipper/anti-zipper | Same (alternatively, referred to as the upper stem) with some differences in the overall length or presence/absence; zipper/anti-zipper alternatively referred to as "upper stem" |
| Stitch/anti-stitch | The anti-stitch comprises the 5' "T" of the nexus in the original nomenclature, which "T" can, in some embodiments, wobble base pair with the (G/A) of the stitch ($G_{R1}$ in original nomenclature) |
| Hairpin sequence | Some of the 5' nucleotides of the hairpin sequence are re-assigned to the nexus |

Accordingly, in one aspect of the invention a synthetic trans-encoded CRISPR (tracr) nucleic acid (e.g., tracrRNA, tracrDNA) construct is provided, said construct comprising, consisting essentially of, or consisting of from 5' to 3', an anti-zipper sequence comprising, consisting essentially of or consisting of at least about three nucleotides; a bulge sequence comprising at least about three nucleotides; an anti-stitch sequence comprising a nucleotide sequence of NNANN: a nexus sequence comprising a nucleotide sequence of TNANNC, T(A/C)A(A/G)(G/A)C (or U(A/C) A(A/G)(G/A)C)), TCAAAC, (or UCAAAC), TAAGGC (or UAAGGC), GATAAGG (or GAUAAGG), GATAAGGCTT (or GAUAAGGCUU) (SEQ ID NO:74), TCAAG (or UCAAG). TCAAGCAA (or UCAAGCAA), T(C/A)AA(A/C)(C/A)(A/G)(AT) (or U(C/A)AA(A/C)(C/A)(A/G)(A/U)), GATAAGGCCATGCC (SEQ ID NO:75), TAAGGCTAGTCC (SEQ ID NO:76), TCAAGCAAAGC (SEQ ID NO:77), or TCAAACAAAGCTTCAGC (SEQ ID NO:78); and a hairpin sequence comprising a nucleotide sequence having at least one hairpin, said hairpin comprising at least three matched base pairs, wherein the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence. In some embodiments, the anti-stitch sequence an comprise, consist essentially of, or consist of a nucleotide sequence of NNANN, ACAAA, TAAAA, (T/C)(A/G)T(A/G)(A/G), TAAAA, TGAAA.

In a further embodiment, a synthetic trans-encoded CRISPR(tracr) nucleic acid construct is provided, comprising, consisting essentially of, or consisting of from 5' to 3', an anti-zipper sequence comprising at least about three nucleotides: a bulge sequence comprising at least about three nucleotides: an anti-stitch sequence comprising a nucleotide sequence of NNANN; a nexus sequence comprising consisting essentially of, or consisting of a nucleotide sequence of TNANNC, T(A/C)A(A/G)(G/A)C (or U(A/C)A(A/G)(G/A)C)), TCAAAC, (or UCAAAC), TAAGGC (or UAAGGC), GATAAGG (or GAUAAGG), GATAAGGCTT (or GAUAAGGCUU) (SEQ ID NO:74), TCAAG (or UCAAG), TCAAGCAA (or UCAAGCAA). T(C/A)AA(A/C)(C/A)(A/G)(A/T) (or U(C/A)AA(A/C)(C/A)(A/G)(A/U)), GATAAGGCCATGCC (SEQ ID NO:75), TAAGGCTAGTCC (SEQ ID NO:76), TCAAGCAAAGC (SEQ ID NO:77), or TCAAACAAAGCTTCAGC (SEQ ID NO:78), and a hairpin sequence comprising a nucleotide sequence having at least one hairpin, said hairpin comprising at least three matched base pairs, wherein the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence.

In some embodiments, the bulge sequence of a synthetic tracr nucleic acid construct comprises, consists essentially of or consists of at least about three nucleotides. In some embodiments, the bulge sequence of a synthetic tracr nucleic acid construct comprises, consists essentially of or consists of at least about four nucleotides. In other embodiments, the bulge sequence of a synthetic tracr nucleic acid construct comprises, consists essentially of or consists of five nucleotides. In other embodiments, the hairpin sequence of a synthetic tracr nucleic acid construct comprises, consists essentially of or consists of at least two hairpins, wherein each hairpin comprises at least three matched base pairs.

In a further aspect, the present invention provides a synthetic CRISPR nucleic acid (e.g., crRNA, crDNA) construct comprising, consisting essentially of, or consisting of from 3' to 5', a zipper sequence comprising, consisting essentially of, or consisting of at least about three nucleotides, a bulge sequence that comprises, consists essentially of, or consists of a nucleotide sequence having at least two nucleotides (e.g., the nucleotide sequence of (—NN—)), a stitch sequence comprising, consisting essentially of, or consisting of a nucleotide sequence of NNTNN (or NNUNN), a $G_{R1}$ comprising, consisting essentially of, or consisting of a nucleotide G or GTT, and a spacer sequence having a 5' end and a 3' end and comprising, consisting essentially of, or consisting of at least seven nucleotides at its 3' end that have 100% identity to a target DNA, and the zipper sequence is located immediately upstream of the bulge sequence, the bulge sequence is located immediately upstream of the stitch sequence, the stitch sequence is located immediately upstream of the $G_{R1}$, and the $G_{R1}$ is located immediately upstream of the spacer sequence.

In a further embodiment, synthetic CRISPR nucleic acid (e.g., crRNA, crDNA) construct is provided, comprising, consisting essentially of, or consisting of, from 3' to 5', a zipper sequence comprising a nucleotide sequence having at least three nucleotides that hybridize to the anti-zipper, a bulge sequence that comprises the nucleotide sequence of at least about two nucleotides, a stitch sequence comprising a nucleotide sequence of NNUNN (and a spacer sequence having a 5' end and a 3' end and comprising at least seven nucleotides at its 3' end having 100% identity to a target DNA, and the zipper sequence is located immediately upstream of the bulge sequence, the bulge sequence is located immediately upstream of the stitch sequence, the stitch sequence is located immediately upstream of the spacer sequence.

In some embodiments, a synthetic CRISPR nucleic acid array is provided, said synthetic CRISPR nucleic acid array comprising, a nucleotide sequence encoding two or more CRISPR nucleic acid constructs of this invention, wherein the two or more CRISPR nucleic acid constructs are located immediately adjacent to one another on said nucleotide sequence, the stitch sequences of said two or more CRISPR nucleic acid constructs are identical, the spacer sequences of said two or more CRISPR nucleic acid constructs are identical or non-identical, and the zipper sequences of said two or more CRISPR nucleic acid constructs are identical.

In other aspects, a chimeric nucleic acid construct (or guide nucleic acid construct) is provided, comprising a synthetic tracr nucleic acid construct and a synthetic CRISPR nucleic acid construct of this invention, wherein the zipper sequence of the synthetic CRISPR nucleic acid construct is at least about 70% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) complementary to and hybridizes to the anti-zipper sequence of said synthetic tracr nucleic acid construct, the stitch sequence of the synthetic CRISPR nucleic acid construct is 100% identical to and hybridized to the anti-stitch sequence of said synthetic tracr nucleic acid construct and the bulge sequence of the synthetic CRISPR nucleic acid construct and the bulge sequence of the synthetic CRISPR nucleic acid construct are non-complementary.

In other embodiments, a chimeric nucleic acid construct is provided comprising, consisting essentially of, or consisting of, a synthetic tracr nucleic acid construct and a synthetic CRISPR nucleic acid construct of this invention, wherein the NNUNN of the stitch sequence of the synthetic CRISPR nucleic acid construct is 100% complementary to and hybridizes to the NNANN of the anti-stitch sequence of said synthetic tracr nucleic acid construct and the (G) of said stitch sequence forms a wobble base pair with the U of said anti-stitch sequence, the bulge sequence of the synthetic CRISPR nucleic acid construct and the bulge sequence of the synthetic CRISPR nucleic acid construct are non-complementary and, when the zipper sequence and anti-zipper sequence are present, the zipper sequence of the synthetic CRISPR nucleic acid construct is hybridized to the anti-zipper sequence of said synthetic tracr nucleic acid construct.

In some embodiments, a chimeric nucleic acid construct can optionally further comprise nucleotides linking the hybridized zipper and the anti-zipper sequence at the end of the hybridized sequences that is distal to the bulge sequences. A linking nucleotide can be any nucleotide (e.g., T, A, G, C) and the number of nucleotides linking the zipper sequence and anti-zipper sequence or the bulge sequence can be about three to about seven.

In further aspects, a synthetic tracr nucleic acid construct, a synthetic CRISPR nucleic acid construct, a CRISPR nucleic acid array, or a chimeric nucleic acid construct of the invention can further comprise a Cas9 nuclease, nucleotide sequence encoding an amino acid sequence having at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to an amino acid sequence encoding a Cas9 nuclease or an amino acid sequence having at least 70% identity to an amino acid sequence encoding a Cas9 nuclease. Cas9 nucleases useful with this invention can be any Cas9 nuclease known to catalyze DNA cleavage in a CRISPR-Cas system. As known in the art, such Cas9 nucleases comprise a HNH motif and a RuvC motif (See, e.g., WO2013/176772; WO/2013/188638). In some embodiments, the HNH motif or the RuvC motif can comprise mutations that reduce or eliminate their activity as compared to wild-type Cas9 nucleases. In some embodiments, just one motif is mutated (e.g., either the HNH motif or the RuvC motif). In other embodiments, both motifs are mutated such that both activities are reduced or eliminated. Any type of mutation including missense mutations, nonsense mutations, frameshift mutations, and the like, can be used to reduce or eliminate the activity of the HNH motif and/or the RuvC motif in a Cas9 nuclease.

The present disclosure identifies several CRISPR-Cas systems and groupings of Cas9 nucleases. These groupings include a *Streptococcus thermophilus* CRISPR 1 (Sth CR1) group of Cas9 nucleases, a *Streptococcus thermophilus* CRISPR 3 (Sth CR3) group of Cas9 nucleases, a *Lactobacillus buchneri* CD034 (Lb) group of Cas9 nucleases, and a *Lactobacillus rhamnosus* GG (Lrh) group of Cas9 nucleases. Non-limiting examples of Sth CR1 group Cas9 nucleases include the Cas9 nucleases encoded by the polypeptide sequences of SEQ ID NOs: 1-9 and 51. Non-limiting examples of Sth CR3 group Cas9 nucleases include the Cas9 nucleases encoded by the polypeptide sequences of SEQ ID NOs: 10-23. Non-limiting examples of Lb group Cas9 nucleases include the Cas9 nucleases encoded by the polypeptide sequences of SEQ ID NOs:28, 30-33, 35, 43, 44, 47, 50 and 52. Non-limiting examples of Lrh group Cas9 nucleases include the Cas9 nucleases encoded by the polypeptide sequences of SEQ ID NOs:24-27, 29, 34, 36-42, 45 and 53. Additional Cas9 nucleases include, but are not limited to, those of *Lactobacillus curvatus* CRL 705. Still further Cas9 nucleases useful with this invention include, but are not limited to, a Cas9 from *Lactobacillus animalis* KCTC 3501, and *Lactobacillus farciminis* WP 010018949.1.

Thus, in some embodiments, the Cas9 nuclease may comprise, consist essentially of, or consist of a Cas9 from a *Streptococcus thermophilus* CRISPR 1 (Sth CR1) group of Cas9 nucleases, a Cas9 from *Streptococcus thermophilus* CRISPR 3 (Sth CR3) group of Cas9 nucleases, a Cas9 nuclease from a *Lactobacillus buchneri* CD034 (Lb) group of Cas9 nucleases, and/or a Cas9 nuclease from a *Lactobacillus rhamnosus* GG (Lrh) group of Cas9 nucleases. In further embodiments, an amino acid sequence encoding a Cas9 nuclease can be an amino acid sequence of any one of SEQ ID NO:1 to SEQ ID NO:53. In still further embodiments, a Cas9 nuclease useful with a synthetic tracr nucleic acid construct, a synthetic CRISPR nucleic acid construct, a synthetic CRISPR nucleic acid array, and/or a chimeric nucleic acid construct of this disclosure comprises, consists essentially of, or consists of a nucleotide sequence encoding an amino acid sequence having at least 70% identity to an amino acid sequence of any one of SEQ ID NO: 1 to SEQ ID NO:53.

Furthermore, in particular embodiments, the Cas9 nuclease can be encoded by a nucleotide sequence that is codon optimized for an organism comprising the target DNA. In still other embodiments, the Cas9 nuclease can comprise at least one nuclear localization sequence.

The present inventors have surprisingly discovered a functional pairing between the nexus sequence of a synthetic tracr nucleic acid construct (tracrRNA, tracrDNA) with particular groups of Cas9 nucleases. Thus, in some embodiments, when the nexus sequence is GATAAGGC or GATAAGGCCATGCC (SEQ ID NO:75), the Cas9 nuclease is from a *Streptococcus thermophilus* CRISPR 1 (STh CR1) group of Cas9 nucleases; when the nexus sequence is TAAGGC or TAAGGCTAGTCC (SEQ ID NO:76), the Cas9 nuclease is from a *Streptococcus thermophilus* CRISPR 3 (Sth CR3) group of Cas9 nucleases; when the nexus sequence is TCAAGC or TCAAGCAAAGC (SEQ ID NO:77), the Cas9 nuclease is from a *Lactobacillus buchneri* CD034 (Lb) group of Cas9 nucleases; or when the nexus sequence is TCAAAC or TCAAACAAAGCTTCAGC (SEQ ID NO:78) and the Cas9 nuclease is from a *Lactobacillus rhamnosus* GG (Lrh) group of Cas9 nucleases.

As described herein, a Cas9 nuclease useful with this invention can comprise a mutation in a HNH motif and/or a RuvC motif, thereby reducing or eliminating the activity of the respective motif. As known in the art, a mutation in the HNH motif reduces/eliminates site-specific nicking of the (+) strand a double stranded target DNA and a mutation in the RucV active site reduces/eliminates site-specific nicking of the (−) strand of the double stranded target DNA. A mutation in both active sites reduces/eliminates cleavage of the DNA (i.e., reduces/eliminates site-specific cleavage of the target DNA). Therefore, in some embodiments, a synthetic tracr nucleic acid construct, a synthetic CRISPR nucleic acid construct, a CRISPR nucleic acid array, and/or a chimeric nucleic acid construct of this disclosure comprises a Cas9 nuclease having a mutation in the RuvC active site motif. In other embodiments, a synthetic tracr nucleic acid construct, a synthetic CRISPR nucleic acid construct, a CRISPR nucleic acid array, and/or a chimeric nucleic acid construct of this disclosure comprises a Cas9 nuclease having a mutation in the HNH active site motif. In still further embodiments, a synthetic tracr nucleic acid construct, a synthetic CRISPR nucleic acid construct, a CRISPR nucleic acid array, and/or a chimeric nucleic acid construct of this disclosure comprises a Cas9 nuclease having a mutation in the HNH active site motif and in the RuvC motif.

In still further embodiments, a Cas9 nuclease having a mutation in the HNH and RuvC motifs, thereby having reduced or eliminated nuclease activity, further comprises a polypeptide of interest fused to the Cas9 nuclease. Such a Cas9-polypeptide of interest fusion protein can be used to direct or target the polypeptide of interest to a particular target DNA.

Further provided herein are methods for using the synthetic tracr nucleic acid constructs, the synthetic CRISPR nucleic acid constructs, the CRISPR nucleic acid arrays, and/or the chimeric nucleic acid constructs of this disclosure. Thus, in some embodiments, a method for site-specific cleavage of a double stranded target DNA is provided, comprising: contacting a chimeric nucleic acid construct of this disclosure or an expression cassette comprising a chimeric nucleic acid construct of this disclosure with the target DNA in the presence of a Cas9 nuclease (e.g., SEQ ID NOs: 1-53), thereby producing a site-specific cleavage of the target DNA in a region defined by complementary hybridization of the spacer sequence to the target DNA. In some embodiments, the site-specific cleavage can be a site-specific nicking of a (+) strand of the double stranded target DNA and said Cas9 nuclease comprises a mutation in a RuvC active site motif, thereby cleaving the (+) strand of the double stranded target and producing a site-specific nick in said (+) strand the double stranded target DNA. In other embodiments, the site-specific cleavage is a site-specific nicking of the (−) strand of the double stranded target DNA and said Cas9 nuclease comprises a point mutation in a HNH active site motif, thereby cleaving the (−) strand of the double stranded target DNA and producing a site-specific nick in said (−) strand the double stranded target DNA.

In additional embodiments, a method for site-specific cleavage of a double stranded target DNA is provided, comprising: contacting a trans-encoded CRISPR (tracr) nucleic acid molecule and a CRISPR nucleic acid molecule with the target DNA in the presence of a Cas9 nuclease (e.g., SEQ ID NOs: 1-53), wherein (a) the tracr nucleic acid molecule is encoded by a nucleotide sequence comprising from 5' to 3', an anti-zipper sequence comprising at least about 3 nucleotides; a bulge sequence comprising at least about three nucleotides: an anti-stitch sequence comprising a nucleotide sequence of NNANN; a nexus sequence comprising a nucleotide sequence of TNANNC, T(A/C)A(A/G)(G/A)C, TCAAAC, TAAGGC, GATAAGG, GATAAGGCTT (SEQ ID NO:74), TCAAG. TCAAGCAA, T(C/A)AA(A/C)(C/A)(A/G)(AT), GATAAGGCCATGCC (SEQ ID NO:75), TAAGGCTAGTCC (SEQ ID NO:76), TCAAGCAAAGC (SEQ ID NO:77), or TCAAACAAAGCTTCAGC (SEQ ID NO:78): and a hairpin sequence comprising a nucleotide sequence comprising, consisting essentially of, or consisting of at least one hairpin, said hairpin comprising at least three matched base pairs, and the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence; and (b) the CRISPR nucleic acid molecule is encoded by a nucleotide sequence comprising from 3' to 5', a zipper sequence comprising at least about 3 nucleotides, a bulge sequence comprising a nucleotide sequence having at least two nucleotides, a stitch sequence comprising a nucleotide sequence of NNTNN (or NNUNN), a $G_{R1}$ comprising a nucleotide G or GTT, and a spacer sequence having a 5' end and a 3' end and comprising at least seven nucleotides at its 3' end having 100% identity to a target DNA, and the zipper sequence is located immediately upstream of the bulge sequence, the bulge sequence is located immediately upstream of the stitch sequence, the stitch sequence is located immediately upstream of the $G_{R1}$, and the $G_{R1}$ is located immediately upstream of the spacer sequence, and further wherein the anti-zipper sequence and anti-stitch sequence of the tracr nucleic acid molecule are at least about 70% complementary to and hybridize to the zipper sequence and the stitch sequence of the CRISPR nucleic acid molecule, respectively, and the spacer sequence of the CRISPR nucleic acid molecule is at least about 80% complementary to and hybridizes to a portion of the target DNA and adjacent to a protospacer adjacent motif (PAM) on the target DNA, thereby resulting in a site-specific cleavage of the target DNA in a region defined by the complementary binding of the spacer sequence of the CRISPR nucleic acid molecule to the target DNA.

In other embodiments, a method for site-specific cleavage of a double stranded target DNA is provided, comprising: contacting the double stranded target DNA with a chimeric nucleic acid comprising, (a) a first nucleotide sequence comprising from 5' to 3', an anti-zipper sequence comprising at least about 9 nucleotides; a bulge sequence comprising at least about 4 nucleotides; an anti-stitch sequence comprising a nucleotide sequence of NNANN; a nexus sequence comprising a nucleotide sequence of TNANNC, T(A/C)A(A/G)(G/A)C, TCAAAC, TAAGGC, GATAAGG, GATAAGGCTT (SEQ ID NO:74), TCAAG, TCAAGCAA, T(C/A)AA(A/C)(C/A)(A/G)(A/T), GATAAGGCCATGCC (SEQ ID NO:75), TAAGGCTAGTCC (SEQ ID NO:76), TCAAGCAAAGC (SEQ ID NO:77), or TCAAACAAAGCTTCAGC (SEQ ID NO:78); and a hairpin sequence comprising a nucleotide sequence having at least one hairpin, said hairpin comprising at least three matched base pairs, and the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence; (b) a second nucleotide sequence comprising from 3' to 5', a zipper sequence comprising at least about 3 nucleotides, a bulge sequence that comprises a nucleotide sequence having at least two nucleotides, a stitch sequence comprising a nucleotide sequence of NNTNN (or NNUNN), a $G_{R1}$ comprising a nucleotide G or GTT, and a spacer sequence having a 5' end and a 3' end and comprising at least seven nucleotides at its 3' end that have 100% identity to a target DNA, and the zipper sequence is located immediately upstream of the bulge sequence, the bulge sequence is located immediately upstream of the stitch sequence, the stitch sequence is located immediately upstream of the $G_{R1}$, and the $G_{R1}$ is located immediately upstream of the spacer sequence; and (c) a third nucleotide sequence encoding an amino acid sequence having at least 80% identity to an amino acid sequence encoding a Cas9 nuclease (e.g., SEQ ID NOs: 1-53), wherein the anti-zipper sequence and the anti-stitch sequence of the first nucleotide sequence hybridize to the zipper sequence and stitch sequence of the second nucleotide sequence and the spacer sequence of the second nucleotide sequence hybridizes to a portion of the target DNA and adjacent to a protospacer adjacent motif (PAM) on the target DNA, thereby resulting in a site-specific cleavage of the target DNA in a region defined by the complementary binding of the spacer sequence of the second nucleotide sequence to the target DNA In a further embodiment, a method of site-specific targeting of a polypeptide of interest to a double stranded (ds) target DNA is provided, comprising contacting a trans-encoded CRISPR (tracr) nucleic acid molecule and a CRISPR nucleic acid molecule with the target DNA in the presence of a Cas9 nuclease (e.g., SEQ ID NOs: 1-53), wherein (a) the tracr nucleic acid molecule is encoded by a nucleotide sequence comprising from 5' to 3', an anti-zipper sequence comprising at least about 3 nucleotides; a bulge sequence comprising at least about three nucleotides; an anti-stitch sequence comprising a nucleotide sequence of NNANN; a nexus sequence comprising a nucleotide sequence of TNANNC, T(A/C)A(A/G)(G/A)C, TCAAAC, TAAGGC, GATAAGG, GATAAGGCTT (SEQ ID NO:74), TCAAG, TCAAGCAA, T(C/A)AA(A/C)(C/A)(A/G)(A/T), GATAAGGCCATGCC (SEQ ID NO:75), TAAGGCTAGTCC (SEQ ID NO:76), TCAAGCAAAGC (SEQ ID NO:77), or TCAAACAAAGCTTCAGC (SEQ ID NO:78); and a hairpin sequence comprising a nucleotide sequence having at one hairpin, said hairpin comprising at least three matched base pairs, and the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence; and (b) the CRISPR nucleic acid molecule is encoded by a nucleotide sequence comprising from 3' to 5', a zipper sequence comprising at least about 3 nucleotides, a bulge sequence comprising at least two nucleotides (e.g., the nucleotide sequence of (—NN—)), a stitch sequence comprising a nucleotide sequence of NNTNN, a $G_{R1}$ comprising a nucleotide G or GTT, and a spacer sequence having a 5' end and a 3' end and comprising at least seven nucleotides at its 3' end having 100% identity to a target DNA, and the zipper sequence is located immediately upstream of the bulge sequence, the bulge sequence is located immediately upstream of the stitch sequence, the stitch sequence is located immediately upstream of the $G_{R1}$, and the $G_{R1}$ is located immediately upstream of the spacer sequence, and further wherein the Cas9 nuclease comprises a mutation in a HNH active site motif, a mutation in a RuvC active site motif, and is fused to a polypeptide of interest, the anti-zipper sequence is about 70% complementary to and hybridizes to the zipper sequence, the stitch sequence is 100% complementary to and hybridizes to the stitch sequence, and the spacer sequence is about 80% complementary to and hybridizes to the target DNA adjacent to a protospacer adjacent motif (PAM) on the target DNA, thereby resulting in a site-specific targeting of the polypeptide of interest to the target DNA in a region defined by the complementary binding of the spacer sequence of the CRISPR nucleic acid molecule to the target DNA.

In representative embodiments, as described herein for a synthetic tracr nucleic acid construct, the bulge sequence of a synthetic tracr nucleic acid molecule or a first nucleotide sequence can comprise, consist essentially of, or consist of about three, four or five nucleotides. In other embodiments, the bulge sequence can comprises, consists essentially of or consists of five nucleotides, and the hairpin sequence can comprise, consist essentially of or consist of at least two hairpins, wherein each hairpin comprises at least three matched base pairs.

In further embodiments, the present invention provides a method for site-specific cleavage of a double stranded target DNA, comprising: contacting a trans-encoded CRISPR (tracr) nucleic acid molecule and a CRISPR nucleic acid molecule with the target DNA in the presence of a Cas9 nuclease, wherein (a) the tracr nucleic acid molecule is encoded by a nucleotide sequence comprising from 5' to 3', an anti-zipper sequence comprising at least about three nucleotides: a bulge sequence comprising at least about three nucleotides; an anti-stitch sequence comprising a nucleotide sequence of NNANN, a nexus sequence comprising a nucleotide sequence of TNANNC, T(A/C)A(A/G)(G/A)C, TCAAAC, TAAGGC, GATAAGG, GATAAGGCTT (SEQ ID NO:74), TCAAG, TCAAGCAA, T(C/A)AA(A/C)(C/A)(A/G)(A/T), GATAAGGCCATGCC (SEQ ID NO:75), TAAGGCTAGTCC (SEQ ID NO:76), TCAAGCAAAGC (SEQ ID NO:77), or TCAAACAAAGCTTCAGC (SEQ ID NO:78) a hairpin sequence comprising a nucleotide sequence having at least one hairpin, said hairpin comprising at least three matched base pairs, and the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence; and (b) the CRISPR nucleic acid molecule is encoded by a nucleotide sequence comprising from 3' to 5', a zipper sequence comprising a nucleotide sequence having at least three nucleotides that hybridize to the anti-zipper, a bulge sequence that comprises the nucleotide sequence of (—NN—), a stitch sequence comprising a nucleotide sequence of NNUNN, and a spacer sequence having a 5' end and a 3' end and comprising at least seven nucleotides at its 3' end having 100% identity to a target DNA, and the zipper sequence is located immediately upstream of the bulge sequence, the bulge sequence is located immediately upstream of the stitch sequence, the stitch sequence is located immediately upstream of the spacer sequence, and further wherein, when the anti-zipper and zipper sequences are present, the anti-zipper sequence hybridizes to the zipper sequence, the NNANN of anti-stitch sequence is complementary to and hybridizes to the NNUNN of the stitch sequence, and the spacer sequence of the CRISPR nucleic acid molecule hybridizes to a portion of the target DNA and adjacent to a protospacer adjacent motif (PAM) on the target DNA, thereby resulting in a site-specific cleavage of the target DNA in a region defined by the hybridization of the spacer sequence of the CRISPR nucleic acid molecule to the target DNA.

In still further embodiments, a method for site-specific cleavage of a double stranded target DNA is provided, the method comprising: contacting the double stranded target DNA with a chimeric nucleic acid comprising, (a) a first nucleotide sequence comprising from 5' to 3', an anti-zipper sequence comprising at least about three nucleotides; a bulge sequence comprising at least about three nucleotides: an anti-stitch sequence comprising a nucleotide sequence of NNANN, a nexus sequence comprising a nucleotide sequence of TNANNC, T(A/C)A(A/G)(G/A)C, TCAAAC, TAAGGC, GATAAGG, GATAAGGCTT (SEQ ID NO:74), TCAAG, TCAAGCAA, T(C/A)AA(A/C)(C/A)(A/G)(A/T), GATAAGGCCATGCC (SEQ ID NO:75), TAAGGCTAGTCC (SEQ ID NO:76). TCAAGCAAAGC (SEQ ID NO:77), or TCAAACAAAGCTTCAGC (SEQ ID NO:78), a hairpin sequence comprising a nucleotide sequence having at least one hairpin, said hairpin comprising at least three matched base pairs, wherein the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence;

(b) a second nucleotide sequence comprising from 3' to 5', a zipper sequence comprising a nucleotide sequence having at least three nucleotides that hybridize to the anti-zipper, a bulge sequence comprising a nucleotide sequence having at least two nucleotides (e.g., the nucleotide sequence of (—NN—)), a stitch sequence comprising a nucleotide sequence of NNUNN, and a spacer sequence having a 5' end and a 3' end and comprising at least seven nucleotides at its 3' end having 100% identity to a target DNA, and the zipper sequence is located immediately upstream of the bulge sequence, the bulge sequence is located immediately upstream of the stitch sequence, the stitch sequence is located immediately upstream of the spacer sequence; and (c) a third nucleotide sequence encoding an amino acid sequence having at least 80% identity to an amino acid sequence encoding a Cas9 nuclease (e.g., SEQ ID NOs: 1-53), wherein, when the zipper sequence and anti-zipper sequence are present, the zipper sequence hybridizes to the anti-zipper sequence, the NNANN of anti-stitch sequence is complementary to and hybridizes to the NNUNN of the stitch sequence, and the spacer sequence of the second nucleotide sequence hybridizes to a portion of the target DNA and adjacent to a protospacer adjacent motif (PAM) on the target DNA, thereby resulting in a site-specific cleavage of the target DNA in a region defined by the hybridization of the spacer sequence of the second nucleotide sequence to the target DNA.

In additional embodiments, a method of site-specific targeting of a polypeptide of interest to a double stranded (ds) target DNA is provided, comprising contacting a trans-encoded CRISPR (tracr) nucleic acid molecule and a CRISPR nucleic acid molecule with the target DNA in the presence of a Cas9 nuclease (e.g., SEQ ID NOs: 1-53), wherein (a) the tracr nucleic acid molecule is encoded by a nucleotide sequence comprising from 5' to 3', an anti-zipper sequence comprising at least about three nucleotides: a bulge sequence comprising at least about three nucleotides; an anti-stitch sequence comprising a nucleotide sequence of NNANN, a nexus sequence comprising a nucleotide sequence of TNANNC, T(A/C)A(A/G)(GA)C, TCAAAC, TAAGGC, GATAAGG, GATAAGGCTT (SEQ ID NO:74), TCAAG, TCAAGCAA, T(C/A)AA(A/C)(C/A)(A/G)(A/T), GATAAGGCCATGCC (SEQ ID NO:75), TAAGGCTAGTCC (SEQ ID NO:76), TCAAGCAAAGC (SEQ ID NO:77), or TCAAACAAAGCTTCAGC (SEQ ID NO:78), a hairpin sequence comprising a nucleotide sequence having at least one hairpin, said hairpin comprising at least three matched base pairs, and the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence; and (b) the CRISPR nucleic acid molecule is encoded by a nucleotide sequence comprising from 3' to 5', a zipper sequence comprising a nucleotide sequence having at least three nucleotides that hybridize to the anti-zipper, a bulge sequence comprising a nucleotide sequence having at least two nucleotides (e.g., the nucleotide sequence of (—NN—)), a stitch sequence comprising a nucleotide sequence of NNUNN, and a spacer sequence having a 5' end and a 3' end and comprising at least seven nucleotides at its 3' end having 100% identity to a target DNA, and the zipper sequence is located immediately upstream of the bulge sequence, the bulge sequence is located immediately upstream of the stitch sequence, the stitch sequence is located immediately upstream of the spacer sequence, and further wherein the Cas9 nuclease comprises a mutation in a HNH active site motif, a mutation in a RuvC active site motif, and is fused to a polypeptide of interest, when the zipper sequence and anti-zipper sequence are present, the zipper sequence hybridizes to the anti-zipper sequence, the NNANN of anti-stitch sequence is complementary to and hybridizes to the NNUNN of the stitch sequence, and the spacer sequence hybridizes to the target DNA adjacent to a protospacer adjacent motif (PAM) on the target DNA, thereby resulting in a site-specific targeting of the polypeptide of interest to the target DNA in a region defined by the hybridization of the spacer sequence of the CRISPR nucleic acid molecule to the target DNA.

In some embodiments, when the anti-zipper and zipper sequences of a tracr nucleic acid molecule and a CRISPR nucleic acid molecule or a first nucleotide sequence and a second nucleotide sequence hybridize, the hybridized sequences can optionally further comprise additional nucleotides at the end of the of the hybridized sequences that is distal to the bulge sequences, thereby linking the hybridized zipper and the anti-zipper sequence. A linking nucleotide can be any nucleotide (e.g., T, A, G, C) and the number of nucleotides linking the zipper and anti-zipper sequences or the bulge sequences can be about three to about seven.

Any wild-type, mutated, codon-optimized Cas9 nuclease or those comprising at least one nuclear localization sequence as described herein can be used with the methods of the invention including but not limited to SEQ ID NOs: 1-53.

Additionally provided herein are expression cassettes and vectors comprising the nucleic acid constructs, the nucleic acid arrays, nucleic acid molecules and/or the nucleotide sequences of this invention, which can be used with the methods of this disclosure.

In further aspects, the nucleic acid constructs, nucleic acid arrays, nucleic acid molecules, and/or nucleotide sequences of this invention can be introduced into a cell of a host organism. Any cell/host organism for which this invention is useful with can be used. Exemplary host organisms include, but are not limited to, a plant, bacteria, archaeon, fungus, animal, mammal, insect, bird, fish, amphibian, cnidarian, human, or non-human primate. In particular embodiments, a host organism can be, but is not limited to *Homo sapiens, Drosophila melanogaster, Mus musculus, Rattus norvegicus, Caenorhabditis elegans, Saccharomyces pombe, Saccharomyces cerevisiae, Glycine max. Zeae maydis, Gossypium hirsutum,* or *Arabidopsis thaliana*. In further embodiments, a cell useful with this invention can be, but is not limited to a stem cell, somatic cell, germ cell, plant cell, animal cell, bacterial cell, archaeon cell, fungal cell, mammalian cell, insect cell, bird cell, fish cell, amphibian cell, cnidarian cell, human cell, or non-human primate cell. In other embodiments, a cell useful with this invention includes but is not limited to a cell from *Homo sapiens, Drosophila melanogaster, Mus musculus, Rattus norvegicus, Caenorhabditis elegans, Saccharomyces pombe, Saccharomyces cerevisiae, Glycine max, Zeae maydis, Gossypium hirsutum,* or *Arabidopsis thaliana*.

In further aspects of the invention, a polypeptide of interest can include but is not limited to a helicase, a nuclease, a methyltransferase, a gyrase, a demethylase, a kinase, a dismutase, an integrase, a transposase, a telomerase, a recombinase, an acetyltransferase, a deacetylase, a polymerase, a phosphatase, a ligase, a ubiquitin ligase, a photolyase or a glycosylase. In other aspects of the invention, a polypeptide of interest comprises depurination activity, oxidation activity, pyrimidine dimer forming activity, alkylation activity, DNA repair activity, DNA damage activity, deubiquitinating activity, adenylation activity, deadenylation activity SUMOylating activity, deSUMOylating activity, ribosylation activity, deribosylation activity, myristoylation activity, demyristoylation activity or telomere repair activity, or deamination activity. In representative embodiments, a polypeptide of interest can be a polypeptide having kinase activity, nuclease activity, methyltransferase activity, demethylase activity, acetyltransferase activity, deacetylase activity, phosphatase activity, ubiquitin ligase activity, deubiquitinating activity, or telomere repair activity.

Further provided herein are kits comprising the nucleic acid constructs, nucleic acid molecules, and/or nucleotide sequences of this invention.

Thus, in one aspect, a kit for site-specific cleavage of double stranded DNA is provided, the kit comprising a synthetic tracr nucleic acid construct, a synthetic CRISPR nucleic acid construct, a CRISPR nucleic acid array or a chimeric nucleic acid construct of this invention. In another aspect, a kit for site-specific targeting of a polypeptide of interest to a double stranded (ds) target DNA is provided, the kit comprising a synthetic tracr nucleic acid construct, a synthetic CRISPR nucleic acid construct, a CRISPR nucleic acid array or a chimeric nucleic acid construct of this invention. In some aspects, the kit can comprise the synthetic tracr nucleic acid construct, the synthetic CRISPR nucleic acid construct, the CRISPR nucleic acid array and/or the chimeric nucleic acid construct of this invention comprised in one or more expression cassettes. In still further aspects, a kit can further comprise a Cas9 nuclease (e.g., SEQ ID NOs: 1-53) for use with the nucleic acid constructs, nucleic acid arrays, nucleic acid molecules, and/or nucleotide sequences of this invention described herein.

In further aspects, a kit can comprise primers said primers comprising portions of CRISPR repeat sequences in both directions. In other embodiments, a kit can comprise primers designed to comprise the boundaries of a CRISPR array (namely the leader end on one side, and the trailer end on the other), and extend through the CRISPR repeat sequence in both directions.

In additional embodiments, a kit can further comprise instructions for use.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. Assessing the Functional Role of Modules Identified in the Guide Sequences Clustered regularly interspaced short palindromic repeats (CRISPR) and associated Cas proteins provide adaptive immunity against invasive genetic elements in bacteria and archaea[1]. In Type II CRISPR-Cas systems, the signature RNA-guided endonuclease Cas9 specifically targets sequences complementary to CRISPR spacers and generates double-stranded DNA breaks (DSBs) using two nickase domains (Makarova, K. S. et al. *Nat Rev Microbiol* 9, 467-477 (2011): Gameau, J. E. et al. *Nature* 468, 67-71 (2010): Sapranauskas, R. et al. *Nucleic Acids Res* 39, 9275-9282 (2011): Gasiunas, G. et al. *Proc Natl Acad Sci* US A 109, E2579-E2586 (2012); Jinek, M. et al., *Science* 337, 816-821 (2012)). Any DNA sequence may be targeted, as long as it is flanked by a Cas9-specific protospacer-adjacent motif (PAM) Gameau, J. E. et al. *Nature* 468. 67-71 (2010); Sapranauskas, R. et al. *Nucleic Acids Res* 39, 9275-9282 (2011): Gasiunas, G. et al. *Proc Natl Acad Sci USA* 109. E2579-E2586 (2012); Jinek, M. et al., *Science* 337, 816-821 (2012): Steinberg, S. H. et al. *Nature* 507, 62 (2014)).

Targeting and cleavage by Cas9 systems rely on a RNA duplex consisting of CRISPR RNA (crRNA) and a transactivating crRNA (tracrRNA)[8]. This native complex can be replaced by a synthetic single guide RNA (sgRNA) chimera which mimics the crRNA:tracrRNA duplex (Jinek, M. et al., *Science* 337, 816-821 (2012)), sgRNAs in combination with Cas9 make convenient, compact, and portable sequence-specific targeting systems that are amenable to engineering and heterologous transfer into a variety of model systems of industrial and translational interest.

Accordingly, the Cas9:sgRNA technology, which provides a compact and practical means to generate double strand breaks (DSBs), has revolutionized genome editing (Mali, P. et al., *Science* 339, 823-826 (2013); Cong, L. et al. *Science* 339, 819-823 (2013): Jiang, W. et al. *Nat. Biotechnol.* 31, 233-239 (2013); Sander, J. D. & Joung, J. K. *Nature Biotechnol.* 32, 347-355, (2014)), opened new avenues for high-throughput genome-wide genetic screens.[13, 14], and expanded the toolbox for transcriptional control (Qi. L. S. et al. *Cell* 152, 1173-1183 (2013); Gilbert, L. A. et al. *Cell* 154, 442-451 (2013)). Furthermore, the absence of cross-interactions between evolutionarily distant Cas9:sgRNAs (Chylinski, K. et al. *RNA biology* 10, 726-737 (2013); Fonfara, I. et al. *Nucleic Acids Res* (2013); Esvelt, K. M. et al. *Nature Methods* (2013)) has allowed multiple, independent targeting to be achieved within a cell when co-existing functional Type II CRISPR-Cas systems function concurrently (Barrangou, R. et al. *Science* 315, 1709-1712 (2007): Horvath, P. et al. *J Bacteriol.* 190, 1401-1412 (2008)). Despite the widespread use of these molecular machines, the critical features of sgRNA guides, and their involvement in defining functionally orthologous Cas9 endonucleases remain to be characterized. Indeed, early attention on Cas9 targeting and cleavage focused on spacer:target complementarity and PAM sequence sensitivity, whereas there remains a paucity of information defining the elements that drive Cas9:sgRNA interactions and that dictate orthogonality between Type II CRISPR-Cas systems. Therefore, we set out to identify and characterize features within sgRNAs that impart Cas9 targeting and cleavage specificity to open new engineering avenues for CRISPR technologies.

Thus, to assess the functional role and implication of the various modules identified in the guides sequences discussed herein (e.g., synthetic tracr nucleic acid constructs, synthetic CRISPR nucleic acid constructs, chimeric nucleic acid constructs (tracr nucleic acid—synthetic CRISPR nucleic acid constructs), we designed mutated variants of guides containing modifications or deletions of each of the aforementioned functional modules. We selected the SthCRISPR3 system as a representative functional model, and first established a positive functional control (Wild Type. WT) using the native guide sequence. We then tested a "stitch" variant in which the stitch is missing, and observed loss of function. The then tested a "bulge" variant in which the bulge is missing and observed loss of function. We then tested a "nexus" variant in which the nexus is missing and observed loss of function. We then tested a "hairpin" variant in which the first hairpin is missing and observed loss of function. Subsequently, we tested sequence specificity and variability sensitivity and established in mutated constructs that the sequence of the nexus is specific, whereas there is variability tolerance for other functional modules, notably the zipper, bulge, hairpin and stitch. The results of these experiments are provided in FIGS. 1-21.

Thus, FIG. 1 shows a multiple sequence alignment for the nexus module and FIG. 2 provides a maximum likelihood tree for the nexus module developed through this research.

Figure 3A:
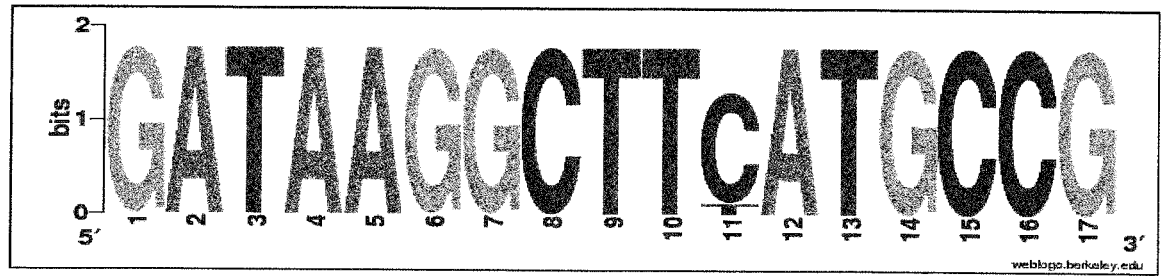
FIG. 3A-3D show consensus sequences for the nexus module.
Figure 3B:
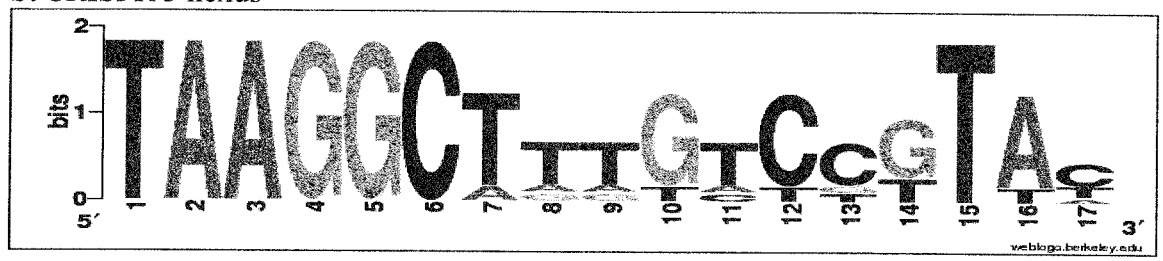
Figure 3C:
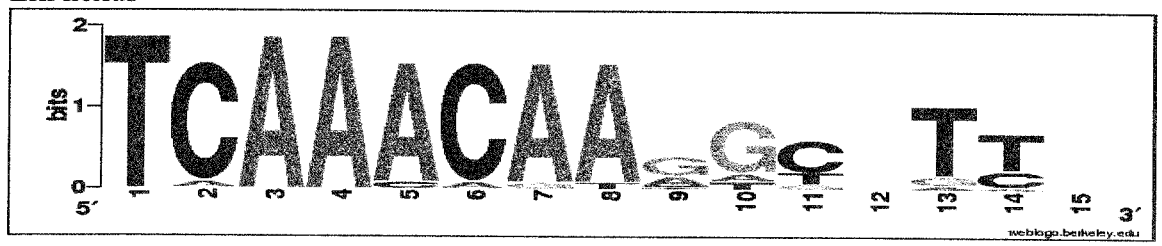
Figure 3D:
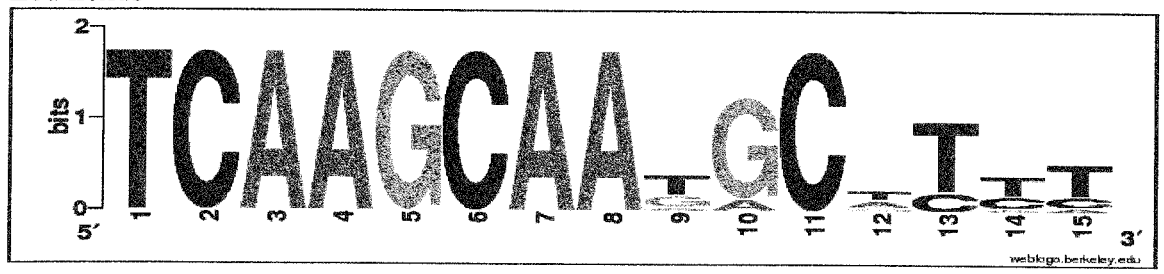

FIG. 3A-3D show consensus sequences for the nexus module for the Sth Cr1 group (FIG. 3A) the Sth Cr3 group (FIG. 3B), for the Lrh group FIG. 3C and for the Lbu group (FIG. 3D).

Figure 6A:
FIG. 6A-6D show consensus sequences for the anti-stitch module.
Figure 6B:
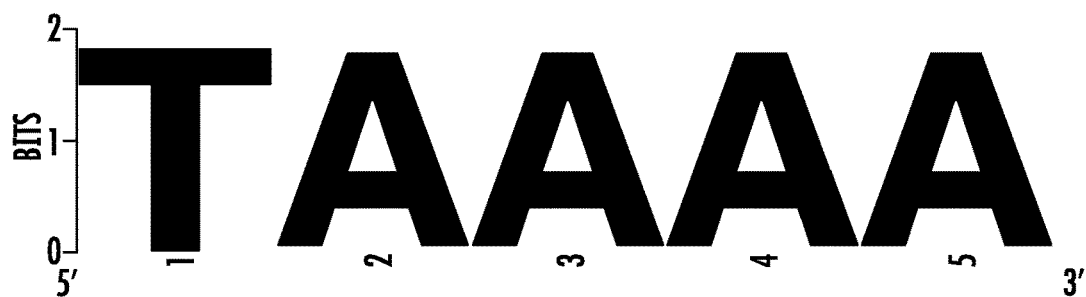
Figure 6C:
Figure 6D:

FIG. 5 shows a multiple sequence alignment for the anti-stitch module, while FIG. 6A-6D show consensus sequences for the anti-stitch module for the Sth Cr1 group (FIG. 6A), for the Sth Cr3 group (FIG. 6B), for the Lrh group (FIG. 6C) and for the Lbu group (FIG. 6D).

Figure 8A:
FIG. 8A-8D show consensus sequences for the bulge module.
Figure 8B:
Figure 8C:
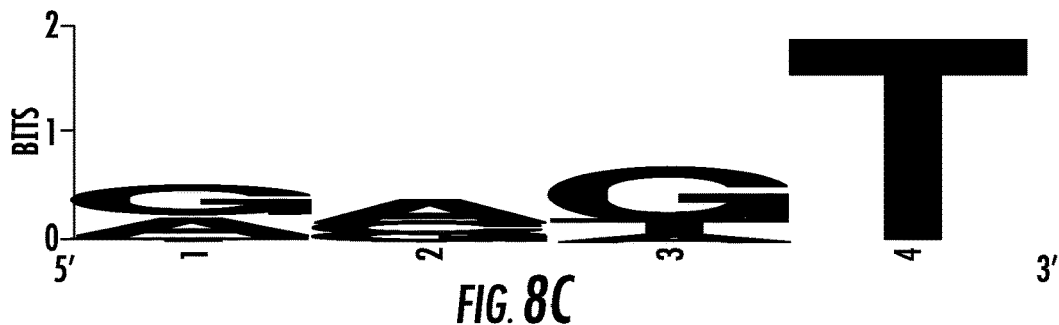
Figure 8D:
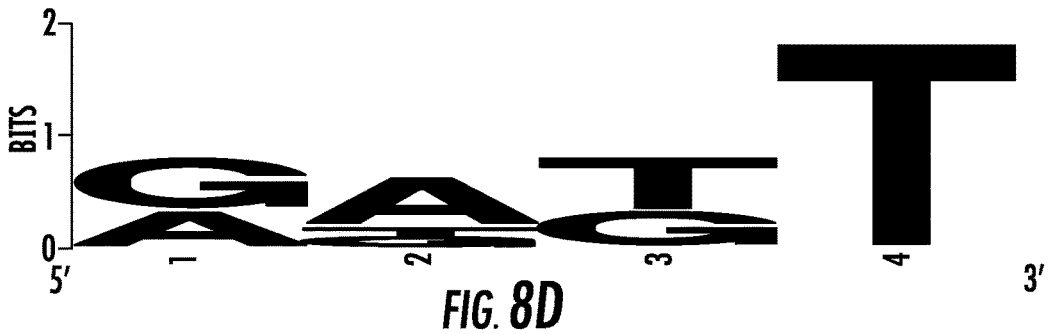

Similarly, a multiple sequence alignment for the bulge module is provided in FIG. 7 with the consensus sequences for the bulge module for the for the Sth Cr1 group is shown in FIG. 8A. FIG. 8B shows the consensus sequence for the bulge module for the Sth Cr3 group. FIG. 8C shows the consensus sequence for the Lrh group and FIG. 8D shows the consensus sequence for bulge module for the Lbu group.

Figure 10:
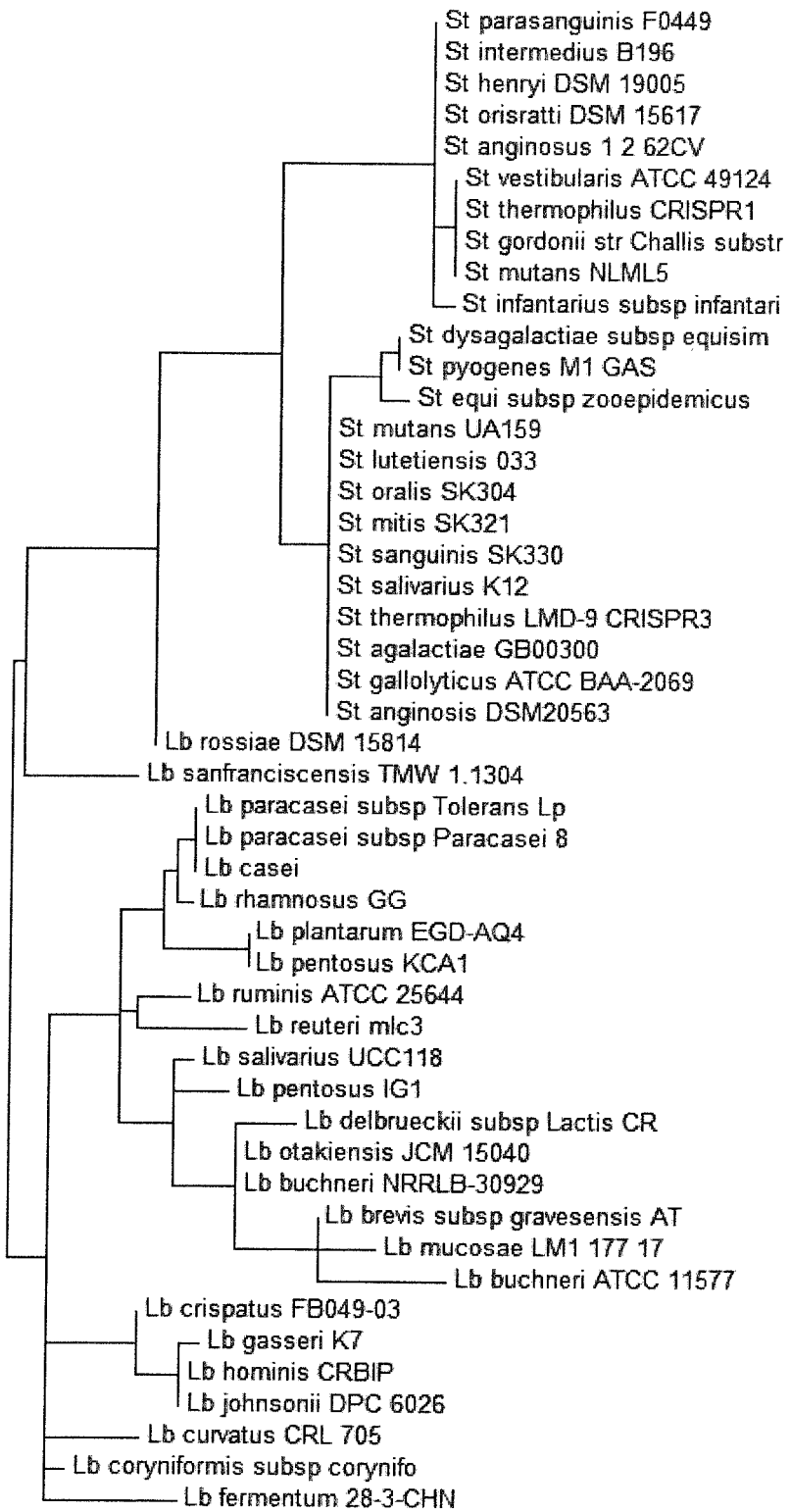
FIG. 10 shows a maximum likelihood tree for the zipper module.
Figure 12:
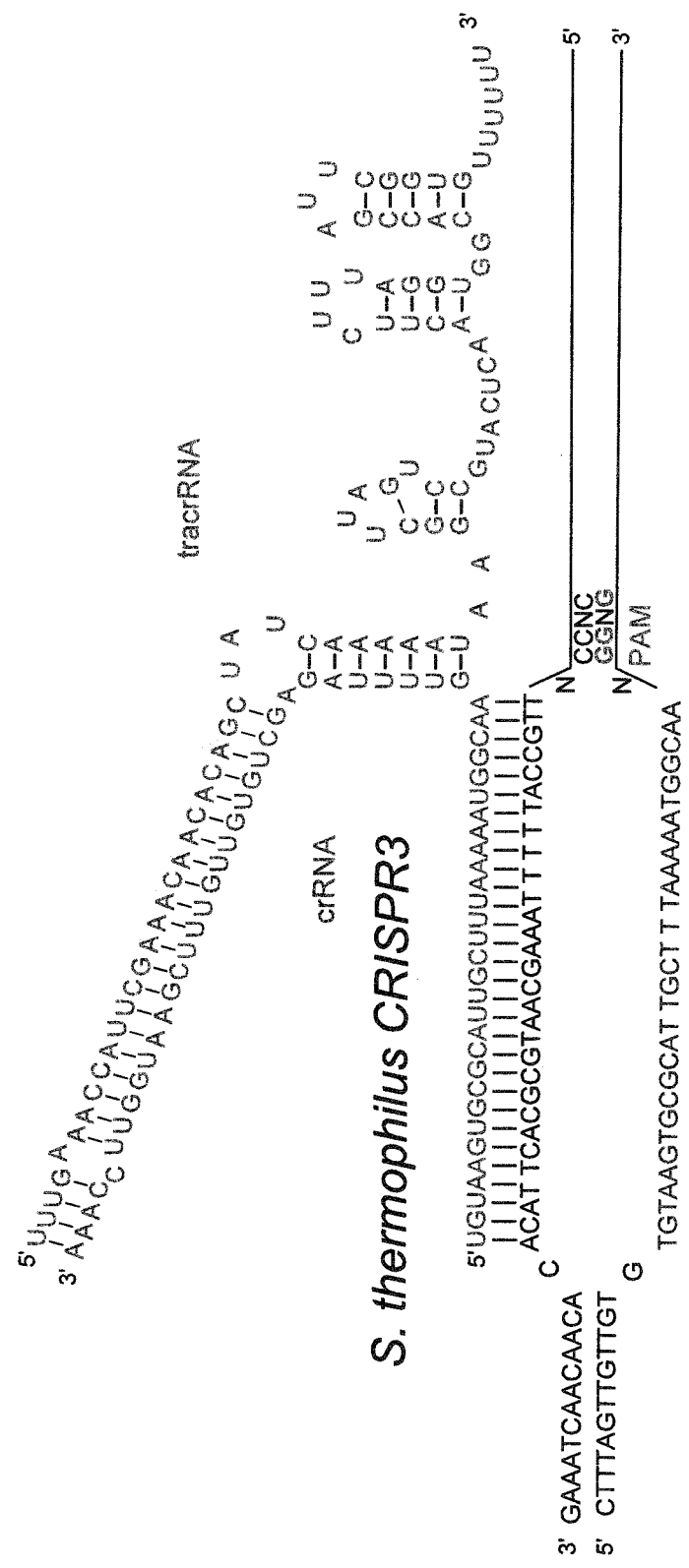
FIG. 12 shows sequence and structural details for CRISPR-Cas system elements for *Streptococcus thermophilus* CR3, representing the Sth CR1 group.
Figure 13:
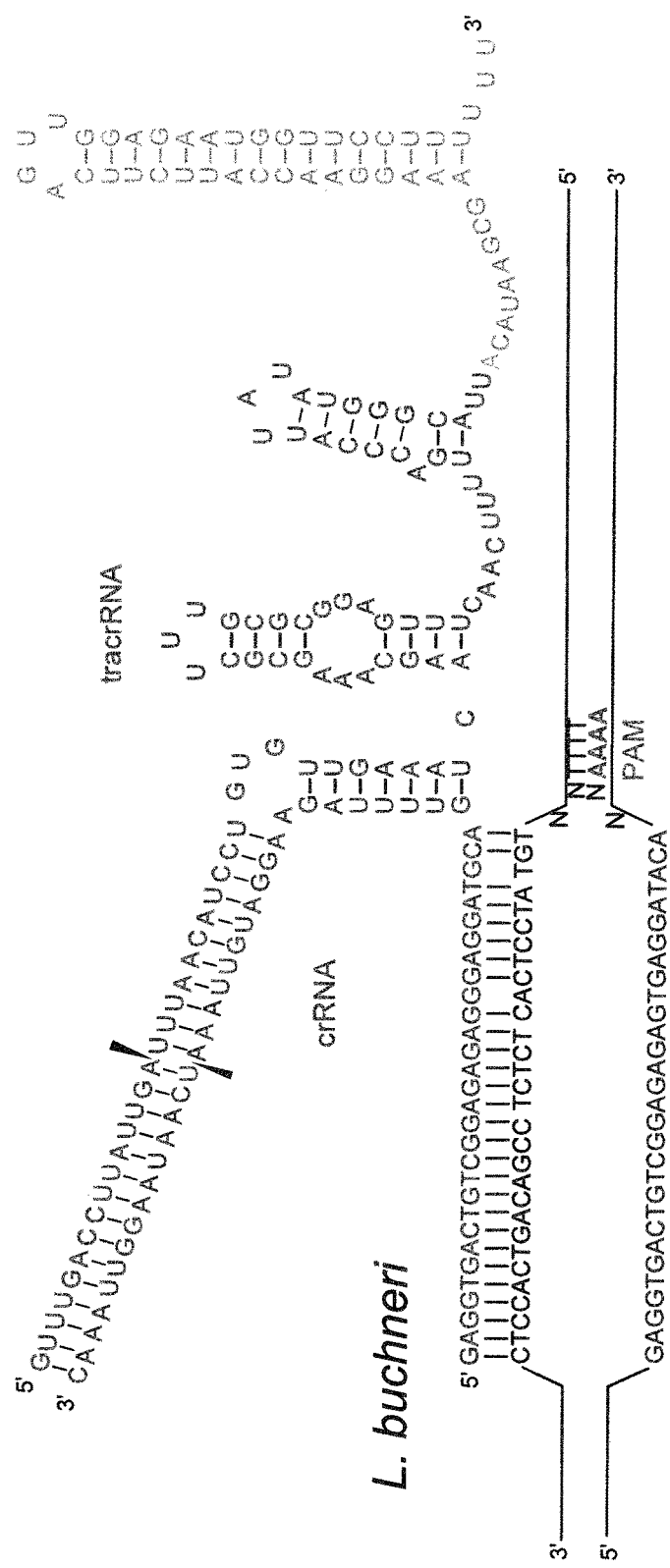
FIG. 13 shows sequence and structural details for CRISPR-Cas system elements for *Lactobacillus buchneri*, representing the Lbu group.
Figure 14:
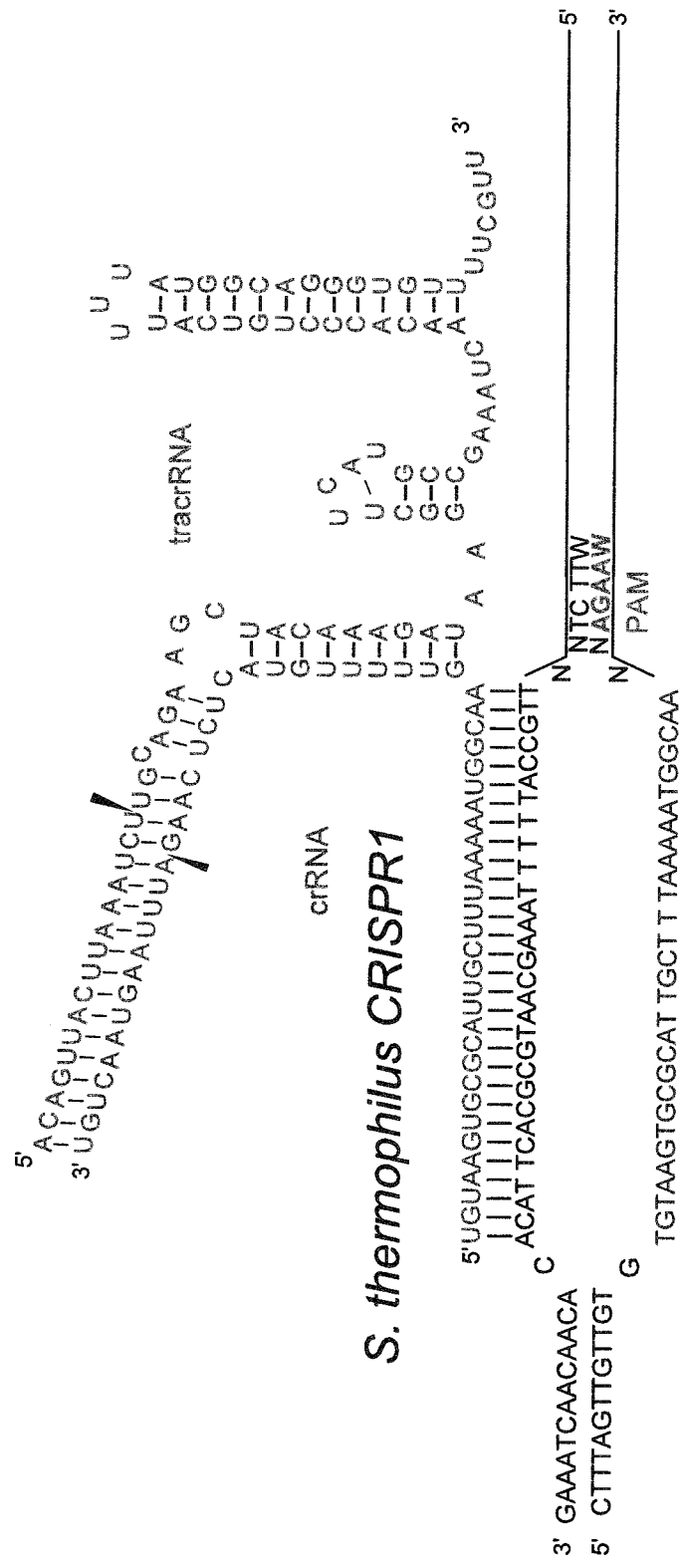
FIG. 14 shows sequence and structural details for CRISPR-Cas system elements for *Streptococcus thermophilus* CR1, representing the Sth CR1 group.
Figure 15:
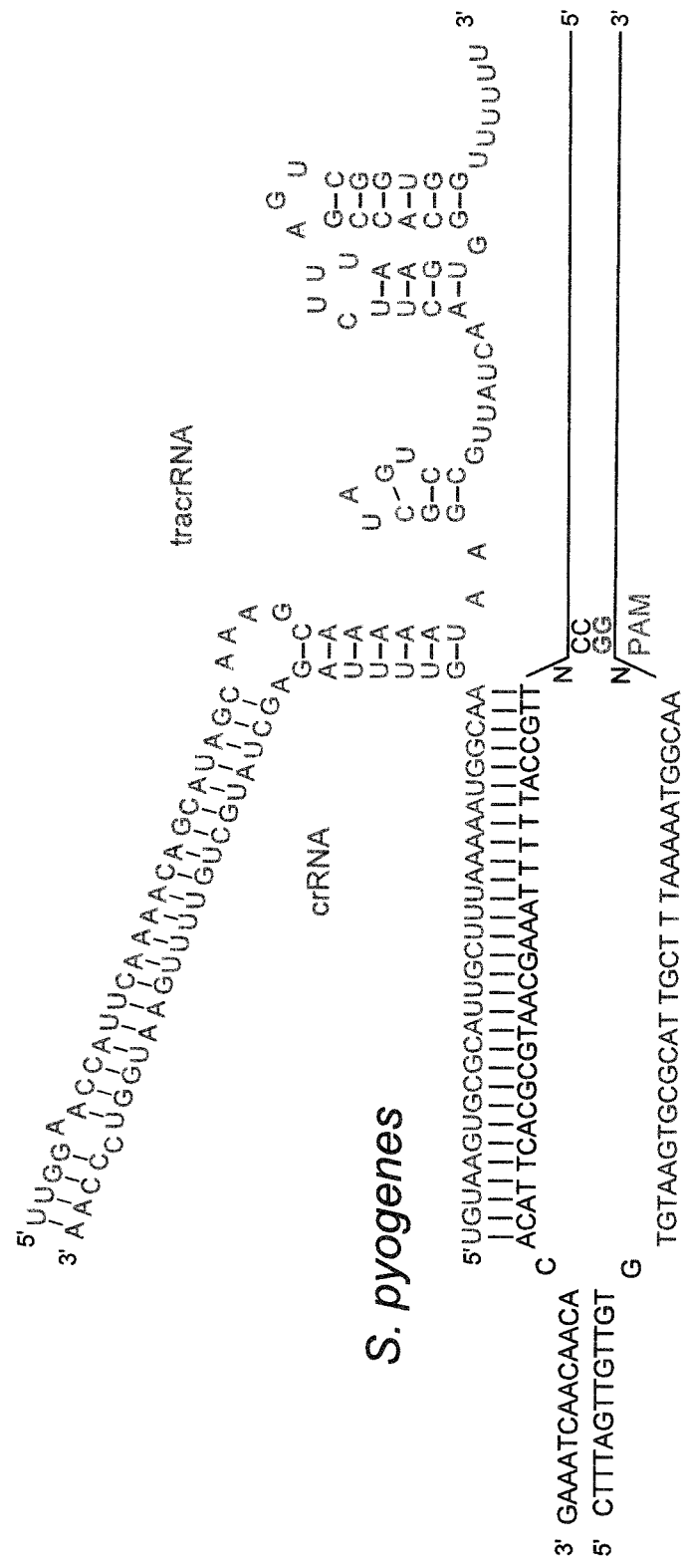
FIG. 15 shows sequence and structural details for CRISPR-Cas system elements for the *Streptococcus pyogenes* M1 GAS, representing the Sth CR3 group.
Figure 16:
FIG. 16 shows sequence and structural details for CRISPR-Cas system elements for the *Lactobacillus rhamnosus*, representing the Lrh group.
Figure 17:
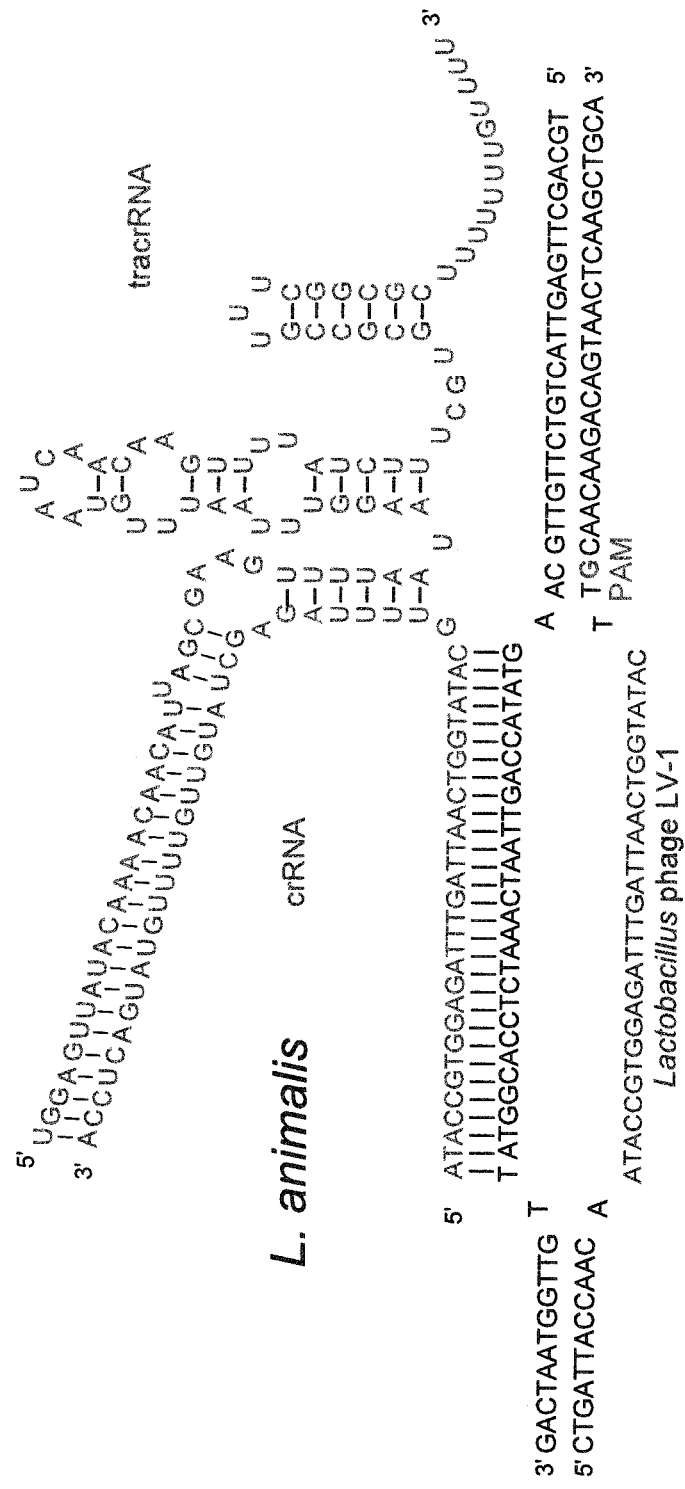
FIG. 17 shows sequence and structural details for CRISPR-Cas system elements for the *Lactobacillus animalis*, representing the Lan group.
Figure 18:
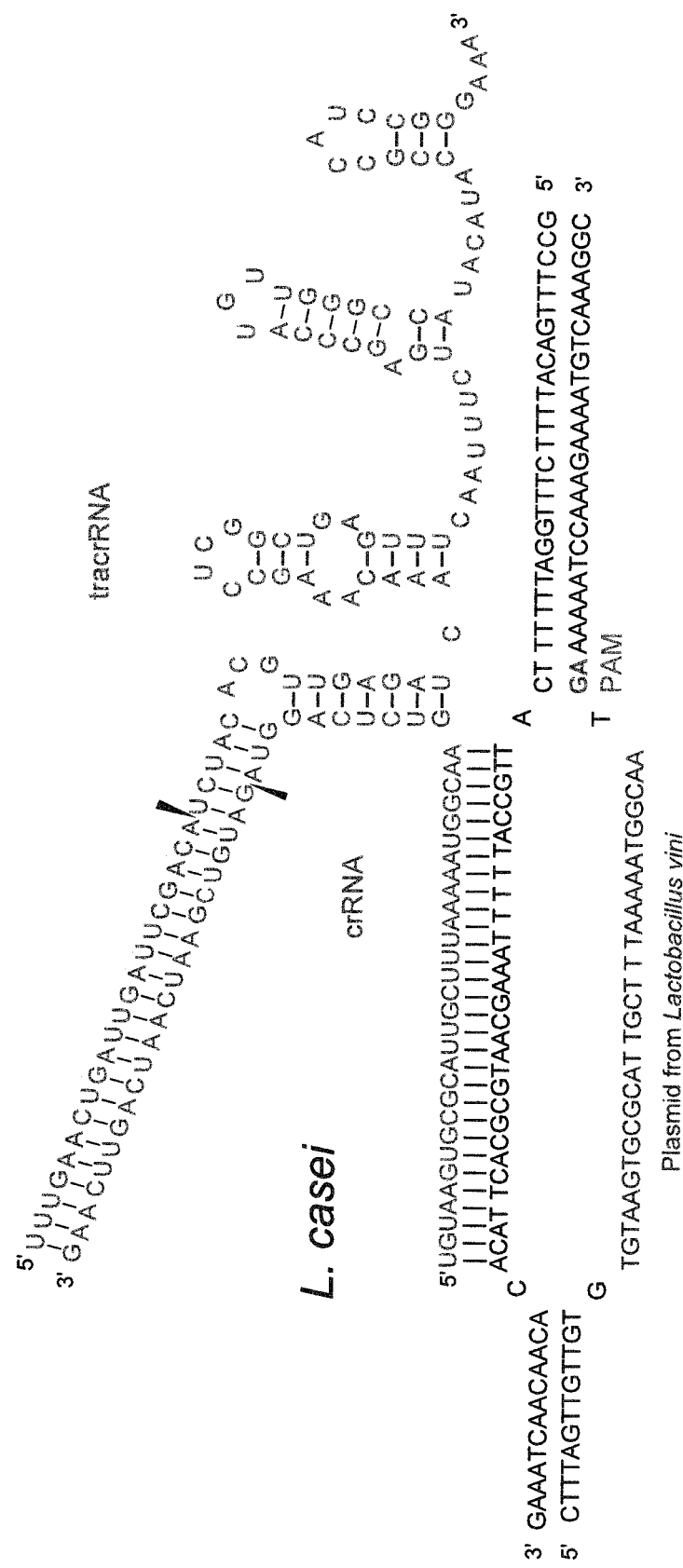
FIG. 18 shows sequence and structural details for CRISPR-Cas system elements for the *Lactobacillus casei*, representing the Lca group.
Figure 19:
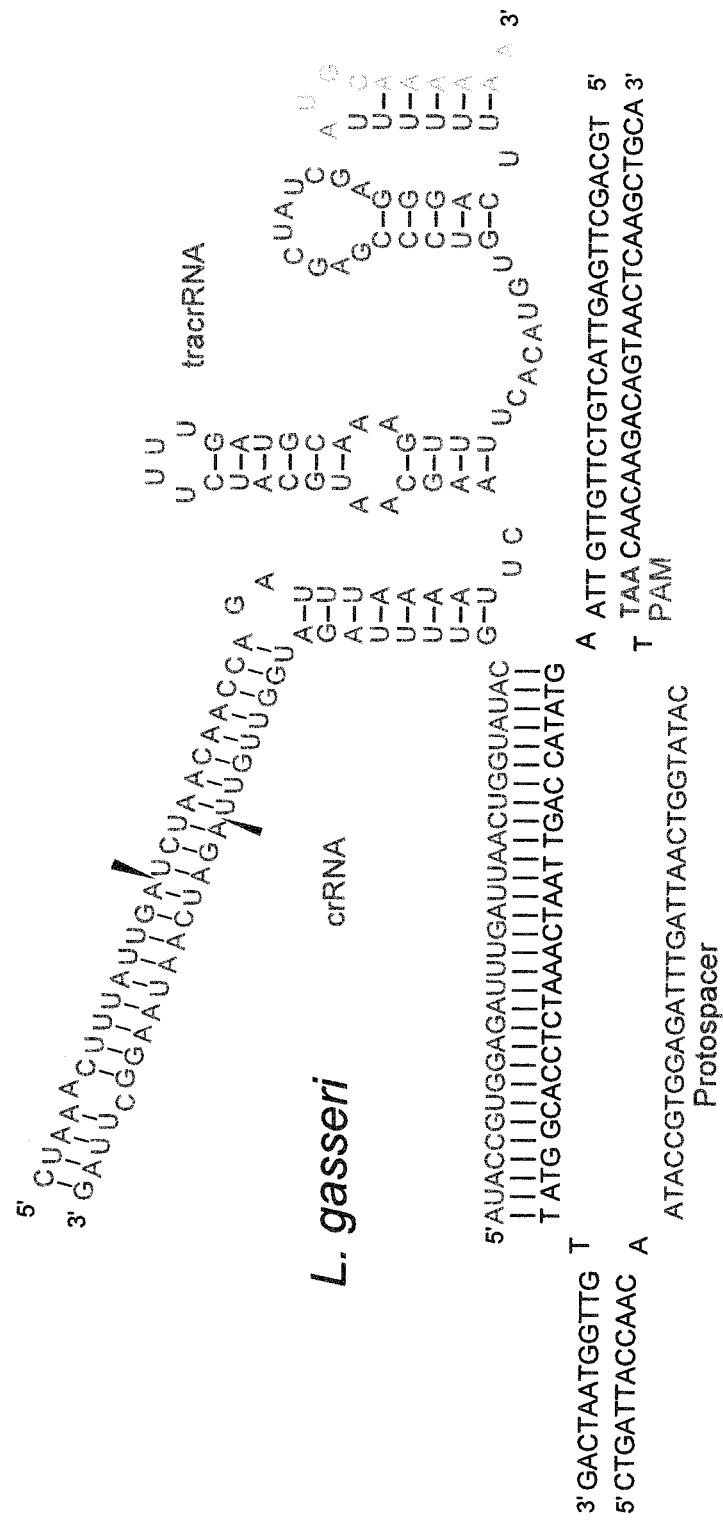
FIG. 19 shows sequence and structural details for CRISPR-Cas system elements for the *Lactobacillus gasseri*, representing the Lga group.

A multiple sequence alignment for the zipper module is provided in FIG. 9 with FIG. 10 showing a maximum likelihood tree for the zipper module.

Figure 4:
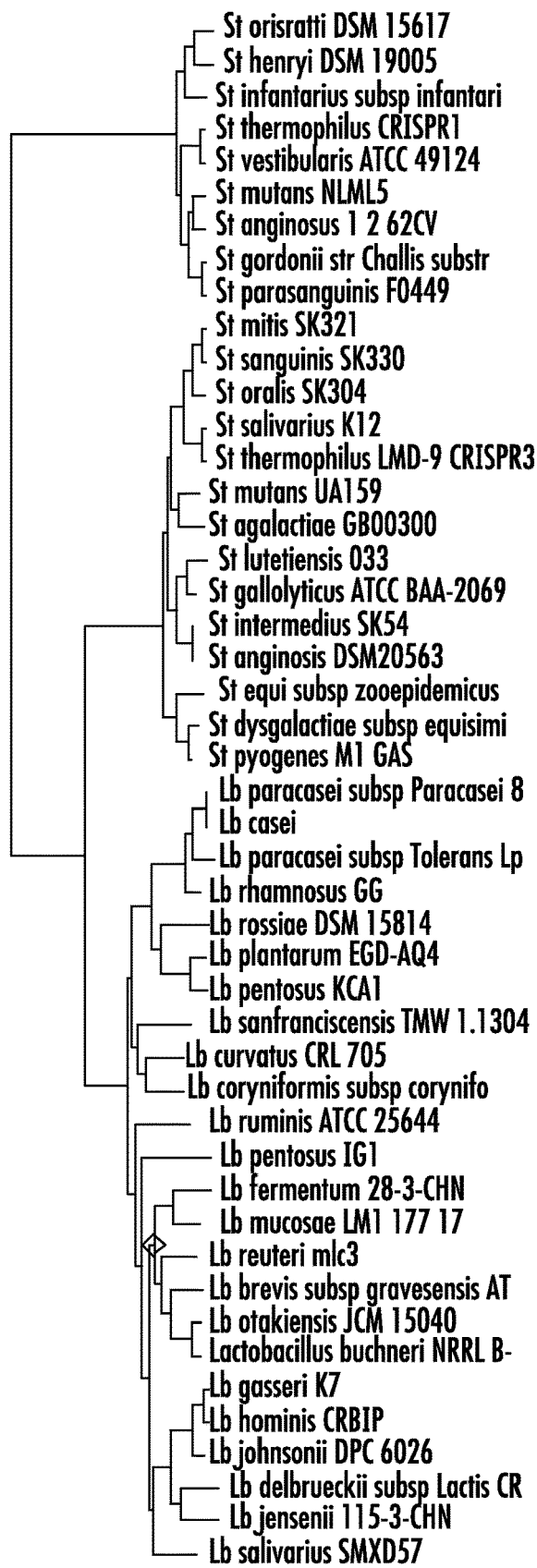
FIG. 4 shows a maximum likelihood tree for Cas9 nucleases.

FIG. 11 shows a multiple sequence alignment for the bulge, anti-stitch and nexus modules. FIG. 4 shows a maximum likelihood tree for Cas9 nucleases.

Figure 21:
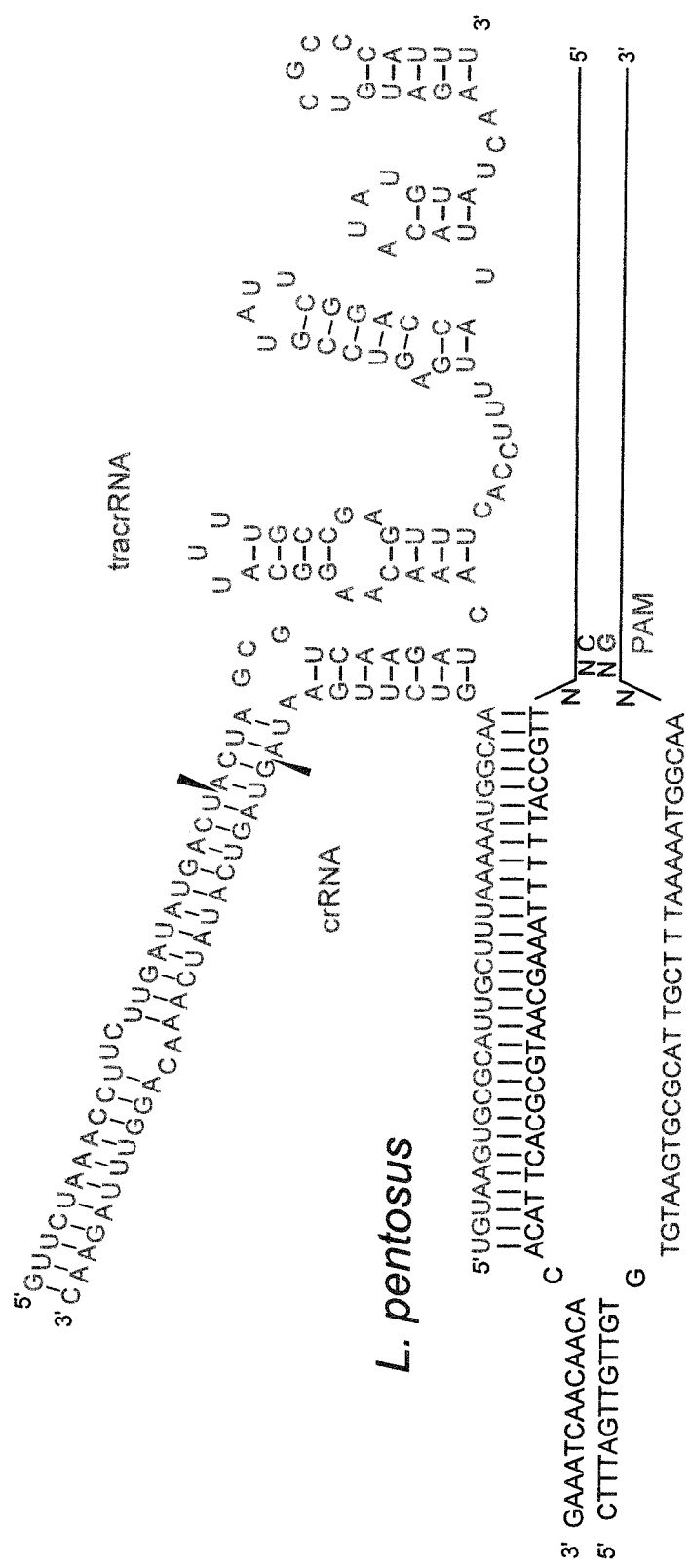
FIG. 21 shows sequence and structural details for CRISPR-Cas system elements for the *Lactobacillus pentosus*, representing the Lpe group.

FIGS. 12-21 show guide sequences and targeting for various cRNA:tracRNA constructs including *Streptococcus thermophilus* CR3, representing the Sth CR1 group (FIG. 12); *Lactobacillus buchneri*, representing the Lbu group (FIG. 13); *Streptococcus thermophilus* CR1, representing the Sth CR1 group (FIG. 14); *Streptococcus pyrogenes* M1 GAS, representing the Sth CR3 group (FIG. 15); *Lactobacillus rhamnosus*, representing the Lrh group (FIG. 16); *Lactobacillus animalis*, representing the Lan group (FIG. 17); *Lactobacillus casei*, representing the Lca group (FIG. 18): *Lactobacillus gasseri*, representing the Lga group (FIG. 19); *Lactobacillus jensenii*, representing the Lje group (FIG. 20); and *Lactobacillus pentosus*, representing the Lpe group (FIG. 21). The lower portion of each of FIGS. 12-21 represents target dsDNA, including the target sequence (open structure) and the flanking (3') PAM. The upper portion of each figure represents the CRISPR RNA (crRNA), which consists of a 5' portion complementary to the target sequence, as well as a 3' portion derived from the CRISPR repeat; and also represents the tracrRNA, which consists of an anti-CRISPR repeat portion, as well as the nexus and 3' hairpins. As shown in each of FIGS. 12-21, the complementary portion of the crRNA:tracrRNA duplex consists of the lower stem (bottom complementary portion), a bulge (herniated mismatch) and upper stem (top complementary portion).

Figure 23:
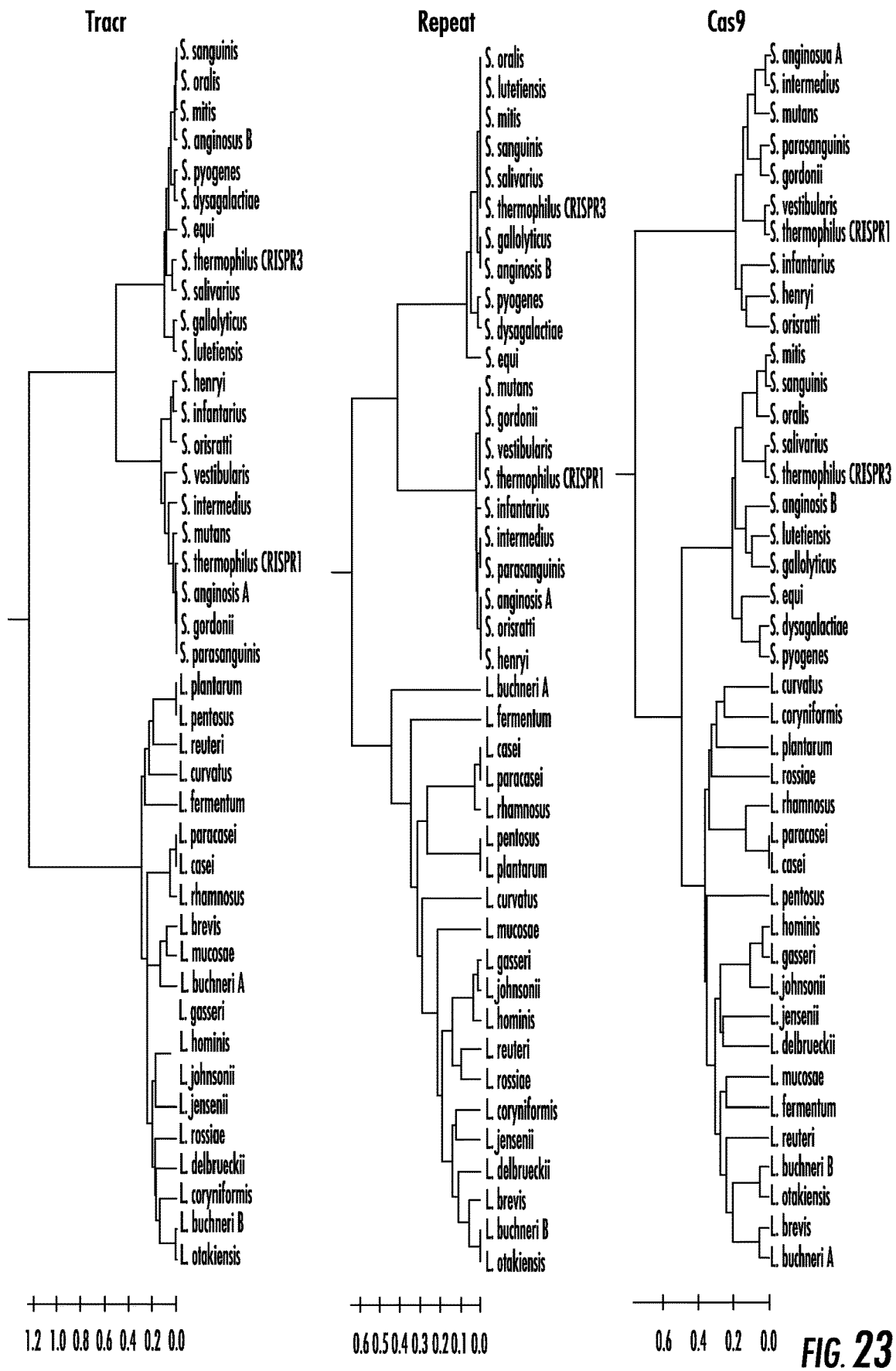
FIG. 23 shows congruence between tracrRNA (left), CRISPR repeat (middle) and Cas9 (right) sequence clustering. Consistent grouping is observed across the three sequence-based phylogenetic trees, into three families.

Example 2. Determination of Guide RNA Sequence Features in Various Additional Type II Systems The findings described in Example 1 establish important modules in sgRNA that are required to support *Streptococcus pyrogenes* Cas9 (SpyCas9) activity. However, while used widely for genome editing, SpyCas9 is merely one of many Cas9 orthologs found naturally (Chylinski, K. et al. *RNA biology* 10, 726-737 (2013); Fonfara, I. et al. *Nucleic Acids Res* (2013)). We therefore next investigated whether the same sgRNA sequence features also occur in other Type II CRISPR-Cas systems. We sampled 41 Cas9 sequences from *Streptococcus* and *Lactobacillus* genomes, in which Type II systems preferentially occur[2] and identified their corresponding CRISPR repeat and predicted tracrRNA sequences. The Cas9 protein sequences clustered into three main sequence groups (FIG. 23). Similar grouping was observed when clustering was carried out using either CRISPR-repeat or predicted tracrRNA sequences (FIG. 24A, FIGS. 23, 25, 26), as anticipated, given the presence of an anti-CRISPR repeat within the tracrRNA, and the intimate molecular relationship between Cas9 and crRNA: tracrRNA pairs (Makarova, K. S. et al. *Nat Rev Microbiol* 9, 467-477 (2011): Deltcheva, E. et al. *Nature* 471, 602-607 (2011); Fonfara, I. et al. *Nucleic Acids Res* (2013)). Within the tracrRNA sequences, we consistently observed the functional modules identified for SpyCas9 (FIG. 24B), with conservation of the overall sgRNAicrRNA:tracrRNA structure between families, and high levels of sequence conservation within clusters.

Figure 24A:
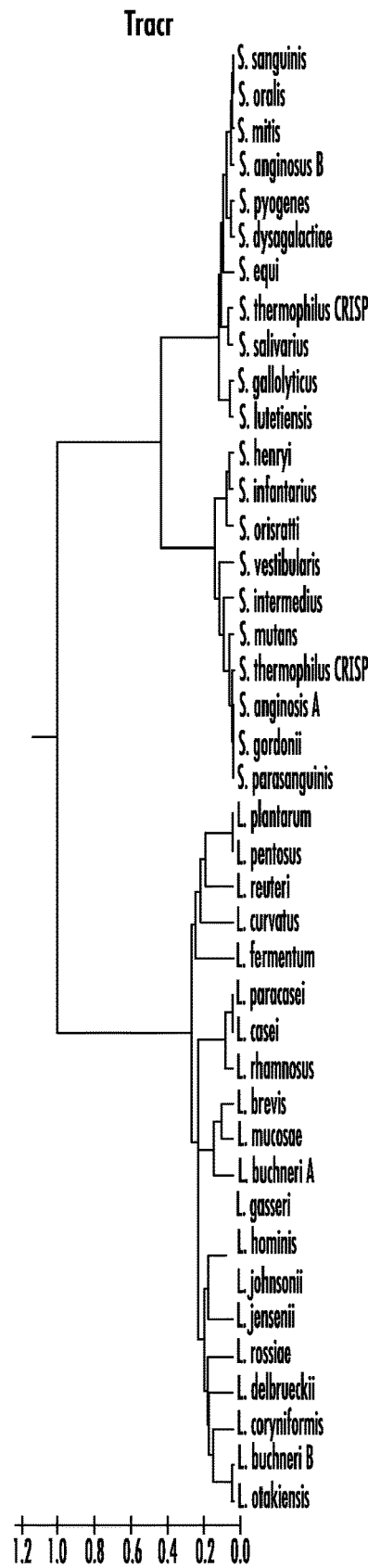
FIG. 24A-24B shows the Cas9:sgRNA families.
Figure 24B:
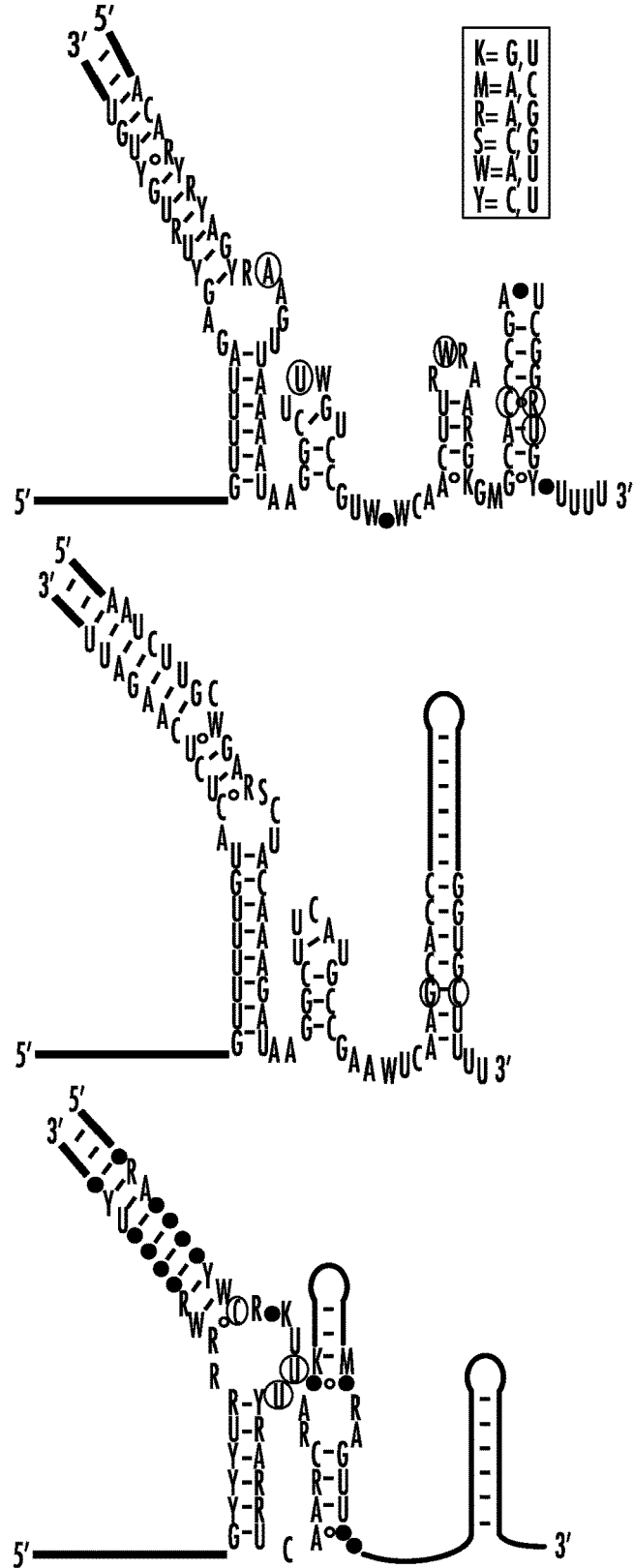
Figures 27A, 27B:
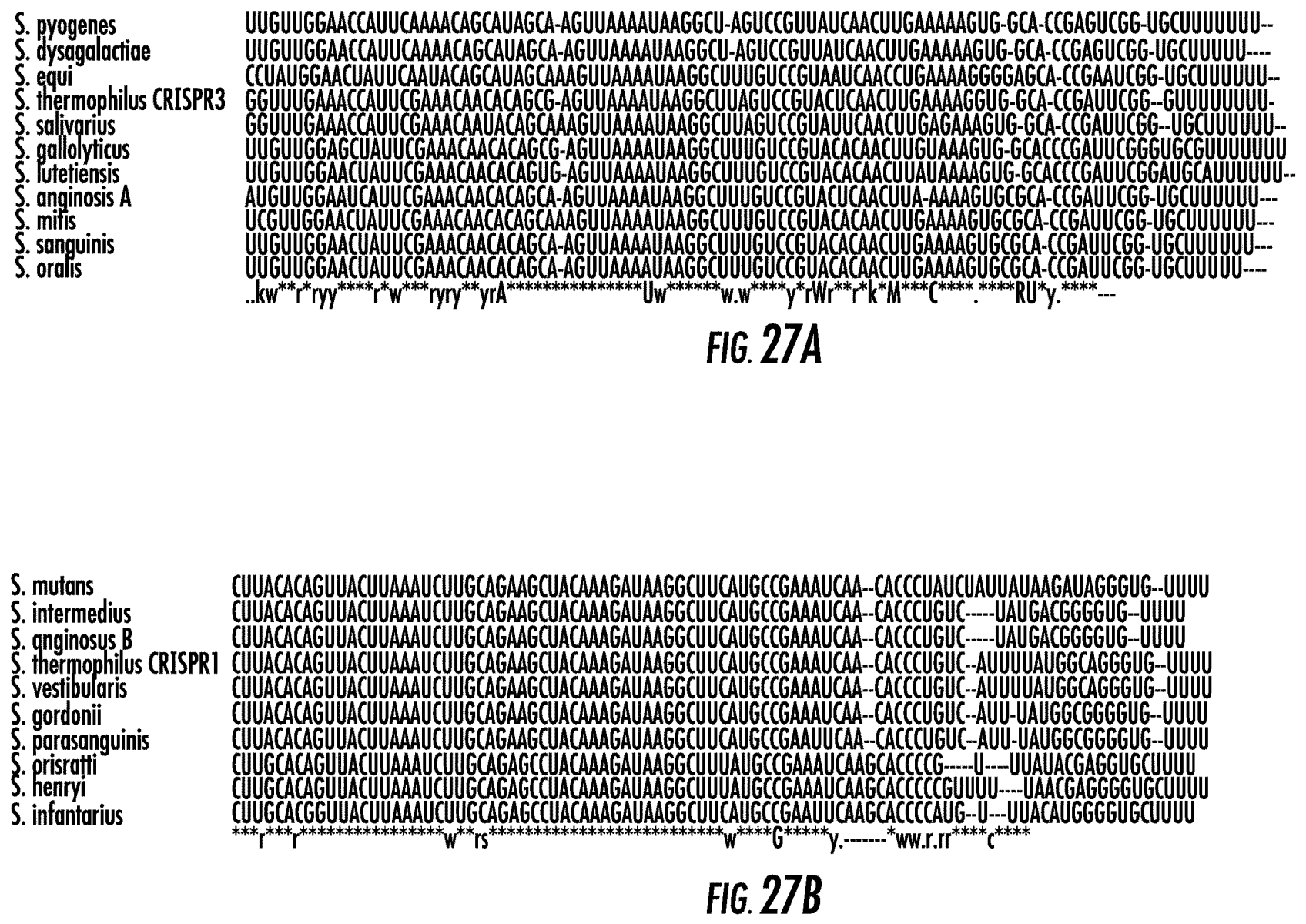
Figure 27C:
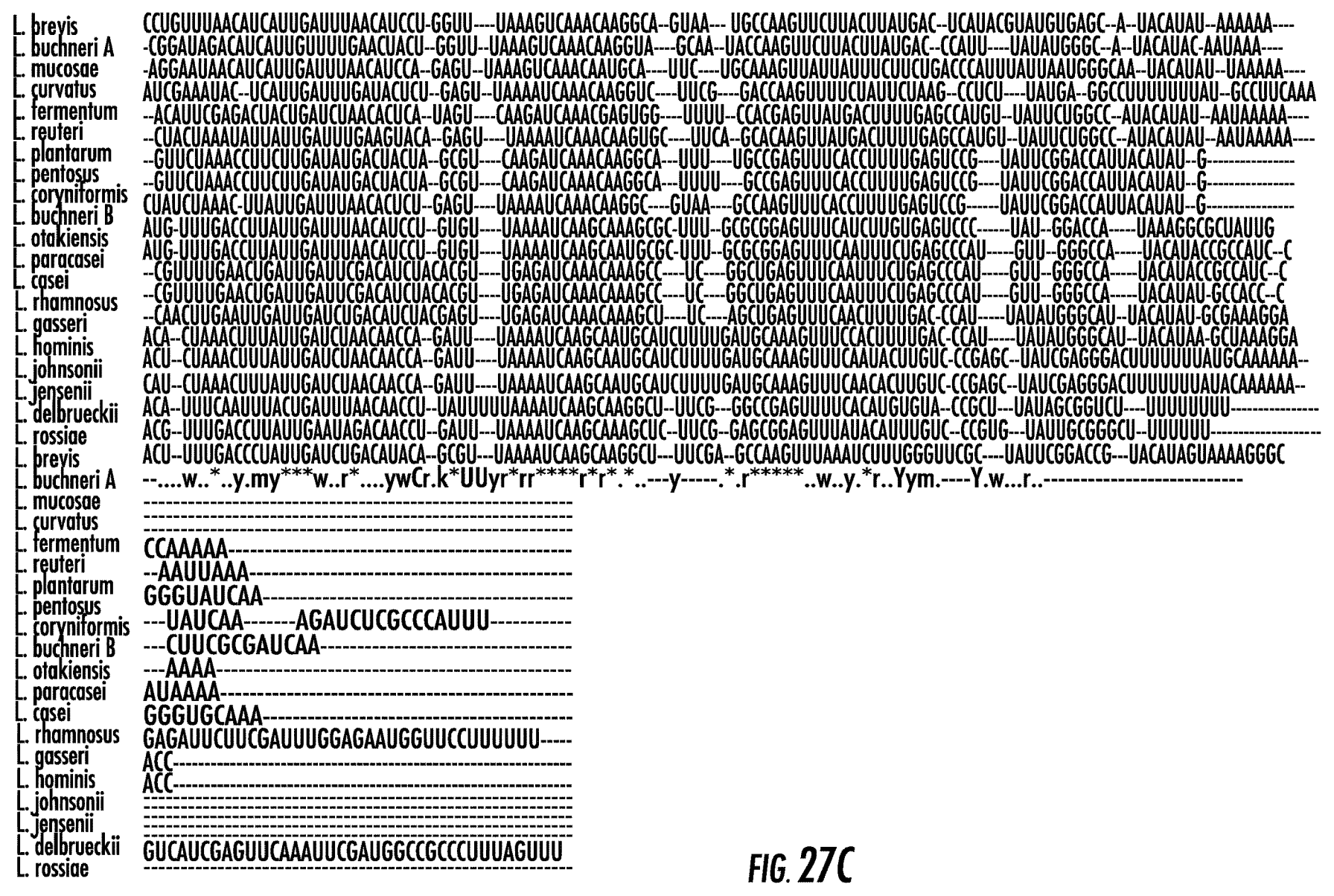

The presence of a bulge with a directional kink between the lower stem (i.e., stitch/anti-stitch) and the upper stem (i.e., zipper/anti-zipper) was observed consistently across a diversity of systems. The length of the lower stem was highly conserved within, and variable between, families. Interestingly, the highest level of conservation was observed for the nexus sequences (FIG. 24B, FIG. 27). The general nexus shape with a GC-rich stem and an offset uracil was shared between the two *Streptococcus* families. In contrast, the idiosyncratic double stem nexus (FIG. 24A-B) was unique to, and ubiquitous in, *Lactobacillus* systems. Remarkably, some bases within the nexus were strictly conserved even between distinct families (FIG. 24A-B), including A52 and C55, further highlighting the critical role of this module. Actually, A52 interacts with the backbone of residues 1103-1107 close to the 5' end of the target strand in the in the crystal structure of SpyCas9, suggesting that the interaction of the nexus with the protein backbone may be required for PAM binding.

Determining the Relationship of Structure of the Guide RNA to Orthogonality of Cas9 Proteins.

Figure 28B:
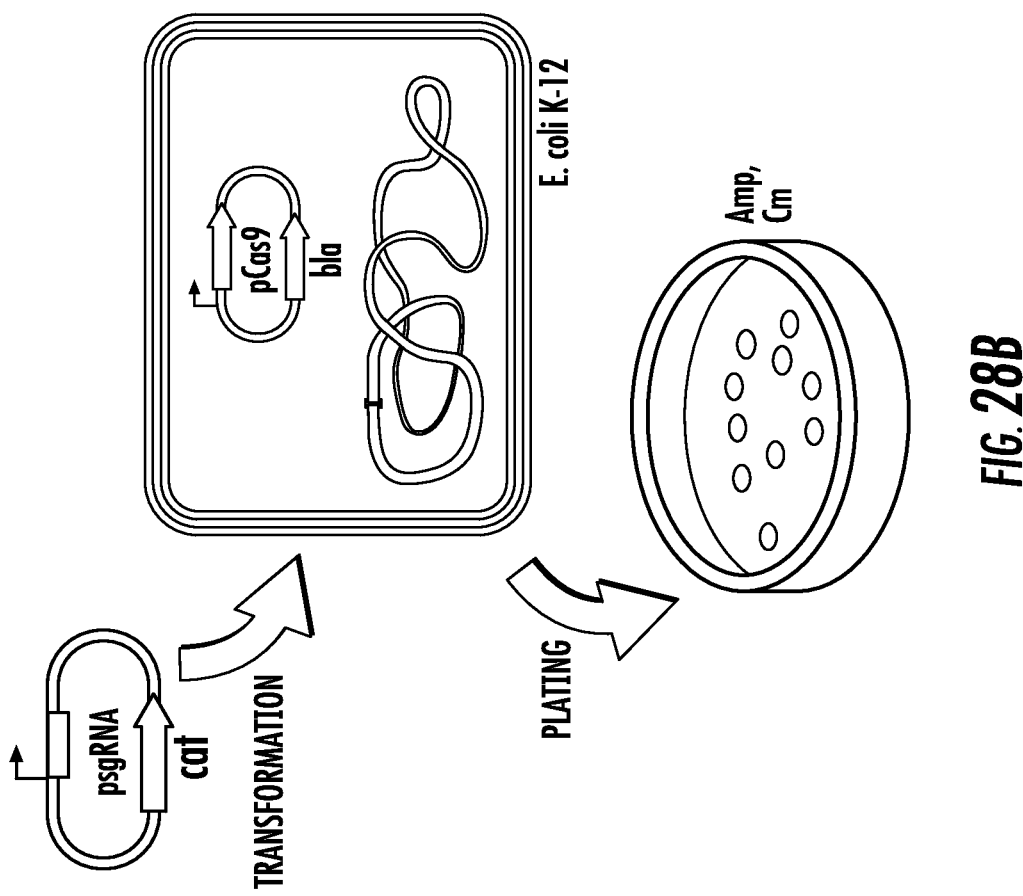
FIG. 28A-B shows a self targeting assay scheme. Orthogonal Cas9 proteins were provided through the pCas9 plasmid (FIG. 28A), and used as described in FIG. 3. Various sgRNA chimera were provided through the psgRNA plasmid (FIG. 28B), and used in combination with each desired Cas9 as described in FIG. 3.
Figure 28A:
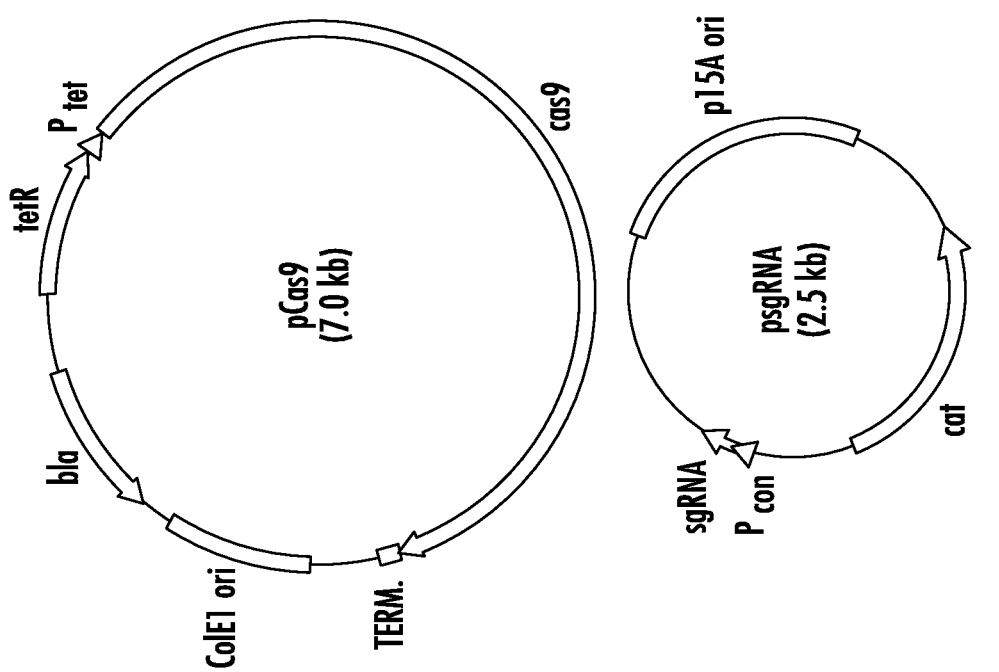

The findings described herein suggest a potential relationship between the structure and sequence of the sgRNA and the diversity of Cas9 proteins. This observation prompted us to determine the sgRNA modules that define Cas9 orthologous groups. Thus, we selected the endonucleases from the two naturally co-existing orthologous *S. thermophilus* Type II systems, namely Sth1Cas9 and Sth3Cas9 (Horvath, P. et al. *J Bacteriol.* 190, 1401-1412 (2008)), to investigate the link between sgRNA composition and Cas9 orthogonality. A series of experiments were designed based on self-targeting activity in *Escherichia coli* (FIG. 28A-B) to test whether specific mutations in a sgRNA could facilitate cleavage activity with a previously orthologous Cas9. We identified a region within the *E. coli* genome that contained overlapping Cas9 target sites for the Sth1Cas9 and Sth3Cas9 systems to ensure that cleavage occurred within one nucleotide (FIG. 29B) and that the PAM sequences were conveniently overlapping. We generated chimeric versions of the two sgRNA backbones and interchanged the spacer, lower stem (ie, stitch/antistitch)-bulge-upper stem (i.e., zipper/anti-zipper), nexus and hairpins (FIG. 29C), and tested their ability to drive self targeting (Gomaa, A. A. et al. *MBio.* 5, e00928-13 (2014)) by either Sth1Cas9 or Sth3Cas9. First, we confirmed that these two systems are indeed orthogonal in this assay system, and that each guide solely drives targeting with its cognate Cas9 (FIG. 29C). Next, we demonstrated that swapping the spacer sequences results in a sgRNA with a CRISPR3 spacer and a CRISPR1 backbone able to support Sth1Cas9 cleavage activity. However, the reverse is not true of Sth3Cas9 activity. A sgRNA containing a CRISPR1 spacer and a CRISPR3 backbone does not support Sth3Cas9 activity (FIG. 29C). We hypothesize that this unidirectional cross-functionality is due to flexibility in the requirement for spacing between the PAM and the protospacer within the SthCRISPR1 system (Chen et al. *J. Biol. Chem.* doi: 10.1074/jbc.M113.539726, (2014)) (FIG. 29C, upper panel). We then demonstrated that functionality between the sgRNA and Cas9 can be switched solely by exchanging the nexus-hairpin combination between two orthogonal systems. A major consequence of re-programming the sgRNA is that the ability to guide the original Cas9 is lost in that process (FIG. 29C, lower panel). This contrasts with the canonical view that the CRISPR repeat sequence plays a key role in defining orthologous CRISPR-Cas systems. Altogether, these results show that chimeric sgRNAs with altered nexus sequences can reprogram orthogonality in a predictable and unidirectional manner, which is critical for further harnessing orthogonal Cas9 proteins associated with different PAMs (Esvelt, K. M. et al. *Nature Methods* (2013)).

Recent structural and biochemical data has begun to shed light on the mechanism of DNA recognition and cleavage by Cas9 (Jinek, M. et al., *Science* 337, 816-821 (2012); Jinek. M. et al., *Science* 343, 6176 (2014); Nishimasu, H. et al. *Cell* 156, 935 (2014)). Electron micrographs of the apo-, RNA-bound and protein/RNA/DNA complexes indicated that upon binding guide RNA, Cas9 undergoes a dramatic conformational change to facilitate target DNA binding and cleavage structures (Jinek, M. et al., *Science* 343, 6176 (2014). Crystal structures show that, consistent with images from the electron microscope, the SpyCas9:sgRNA:DNA: complex and apo-SpyCas9 occupy significantly different conformations, with substantial rearrangement of RNA- and DNA-binding domains taking place between the two structures (Jinek, M. et al., *Science* 343, 6176 (2014): Nishimasu, H. et al. *Cell* 156, 935 (2014)). The nexus occupies a critical position in the SpyCas9-sgRNA:DNA complex, coordinating a number of key components of the protein and sgRNA, positioning both protein and RNA appropriately to receive target DNA duplexes for cleavage. Upon binding sgRNA: DNA, the arginine-rich bridge helix binds to the base of the nexus and to the lower stem. Additionally, the nexus interacts with two small regions (which we propose to establish as Nexus Interacting Region 1 (NIR1) 446-497 and Nexus Interacting Region 2 (NIR2) 1105-1138) from the two lobes of SpyCas9. Both of these regions are disordered in the apoSpyCas9 structure, and notably contain two tryptophan residues identified as being important in PAM recognition[21]. NIR2 also interacts directly with the lower stem, and the face opposite the nexus-binding site lies in close proximity to the 3' end of the target strand, suggesting that interaction with the nexus may be required to order the PAM recognition site. Notably, in the *Actinomyces naeslundii* Cas9 (AnaCas9) apo-structure (Jinek, M. et al., *Science* 343, 6176 (2014)), NIR2 is ordered, and contains an about 50 amino acid insertion. It is tempting to speculate that AnaCas9 may recognize a larger nexus and possibly accompanying PAM sequence.

Altogether, these results reveal that there are six distinct features within guide RNAs and establish the bulge and nexus as structure- and sequence-specific features that guide Cas9 targeting and cleavage. This provides a basis for optimization of sgRNA composition and design with the opportunity to engineer short, minimal guide RNAs that contain smaller regions of double-stranded RNA potentially triggering innate immune responses, and are more amenable to packaging into, for example, adeno-associated viruses. This understanding of Type II CRISPR-Cas systems is corroborated by Briner et al. (*Mol. Cell* 56:333-339 (2014)) and Nishimasu et al. (*Cell* 156:935-949 (2014), wherein it is shown that modifications of the sequences that impact the ability of the modified sequences to guide Cas9. Noteworthy, these studies confirm that the nexus sequence within the guide is critical in guiding Cas9 towards complementary DNA and subsequent cleavage.

The ability to reprogram Cas9 orthogonality using chimeric sgRNAs with altered nexus sequences opens new avenues for the exploitation of novel Cas9 proteins, with the potential to harness the diversity of natural Cas9 orthologs, including short Cas9 variants for convenient packaging and delivery. Additionally, the ability to reprogram Cas9 using chimeric mgRNAs will allow for increased use of various PAMs for flexible management of target frequency (short PAMs with frequent occurrence) and specificity by reducing off-target cleavage (longer PAMs with infrequent occurrence). This also expands multiplexing opportunities, by using a single Cas9 with various chimeric guides, or by concurrently using orthogonal systems with different combinations of standard or chimeric sgRNAs. Collectively, our findings open up new avenues for Cas9-dependent DNA targeting, and set the stage for the development of next-generation CRISPR-based technologies.

Example 3

The cas9 genes from the CRISPR1 locus and the CRISPR3 locus were PCR amplified from genomic DNA from *S. thermophilus* LMD-9, and cloned into pwtCas9-Bacteria (Addgene #44250)) (Qi, L. S. et al. *Cell* 152, 1173-1183 (2013)). To construct the sgRNA-expressing plasmids, the SpeI restriction site in the pdCas9-bacteria plasmid (Addgene #44249) (Id.) was removed and a gBlock (IDT) encoding a zraP-targeting sgRNA based on the CRISPR1 or the CRISPR3 locus was combined with the PCR-amplified backbone of the pgRNA-bacteria plasmid (Addgene #44251) (Id.). *E. coli* K-12 was used for transformation assays, and transformation efficiency was calculated by dividing the number of transformants for the tested sgRNA plasmid by the number of transformants for the psgRNA-C1-T4 control plasmid, as described previously (Gomaa, A. A. et al. MBio. 5, e00928-13 (2014)).

Plasmid Construction.

To construct the Cas9-expressing plasmids, the Cas9 genes from the CRISPR1 locus (Sth1-Cas9) and the CRISPR3 locus (Sth3-Cas9) were PCR amplified from genomic DNA extracted from *S. thermophilus* LMD-9. Each PCR product was combined with the PCR-amplified backbone of pwtCas9-Bacteria (Addgene #44250) (Qi, L. S. et al. (*Cell* 152, 1173-1183 (2013)) by Gibson assembly. To construct the sgRNA-expressing plasmids, the SpeI restriction site in the pdCas9-bacteria plasmid (Addgene #44249) (Id.) was removed by digesting the plasmid with SpeI, blunt ending, and religating to generate the pdCas9ΔSpeI plasmid. Separately, a gBlock (IDT) encoding a zraP-targeting sgRNA based on the CRISPR1 (C1) locus or the CRISPR3 (C3) locus in *S. thermophilus* LMD-9 was combined with the PCR-amplified backbone of the pgRNA-bacteria plasmid (Addgene #44251) (Id.) by Gibson assembly, thereby replacing the original *S. pyogenes* sgRNA sequence with the designed sgRNA sequence. The resulting sgRNA plasmids and the pdCas9ΔSpeI backbone were then digested with AatII and XhoI, and the gel-extracted fragment of each sgRNA plasmid and the pdCas9ΔSpeI plasmid were ligated together, forming psgRNA-SthC1 and psgRNA-SthC3. To modify the sgRNA sequences, 5' phosphorylated oligonucleotides were annealed and ligated into the SpeI/KpnI or KpnI:HindIII sites of the psgRNA-C1 plasmid or the psgRNA-C3 plasmid. All plasmid modifications were verified by sequencing.

Strains and Growth Conditions.

E. coli K-12 subst. MG1655 (genotype: E. coli K-12 F λ-ilvG-rfb-5C rph-1) was used for all transformation assays. The strain was grown aerobically in LB medium (10 g/L tryptone, 5 g/L yeast extract, 10 g/L sodium chloride) at 37° C. and 250 RPM unless indicated otherwise. The medium was supplemented with antibiotics (34 µg/ml of chloramphenicol, 50 µg/ml Ampicillin) as appropriate.

Transformation Assay.

Figure 30:
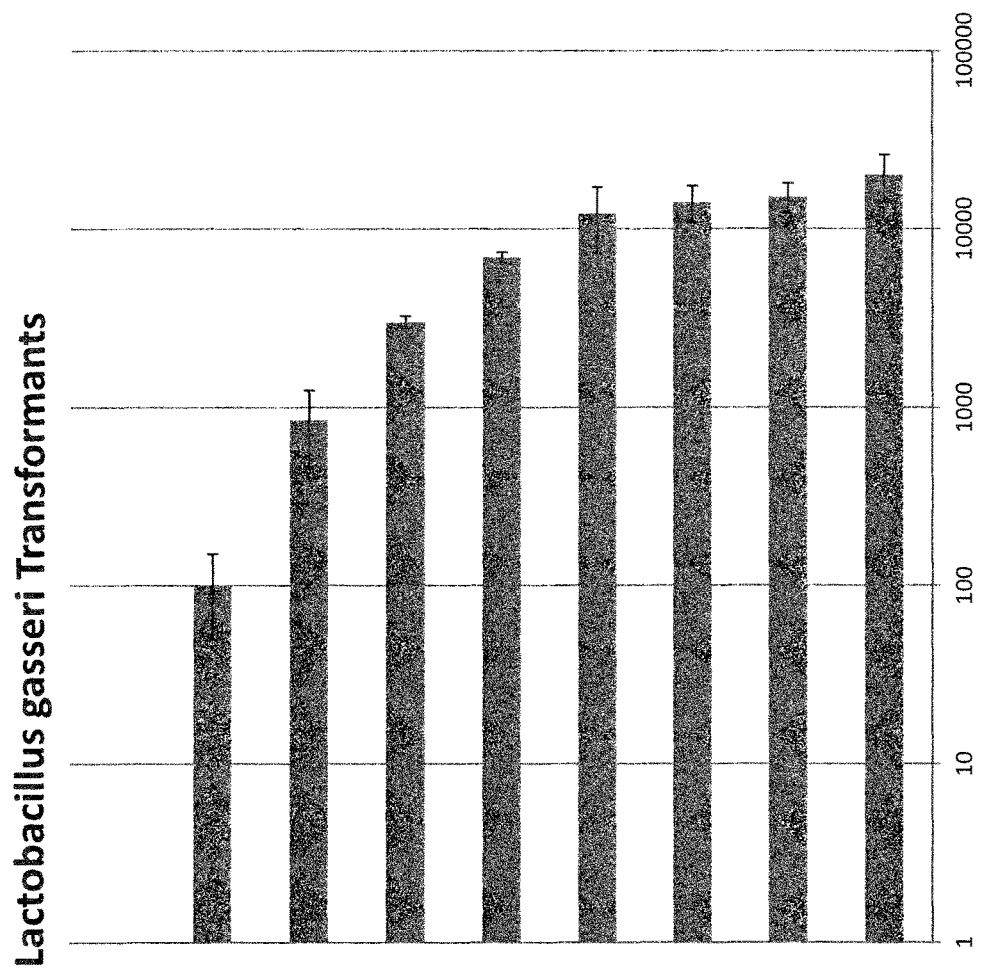
FIG. 30 shows CRISPR interference against complementary DNA, as inability to transform plasmids that contain protospacer sequences that match the first wild type CRISPR spacer sequence, in *Lactobacillus gasseri*. The bold sequence, flanked by a PAM (light grey, italicized nucleotides) and variants thereof (single nucleotide polymorphisms (SNPs); black underlined nucleotides) is the protospacer. Low transformant counts represent an active Lga CRISPR systems which precludes transformation of complementary target DNA.
Figure 31:
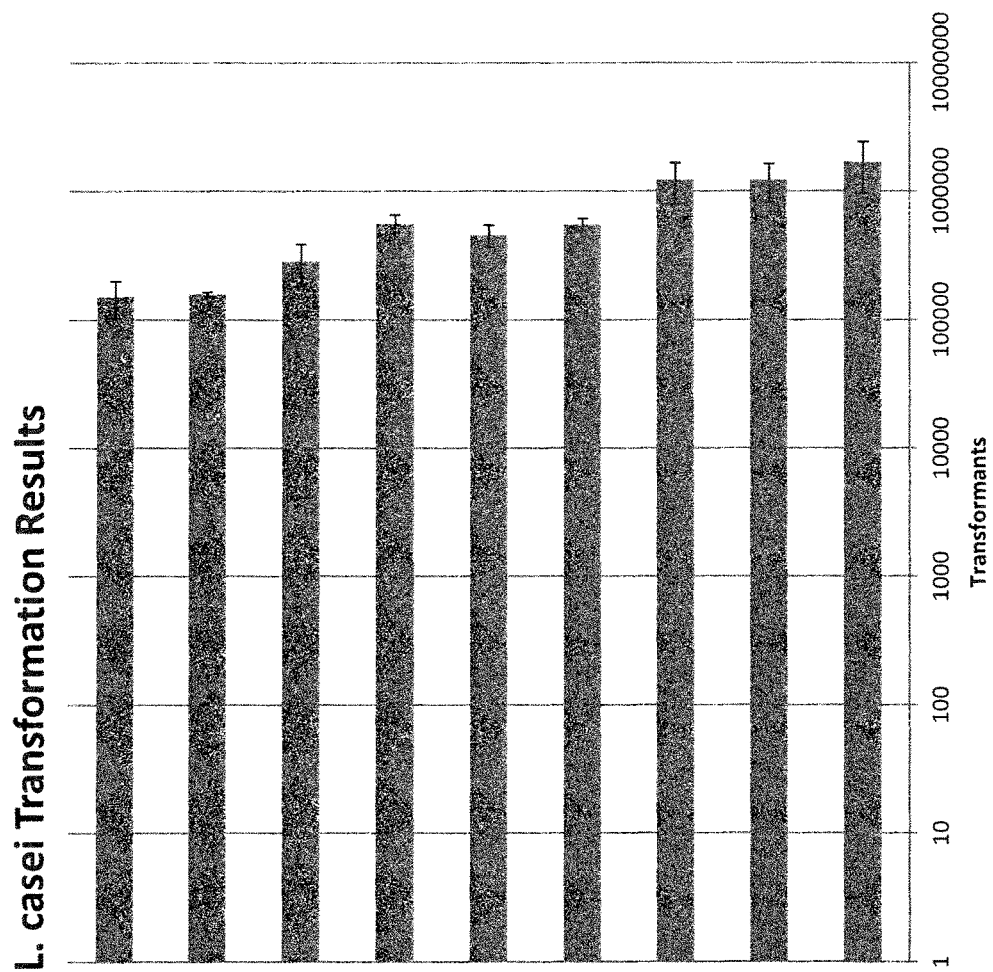
FIG. 31 shows CRISPR interference against complementary DNA, as inability to transform plasmids that contain protospacer sequences that match the first wild type CRISPR spacer sequence, in *Lactobacillus casei*. The bold sequence, flanked by a PAM (light grey, italicized nucleotides) and variants thereof (SNPs, black underlined nucleotides) is the protospacer. Low transformant counts represent an active Lca CRISPR systems which precludes transformation of complementary target DNA.
Figure 32:
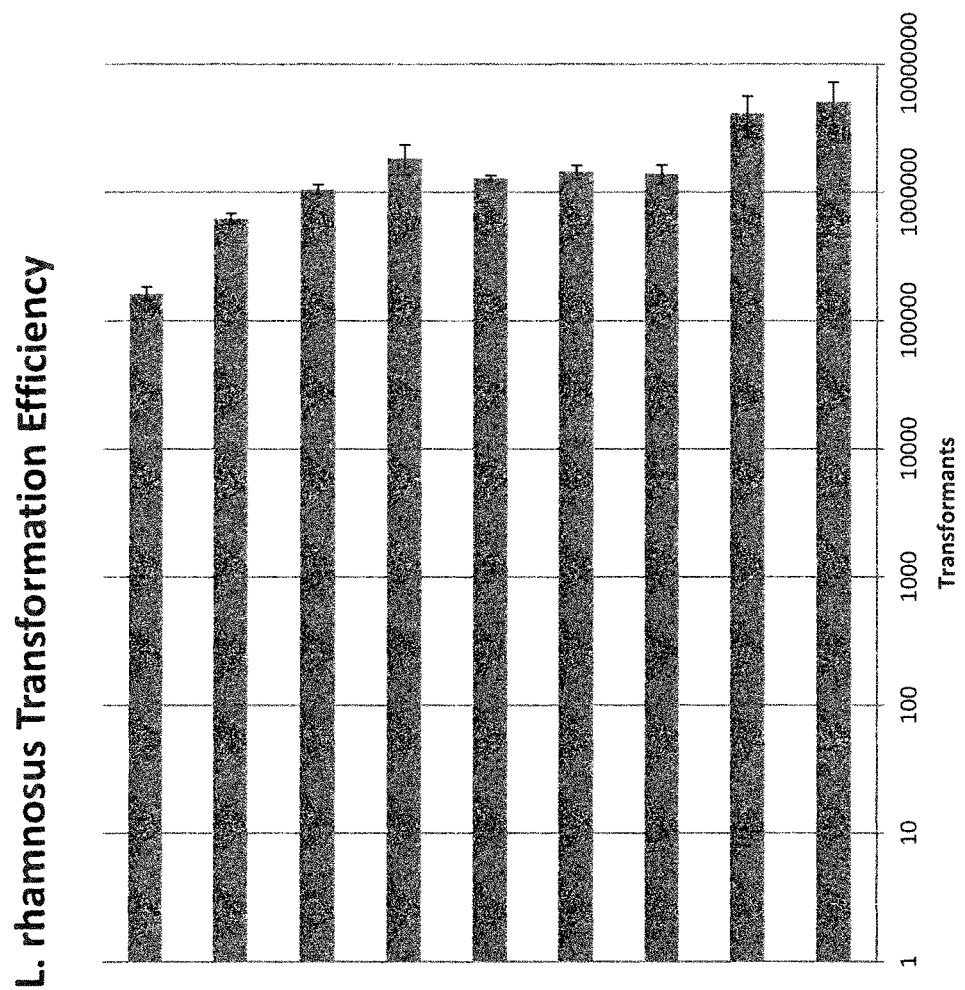
FIG. 32 shows CRISPR interference against complementary DNA, as inability to transform plasmids that contain protospacer sequences that match the first wild type CRISPR spacer sequence, in *Lactobacillus rhamnosus*. The bold sequence, flanked by a PAM light grey, italicized nucleotides) and variants thereof (SNPs, black underlined nucleotides) is the protospacer. Low transformant counts represent an active Lra CRISPR systems which precludes transformation of complementary target DNA.

Freezer stocks of cells harboring the indicated Cas9-expressing plasmid were streaked to isolation and individual colonies were inoculated into 3 ml of LB medium and cultured overnight. The resulting cultures were back-diluted into 45 ml of LB medium and grown to an $ABS_{60}$ of 0.6-0.8 as measured on a Nanodrop 2000c spectrophotometer (Thermo Scientific). The cultures were then pelleted and washed with ice-cold 10% glycerol twice before being resuspended in 200-400 µl of 10% glycerol. Suspended cells (50 µl) were transformed with 25 ng of the indicated sgRNA-expressing plasmid using a MicroPulser Electroporator (BioRad) and recovered in 300 µl of SOC medium (Quality Biological) for 1 hour. After recovery. 200 µl of cultures with different amounts of LB medium were plated on LB agar with 100 ng/ml of anhydrotetracycline. The transformation efficiency was calculated by dividing the number of transformants for the tested DgRNA plasmid by the number of transformants for the psgRNA-C1-T4 control plasmid, as described previously (Gomaa, A. A. et al. MBio. 5, e00928-13 (2014)). In order to reduce experiment-to-experiment variability in transformation efficiency, the tested sgRNA plasmid and the control plasmid were transformed into the same batch of electrocompetent cells. Similarly, for FIGS. 30-32, transformation assays were used to test the ability of a plasmid to be electroporated into lactobacillus strains that carry active CRISPR-Cas systems (Lbu—Lactobacillus buchneri. FIG. 30; Lrh—Lactobacillus rhamnosus, FIG. 32; Lca—Lactobacillus casei. FIG. 31. The plasmid was engineered as to contain a protospacer sequence identical to the first spacer sequence in the CRISPR locus of the host. Various plasmids were engineered as to flank the protospacer with a perfect PAM (NTAAC for Lga; NNGAA for Lca; NGAAA for Lrh: the PAM region is the underlined nucleotides in FIGS. 30-32, and mutated variants thereof (the nucleotides being tested for efficiency are italicized). Experiments also included a control non-targeting sequence (next to last entry for each experiment shown in FIGS. 30-32, as well as a control plasmid with no target sequence (last entry for each experiment shown in FIGS. 30-32. The ability of the native CRISPR-Cas system to interfere with plasmid uptake by DNA targeting is measured as the difference in transformation efficiency between the test sequence and that of the two aforementioned controls.

---

That which is claimed is:

1. A chimeric nucleic acid construct comprising (a) a synthetic trans-encoded CRISPR (tracr) nucleic acid construct and (b) a synthetic CRISPR nucleic acid construct, the synthetic tracr nucleic acid construct comprising, from 5' to 3', nucleotides 4 to 112 of SEQ ID NO: 69, wherein the synthetic tracr nucleic acid construct comprises an anti-zipper sequence comprising at least four nucleotides, wherein the at least four nucleotides comprises nucleotides 22-25 of SEQ ID NO: 69; a bulge sequence comprising nucleotides 29-30 of SEQ ID NO: 69; an anti-stitch sequence comprising nucleotides 31-38 of SEQ ID NO: 69; a nexus sequence comprising nucleotides 39-68 of SEQ ID NO: 69; said nexus forms a hairpin structure comprising a double stranded double stem; and a hairpin sequence comprising a nucleotide sequence having two hairpins, each hairpin comprising a stem having at least five matched base pairs, wherein the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence: and the synthetic CRISPR nucleic acid construct comprising, from 3' to 5', a zipper sequence comprising at least four nucleotides, wherein the at least four nucleotides comprises the nucleotide sequence of UGGU, a stitch sequence comprising a nucleotide sequence of AGAUUUUG, and a spacer sequence having a 5' end and a 3' end and comprising at least seven nucleotides at its 3' end having 100% complementarity to a target DNA, and the zipper sequence is located immediately upstream of the stitch sequence, the stitch sequence is located immediately upstream of the spacer sequence, wherein the stitch sequence of the synthetic CRISPR nucleic acid construct is 100% complementary to and is hybridized to the anti-stitch sequence of said synthetic tracr nucleic acid construct and the zipper sequence of the synthetic CRISPR nucleic acid construct is at least about 90% complementary to and is hybridized to the anti-zipper sequence of said synthetic tracr nucleic acid construct, wherein the chimeric nucleic acid construct is functional with a Cas9 polypeptide having at least 90% identity to the amino acid sequence of SEQ ID NO:30.

2. The chimeric nucleic acid construct of claim 1, wherein the chimeric nucleic acid construct is capable of forming a nucleic acid-protein complex with a Cas9 polypeptide having at least 90% identity to the amino acid sequence of SEQ ID NO:30.

3. The chimeric nucleic acid construct of claim 2, wherein the Cas9 nuclease is a Cas9 from a *Lactobacillus* gasseri (Lga) group of Cas9 nucleases.

4. The chimeric nucleic acid construct of claim 2, wherein the Cas9 nuclease comprises a mutation in the RuvC active site motif.

5. The chimeric nucleic acid construct of claim 2, wherein the Cas9 nuclease comprises a mutation in the HNH active site motif.

6. The chimeric nucleic acid construct of claim 2, wherein the Cas9 nuclease comprises a mutation in the HNH active site motif and in the RuvC active site motif and is fused to a polypeptide of interest.

7. An expression cassette encoding the chimeric nucleic acid construct of claim 1.

8. A cell comprising the expression cassette of claim 7.

9. A method for site-specific cleavage of a double stranded target DNA, comprising:
  contacting the chimeric nucleic acid construct of claim 1 with the target DNA in the presence of a Cas9 nuclease, and the spacer sequence of the synthetic CRISPR nucleic acid construct hybridizes to a portion of the target DNA and adjacent to a protospacer adjacent motif (PAM) on the target DNA, thereby producing a site-specific cleavage of the target DNA in a region defined by complementary hybridization of the spacer sequence to the target DNA.

10. The method of claim 9, wherein the site-specific cleavage is a site-specific nicking of a (+) strand of the double stranded target DNA and said Cas9 nuclease comprises a mutation in a RuvC active site motif, thereby cleaving the (+) strand of the double stranded target and producing a site-specific nick in said (+) strand the double stranded target DNA, or the site-specific cleavage is a site-specific nicking of the (−) strand of the double stranded target DNA and said Cas9 nuclease comprises a point mutation in a HNH active site motif, thereby cleaving the (−) strand of the double stranded target DNA and producing a site-specific nick in said (−) strand the double stranded target DNA.

11. A method of site-specific targeting of a polypeptide of interest to a double stranded (ds) target DNA, comprising
  contacting the chimeric nucleic acid construct of claim 6, thereby targeting the polypeptide of interest fused to the Cas9 to a specific site on the target DNA, said site defined by complementary hybridization of the spacer sequence to the target DNA.

12. The method of claim 9, wherein the PAM comprises the nucleotide sequence of CTAA, TAA or GAA.

13. The method of claim 9, wherein the Cas9 nuclease is encoded by a nucleotide sequence that is codon optimized for an organism comprising the target DNA.

14. The method of claim 9, wherein the Cas9 nuclease comprises at least one nuclear localization sequence.

15. A target nucleic acid modification system, comprising a chimeric nucleic acid construct comprising (a) a synthetic trans-encoded CRISPR (tracr) nucleic acid construct and (b) a synthetic CRISPR nucleic acid (e.g., crRNA, crDNA) construct, the synthetic tracr nucleic acid construct comprising, from 5' to 3', nucleotides 4 to 112 of SEQ ID NO:69, wherein the synthetic tracr nucleic acid construct comprises an anti-zipper sequence comprising at least four nucleotides, wherein the at least four nucleotides comprises nucleotides 22-25 of SEQ ID NO: 69; a bulge sequence comprising nucleotides 29-30 of SEQ ID NO: 69; an anti-stitch sequence comprising nucleotides 31-38 of SEQ ID NO: 69; a nexus sequence comprising nucleotides 39-68 of SEQ ID NO: 69; said nexus forms a hairpin structure comprising a double stranded double stem; and a hairpin sequence comprising a nucleotide sequence having two hairpins, each hairpin comprising a stem having at least five matched base pairs, wherein the anti-zipper sequence is located immediately upstream of the bulge sequence, the bulge sequence is located immediately upstream of the anti-stitch sequence, the anti-stitch sequence is located immediately upstream of the nexus sequence, and the nexus sequence is located immediately upstream of the hairpin sequence; and
  the synthetic CRISPR nucleic acid construct comprising, from 3' to 5', a zipper sequence comprising at least four nucleotides, wherein the at least four nucleotides comprises the nucleotide sequence of UGGU, a stitch sequence comprising a nucleotide sequence of AGAUUUUG, and a spacer sequence having a 5' end and a 3' end and comprising at least seven nucleotides at its 3' end having 100% complementarity to a target nucleic acid, and the zipper sequence is located immediately upstream of the stitch sequence, the stitch sequence is located immediately upstream of the spacer sequence,
  wherein the stitch sequence of the synthetic CRISPR nucleic acid construct is 100% complementary to and is hybridized to the anti-stitch sequence of said synthetic tracr nucleic acid construct and the zipper sequence of the synthetic CRISPR nucleic acid construct is at least about 90% complementary to and is hybridized to the anti-zipper sequence of said synthetic tracr nucleic acid construct; and
  (c) a Cas9 nuclease having at least 90% identity to the amino acid sequence of SEQ ID NO: 30,
  wherein the Cas9 nuclease binds to and is capable of forming a complex with the chimeric nucleic acid, and the spacer sequence of the synthetic CRISPR nucleic acid construct hybridizes to a portion of the target nucleic acid and adjacent to a protospacer adjacent motif (PAM) on the target nucleic acid, thereby the Cas9 is guided to the target nucleic acid and modifies the target nucleic acid.

16. The system of claim 15, wherein the Cas9 nuclease having at least 90% identity to the amino acid sequence of SEQ ID NO:30 is a Cas9 from a *Lactobacillus* gasseri (Lga) group of Cas9 nucleases.

17. The system of claim 15, wherein the Cas9 nuclease comprises a mutation in the RuvC active site motif.

18. The system of claim 15, wherein the Cas9 nuclease comprises a mutation in the HNH active site motif.

19. The system of claim 15, wherein the nucleic acid modification is a site-specific cleavage of a double stranded target DNA.

20. The system of claim 15, wherein the Cas9 nuclease comprises a mutation in the HNH active site motif and in the RuvC active site motif and is fused to a polypeptide of interest.

21. The system of claim 15, wherein the PAM comprises the nucleotide sequence of CTAA, TAA or GAA.

\* \* \* \* \*

UNITED STATES PATENT AND TRADEMARK OFFICE
CERTIFICATE OF CORRECTION

PATENT NO. : 10,787,654 B2
APPLICATION NO. : 15/113656
DATED : September 29, 2020
INVENTOR(S) : Barrangou et al.

It is certified that error appears in the above-identified patent and that said Letters Patent is hereby corrected as shown below:

On the Title Page

(56) References Cited, OTHER PUBLICATIONS, Page 3, Column 1, Line 42, Salle K. Barrangou R. cite: Please correct "Salle" to read -- Selle --

(56) References Cited, OTHER PUBLICATIONS, Page 3, Column 1, Line 48, Salle, K. et al. cite: Please correct "Salle" to read -- Selle --

(56) References Cited, OTHER PUBLICATIONS, Page 3, Column 2, Line 4: Please correct "SMU_L1405c" to read -- SMU_1405c --

(56) References Cited, OTHER PUBLICATIONS, Page 3, Column 2, Line 12: Please correct "CCD034" to read -- CD034 --

(56) References Cited, OTHER PUBLICATIONS, Page 4, Column 1, Lines 32-33: Please correct "PCT/US2018/934322" to read -- PCT/US2018/034322 --

(56) References Cited, OTHER PUBLICATIONS, Page 4, Column 2, Line 29: Please correct "Gasiijnas" to read -- Gasiunas --

In the Specification

Column 1, Line 47: Please correct "Tems" to read -- Terns --

Column 1, Line 60: Please correct "Gameau" to read -- Garneau --

Column 3, Line 56: Please correct "(G/A)C." to read -- (G/A)C, --

Column 5, Line 47: Please correct "TCAAAC." to read -- TCAAAC, --

Signed and Sealed this
Ninth Day of March, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,787,654 B2

Column 11, Line 13: Please correct "990/identical" to read -- 99% identical --

Column 14, Line 12: Please correct "95%. 97%" to read -- 95%, 97% --

Column 14, Line 20: Please correct "990%" to read -- 99% --

Column 14, Line 28: Please correct "75%/0" to read -- 75% --

Column 14, Line 29: Please correct "82%/0" to read -- 82% --

Column 14, Line 30: Please correct "999%" to read -- 99% --

Column 16, Line 3: Please correct "TTTTTA" to read -- TTTTA --

Column 16, Line 24: Please correct "81%.," to read -- 81%, --

Column 16, Line 24: Please correct "88%.," to read -- 88%, --

Column 16, Line 25: Please correct "90° %" to read -- 90% --

Column 16, Line 48: Please correct "70° %" to read -- 70% --

Column 19, Line 23: Please correct "(SDS)." to read -- (SDS), --

Column 24, Line 64: Please correct "UCAAG)." to read -- UCAAG), --

Column 24, Line 65: Please correct "(AT)" to read -- (A/T) --

Column 29, Line 34: Please correct "(AT)" to read -- (A/T) --

Column 33, Line 32: Please correct "(GA)" to read -- (G/A) --

Column 35, Line 57: Please correct "Gameau" to read -- Garneau --

Column 35, Line 63: Please correct "Gameau" to read -- Garneau --

Column 36, Line 51: Please correct "(Wild Type. WT)" to read -- (Wild Type, WT) --

Column 38, Line 10: Please correct "sgRNAicrRNA" to read -- sgRNA/crRNA --

Column 39, Line 30: Please correct "(2014): Nishimasu" to read -- (2014); Nishimasu --

Column 40, Line 14: Please correct "$ABS_{60}$" to read -- $ABS_{600}$ --

SEQUENCE LISTING

```
<160> NUMBER OF SEQ ID NOS: 79

<210> SEQ ID NO 1
<211> LENGTH: 1121
<212> TYPE: PRT
<213> ORGANISM: Streptococcus thermophilus

<400> SEQUENCE: 1

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Ala Arg Arg Lys Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Asp Gly
        115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190
```

```
Ala Leu Arg Ile Leu Gln Thr Gln Gln Glu Phe Asn Pro Gln Ile Thr
    195                 200                 205
Asp Glu Phe Ile Asn Arg Tyr Leu Glu Ile Leu Thr Gly Lys Arg Lys
210                 215                 220
Tyr Tyr His Gly Pro Gly Asn Glu Lys Ser Arg Thr Asp Tyr Gly Arg
225                 230                 235                 240
Tyr Arg Thr Ser Gly Glu Thr Leu Asp Asn Ile Phe Gly Ile Leu Ile
                245                 250                 255
Gly Lys Cys Thr Phe Tyr Pro Asp Glu Phe Arg Ala Ala Lys Ala Ser
            260                 265                 270
Tyr Thr Ala Gln Glu Phe Asn Leu Leu Asn Asp Leu Asn Asn Leu Thr
        275                 280                 285
Val Pro Thr Glu Thr Lys Lys Leu Ser Lys Glu Gln Lys Asn Gln Ile
    290                 295                 300
Ile Asn Tyr Val Lys Asn Glu Lys Ala Met Gly Pro Ala Lys Leu Phe
305                 310                 315                 320
Lys Tyr Ile Ala Lys Leu Leu Ser Cys Asp Val Ala Asp Ile Lys Gly
                325                 330                 335
Tyr Arg Ile Asp Lys Ser Gly Lys Ala Glu Ile His Thr Phe Glu Ala
            340                 345                 350
Tyr Arg Lys Met Lys Thr Leu Glu Thr Leu Asp Ile Glu Gln Met Asp
        355                 360                 365
Arg Glu Thr Leu Asp Lys Leu Ala Tyr Val Leu Thr Leu Asn Thr Glu
    370                 375                 380
Arg Glu Gly Ile Gln Glu Ala Leu Glu His Glu Phe Ala Asp Gly Ser
385                 390                 395                 400
Phe Ser Gln Lys Gln Val Asp Glu Leu Val Gln Phe Arg Lys Ala Asn
                405                 410                 415
Ser Ser Ile Phe Gly Lys Gly Trp His Asn Phe Ser Val Lys Leu Met
            420                 425                 430
Met Glu Leu Ile Pro Glu Leu Tyr Glu Thr Ser Glu Glu Gln Met Thr
        435                 440                 445
Ile Leu Thr Arg Leu Gly Lys Gln Lys Thr Thr Ser Ser Ser Asn Lys
    450                 455                 460
Thr Lys Tyr Ile Asp Glu Lys Leu Leu Thr Glu Glu Ile Tyr Asn Pro
465                 470                 475                 480
Val Val Ala Lys Ser Val Arg Gln Ala Ile Lys Ile Val Asn Ala Ala
                485                 490                 495
Ile Lys Glu Tyr Gly Asp Phe Asp Asn Ile Val Ile Glu Met Ala Arg
            500                 505                 510
Glu Thr Asn Glu Asp Asp Glu Lys Lys Ala Ile Gln Lys Ile Gln Lys
        515                 520                 525
Ala Asn Lys Asp Glu Lys Asp Ala Ala Met Leu Lys Ala Ala Asn Gln
    530                 535                 540
Tyr Asn Gly Lys Ala Glu Leu Pro His Ser Val Phe His Gly His Lys
545                 550                 555                 560
Gln Leu Ala Thr Lys Ile Arg Leu Trp His Gln Gln Gly Glu Arg Cys
                565                 570                 575
Leu Tyr Thr Gly Lys Thr Ile Ser Ile His Asp Leu Ile Asn Asn Ser
            580                 585                 590
Asn Gln Phe Glu Val Asp His Ile Leu Pro Leu Ser Ile Thr Phe Asp
        595                 600                 605
```

```
Asp Ser Leu Ala Asn Lys Val Leu Val Tyr Ala Thr Ala Asn Gln Glu
610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
            645                 650                 655

Ser Asn Lys Lys Lys Glu Tyr Leu Leu Thr Glu Glu Asp Ile Ser Lys
            660                 665                 670

Phe Asp Val Arg Lys Lys Phe Ile Glu Arg Asn Leu Val Asp Thr Arg
        675                 680                 685

Tyr Ala Ser Arg Val Val Leu Asn Ala Leu Gln Glu His Phe Arg Ala
    690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
                725                 730                 735

His His Ala Val Asp Ala Leu Ile Ile Ala Ala Ser Ser Gln Leu Asn
            740                 745                 750

Leu Trp Lys Lys Gln Lys Asn Thr Leu Val Ser Tyr Ser Glu Asp Gln
        755                 760                 765

Leu Leu Asp Ile Glu Thr Gly Glu Leu Ile Ser Asp Asp Glu Tyr Lys
    770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
                805                 810                 815

Lys Phe Asn Arg Lys Ile Ser Asp Ala Thr Ile Tyr Ala Thr Arg Gln
            820                 825                 830

Ala Lys Val Gly Lys Asp Lys Ala Asp Glu Thr Tyr Val Leu Gly Lys
        835                 840                 845

Ile Lys Asp Ile Tyr Thr Gln Asp Gly Tyr Asp Ala Phe Met Lys Ile
    850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
                885                 890                 895

Gln Ile Asn Glu Lys Gly Lys Glu Val Pro Cys Asn Pro Phe Leu Lys
            900                 905                 910

Tyr Lys Glu Glu His Gly Tyr Ile Arg Lys Tyr Ser Lys Lys Gly Asn
        915                 920                 925

Gly Pro Glu Ile Lys Ser Leu Lys Tyr Tyr Asp Ser Lys Leu Gly Asn
    930                 935                 940

His Ile Asp Ile Thr Pro Lys Asp Ser Asn Asn Lys Val Val Leu Gln
945                 950                 955                 960

Ser Val Ser Pro Trp Arg Ala Asp Val Tyr Phe Asn Lys Thr Thr Gly
                965                 970                 975

Lys Tyr Glu Ile Leu Gly Leu Lys Tyr Ala Asp Leu Gln Phe Glu Lys
            980                 985                 990

Gly Thr Gly Thr Tyr Lys Ile Ser  Gln Glu Lys Tyr Asn  Asp Ile Lys
            995                 1000                1005

Lys Lys  Glu Gly Val Asp Ser  Asp Ser Glu Phe Lys  Phe Thr Leu
    1010                1015                1020

Tyr Lys  Asn Asp Leu Leu Leu  Val Lys Asp Thr Glu  Thr Lys Glu
```

```
                1025                1030                1035

Gln Gln Leu Phe Arg Phe Leu Ser Arg Thr Met Pro Lys Gln Lys
        1040                1045                1050

His Tyr Val Glu Leu Lys Pro Tyr Asp Lys Gln Lys Phe Glu Gly
    1055                1060                1065

Gly Glu Ala Leu Ile Lys Val Leu Gly Asn Val Ala Asn Ser Gly
    1070                1075                1080

Gln Cys Lys Lys Gly Leu Gly Lys Ser Asn Ile Ser Ile Tyr Lys
    1085                1090                1095

Val Arg Thr Asp Val Leu Gly Asn Gln His Ile Ile Lys Asn Glu
    1100                1105                1110

Gly Asp Lys Pro Lys Leu Asp Phe
    1115                1120

<210> SEQ ID NO 2
<211> LENGTH: 1128
<212> TYPE: PRT
<213> ORGANISM: Streptococcus vestibularis ATCC 49124

<400> SEQUENCE: 2

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Val Glu Arg Arg Thr
        35                  40                  45

Asn Arg Gln Gly Arg Arg Leu Thr Arg Arg Lys Lys His Arg Arg Val
    50                  55                  60

Arg Leu Asn His Leu Phe Glu Glu Ser Gly Leu Ile Thr Asp Phe Thr
65                  70                  75                  80

Lys Val Ser Ile Asn Leu Asn Pro Tyr Gln Leu Arg Val Lys Gly Leu
                85                  90                  95

Ile Asp Glu Leu Ser Asn Glu Leu Phe Ile Ala Leu Lys Asn Met
            100                 105                 110

Val Lys His Arg Gly Ile Ser Tyr Leu Asp Asp Ala Ser Asp Asp Gly
        115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Lys Tyr Gly Gln Leu Arg Gly Asp Phe Thr Val Glu Glu Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Lys Glu Phe Asn Pro Gln Ile Thr
        195                 200                 205

Asp Glu Phe Ile Asn Arg Tyr Leu Glu Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Tyr Thr Thr Lys Lys Asp Ser Glu Asn Glu Tyr Ile Thr Leu Asp Asn
                245                 250                 255

Ile Phe Gly Ile Leu Ile Gly Lys Cys Thr Phe Tyr Pro Glu Glu Tyr
            260                 265                 270
```

```
Arg Ala Ala Lys Ala Ser Tyr Thr Ala Gln Glu Phe Asn Leu Leu Asn
            275                 280                 285

Asp Leu Asn Asn Leu Thr Val Pro Thr Glu Thr Lys Lys Leu Ser Glu
    290                 295                 300

Glu Gln Lys Asn Gln Ile Ile Asn Tyr Val Lys Asn Glu Lys Ala Met
305                 310                 315                 320

Gly Pro Ala Lys Leu Phe Lys Tyr Ile Ala Lys Leu Leu Ser Cys Asp
                325                 330                 335

Val Ala Asp Ile Lys Gly Tyr Arg Ile Asp Lys Ser Asp Lys Ala Glu
            340                 345                 350

Ile His Thr Phe Glu Ala Tyr Arg Lys Met Lys Thr Leu Glu Thr Ile
        355                 360                 365

Asp Phe Glu Lys Met Ser Arg Asp Gln Leu Asp Lys Leu Ala Tyr Val
    370                 375                 380

Leu Thr Leu Asn Thr Glu Arg Glu Gly Ile Gln Glu Ala Leu Asp His
385                 390                 395                 400

Glu Phe Ala Asp Gly Asn Phe Ser Gln Glu Gln Ile Asp Glu Leu Val
                405                 410                 415

Gln Phe Arg Lys Ala Asn Ser Ser Ile Phe Gly Lys Gly Trp His Asn
            420                 425                 430

Phe Ser Val Lys Leu Met Met Glu Leu Ile Pro Glu Leu Tyr Ala Thr
        435                 440                 445

Ser Glu Glu Gln Met Thr Ile Leu Thr Arg Leu Gly Lys Gln Lys Thr
    450                 455                 460

Thr Ser Ser Ser Asn Lys Thr Lys Tyr Ile Asp Glu Lys Leu Leu Thr
465                 470                 475                 480

Glu Glu Ile Tyr Asn Pro Val Val Ala Lys Ser Val Arg Gln Ala Ile
                485                 490                 495

Lys Ile Val Asn Ala Ala Ile Lys Glu Tyr Gly Asp Phe Asp Asn Ile
            500                 505                 510

Val Ile Glu Met Ala Arg Glu Thr Asn Glu Asp Asp Glu Lys Lys Ala
        515                 520                 525

Ile Gln Lys Ile Gln Lys Ala Asn Lys Asp Glu Lys Asp Ala Ala Met
    530                 535                 540

Leu Lys Ala Ala Asn Gln Tyr Asn Gly Arg Ala Glu Leu Pro His Ser
545                 550                 555                 560

Val Phe His Gly His Lys Gln Leu Ala Thr Lys Ile Arg Leu Trp His
                565                 570                 575

Gln Gln Gly Glu Arg Cys Leu Tyr Thr Gly Lys Thr Ile Ser Ile His
            580                 585                 590

Asp Leu Ile Asn Asn Pro Asn Gln Phe Glu Ile Asp His Ile Leu Pro
        595                 600                 605

Leu Ser Ile Thr Phe Asp Asp Ser Leu Ala Asn Lys Val Leu Val Tyr
    610                 615                 620

Ala Thr Ala Asn Gln Glu Lys Gly Gln Arg Thr Pro Tyr Gln Ala Leu
625                 630                 635                 640

Asp Ser Met Asp Asp Ala Trp Ser Phe Arg Glu Leu Lys Ala Phe Val
                645                 650                 655

Arg Glu Ser Lys Ser Leu Ser Asn Lys Lys Lys Glu Tyr Leu Leu Thr
            660                 665                 670

Glu Glu Asp Ile Ser Arg Phe Asp Val Arg Lys Lys Phe Ile Glu Arg
        675                 680                 685

Asn Leu Val Asp Thr Arg Tyr Ala Ser Arg Val Val Leu Asn Ala Leu
```

```
            690              695             700
    Gln Glu His Phe Arg Ala His Lys Thr Asp Thr Lys Val Ser Val Val
    705                 710             715                 720
    Arg Gly Gln Phe Thr Ser Gln Leu Arg Arg His Trp Gly Ile Glu Lys
                        725             730                 735
    Thr Arg Asp Thr Tyr His His His Ala Val Asp Ala Leu Ile Ile Ala
                    740             745                 750
    Ala Ser Ser Gln Leu Asn Leu Trp Lys Lys Gln Lys Asn Thr Leu Val
                755             760                 765
    Asn Tyr Ser Glu Asn Gln Leu Leu Asp Ile Glu Thr Gly Glu Leu Ile
            770             775                 780
    Ser Asp Asp Glu Tyr Lys Glu Ser Val Phe Lys Ala Pro Tyr Gln His
    785                 790             795                 800
    Phe Val Asp Thr Leu Lys Ser Lys Glu Phe Glu Asp Ser Ile Leu Phe
                        805             810                  815
    Ser Tyr Gln Val Asp Ser Lys Phe Asn Arg Lys Ile Ser Asp Ala Thr
                    820             825                 830
    Ile Tyr Ala Thr Arg Gln Ala Lys Val Gly Lys Asp Lys Lys Asp Glu
                835             840                 845
    Thr Tyr Val Leu Gly Lys Ile Lys Asp Ile Tyr Ser Gln Thr Gly Tyr
            850             855                 860
    Asp Ala Phe Ile Lys Ile Tyr Gln Lys Asp Lys Ser Lys Phe Leu Met
    865                 870             875                 880
    Tyr Arg His Asp Pro Gln Thr Phe Glu Lys Val Ile Glu Pro Ile Leu
                        885             890                 895
    Glu Asn Tyr Pro Asn Lys Glu Met Asn Glu Lys Gly Lys Glu Val Pro
                    900             905                 910
    Cys Asn Pro Phe Leu Lys Tyr Lys Glu His Gly Asp Tyr Ile Arg
                915             920             925
    Lys Tyr Ser Lys Lys Gly Asn Gly Pro Glu Ile Lys Ser Leu Lys Tyr
            930             935                 940
    Tyr Asp Ser Lys Leu Gly Asn His Ile Asp Ile Thr Pro Lys Asp Ser
    945                 950             955                 960
    Asn Asn Lys Val Val Leu Gln Ser Val Ser Pro Trp Arg Ala Asp Val
                        965             970                 975
    Tyr Phe Asn Lys Thr Thr Gly Lys Tyr Glu Ile Leu Gly Leu Lys Tyr
                    980             985                 990
    Ala Asp Leu Gln Phe Glu Lys Gly  Thr Gly Thr Tyr Lys Ile Ser Gln
                995              1000            1005
    Glu Lys  Tyr Asn Val Ile Lys  Lys Lys Glu Gly Val  Asp Ser Asp
        1010             1015             1020
    Ser Glu Phe Lys Phe Thr Leu  Tyr Lys Asn Asp Leu  Leu Leu Ile
        1025            1030             1035
    Lys Asp  Thr Glu Thr Lys Glu  Gln Gln Leu Phe Arg  Phe Leu Ser
        1040            1045              1050
    Arg Thr Lys Pro Asn Val Lys  His Tyr Val Glu Leu  Lys Pro Tyr
        1055            1060             1065
    Asp Lys  Gln Lys Phe Glu Gly  Asn Glu Ser Leu Ile  Asn Val Leu
        1070            1075             1080
    Gly Ala  Val Ala Lys Gly Gly  Gln Cys Gln Lys Gly  Ile Asn Lys
        1085            1090             1095
    Pro Asn  Ile Ser Ile Tyr Lys  Val Arg Thr Asp Val  Leu Gly Asn
        1100            1105             1110
```

```
Gln His Ile Ile Lys Asn Glu Gly Asp Lys Pro Lys Leu Asp Phe
    1115                1120                1125

<210> SEQ ID NO 3
<211> LENGTH: 1128
<212> TYPE: PRT
<213> ORGANISM: Streptococcus mutans NLML5

<400> SEQUENCE: 3

Met Ala Asn Ser Lys Ile Leu Gly Leu Asp Ile Gly Ile Ala Ser Val
 1               5                  10                  15

Gly Val Gly Ile Ile Asp Lys Glu Thr Gly Lys Ile Ile His Val Asn
            20                  25                  30

Ser Arg Ile Phe Pro Ala Ala Thr Ala Asp Ser Asn Val Glu Arg Arg
        35                  40                  45

Gly Phe Arg Gln Gly Arg Arg Leu Val Arg Arg Lys His Arg Lys
    50                  55                  60

Val Arg Leu Ala Asp Leu Phe Leu Asp Ser Asn Leu Leu Thr Asp Phe
65                  70                  75                  80

Ser Lys Val Ser Leu Asn Leu Asn Pro Tyr Gln Leu Arg Val Lys Gly
                85                  90                  95

Leu Asn Glu Glu Leu Ser Asn Glu Glu Leu Phe Ile Ala Leu Lys Ser
            100                 105                 110

Ile Val Ser Arg Arg Gly Ile Ser Tyr Leu Asp Asp Ala Ser Glu Asp
        115                 120                 125

Ser Gly Ala Asn Ser Ser Glu Tyr Gly Lys Ala Val Glu Glu Asn Arg
    130                 135                 140

Lys Leu Leu Glu Asp Arg Thr Pro Gly Gln Ile Gln Leu Glu Arg Phe
145                 150                 155                 160

Glu Lys Tyr Gly Lys Val Arg Gly Asp Phe Thr Val Val Glu Asn Gly
                165                 170                 175

Glu Asn His Arg Leu Ile Asn Val Phe Ser Thr Ser Ala Tyr Lys Lys
            180                 185                 190

Glu Ala Glu Arg Ile Leu Arg Arg Gln Gln Glu Phe Asn Ile Arg Ile
        195                 200                 205

Ala Asp Glu Phe Ile Glu Ala Tyr Leu Thr Ile Leu Thr Gly Lys Arg
    210                 215                 220

Lys Tyr Tyr His Gly Pro Gly Asn Glu Lys Ser Arg Thr Asp Tyr Gly
225                 230                 235                 240

Arg Phe Arg Thr Asp Gly Thr Thr Leu Asp Asn Ile Phe Gly Ile Leu
                245                 250                 255

Ile Gly Lys Cys Thr Phe Tyr Pro Asp Glu Tyr Arg Ala Ala Lys Ala
            260                 265                 270

Ser Tyr Thr Ala Gln Glu Phe Asn Leu Leu Asn Asp Leu Asn Asn Leu
        275                 280                 285

Thr Val Pro Thr Glu Thr Lys Lys Leu Ser Glu Gln Lys Arg Gln
    290                 295                 300

Ile Ile Glu His Ala Lys Thr Val Lys Thr Leu Gly Ala Pro Thr Leu
305                 310                 315                 320

Leu Lys Tyr Ile Ala Lys Leu Val Gly Cys Ser Ala Asp Asp Ile Lys
                325                 330                 335

Gly Tyr Arg Ile Asp Lys Ser Asp Lys Pro Glu Ile His Thr Phe Glu
            340                 345                 350

Ala Tyr Arg Lys Met Arg Thr Met Glu Leu Ile Lys Val Ala Asp Leu
```

```
                355                 360                 365
Ser Arg Glu Ser Leu Asp Ala Leu Ala His Ile Leu Thr Leu Asn Thr
370                 375                 380

Glu Arg Glu Gly Ile Glu Glu Ala Ile Arg Asp Arg Phe Thr Asn Lys
385                 390                 395                 400

Glu Phe Asn Gln Glu Gln Ile Asn Glu Leu Val Leu Phe Arg Lys Asn
                405                 410                 415

Asn Ser Ser Leu Phe Gly Lys Gly Trp His Asn Phe Ser Leu Lys Leu
            420                 425                 430

Met Lys Glu Leu Ile Pro Glu Leu Tyr Glu Thr Ser Glu Glu Gln Met
            435                 440                 445

Thr Ile Leu Thr Arg Leu Gly Lys Gln Arg Val Lys Lys Ser Ser Asn
            450                 455                 460

Arg Thr Asn Tyr Ile Asp Glu Lys Glu Leu Thr Glu Glu Ile Tyr Asn
465                 470                 475                 480

Pro Val Val Ala Lys Ser Val Arg Gln Ala Ile Lys Ile Ile Asn Leu
                485                 490                 495

Ala Thr Lys Lys Tyr Gly Val Phe Asp Asn Ile Val Ile Glu Met Ala
            500                 505                 510

Arg Glu Ser Asn Glu Asp Asp Glu Lys Lys Ala Ile Gln Asn Ala Gln
            515                 520                 525

Lys Ala Asn Glu Asp Glu Lys Glu Ala Ala Leu Leu Lys Ala Ala His
530                 535                 540

Gln Phe Asn Gly Lys Glu Glu Leu Pro Asp Ser Ile Phe His Gly His
545                 550                 555                 560

Lys Glu Leu Leu Thr Lys Ile Arg Leu Trp His Gln Gln Gly Glu Lys
                565                 570                 575

Cys Leu Tyr Thr Gly Lys Thr Ile Phe Ile Asn Asp Leu Ile His Asn
            580                 585                 590

Pro Tyr Lys Tyr Glu Ile Asp His Ile Leu Pro Leu Ser Leu Ser Phe
            595                 600                 605

Asp Asp Ser Leu Ala Asn Lys Val Leu Val Leu Ser Thr Ala Asn Gln
            610                 615                 620

Glu Lys Gly Gln Arg Thr Pro Phe Gln Ser Leu Asp Ser Met Asp Gly
625                 630                 635                 640

Ala Trp Thr Tyr Arg Glu Phe Lys Ala Tyr Val Lys Gly Leu Lys Thr
                645                 650                 655

Leu Ser Asn Lys Lys Asp Tyr Leu Leu Asn Glu Glu Asp Ile Asn
            660                 665                 670

Lys Asn Glu Val Lys Gln Lys Phe Ile Glu Arg Asn Leu Val Asp Thr
            675                 680                 685

Arg Tyr Ser Ser Arg Val Val Leu Asn Thr Leu Gln Asp Phe Tyr Lys
            690                 695                 700

Lys Arg Glu Phe Asp Thr Lys Ile Ser Val Val Arg Gly Gln Phe Thr
705                 710                 715                 720

Ser Gln Ile Arg Arg Lys Trp Arg Ile Glu Lys Thr Arg Glu Thr Tyr
                725                 730                 735

His His His Ala Val Asp Ala Leu Ile Ile Ala Ala Ser Ser Gln Leu
            740                 745                 750

Asn Leu Trp Lys Lys Gln Asn Asn Pro Leu Ile Ser Tyr Lys Glu Asp
            755                 760                 765

Gln Phe Val Asp Pro Glu Thr Gly Glu Ile Leu Ser Leu Ser Asp Asp
770                 775                 780
```

Glu Tyr Lys Glu Leu Val Phe Lys Ala Pro Tyr Asp His Phe Val Asp
785                 790                 795                 800

Thr Leu Lys Ser Lys Lys Phe Glu Asp Ser Ile Leu Phe Ser Tyr Gln
                805                 810                 815

Val Asp Ser Lys Tyr Asn Arg Lys Ile Ser Asp Ala Thr Ile Tyr Gly
            820                 825                 830

Thr Arg Lys Ala Arg Leu Gly Lys Asp Ser Gln Glu Glu Thr Tyr Val
        835                 840                 845

Leu Gly Lys Ile Lys Asp Ile Tyr Ser Gln Lys Gly Tyr Glu Asp Phe
    850                 855                 860

Ile Lys Lys Tyr Lys Lys Asp Lys Thr Gln Phe Leu Met Tyr His Lys
865                 870                 875                 880

Asp Pro Gln Thr Phe Glu Lys Val Ile Glu Ile Leu Lys Thr Tyr
                885                 890                 895

Ser Asp Lys Glu Leu Asn Glu Lys Gly Lys Glu Val Pro Cys Asn Pro
            900                 905                 910

Phe Glu Lys Tyr Arg Gln Glu Asn Gly Pro Val Arg Lys Tyr Ser Lys
        915                 920                 925

Lys Gly Asn Gly Pro Glu Ile Lys Ser Ile Lys Tyr Tyr Asp Asn Lys
    930                 935                 940

Leu Gly Asn His Ile Asp Ile Thr Pro Asn Asn Ser His His Gln Val
945                 950                 955                 960

Val Leu Gln Ser Leu Lys Pro Trp Arg Thr Asp Val Tyr Phe Asn Pro
                965                 970                 975

Lys Ser Gly Lys Tyr Glu Leu Met Gly Leu Lys Tyr Ser Asp Leu Arg
            980                 985                 990

Phe Glu Lys Val Ser Gly Asp Tyr Gly Ile Ser Val Lys Lys Tyr Asn
        995                 1000                1005

Glu Ile Lys Ser Lys Glu Gly Val Asp Glu Asn Ser Glu Phe Lys
    1010                1015                1020

Phe Thr Leu Tyr Lys Asn Asp Leu Ile Leu Ile Lys Asp Thr Glu
    1025                1030                1035

Ser Gly Glu Gln Glu Leu Phe Arg Phe Leu Ser Arg Thr Met Pro
    1040                1045                1050

Asn Gln Lys His Tyr Val Glu Leu Lys Pro Tyr Asp Lys Ser Lys
    1055                1060                1065

Phe Glu Gly His Gln Lys Leu Met Asp Ile Phe Gly Glu Val Ala
    1070                1075                1080

Lys Gly Gly Gln Cys Leu Lys Gly Leu Asn Lys Ser Asn Ile Ser
    1085                1090                1095

Ile Tyr Lys Val Lys Thr Asp Val Leu Gly Asn Lys Tyr Phe Ile
    1100                1105                1110

Lys Lys Glu Gly Asp Gln Pro Gln Leu Asn Phe Lys Lys Ile
    1115                1120                1125

<210> SEQ ID NO 4
<211> LENGTH: 1125
<212> TYPE: PRT
<213> ORGANISM: Streptococcus anginosus 1 2 62CV

<400> SEQUENCE: 4

Met Asn Gly Leu Val Leu Gly Leu Asp Ile Gly Ile Ala Ser Val Gly
1               5                   10                  15

Val Gly Ile Leu Asn Lys Glu Thr Gly Glu Ile Ile His Ala Asn Ser

```
            20                  25                  30
Arg Ile Phe Pro Ala Ala Thr Ala Asp Ser Asn Val Glu Arg Arg Gly
            35                  40                  45
Phe Arg Gln Gly Arg Arg Leu Gly Arg Lys Lys His Arg Ser Ala
 50                  55                  60
Arg Leu Asn Asn Leu Phe Glu Glu Phe Gly Phe Ile Thr Asp Phe Ser
 65                  70                  75                  80
Ala Ile Pro Leu Asn Leu Asn Pro Tyr Ala Leu Arg Val Lys Gly Leu
                    85                  90                  95
Ser Glu Glu Leu Thr Asn Glu Glu Leu Phe Ile Ala Leu Lys Asn Ile
                    100                 105                 110
Ile Lys Arg Arg Gly Ile Ser Tyr Leu Asp Asp Ala Ser Glu Asp Gly
                    115                 120                 125
Glu Thr Ala Ser Asn Glu Tyr Gly Lys Ala Val Glu Glu Asn Arg Lys
                    130                 135                 140
Leu Leu Ala Asp Lys Thr Pro Gly Gln Ile Gln Leu Glu Arg Phe Glu
 145                 150                 155                 160
Lys Tyr Gly Gln Val Arg Gly Asp Phe Thr Val Val Glu Asn Gly Glu
                    165                 170                 175
Asn His Arg Leu Ile Asn Val Phe Ser Thr Ser Ala Tyr Lys Lys Glu
                    180                 185                 190
Ala Glu Arg Ile Leu Arg Arg Gln Gln Glu Phe Asn Val Arg Ile Ser
                    195                 200                 205
Asp Glu Phe Ile Glu Ala Tyr Leu Thr Ile Leu Thr Gly Lys Arg Lys
                    210                 215                 220
Tyr Tyr His Gly Pro Gly Asn Glu Lys Ser Arg Thr Asp Tyr Gly Arg
 225                 230                 235                 240
Phe Arg Thr Asp Gly Thr Thr Leu Asp Asn Ile Phe Gly Ile Leu Ile
                    245                 250                 255
Gly Lys Cys Thr Phe Tyr Pro Asp Glu Tyr Arg Ala Ala Lys Ala Ser
                    260                 265                 270
Tyr Thr Ala Gln Glu Phe Asn Leu Leu Asn Asp Leu Asn Asn Leu Thr
                    275                 280                 285
Val Pro Thr Glu Thr Lys Lys Leu Ser Pro Glu Gln Lys Arg Gln Ile
                    290                 295                 300
Val Glu Tyr Ala Arg Thr Ala Lys Thr Leu Gly Thr Pro Thr Leu Leu
 305                 310                 315                 320
Lys Tyr Ile Ala Lys Leu Val Asp Gly Ser Ile Asp Asp Ile Lys Gly
                    325                 330                 335
Tyr Arg Ile Asp Lys Ser Asp Lys Pro Glu Met His Thr Phe Asp Ala
                    340                 345                 350
Tyr Arg Lys Met Arg Thr Leu Asp Leu Val Asn Ile Asp Ala Leu Ser
                    355                 360                 365
Arg Glu Thr Leu Asp Asp Leu Ala His Ile Leu Thr Leu Asn Thr Glu
                    370                 375                 380
Ser Glu Gly Ile Leu Glu Ala Leu Asn Ser Lys Met Pro Ser Thr Phe
 385                 390                 395                 400
Thr Lys Glu Gln Ile Asp Glu Leu Ile Gln Phe Arg Lys Lys Asn Ser
                    405                 410                 415
Ala Val Phe Gly Lys Gly Trp His Asn Phe Ser Leu Lys Leu Met Asn
                    420                 425                 430
Glu Leu Ile Ser Glu Leu Tyr Glu Thr Ser Glu Glu Gln Met Thr Ile
                    435                 440                 445
```

```
Leu Thr Arg Leu Gly Lys Gln Arg Ser Arg Glu Ile Ser Lys Arg Thr
    450                 455                 460
Lys Tyr Ile Asp Glu Lys Glu Leu Thr Glu Glu Ile Tyr Asn Pro Val
465                 470                 475                 480
Val Ala Lys Ser Val Arg Gln Ala Ile Lys Ile Ile Asn Glu Ala Thr
                485                 490                 495
Lys Arg Tyr Gly Ile Phe Asp Asn Ile Val Ile Glu Met Ala Arg Glu
                500                 505                 510
Asn Asn Glu Glu Asp Ala Lys Lys Asp Tyr Ile Lys Arg Gln Lys Ala
            515                 520                 525
Asn Gln Asp Glu Lys Asn Ala Ser Met Glu Lys Ala Ala Phe Gln Tyr
        530                 535                 540
Asn Gly Lys Lys Glu Leu Pro Asp Ser Ile Phe His Gly His Lys Glu
545                 550                 555                 560
Leu Ala Thr Lys Ile Arg Leu Trp His Gln Gln Gly Glu Arg Cys Leu
                565                 570                 575
Tyr Thr Gly Lys Asn Ile Ser Ile Arg Asp Leu Ile His Asn Pro His
                580                 585                 590
Gln Tyr Glu Ile Asp His Ile Leu Pro Leu Ser Leu Ser Phe Asp Asp
        595                 600                 605
Gly Leu Ala Asn Lys Val Leu Val Leu Ala Thr Ala Asn Gln Glu Lys
610                 615                 620
Gly Gln Arg Thr Pro Phe Gln Ala Ile Asp Ser Met Asp Asp Ala Trp
625                 630                 635                 640
Ser Tyr Arg Glu Phe Lys Gln Tyr Val Arg Asn Ser Lys Ser Leu Ser
                645                 650                 655
Asn Lys Lys Lys Asp Tyr Leu Leu Thr Glu Glu Asp Ile Ser Lys Ile
                660                 665                 670
Glu Val Lys Gln Lys Phe Ile Glu Arg Asn Leu Val Asp Thr Arg Tyr
            675                 680                 685
Ser Ser Arg Val Val Leu Asn Thr Leu Gln Glu Phe Tyr Lys Thr Asn
    690                 695                 700
Asp Phe Asp Thr Lys Ile Ser Val Val Arg Gly Gln Phe Thr Ser Gln
705                 710                 715                 720
Leu Arg Arg Lys Trp Lys Ile Glu Lys Ser Arg Asp Thr Tyr His His
                725                 730                 735
His Ala Val Asp Ala Leu Ile Ile Ala Ala Ser Ser Gln Leu Arg Leu
                740                 745                 750
Trp Lys Lys Gln Asn Asn Pro Leu Ile Ser Tyr Lys Glu Gly Gln Phe
            755                 760                 765
Val Asp Pro Glu Thr Gly Glu Ile Leu Ser Leu Thr Asp Asp Glu Tyr
        770                 775                 780
Lys Glu Leu Val Phe Arg Pro Pro Tyr Asp Tyr Phe Val Asp Thr Leu
785                 790                 795                 800
Lys Ser Lys Ser Phe Glu Asp Ser Ile Leu Phe Ser Tyr Gln Val Asp
                805                 810                 815
Ser Lys Tyr Asn Arg Lys Ile Ser Asp Ala Thr Ile Tyr Gly Thr Arg
                820                 825                 830
Lys Ala Gln Leu Gly Lys Asp Lys Gln Glu Glu Thr Tyr Val Leu Gly
            835                 840                 845
Lys Ile Lys Asp Ile Tyr Ser Gln Lys Gly Tyr Glu Asp Phe Ile Lys
    850                 855                 860
```

```
Arg Tyr Asn Lys Asp Glu Thr Gln Phe Leu Ile Tyr His Lys Asp Pro
865                 870                 875                 880

Gln Thr Phe Glu Lys Val Ile Glu Glu Ile Leu Lys Thr Tyr Pro Asp
            885                 890                 895

Lys Glu Leu Asn Glu Lys Gly Lys Glu Ile Pro Cys Asn Pro Phe Glu
            900                 905                 910

Lys Tyr Arg Gln Glu Asn Gly Pro Ile Arg Lys Tyr Ser Lys Lys Gly
            915                 920                 925

Lys Gly Pro Glu Ile Lys Ser Leu Lys Tyr Tyr Asp Asn Lys Leu Gly
            930                 935                 940

Asn His Ile Asp Ile Thr Pro Val Asn Ser Gln Asn Gln Val Val Leu
945                 950                 955                 960

Gln Ser Leu Lys Pro Trp Arg Thr Asp Val Tyr Phe Asn Pro Arg Thr
            965                 970                 975

Ser Lys Tyr Glu Leu Met Gly Leu Lys Tyr Ser Asp Leu Arg Phe Glu
            980                 985                 990

Lys Gly Ser Gly Ser Tyr Gly Ile Ser Pro Glu Lys Tyr Asn Lys Val
            995                 1000                1005

Lys Ala Lys Glu Gly Val Asn Glu Asp Ser Glu Phe Lys Phe Thr
    1010                1015                1020

Leu Tyr Lys Asn Asp Leu Ile Leu Ile Lys Asp Thr Glu Thr Gly
    1025                1030                1035

Glu Gln Gln Leu Phe Arg Tyr Gly Ser Arg Asn Asp Thr Ser Lys
    1040                1045                1050

His Tyr Val Glu Leu Lys Pro Tyr Glu Lys Ala Lys Phe Glu Gly
    1055                1060                1065

Asn Gln Gln Leu Met Asn Leu Leu Gly Thr Val Ala Lys Gly Gly
    1070                1075                1080

Gln Cys Leu Lys Gly Ile Asn Lys Pro Asn Leu Ser Ile Tyr Lys
    1085                1090                1095

Val Lys Thr Asp Val Leu Gly Asn Lys Tyr Phe Ile Lys Lys Glu
    1100                1105                1110

Gly Asp Gln Pro Gln Leu Asn Phe Lys Lys Lys Phe
    1115                1120                1125

<210> SEQ ID NO 5
<211> LENGTH: 1136
<212> TYPE: PRT
<213> ORGANISM: Streptococcus gordonii str. Challis substr. CH1

<400> SEQUENCE: 5

Met Asn Gly Leu Val Leu Gly Leu Asp Ile Gly Ile Ala Ser Val Gly
1               5                   10                  15

Val Gly Ile Leu Glu Lys Asp Thr Gly Lys Ile Ile His Ala Ser Ser
            20                  25                  30

Arg Leu Phe Pro Ala Ala Thr Ala Asp Asn Asn Val Glu Arg Arg Ser
            35                  40                  45

Asn Arg Gln Gly Arg Arg Leu Asn Arg Arg Lys His Arg Ser Val
            50                  55                  60

Arg Leu Gln Asp Leu Phe Glu Gly Tyr Gly Leu Leu Thr Asp Phe Ser
65                  70                  75                  80

Lys Val Ser Met Asn Leu Asn Pro Tyr Gln Leu Arg Val Gln Gly Met
                85                  90                  95

Glu Asn Gln Leu Thr Asn Glu Glu Leu Phe Val Ala Leu Lys Asn Ile
                100                 105                 110
```

```
Val Lys Arg Arg Gly Ile Ser Tyr Leu Asp Asp Ala Ser Glu Asp Gly
            115                 120                 125

Gly Thr Val Ser Ser Asp Tyr Gly Lys Ala Val Glu Glu Asn Arg Lys
        130                 135                 140

Leu Leu Ala Glu Lys Thr Pro Gly Gln Ile Gln Leu Glu Arg Phe Glu
145                 150                 155                 160

Lys Tyr Gly Gln Leu Arg Gly Asp Phe Thr Val Glu Glu Asn Gly Glu
                165                 170                 175

Lys His Arg Leu Ile Asn Val Phe Ser Thr Ala Tyr Arg Lys Glu
            180                 185                 190

Ala Glu Arg Ile Leu Arg Lys Gln Gln Glu Phe Asn Ser Lys Ile Thr
        195                 200                 205

Asp Glu Phe Ile Glu Asp Tyr Leu Ile Ile Leu Thr Gly Lys Arg Lys
210                 215                 220

Tyr Tyr His Gly Pro Gly Asn Glu Lys Ser Arg Thr Asp Tyr Gly Arg
225                 230                 235                 240

Phe Arg Thr Asp Gly Thr Thr Leu Asp Asn Ile Phe Gly Ile Leu Ile
                245                 250                 255

Gly Lys Cys Thr Phe Tyr Thr Glu Glu Tyr Arg Ala Ser Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Glu Glu Gln Lys Lys Leu Ile
290                 295                 300

Ile Glu Tyr Ala Lys Ser Ala Lys Thr Leu Gly Ala Ser Thr Leu Leu
305                 310                 315                 320

Lys Tyr Ile Ala Lys Met Ile Asp Ala Ser Val Asp Gln Ile Arg Gly
                325                 330                 335

Tyr Arg Val Asp Val Asn Asn Lys Pro Glu Met His Thr Phe Glu Val
            340                 345                 350

Tyr Arg Lys Met Gln Ser Leu Glu Thr Ile Lys Val Glu Glu Leu Pro
        355                 360                 365

Arg Lys Val Leu Asp Glu Leu Ala His Ile Leu Thr Leu Asn Thr Glu
370                 375                 380

Arg Glu Gly Ile Glu Glu Ala Ile Asn Ser Lys Leu Lys Asp Ile Phe
385                 390                 395                 400

Asn Arg Asp Gln Val Leu Glu Leu Val Gln Phe Arg Lys Asn Asn Ser
                405                 410                 415

Ser Leu Phe Ser Lys Gly Trp His Asn Phe Ser Ile Lys Leu Met Met
            420                 425                 430

Glu Leu Ile Pro Glu Leu Tyr Glu Thr Ser Glu Glu Gln Met Thr Ile
        435                 440                 445

Leu Thr Arg Leu Gly Lys Gln Arg Ser Lys Glu Thr Ser Lys Arg Thr
450                 455                 460

Lys Tyr Ile Asp Glu Lys Leu Thr Glu Glu Ile Tyr Asn Pro Val
465                 470                 475                 480

Val Ala Lys Ser Val Arg Gln Ala Ile Lys Ile Asn Glu Ala Thr
                485                 490                 495

Lys Lys Tyr Gly Ile Phe Asp Asn Ile Val Ile Glu Met Ala Arg Glu
            500                 505                 510

Asn Asn Glu Glu Asp Ala Lys Lys Asp Tyr Ile Lys Arg Gln Lys Ala
        515                 520                 525
```

-continued

```
Asn Gln Asp Glu Lys Asn Ala Ala Met Glu Lys Ala Ala Phe Gln Tyr
    530                 535                 540
Asn Gly Lys Lys Glu Leu Pro Asp Asn Ile Phe His Gly His Lys Glu
545                 550                 555                 560
Leu Thr Thr Lys Ile Arg Leu Trp His Gln Gln Gly Glu Lys Cys Leu
                565                 570                 575
Tyr Thr Gly Lys Asn Ile Pro Ile Ser Asp Leu Ile His Asn Gln Tyr
            580                 585                 590
Lys Tyr Glu Ile Asp His Ile Leu Pro Leu Ser Leu Ser Phe Asp Asp
        595                 600                 605
Ser Leu Ser Asn Lys Val Leu Val Leu Ala Thr Ala Asn Gln Glu Lys
    610                 615                 620
Gly Gln Arg Thr Pro Phe Gln Ala Leu Asp Ser Met Asp Asp Ala Trp
625                 630                 635                 640
Ser Tyr Arg Glu Phe Lys Ser Tyr Val Lys Asp Ser Lys Leu Leu Ser
                645                 650                 655
Asn Lys Lys Lys Asp Tyr Leu Leu Thr Glu Glu Asp Ile Ser Lys Ile
            660                 665                 670
Glu Val Lys Gln Lys Phe Ile Glu Arg Asn Leu Val Asp Thr Arg Tyr
        675                 680                 685
Ser Ser Arg Val Val Leu Asn Ala Leu Gln Asp Phe Tyr Lys Ser His
    690                 695                 700
Gln Leu Asp Thr Thr Ile Ser Val Val Arg Gly Gln Phe Thr Ser Gln
705                 710                 715                 720
Leu Arg Arg Lys Trp Gly Ile Glu Lys Ser Arg Glu Thr Tyr His His
                725                 730                 735
His Ala Val Asp Ala Leu Ile Ile Ala Ala Ser Ser Gln Leu Arg Leu
            740                 745                 750
Trp Lys Lys His Ser Asn Pro Leu Ile Ala Tyr Lys Glu Gly Gln Phe
        755                 760                 765
Val Asp Ser Glu Thr Gly Glu Ile Val Ser Leu Ser Asp Glu Glu Tyr
    770                 775                 780
Lys Glu Leu Val Phe Lys Ala Pro Tyr Asp His Phe Val Asp Thr Leu
785                 790                 795                 800
Arg Ser Lys Lys Phe Glu Asp Ser Ile Leu Phe Ser Tyr Gln Val Asp
                805                 810                 815
Ser Lys Tyr Asn Arg Lys Ile Ser Asp Ala Thr Ile Tyr Ala Thr Arg
            820                 825                 830
Lys Ala Lys Leu Asp Lys Glu Lys Lys Glu Tyr Thr Tyr Thr Leu Gly
        835                 840                 845
Lys Ile Lys Asp Ile Tyr Ala Leu Gly Thr Lys Thr Pro Ser Lys Thr
    850                 855                 860
Gly Phe Tyr Lys Phe Leu Asp Leu Tyr Lys Thr Asp Lys Ser Gln Phe
865                 870                 875                 880
Leu Met Tyr Gln Lys Asp Arg Lys Thr Trp Asp Glu Val Ile Glu Lys
                885                 890                 895
Ile Ile Glu Gln Tyr Arg Pro Phe Lys Glu Tyr Asp Lys Asn Gly Lys
            900                 905                 910
Glu Val Asp Phe Asn Pro Phe Glu Lys Tyr Arg Ile Gly Asn Gly Pro
        915                 920                 925
Ile Arg Lys Tyr Ser Lys Gly Asn Gly Pro Glu Ile Lys Ser Leu
    930                 935                 940
Lys Tyr Tyr Asp Ile Leu Leu Gly Lys His Lys Asn Ile Thr Pro Asp
```

945                 950                 955                 960
Gly Ser Arg Asn Thr Val Ala Leu Leu Ser Leu Asn Pro Trp Arg Thr
                        965                 970                 975
Asp Val Tyr Tyr Asn Ser Glu Thr Lys Lys Tyr Glu Phe Leu Gly Leu
                980                 985                 990
Lys Tyr Ala Asp Leu Cys Phe Glu Glu Gly Gly Ala Tyr Gly Ile Ser
                995                 1000                1005
Glu Val Lys Tyr Lys Lys Ile Arg Glu Lys Glu Gly Ile Gly Lys
    1010                1015                1020
Asn Ser Glu Phe Lys Phe Thr Leu Tyr Lys Asn Asp Leu Ile Leu
    1025                1030                1035
Ile Lys Asp Thr Glu Thr Asn Cys Gln Gln Phe Phe Arg Phe Trp
    1040                1045                1050
Ser Arg Thr Gly Lys Asp Asn Pro Lys Ser Phe Glu Lys His Lys
    1055                1060                1065
Ile Glu Leu Lys Pro Tyr Glu Lys Ala Lys Phe Glu Lys Gly Glu
    1070                1075                1080
Glu Leu Lys Val Leu Gly Lys Val Pro Pro Ser Ser Asn Gln Phe
    1085                1090                1095
Gln Lys Asn Met Gln Ile Glu Asn Leu Ser Ile Tyr Lys Val Lys
    1100                1105                1110
Thr Asp Ile Leu Gly Asn Lys His Phe Ile Lys Lys Glu Gly Asp
    1115                1120                1125
Glu Pro Lys Leu Lys Phe Lys Lys
    1130                1135

<210> SEQ ID NO 6
<211> LENGTH: 1140
<212> TYPE: PRT
<213> ORGANISM: Streptococcus parasanguinis F0449

<400> SEQUENCE: 6

Met Asn Gly Leu Val Leu Gly Leu Asp Ile Gly Ile Ala Ser Val Gly
1               5                   10                  15

Val Gly Ile Leu Lys Lys Asp Ile Gly Glu Ile Ile His Thr Asn Ser
            20                  25                  30

Arg Leu Phe Ser Ala Ala Thr Ala Asp Ser Asn Ile Glu Arg Arg Gly
        35                  40                  45

His Arg Gly Gly Lys Arg Leu Thr Arg Arg Lys His Arg Ser Ile
    50                  55                  60

Arg Leu His Asp Leu Phe Glu Asp Phe Gly Leu Leu Thr Asp Phe Ser
65                  70                  75                  80

Lys Val Ser Ile Asn Leu Asn Pro Tyr Gln Leu Arg Val Gln Gly Leu
                85                  90                  95

Asp Asn Gln Leu Thr Asn Glu Glu Leu Phe Ile Ala Leu Lys Asn Ile
            100                 105                 110

Val Lys Arg Arg Gly Ile Ser Tyr Leu Asp Asp Ala Ser Glu Asp Gly
        115                 120                 125

Gly Thr Val Ser Ser Asp Tyr Gly Lys Ala Val Glu Glu Asn Arg Lys
    130                 135                 140

Leu Leu Ala Glu Gln Thr Pro Gly Gln Ile Gln Leu Asp Arg Phe Glu
145                 150                 155                 160

Lys Tyr Gly Gln Val Arg Gly Asp Phe Asn Val Val Glu Asn Gly Glu
                165                 170                 175

```
Lys Arg Arg Leu Ile Asn Val Phe Thr Thr Ser Ala Tyr Ser Lys Glu
                180                 185                 190

Ala Glu Arg Ile Leu Arg Lys Gln Gln Glu Phe Asn Lys Lys Ile Thr
            195                 200                 205

Asp Glu Phe Ile Glu Asp Tyr Leu Thr Ile Leu Thr Gly Lys Arg Lys
        210                 215                 220

Tyr Tyr His Gly Pro Gly Asn Glu Lys Ser Arg Thr Asp Tyr Gly Arg
225                 230                 235                 240

Tyr Thr Thr Lys Lys Asp Pro Glu Gly Lys Tyr Ile Thr Leu Asp Asn
                245                 250                 255

Ile Phe Gly Ile Leu Ile Gly Lys Cys Thr Phe Tyr Pro Asp Glu Tyr
                260                 265                 270

Arg Ala Ser Lys Ala Ser Tyr Thr Ala Gln Glu Phe Asn Leu Leu Asn
            275                 280                 285

Asp Leu Asn Asn Leu Thr Val Pro Thr Glu Thr Lys Lys Leu Ser Glu
        290                 295                 300

Glu Gln Lys Lys Thr Ile Ile Lys Tyr Ala Lys Thr Ala Lys Thr Leu
305                 310                 315                 320

Gly Ala Ser Thr Leu Leu Lys Tyr Ile Ala Lys Leu Ile Gly Ala Ser
                325                 330                 335

Val Asp Gln Ile His Gly Tyr Arg Ile Asp Pro Asn Lys Lys Pro Glu
                340                 345                 350

Met His Thr Phe Glu Thr Tyr Arg Lys Met Gln Ser Leu Glu Thr Ile
            355                 360                 365

Ser Val Glu Glu Leu Pro Arg Lys Val Leu Asp Glu Leu Ala His Ile
370                 375                 380

Leu Thr Leu Asn Thr Glu Arg Glu Gly Ile Glu Glu Ala Ile Asn Ala
385                 390                 395                 400

Thr Leu Lys Asp Thr Phe Ser Gln Asp Gln Val Glu Leu Val Gln
                405                 410                 415

Phe Arg Lys Asn Asn Ser Ser Leu Phe Ser Lys Gly Trp His Ser Phe
                420                 425                 430

Ser Leu Lys Leu Met Met Glu Leu Ile Pro Glu Leu Tyr Glu Thr Ser
            435                 440                 445

Glu Glu Gln Met Thr Ile Leu Thr Arg Leu Gly Lys Gln Lys Ser Lys
        450                 455                 460

Glu Thr Ser Lys Arg Thr Lys Tyr Ile Asp Glu Lys Glu Leu Thr Glu
465                 470                 475                 480

Glu Ile Tyr Asn Pro Val Val Ala Lys Ser Val Arg Gln Ala Ile Lys
                485                 490                 495

Ile Ile Asn Glu Ala Thr Lys Lys Tyr Gly Ile Phe Asp Asn Ile Val
                500                 505                 510

Ile Glu Met Ala Arg Glu Asn Asn Glu Glu Asp Ala Lys Lys Glu Tyr
            515                 520                 525

Ile Lys Arg Gln Lys Ala Asn Leu Asp Glu Lys Asn Ala Ala Met Glu
        530                 535                 540

Lys Ala Ala Phe Gln Tyr Asn Gly Lys Lys Glu Leu Pro Asp Asn Val
545                 550                 555                 560

Phe His Gly His Lys Glu Leu Ala Thr Lys Ile Arg Leu Trp His Gln
                565                 570                 575

Gln Gly Glu Lys Cys Leu Tyr Thr Gly Lys Asn Ile Pro Ile Ser Asp
            580                 585                 590

Leu Ile Gln Asn Gln Tyr Lys Tyr Glu Ile Asp His Ile Leu Pro Leu
```

```
            595                 600                 605
Ser Leu Ser Phe Asp Asp Ser Leu Ser Asn Lys Val Leu Val Leu Ala
    610                 615                 620
Thr Ala Asn Gln Glu Lys Gly Gln Arg Thr Pro Phe Gln Ala Leu Asp
625                 630                 635                 640
Ser Met Asp Asp Ala Trp Ser Tyr Arg Glu Phe Lys Ser Tyr Val Lys
                645                 650                 655
Asp Ser Lys Leu Leu Gly Asn Lys Lys Glu Tyr Leu Leu Thr Glu
                660                 665                 670
Glu Asp Ile Ser Lys Ile Glu Val Lys Gln Lys Phe Ile Glu Arg Asn
            675                 680                 685
Leu Val Asp Thr Arg Tyr Ser Ser Arg Val Val Leu Asn Ala Leu Gln
        690                 695                 700
Asp Phe Tyr Lys Glu His Gln Phe Asp Thr Thr Ile Ser Val Val Arg
705                 710                 715                 720
Gly Gln Phe Thr Ser Gln Leu Arg Arg Lys Trp Gly Leu Glu Lys Ser
                725                 730                 735
Arg Glu Thr Tyr His His His Ala Val Asp Ala Leu Ile Ile Ala Ala
                740                 745                 750
Ser Ser Gln Leu Arg Leu Trp Lys Lys Gln Asn Asn Pro Leu Ile Ser
        755                 760                 765
Tyr Thr Glu Gly Gln Phe Val Asp Gln Val Thr Gly Glu Ile Ile Ser
    770                 775                 780
Leu Ser Asp Asp Glu Tyr Lys Glu Leu Val Phe Lys Ala Pro Tyr Asp
785                 790                 795                 800
His Phe Val Asp Thr Leu Lys Ser Lys Lys Phe Glu Asp Ser Ile Leu
                805                 810                 815
Phe Ser Tyr Gln Val Asp Ser Lys Tyr Asn Arg Lys Ile Ser Asp Ala
                820                 825                 830
Thr Ile Tyr Ala Thr Arg Lys Ala Lys Leu Asp Lys Glu Asn Lys Glu
        835                 840                 845
Tyr Thr Tyr Thr Leu Gly Lys Ile Lys Asp Ile Tyr Ala Leu Gly Thr
    850                 855                 860
Lys Ser Pro Ser Lys Thr Gly Phe Tyr Lys Phe Leu Asp Leu Tyr Asn
865                 870                 875                 880
Lys Asp Lys Ser Gln Phe Leu Met Phe Gln Lys Asp Arg Lys Thr Trp
                885                 890                 895
Asp Glu Val Ile Glu Lys Ile Ile Glu Gln Tyr Arg Pro Phe Lys Glu
                900                 905                 910
Tyr Asp Glu Asn Gly Lys Glu Val Asp Phe Asn Pro Phe Glu Lys Tyr
        915                 920                 925
Arg Ile Glu Asn Gly Pro Ile Arg Lys Tyr Ser Lys Lys Gly Asn Gly
    930                 935                 940
Pro Glu Ile Lys Ser Leu Lys Tyr Tyr Asp Asn Leu Leu Gly Lys Phe
945                 950                 955                 960
Val Asp Ile Thr Pro Ser Glu Ser Lys Asn Pro Val Ala Leu Leu Ser
                965                 970                 975
Leu Asn Pro Trp Arg Thr Asp Val Tyr Tyr Asn Thr Glu Thr Ser Lys
                980                 985                 990
Tyr Glu Phe Leu Gly Leu Lys Tyr Ala Asp Leu Cys Phe Glu Lys Gly
        995                 1000                1005
Gly Ala Tyr Gly Ile Ser Glu Val Lys Tyr Asn Lys Ile Arg Glu
    1010                1015                1020
```

```
Lys Glu Gly Ile Gly Lys Glu Ser Glu Phe Lys Phe Thr Leu Tyr
       1025                1030                1035

Lys Asn Asp Leu Ile Leu Ile Lys Asp Thr Glu Thr Asn Cys Gln
       1040                1045                1050

Gln Ile Phe Arg Phe Trp Ser Arg Thr Gly Lys Asp Asn Pro Lys
       1055                1060                1065

Ser Phe Glu Lys His Lys Ile Glu Leu Lys Pro Tyr Glu Lys Ala
       1070                1075                1080

Arg Phe Glu Lys Gly Glu Glu Leu Glu Val Leu Gly Lys Val Pro
       1085                1090                1095

Pro Ser Ser Asn Gln Leu Gln Lys Asn Met Gln Ile Glu Asn Leu
       1100                1105                1110

Ser Ile Tyr Lys Val Lys Thr Asp Val Leu Gly Asn Lys His Phe
       1115                1120                1125

Ile Lys Lys Glu Gly Glu Glu Pro Lys Leu Lys Phe
       1130                1135                1140

<210> SEQ ID NO 7
<211> LENGTH: 1129
<212> TYPE: PRT
<213> ORGANISM: Streptococcus orisratti DSM 15617

<400> SEQUENCE: 7

Met Thr Asn Gly Lys Ile Leu Gly Leu Asp Ile Gly Ile Ala Ser Val
 1               5                  10                  15

Gly Val Gly Val Ile Glu Ala Asp Thr Gly Lys Val Val His Ala Ser
                20                  25                  30

Ser Arg Leu Phe Pro Ser Ala Asn Ala Asp Asn Asn Ala Glu Arg Arg
            35                  40                  45

Gly Phe Arg Gly Gly Arg Arg Leu Ile Arg Arg Lys Lys His Arg Met
        50                  55                  60

Lys Arg Val Lys Asp Leu Phe Glu Glu Tyr Lys Leu Glu Thr Arg Phe
 65                  70                  75                  80

Asn Asn Leu Asn Leu Asn Pro Tyr Glu Leu Arg Val Arg Gly Leu Thr
                 85                  90                  95

Glu Lys Leu Ala Pro Glu Glu Leu Phe Ala Ala Leu Lys Asn Leu Ser
            100                 105                 110

Lys His Arg Gly Ile Ser Tyr Leu Asp Asp Ala Glu Asp Asn Ala
        115                 120                 125

Ser Ala Lys Thr Asn Tyr Ala Lys Ser Val Leu Ala Asn Lys Glu Leu
    130                 135                 140

Leu Lys Thr Arg Thr Pro Gly Gln Ile Gln Trp Glu Arg Phe Glu Lys
145                 150                 155                 160

Tyr Gly Gln Ile Arg Gly Asp Phe Asp Ile Val Thr Pro Glu Gly Glu
                165                 170                 175

Gln Gln Arg Ile Ile Asn Val Phe Ser Thr Thr Asp Tyr Lys Lys Glu
            180                 185                 190

Ala Glu Gln Ile Leu Glu Thr Gln Ala Leu Tyr Tyr Pro Gln Ile Ser
        195                 200                 205

Ser Glu Phe Ile Glu Asp Phe Ile Thr Ile Leu Thr Ser Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Asp Gly Thr Thr Leu Asp Asn Ile Phe Asp Ile Leu Val
```

```
                245                 250                 255
Gly Lys Cys Gly Ile Tyr Pro Asp Glu Tyr Arg Ala Ala Lys Ala Ser
            260                 265                 270

Tyr Thr Ala Gln Glu Phe Asn Phe Leu Asn Asp Leu Asn Asn Leu Thr
        275                 280                 285

Leu Pro Thr Glu Thr Lys Arg Leu Ser Thr Asp Gln Lys Lys Asp Leu
290                 295                 300

Val Arg Phe Ala Thr Thr Ala Ala Thr Leu Gly Pro Asp Lys Leu Leu
305                 310                 315                 320

Lys Glu Ile Ala Arg Met Val Gly Cys Ser Lys Asp Asp Ile Lys Gly
                325                 330                 335

Tyr Arg Ile Asp Asn Lys Glu Lys Pro Asp Leu His Thr Phe Glu Ala
            340                 345                 350

Tyr Arg Ala Met Thr Lys Leu Asn Thr Phe Asp Val Ala Thr Phe Ser
        355                 360                 365

Arg Glu Met Ile Asp Glu Leu Ala Arg Ile Leu Thr Leu Asn Thr Asp
    370                 375                 380

Arg Glu Gly Ile Glu Glu Ala Ile Val Asn Asp Phe Pro Asn Leu Phe
385                 390                 395                 400

Ser Arg Glu Gln Ile Asp Glu Leu Ile Gln Phe Arg Lys Ser Lys Ser
                405                 410                 415

Gln Leu Phe Gly Lys Gly Trp His Ser Phe Ser Leu Lys Leu Met Ser
            420                 425                 430

Glu Leu Ile Pro Glu Leu Tyr Ala Thr Ser Glu Glu Gln Met Thr Ile
        435                 440                 445

Leu Thr Arg Leu Asn Lys Met Ser Pro Glu Arg Lys Val Thr Leu Arg
    450                 455                 460

Thr Lys Tyr Ile Asn Glu Gln Asp Ala Thr Glu Ile Tyr Asn Pro
465                 470                 475                 480

Val Val Ala Lys Ser Val Arg Gln Ala Ile Lys Ile Asn Glu Cys
                485                 490                 495

Ile Lys Lys Trp Gly Glu Phe Asp Gln Ile Val Ile Glu Met Pro Arg
            500                 505                 510

Asp Lys Asn Glu Asp Asp Glu Lys Lys Arg Ile Ala Asp Gly Gln Lys
        515                 520                 525

Ala Asn Ala Lys Glu Lys Ala Ser Ala Thr Glu Phe Ala Ala Ser Leu
    530                 535                 540

Tyr Asn Gly Lys Lys Glu Leu Pro Asp Glu Val Phe His Gly His Lys
545                 550                 555                 560

Gln Leu Ala Thr Lys Ile Arg Leu Trp Tyr Gln Gln Asp Gly Lys Cys
                565                 570                 575

Leu Tyr Thr Gly Gln Asp Ile Ser Ile His Asp Leu Ile His Asn Gln
            580                 585                 590

Asn Gln Tyr Glu Ile Asp His Ile Met Pro Leu Ser Leu Ser Phe Asp
        595                 600                 605

Asp Ser Leu Ser Asn Lys Val Leu Val Leu Ala Thr Ala Asn Gln Glu
    610                 615                 620

Lys Gly Gln Gln Thr Pro Tyr Gln Ala Ile Pro Lys Met Lys Ser Ala
625                 630                 635                 640

Trp Ser Tyr Arg Glu Phe Lys Ala Phe Val Leu Asp Cys Lys Arg Leu
                645                 650                 655

Ser Lys Lys Lys Arg Glu Tyr Leu Leu Thr Glu Glu Asp Ile Asp Lys
            660                 665                 670
```

```
Ile Glu Val Arg Arg Lys Phe Ile Ala Arg Asn Leu Val Asp Thr Arg
        675                 680                 685

Tyr Ala Ser Arg Val Val Leu Thr Thr Leu Gln Asp Ala Leu Glu Val
        690                 695                 700

Met Asn Lys Glu Thr Lys Val Ser Val Val Arg Gly Gln Phe Thr Ser
705                 710                 715                 720

Gln Leu Arg Arg Gln Trp Lys Ile Asp Lys Thr Arg Asp Thr Tyr His
                725                 730                 735

His His Ala Ile Asp Ala Leu Ile Ile Ala Ala Ser Ser Gln Leu Lys
            740                 745                 750

Leu Trp Lys Lys Gln Asp Asn Pro Met Phe Glu Glu Tyr Glu Gln Gly
        755                 760                 765

Gln Lys Ile Asn Leu Glu Thr Gly Glu Ile Leu Ser Asp Asp Asp Tyr
    770                 775                 780

Lys Lys Leu Val Phe Gln Ser Pro Tyr Gln Gly Phe Val His Thr Ile
785                 790                 795                 800

Ser Ser Lys Ser Phe Glu Asp Glu Ile Leu Phe Ser Tyr Gln Ile Asp
                805                 810                 815

Ser Lys Val Asn Arg Lys Ile Ser Asp Ala Thr Ile Tyr Ala Thr Arg
            820                 825                 830

Gln Ala Gln Leu Ser Arg Asp Arg Lys Lys Glu Thr Tyr Val Leu Gly
        835                 840                 845

Lys Ile Lys Asp Ile Tyr Ser Gln Thr Gly Tyr Asp Ala Phe Arg Lys
    850                 855                 860

Arg Tyr Asp Lys Asp Lys Thr Val Phe Leu Met Tyr Gln Lys Asp Pro
865                 870                 875                 880

Leu Thr Trp Glu Lys Val Ile Glu Val Ile Leu Arg Asp Tyr Lys Glu
                885                 890                 895

Phe Asp Asp Lys Gly Lys Glu Val Gly Asn Pro Phe Glu Arg Tyr Arg
            900                 905                 910

Gln Gln Asn Gly Leu Met Thr Lys Tyr Ser Arg Lys Asn Lys Gly Thr
        915                 920                 925

Pro Ile Lys Ala Leu Lys Tyr Tyr Asp Asn Lys Leu Gly Asn His Val
    930                 935                 940

Asp Val Thr Pro Asp Asp Ser Lys Asn Pro Val Val Leu Gln Ser Ile
945                 950                 955                 960

Asn Pro Trp Arg Ala Asp Leu Tyr Phe Asn Pro Lys Thr Ala Lys Tyr
                965                 970                 975

Glu Leu Leu Gly Leu Lys Tyr Ala Asp Leu Ser Phe Glu Lys Gly Thr
            980                 985                 990

Gly Asn Tyr Thr Ile Ser Gln Glu Lys Tyr Asp Glu Ile Lys Lys Arg
        995                 1000                1005

Glu Gly Ile Ser Ala Glu Ser Glu Phe Lys Phe Thr Leu Tyr Lys
        1010                1015                1020

Asn Asp Leu Leu Leu Ile Lys Asp Ile Glu Asn Gly Glu Glu Gln
        1025                1030                1035

Val Phe Arg Phe Leu Ser Arg Thr Met Pro Asn Gln Lys His Tyr
        1040                1045                1050

Val Glu Leu Lys Pro Tyr Asp Lys Ala Lys Phe Asp Gly Gly Gln
        1055                1060                1065

Ser Leu Leu Thr Val Leu Gly Thr Val Ala Lys Gly Gly Gln Cys
        1070                1075                1080
```

-continued

```
Leu Lys Ser Leu Asn Lys Val Gly Ile Ser Ile Tyr Lys Val Lys
    1085                1090                1095

Thr Asp Val Leu Gly Tyr Gln His Phe Ile Lys Lys Glu Gly Asn
    1100                1105                1110

Gln Pro Lys Leu Ser Phe Glu Asn Ser Ile Lys Arg His Lys Asn
    1115                1120                1125

Lys

<210> SEQ ID NO 8
<211> LENGTH: 1126
<212> TYPE: PRT
<213> ORGANISM: Streptococcus henryi DSM 19005

<400> SEQUENCE: 8

Met Thr Asn Gly Leu Val Leu Gly Leu Asp Ile Gly Ile Ala Ser Val
1               5                   10                  15

Gly Val Gly Ile Ile Glu Ala Glu Thr Gly Lys Val Ile His Ala Ser
                20                  25                  30

Ser Arg Ile Phe Pro Ala Ala Asn Ala Asp Asn Asn Ala Glu Arg Arg
            35                  40                  45

Gly Phe Arg Gly Arg Arg Leu Thr Arg Arg Lys Lys His Arg Val
        50                  55                  60

Lys Arg Val Arg Asp Leu Phe Asp Asp Tyr Asn Ile Ala Thr Asp Phe
65                  70                  75                  80

Ser Asn Leu Asn Leu Asn Pro Tyr Glu Leu Arg Val Lys Gly Leu Thr
                85                  90                  95

Glu Glu Leu Thr Asn Glu Glu Leu Phe Ala Ala Leu Arg Asn Ile Ser
                100                 105                 110

Lys Arg Arg Gly Ile Ser Tyr Leu Asp Asp Ala Glu Asp Ala Asn
            115                 120                 125

Ser Gly Lys Thr Asp Tyr Ala Lys Ser Val Leu Ala Asn Lys Glu Leu
130                 135                 140

Leu Lys Thr Gln Thr Pro Gly Gln Ile Gln Leu Asp Arg Leu Asn Lys
145                 150                 155                 160

Tyr Gly Gln Leu Arg Gly Asp Phe Asp Val Val Asp Glu Asn Gly Glu
                165                 170                 175

Ile His Arg Val Ile Asn Val Phe Ser Thr Ser Asp Tyr Arg Lys Glu
            180                 185                 190

Ala Glu Lys Ile Leu Gln Thr Gln Ser Gln Phe Asn Asn Ala Ile Asn
        195                 200                 205

Gln Glu Phe Ile Asn Asp Tyr Ile Asp Ile Leu Val Ser Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Asp Gly Arg Thr Leu Glu Asn Ile Phe Asp Ile Leu Val
                245                 250                 255

Gly Lys Cys Thr Phe Tyr Pro Glu Glu Tyr Arg Ala Ala Lys Ala Ser
            260                 265                 270

Tyr Thr Ala Gln Glu Phe Asn Phe Leu Asn Asp Leu Asn Asn Leu Thr
        275                 280                 285

Leu Pro Thr Glu Thr Lys Lys Leu Ser Ile Glu Glu Lys Leu Tyr Leu
    290                 295                 300

Val Asp Tyr Ala Lys Asn Thr Pro Val Leu Gly Pro Asp Lys Leu Leu
305                 310                 315                 320
```

-continued

Lys Glu Ile Ala Lys Leu Val Asp Cys Lys Lys Glu Asp Ile Lys Gly
            325                 330                 335

Phe Arg Ile Asp Asn Lys Glu Lys Pro Asp Met His Thr Phe Glu Val
            340                 345                 350

Tyr Arg Thr Met Ser Lys Leu Asp Lys Val Asp Ile Gln Thr Leu Ser
            355                 360                 365

Arg Glu Thr Phe Asp Glu Leu Ala Arg Ile Leu Thr Leu Asn Thr Glu
            370                 375                 380

Arg Glu Gly Ile Glu Glu Ala Ile Leu Lys Asp Leu Pro Asn Gln Phe
385                 390                 395                 400

Thr Asn Glu Gln Ile Glu Glu Leu Ile Lys Phe Arg Lys Asp Lys Ser
            405                 410                 415

Gln Ile Phe Gly Lys Gly Trp His Asn Phe Ser Val Lys Leu Met Leu
            420                 425                 430

Glu Leu Ile Pro Glu Leu Tyr Asp Thr Ser Glu Glu Gln Met Thr Ile
            435                 440                 445

Leu Thr Arg Leu Gly Lys Thr Ser Ala Asn Lys Lys Glu Val Lys Arg
            450                 455                 460

Thr Lys Tyr Ile Asn Glu Asn Asp Val Thr Glu Glu Ile Tyr Asn Pro
465                 470                 475                 480

Val Val Val Lys Ser Val Arg Gln Ala Ile Lys Ile Ile Asn Ala Ser
            485                 490                 495

Val Lys Glu Trp Gly Glu Phe Asp Asn Ile Val Ile Glu Met Pro Arg
            500                 505                 510

Glu Thr Asn Ala Asp Asp Glu Arg Lys Phe Ile Lys Lys Met Gln Asp
            515                 520                 525

Ala Asn Ala Lys Glu Lys Lys Asp Ser Glu Glu Arg Ala Ala Thr Leu
            530                 535                 540

Tyr Asn Gly Lys Thr Glu Leu Pro Ser Asn Ile Phe His Gly His Asn
545                 550                 555                 560

Gln Leu Ala Thr Lys Ile Arg Leu Trp Tyr Gln Gln Gly Glu Arg Cys
            565                 570                 575

Ile Tyr Thr Gly Gln Lys Ile Asp Ile Asn Asp Leu Ile His Asn His
            580                 585                 590

Asn Met Tyr Glu Ile Asp His Val Leu Pro Leu Ser Leu Ser Phe Asp
            595                 600                 605

Asp Ser Leu Ala Asn Lys Val Leu Val Leu Ala Thr Ala Asn Gln Glu
            610                 615                 620

Lys Gly Gln Lys Thr Pro Phe Gln Ser Ile Pro Gln Met Lys Ser Ala
625                 630                 635                 640

Trp Ser Tyr Arg Glu Phe Lys Ser Tyr Val Leu Gly Cys Lys Gly Leu
            645                 650                 655

Ser Lys Lys Lys Arg Glu Tyr Leu Leu Thr Glu Glu Asp Ile Asn Lys
            660                 665                 670

Ile Glu Val Lys Gln Lys Phe Ile Glu Arg Asn Leu Val Asp Thr Arg
            675                 680                 685

Tyr Ala Ser Arg Val Val Leu Asn Thr Leu Gln Asp Ser Leu Lys Ala
            690                 695                 700

Met Asn Lys Lys Thr Arg Val Ser Val Val Arg Gly Gln Phe Thr Ser
705                 710                 715                 720

Gln Leu Arg Arg Gln Trp Lys Ile Asp Lys Ser Arg Glu Thr Tyr His
            725                 730                 735

His His Ala Ile Asp Ala Leu Ile Ile Ala Ala Ser Ser Gln Leu Arg

```
                    740                 745                 750
Leu Trp Lys Lys Gln Gly Asp Thr Met Phe Glu Asp Tyr Lys Asn Gly
            755                 760                 765

Gln Lys Val Asp Leu Glu Thr Gly Glu Leu Leu Ser Asp Asn Glu Tyr
        770                 775                 780

Lys Glu Leu Val Phe Gln Ser Pro Tyr Gln Gly Phe Val Asn Thr Ile
785                 790                 795                 800

Ser Ser Lys Ala Phe Glu Asp Glu Ile Leu Phe Ser Tyr Gln Val Asp
                805                 810                 815

Ser Lys Val Asn Arg Lys Ile Ser Asp Ala Thr Ile Tyr Ala Thr Arg
            820                 825                 830

Gln Ala Lys Leu Thr Lys Asp Lys Glu Glu Thr Tyr Val Leu Gly
        835                 840                 845

Lys Ile Lys Asp Ile Tyr Ser Gln Ala Gly Tyr Asp Ala Phe Arg Lys
        850                 855                 860

Arg Tyr Glu Lys Asp Lys Ser Ala Phe Leu Met Tyr Gln Lys Asp Pro
865                 870                 875                 880

Met Thr Trp Glu Lys Val Ile Glu Val Ile Leu Asn Asp Tyr Cys Glu
                885                 890                 895

Phe Asp Asp Lys Gly Lys Glu Thr Gly Asn Pro Phe Glu Lys Tyr Arg
            900                 905                 910

Asn Glu Asn Gly Tyr Ile Arg Lys Tyr Ser Arg Lys Gly Lys Gly Thr
        915                 920                 925

Glu Ile Lys Ser Leu Lys Tyr Tyr Asp Ser Lys Leu Gly Asn His Ile
        930                 935                 940

Asp Ile Thr Pro Glu Asn Ser Lys Asn Ser Val Val Leu Gln Ser Ile
945                 950                 955                 960

Asn Pro Trp Arg Ala Asp Leu Tyr Phe Asn Pro Lys Thr Leu Lys Tyr
                965                 970                 975

Glu Leu Met Gly Leu Lys Tyr Ser Asp Leu Ser Phe Glu Lys Gly Thr
            980                 985                 990

Gly Asn Tyr Ser Ile Ser Gln Asp Lys Tyr Asp Glu Ile Lys Ser Arg
        995                 1000                1005

Glu Gly Ile Ser Pro Lys Ser Glu Phe Lys Phe Thr Leu Tyr Lys
        1010                1015                1020

Asn Asp Leu Ile Leu Ile Lys Asp Thr Ile Asn Asn Lys Thr Leu
        1025                1030                1035

Thr Ala Arg Phe Asn Ser Lys Asn Asp Thr Ser Lys His Tyr Val
        1040                1045                1050

Glu Leu Lys Pro Asp Ser Lys Ala Lys Tyr Asp Ser Glu Glu Val
        1055                1060                1065

Leu Ile Pro Val Phe Gly Lys Val Ala Lys Ser Gly Arg Phe Ile
        1070                1075                1080

Lys Gly Ile Asn Lys Thr Gly Ile Ser Ile Tyr Lys Ile Lys Thr
        1085                1090                1095

Asp Ile Leu Gly Arg Lys His Phe Ile Lys Glu Glu Gly Asp Gln
        1100                1105                1110

Pro Lys Leu Glu Phe Met Lys Ser Ser Lys Asn Asn Lys
        1115                1120                1125

<210> SEQ ID NO 9
<211> LENGTH: 1129
<212> TYPE: PRT
<213> ORGANISM: Streptococcus infantarius subsp. infantarius
```

<400> SEQUENCE: 9

```
Met Ser Asn Gly Lys Ile Leu Gly Leu Asp Ile Gly Val Ala Ser Val
1               5                   10                  15

Gly Val Gly Ile Ile Asp Ser Lys Thr Gly Asn Val Ile His Ala Asn
            20                  25                  30

Ser Arg Leu Phe Ser Ala Ala Asn Ala Glu Asn Asn Ala Glu Arg Arg
        35                  40                  45

Gly Phe Arg Gly Ala Arg Arg Leu Thr Arg Arg Lys Lys His Arg Val
    50                  55                  60

Lys Arg Val Arg Asp Leu Phe Glu Lys Tyr Asp Ile Ser Thr Asp Phe
65                  70                  75                  80

Arg Asn Leu Asn Leu Asn Pro Tyr Glu Leu Arg Val Lys Gly Leu Thr
                85                  90                  95

Glu Gln Leu Thr Asn Glu Glu Leu Phe Ala Ala Leu Arg Thr Ile Ala
            100                 105                 110

Lys Arg Arg Gly Ile Ser Tyr Leu Asp Asp Ala Glu Asp Asp Ser Thr
        115                 120                 125

Gly Ser Ser Asp Tyr Ala Lys Ser Ile Asp Glu Asn Arg Arg Leu Leu
    130                 135                 140

Lys Thr Lys Thr Pro Gly Gln Ile Gln Leu Glu Arg Leu Glu Lys Tyr
145                 150                 155                 160

Gly Gln Leu Arg Gly Asn Phe Thr Val Tyr Asp Glu Asn Gly Glu Ala
                165                 170                 175

His Arg Leu Ile Asn Val Phe Ser Thr Ser Asp Tyr Lys Asn Glu Ala
            180                 185                 190

Arg Lys Ile Leu Glu Thr Gln Ser Asn Tyr Asn Lys Gln Ile Thr Asp
        195                 200                 205

Glu Phe Ile Glu Asp Tyr Ile Glu Ile Leu Thr Gln Lys Arg Lys Tyr
    210                 215                 220

Tyr His Gly Pro Gly Asn Glu Lys Ser Arg Thr Asp Tyr Gly Arg Phe
225                 230                 235                 240

Arg Thr Asp Gly Thr Thr Leu Glu Asn Ile Phe Gly Ile Leu Ile Gly
                245                 250                 255

Lys Cys Ser Phe Tyr Pro Glu Glu Tyr Arg Ala Ser Lys Ala Ser Tyr
            260                 265                 270

Thr Ala Gln Glu Phe Asn Phe Leu Asn Asp Leu Asn Asn Leu Lys Val
        275                 280                 285

Pro Thr Glu Thr Gly Lys Leu Ser Thr Glu Gln Lys Glu Tyr Leu Val
    290                 295                 300

Asp Phe Ala Lys Lys Ser Lys Ala Leu Gly Ala Ser Lys Leu Leu Lys
305                 310                 315                 320

Glu Ile Ala Lys Ile Val Asp Cys Ser Val Asp Ile Lys Gly Tyr
                325                 330                 335

Arg Val Asp Asn Lys Asp Lys Pro Asp Leu His Thr Phe Glu Pro Tyr
            340                 345                 350

Arg Lys Leu Lys Phe Asn Leu Ser Ser Ile Asp Ile Asp Glu Leu Ser
        355                 360                 365

Arg Glu Thr Leu Asp Lys Leu Ala Asp Ile Leu Thr Leu Asn Thr Glu
    370                 375                 380

Arg Glu Gly Ile Glu Asp Ala Ile Lys Arg Asn Leu Pro Ser Gln Phe
385                 390                 395                 400

Thr Glu Glu Gln Ile Ser Glu Ile Val Gln Ile Arg Lys Asn Gln Ser
```

```
            405                 410                 415
Ser Ala Phe Asn Lys Gly Trp His Ser Phe Ser Ala Lys Leu Met Asn
                420                 425                 430

Glu Leu Ile Pro Glu Leu Tyr Val Thr Ser Glu Gln Met Thr Ile
                435                 440                 445

Leu Thr Arg Leu Glu Lys Phe Lys Val Asn Lys Ser Ser Lys Asn
            450                 455                 460

Thr Lys Thr Ile Asp Glu Lys Glu Ile Thr Asp Glu Ile Tyr Asn Pro
465                 470                 475                 480

Val Val Ala Lys Ser Val Arg Gln Thr Ile Lys Ile Asn Ala Ala
                485                 490                 495

Val Lys Lys Tyr Gly Asp Phe Asp Lys Ile Val Ile Glu Met Pro Arg
                500                 505                 510

Asp Lys Asn Ala Glu Asp Glu Lys Lys Phe Ile Asp Lys Lys Gln Lys
                515                 520                 525

Glu Asn Lys Lys Glu Lys Asp Asp Ser Leu Lys Arg Ala Ala Phe Leu
                530                 535                 540

Tyr Asn Gly Thr Asp Asn Leu Pro Asp Gly Val Phe His Gly Asn Lys
545                 550                 555                 560

Glu Leu Lys Thr Lys Ile Arg Leu Trp Tyr Gln Gln Gly Glu Arg Cys
                565                 570                 575

Leu Tyr Ser Gly Lys Leu Ile Ser Ile His Asp Leu Val His Asn Ser
                580                 585                 590

Asn Lys Phe Glu Ile Asp His Ile Leu Pro Leu Ser Leu Ser Phe Asp
                595                 600                 605

Asp Ser Leu Ala Asn Lys Val Leu Val Tyr Ala Trp Thr Asn Gln Glu
                610                 615                 620

Lys Gly Gln Lys Thr Pro Tyr Gln Val Ile Asp Ser Met Asp Thr Ala
625                 630                 635                 640

Trp Ser Phe Arg Glu Met Lys Asp Tyr Val Leu Lys Gln Lys Gly Leu
                645                 650                 655

Gly Lys Lys Lys Cys Glu Tyr Leu Leu Thr Thr Glu Asn Ile Asp Lys
                660                 665                 670

Ile Glu Val Lys Lys Lys Phe Ile Glu Arg Asn Leu Val Asp Thr Arg
                675                 680                 685

Tyr Ala Ser Arg Val Val Leu Asn Ser Leu Gln Thr Ala Leu Lys Glu
                690                 695                 700

Leu Gly Lys Asp Thr Lys Val Ser Val Arg Gly Gln Phe Thr Ser
705                 710                 715                 720

Gln Leu Arg Arg Lys Trp Asn Ile Asp Lys Ser Arg Glu Thr Tyr His
                725                 730                 735

His His Ala Val Asp Ala Leu Ile Ile Ala Ala Ser Ser Gln Leu Lys
                740                 745                 750

Leu Trp Gln Lys Gln Glu Asn Pro Met Phe Glu Ser Tyr Gly Glu Asn
                755                 760                 765

Gln Val Val Asn Lys Glu Thr Gly Glu Ile Leu Ser Ile Ser Asp Asp
                770                 775                 780

Lys Tyr Lys Glu Leu Val Phe Gln Pro Pro Tyr Gln Gly Phe Val Asn
785                 790                 795                 800

Thr Ile Ser Ser Lys Gly Phe Glu Asp Glu Ile Leu Phe Ser Tyr Gln
                805                 810                 815

Val Asp Ser Lys Phe Asn Arg Lys Val Ser Asp Ala Thr Ile Tyr Ser
                820                 825                 830
```

```
Thr Arg Lys Ala Lys Leu Gly Lys Asp Lys Asp Glu Thr Tyr Val
        835                 840                 845

Leu Gly Lys Ile Lys Asp Ile Tyr Ser Gln Asp Gly Phe Asp Thr Phe
850                 855                 860

Ile Lys Arg Tyr Lys Lys Asp Lys Thr Gln Phe Leu Met Tyr Gln Lys
865                 870                 875                 880

Asp Pro Leu Thr Trp Glu Asn Val Ile Glu Val Ile Leu Arg Asp Tyr
                885                 890                 895

Pro Ser Glu Lys Leu Ser Glu Asp Gly Lys Lys Thr Val Lys Cys Asn
                900                 905                 910

Pro Phe Glu Tyr Arg Arg Glu Asn Gly Leu Ile Cys Lys Tyr Ser
                915                 920                 925

Lys Lys Gly Asn Gly Thr Pro Ile Lys Ser Leu Lys Tyr Tyr Asp Lys
        930                 935                 940

Lys Leu Gly Asn Cys Ile Asp Ile Thr Pro Glu Lys Ser Lys Asn Arg
945                 950                 955                 960

Val Val Leu Arg Gln Ile Ser Pro Trp Arg Ala Asp Ile Tyr Phe Asn
                965                 970                 975

Leu Glu Thr Leu Lys Tyr Glu Leu Met Gly Leu Lys Tyr Ser Asp Leu
                980                 985                 990

Ser Phe Glu Lys Gly Thr Gly Lys Tyr His Ile Ser Gln Glu Lys Tyr
            995                 1000                1005

Asp Ala Ile Arg Glu Lys Glu Gly Ile Gly Lys Lys Ser Glu Phe
        1010                1015                1020

Lys Phe Thr Leu Tyr Arg Asn Asp Leu Ile Leu Ile Lys Asp Thr
        1025                1030                1035

Leu Asn Asn Cys Glu Arg Met Leu Arg Phe Gly Ser Lys Asn Asp
        1040                1045                1050

Thr Ser Lys His Tyr Val Glu Leu Lys Pro Leu Glu Lys Gly Thr
        1055                1060                1065

Phe Asp Ser Glu Glu Glu Ile Leu Pro Val Leu Gly Lys Val Ala
        1070                1075                1080

Lys Ser Gly Gln Phe Ile Lys Gly Leu Asn Lys Pro Asn Ile Ser
        1085                1090                1095

Ile Tyr Lys Val Arg Thr Asp Val Leu Gly Asn Lys Phe Phe Ile
        1100                1105                1110

Lys Lys Glu Gly Asp Lys Pro Lys Leu Asp Phe Lys Asn Asn Asn
        1115                1120                1125

Lys

<210> SEQ ID NO 10
<211> LENGTH: 1388
<212> TYPE: PRT
<213> ORGANISM: Streptococcus thermophilus LMD-9

<400> SEQUENCE: 10

Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60
```

-continued

```
Lys Arg Thr Ala Arg Arg Tyr Thr Arg Arg Asn Arg Ile Leu
 65                  70                  75                  80

Tyr Leu Gln Glu Ile Phe Ser Thr Glu Met Ala Thr Leu Asp Asp Ala
                     85                  90                  95

Phe Phe Gln Arg Leu Asp Asp Ser Phe Leu Val Pro Asp Lys Arg
                100                 105                 110

Asp Ser Lys Tyr Pro Ile Phe Gly Asn Leu Val Glu Glu Lys Ala Tyr
            115                 120                 125

His Asp Glu Phe Pro Thr Ile Tyr His Leu Arg Lys Tyr Leu Ala Asp
        130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
    290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Glu Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480
```

```
Val Ile Asp Lys Glu Ser Ser Ala Glu Ala Phe Ile Asn Arg Met Thr
                485             490                 495
Ser Phe Asp Leu Tyr Leu Pro Glu Glu Lys Val Leu Pro Lys His Ser
            500                 505                 510
Leu Leu Tyr Glu Thr Phe Asn Val Tyr Asn Glu Leu Thr Lys Val Arg
            515                 520                 525
Phe Ile Ala Glu Ser Met Arg Asp Tyr Gln Phe Leu Asp Ser Lys Gln
            530                 535                 540
Lys Lys Asp Ile Val Arg Leu Tyr Phe Lys Asp Lys Arg Lys Val Thr
545                 550                 555                 560
Asp Lys Asp Ile Ile Glu Tyr Leu His Ala Ile Tyr Gly Tyr Asp Gly
                565                 570                 575
Ile Glu Leu Lys Gly Ile Glu Lys Gln Phe Asn Ser Ser Leu Ser Thr
            580                 585                 590
Tyr His Asp Leu Leu Asn Ile Ile Asn Asp Lys Glu Phe Leu Asp Asp
            595                 600                 605
Ser Ser Asn Glu Ala Ile Ile Glu Glu Ile Ile His Thr Leu Thr Ile
            610                 615                 620
Phe Glu Asp Arg Glu Met Ile Lys Gln Arg Leu Ser Lys Phe Glu Asn
625                 630                 635                 640
Ile Phe Asp Lys Ser Val Leu Lys Lys Leu Ser Arg Arg His Tyr Thr
                645                 650                 655
Gly Trp Gly Lys Leu Ser Ala Lys Leu Ile Asn Gly Ile Arg Asp Glu
            660                 665                 670
Lys Ser Gly Asn Thr Ile Leu Asp Tyr Leu Ile Asp Asp Gly Ile Ser
            675                 680                 685
Asn Arg Asn Phe Met Gln Leu Ile His Asp Asp Ala Leu Ser Phe Lys
            690                 695                 700
Lys Lys Ile Gln Lys Ala Gln Ile Ile Gly Asp Glu Asp Lys Gly Asn
705                 710                 715                 720
Ile Lys Glu Val Val Lys Ser Leu Pro Gly Ser Pro Ala Ile Lys Lys
                725                 730                 735
Gly Ile Leu Gln Ser Ile Lys Ile Val Asp Glu Leu Val Lys Val Met
            740                 745                 750
Gly Gly Arg Lys Pro Glu Ser Ile Val Val Glu Met Ala Arg Glu Asn
            755                 760                 765
Gln Tyr Thr Asn Gln Gly Lys Ser Asn Ser Gln Gln Arg Leu Lys Arg
            770                 775                 780
Leu Glu Lys Ser Leu Lys Glu Leu Gly Ser Lys Ile Leu Lys Glu Asn
785                 790                 795                 800
Ile Pro Ala Lys Leu Ser Lys Ile Asp Asn Asn Ala Leu Gln Asn Asp
                805                 810                 815
Arg Leu Tyr Leu Tyr Tyr Leu Gln Asn Gly Lys Asp Met Tyr Thr Gly
            820                 825                 830
Asp Asp Leu Asp Ile Asp Arg Leu Ser Asn Tyr Asp Ile Asp His Ile
            835                 840                 845
Ile Pro Gln Ala Phe Leu Lys Asp Asn Ser Ile Asp Asn Lys Val Leu
            850                 855                 860
Val Ser Ser Ala Ser Asn Arg Gly Lys Ser Asp Asp Val Pro Ser Leu
865                 870                 875                 880
Glu Val Val Lys Lys Arg Lys Thr Phe Trp Tyr Gln Leu Leu Lys Ser
                885                 890                 895
Lys Leu Ile Ser Gln Arg Lys Phe Asp Asn Leu Thr Lys Ala Glu Arg
```

-continued

```
                900             905                 910
Gly Gly Leu Ser Pro Glu Asp Lys Ala Gly Phe Ile Gln Arg Gln Leu
            915                 920                 925

Val Glu Thr Arg Gln Ile Thr Lys His Val Ala Arg Leu Leu Asp Glu
        930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
            965                 970                 975

Phe Glu Leu Tyr Lys Val Arg Glu Ile Asn Asp Phe His His Ala His
        980                 985                 990

Asp Ala Tyr Leu Asn Ala Val Val  Ala Ser Ala Leu Leu  Lys Lys Tyr
        995                 1000                1005

Pro Lys Leu Glu Pro Glu Phe  Val Tyr Gly Asp Tyr  Pro Lys Tyr
    1010                1015                1020

Asn Ser  Phe Arg Glu Arg Lys  Ser Ala Thr Glu Lys  Val Tyr Phe
    1025                1030                1035

Tyr Ser  Asn Ile Met Asn Ile  Phe Lys Lys Ser Ile  Ser Leu Ala
    1040                1045                1050

Asp Gly  Arg Val Ile Glu Arg  Pro Leu Ile Glu Val  Asn Glu Glu
    1055                1060                1065

Thr Gly  Glu Ser Val Trp Asn  Lys Glu Ser Asp Leu  Ala Thr Val
    1070                1075                1080

Arg Arg  Val Leu Ser Tyr Pro  Gln Val Asn Val Val  Lys Lys Val
    1085                1090                1095

Glu Glu  Gln Asn His Gly Leu  Asp Arg Gly Lys Pro  Lys Gly Leu
    1100                1105                1110

Phe Asn  Ala Asn Leu Ser Ser  Lys Pro Lys Pro Asn  Ser Asn Glu
    1115                1120                1125

Asn Leu  Val Gly Ala Lys Glu  Tyr Leu Asp Pro Lys  Lys Tyr Gly
    1130                1135                1140

Gly Tyr  Ala Gly Ile Ser Asn  Ser Phe Thr Val Leu  Val Lys Gly
    1145                1150                1155

Thr Ile  Glu Lys Gly Ala Lys  Lys Lys Ile Thr Asn  Val Leu Glu
    1160                1165                1170

Phe Gln  Gly Ile Ser Ile Leu  Asp Arg Ile Asn Tyr  Arg Lys Asp
    1175                1180                1185

Lys Leu  Asn Phe Leu Leu Glu  Lys Gly Tyr Lys Asp  Ile Glu Leu
    1190                1195                1200

Ile Ile  Glu Leu Pro Lys Tyr  Ser Leu Phe Glu Leu  Ser Asp Gly
    1205                1210                1215

Ser Arg  Arg Met Leu Ala Ser  Ile Leu Ser Thr Asn  Asn Lys Arg
    1220                1225                1230

Gly Glu  Ile His Lys Gly Asn  Gln Ile Phe Leu Ser  Gln Lys Phe
    1235                1240                1245

Val Lys  Leu Leu Tyr His Ala  Lys Arg Ile Ser Asn  Thr Ile Asn
    1250                1255                1260

Glu Asn  His Arg Lys Tyr Val  Glu Asn His Lys Lys  Glu Phe Glu
    1265                1270                1275

Glu Leu  Phe Tyr Tyr Ile Leu  Glu Phe Asn Glu Asn  Tyr Val Gly
    1280                1285                1290

Ala Lys  Lys Asn Gly Lys Leu  Leu Asn Ser Ala Phe  Gln Ser Trp
    1295                1300                1305
```

Gln Asn His Ser Ile Asp Glu Leu Cys Ser Ser Phe Ile Gly Pro
    1310            1315                1320

Thr Gly Ser Glu Arg Lys Gly Leu Phe Glu Leu Thr Ser Arg Gly
    1325            1330                1335

Ser Ala Ala Asp Phe Glu Phe Leu Gly Val Lys Ile Pro Arg Tyr
    1340            1345                1350

Arg Asp Tyr Thr Pro Ser Ser Leu Leu Lys Asp Ala Thr Leu Ile
    1355            1360                1365

His Gln Ser Val Thr Gly Leu Tyr Glu Thr Arg Ile Asp Leu Ala
    1370            1375                1380

Lys Leu Gly Glu Gly
    1385

<210> SEQ ID NO 11
<211> LENGTH: 1385
<212> TYPE: PRT
<213> ORGANISM: Streptococcus salivarius K12

<400> SEQUENCE: 11

Met Thr Lys Pro Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Ala Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Val Tyr
        115                 120                 125

His Asp Glu Phe Pro Thr Ile Tyr His Leu Arg Lys His Leu Ala Asp
    130                 135                 140

Ser Ser Lys Lys Ala Asp Leu Arg Leu Val Tyr Leu Ala Leu Ala His
145                 150                 155                 160

Met Ile Lys Tyr Arg Gly His Phe Leu Ile Glu Gly Asp Phe Asn Ser
                165                 170                 175

Lys Asn Asn Asp Leu Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Ser Ala Lys Lys Asp Arg
    210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Tyr Phe
                245                 250                 255

Asn Leu Asp Glu Lys Thr Ser Leu Gln Phe Ser Lys Glu Ser Tyr Asp
            260                 265                 270

Glu Asp Leu Glu Thr Leu Leu Gly His Ile Gly Asp Asp Tyr Ser Asp

-continued

```
            275                 280                 285
Val Phe Leu Lys Ala Lys Lys Leu Tyr Asp Ala Ile Leu Leu Ser Gly
290                 295                 300

Ile Leu Thr Val Thr Asp Asn Gly Thr Glu Ala Pro Leu Ser Ser Ala
305                 310                 315                 320

Met Ile Met Arg Tyr Lys Glu His Glu Glu Asp Leu Ala Leu Leu Lys
                325                 330                 335

Ala Tyr Ile Arg Asn Ile Ser Leu Glu Thr Tyr Asn Glu Val Phe Lys
                340                 345                 350

Asp Asn Thr Lys Asn Gly Tyr Ala Gly Tyr Ile Asp Gly Lys Thr Ser
                355                 360                 365

Gln Glu Asp Phe Tyr Val Tyr Leu Lys Arg Leu Leu Ala Gly Leu Glu
370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile Tyr Leu
                405                 410                 415

Gln Glu Met Arg Ala Ile Leu Asp Lys Gln Ala Lys Phe Tyr Pro Phe
                420                 425                 430

Leu Ala Lys Asn Lys Glu Arg Ile Glu Lys Ile Leu Thr Phe Arg Ile
                435                 440                 445

Pro Tyr Tyr Val Gly Pro Leu Ala Arg Gly Asn Ser Asp Phe Ala Trp
450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
                500                 505                 510

Leu Leu Tyr Glu Asn Phe Thr Val Tyr Asn Glu Leu Thr Lys Val Arg
                515                 520                 525

Phe Ile Ala Glu Gly Met Arg Asp Tyr Gln Phe Leu Asp Ser Lys Gln
530                 535                 540

Lys Lys Asp Ile Val Arg Leu Tyr Phe Lys Gly Lys Arg Lys Val Thr
545                 550                 555                 560

Asp Lys Asp Ile Ile Glu Tyr Leu His Ala Ile Asp Gly Tyr Asp Gly
                565                 570                 575

Ile Glu Leu Lys Gly Ile Glu Lys Gln Phe Asn Ser Ser Leu Ser Thr
                580                 585                 590

Tyr His Asp Leu Leu Asn Ile Ile Asn Asp Lys Glu Phe Leu Asp Asp
                595                 600                 605

Ser Ser Asn Glu Thr Ile Ile Glu Glu Ile Ile His Thr Leu Thr Met
610                 615                 620

Phe Glu Asp Arg Glu Met Ile Lys Gln Arg Leu Ser Lys Phe Asp Asn
625                 630                 635                 640

Ile Phe Asp Lys Ser Val Leu Lys Lys Leu Ser Arg Arg His Tyr Thr
                645                 650                 655

Gly Trp Gly Lys Leu Ser Ala Lys Leu Ile Asn Gly Ile Arg Asp Glu
                660                 665                 670

Lys Ser Gly Asn Thr Ile Leu Asp Tyr Leu Ile Asp Asp Gly Val Ser
                675                 680                 685

Asn Arg Asn Phe Met Gln Leu Ile His Asp Asp Ala Leu Ser Phe Lys
690                 695                 700
```

-continued

Lys Lys Ile Lys Lys Ala Gln Ile Ile Gly Asp Lys Asp Asn Ile Lys
705                 710                 715                 720

Gln Val Val Lys Ser Leu Pro Gly Ser Pro Ala Ile Lys Lys Gly Ile
            725                 730                 735

Leu Gln Ser Ile Lys Ile Val Asp Glu Leu Val Lys Val Met Gly Arg
            740                 745                 750

Glu Pro Glu Ser Ile Val Val Glu Met Ala Arg Glu Asn Gln Tyr Thr
            755                 760                 765

Asn Gln Gly Lys Ser Asn Ser Gln Gln Arg Leu Lys Arg Leu Glu Glu
770                 775                 780

Ser Leu Lys Gly Leu Gly Ser Lys Ile Leu Lys Glu Asn Val Pro Thr
785                 790                 795                 800

Arg Leu Ser Lys Ile Asp Asn Asn Ala Leu Gln Asn Asp Arg Leu Tyr
                805                 810                 815

Leu Tyr Tyr Leu Gln Asn Gly Lys Asp Met Tyr Thr Gly Glu Glu Leu
                820                 825                 830

Asp Ile Asp Arg Leu Ser Asn Tyr Asp Ile Asp His Ile Ile Pro Gln
            835                 840                 845

Ala Phe Leu Lys Asp Asp Ser Ile Asp Asn Lys Val Leu Val Ser Ser
850                 855                 860

Ala Ser Asn Arg Gly Lys Ser Asp Asp Val Pro Ser Leu Glu Val Val
865                 870                 875                 880

Lys Lys Arg Lys Thr Leu Trp Tyr Gln Leu Leu Lys Ser Lys Leu Ile
                885                 890                 895

Ser Gln Arg Lys Phe Asp Asn Leu Thr Lys Ala Glu Arg Gly Gly Leu
            900                 905                 910

Ser Gln Glu Glu Lys Ala Gly Phe Ile Gln Arg Gln Leu Val Glu Thr
            915                 920                 925

Arg Gln Ile Thr Lys His Val Ala Arg Leu Leu Asp Glu Arg Phe Asn
930                 935                 940

Asn Lys Lys Asp Glu Asn Asn Arg Thr Leu Arg Thr Val Lys Ile Ile
945                 950                 955                 960

Thr Leu Lys Ser Ser Leu Val Ser Gln Phe Arg Lys Asp Phe Glu Leu
                965                 970                 975

Tyr Lys Val Arg Glu Ile Asn Asp Phe His His Ala His Asp Ala Tyr
                980                 985                 990

Leu Asn Ala Val Val Ala Ser Ala Leu Leu Lys Lys Tyr Pro Lys Leu
            995                 1000                1005

Glu Pro Glu Phe Val Tyr Gly Asp Tyr Pro Lys Tyr Asn Ser Phe
    1010                1015                1020

Arg Glu Arg Lys Ser Ala Thr Glu Lys Val Tyr Phe Tyr Ser Asn
    1025                1030                1035

Ile Met Asn Ile Phe Lys Lys Ser Ile Pro Leu Ala Asp Gly Thr
    1040                1045                1050

Val Ile Asp Arg Pro Leu Ile Glu Val Asn Glu Glu Thr Gly Glu
    1055                1060                1065

Ser Val Trp Asn Lys Val Ala Asp Leu Asn Thr Val Arg Lys Val
    1070                1075                1080

Leu Ser Tyr Ser Gln Val Asn Ile Val Lys Lys Val Glu Glu Gln
    1085                1090                1095

Asn His Gly Leu Asp Arg Gly Lys Pro Lys Gly Leu Phe Asn Ala
    1100                1105                1110

Asn Leu Ser Ser Lys Pro Lys Pro Asn Ser Lys Glu Asn Leu Val
    1115                1120                1125

Gly Ala Lys Glu Tyr Leu Asp Pro Lys Tyr Gly Gly Tyr Ala
    1130                1135                1140

Gly Ile Ser Asn Ser Phe Ala Ile Leu Val Lys Gly Thr Ile Glu
    1145                1150                1155

Lys Gly Ala Lys Lys Ile Thr Asn Val Leu Glu Phe Gln Gly
    1160                1165                1170

Ile Ser Ile Leu Asp Arg Ile Tyr Tyr Arg Lys Asp Lys Leu Asn
    1175                1180                1185

Phe Leu Leu Glu Lys Gly Tyr Lys Asp Ile Glu Leu Ile Ile Glu
    1190                1195                1200

Leu Pro Lys Tyr Ser Leu Phe Glu Leu Ser Asp Gly Ser Arg Arg
    1205                1210                1215

Met Leu Ala Ser Ile Leu Ser Thr Asn Asn Lys Arg Gly Glu Ile
    1220                1225                1230

His Lys Gly Asn Gln Ile Phe Ile Ser Gln Lys Phe Val Lys Leu
    1235                1240                1245

Leu Tyr His Ala Lys Arg Ile Ser Ser Thr Phe Asn Glu Asn His
    1250                1255                1260

Arg Lys Tyr Val Glu Asn His Lys Lys Glu Phe Glu Glu Leu Phe
    1265                1270                1275

Tyr Tyr Ile Leu Glu Phe Asn Glu Asn Tyr Val Gly Ala Lys Lys
    1280                1285                1290

Asn Gly Glu Leu Leu Lys Ser Ala Phe Gln Ser Trp Gln Asn His
    1295                1300                1305

Ser Ile Asp Glu Leu Cys Ser Ser Phe Ile Gly Pro Thr Gly Ser
    1310                1315                1320

Glu Arg Lys Gly Leu Phe Glu Leu Thr Ser Arg Gly Gly Ala Ala
    1325                1330                1335

Asp Phe Glu Phe Leu Gly Val Lys Ile Pro Arg Tyr Arg Asp Tyr
    1340                1345                1350

Thr Pro Ser Ser Leu Leu Lys Asp Ala Thr Leu Ile His Gln Ser
    1355                1360                1365

Val Thr Gly Leu Tyr Glu Thr Arg Ile Asp Leu Gly Lys Leu Gly
    1370                1375                1380

Glu Asp
    1385

<210> SEQ ID NO 12
<211> LENGTH: 1392
<212> TYPE: PRT
<213> ORGANISM: Streptococcus sanguinis SK330

<400> SEQUENCE: 12

Met Glu Asn Lys Asn Tyr Ser Ile Gly Leu Asp Ile Gly Thr Asn Ser
1               5                   10                  15

Val Gly Trp Ala Val Ile Thr Asp Asp Tyr Lys Val Pro Ser Lys Lys
            20                  25                  30

Met Lys Val Phe Gly Asn Thr Asp Lys His Phe Ile Lys Lys Asn Leu
        35                  40                  45

Ile Gly Ala Leu Leu Phe Asp Glu Gly Ala Thr Ala Glu Asp Arg Arg
    50                  55                  60

Leu Lys Arg Thr Ala Arg Arg Arg Tyr Thr Arg Arg Lys Asn Arg Leu
65                  70                  75                  80

```
Arg Tyr Leu Gln Glu Ile Phe Ser Glu Ile Ser Lys Leu Asp Ser
                 85                  90                  95

Ser Phe Phe His Arg Leu Asp Asp Ser Phe Leu Val Pro Lys Asp Lys
            100                 105                 110

Arg Gly Ser Lys Tyr Pro Ile Phe Ala Thr Leu Glu Glu Lys Glu
        115                 120                 125

Tyr His Lys Lys Phe Pro Thr Ile Tyr His Leu Arg Lys His Leu Ala
    130                 135                 140

Asp Ser Lys Glu Lys Thr Asp Leu Arg Leu Ile Tyr Leu Ala Leu Ala
145                 150                 155                 160

His Met Ile Lys Tyr Arg Gly His Phe Leu Tyr Glu Glu Ser Phe Asp
                165                 170                 175

Ile Lys Asn Asn Asp Ile Gln Lys Ile Phe Asn Glu Phe Ile Ser Ile
                180                 185                 190

Tyr Asp Asn Thr Phe Glu Gly Ser Ser Leu Ser Gly Gln Asn Ala Gln
            195                 200                 205

Val Glu Ala Ile Phe Thr Asp Lys Ile Ser Lys Ser Ala Lys Arg Glu
        210                 215                 220

Arg Val Leu Lys Leu Phe Ser Asp Glu Lys Ser Thr Ser Leu Phe Ser
225                 230                 235                 240

Glu Phe Leu Lys Leu Ile Val Gly Asn Gln Ala Asp Phe Lys Lys His
                245                 250                 255

Phe Asp Leu Glu Glu Lys Ala Pro Leu Gln Phe Ser Lys Asp Thr Tyr
            260                 265                 270

Asp Glu Asp Leu Glu Asn Leu Leu Gly Gln Ile Gly Asp Gly Phe Thr
        275                 280                 285

Asp Leu Phe Leu Val Ala Lys Lys Leu Tyr Asp Ala Ile Leu Leu Ser
        290                 295                 300

Gly Ile Leu Thr Val Thr Asp Pro Ser Thr Lys Ala Pro Leu Ser Ala
305                 310                 315                 320

Ser Met Ile Glu Arg Tyr Glu Ser His Gln Lys Asp Leu Ala Ala Leu
                325                 330                 335

Lys Gln Phe Ile Lys Asn Asn Leu Pro Lys Arg Tyr Asn Glu Val Phe
            340                 345                 350

Ser Asp Gln Ser Lys Asp Gly Tyr Ala Gly Tyr Ile Asp Gly Lys Thr
        355                 360                 365

Thr Gln Glu Ala Phe Tyr Lys Tyr Ile Lys Asn Leu Leu Ser Lys Phe
    370                 375                 380

Glu Gly Ala Asp Tyr Phe Leu Asp Lys Ile Glu Arg Glu Asp Phe Leu
385                 390                 395                 400

Arg Lys Gln Arg Thr Phe Asp Asn Gly Ser Ile Pro His Gln Ile His
                405                 410                 415

Leu Gln Glu Met Asn Ala Ile Leu Arg Arg Gln Gly Glu His Tyr Pro
            420                 425                 430

Phe Leu Lys Glu Asn Arg Glu Lys Ile Glu Lys Ile Leu Thr Phe Arg
        435                 440                 445

Ile Pro Tyr Tyr Val Gly Pro Leu Ala Arg Gly Asn Arg Asp Phe Ala
    450                 455                 460

Trp Leu Thr Arg Asn Ser Asp Gln Ala Ile Arg Pro Trp Asn Phe Glu
465                 470                 475                 480

Glu Ile Val Asp Lys Ala Ser Ser Ala Glu Glu Phe Ile Asn Lys Met
                485                 490                 495
```

-continued

```
Thr Asn Tyr Asp Leu Tyr Leu Pro Glu Lys Val Leu Pro Lys His
            500                 505                 510

Ser Leu Leu Tyr Glu Thr Phe Ala Val Tyr Asn Glu Leu Thr Lys Val
        515                 520                 525

Lys Phe Ile Ala Glu Gly Leu Arg Asp Tyr Gln Phe Leu Asp Ser Gly
    530                 535                 540

Gln Lys Lys Gln Ile Val Asn Gln Leu Phe Lys Glu Arg Lys Val
545                 550                 555                 560

Thr Glu Lys Asp Ile Ile His Tyr Leu His Asn Val Asp Gly Tyr Asp
                565                 570                 575

Gly Ile Glu Leu Lys Gly Ile Glu Lys Gln Phe Asn Ala Ser Leu Ser
            580                 585                 590

Thr Tyr His Asp Leu Leu Lys Ile Ile Lys Asp Lys Glu Phe Met Asp
        595                 600                 605

Asp Pro Lys Asn Glu Glu Ile Leu Glu Asn Ile Val His Thr Leu Thr
    610                 615                 620

Ile Phe Glu Asp Arg Glu Met Ile Lys Gln Arg Leu Ala Gln Tyr Asp
625                 630                 635                 640

Ser Ile Phe Asp Glu Lys Val Ile Lys Ala Leu Thr Arg Arg His Tyr
                645                 650                 655

Thr Gly Trp Gly Lys Leu Ser Ala Lys Leu Ile Asn Gly Ile Cys Asp
            660                 665                 670

Lys Gln Thr Gly Asp Thr Ile Leu Asp Tyr Leu Ile Asp Asp Gly Lys
        675                 680                 685

Ile Asn Arg Asn Phe Met Gln Leu Ile Asn Asp Asp Gly Leu Ser Phe
    690                 695                 700

Lys Glu Ile Ile Gln Lys Ala Gln Val Val Gly Lys Thr Asp Asp Val
705                 710                 715                 720

Lys Gln Val Val Gln Glu Leu Pro Gly Ser Pro Ala Ile Lys Lys Gly
                725                 730                 735

Ile Leu Gln Ser Ile Lys Ile Val Asp Glu Leu Val Lys Val Met Gly
            740                 745                 750

Tyr Ala Pro Glu Ser Ile Val Ile Glu Met Ala Arg Glu Asn Gln Thr
        755                 760                 765

Thr Ala Arg Gly Lys Lys Asn Ser Gln Gln Arg Tyr Lys Arg Ile Glu
    770                 775                 780

Asp Ser Leu Lys Asn Leu Ala Pro Gly Leu Asp Ser Asn Ile Leu Lys
785                 790                 795                 800

Glu Asn Pro Thr Asp Asn Ile Gln Leu Gln Asn Asp Arg Leu Phe Leu
                805                 810                 815

Tyr Tyr Leu Gln Asn Gly Lys Asp Met Tyr Thr Gly Lys Pro Leu Asp
            820                 825                 830

Ile Asp Gln Leu Ser Ser Tyr Asp Ile Asp His Ile Ile Pro Gln Ala
        835                 840                 845

Phe Ile Lys Asp Asp Ser Ile Asp Asn Arg Val Leu Thr Ser Ser Lys
    850                 855                 860

Asp Asn Arg Gly Lys Ser Asp Asn Val Pro Ser Leu Glu Val Val Gln
865                 870                 875                 880

Lys Arg Lys Ala Phe Trp Gln Gln Leu Leu Asp Ser Lys Leu Ile Ser
                885                 890                 895

Glu Arg Lys Phe Asn Asn Leu Thr Lys Ala Glu Arg Gly Gly Leu Asp
            900                 905                 910

Glu Arg Asp Lys Val Gly Phe Ile Arg Arg Gln Leu Val Glu Thr Arg
```

-continued

```
            915                 920                 925
Gln Ile Thr Lys His Val Ala Gln Ile Leu Asp Ala Ser Phe Asn Thr
        930                 935                 940
Glu Val Asn Glu Lys Asn Gln Lys Ile Arg Thr Val Lys Ile Ile Thr
945                 950                 955                 960
Leu Lys Ser Asn Leu Val Ser Asn Phe Arg Lys Glu Phe Glu Leu Tyr
                965                 970                 975
Lys Val Arg Glu Ile Asn Asp Tyr His His Ala His Asp Ala Tyr Leu
            980                 985                 990
Asn Ala Val Val Ala Lys Ala Ile Leu Lys Lys Tyr Pro Lys Leu Glu
                995                 1000                1005
Pro Glu Phe Val Tyr Gly Asp Tyr Gln Lys Tyr Asp Leu Lys Arg
    1010                1015                1020
Tyr Ile Ser Arg Phe Lys Pro Ser Lys Glu Ile Glu Lys Ala Thr
    1025                1030                1035
Glu Lys Tyr Phe Phe Tyr Ser Asn Leu Leu Asn Phe Phe Lys Glu
    1040                1045                1050
Glu Val His Tyr Ala Asp Gly Ile Ile Val Lys Arg Glu Asn Ile
    1055                1060                1065
Glu Tyr Ser Lys Asp Thr Gly Glu Ile Ala Trp Asn Lys Glu Lys
    1070                1075                1080
Asp Phe Ala Thr Ile Lys Lys Val Leu Ser Tyr Pro Gln Val Asn
    1085                1090                1095
Ile Val Lys Lys Thr Glu Ile Gln Thr His Gly Leu Asp Arg Gly
    1100                1105                1110
Lys Pro Lys Gly Leu Phe Asn Ser Asn Pro Ser Pro Lys Pro Ser
    1115                1120                1125
Glu Asp Ser Lys Glu Asn Leu Val Pro Ile Lys Gln Gly Leu Asp
    1130                1135                1140
Pro Arg Lys Tyr Gly Gly Tyr Ala Gly Ile Ser Asn Ser Tyr Ala
    1145                1150                1155
Val Leu Val Lys Ala Ile Val Glu Lys Gly Ala Lys Lys Gln Gln
    1160                1165                1170
Lys Thr Ile Leu Glu Phe Gln Gly Ile Ser Ile Leu Asp Lys Ile
    1175                1180                1185
Asn Phe Glu Asn Asn Lys Glu Asn Tyr Leu Leu Lys Lys Arg Tyr
    1190                1195                1200
Ile Glu Ile Leu Ser Thr Ile Thr Leu Pro Lys Tyr Ser Leu Phe
    1205                1210                1215
Glu Phe Pro Asp Gly Thr Arg Arg Arg Leu Ala Ser Ile Leu Ser
    1220                1225                1230
Thr Asn Asn Lys Arg Gly Glu Ile His Lys Gly Asn Glu Leu Val
    1235                1240                1245
Leu Pro Gly Lys Tyr Thr Thr Leu Leu Tyr His Ala Lys Asn Ile
    1250                1255                1260
Asn Lys Lys Leu Glu Pro Glu His Leu Glu Tyr Val Glu Lys His
    1265                1270                1275
Arg Asn Asp Phe Ala Lys Leu Leu Glu Cys Val Leu Asn Phe Asn
    1280                1285                1290
Asp Lys Tyr Val Gly Ala Leu Lys Asn Gly Glu Arg Ile Arg Gln
    1295                1300                1305
Ala Phe Thr Asp Trp Glu Thr Val Asp Ile Glu Lys Leu Cys Phe
    1310                1315                1320
```

-continued

Ser Phe Ile Gly Pro Glu Asn Ser Lys Asn Ala Gly Leu Phe Glu
      1325                1330                1335

Leu Thr Ser Gln Gly Ser Ala Ser Asp Phe Glu Phe Leu Gly Val
     1340                1345                1350

Lys Ile Pro Arg Tyr Arg Asp Tyr Ala Pro Ser Ser Leu Leu Lys
     1355                1360                1365

Ala Thr Leu Ile His Gln Ser Ile Thr Gly Leu Tyr Glu Thr Arg
     1370                1375                1380

Ile Asp Leu Ser Lys Leu Gly Glu Asp
     1385                1390

<210> SEQ ID NO 13
<211> LENGTH: 1392
<212> TYPE: PRT
<213> ORGANISM: Streptococcus mitis SK321

<400> SEQUENCE: 13

Met Asn Asn Asn Tyr Ser Ile Gly Leu Asp Ile Gly Thr Asn Ser
1               5                   10                  15

Val Gly Trp Ala Val Ile Thr Asp Asp Tyr Lys Val Pro Ser Lys Lys
            20                  25                  30

Met Lys Val Leu Gly Asn Thr Asp Lys His Phe Ile Lys Lys Asn Leu
        35                  40                  45

Ile Gly Ala Leu Leu Phe Asp Glu Gly Ala Thr Ala Glu Asp Arg Arg
    50                  55                  60

Phe Lys Arg Thr Ala Arg Arg Arg Tyr Thr Arg Arg Lys Asn Arg Leu
65                  70                  75                  80

Arg Tyr Leu Gln Glu Ile Phe Ser Glu Glu Met Ser Lys Val Asp Ser
                85                  90                  95

Ser Phe Phe His Arg Leu Asp Asp Ser Phe Leu Val Pro Glu Asp Lys
            100                 105                 110

Arg Gly Ser Lys Tyr Pro Ile Phe Ala Thr Leu Ala Glu Glu Lys Glu
        115                 120                 125

Tyr His Lys Lys Phe Pro Thr Ile Tyr His Leu Arg Lys His Leu Ala
    130                 135                 140

Asp Ser Lys Glu Lys Thr Asp Leu Arg Leu Ile Tyr Leu Ala Leu Ala
145                 150                 155                 160

His Met Ile Lys Tyr Arg Gly His Phe Leu Tyr Glu Glu Ser Phe Asp
                165                 170                 175

Ile Lys Asn Asn Asp Ile Gln Lys Ile Phe Ser Glu Phe Ile Ser Ile
            180                 185                 190

Tyr Asp Asn Thr Phe Glu Gly Ser Ser Leu Ser Gly Gln Asn Ala Gln
        195                 200                 205

Val Glu Ala Ile Phe Thr Asp Lys Ile Ser Lys Ser Ala Lys Arg Glu
    210                 215                 220

Arg Ile Leu Lys Leu Phe Ala Tyr Glu Lys Ser Thr Asp Leu Phe Ser
225                 230                 235                 240

Glu Phe Leu Lys Leu Ile Val Gly Asn Gln Ala Asp Phe Lys Lys His
                245                 250                 255

Phe Asp Leu Glu Glu Lys Ala Pro Leu Gln Phe Ser Lys Asp Thr Tyr
            260                 265                 270

Asp Glu Asp Leu Glu Asn Leu Leu Gly Gln Ile Gly Asp Asp Phe Ala
        275                 280                 285

Asp Leu Phe Leu Val Ala Lys Lys Leu Tyr Asp Ala Ile Leu Leu Ser

```
                290                 295                 300
Gly Ile Leu Thr Val Thr Asp Ser Ser Thr Lys Ala Pro Leu Ser Ala
305                 310                 315                 320

Ser Met Ile Glu Arg Tyr Glu Asn His Gln Lys Asp Leu Ala Ala Leu
                325                 330                 335

Lys Gln Phe Ile Gln Asn Asn Leu Gln Glu Lys Tyr Asp Glu Val Phe
                340                 345                 350

Ser Asp Gln Ser Lys Asp Gly Tyr Ala Arg Tyr Ile Asn Gly Lys Thr
                355                 360                 365

Thr Gln Glu Ala Phe Tyr Lys Tyr Ile Lys Asn Leu Leu Ser Lys Phe
370                 375                 380

Glu Gly Ser Asp Tyr Phe Leu Asp Lys Ile Glu Arg Glu Asp Phe Leu
385                 390                 395                 400

Arg Lys Gln Arg Thr Phe Asp Asn Gly Ser Ile Pro His Gln Ile His
                405                 410                 415

Leu Gln Glu Met Asn Ala Ile Ile Arg Arg Gln Gly Glu His Tyr Pro
                420                 425                 430

Phe Leu Lys Glu Tyr Lys Glu Lys Ile Glu Thr Ile Leu Thr Phe Arg
                435                 440                 445

Ile Pro Tyr Tyr Val Gly Pro Leu Ala Arg Gly Asn Arg Asn Phe Ala
450                 455                 460

Trp Leu Thr Arg Asn Ser Asp Gln Ala Ile Arg Pro Trp Asn Phe Glu
465                 470                 475                 480

Glu Ile Val Asp Gln Ala Ser Ser Ala Glu Glu Phe Ile Asn Lys Met
                485                 490                 495

Thr Asn Tyr Asp Leu Tyr Leu Pro Glu Glu Lys Val Leu Pro Lys His
                500                 505                 510

Ser Leu Leu Tyr Glu Thr Phe Ala Val Tyr Asn Glu Leu Thr Lys Val
                515                 520                 525

Lys Phe Ile Ser Glu Gly Leu Arg Asp Tyr Gln Phe Leu Asp Ser Gly
                530                 535                 540

Gln Lys Lys Gln Ile Val Asn Gln Leu Phe Lys Glu Lys Arg Lys Val
545                 550                 555                 560

Thr Glu Lys Asp Ile Ile Gln Tyr Leu His Asn Val Asp Gly Tyr Asp
                565                 570                 575

Gly Ile Glu Leu Lys Gly Ile Glu Lys Gln Phe Asn Ala Ser Leu Ser
                580                 585                 590

Thr Tyr His Asp Leu Leu Lys Ile Ile Lys Asp Lys Glu Phe Met Asp
                595                 600                 605

Asp Pro Lys Asn Glu Glu Ile Leu Glu Asn Ile Val His Thr Leu Thr
610                 615                 620

Ile Phe Glu Asp Arg Glu Met Ile Lys Gln Arg Leu Ala Gln Tyr Ala
625                 630                 635                 640

Ser Ile Phe Asp Lys Lys Val Ile Lys Ala Leu Thr Arg Arg His Tyr
                645                 650                 655

Thr Gly Trp Gly Lys Leu Ser Ala Lys Leu Ile Asn Gly Ile Cys Asp
                660                 665                 670

Lys Lys Thr Gly Lys Thr Ile Leu Asp Tyr Leu Ile Asp Asp Gly Tyr
                675                 680                 685

Ser Asn Arg Asn Phe Met Gln Leu Ile Asn Asp Asp Gly Leu Ser Phe
                690                 695                 700

Lys Asp Ile Ile Gln Lys Ala Gln Val Val Gly Lys Thr Asn Asp Val
705                 710                 715                 720
```

-continued

Lys Gln Val Val Gln Glu Leu Pro Gly Ser Pro Ala Ile Lys Gly
            725                 730                 735

Ile Leu Gln Ser Ile Lys Leu Val Asp Glu Leu Val Lys Val Met Gly
            740                 745                 750

His Ala Pro Glu Ser Ile Val Ile Glu Ile Ala Arg Glu Asn Gln Thr
            755                 760                 765

Thr Ala Arg Gly Lys Lys Asn Ser Gln Gln Arg Tyr Lys Arg Ile Glu
            770                 775                 780

Asp Ala Leu Lys Asn Leu Ala Pro Gly Leu Asp Ser Asn Ile Leu Lys
785                 790                 795                 800

Glu His Pro Thr Asp Asn Ile Gln Leu Gln Asn Asp Arg Leu Phe Leu
                805                 810                 815

Tyr Tyr Leu Gln Asn Gly Lys Asp Met Tyr Thr Gly Glu Ala Leu Asp
                820                 825                 830

Ile Asn Gln Leu Ser Ser Tyr Asp Ile Asp His Ile Val Pro Gln Ala
            835                 840                 845

Phe Ile Lys Asp Asp Ser Leu Asp Asn Arg Val Leu Thr Ser Ser Lys
        850                 855                 860

Asp Asn Arg Gly Lys Ser Asp Asn Val Pro Ser Leu Glu Val Val Gln
865                 870                 875                 880

Lys Arg Lys Ala Phe Trp Gln Gln Leu Leu Asp Ser Lys Leu Ile Ser
                885                 890                 895

Glu His Lys Phe Asn Asn Leu Thr Lys Ala Glu Arg Gly Gly Leu Asp
                900                 905                 910

Glu Arg Asp Lys Val Gly Phe Ile Arg Arg Gln Leu Val Glu Thr Arg
            915                 920                 925

Gln Ile Thr Lys His Val Ala Gln Ile Leu Asp Ala Arg Phe Asn Thr
930                 935                 940

Glu Val Asn Glu Lys Asp Lys Lys Asn Arg Thr Val Lys Ile Ile Thr
945                 950                 955                 960

Leu Lys Ser Asn Leu Val Ser Asn Phe Arg Lys Glu Phe Lys Leu Tyr
                965                 970                 975

Lys Val Arg Glu Ile Asn Asp Tyr His His Ala His Asp Ala Tyr Leu
            980                 985                 990

Asn Ala Val Val Ala Lys Ala Ile Leu Lys Lys Tyr Pro Lys Leu Glu
            995                 1000                1005

Pro Gly Phe Val Tyr Gly Asp Tyr Gln Lys Tyr Asp Ile Lys Arg
    1010                1015                1020

Tyr Ile Ser Arg Ser Lys Asp Pro Lys Glu Val Glu Lys Ala Thr
    1025                1030                1035

Glu Lys Tyr Phe Phe Tyr Ser Asn Leu Leu Asn Phe Phe Lys Glu
    1040                1045                1050

Glu Val His Tyr Ala Asp Gly Thr Ile Val Lys Arg Glu Asn Ile
    1055                1060                1065

Glu Tyr Ser Lys Asp Thr Gly Glu Ile Ala Trp Asn Lys Glu Lys
    1070                1075                1080

Asp Phe Ala Thr Ile Lys Lys Val Leu Ser Leu Pro Gln Val Asn
    1085                1090                1095

Ile Val Lys Lys Thr Glu Ile Gln Thr His Gly Leu Asp Arg Gly
    1100                1105                1110

Lys Pro Arg Gly Leu Phe Asn Ser Asn Pro Ser Pro Lys Pro Ser
    1115                1120                1125

Glu Asp Arg Lys Glu Asn Leu Val Pro Ile Lys Gln Gly Leu Asp
   1130                1135                1140

Pro Arg Lys Tyr Gly Gly Tyr Ala Gly Ile Ser Asn Ser Tyr Ala
   1145                1150                1155

Val Leu Val Lys Ala Ile Ile Glu Lys Gly Ala Lys Lys Gln Gln
   1160                1165                1170

Lys Thr Val Leu Glu Phe Gln Gly Ile Ser Ile Leu Asp Lys Ile
   1175                1180                1185

Asn Phe Glu Lys Asn Lys Glu Asn Tyr Leu Leu Glu Lys Gly Tyr
   1190                1195                1200

Ile Lys Ile Leu Ser Thr Ile Thr Leu Pro Lys Tyr Ser Leu Phe
   1205                1210                1215

Glu Phe Pro Asp Gly Thr Arg Arg Leu Ala Ser Ile Leu Ser
   1220                1225                1230

Thr Asn Asn Lys Arg Gly Glu Ile His Lys Gly Asn Glu Leu Val
   1235                1240                1245

Ile Pro Glu Lys Tyr Thr Thr Leu Leu Tyr His Ala Lys Asn Ile
   1250                1255                1260

Asn Lys Thr Leu Glu Pro Glu His Leu Glu Tyr Val Glu Lys His
   1265                1270                1275

Arg Asn Asp Phe Ala Lys Leu Leu Glu Tyr Val Leu Asn Phe Asn
   1280                1285                1290

Asp Lys Tyr Val Gly Ala Leu Lys Asn Gly Glu Arg Ile Arg Gln
   1295                1300                1305

Ala Phe Ile Asp Trp Glu Thr Val Asp Ile Glu Lys Leu Cys Phe
   1310                1315                1320

Ser Phe Ile Gly Pro Arg Asn Ser Lys Asn Ala Gly Leu Phe Glu
   1325                1330                1335

Leu Thr Ser Gln Gly Ser Ala Ser Asp Phe Glu Phe Leu Gly Val
   1340                1345                1350

Lys Ile Pro Arg Tyr Arg Asp Tyr Thr Pro Ser Ser Leu Leu Asn
   1355                1360                1365

Ala Thr Leu Ile His Gln Ser Ile Thr Gly Leu Tyr Glu Thr Arg
   1370                1375                1380

Ile Asp Leu Ser Lys Leu Gly Glu Asp
   1385                1390

<210> SEQ ID NO 14
<211> LENGTH: 1373
<212> TYPE: PRT
<213> ORGANISM: Streptococcus oralis SK304

<400> SEQUENCE: 14

Met Glu Asn Lys Asn Tyr Ser Ile Gly Leu Asp Ile Gly Thr Asn Ser
  1               5                  10                  15

Val Gly Trp Ala Val Ile Thr Asp Asp Tyr Lys Val Pro Ser Lys Lys
             20                  25                  30

Met Lys Val Leu Gly Asn Thr Asp Lys Arg Phe Ile Lys Lys Asn Leu
         35                  40                  45

Ile Gly Ala Leu Leu Phe Asp Glu Gly Thr Thr Ala Glu Ala Arg Arg
     50                  55                  60

Leu Lys Arg Thr Ala Arg Arg Arg Tyr Thr Arg Arg Lys Asn Arg Leu
 65                  70                  75                  80

Arg Tyr Leu Gln Glu Ile Phe Ala Glu Glu Met Ser Lys Val Asp Ser
                 85                  90                  95

```
Ser Phe Phe His Arg Leu Asp Asp Ser Phe Leu Ile Pro Glu Asp Lys
                100                 105                 110

Lys Gly Ser Lys Tyr Pro Ile Phe Ala Thr Leu Ile Glu Glu Lys Glu
            115                 120                 125

Tyr His Lys Gln Phe Pro Thr Ile Tyr His Leu Arg Lys Gln Leu Ala
        130                 135                 140

Asp Ser Lys Glu Lys Thr Asp Leu Arg Leu Ile Tyr Leu Ala Leu Ala
145                 150                 155                 160

His Met Ile Lys Tyr Arg Gly His Phe Leu Tyr Glu Asp Thr Phe Asp
                165                 170                 175

Ile Lys Asn Asn Asp Ile Gln Lys Ile Phe Asn Glu Phe Ile Ser Ile
            180                 185                 190

Tyr Asn Asn Thr Phe Glu Gly Asn Ser Leu Ser Gly Gln Asn Val Gln
        195                 200                 205

Val Glu Ala Ile Phe Thr Asp Lys Ile Ser Lys Ser Ala Lys Arg Glu
210                 215                 220

Arg Val Leu Lys Leu Phe Pro Asp Glu Lys Ser Thr Gly Leu Phe Ser
225                 230                 235                 240

Glu Phe Leu Lys Leu Ile Val Gly Asn Gln Ala Asp Phe Lys Lys His
                245                 250                 255

Phe Asp Leu Glu Glu Lys Ala Pro Leu Gln Phe Ser Arg Asp Thr Tyr
            260                 265                 270

Asp Glu Asp Leu Glu Asn Leu Leu Gly Gln Ile Gly Asp Asp Phe Ala
        275                 280                 285

Asp Leu Phe Val Ala Ala Lys Lys Leu Tyr Asp Ala Ile Leu Leu Ser
        290                 295                 300

Gly Ile Leu Thr Val Thr Asp Pro Ser Thr Lys Ala Pro Leu Ser Ala
305                 310                 315                 320

Ser Met Ile Glu Arg Tyr Glu Asn His Gln Lys Asp Leu Ala Thr Leu
                325                 330                 335

Lys Gln Phe Ile Lys Thr Asn Leu Pro Glu Lys Tyr Asp Glu Val Phe
            340                 345                 350

Ser Asp Gln Ser Lys Asp Gly Tyr Ala Gly Tyr Ile Asp Gly Lys Thr
        355                 360                 365

Thr Gln Glu Ser Phe Tyr Lys Tyr Ile Lys Asn Leu Leu Ser Lys Phe
        370                 375                 380

Glu Gly Ala Asp Tyr Phe Leu Glu Lys Ile Glu Arg Glu Asp Phe Leu
385                 390                 395                 400

Arg Lys Gln Arg Thr Phe Asp Asn Gly Ser Ile Pro His Gln Ile His
                405                 410                 415

Leu Gln Glu Met Asn Ala Ile Leu Arg Arg Gln Gly His Tyr Pro
            420                 425                 430

Phe Leu Lys Glu Asn Lys Glu Lys Ile Glu Lys Ile Leu Thr Phe Arg
        435                 440                 445

Ile Pro Tyr Tyr Val Gly Pro Leu Ala Arg Gly Asn Arg Asp Phe Ala
        450                 455                 460

Trp Leu Thr Arg Asn Ser Asp Gln Ala Ile Arg Pro Trp Asn Phe Glu
465                 470                 475                 480

Glu Ile Val Asp Lys Ala Ser Ser Ala Glu Ser Phe Ile Asn Lys Met
                485                 490                 495

Thr Asn Tyr Asp Leu Tyr Leu Pro Glu Glu Lys Val Leu Pro Lys His
            500                 505                 510
```

-continued

```
Ser Leu Leu Tyr Glu Thr Phe Ala Val Tyr Asn Glu Leu Thr Lys Val
            515                 520                 525

Lys Phe Ile Ala Glu Gly Leu Arg Asp Tyr Gln Phe Leu Asp Ser Arg
    530                 535                 540

Gln Lys Lys Asp Ile Phe Tyr Thr Leu Phe Lys Ala Glu Asp Lys Arg
545                 550                 555                 560

Lys Val Thr Glu Lys Asp Ile Ile Gln Tyr Leu His Thr Val Asp Gly
                565                 570                 575

Tyr Asp Gly Ile Glu Leu Lys Gly Ile Glu Lys Gln Phe Asn Ala Ser
            580                 585                 590

Leu Ser Thr Tyr His Asp Leu Leu Lys Ile Ile Lys Asp Lys Glu Phe
        595                 600                 605

Met Asp Asp Pro Asn Asn Glu Glu Ile Leu Glu Asn Ile Val His Thr
    610                 615                 620

Leu Thr Ile Phe Glu Asp Arg Glu Met Ile Lys Gln Arg Leu Ala Gln
625                 630                 635                 640

Tyr Asp Ser Leu Phe Asp Glu Lys Val Ile Lys Ala Leu Thr Arg Arg
                645                 650                 655

His Tyr Thr Gly Trp Gly Lys Leu Ser Ser Lys Leu Ile Asn Gly Ile
            660                 665                 670

Arg Asp Lys Gln Thr Gly Lys Thr Ile Leu Asp Tyr Leu Met Asp Asp
        675                 680                 685

Gly Tyr Asn Asn Arg Asn Phe Met Gln Leu Ile Asn Asp Asp Glu Leu
    690                 695                 700

Ser Phe Lys Glu Ile Ile Lys Lys Ala Gln Val Val Gly Lys Thr Asp
705                 710                 715                 720

Asp Val Lys Gln Val Val Gln Glu Leu Pro Gly Ser Pro Ala Ile Lys
                725                 730                 735

Lys Gly Ile Leu Gln Ser Ile Lys Leu Val Asp Glu Leu Val Lys Val
            740                 745                 750

Met Gly His Glu Pro Glu Ser Ile Val Ile Glu Met Ala Arg Glu Asn
        755                 760                 765

Gln Thr Thr Ala Arg Gly Lys Lys Asn Ser Gln Gln Arg Tyr Lys Arg
    770                 775                 780

Ile Glu Asp Ser Leu Lys Ile Leu Ala Ser Gly Leu Asn Ala Lys Ile
785                 790                 795                 800

Leu Lys Glu His Pro Thr Asp Asn Ile Gln Leu Gln Asn Asp Arg Leu
                805                 810                 815

Phe Leu Tyr Tyr Leu Gln Asn Gly Arg Asp Met Tyr Thr Gly Lys Pro
            820                 825                 830

Leu Asp Ile Asn Gln Leu Ser Ser Tyr Asp Ile Asp His Ile Val Pro
        835                 840                 845

Gln Ala Phe Ile Lys Asp Asp Ser Leu Asp Asn Arg Val Leu Thr Ser
    850                 855                 860

Leu Lys Asp Asn Arg Gly Lys Ser Asp Asn Val Pro Ser Leu Glu Val
865                 870                 875                 880

Val Glu Lys Met Lys Thr Phe Trp Gln Gln Leu Leu Asp Ser Lys Leu
                885                 890                 895

Ile Ser Tyr Arg Lys Phe Asn Asn Leu Thr Lys Ala Glu Arg Gly Gly
            900                 905                 910

Leu Asp Glu Arg Asp Lys Val Gly Phe Ile Lys Arg Gln Leu Val Glu
        915                 920                 925

Thr Arg Gln Ile Thr Lys His Val Ala Gln Ile Leu Asp Ala Arg Tyr
```

-continued

```
                930                 935                 940
Asn Thr Glu Val Asn Glu Lys Asp Lys Lys Asn Arg Thr Val Lys Ile
945                 950                 955                 960
Ile Thr Leu Lys Ser Asn Leu Val Ser Asn Phe Arg Lys Glu Phe Arg
                965                 970                 975
Leu Tyr Lys Ile Arg Glu Ile Asn Asp Tyr His His Ala His Asp Ala
                980                 985                 990
Tyr Leu Asn Ala Val Val Ala Lys Ala Ile Leu Lys Lys Tyr Pro Lys
            995                1000                1005
Leu Glu Pro Glu Phe Val Tyr Gly Asp Tyr Gln Lys Tyr Asp Leu
       1010                1015                1020
Lys Arg Tyr Ile Ser Arg Ser Lys Asp Pro Lys Glu Ile Glu Lys
       1025                1030                1035
Ala Thr Glu Lys Tyr Phe Phe Tyr Ser Asn Leu Leu Asn Phe Phe
       1040                1045                1050
Lys Glu Glu Val His Tyr Ala Asp Gly Thr Ile Val Lys Arg Glu
       1055                1060                1065
Asn Ile Glu Tyr Ser Lys Asp Thr Gly Glu Ile Ala Trp Asn Lys
       1070                1075                1080
Glu Lys Asp Phe Ala Thr Ile Lys Lys Val Leu Ser Leu Pro Gln
       1085                1090                1095
Val Asn Ile Val Lys Lys Arg Glu Val Gln Thr Gly Gly Phe Ser
       1100                1105                1110
Lys Glu Ser Ile Leu Pro Lys Gly Asn Ser Asp Lys Leu Ile Pro
       1115                1120                1125
Arg Lys Thr Lys Asp Ile Leu Trp Asp Thr Thr Lys Tyr Gly Gly
       1130                1135                1140
Phe Asp Ser Pro Val Ile Ala Tyr Ser Ile Leu Leu Ile Ala Asp
       1145                1150                1155
Ile Glu Lys Gly Lys Ala Lys Arg Leu Lys Thr Val Lys Thr Leu
       1160                1165                1170
Val Gly Ile Thr Ile Met Glu Lys Ala Thr Phe Glu Lys Ser Pro
       1175                1180                1185
Ile Ala Phe Leu Glu Asn Lys Gly Tyr His Asn Val Arg Lys Glu
       1190                1195                1200
Asn Ile Leu Cys Leu Pro Lys Tyr Ser Leu Phe Glu Leu Lys Asn
       1205                1210                1215
Gly Arg Arg Arg Met Leu Ala Ser Ala Lys Glu Leu Gln Lys Gly
       1220                1225                1230
Asn Glu Ile Val Leu Pro Val His Leu Thr Thr Leu Leu Tyr His
       1235                1240                1245
Ala Lys Asn Ile His Arg Leu Asp Glu Pro Glu His Leu Glu Tyr
       1250                1255                1260
Ile Gln Lys His Arg Asn Glu Phe Lys Gly Leu Leu Asn Leu Val
       1265                1270                1275
Ser Glu Phe Ser Gln Lys Tyr Val Leu Ala Asp Ala Asn Leu Glu
       1280                1285                1290
Lys Ile Lys Asn Leu Tyr Ala Asp Asn Glu Gln Ala Asp Ile Glu
       1295                1300                1305
Ile Leu Ala Asn Ser Phe Ile Asn Leu Leu Thr Phe Thr Ala Leu
       1310                1315                1320
Gly Ala Pro Ala Ala Phe Lys Phe Phe Gly Lys Asp Val Asp Arg
       1325                1330                1335
```

```
Lys Arg Tyr Thr Thr Val Ser Glu Ile Leu Asn Ala Thr Leu Ile
    1340                1345                1350

His Gln Ser Ile Thr Gly Leu Tyr Glu Thr Arg Ile Asp Leu Ser
    1355                1360                1365

Lys Leu Gly Glu Asp
    1370

<210> SEQ ID NO 15
<211> LENGTH: 1370
<212> TYPE: PRT
<213> ORGANISM: Streptococcus agalactiae GB00300

<400> SEQUENCE: 15

Met Asn Lys Pro Tyr Ser Ile Gly Leu Asp Ile Gly Thr Asn Ser Val
1               5                   10                  15

Gly Trp Ser Ile Ile Thr Asp Asp Tyr Lys Val Pro Ala Lys Lys Ile
            20                  25                  30

Arg Val Leu Gly Asn Thr Asp Lys Glu Tyr Ile Lys Lys Asn Leu Ile
        35                  40                  45

Gly Ala Leu Leu Phe Asp Gly Gly Asn Thr Ala Ala Asp Arg Arg Leu
    50                  55                  60

Lys Arg Thr Ala Arg Arg Arg Tyr Thr Arg Arg Asn Arg Ile Leu
65                  70                  75                  80

Tyr Leu Gln Glu Ile Phe Ala Glu Glu Met Ser Lys Val Asp Asp Ser
                85                  90                  95

Phe Phe His Arg Leu Glu Asp Ser Phe Leu Val Glu Glu Asp Lys Arg
            100                 105                 110

Gly Ser Lys Tyr Pro Ile Phe Ala Thr Leu Gln Glu Glu Lys Tyr Tyr
        115                 120                 125

His Glu Lys Phe Pro Thr Ile Tyr His Leu Arg Lys Glu Leu Ala Asp
    130                 135                 140

Lys Lys Glu Lys Ala Asp Leu Arg Leu Val Tyr Leu Ala Leu Ala His
145                 150                 155                 160

Ile Ile Lys Phe Arg Gly His Phe Leu Ile Glu Asp Asp Arg Phe Asp
                165                 170                 175

Val Arg Asn Thr Asp Ile Gln Lys Gln Tyr Gln Ala Phe Leu Glu Ile
            180                 185                 190

Phe Asp Thr Thr Phe Glu Asn Asn Asp Leu Leu Ser Gln Asp Val Asp
        195                 200                 205

Val Glu Ala Ile Leu Thr Asp Lys Ile Ser Lys Ser Ala Lys Lys Asp
    210                 215                 220

Arg Ile Leu Ala Gln Tyr Pro Asn Gln Lys Ser Thr Gly Ile Phe Ala
225                 230                 235                 240

Glu Phe Leu Lys Leu Ile Val Gly Asn Gln Ala Asp Phe Lys Lys His
                245                 250                 255

Phe Asn Leu Glu Asp Lys Thr Pro Leu Gln Phe Ala Lys Asp Ser Tyr
            260                 265                 270

Asp Glu Asp Leu Glu Asn Leu Leu Gly Gln Ile Gly Asp Glu Phe Ala
        275                 280                 285

Asp Leu Phe Ser Ala Ala Lys Lys Leu Tyr Asp Ser Val Leu Leu Ser
    290                 295                 300

Gly Ile Leu Thr Val Thr Asp Leu Ser Thr Lys Ala Pro Leu Ser Ala
305                 310                 315                 320

Ser Met Ile Gln Arg Tyr Asp Glu His Arg Glu Asp Leu Lys Gln Leu
```

-continued

```
                325                 330                 335
Lys Gln Phe Val Lys Ala Ser Leu Pro Glu Lys Tyr Gln Glu Ile Val
                340                 345                 350
Ala Asp Ser Ser Lys Asp Gly Tyr Ala Gly Tyr Ile Glu Gly Lys Thr
                355                 360                 365
Asn Gln Glu Ala Phe Tyr Lys Tyr Leu Ser Lys Leu Leu Thr Lys Gln
                370                 375                 380
Glu Gly Ser Glu Tyr Phe Leu Glu Lys Ile Lys Asn Glu Asp Phe Leu
385                 390                 395                 400
Arg Lys Gln Arg Thr Phe Asp Asn Gly Ser Ile Pro His Gln Val His
                405                 410                 415
Leu Thr Glu Leu Arg Ala Ile Ile Arg Arg Gln Ser Glu Tyr Tyr Pro
                420                 425                 430
Phe Leu Lys Glu Asn Leu Asp Arg Ile Glu Lys Ile Leu Thr Phe Arg
                435                 440                 445
Ile Pro Tyr Tyr Val Gly Pro Leu Ala Arg Glu Lys Ser Asp Phe Ala
                450                 455                 460
Trp Met Thr Arg Lys Thr Asp Asp Ser Ile Arg Pro Trp Asn Phe Glu
465                 470                 475                 480
Asp Leu Val Asp Lys Glu Lys Ser Ala Glu Ala Phe Ile His Arg Met
                485                 490                 495
Thr Asn Asn Asp Leu Tyr Leu Pro Glu Glu Lys Val Leu Pro Lys His
                500                 505                 510
Ser Leu Ile Tyr Glu Lys Phe Thr Val Tyr Asn Glu Leu Thr Lys Val
                515                 520                 525
Arg Phe Leu Ala Glu Gly Phe Lys Asp Phe Gln Phe Leu Asn Arg Lys
                530                 535                 540
Gln Lys Glu Thr Ile Phe Asn Ser Leu Phe Lys Glu Lys Arg Lys Val
545                 550                 555                 560
Thr Glu Lys Asp Ile Ile Ser Phe Leu Asn Lys Val Asp Gly Tyr Glu
                565                 570                 575
Gly Ile Ala Ile Lys Gly Ile Glu Lys Gln Phe Asn Ala Ser Leu Ser
                580                 585                 590
Thr Tyr His Asp Leu Lys Lys Ile Leu Gly Lys Asp Phe Leu Asp Asn
                595                 600                 605
Thr Asp Asn Glu Leu Ile Leu Glu Asp Ile Val Gln Thr Leu Thr Leu
                610                 615                 620
Phe Glu Asp Arg Glu Met Ile Lys Lys Arg Leu Asp Ile Tyr Lys Asp
625                 630                 635                 640
Phe Phe Thr Glu Ser Gln Leu Lys Lys Leu Tyr Arg Arg His Tyr Thr
                645                 650                 655
Gly Trp Gly Arg Leu Ser Ala Lys Leu Ile Asn Gly Ile Arg Asn Lys
                660                 665                 670
Glu Asn Gln Lys Thr Ile Leu Asp Tyr Leu Ile Asp Asp Gly Ser Ala
                675                 680                 685
Asn Arg Asn Phe Met Gln Leu Ile Lys Asp Ala Gly Leu Ser Phe Lys
                690                 695                 700
Pro Ile Ile Asp Lys Ala Arg Thr Gly Ser His Ser Asn Leu Lys
705                 710                 715                 720
Glu Val Ile Gly Glu Leu Ala Gly Ser Pro Ala Ile Lys Lys Gly Ile
                725                 730                 735
Leu Gln Ser Leu Lys Ile Val Asp Glu Leu Val Lys Val Met Gly Tyr
                740                 745                 750
```

-continued

```
Glu Pro Glu Gln Ile Val Val Glu Met Ala Arg Glu Asn Gln Thr Thr
            755                 760                 765

Ala Lys Gly Leu Ser Arg Ser Arg Gln Arg Leu Thr Thr Leu Arg Glu
    770                 775                 780

Ser Leu Ala Asn Leu Lys Ser Asn Ile Leu Glu Glu Lys Lys Pro Lys
785                 790                 795                 800

Tyr Val Lys Asp Gln Val Glu Asn His His Leu Ser Asp Asp Arg Leu
            805                 810                 815

Phe Leu Tyr Tyr Leu Gln Asn Gly Lys Asp Met Tyr Thr Asp Asp Glu
            820                 825                 830

Leu Asp Ile Asp Asn Leu Ser Gln Tyr Asp Ile Asp His Ile Ile Pro
            835                 840                 845

Gln Ala Phe Ile Lys Asp Asp Ser Ile Asp Asn Arg Val Leu Val Ser
            850                 855                 860

Ser Ala Lys Asn Arg Gly Lys Ser Asp Asp Val Pro Ser Leu Glu Ile
865                 870                 875                 880

Val Lys Asp Cys Lys Val Phe Trp Lys Lys Leu Leu Asp Ala Lys Leu
                885                 890                 895

Met Ser Gln Arg Lys Tyr Asp Asn Leu Thr Lys Ala Glu Arg Gly Gly
            900                 905                 910

Leu Thr Ser Asp Asp Lys Ala Arg Phe Ile Gln Arg Gln Leu Val Glu
            915                 920                 925

Thr Arg Gln Ile Thr Lys His Val Ala Arg Ile Leu Asp Glu Arg Phe
            930                 935                 940

Asn Asn Glu Leu Asp Ser Lys Gly Arg Arg Ile Arg Lys Val Lys Ile
945                 950                 955                 960

Val Thr Leu Lys Ser Asn Leu Val Ser Asn Phe Arg Lys Glu Phe Val
                965                 970                 975

Phe Tyr Lys Ile Arg Glu Val Asn Asn Tyr His His Ala His Asp Ala
            980                 985                 990

Tyr Leu Asn Ala Val Val Ala Lys Ala Ile Leu Thr Lys Tyr Pro Gln
            995                1000                1005

Leu Glu Pro Glu Phe Val Tyr Gly Asp Tyr Pro Lys Tyr Asn Ser
    1010                1015                1020

Tyr Lys Thr Arg Lys Ser Ala Thr Glu Lys Leu Phe Phe Tyr Ser
    1025                1030                1035

Asn Ile Met Asn Phe Phe Lys Thr Lys Val Thr Leu Ala Asp Gly
    1040                1045                1050

Thr Val Val Val Lys Asp Asp Ile Glu Val Asn Asn Asp Thr Gly
    1055                1060                1065

Glu Ile Val Trp Asp Lys Lys Lys His Phe Ala Thr Val Arg Lys
    1070                1075                1080

Val Leu Ser Tyr Pro Gln Val Asn Ile Val Lys Lys Thr Glu Ile
    1085                1090                1095

Gln Thr Gly Gly Phe Ser Lys Glu Ser Ile Leu Ala His Gly Asn
    1100                1105                1110

Ser Asp Lys Leu Ile Pro Arg Lys Thr Lys Asp Ile Tyr Leu Asp
    1115                1120                1125

Pro Lys Lys Tyr Gly Gly Phe Asp Ser Pro Ile Val Ala Tyr Ser
    1130                1135                1140

Val Leu Val Val Ala Asp Ile Lys Lys Gly Lys Ala Gln Lys Leu
    1145                1150                1155
```

```
Lys Thr Val Thr Glu Leu Leu Gly Ile Thr Ile Met Glu Arg Ser
    1160                1165                1170

Arg Phe Glu Lys Asn Pro Ser Ala Phe Leu Glu Ser Lys Gly Tyr
    1175                1180                1185

Leu Asn Ile Arg Thr Asp Lys Leu Ile Ile Leu Pro Lys Tyr Ser
    1190                1195                1200

Leu Phe Glu Leu Glu Asn Gly Arg Arg Arg Leu Leu Ala Ser Ala
    1205                1210                1215

Gly Glu Leu Gln Lys Gly Asn Glu Leu Ala Leu Pro Thr Gln Phe
    1220                1225                1230

Met Lys Phe Leu Tyr Leu Ala Ser Arg Tyr Asn Glu Ser Lys Gly
    1235                1240                1245

Lys Pro Glu Glu Ile Glu Lys Lys Gln Glu Phe Val Asn Gln His
    1250                1255                1260

Val Ser Tyr Phe Asp Asp Ile Phe Gln Ile Ile Asn Asp Phe Ser
    1265                1270                1275

Lys Arg Val Ile Leu Ala Asp Ala Asn Leu Glu Lys Ile Asn Arg
    1280                1285                1290

Leu Tyr Gln Asp Asn Lys Glu Asn Ile Pro Val Asp Glu Leu Ala
    1295                1300                1305

Asn Asn Ile Ile Asn Leu Phe Thr Phe Thr Ser Leu Gly Ala Pro
    1310                1315                1320

Ala Ala Phe Lys Phe Phe Asp Lys Ile Val Asp Arg Lys Arg Tyr
    1325                1330                1335

Thr Ser Thr Lys Glu Val Leu Asn Ser Thr Leu Ile His Gln Ser
    1340                1345                1350

Ile Thr Gly Leu Tyr Glu Thr Arg Ile Asp Leu Gly Lys Leu Gly
    1355                1360                1365

Glu Asp
    1370

<210> SEQ ID NO 16
<211> LENGTH: 1368
<212> TYPE: PRT
<213> ORGANISM: Streptococcus pyogenes M1 GAS

<400> SEQUENCE: 16

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140
```

```
Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
            165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560
```

-continued

```
Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
```

-continued

Val Gly Thr Ala Leu Ile Lys Lys Tyr Pro Lys Leu Glu Ser Glu Phe
              980             985             990
    Val Tyr Gly Asp Tyr Lys Val Tyr Asp Val Arg Lys Met Ile Ala
         995            1000            1005
    Lys Ser Glu Gln Glu Ile Gly Lys Ala Thr Ala Lys Tyr Phe Phe
        1010            1015            1020
    Tyr Ser Asn Ile Met Asn Phe Phe Lys Thr Glu Ile Thr Leu Ala
        1025            1030            1035
    Asn Gly Glu Ile Arg Lys Arg Pro Leu Ile Glu Thr Asn Gly Glu
        1040            1045            1050
    Thr Gly Glu Ile Val Trp Asp Lys Gly Arg Asp Phe Ala Thr Val
        1055            1060            1065
    Arg Lys Val Leu Ser Met Pro Gln Val Asn Ile Val Lys Lys Thr
        1070            1075            1080
    Glu Val Gln Thr Gly Gly Phe Ser Lys Glu Ser Ile Leu Pro Lys
        1085            1090            1095
    Arg Asn Ser Asp Lys Leu Ile Ala Arg Lys Lys Asp Trp Asp Pro
        1100            1105            1110
    Lys Lys Tyr Gly Gly Phe Asp Ser Pro Thr Val Ala Tyr Ser Val
        1115            1120            1125
    Leu Val Val Ala Lys Val Glu Lys Gly Lys Ser Lys Lys Leu Lys
        1130            1135            1140
    Ser Val Lys Glu Leu Leu Gly Ile Thr Ile Met Glu Arg Ser Ser
        1145            1150            1155
    Phe Glu Lys Asn Pro Ile Asp Phe Leu Glu Ala Lys Gly Tyr Lys
        1160            1165            1170
    Glu Val Lys Lys Asp Leu Ile Ile Lys Leu Pro Lys Tyr Ser Leu
        1175            1180            1185
    Phe Glu Leu Glu Asn Gly Arg Lys Arg Met Leu Ala Ser Ala Gly
        1190            1195            1200
    Glu Leu Gln Lys Gly Asn Glu Leu Ala Leu Pro Ser Lys Tyr Val
        1205            1210            1215
    Asn Phe Leu Tyr Leu Ala Ser His Tyr Glu Lys Leu Lys Gly Ser
        1220            1225            1230
    Pro Glu Asp Asn Glu Gln Lys Gln Leu Phe Val Glu Gln His Lys
        1235            1240            1245
    His Tyr Leu Asp Glu Ile Ile Glu Gln Ile Ser Glu Phe Ser Lys
        1250            1255            1260
    Arg Val Ile Leu Ala Asp Ala Asn Leu Asp Lys Val Leu Ser Ala
        1265            1270            1275
    Tyr Asn Lys His Arg Asp Lys Pro Ile Arg Glu Gln Ala Glu Asn
        1280            1285            1290
    Ile Ile His Leu Phe Thr Leu Thr Asn Leu Gly Ala Pro Ala Ala
        1295            1300            1305
    Phe Lys Tyr Phe Asp Thr Thr Ile Asp Arg Lys Arg Tyr Thr Ser
        1310            1315            1320
    Thr Lys Glu Val Leu Asp Ala Thr Leu Ile His Gln Ser Ile Thr
        1325            1330            1335
    Gly Leu Tyr Glu Thr Arg Ile Asp Leu Ser Gln Leu Gly Gly Asp
        1340            1345            1350

<210> SEQ ID NO 17

<211> LENGTH: 1371
<212> TYPE: PRT
<213> ORGANISM: Streptococcus dysgalactiae subsp. equisimilis

<400> SEQUENCE: 17

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Arg
65                  70                  75                  80

Tyr Leu Gln Glu Ile Phe Ser Ser Glu Met Ser Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Met Asp Lys Leu Phe Ile Gln Leu Val Gln Thr Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Ala Lys Leu Asn Arg Glu Asp Leu Leu Arg

-continued

```
            385                 390                 395                 400
Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Glu Phe Leu Ser Gly Lys Gln
            530                 535                 540

Lys Glu Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Lys Glu Met Ile Glu Glu Arg Leu Lys Thr Tyr Ala
625                 630                 635                 640

His Leu Phe Asp Asp Lys Val Met Lys Gln Leu Lys Arg Arg His Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Ile Gln Leu Ile His Asp Asp Ser Leu Thr Phe
            690                 695                 700

Lys Glu Ala Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
                725                 730                 735

Ile Leu Gln Ser Val Lys Val Val Asp Glu Leu Val Lys Val Met Gly
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
        770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815
```

```
Asn Gly Arg Asp Met Tyr Val Asp Gln Glu Leu Asp Ile Asn Arg Leu
        820                 825                 830

Ser Asp Tyr Asp Val Asp His Ile Val Pro Gln Ser Phe Ile Lys Asp
        835                 840                 845

Asp Ser Ile Asp Asn Lys Val Leu Thr Arg Ser Asp Lys Asn Arg Gly
850                 855                 860

Lys Ser Asp Asp Val Pro Ser Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
        900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
        930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
                980                 985                 990

Gly Thr Ala Leu Ile Lys Lys Tyr  Pro Lys Leu Glu Ser  Glu Phe Val
            995                 1000                1005

Tyr Gly Asp Tyr Lys Val Tyr  Asp Val Arg Lys Met  Ile Ala Lys
    1010                1015                1020

Ser Glu Gln Glu Ile Gly Lys  Ala Thr Ala Lys Arg  Phe Phe Tyr
    1025                1030                1035

Ser Asn Ile Met Asn Phe Phe  Lys Thr Glu Ile Thr  Leu Ala Asn
    1040                1045                1050

Gly Glu Ile Arg Lys Arg Pro  Leu Ile Glu Thr Asn  Gly Glu Thr
    1055                1060                1065

Gly Glu Ile Val Trp Asn Lys  Gly Arg Asp Phe Ala  Thr Val Arg
    1070                1075                1080

Lys Val Leu Ser Met Pro Gln  Val Asn Ile Val Lys  Lys Thr Glu
    1085                1090                1095

Val Gln Thr Gly Ala Leu Thr  Asn Glu Ser Ile Tyr  Ala Arg Gly
    1100                1105                1110

Ser Phe Asp Lys Leu Ile Ser  Arg Lys His Arg Phe  Glu Ser Ser
    1115                1120                1125

Lys Tyr Gly Gly Phe Gly Ser  Pro Thr Val Thr Tyr  Ser Val Leu
    1130                1135                1140

Val Val Ala Lys Ser Lys Val  Gln Asp Gly Lys Val  Lys Lys Ile
    1145                1150                1155

Lys Thr Gly Lys Glu Leu Ile  Gly Ile Thr Leu Leu  Asp Lys Leu
    1160                1165                1170

Val Phe Glu Lys Asn Pro Leu  Lys Phe Ile Glu Asp  Lys Gly Tyr
    1175                1180                1185

Gly Asn Val Gln Ile Asp Lys  Cys Ile Lys Leu Pro  Lys Tyr Ser
    1190                1195                1200

Leu Phe Glu Phe Glu Asn Gly  Thr Arg Arg Met Leu  Ala Ser Val
    1205                1210                1215
```

```
Met Ala Asn Asn Asn Ser Arg Gly Asp Leu Gln Lys Ala Asn Glu
    1220                1225                1230

Met Phe Leu Pro Ala Lys Leu Val Thr Leu Leu Tyr His Ala His
    1235                1240                1245

Lys Ile Glu Ser Ser Lys Glu Leu Glu His Glu Ala Tyr Ile Leu
    1250                1255                1260

Asp His Tyr Asn Asp Leu Tyr Gln Leu Leu Ser Tyr Ile Glu Arg
    1265                1270                1275

Phe Ala Ser Leu Tyr Val Asp Val Glu Lys Asn Ile Ser Lys Val
    1280                1285                1290

Lys Glu Leu Phe Ser Asn Ile Glu Ser Tyr Ser Ile Ser Glu Ile
    1295                1300                1305

Cys Ser Ser Val Ile Asn Leu Leu Thr Leu Thr Ala Ser Gly Ala
    1310                1315                1320

Pro Ala Asp Phe Lys Phe Leu Gly Thr Thr Ile Pro Arg Lys Arg
    1325                1330                1335

Tyr Gly Ser Pro Gln Ser Ile Leu Ser Ser Thr Leu Ile His Gln
    1340                1345                1350

Ser Ile Thr Gly Leu Tyr Glu Thr Arg Ile Asp Leu Ser Gln Leu
    1355                1360                1365

Gly Gly Asp
    1370

<210> SEQ ID NO 18
<211> LENGTH: 1348
<212> TYPE: PRT
<213> ORGANISM: Streptococcus equi subsp. zooepidemicus

<400> SEQUENCE: 18

Met Lys Lys Pro Tyr Thr Ile Ala Leu Asp Ile Gly Thr Asn Ser
  1               5                  10                 15

Gly Trp Val Val Val Thr Asp Asp Tyr Arg Val Pro Thr Lys Lys Met
                 20                  25                  30

Lys Val Leu Gly Asn Thr Glu Arg Lys Thr Ile Lys Lys Asn Leu Ile
             35                  40                  45

Gly Ala Leu Leu Phe Asp Ser Gly Asp Thr Ala Glu Gly Thr Arg Leu
         50                  55                  60

Lys Arg Thr Ala Arg Arg Arg Tyr Thr Arg Arg Lys Asn Arg Leu Arg
 65                  70                  75                  80

Tyr Leu Lys Glu Ile Phe Thr Glu Glu Met Ala Lys Val Asp Asp Gly
                 85                  90                  95

Phe Phe Gln Arg Leu Glu Asp Ser Phe Tyr Val Leu Glu Asp Lys Glu
                100                 105                 110

Gly Asn Lys His Pro Ile Phe Ala Asn Leu Ala Asp Glu Val Ala Tyr
            115                 120                 125

His Lys Lys Tyr Pro Thr Ile Tyr His Leu Arg Lys Glu Leu Val Asp
        130                 135                 140

Asn Pro Gln Lys Ala Asp Leu Arg Leu Ile Tyr Leu Ala Val Ala His
145                 150                 155                 160

Ile Ile Lys Phe Arg Gly His Phe Leu Ile Glu Gly Thr Leu Ser Ser
                165                 170                 175

Lys Asn Asn Asn Leu Gln Lys Ser Phe Asp His Leu Val Asp Thr Tyr
            180                 185                 190

Asn Leu Leu Phe Glu Glu Gln Arg Leu Leu Thr Glu Gly Ile Asn Ala
        195                 200                 205
```

```
Lys Glu Leu Leu Ser Ala Ala Leu Ser Lys Ser Lys Arg Leu Glu Asn
    210                 215                 220

Leu Ile Ser Leu Ile Pro Gly Gln Lys Lys Thr Gly Ile Phe Gly Asn
225                 230                 235                 240

Ile Ile Ala Leu Ser Leu Gly Leu Thr Pro Asn Phe Lys Ala Asn Phe
                245                 250                 255

Gly Leu Ser Lys Asp Val Lys Leu Gln Leu Ala Lys Asp Thr Tyr Ala
                260                 265                 270

Asp Asp Leu Asp Ser Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
    290                 295                 300

Ile Leu Thr Glu Ser Asp Glu Ile Thr Arg Ala Pro Leu Ser Ala Ser
305                 310                 315                 320

Met Val Lys Arg Tyr Arg Glu His His Lys Asp Leu Val Thr Leu Lys
                325                 330                 335

Thr Leu Ile Lys Asp Gln Leu Pro Glu Lys Tyr Gln Glu Ile Phe Leu
                340                 345                 350

Asp Lys Thr Lys Asn Gly Tyr Ala Gly Tyr Ile Glu Gly Gln Val Ser
            355                 360                 365

Gln Glu Glu Phe Tyr Lys Tyr Leu Lys Pro Ile Leu Ala Arg Leu Asp
    370                 375                 380

Gly Ser Glu Pro Leu Leu Leu Lys Ile Asp Arg Glu Asp Phe Leu Arg
385                 390                 395                 400

Lys Gln Arg Thr Phe Asp Asn Gly Ser Ile Pro His Gln Ile His Leu
                405                 410                 415

Glu Glu Leu His Ala Ile Leu Arg Arg Gln Glu Val Phe Tyr Pro Phe
                420                 425                 430

Leu Lys Asp Asn Arg Lys Lys Ile Glu Ser Leu Leu Thr Phe Arg Ile
            435                 440                 445

Pro Tyr Tyr Val Gly Pro Leu Ala Arg Gly His Ser Arg Phe Ala Trp
    450                 455                 460

Val Lys Arg Lys Phe Asp Gly Ala Ile Arg Pro Trp Asn Phe Glu Glu
465                 470                 475                 480

Ile Val Asp Glu Glu Ala Ser Ala Gln Ile Phe Ile Glu Lys Met Thr
                485                 490                 495

Lys Asn Asp Leu Tyr Leu Pro Asn Glu Lys Val Leu Pro Lys His Ser
            500                 505                 510

Leu Leu Tyr Glu Thr Phe Thr Val Tyr Asn Glu Leu Thr Lys Val Lys
    515                 520                 525

Tyr Ala Thr Glu Gly Met Thr Arg Pro Gln Phe Leu Ser Ala Asp Gln
530                 535                 540

Lys Gln Ala Ile Val Asp Leu Leu Phe Lys Thr Asn Arg Lys Val Thr
545                 550                 555                 560

Val Lys Gln Leu Lys Glu Asn Tyr Phe Lys Lys Ile Glu Cys Trp Asp
                565                 570                 575

Ser Val Glu Ile Thr Gly Val Glu Asp Ser Phe Asn Ala Ser Leu Gly
                580                 585                 590

Thr Tyr His Asp Leu Leu Lys Ile Ile Gln Asp Lys Asp Phe Leu Asp
            595                 600                 605

Asn Pro Asp Asn Gln Lys Ile Ile Glu Asp Ile Ile Leu Thr Leu Thr
610                 615                 620
```

```
Leu Phe Glu Asp Lys Lys Met Ile Ser Lys Arg Leu Asp Gln Tyr Ala
625                 630                 635                 640

His Leu Phe Asp Lys Val Val Leu Asn Lys Leu Glu Arg His His Tyr
            645                 650                 655

Thr Gly Trp Gly Arg Leu Ser Gly Lys Leu Ile Asn Gly Ile Arg Asp
        660                 665                 670

Lys Gln Ser Gly Lys Thr Ile Leu Asp Phe Leu Lys Ala Asp Gly Phe
            675                 680                 685

Ala Asn Arg Asn Phe Met Gln Leu Ile His Asp Ser Glu Leu Ser Phe
690                 695                 700

Ile Asp Glu Ile Ala Lys Ala Gln Val Ile Gly Lys Thr Glu Tyr Ser
705                 710                 715                 720

Lys Asp Leu Val Gly Asn Leu Ala Ser Ser Pro Ala Ile Lys Lys Gly
            725                 730                 735

Ile Ser Gln Thr Ile Lys Ile Val Asp Glu Leu Val Lys Ile Met Gly
            740                 745                 750

Tyr Leu Pro Gln Gln Ile Val Ile Glu Met Ala Arg Glu Asn Gln Thr
        755                 760                 765

Thr Ala Gln Gly Ile Lys Asn Ala Arg Gln Arg Met Arg Lys Leu Glu
770                 775                 780

Glu Thr Ala Lys Lys Leu Gly Ser Asn Ile Leu Lys Glu His Pro Val
785                 790                 795                 800

Asp Asn Ser Gln Leu Gln Asn Asp Lys Arg Tyr Leu Tyr Tyr Leu Gln
            805                 810                 815

Asn Gly Lys Asp Met Tyr Thr Gly Asp Asp Leu Asp Ile Asp Tyr Leu
            820                 825                 830

Ser Ser Tyr Asp Ile Asp His Ile Ile Pro Gln Ser Phe Ile Lys Asn
            835                 840                 845

Asn Ser Ile Asp Asn Lys Val Leu Thr Ser Gln Gly Ala Asn Arg Gly
850                 855                 860

Lys Leu Asp Asn Val Pro Ser Glu Ala Ile Val Arg Lys Met Lys Gly
865                 870                 875                 880

Tyr Trp Gln Ser Leu Leu Arg Ala Gly Ala Ile Ser Lys Gln Lys Phe
            885                 890                 895

Asp Asn Leu Thr Lys Ala Glu Arg Gly Gly Leu Thr Gln Val Asp Lys
            900                 905                 910

Ala Gly Phe Ile Gln Arg Gln Leu Val Glu Thr Arg Gln Ile Thr Lys
        915                 920                 925

His Val Ala Gln Ile Leu Asp Ser Arg Phe Asn Thr Glu Phe Asp Asp
930                 935                 940

His Asn Lys Arg Ile Arg Lys Val His Ile Ile Thr Leu Lys Ser Lys
945                 950                 955                 960

Leu Val Ser Asp Phe Arg Lys Glu Phe Gly Leu Tyr Lys Ile Arg Asp
            965                 970                 975

Ile Asn His Tyr His His Ala His Asp Ala Tyr Leu Asn Ala Val Val
        980                 985                 990

Ala Lys Ala Ile Leu Gly Lys Tyr Pro Gln Leu Ala Pro Glu Phe Val
        995                 1000                1005

Tyr Gly Asp Tyr Pro Lys Tyr Asn Ser Phe Lys Glu Arg Gln Lys
        1010                1015                1020

Ala Thr Gln Lys Thr Leu Phe Tyr Ser Asn Ile Leu Lys Phe Phe
        1025                1030                1035

Lys Asp Gln Glu Ser Leu His Val Asn Ser Asp Gly Glu Glu Ile
```

Trp Asn Ala Asn Lys His Leu Pro Ile Ile Lys Asn Val Leu Ser
                1055                1060                1065

Ile Pro Gln Val Asn Ile Val Lys Lys Thr Glu Val Gln Thr Gly
    1070                1075                1080

Gly Phe Tyr Lys Glu Ser Ile Leu Ser Lys Gly Asn Ser Asp Lys
        1085                1090                1095

Leu Ile Pro Arg Lys Asn Asn Trp Asp Thr Arg Lys Tyr Gly Gly
    1100                1105                1110

Phe Asp Ser Pro Thr Val Ala Tyr Ser Val Leu Val Ile Ala Lys
    1115                1120                1125

Met Glu Lys Gly Lys Ala Lys Val Leu Lys Pro Val Lys Glu Met
    1130                1135                1140

Val Gly Ile Thr Ile Met Glu Arg Ile Ala Phe Glu Glu Asn Pro
    1145                1150                1155

Val Val Phe Leu Glu Ala Lys Gly Tyr Arg Glu Ile Gln Glu His
    1160                1165                1170

Leu Ile Ile Lys Leu Pro Lys Tyr Ser Leu Phe Glu Leu Glu Asn
    1175                1180                1185

Gly Arg Arg Arg Leu Leu Ala Ser Ala Ser Glu Leu Gln Lys Gly
    1190                1195                1200

Asn Glu Leu Phe Leu Pro Val Asp Tyr Met Thr Phe Leu Tyr Leu
    1205                1210                1215

Ala Ala His Tyr His Glu Leu Thr Gly Ser Ser Glu Asp Val Leu
    1220                1225                1230

Arg Lys Lys Tyr Phe Val Glu Arg His Leu His Tyr Phe Asp Asp
    1235                1240                1245

Ile Ile Gln Met Ile Asn Asp Phe Ala Glu Arg His Ile Leu Ala
    1250                1255                1260

Ser Ser Asn Leu Glu Lys Ile Asn His Thr Tyr His Asn Asn Ser
    1265                1270                1275

Asp Leu Pro Ile Asn Glu Arg Ala Glu Asn Ile Ile Asn Val Phe
    1280                1285                1290

Thr Phe Val Ala Leu Gly Ala Pro Ala Ala Phe Lys Phe Phe Asp
    1295                1300                1305

Ala Thr Ile Asp Arg Lys Arg Tyr Thr Ser Thr Lys Glu Val Leu
    1310                1315                1320

Asn Ala Thr Leu Ile His Gln Ser Val Thr Gly Leu Tyr Glu Thr
    1325                1330                1335

Arg Ile Asp Leu Ser Gln Leu Gly Glu Asn
    1340                1345

<210> SEQ ID NO 19
<211> LENGTH: 1396
<212> TYPE: PRT
<213> ORGANISM: Streptococcus anginosis DSM20563

<400> SEQUENCE: 19

Met Thr Lys Pro Tyr Ser Ile Gly Leu Asp Ile Gly Thr Asn Ser Val
1               5                   10                  15

Gly Trp Ala Val Ile Thr Asp Asp Tyr Lys Val Pro Ala Lys Lys Met
            20                  25                  30

Lys Val Leu Gly Asn Thr Asn Arg Asp Tyr Ile Lys Lys Asn Leu Leu
        35                  40                  45

```
Gly Ala Leu Leu Phe Asp Gly Gly Glu Thr Ala Glu Gly Arg Arg Leu
    50                  55                  60

Lys Arg Thr Ala Arg Arg Tyr Thr Arg Arg Lys Asn Arg Leu Arg
65              70                  75                  80

Tyr Leu Gln Glu Ile Phe Ala Glu Glu Met Met Gln Val Asp Glu Ser
                85                  90                  95

Phe Phe Gln Arg Leu Asp Asp Ser Phe Leu Val Glu Glu Asp Lys Gln
            100                 105                 110

Gly Ser Lys Tyr Pro Ile Phe Gly Thr Leu Lys Glu Glu Lys Glu Tyr
        115                 120                 125

His Lys Lys Phe Lys Thr Ile Tyr His Leu Arg Glu Glu Leu Ala Asn
    130                 135                 140

Ser Lys Glu Lys Ala Asp Leu Arg Leu Val Tyr Leu Ala Leu Ala His
145                 150                 155                 160

Met Ile Lys Phe Arg Gly His Phe Leu Tyr Glu Gly Asp Leu Lys Ala
                165                 170                 175

Glu Asn Thr Asp Val Gln Ala Leu Phe Lys Asp Phe Val Glu Glu Tyr
            180                 185                 190

Asp Lys Thr Ile Glu Glu Ser His Leu Ser Glu Ile Thr Val Asp Ala
        195                 200                 205

Leu Ser Ile Leu Thr Glu Lys Val Ser Lys Ser Ser Arg Leu Glu Asn
210                 215                 220

Leu Ile Ala His Tyr Pro Thr Glu Lys Lys Asn Thr Leu Phe Gly Asn
225                 230                 235                 240

Leu Ile Ala Leu Ser Leu Gly Leu Gln Ala Asn Phe Lys Thr Asn Phe
                245                 250                 255

Gln Leu Ser Glu Asp Ala Lys Leu Gln Phe Ser Lys Asp Thr Tyr Glu
            260                 265                 270

Glu Asp Leu Glu Gly Leu Leu Gly Glu Val Gly Asp Glu Tyr Ala Asp
        275                 280                 285

Leu Phe Val Ser Ala Lys Asn Leu Tyr Asp Ala Ile Leu Leu Ser Gly
    290                 295                 300

Ile Leu Thr Val Asp Asp Asn Ser Thr Lys Ala Pro Leu Ser Ala Ser
305                 310                 315                 320

Met Val Lys Arg Tyr Lys Glu His Lys Glu Glu Leu Ala Ala Phe Lys
                325                 330                 335

Arg Phe Ile Lys Glu Lys Leu Pro Lys Lys Tyr Glu Glu Ile Phe Lys
            340                 345                 350

Asp Asp Thr Lys Asn Gly Tyr Ala Gly Tyr Val Gly Ala Asp Lys Lys
        355                 360                 365

Leu Arg Lys Arg Ser Gly Lys Leu Ala Thr Glu Glu Phe Tyr Lys
    370                 375                 380

Tyr Val Lys Gly Ile Leu Asn Lys Val Glu Gly Ala Asp Tyr Phe Leu
385                 390                 395                 400

Asp Lys Ile Asp Arg Glu Asp Phe Leu Arg Lys Gln Arg Thr Phe Asp
                405                 410                 415

Asn Gly Ser Ile Pro His Gln Ile His Leu Gln Glu Met His Ala Ile
            420                 425                 430

Leu Arg Arg Gln Gly Glu His Tyr Pro Phe Leu Lys Glu Asn Gln Asp
        435                 440                 445

Lys Ile Glu Lys Ile Leu Thr Phe Arg Ile Pro Tyr Tyr Val Gly Pro
    450                 455                 460

Leu Ala Arg Lys Gly Ser Arg Phe Ala Trp Ala Glu Tyr Lys Ala Asp
```

-continued

```
            465                 470                 475                 480
        Glu Lys Ile Thr Pro Trp Asn Phe Asp Asp Ile Leu Asp Lys Glu Lys
                            485                 490                 495

Ser Ala Glu Lys Phe Ile Thr Arg Met Thr Leu Asn Asp Leu Tyr Leu
                        500                 505                 510

Pro Glu Glu Lys Val Leu Pro Lys His Ser Pro Leu Tyr Glu Thr Phe
                        515                 520                 525

Thr Val Tyr Asn Glu Leu Thr Lys Val Lys Tyr Val Asn Glu Gln Gly
                    530                 535                 540

Glu Ala Lys Phe Phe Asp Thr Asn Met Lys Gln Glu Ile Phe Asp His
        545                 550                 555                 560

Val Phe Lys Glu Asn Arg Lys Val Thr Lys Asp Lys Leu Leu Asn Tyr
                            565                 570                 575

Leu Asn Lys Glu Phe Glu Glu Phe Arg Ile Val Asn Leu Thr Gly Leu
                        580                 585                 590

Asp Lys Glu Asn Lys Ala Phe Asn Ala Ser Leu Gly Thr Tyr His Asp
                        595                 600                 605

Leu Arg Lys Ile Leu Asp Lys Ser Phe Leu Asp Asp Lys Val Asn Glu
                    610                 615                 620

Lys Ile Ile Glu Asp Ile Ile Gln Thr Leu Thr Leu Phe Glu Asp Arg
        625                 630                 635                 640

Glu Met Ile Arg Gln Arg Leu Gln Lys Tyr Ser Asp Ile Phe Thr Thr
                            645                 650                 655

Gln Gln Leu Lys Glu Leu Glu Arg Arg His Tyr Thr Gly Trp Gly Arg
                        660                 665                 670

Leu Ser Tyr Lys Leu Ile Asn Gly Ile Arg Asn Lys Glu Asn Lys Lys
                        675                 680                 685

Thr Ile Leu Asp Tyr Leu Ile Asp Asp Gly Tyr Ala Asn Arg Asn Phe
                    690                 695                 700

Met Gln Leu Ile Asn Asp Asp Ala Leu Ser Phe Lys Glu Glu Ile Ala
        705                 710                 715                 720

Arg Ala Gln Ile Ile Gly Asp Val Asp Asp Ile Ala Asn Val Val His
                            725                 730                 735

Asp Leu Pro Gly Ser Pro Ala Ile Lys Lys Gly Ile Leu Gln Ser Val
                        740                 745                 750

Lys Ile Val Asp Glu Leu Val Lys Val Met Gly His Asn Pro Thr Asn
                        755                 760                 765

Ile Ile Ile Glu Met Ala Arg Glu Asn Gln Thr Thr Asp Lys Gly Arg
                    770                 775                 780

Arg Asn Ser Gln Gln Arg Leu Lys Leu Leu Gln Asp Ser Leu Lys Asn
        785                 790                 795                 800

Leu Asp Asn Pro Val Asn Ile Lys Asn Val Glu Asn Gln Gln Leu Gln
                            805                 810                 815

Asn Asp Arg Leu Phe Leu Tyr Tyr Ile Gln Asn Gly Lys Asp Met Tyr
                        820                 825                 830

Thr Gly Glu Thr Leu Asp Ile Asn Asn Leu Ser Gln Tyr Asp Ile Asp
                        835                 840                 845

His Ile Ile Pro Gln Ala Phe Ile Lys Asp Asn Ser Leu Asp Asn Arg
                    850                 855                 860

Val Leu Thr Arg Ser Asp Lys Asn Arg Gly Lys Ser Asp Asp Val Pro
        865                 870                 875                 880

Ser Ile Glu Val Val His Glu Met Lys Ser Phe Trp Ser Lys Leu Leu
                            885                 890                 895
```

```
Ser Val Lys Leu Ile Thr Gln Arg Lys Phe Asp Asn Leu Thr Lys Ala
        900                 905                 910

Glu Arg Gly Gly Leu Thr Glu Asn Asp Lys Ala Gly Phe Ile Lys Arg
        915                 920                 925

Gln Leu Val Glu Thr Arg Gln Ile Thr Lys His Val Ala Gln Val Leu
        930                 935                 940

Asp Ala Arg Phe Asn Ala Lys His Asp Glu Asn Lys Lys Val Ile Arg
945                 950                 955                 960

Asp Val Lys Ile Ile Thr Leu Lys Ser Asn Leu Val Ser Gln Phe Arg
                965                 970                 975

Lys Asp Phe Lys Phe Tyr Lys Val Arg Glu Ile Asn Asp Tyr His His
            980                 985                 990

Ala His Asp Ala Tyr Leu Asn Ala Val Ile Gly Thr Ala Leu Leu Lys
            995                 1000                1005

Lys Tyr Pro Lys Leu Ala Ser Glu Phe Val Tyr Gly Glu Phe Lys
    1010                1015                1020

Lys Tyr Asp Val Arg Lys Phe Ile Ala Lys Ser Asp Lys Glu Ile
    1025                1030                1035

Gly Lys Ala Thr Ala Lys Tyr Phe Phe Tyr Ser Asn Leu Met Asn
    1040                1045                1050

Phe Phe Lys Lys Glu Val Lys Phe Ala Asp Gly Thr Val Val Glu
    1055                1060                1065

Arg Pro Asp Ile Glu Thr Ser Glu Asp Gly Glu Ile Ala Trp Asn
    1070                1075                1080

Lys Gln Thr Asp Phe Lys Ile Val Arg Lys Val Leu Ser Tyr Pro
    1085                1090                1095

Gln Val Asn Ile Val Lys Lys Thr Glu Val Gln Thr His Gly Leu
    1100                1105                1110

Asp Arg Gly Lys Pro Arg Gly Leu Phe Asn Ala Asn Pro Ser Pro
    1115                1120                1125

Lys Pro Lys Pro Asp Ser Ser Glu Asn Leu Val Gly Ile Lys Arg
    1130                1135                1140

Asn Leu Asp Pro Lys Lys Tyr Gly Gly Tyr Ala Gly Ile Ser Asn
    1145                1150                1155

Ser Tyr Ala Val Leu Val Lys Ala Ile Ile Glu Lys Gly Val Lys
    1160                1165                1170

Lys Lys Glu Thr Met Val Leu Glu Phe Gln Gly Ile Ser Ile Leu
    1175                1180                1185

Asp Arg Ile Thr Phe Glu Lys Asp Lys Arg Ala Phe Leu Leu Gly
    1190                1195                1200

Lys Gly Tyr Lys Asp Ile Lys Lys Ile Ile Glu Leu Pro Lys Tyr
    1205                1210                1215

Ser Leu Phe Glu Leu Lys Asp Gly Ser Arg Arg Met Leu Ala Ser
    1220                1225                1230

Ile Leu Ser Thr Asn Asn Lys Arg Gly Glu Ile His Lys Gly Asn
    1235                1240                1245

Glu Leu Phe Val Pro Gln Lys Phe Thr Thr Leu Leu Tyr His Ala
    1250                1255                1260

Lys Arg Ile Asn Asn Pro Ile Asn Lys Asp His Ile Glu Tyr Val
    1265                1270                1275

Lys Lys His Arg Asp Asp Phe Lys Glu Leu Leu Asn Tyr Val Leu
    1280                1285                1290
```

-continued

```
Glu Phe Asn Glu Lys Tyr Val Gly Ala Thr Lys Asn Gly Glu Arg
    1295                1300                1305

Leu Lys Glu Ala Val Ala Asp Phe Asp Ser Lys Ser Asn Glu Glu
    1310                1315                1320

Ile Cys Thr Ser Phe Leu Gly Ala Val Asn Ser Lys Asn Ala Gly
    1325                1330                1335

Leu Phe Glu Leu Thr Ser Leu Gly Ser Ala Ser Asp Phe Glu Phe
    1340                1345                1350

Leu Gly Val Lys Ile Pro Arg Tyr Arg Asp Tyr Thr Pro Ser Ser
    1355                1360                1365

Leu Leu Lys Asp Ser Ile Leu Ile His Gln Ser Ile Thr Gly Leu
    1370                1375                1380

Tyr Glu Thr Arg Ile Asp Leu Ser Lys Leu Gly Glu Asp
    1385                1390                1395

<210> SEQ ID NO 20
<211> LENGTH: 1345
<212> TYPE: PRT
<213> ORGANISM: Streptococcus mutans UA159

<400> SEQUENCE: 20

Met Lys Lys Pro Tyr Ser Ile Gly Leu Asp Ile Gly Thr Asn Ser Val
  1               5                  10                  15

Gly Trp Ala Val Val Thr Asp Asp Tyr Lys Val Pro Ala Lys Lys Met
                 20                  25                  30

Lys Val Leu Gly Asn Thr Asp Lys Ser His Ile Glu Lys Asn Leu Leu
             35                  40                  45

Gly Ala Leu Leu Phe Asp Ser Gly Asn Thr Ala Glu Asp Arg Arg Leu
         50                  55                  60

Lys Arg Thr Ala Arg Arg Arg Tyr Thr Arg Arg Asn Arg Ile Leu
 65                  70                  75                  80

Tyr Leu Gln Glu Ile Phe Ser Glu Glu Met Gly Lys Val Asp Asp Ser
                 85                  90                  95

Phe Phe His Arg Leu Glu Asp Ser Phe Leu Val Thr Glu Asp Lys Arg
            100                 105                 110

Gly Glu Arg His Pro Ile Phe Gly Asn Leu Glu Glu Val Lys Tyr
            115                 120                 125

His Glu Asn Phe Pro Thr Ile Tyr His Leu Arg Gln Tyr Leu Ala Asp
        130                 135                 140

Asn Pro Glu Lys Val Asp Leu Arg Leu Val Tyr Leu Ala Leu Ala His
145                 150                 155                 160

Ile Ile Lys Phe Arg Gly His Phe Leu Ile Glu Gly Lys Phe Asp Thr
                165                 170                 175

Arg Asn Asn Asp Val Gln Arg Leu Phe Gln Glu Phe Leu Ala Val Tyr
            180                 185                 190

Asp Asn Thr Phe Glu Asn Ser Ser Leu Gln Glu Gln Asn Val Gln Val
        195                 200                 205

Glu Glu Ile Leu Thr Asp Lys Ile Ser Lys Ser Ala Lys Lys Asp Arg
    210                 215                 220

Val Leu Lys Leu Phe Pro Asn Glu Lys Ser Asn Gly Arg Phe Ala Glu
225                 230                 235                 240

Phe Leu Lys Leu Ile Val Gly Asn Gln Ala Asp Phe Lys Lys His Phe
                245                 250                 255

Glu Leu Glu Glu Lys Ala Pro Leu Gln Phe Ser Lys Asp Thr Tyr Glu
            260                 265                 270
```

-continued

Glu Glu Leu Glu Val Leu Leu Ala Gln Ile Gly Asp Asn Tyr Ala Glu
            275                 280                 285

Leu Phe Leu Ser Ala Lys Lys Leu Tyr Asp Ser Ile Leu Leu Ser Gly
    290                 295                 300

Ile Leu Thr Val Thr Asp Val Gly Thr Lys Ala Pro Leu Ser Ala Ser
305                 310                 315                 320

Met Ile Gln Arg Tyr Asn Glu His Gln Met Asp Leu Ala Gln Leu Lys
                325                 330                 335

Gln Phe Ile Arg Gln Lys Leu Ser Asp Lys Tyr Asn Glu Val Phe Ser
                340                 345                 350

Asp Val Ser Lys Asp Gly Tyr Ala Gly Tyr Ile Asp Gly Lys Thr Asn
            355                 360                 365

Gln Glu Ala Phe Tyr Lys Tyr Leu Lys Gly Leu Leu Asn Lys Ile Glu
        370                 375                 380

Gly Ser Gly Tyr Phe Leu Asp Lys Ile Glu Arg Glu Asp Phe Leu Arg
385                 390                 395                 400

Lys Gln Arg Thr Phe Asp Asn Gly Ser Ile Pro His Gln Ile His Leu
                405                 410                 415

Gln Glu Met Arg Ala Ile Ile Arg Arg Gln Ala Glu Phe Tyr Pro Phe
            420                 425                 430

Leu Ala Asp Asn Gln Asp Arg Ile Glu Lys Leu Leu Thr Phe Arg Ile
        435                 440                 445

Pro Tyr Tyr Val Gly Pro Leu Ala Arg Gly Lys Ser Asp Phe Ala Trp
    450                 455                 460

Leu Ser Arg Lys Ser Ala Asp Lys Ile Thr Pro Trp Asn Phe Asp Glu
465                 470                 475                 480

Ile Val Asp Lys Glu Ser Ser Ala Glu Ala Phe Ile Asn Arg Met Thr
                485                 490                 495

Asn Tyr Asp Leu Tyr Leu Pro Asn Gln Lys Val Leu Pro Lys His Ser
            500                 505                 510

Leu Leu Tyr Glu Lys Phe Thr Val Tyr Asn Glu Leu Thr Lys Val Lys
        515                 520                 525

Tyr Lys Thr Glu Gln Gly Lys Thr Ala Phe Phe Asp Ala Asn Met Lys
    530                 535                 540

Gln Glu Ile Phe Asp Gly Val Phe Lys Val Tyr Arg Lys Val Thr Lys
545                 550                 555                 560

Asp Lys Leu Met Asp Phe Leu Glu Lys Glu Phe Asp Glu Phe Arg Ile
                565                 570                 575

Val Asp Leu Thr Gly Leu Asp Lys Glu Asn Lys Val Phe Asn Ala Ser
            580                 585                 590

Tyr Gly Thr Tyr His Asp Leu Cys Lys Ile Leu Asp Lys Asp Phe Leu
        595                 600                 605

Asp Asn Ser Lys Asn Glu Lys Ile Leu Glu Asp Ile Val Leu Thr Leu
    610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
                645                 650                 655

Tyr Thr Gly Trp Gly Arg Leu Ser Ala Glu Leu Ile His Gly Ile Arg
            660                 665                 670

Asn Lys Glu Ser Arg Lys Thr Ile Leu Asp Tyr Leu Ile Asp Asp Gly
        675                 680                 685

-continued

Asn Ser Asn Arg Asn Phe Met Gln Leu Ile Asn Asp Asp Ala Leu Ser
690                 695                 700

Phe Lys Glu Glu Ile Ala Lys Ala Gln Val Ile Gly Glu Thr Asp Asn
705                 710                 715                 720

Leu Asn Gln Val Val Ser Asp Ile Ala Gly Ser Pro Ala Ile Lys Lys
            725                 730                 735

Gly Ile Leu Gln Ser Leu Lys Ile Val Asp Glu Leu Val Lys Ile Met
            740                 745                 750

Gly His Gln Pro Glu Asn Ile Val Glu Met Ala Arg Glu Asn Gln
        755                 760                 765

Phe Thr Asn Gln Gly Arg Arg Asn Ser Gln Gln Arg Leu Lys Gly Leu
770                 775                 780

Thr Asp Ser Ile Lys Glu Phe Gly Ser Gln Ile Leu Lys Glu His Pro
785                 790                 795                 800

Val Glu Asn Ser Gln Leu Gln Asn Asp Arg Leu Phe Leu Tyr Tyr Leu
                805                 810                 815

Gln Asn Gly Arg Asp Met Tyr Thr Gly Glu Glu Leu Asp Ile Asp Tyr
            820                 825                 830

Leu Ser Gln Tyr Asp Ile Asp His Ile Ile Pro Gln Ala Phe Ile Lys
            835                 840                 845

Asp Asn Ser Ile Asp Asn Arg Val Leu Thr Ser Ser Lys Glu Asn Arg
850                 855                 860

Gly Lys Ser Asp Asp Val Pro Ser Lys Asp Val Val Arg Lys Met Lys
865                 870                 875                 880

Ser Tyr Trp Ser Lys Leu Leu Ser Ala Lys Leu Ile Thr Gln Arg Lys
                885                 890                 895

Phe Asp Asn Leu Thr Lys Ala Glu Arg Gly Gly Leu Thr Asp Asp Asp
            900                 905                 910

Lys Ala Gly Phe Ile Lys Arg Gln Leu Val Glu Thr Arg Gln Ile Thr
            915                 920                 925

Lys His Val Ala Arg Ile Leu Asp Glu Arg Phe Asn Thr Glu Thr Asp
930                 935                 940

Glu Asn Asn Lys Lys Ile Arg Gln Val Lys Ile Val Thr Leu Lys Ser
945                 950                 955                 960

Asn Leu Val Ser Asn Phe Arg Lys Glu Phe Glu Leu Tyr Lys Val Arg
                965                 970                 975

Glu Ile Asn Asp Tyr His His Ala His Asp Ala Tyr Leu Asn Ala Val
            980                 985                 990

Ile Gly Lys Ala Leu Leu Gly Val Tyr Pro Gln Leu Glu Pro Glu Phe
            995                 1000                1005

Val Tyr Gly Asp Tyr Pro His Phe His Gly His Lys Glu Asn Lys
    1010                1015                1020

Ala Thr Ala Lys Lys Phe Phe Tyr Ser Asn Ile Met Asn Phe Phe
    1025                1030                1035

Lys Lys Asp Asp Val Arg Thr Asp Lys Asn Gly Glu Ile Ile Trp
    1040                1045                1050

Lys Lys Asp Glu His Ile Ser Asn Ile Lys Lys Val Leu Ser Tyr
    1055                1060                1065

Pro Gln Val Asn Ile Val Lys Val Glu Glu Gln Thr Gly Gly
    1070                1075                1080

Phe Ser Lys Glu Ser Ile Leu Pro Lys Gly Asn Ser Asp Lys Leu
    1085                1090                1095

Ile Pro Arg Lys Thr Lys Lys Phe Tyr Trp Asp Thr Lys Lys Tyr

```
                1100               1105                1110
Gly Gly Phe Asp Ser Pro Ile Val Ala Tyr Ser Ile Leu Val Ile
        1115                1120                1125

Ala Asp Ile Glu Lys Gly Lys Ser Lys Lys Leu Lys Thr Val Lys
    1130                1135                1140

Ala Leu Val Gly Val Thr Ile Met Glu Lys Met Thr Phe Glu Arg
    1145                1150                1155

Asp Pro Val Ala Phe Leu Glu Arg Lys Gly Tyr Arg Asn Val Gln
    1160                1165                1170

Glu Glu Asn Ile Ile Lys Leu Pro Lys Tyr Ser Leu Phe Lys Leu
    1175                1180                1185

Glu Asn Gly Arg Lys Arg Leu Leu Ala Ser Ala Arg Glu Leu Gln
    1190                1195                1200

Lys Gly Asn Glu Ile Val Leu Pro Asn His Leu Gly Thr Leu Leu
    1205                1210                1215

Tyr His Ala Lys Asn Ile His Lys Val Asp Glu Pro Lys His Leu
    1220                1225                1230

Asp Tyr Val Asp Lys His Lys Asp Glu Phe Lys Glu Leu Leu Asp
    1235                1240                1245

Val Val Ser Asn Phe Ser Lys Lys Tyr Thr Leu Ala Glu Gly Asn
    1250                1255                1260

Leu Glu Lys Ile Lys Glu Leu Tyr Ala Gln Asn Asn Gly Glu Asp
    1265                1270                1275

Leu Lys Glu Leu Ala Ser Ser Phe Ile Asn Leu Leu Thr Phe Thr
    1280                1285                1290

Ala Ile Gly Ala Pro Ala Thr Phe Lys Phe Phe Asp Lys Asn Ile
    1295                1300                1305

Asp Arg Lys Arg Tyr Thr Ser Thr Thr Glu Ile Leu Asn Ala Thr
    1310                1315                1320

Leu Ile His Gln Ser Ile Thr Gly Leu Tyr Glu Thr Arg Ile Asp
    1325                1330                1335

Leu Asn Lys Leu Gly Gly Asp
    1340                1345

<210> SEQ ID NO 21
<211> LENGTH: 1370
<212> TYPE: PRT
<213> ORGANISM: Streptococcus gallolyticus ATCC BAA-2069

<400> SEQUENCE: 21

Met Thr Lys Lys Asn Tyr Ser Ile Gly Leu Asp Ile Gly Thr Asn Ser
1               5                   10                  15

Val Gly Trp Ala Val Ile Thr Asp Asp Tyr Lys Val Pro Ala Lys Lys
            20                  25                  30

Met Lys Val Leu Gly Asn Thr Asp Lys Lys Tyr Ile Lys Lys Asn Leu
        35                  40                  45

Leu Gly Ala Leu Leu Phe Asp Ser Gly Glu Thr Ala Glu Ala Thr Arg
    50                  55                  60

Leu Lys Arg Thr Ala Arg Arg Arg Tyr Thr Arg Arg Lys Asn Arg Leu
65                  70                  75                  80

Arg Tyr Leu Gln Glu Ile Phe Ala Glu Glu Met Thr Lys Val Asp Glu
                85                  90                  95

Ser Phe Phe Tyr Arg Leu Asp Glu Ser Phe Leu Thr Asp Glu Lys
            100                 105                 110
```

```
Asp Phe Glu Arg His Pro Ile Phe Gly Asn Lys Ala Glu Asp Ala
            115                 120                 125

Tyr His Gln Lys Phe Pro Thr Ile Tyr His Leu Arg Asn Tyr Leu Ala
        130                 135                 140

Asp Ser Ser Glu Lys Ala Asp Leu Arg Leu Val Tyr Leu Ala Leu Ala
145                 150                 155                 160

His Met Ile Lys Tyr Arg Gly His Phe Leu Ile Glu Gly Lys Leu Asn
                165                 170                 175

Ala Glu Asn Thr Asp Val Gln Lys Leu Phe Thr Asp Phe Val Gly Val
            180                 185                 190

Tyr Asp Arg Thr Phe Asp Asp Ser His Leu Ser Glu Ile Thr Val Asp
        195                 200                 205

Val Ala Ser Thr Leu Thr Glu Lys Ile Ser Lys Ser Arg Arg Leu Glu
210                 215                 220

Asn Leu Ile Lys Tyr Tyr Pro Thr Glu Lys Lys Asn Thr Leu Phe Gly
225                 230                 235                 240

Asn Leu Ile Ala Leu Ala Leu Gly Leu Gln Pro Asn Phe Lys Met Asn
            245                 250                 255

Phe Lys Leu Ser Glu Asp Ala Lys Leu Gln Phe Ser Lys Asp Thr Tyr
        260                 265                 270

Glu Glu Asp Leu Glu Glu Leu Leu Gly Lys Ile Gly Asp Asp Tyr Ala
        275                 280                 285

Asp Leu Phe Thr Ser Ala Lys Asn Leu Tyr Asp Ala Ile Leu Leu Ser
        290                 295                 300

Gly Ile Leu Thr Val Asp Asp Asn Ser Thr Lys Ala Pro Leu Ser Ala
305                 310                 315                 320

Ser Met Ile Lys Arg Tyr Val Glu His His Glu Asp Leu Glu Lys Leu
                325                 330                 335

Lys Glu Phe Ile Lys Ala Asn Lys Ser Glu Leu Tyr His Asp Ile Phe
            340                 345                 350

Lys Asp Lys Asn Lys Asn Gly Tyr Ala Gly Tyr Ile Glu Asn Gly Val
        355                 360                 365

Lys Gln Asp Glu Phe Tyr Lys Tyr Leu Lys Asn Thr Leu Ser Lys Ile
370                 375                 380

Asp Gly Ser Asp Tyr Phe Leu Asp Lys Ile Glu Arg Glu Asp Phe Leu
385                 390                 395                 400

Arg Lys Gln Arg Thr Phe Asp Asn Gly Ser Ile Pro His Gln Ile His
            405                 410                 415

Leu Gln Glu Met His Ala Ile Leu Arg Arg Gln Gly Asp Tyr Tyr Pro
        420                 425                 430

Phe Leu Lys Glu Lys Gln Asp Arg Ile Glu Lys Ile Leu Thr Phe Arg
        435                 440                 445

Ile Pro Tyr Tyr Val Gly Pro Leu Val Arg Lys Asp Ser Arg Phe Ala
450                 455                 460

Trp Ala Glu Tyr Arg Ser Asp Glu Lys Ile Thr Pro Trp Asn Phe Asp
465                 470                 475                 480

Lys Val Ile Asp Lys Glu Lys Ser Ala Glu Lys Phe Ile Thr Arg Met
                485                 490                 495

Thr Leu Asn Asp Leu Tyr Leu Pro Glu Glu Lys Val Leu Pro Lys His
            500                 505                 510

Ser His Val Tyr Glu Thr Tyr Ala Val Tyr Asn Glu Leu Thr Lys Ile
        515                 520                 525

Lys Tyr Val Asn Glu Gln Gly Lys Glu Ser Phe Phe Asp Ser Asn Met
```

-continued

```
            530                 535                 540
Lys Gln Glu Ile Phe Asp His Val Phe Lys Glu Asn Arg Lys Val Thr
545                 550                 555                 560

Lys Glu Lys Leu Leu Asn Tyr Leu Asn Lys Glu Phe Pro Glu Tyr Arg
                565                 570                 575

Ile Lys Asp Leu Ile Gly Leu Asp Lys Glu Asn Lys Ser Phe Asn Ala
                580                 585                 590

Ser Leu Gly Thr Tyr His Asp Leu Lys Lys Ile Leu Asp Lys Ala Phe
                595                 600                 605

Leu Asp Asp Lys Val Asn Glu Glu Val Ile Glu Asp Ile Ile Lys Thr
            610                 615                 620

Leu Thr Leu Phe Glu Asp Lys Asp Met Ile His Glu Arg Leu Gln Lys
625                 630                 635                 640

Tyr Ser Asp Ile Phe Thr Ala Asn Gln Leu Lys Lys Leu Glu Arg Arg
                645                 650                 655

His Tyr Thr Gly Trp Gly Arg Leu Ser Tyr Lys Leu Ile Asn Gly Ile
                660                 665                 670

Arg Asn Lys Glu Asn Asn Lys Thr Ile Leu Asp Tyr Leu Ile Asp Asp
                675                 680                 685

Gly Ser Ala Asn Arg Asn Phe Met Gln Leu Ile Asn Asp Asp Thr Leu
            690                 695                 700

Pro Phe Lys Gln Ile Ile Gln Lys Ser Gln Val Val Gly Asp Val Asp
705                 710                 715                 720

Asp Ile Glu Ala Val Val His Asp Leu Pro Gly Ser Pro Ala Ile Lys
                725                 730                 735

Lys Gly Ile Leu Gln Ser Val Lys Ile Val Asp Glu Leu Val Lys Val
                740                 745                 750

Met Gly Asp Asn Pro Asp Asn Ile Val Ile Glu Met Ala Arg Glu Asn
            755                 760                 765

Gln Thr Thr Asn Arg Gly Arg Ser Gln Ser Gln Arg Leu Lys Lys Leu
770                 775                 780

Leu Gln Ser Ser Leu Lys Glu Leu Gly Ser Asn Ile Leu Asn Glu Glu
785                 790                 795                 800

Lys Pro Ser Tyr Ile Glu Asp Lys Val Glu Asn Ser His Leu Gln Asn
                805                 810                 815

Asp Gln Leu Phe Leu Tyr Tyr Ile Gln Asn Gly Lys Asp Met Tyr Thr
                820                 825                 830

Gly Asp Glu Leu Asp Ile Asp His Leu Ser Asp Tyr Asp Ile Asp His
                835                 840                 845

Ile Ile Pro Gln Ala Phe Ile Lys Asp Asp Ser Ile Asp Asn Arg Val
850                 855                 860

Leu Thr Ser Ser Ala Lys Asn Arg Gly Lys Ser Asp Asp Val Pro Ser
865                 870                 875                 880

Leu Asp Ile Val Arg Ala Arg Lys Ala Glu Trp Val Arg Leu Tyr Lys
                885                 890                 895

Ser Gly Leu Ile Ser Lys Arg Lys Phe Asp Asn Leu Thr Lys Ala Glu
                900                 905                 910

Arg Gly Gly Leu Thr Glu Ala Asp Lys Ala Gly Phe Ile Lys Arg Gln
                915                 920                 925

Leu Val Glu Thr Arg Gln Ile Thr Lys His Val Ala Gln Ile Leu Asp
            930                 935                 940

Ala Arg Phe Asn Thr Glu His Asp Glu Asn Asp Lys Val Ile Arg Asp
945                 950                 955                 960
```

-continued

Val Lys Val Ile Thr Leu Lys Ser Asn Leu Val Ser Gln Phe Arg Lys
              965                 970                 975

Asp Phe Glu Phe Tyr Lys Val Arg Glu Ile Asn Asp Tyr His His Ala
              980                 985                 990

His Asp Ala Tyr Leu Asn Ala Val Val Gly Thr Ala Leu Leu Lys Lys
              995                1000                1005

Tyr Pro Lys Leu Ala Ser Glu Phe Val Tyr Gly Glu Tyr Lys Lys
         1010                1015                1020

Tyr Asp Ile Arg Lys Phe Ile Thr Asn Ser Ser Asp Lys Ala Thr
         1025                1030                1035

Ala Lys Tyr Phe Phe Tyr Ser Asn Leu Met Asn Phe Phe Lys Thr
         1040                1045                1050

Lys Val Lys Tyr Ala Asp Gly Thr Val Phe Glu Arg Pro Ile Ile
         1055                1060                1065

Glu Thr Asn Ala Asp Gly Glu Ile Ala Trp Asn Lys Gln Ile Asp
         1070                1075                1080

Phe Glu Lys Val Arg Lys Val Leu Ser Tyr Pro Gln Val Asn Ile
         1085                1090                1095

Val Lys Lys Val Glu Thr Gln Thr Gly Gly Phe Ser Lys Glu Ser
         1100                1105                1110

Ile Leu Pro Lys Gly Asp Ser Asp Lys Leu Ile Pro Arg Lys Thr
         1115                1120                1125

Lys Lys Val Tyr Trp Asp Thr Lys Lys Tyr Gly Gly Phe Asp Ser
         1130                1135                1140

Pro Thr Val Ala Tyr Ser Val Phe Val Val Ala Asp Val Glu Lys
         1145                1150                1155

Gly Lys Ala Lys Lys Leu Lys Thr Val Lys Glu Leu Val Gly Ile
         1160                1165                1170

Ser Ile Met Glu Arg Ser Phe Phe Glu Glu Asn Pro Val Glu Phe
         1175                1180                1185

Leu Glu Asn Lys Gly Tyr His Asn Ile Arg Glu Asp Lys Leu Ile
         1190                1195                1200

Lys Leu Pro Lys Tyr Ser Leu Phe Glu Phe Glu Gly Gly Arg Arg
         1205                1210                1215

Arg Leu Leu Ala Ser Ala Ser Glu Leu Gln Lys Gly Asn Glu Met
         1220                1225                1230

Val Leu Pro Gly Tyr Leu Val Glu Leu Leu Tyr His Ala His Arg
         1235                1240                1245

Ala Asp Asn Phe Asn Ser Thr Glu Tyr Leu Asn Tyr Val Ser Glu
         1250                1255                1260

His Lys Lys Glu Phe Glu Lys Val Leu Ser Cys Val Glu Asp Phe
         1265                1270                1275

Ala Asn Leu Tyr Val Asp Val Glu Lys Asn Leu Ser Lys Ile Arg
         1280                1285                1290

Ala Val Ala Asp Ser Met Asp Asn Phe Ser Ile Glu Glu Ile Ser
         1295                1300                1305

Asn Ser Phe Ile Asn Leu Leu Thr Leu Thr Ala Leu Gly Ala Pro
         1310                1315                1320

Ala Asp Phe Asn Phe Leu Gly Glu Lys Ile Pro Arg Lys Arg Tyr
         1325                1330                1335

Thr Ser Thr Lys Glu Cys Leu Thr Ala Thr Leu Ile His Gln Ser
         1340                1345                1350

Ile Thr Gly Leu Tyr Glu Thr Arg Ile Asp Leu Ser Lys Leu Gly
        1355                1360                1365

Glu Glu
    1370

<210> SEQ ID NO 22
<211> LENGTH: 1373
<212> TYPE: PRT
<213> ORGANISM: Streptococcus lutetiensis 033

<400> SEQUENCE: 22

Met Glu Lys Thr Tyr Ser Ile Gly Leu Asp Ile Gly Thr Asn Ser Val
1               5                   10                  15

Gly Trp Ser Val Ile Thr Asp Asp Tyr Lys Val Pro Ala Lys Lys Met
            20                  25                  30

Lys Val Leu Gly Asn Thr Asp Lys Lys Tyr Ile Lys Lys Asn Leu Leu
        35                  40                  45

Gly Ala Leu Leu Phe Asp Ser Gly Glu Thr Ala Glu Val Thr Arg Leu
    50                  55                  60

Lys Arg Thr Ala Arg Arg Arg Tyr Thr Arg Arg Lys Asn Arg Leu Arg
65                  70                  75                  80

Tyr Leu Gln Glu Ile Phe Ala Lys Glu Met Ala Lys Val Asp Glu Ser
                85                  90                  95

Phe Phe Gln Arg Leu Glu Glu Ser Phe Leu Thr Asp Asp Lys Thr
            100                 105                 110

Phe Asp Ser His Pro Ile Phe Gly Asn Lys Ala Glu Glu Asp Ala Tyr
        115                 120                 125

His Gln Glu Phe Pro Thr Ile Tyr His Leu Arg Lys His Leu Ala Asp
    130                 135                 140

Ser Ser Glu Lys Ala Asp Leu Arg Leu Val Tyr Leu Ala Leu Ala His
145                 150                 155                 160

Met Ile Lys Phe Arg Gly His Phe Leu Ile Glu Gly Glu Leu Asn Ala
                165                 170                 175

Glu Asn Thr Asp Ile Gln Lys Leu Phe Asn Asp Phe Val Glu Thr Tyr
            180                 185                 190

Asp Lys Ile Ala Asp Glu Ser His Leu Ser Glu Val Asp Ala Ser Ser
        195                 200                 205

Ile Leu Thr Asn Lys Ile Ser Lys Ser Arg Arg Leu Glu Asn Leu Ile
    210                 215                 220

Lys Gln Tyr Pro Thr Glu Lys Lys Asn Thr Leu Phe Gly Asn Leu Val
225                 230                 235                 240

Ala Leu Val Leu Gly Leu Gln Pro Asn Phe Lys Thr Asn Phe Lys Leu
                245                 250                 255

Ser Glu Asp Ala Lys Leu Gln Phe Ser Lys Asp Thr Tyr Asp Glu Asp
            260                 265                 270

Leu Glu Glu Leu Leu Gly Lys Ile Gly Asp Asp Tyr Ala Asp Leu Phe
        275                 280                 285

Thr Ala Ala Lys Asn Leu Tyr Asp Ala Ile Leu Leu Ser Gly Ile Leu
    290                 295                 300

Thr Val Asp Asp Asn Ser Thr Lys Ala Pro Leu Ser Ala Ser Met Ile
305                 310                 315                 320

Lys Arg Tyr Glu Glu His His Glu Asp Leu Glu Lys Leu Lys Lys Phe
                325                 330                 335

Ile Lys Val Asn Asn Phe Asp Lys Tyr His Glu Ile Phe Lys Asp Lys
            340                 345                 350

```
Ser Lys Asn Gly Tyr Ala Gly Tyr Ile Glu Asn Gly Val Lys Gln Asp
            355                 360                 365

Ile Phe Tyr Lys His Leu Lys Ser Ile Ile Ser Glu Lys Asn Gly Gly
            370                 375                 380

Gln Tyr Phe Leu Asp Lys Ile Glu Arg Glu Asp Phe Leu Arg Lys Gln
385                 390                 395                 400

Arg Thr Phe Asp Asn Gly Ser Ile Pro His Gln Ile His Leu Gln Glu
                405                 410                 415

Met Arg Ala Ile Leu Arg Arg Gln Gly Glu Tyr Tyr Pro Phe Leu Lys
                420                 425                 430

Glu Asn Gln Ala Lys Ile Glu Lys Ile Leu Thr Phe Arg Ile Pro Tyr
            435                 440                 445

Tyr Val Gly Pro Leu Ala Arg Lys Asp Ser Arg Phe Ala Trp Ala Asn
            450                 455                 460

Tyr His Ser Asp Glu Pro Ile Thr Pro Trp Asn Phe Asp Glu Val Val
465                 470                 475                 480

Asp Lys Glu Lys Ser Ala Glu Lys Phe Ile Thr Arg Met Thr Leu Asn
                485                 490                 495

Asp Leu Tyr Leu Pro Glu Glu Lys Val Leu Pro Lys His Ser His Val
            500                 505                 510

Tyr Glu Thr Phe Thr Val Tyr Asn Glu Leu Thr Lys Ile Lys Tyr Val
            515                 520                 525

Asn Glu Gln Gly Glu Ser Phe Phe Phe Asp Ala Asn Met Lys Gln Glu
            530                 535                 540

Ile Phe Asp His Val Phe Lys Glu Asn Arg Lys Val Thr Lys Ala Lys
545                 550                 555                 560

Leu Leu Ser Tyr Leu Asn Asn Glu Phe Glu Glu Phe Arg Ile Asn Asp
                565                 570                 575

Leu Ile Gly Leu Asp Lys Asp Ser Lys Ser Phe Asn Ala Ser Leu Gly
                580                 585                 590

Thr Tyr His Asp Leu Lys Lys Ile Leu Asp Lys Ser Phe Leu Asp Asp
            595                 600                 605

Lys Thr Asn Glu Gln Ile Ile Glu Asp Ile Val Leu Thr Leu Thr Leu
            610                 615                 620

Phe Glu Asp Arg Asp Met Ile His Glu Arg Leu Gln Lys Tyr Ser Asp
625                 630                 635                 640

Phe Phe Thr Ser Gln Gln Leu Lys Lys Leu Glu Arg Arg His Tyr Thr
                645                 650                 655

Gly Trp Gly Arg Leu Ser Tyr Lys Leu Ile Asn Gly Ile Arg Asn Lys
                660                 665                 670

Glu Asn Asn Lys Thr Ile Leu Asp Phe Leu Ile Asp Asp Gly His Ala
            675                 680                 685

Asn Arg Asn Phe Met Gln Leu Ile Asn Asp Glu Ser Leu Ser Phe Lys
            690                 695                 700

Thr Ile Ile Gln Glu Ala Gln Val Val Gly Asp Val Asp Asp Ile Glu
705                 710                 715                 720

Ala Val Val His Asp Leu Pro Gly Ser Pro Ala Ile Lys Lys Gly Ile
                725                 730                 735

Leu Gln Ser Val Lys Ile Val Asp Glu Leu Val Lys Val Met Gly Asp
            740                 745                 750

Asn Pro Asp Asn Ile Val Ile Glu Met Ala Arg Glu Asn Gln Thr Thr
            755                 760                 765
```

```
Asn Arg Glu Arg Ser Gln Ser Gln Gln Arg Leu Lys Lys Leu Gln Asn
770                 775                 780

Ser Leu Lys Glu Leu Gly Ser Asn Ile Leu Asn Glu Glu Lys Pro Ser
785                 790                 795                 800

Tyr Ile Glu Asp Lys Val Glu Asn Ser His Leu Gln Asn Asp Gln Leu
                805                 810                 815

Phe Leu Tyr Tyr Ile Gln Asn Gly Lys Asp Met Tyr Thr Gly Asp Glu
                820                 825                 830

Leu Asp Ile Asp His Leu Ser Asp Tyr Asp Ile Asp His Ile Ile Pro
                835                 840                 845

Gln Ala Phe Ile Lys Asp Asn Ser Ile Asp Asn Arg Val Leu Thr Ser
850                 855                 860

Ser Ala Lys Asn Arg Gly Lys Ser Asp Asp Val Pro Ser Leu Asp Ile
865                 870                 875                 880

Val Arg Ala Arg Lys Ala Glu Trp Val Arg Leu Tyr Lys Ser Gly Leu
                885                 890                 895

Ile Ser Lys Arg Lys Phe Asp Asn Leu Thr Lys Ala Glu Arg Gly Gly
                900                 905                 910

Leu Thr Glu Ala Asp Lys Ala Gly Phe Ile Lys Arg Gln Leu Val Glu
                915                 920                 925

Thr Arg Gln Ile Thr Lys His Val Ala Gln Ile Leu Asp Ala Arg Phe
930                 935                 940

Asn Thr Lys Arg Asp Glu Asn Asp Lys Val Ile Arg Asp Val Lys Val
945                 950                 955                 960

Ile Thr Leu Lys Ser Asn Leu Val Ser Gln Phe Arg Lys Glu Phe Lys
                965                 970                 975

Phe Tyr Lys Val Arg Glu Ile Asn Asp Tyr His His Ala His Asp Ala
                980                 985                 990

Tyr Leu Asn Ala Val Val Gly Thr Ala Leu Leu Lys Lys Tyr Pro Lys
                995                 1000                1005

Leu Thr Pro Glu Phe Val Tyr Gly Glu Tyr Lys Lys Tyr Asp Val
        1010                1015                1020

Arg Lys Leu Ile Ala Lys Ser Ser Asp Asp Tyr Ser Glu Met Gly
        1025                1030                1035

Lys Ala Thr Ala Lys Tyr Phe Phe Tyr Ser Asn Leu Met Asn Phe
        1040                1045                1050

Phe Lys Thr Glu Val Lys Tyr Ala Asp Gly Arg Val Phe Glu Arg
        1055                1060                1065

Pro Asp Ile Glu Thr Asn Ala Asp Gly Glu Val Val Trp Asn Lys
        1070                1075                1080

Gln Lys Asp Phe Asp Ile Val Arg Lys Val Leu Ser Tyr Pro Gln
        1085                1090                1095

Val Asn Ile Val Lys Lys Val Glu Glu Gln Thr Val Gly Gln Asn
        1100                1105                1110

Gly Gly Leu Phe Asp Asn Asn Ile Leu Ala Lys Pro Glu Lys Asp
        1115                1120                1125

Asp Lys Lys Lys Leu Phe Pro Ile Lys Lys Ser Leu Ser Thr Thr
        1130                1135                1140

Ser Tyr Gly Gly Tyr Ala Arg Ala Thr Ile Ala Tyr Ser Ile Leu
        1145                1150                1155

Ile Val Ser Glu Phe Gly Lys Asn Lys Glu Leu Lys Leu Leu Gly
        1160                1165                1170

Leu Pro Leu Leu Asp Lys Val Lys Tyr Glu Lys Asn Pro Ile Ala
```

```
                    1175                1180                1185

Tyr Leu Asn Ser Ile Gly Ile Ile Asn Val Lys Ser Ile Phe Lys
        1190                1195                1200

Leu Pro Lys Tyr Cys Leu Phe Glu Phe Gln Glu Lys Asn Thr Asn
        1205                1210                1215

Tyr Arg Arg Tyr Met Val Ser Asn Gln Glu Leu Lys Arg Ala Asn
        1220                1225                1230

Gln Leu Phe Leu Thr Cys Lys Glu Thr Glu Leu Val Tyr Lys Tyr
        1235                1240                1245

Ile Lys Ser Asp Asn Asp Asn Thr His Leu Val Gly Asn Glu Lys
        1250                1255                1260

Thr Ile Leu Ser Ile Trp Asn Lys Leu Val Ile Phe Met Glu Arg
        1265                1270                1275

Thr Lys Leu Ile Asp Lys Lys Leu Phe Ala Ser Leu Lys Gln Leu
        1280                1285                1290

Lys Asp Glu Val Asp Leu Ile Asn Ile Leu Asp Met Thr Ala Lys
        1295                1300                1305

Ser Leu Asp Phe Thr Lys Ile Ser Ala Gly Gln Lys Lys Ile Thr
        1310                1315                1320

Ile Ser Asp Ser Leu Ser Leu Pro Ile Lys Arg Trp Gln Phe Ser
        1325                1330                1335

Ser Asp Glu Lys Met Leu Lys Gln Leu Lys Thr Ala Thr Leu Ile
        1340                1345                1350

His Gln Ser Val Thr Gly Leu Tyr Glu Thr Arg Ile Asp Leu Ser
        1355                1360                1365

Lys Leu Gly Glu Glu
        1370

<210> SEQ ID NO 23
<211> LENGTH: 1246
<212> TYPE: PRT
<213> ORGANISM: Streptococcus intermedius SK54

<400> SEQUENCE: 23

Met Arg Leu Val Tyr Leu Ala Leu Ala His Met Ile Lys Phe Arg Gly
1               5                   10                  15

His Phe Leu Tyr Glu Gly Asp Leu Lys Ala Glu Asn Thr Asp Val Gln
                20                  25                  30

Ala Leu Phe Lys Asp Phe Val Glu Glu Tyr Asp Lys Thr Ile Glu Glu
            35                  40                  45

Ser His Leu Ser Glu Ile Thr Val Asp Ala Leu Ser Ile Leu Thr Glu
        50                  55                  60

Lys Val Ser Lys Ser Arg Leu Glu Asn Leu Ile Ala His Tyr Pro
65                  70                  75                  80

Thr Glu Lys Lys Asn Thr Leu Phe Gly Asn Leu Ile Ala Leu Ser Leu
                85                  90                  95

Gly Leu Gln Ala Asn Phe Lys Thr Asn Phe Gln Leu Ser Glu Asp Ala
            100                 105                 110

Lys Leu Gln Phe Ser Lys Asp Thr Tyr Glu Glu Asp Leu Glu Gly Leu
        115                 120                 125

Leu Gly Glu Val Gly Asp Glu Tyr Ala Asp Leu Phe Val Ser Ala Lys
    130                 135                 140

Asn Leu Tyr Asp Ala Ile Leu Leu Ser Gly Ile Leu Thr Val Asp Asp
145                 150                 155                 160
```

```
Asn Ser Thr Lys Ala Pro Leu Ser Ala Ser Met Val Lys Arg Tyr Lys
            165                 170                 175
Glu His Lys Glu Glu Leu Ala Ala Phe Lys Arg Phe Ile Lys Glu Lys
        180                 185                 190
Leu Pro Lys Lys Tyr Glu Glu Ile Phe Lys Asp Asp Thr Lys Asn Gly
        195                 200                 205
Tyr Ala Gly Tyr Val Gly Ala Asp Lys Lys Leu Arg Lys Arg Ser Gly
        210                 215                 220
Lys Leu Ala Thr Glu Glu Phe Tyr Lys Tyr Val Lys Gly Ile Leu
225                 230                 235                 240
Asn Lys Val Glu Gly Ala Asp Tyr Phe Leu Asp Lys Ile Asp Arg Glu
            245                 250                 255
Asp Phe Leu Arg Lys Gln Arg Thr Phe Asp Asn Gly Ser Ile Pro His
            260                 265                 270
Gln Ile His Leu Gln Glu Met His Ala Ile Leu Arg Arg Gln Gly Glu
        275                 280                 285
His Tyr Pro Phe Leu Lys Glu Asn Gln Asp Lys Ile Glu Lys Ile Leu
290                 295                 300
Thr Phe Arg Ile Pro Tyr Tyr Val Gly Pro Leu Ala Arg Lys Gly Ser
305                 310                 315                 320
Arg Phe Ala Trp Ala Glu Tyr Lys Ala Asp Glu Lys Ile Thr Pro Trp
            325                 330                 335
Asn Phe Asp Asp Ile Leu Asp Lys Glu Lys Ser Ala Glu Lys Phe Ile
            340                 345                 350
Thr Arg Met Thr Leu Asn Asp Leu Tyr Leu Pro Glu Glu Lys Val Leu
        355                 360                 365
Pro Lys His Ser Pro Leu Tyr Glu Thr Phe Thr Val Tyr Asn Glu Leu
        370                 375                 380
Thr Lys Val Lys Tyr Val Asn Glu Gln Gly Glu Ala Lys Phe Phe Asp
385                 390                 395                 400
Thr Asn Met Lys Gln Glu Ile Phe Asp His Val Phe Lys Glu Asn Arg
            405                 410                 415
Lys Val Thr Lys Asp Lys Leu Leu Asn Tyr Leu Asn Lys Glu Phe Glu
        420                 425                 430
Glu Phe Arg Ile Val Asn Leu Thr Gly Leu Asp Lys Glu Asn Lys Ala
        435                 440                 445
Phe Asn Ala Ser Leu Gly Thr Tyr His Asp Leu Arg Lys Ile Leu Asp
450                 455                 460
Lys Ser Phe Leu Asp Asp Lys Val Asn Glu Lys Ile Ile Glu Asp Ile
465                 470                 475                 480
Ile Gln Thr Leu Thr Leu Phe Glu Asp Arg Glu Met Ile Arg Gln Arg
            485                 490                 495
Leu Gln Lys Tyr Ser Asp Ile Phe Thr Thr Gln Leu Lys Glu Leu
        500                 505                 510
Glu Arg Arg His Tyr Thr Gly Trp Gly Arg Leu Ser Tyr Lys Leu Ile
        515                 520                 525
Asn Gly Ile Arg Asn Lys Glu Asn Lys Lys Thr Ile Leu Asp Tyr Leu
530                 535                 540
Ile Asp Asp Gly Tyr Ala Asn Arg Asn Phe Met Gln Leu Ile Asn Asp
545                 550                 555                 560
Asp Ala Leu Ser Phe Lys Glu Glu Ile Ala Arg Ala Gln Ile Ile Gly
            565                 570                 575
Asp Val Asp Asp Ile Ala Asn Val Val His Asp Leu Pro Gly Ser Pro
```

```
                580                 585                 590
Ala Ile Lys Lys Gly Ile Leu Gln Ser Val Lys Ile Val Asp Glu Leu
            595                 600                 605

Val Lys Val Met Gly His Asn Pro Thr Asn Ile Ile Glu Met Ala
        610                 615                 620

Arg Glu Asn Gln Thr Thr Asp Lys Gly Arg Asn Ser Gln Gln Arg
625                 630                 635                 640

Leu Lys Leu Leu Gln Asp Ser Leu Lys Asn Leu Asp Asn Pro Val Asn
                645                 650                 655

Ile Lys Asn Val Glu Asn Gln Gln Leu Gln Asn Asp Arg Leu Phe Leu
            660                 665                 670

Tyr Tyr Ile Gln Asn Gly Lys Asp Met Tyr Thr Gly Glu Thr Leu Asp
            675                 680                 685

Ile Asn Asn Leu Ser Gln Tyr Asp Ile Asp His Ile Ile Pro Gln Ala
            690                 695                 700

Phe Ile Lys Asp Asn Ser Leu Asp Asn Arg Val Leu Thr Arg Ser Asp
705                 710                 715                 720

Lys Asn Arg Gly Lys Ser Asp Asp Val Pro Ser Ile Glu Val Val His
                725                 730                 735

Glu Met Lys Ser Phe Trp Ser Lys Leu Leu Ser Val Lys Leu Ile Thr
            740                 745                 750

Gln Arg Lys Phe Asp Asn Leu Thr Lys Ala Glu Arg Gly Gly Leu Thr
            755                 760                 765

Glu Asn Asp Lys Ala Gly Phe Ile Lys Arg Gln Leu Val Glu Thr Arg
        770                 775                 780

Gln Ile Thr Lys His Val Ala Gln Val Leu Asp Ala Arg Phe Asn Ala
785                 790                 795                 800

Lys His Asp Glu Asn Lys Lys Val Ile Arg Asp Val Lys Ile Ile Thr
                805                 810                 815

Leu Lys Ser Asn Leu Val Ser Gln Phe Arg Lys Asp Phe Lys Phe Tyr
            820                 825                 830

Lys Val Arg Glu Ile Asn Asp Tyr His His Ala His Asp Ala Tyr Leu
        835                 840                 845

Asn Ala Val Ile Gly Thr Ala Leu Leu Lys Lys Tyr Pro Lys Leu Ala
    850                 855                 860

Ser Glu Phe Val Tyr Gly Glu Phe Lys Lys Tyr Asp Val Arg Lys Phe
865                 870                 875                 880

Ile Ala Lys Ser Asp Lys Glu Ile Gly Lys Ala Thr Ala Lys Tyr Phe
                885                 890                 895

Phe Tyr Ser Asn Leu Met Asn Phe Phe Lys Glu Val Lys Phe Ala
            900                 905                 910

Asp Gly Thr Val Val Glu Arg Pro Asp Ile Glu Thr Ser Glu Asp Gly
        915                 920                 925

Glu Ile Ala Trp Asn Lys Gln Thr Asp Phe Lys Ile Val Arg Lys Val
        930                 935                 940

Leu Ser Tyr Pro Gln Val Asn Ile Val Lys Lys Thr Glu Val Gln Thr
945                 950                 955                 960

His Gly Leu Asp Arg Gly Lys Pro Arg Gly Leu Phe Asn Ala Asn
            965                 970                 975

Ser Pro Lys Pro Lys Pro Asp Ser Ser Glu Asn Leu Val Gly Ile Lys
            980                 985                 990

Arg Asn Leu Asp Pro Lys Lys Tyr Gly Gly Tyr Ala Gly Ile Ser Asn
            995                 1000                1005
```

Ser Tyr Ala Val Leu Val Lys Ala Ile Ile Glu Lys Gly Val Lys
   1010                1015                1020

Lys Lys Glu Thr Met Val Leu Glu Phe Gln Gly Ile Ser Ile Leu
   1025                1030                1035

Asp Arg Ile Thr Phe Glu Lys Asp Lys Arg Ala Phe Leu Leu Gly
   1040                1045                1050

Lys Gly Tyr Lys Asp Ile Lys Lys Ile Ile Glu Leu Pro Lys Tyr
   1055                1060                1065

Ser Leu Phe Glu Leu Lys Asp Gly Ser Arg Arg Met Leu Ala Ser
   1070                1075                1080

Ile Leu Ser Thr Asn Asn Lys Arg Gly Glu Ile His Lys Gly Asn
   1085                1090                1095

Glu Leu Phe Val Pro Gln Lys Phe Thr Thr Leu Leu Tyr His Ala
   1100                1105                1110

Lys Arg Ile Asn Asn Pro Ile Asn Lys Asp His Ile Glu Tyr Val
   1115                1120                1125

Lys Lys His Arg Asp Asp Phe Lys Glu Leu Leu Asn Tyr Val Leu
   1130                1135                1140

Glu Phe Asn Glu Lys Tyr Val Gly Ala Thr Lys Asn Gly Glu Arg
   1145                1150                1155

Leu Lys Glu Ala Val Ala Asp Phe Asp Ser Lys Ser Asn Glu Glu
   1160                1165                1170

Ile Cys Thr Ser Phe Leu Gly Ala Val Asn Ser Lys Asn Ala Gly
   1175                1180                1185

Leu Phe Glu Leu Thr Ser Leu Gly Ser Ala Ser Asp Phe Glu Phe
   1190                1195                1200

Leu Gly Val Lys Ile Pro Arg Tyr Arg Asp Tyr Thr Pro Ser Ser
   1205                1210                1215

Leu Leu Lys Asp Ser Ile Leu Ile His Gln Ser Ile Thr Gly Leu
   1220                1225                1230

Tyr Glu Thr Arg Ile Asp Leu Ser Lys Leu Gly Glu Asp
   1235                1240                1245

<210> SEQ ID NO 24
<211> LENGTH: 1377
<212> TYPE: PRT
<213> ORGANISM: Lactobacillus brevis subsp. gravesensis ATCC 27305

<400> SEQUENCE: 24

Met Glu Ser Asn His Asp Gly Glu Gln Val Lys Tyr Thr Leu Gly
1               5                   10                  15

Asp Ile Gly Thr Ser Ser Ile Gly Tyr Ala Ala Ile Asp Lys His Gln
            20                  25                  30

Lys Pro Ile Arg Ala Lys Gly Lys His Val Ile Gly Val Arg Leu Phe
        35                  40                  45

Gln Glu Gly Gln Thr Ala Ala Asp Arg Arg Ala Phe Arg Thr Thr Arg
    50                  55                  60

Arg Arg Leu Lys Arg Arg Lys Trp Arg Leu Asn Leu Leu Asn Arg Leu
65                  70                  75                  80

Phe Asp Pro Tyr Leu Ser Glu Val Asp Pro Asn Phe Leu Pro Arg Leu
                85                  90                  95

Arg Gln Ser Asn Leu Ser Pro Lys Asp Asn Lys His Phe Asn Gly
            100                 105                 110

Ser Thr Leu Phe Pro Asp Lys Thr Asp Ala Ala Phe Tyr Arg Gln Tyr

-continued

```
                115                 120                 125
Pro Thr Met Tyr His Leu Arg Tyr Ala Leu Met Thr Glu Lys Arg Lys
130                 135                 140

Phe Asp Ile Arg Glu Val Tyr Leu Ala Ile His His Ile Val Lys Tyr
145                 150                 155                 160

Arg Gly Asn Phe Leu Asn Ser Ala Thr Val Asp Ser Phe Lys Thr Ser
                165                 170                 175

Asn Ile Asp Phe Thr Ser Gln Phe Asp Arg Leu Asn Glu Leu Tyr Arg
                180                 185                 190

Gln Val Ile Leu Asp Glu Pro Phe Gln Ile Asn Met Asp Gln Val Asp
                195                 200                 205

Glu Met Thr Asn Lys Leu Leu Asp Asn Asp Ala Leu Lys Leu Asp Thr
210                 215                 220

Gln Lys Gln Val Ala Lys Leu Leu Pro Val Ile Tyr Asn Asp Lys Pro
225                 230                 235                 240

Ile Asp Lys Gln Tyr Thr Arg Ile Ala Thr Glu Phe Ser Lys Ala Ile
                245                 250                 255

Leu Gly Tyr Lys Thr Lys Leu Asp Val Ile Leu Asn Leu Asp Thr Gln
                260                 265                 270

Asn Ala Lys Asp Trp Val Ile Arg Leu Asp Glu Asp Ile Asp Asp
                275                 280                 285

Lys Leu Pro Ala Leu Val Glu Asn Leu Asp Glu Ser Arg Gln Glu Ile
290                 295                 300

Val Thr Ile Ile Arg Asp Leu Tyr Ala Gln Ile Thr Leu Asn Ala Ile
305                 310                 315                 320

Val Pro Lys Gly Lys Ser Leu Ser Glu Ser Met Val Asp Lys Tyr Asn
                325                 330                 335

Asp His Lys Asp His Leu Asp Leu Leu Met Gly Leu Ile His Glu Leu
                340                 345                 350

Gly Asp Asp Ser Ala Lys Gly Ile Lys Leu Arg Glu Ala Tyr Thr Gln
                355                 360                 365

Tyr Val Gly Lys Ser Asp Asp Lys Thr Leu Asn Gln Asp Asp Phe Tyr
370                 375                 380

Ala Ala Ile Lys Lys Asn Leu Asp Glu Asp Ser Lys Arg Ser Pro Lys
385                 390                 395                 400

Ile Gln Arg Leu Ile Glu Gln Ala Ser Phe Met Pro Lys Gln Arg Thr
                405                 410                 415

Ser Ala Asn Gly Val Ile Pro His Gln Leu His Gln Leu Glu Leu Asp
                420                 425                 430

Arg Ile Ile Glu Asn Gln Gly Arg Tyr Tyr Pro Phe Leu Lys Lys Pro
                435                 440                 445

Asn Pro Asn Thr His Lys Pro Asn Gly Gly Lys Tyr Lys Leu Asp Glu
                450                 455                 460

Leu Val Ala Phe Arg Ile Pro Tyr Tyr Val Gly Pro Leu Ile Thr Lys
465                 470                 475                 480

Arg Asp Gln Glu Lys Thr Ser Gly Ala Asp Phe Ala Trp Met Ile Arg
                485                 490                 495

Lys Pro Gly Gln Glu Gly Glu Ile Thr Pro Trp Asn Phe Asp Gln Lys
                500                 505                 510

Val Asp Arg Met Ala Ser Ala Asn Arg Phe Ile Arg Arg Met Thr Thr
                515                 520                 525

Lys Asp Ser Tyr Leu Val Ala Glu Asp Val Leu Pro Asp Ala Ser Leu
530                 535                 540
```

```
Ile Tyr Glu Lys Phe Lys Ala Leu Asn Glu Leu Asn Met Leu Lys Val
545                 550                 555                 560

Asn Asp Ser Arg Leu Ser Pro Ser Gln Lys Gln Asp Leu Phe Asn Asn
            565                 570                 575

Leu Phe Lys Lys Gln Lys Thr Ile Arg Thr Lys Lys Leu Gln Thr Tyr
        580                 585                 590

Ile Arg Thr Asn Trp Glu Leu Pro Ser Val Met Ile Ser Gly Leu Ala
    595                 600                 605

Asp Pro Asp Lys Phe Asn Ser Ser Leu Ser Thr Tyr Ile Asp Phe Arg
610                 615                 620

Asp Ile Phe Gly Glu Lys Val Asp Pro Asn Arg Gln Ala Asp Tyr
625                 630                 635                 640

Glu Glu Ile Ile Glu Trp Ser Thr Val Phe Glu Asp Arg Lys Ile Tyr
                645                 650                 655

Gln Ala Lys Leu Asn Gln Leu Asp Trp Leu Thr Glu Pro Gln Arg Lys
            660                 665                 670

Ala Leu Leu Thr Lys Arg Tyr Thr Gly Trp Gly Arg Leu Ser Lys Lys
        675                 680                 685

Leu Leu Thr Gly Leu Lys Asp Gln Asn Gly Asp Ser Ile Leu Asp Gln
    690                 695                 700

Leu Trp Lys Thr Asn Asp Asn Phe Met Gln Ile Gln Ser Arg Asp Glu
705                 710                 715                 720

Phe Ala Lys Gln Ile His Asp Glu Asn Ala Lys Gln Phe His Glu Ala
                725                 730                 735

Asn Asn Val Asp Asp Ile Leu Asp Asp Ala Phe Thr Ser Pro Gln Asn
            740                 745                 750

Lys Lys Ala Ile Arg Gln Val Asp Lys Val Val Gln Asp Val Val Lys
        755                 760                 765

Ala Val Gly Tyr Ala Pro Asp Lys Ile Ala Ile Glu Phe Thr Arg Ser
    770                 775                 780

Leu Glu Asn Asn Pro Gln Arg Thr Val Ser Arg Gln Arg Gln Leu Gln
785                 790                 795                 800

Ala Ala Tyr Lys Asn Ile Pro Arg Glu Ile Met Lys Ser Gly Leu Met
                805                 810                 815

Ala Glu Leu Gly Ser Val Ala Asp Ser Lys Lys Val Leu Ser Asp Lys
            820                 825                 830

Leu Tyr Leu Tyr Phe Thr Gln Met Gly Lys Asp Met Tyr Glu Asp Lys
        835                 840                 845

Thr Ile Asn Ile Asp Asn Leu Pro Asn Tyr Asp Ile Asp His Ile Leu
    850                 855                 860

Pro Gln Ala Phe Ile Lys Asp Asp Ser Ile Asp Asn Arg Val Leu Ile
865                 870                 875                 880

Ser Lys Glu Glu Asn Ala Arg Lys Ser Asn Arg Val Pro Leu Lys Phe
                885                 890                 895

Phe Gly Ala Lys Arg Met Gly Phe Trp Lys Asp Leu Leu Asn Asn Gly
            900                 905                 910

Leu Ile Ser Asn Arg Lys Phe Gln Asn Leu Thr Thr Asp Pro Glu Lys
        915                 920                 925

Ile Ser Lys Tyr Ser Ala Lys Gly Phe Ile His Arg Gln Leu Val Glu
    930                 935                 940

Thr Ser Gln Val Ile Arg Leu Val Ala Asn Ile Leu Gly Asn Glu Tyr
945                 950                 955                 960
```

-continued

```
Ser Gln Ala Gly Thr Thr Ile Ile Glu Val Ser Ala Lys Met Asn Arg
                965                 970                 975
Gln Leu Arg Glu Asp Phe His Leu Ile Lys Asn Arg Asn Val Asn Asp
            980                 985                 990
Tyr His His Ala Met Asp Ala Tyr Leu Thr Ala Tyr Val Gly Asp Tyr
        995                 1000                1005
Leu Tyr Leu Arg Tyr Pro Lys Leu Arg Pro Tyr Phe Val Tyr Gly
    1010                1015                1020
Asp Phe Lys Lys Ala Glu Asp Gln Asp Leu Asn Ile Arg Asn Phe
    1025                1030                1035
Asn Phe Leu His Asp Leu Lys Asp Asn Glu Ser Leu Asp Lys Ile
    1040                1045                1050
Val Asp Ser Glu Thr Gly Glu Ile Val Trp Glu Lys His Gly Ser
    1055                1060                1065
Val Lys Gln Leu Lys Lys Val Tyr His Tyr Lys Phe Met Leu Val
    1070                1075                1080
Ser Gln Glu Val Tyr Thr Arg Gln Asp Ala Leu Phe Asn Gln Thr
    1085                1090                1095
Ile Tyr Pro Ala Ser Asp Ala Asp Lys Arg Lys Leu Ile Pro Ile
    1100                1105                1110
Lys Asn Ser Lys Pro Val Asp Val Tyr Gly Gly Tyr Ser Gly Asn
    1115                1120                1125
Ile Asp Ala Tyr Met Ala Ile Val Arg Val His Gly Lys Lys Glu
    1130                1135                1140
Asp Asn Tyr Lys Val Val Gly Ile Pro Met Arg Ala Val Thr Lys
    1145                1150                1155
Leu Lys Lys Ala Glu Lys Glu Gly His Asp Ser Tyr Leu Asn Ala
    1160                1165                1170
Val His Glu Val Leu Lys Pro Gln Phe Thr Lys Lys Lys Asn
    1175                1180                1185
Arg Lys Thr Gly Glu Ile Thr Glu Thr Val Asp Glu Phe Asp Val
    1190                1195                1200
Leu Leu Gly Lys Val Tyr Tyr Arg Gln Leu Ile Val Asp Gly Asn
    1205                1210                1215
Lys Lys Phe Met Leu Gly Ser Ser Tyr Gln Tyr Asn Ala Lys
    1220                1225                1230
Gln Leu Val Leu Ser Asp Lys Ala Met Gln Val Leu Ser Lys Asn
    1235                1240                1245
Gly Lys Val Lys Ser Gln Asp Glu Asn Gln Asn Leu Ile Asp Val
    1250                1255                1260
Tyr Asp Glu Ile Leu Glu Lys Val Asp Gln Tyr Phe Glu Leu Tyr
    1265                1270                1275
Asp Gln Arg His Tyr Arg Glu Ser Leu His Lys Gly Arg Gly Ile
    1280                1285                1290
Phe Val Asn Leu Pro Leu Ser Asn Gln Tyr Asp Gly Ser Lys Leu
    1295                1300                1305
Thr Ser Tyr Gly Lys Tyr Glu Thr Ile Asp Ala Ile Leu Asn Gly
    1310                1315                1320
Leu His Ala Asn Ala Thr Met Ser Asn Leu Arg Tyr Leu Gly Ile
    1325                1330                1335
Ser Ser Pro Phe Gly Lys Met Gln Ala Ser Asn Gly Leu Thr Ile
    1340                1345                1350
Asp Pro Asp Ser Ile Ile Cys Tyr Gln Ser Pro Thr Gly Leu Phe
```

-continued

```
                1355                1360                1365
Glu Arg Gln Ile Lys Leu Ser Asp Leu
        1370                1375

<210> SEQ ID NO 25
<211> LENGTH: 1362
<212> TYPE: PRT
<213> ORGANISM: Lactobacillus casei

<400> SEQUENCE: 25

Met Thr Lys Leu Gly Lys Pro Tyr Gly Ile Gly Val Asp Ile Gly Ser
1               5                   10                  15

Asn Ser Ile Gly Phe Ala Ala Val Asp Glu Asn Ser His Leu Ile Arg
            20                  25                  30

Leu Lys Gly Lys Thr Val Ile Gly Ala Arg Leu Phe Glu Glu Gly Lys
        35                  40                  45

Ala Ala Ala Lys Arg Arg Ala Gly Arg Thr Thr Arg Arg Arg Leu Ser
    50                  55                  60

Arg Asn Arg Trp Arg Leu Ser Phe Leu Arg Asp Phe Phe Glu Ser His
65                  70                  75                  80

Ile Thr Pro Thr Asp Pro Asn Phe Phe Met Arg Gln Lys Tyr Ser Glu
                85                  90                  95

Ile Ser Pro Lys Asp Lys Ala Arg Tyr Lys Tyr Glu Lys Arg Leu Phe
            100                 105                 110

Asn Asp Arg Thr Asp Ala Glu Phe Tyr Gln Gln Tyr Ser Thr Met Tyr
        115                 120                 125

His Leu Arg Asn Arg Leu Met Thr Asp Pro Ser Arg Ala Asp Val Arg
130                 135                 140

Glu Ile Tyr Phe Ala Ile His His Ile Leu Lys Ser Arg Gly His Phe
145                 150                 155                 160

Leu Thr Pro Gly Asp Ala Lys Asp Phe Asn Thr Asn Asp Val Ala Leu
                165                 170                 175

Asp Glu Ile Phe Pro Ala Leu Gln Asp Ala Tyr Ala Gln Val Tyr Pro
            180                 185                 190

Asp Leu Gly Ile Thr Phe Asp Glu Asp Lys Ala Asn Glu Phe Lys Thr
        195                 200                 205

Ile Leu Leu Asn Glu Ile Ala Thr Ser Ile Asp Thr Gln Arg Ala Leu
    210                 215                 220

Val Lys Leu Leu Leu Ala Glu Glu Asp Lys Asp Ile Leu Lys Gln
225                 230                 235                 240

Gln Lys Gln Val Leu Thr Glu Phe Ala Lys Ala Val Val Gly Leu Lys
                245                 250                 255

Thr Lys Leu Asn Leu Ala Leu Gly Thr Glu Val Asp Ser Ser Glu Ala
            260                 265                 270

Thr Ala Trp Asn Phe Ser Leu Gly Gln Leu Asp Asp Lys Trp Ala Gly
        275                 280                 285

Ile Glu Ser Ala Met Thr Asp Glu Gly Thr Glu Ile Leu Asp Gln Ile
    290                 295                 300

Arg Asp Leu Tyr Arg Ala Arg Leu Leu Asn Gly Ile Val Pro Thr Gly
305                 310                 315                 320

Lys Thr Leu Ser Gln Ala Lys Val Asp Asp Tyr Thr Gln His His Glu
                325                 330                 335

Asp Leu Gln Leu Phe Lys Ala Tyr Leu Lys Gln Leu Gly Asp Asp Gly
            340                 345                 350
```

```
Thr Ala Lys Ala Ile Arg Gln Leu Tyr Asp Arg Tyr Ile Asp Gly Asp
            355                 360                 365

Asp Ala Ala Pro Phe Leu Arg Glu Asn Phe Val Lys Ala Leu Thr Lys
        370                 375                 380

Asp Val Thr Ala His Pro Asn Thr Lys Ser Pro Glu Leu Leu Glu Arg
385                 390                 395                 400

Leu Ala Gln Pro Asp Phe Met Leu Lys Gln Arg Asn Lys Ala Asn Gly
            405                 410                 415

Ala Ile Pro Val Gln Met Gln Gln Arg Glu Leu Asp Gln Ile Ile Lys
            420                 425                 430

Asn Gln Ala Val Tyr Tyr Asp Trp Leu Ala Ala Pro Asn Pro Val Glu
        435                 440                 445

Lys His Arg Lys Ser Met Pro Tyr Gln Leu Asp Glu Leu Leu Asn Phe
    450                 455                 460

Arg Ile Pro Tyr Tyr Val Gly Pro Leu Val Thr Ala Lys Glu Gln Lys
465                 470                 475                 480

Ala Ala Gln Gly Gly Val Phe Ala Trp Met Val Arg Lys Asp Pro Glu
            485                 490                 495

Gly Asn Ile Thr Pro Tyr Asn Phe Asp Glu Lys Val Asp Arg Glu Ala
        500                 505                 510

Ser Ala Asn Thr Phe Ile Gln Arg Met Lys Thr Thr Asp Thr Tyr Leu
    515                 520                 525

Ile Gly Glu Asp Val Leu Pro Lys Gln Ser Leu Leu Tyr Gln Arg Tyr
    530                 535                 540

Glu Val Leu Asn Glu Leu Asn Asn Val Arg Val Asn Asn Glu Lys Leu
545                 550                 555                 560

Ser Ile Glu Gln Lys Gln Gln Val Ile Arg Glu Leu Phe Glu Arg His
            565                 570                 575

Asn Ser Val Thr Ile Lys Gln Phe Ala Glu Asn Leu Arg Ala His Gly
        580                 585                 590

Asp Tyr Ala His Ile Pro Glu Ile Arg Gly Leu Ala Asp Glu Lys Arg
    595                 600                 605

Phe Leu Ser Ser Leu Ser Thr Tyr Arg Gln Leu Lys Ser Leu Leu Pro
    610                 615                 620

Glu Ala Ile Asp Asp Pro Ala Lys Gln Ala Asp Ile Glu Asn Ile Ile
625                 630                 635                 640

Ala Trp Ser Thr Val Phe Glu Asp Ala Ala Ile Phe Lys Thr Lys Leu
            645                 650                 655

Lys Glu Ile Ser Trp Leu Gly Ser Glu Ala Ile Thr Lys Leu Ser Asn
        660                 665                 670

Ile Arg Tyr Arg Gly Trp Gly Gln Phe Ser Arg Lys Phe Leu Asn Gly
    675                 680                 685

Leu Thr Leu Gly Asn Gly His Thr Ile Ile Gln Glu Leu Leu Leu Ser
    690                 695                 700

Thr Asn Asn Leu Met Gln Ile Leu Thr Asp Glu Thr Leu Gln Lys Lys
705                 710                 715                 720

Met Thr Glu Leu Asn Ala Asp Lys Leu Lys Thr Ala Asn Ile Asn Asp
            725                 730                 735

Ala Ile Asp Asn Ala Tyr Thr Ser Pro Ser Asn Lys Lys Ala Leu Arg
        740                 745                 750

Gln Val Leu Arg Val Val Asp Asp Ile Lys Arg Ala Ala Asp Gly Gln
    755                 760                 765

Asp Pro Ser Trp Leu Tyr Val Glu Thr Ala Asp Gly Gly Gly Thr Pro
```

```
                770               775               780
Gly Lys Arg Thr Arg Ala Arg Gln His Gln Leu Gln Glu Ile Tyr Ala
785               790               795               800

Asn Ala Ala His Glu Leu Ile Asp Thr Ala Val Arg Gly Glu Leu Glu
                805               810               815

Asp Lys Ile Ser Asp Lys Ala Asp Phe Asn Asp Arg Leu Val Leu Tyr
                820               825               830

Phe Met Gln Gly Gly Arg Asp Ile Tyr Thr Gly Ala Pro Leu Asn Ile
                835               840               845

Asp Gln Leu Ser Ser Tyr Asp Ile Asp His Ile Leu Pro Gln Ser Leu
                850               855               860

Ile Lys Asp Asn Ser Leu Asp Asn Arg Val Leu Val His Ala Ile Ile
865               870               875               880

Asn Arg Glu Lys Asn Ala Thr Phe Ala Ser Thr Ile Tyr Ala Gln Lys
                885               890               895

Met Asn Ala Thr Trp Arg Gln Trp His Glu Ala Gly Leu Ile Ser Gly
                900               905               910

Arg Lys Leu Arg Asn Leu Gln Met Arg Pro Asp Gln Ile Asp Lys Tyr
                915               920               925

Ala Ser Gly Phe Val Ala Arg Gln Leu Val Glu Thr Arg Gln Ile Ile
                930               935               940

Lys Leu Thr Glu Gln Ile Val Ala Ala Gln Tyr Pro Asp Thr Lys Ile
945               950               955               960

Ile Ala Val Lys Ala Gly Leu Ser His Gln Leu Arg Glu Glu Leu Glu
                965               970               975

Phe Pro Lys Asn Arg Asp Val Asn His Tyr His His Ala Phe Asp Ala
                980               985               990

Phe Leu Ala Ala Arg Ile Gly Thr Tyr Leu Leu Lys Arg Phe Pro Asn
                995               1000              1005

Leu Gln Ala Phe Phe Thr Tyr Gly Lys Phe Thr Lys Ala Asp Val
    1010              1015              1020

Lys Lys Leu Arg Gly Phe Asn Phe Ile Arg Asp Ile Thr His Ala
    1025              1030              1035

Glu Asp Lys Ile Val Ala Lys Asp Thr Gly Glu Val Val Trp Asp
    1040              1045              1050

Lys Gln Arg Asp Val Asp Glu Leu Asp Arg Ile Tyr Asn Phe Lys
    1055              1060              1065

Arg Met Leu Ile Thr His Val Arg Phe Glu Thr Ala Asp Leu
    1070              1075              1080

Phe Lys Gln Thr Val Tyr Gly Ala Arg Asp Ser Lys Glu Ala Gly
    1085              1090              1095

Gly Ser Lys Gln Leu Ile Pro Lys Lys Lys Gly Tyr Pro Val Asp
    1100              1105              1110

Ile Tyr Gly Gly Tyr Phe Arg Glu Asn Thr Ala Tyr Leu Ala Val
    1115              1120              1125

Val Lys Val Thr Lys Lys Thr Glu Thr Ile Phe Lys Val Val Lys
    1130              1135              1140

Ile Ala Thr Ser Gln Val Ala Leu Asn Lys Ala Arg Ser Arg
    1145              1150              1155

Ser Thr Ala Glu Glu Leu Ser Val Leu Thr Glu Leu Leu Lys Pro
    1160              1165              1170

Lys Phe Ser Lys Val Gly Lys Asn Gly Lys Ile Thr Asp Thr Pro
    1175              1180              1185
```

```
Phe Glu Val Val Leu Pro Arg Val Pro Arg Glu Gln Leu Phe Tyr
    1190                1195                1200

Asn Ala Lys Tyr Gly Phe Phe Met Val Asn Ser Asp Thr Met Phe
    1205                1210                1215

His Asn Phe Gln Glu Ile Trp Val Ser Arg Ser Asp Gln Lys Ile
    1220                1225                1230

Leu Gln Gln Ile Arg Lys Ala Lys Ile Asp Tyr Pro Asn Val Asp
    1235                1240                1245

Gln Asp Leu Asp Asn Leu Phe His Asn Leu Ala Asp Gln Ile Val
    1250                1255                1260

Lys Tyr Phe Asp Leu Tyr Ser Ile Ala Gly Phe Lys Glu Lys Ile
    1265                1270                1275

Ser Gln Ser Gln Asn Thr Phe Asn Asp Leu Ala Val Asp Asp Thr
    1280                1285                1290

Asp Gln Ser Val Gly Lys Ile Thr Val Ile Asn Glu Leu Leu Lys
    1295                1300                1305

Gly Ala Gln Ala Asn Gly Met Thr Gly Ser Leu Lys Val Leu Lys
    1310                1315                1320

Ile Ser Thr Pro Phe Gly Phe Thr Gln Asp Lys Ser Gly Val Leu
    1325                1330                1335

Thr Lys Asp Ser Ser Ile Ile Tyr Gln Ser Pro Thr Gly Leu Phe
    1340                1345                1350

Glu Arg Ser Val Arg Leu Thr Asp Leu
    1355                1360
```

<210> SEQ ID NO 26
<211> LENGTH: 1354
<212> TYPE: PRT
<213> ORGANISM: Lactobacillus coryniformis subsp. coryniformis KCTC 3167

<400> SEQUENCE: 26

```
Met Thr Leu His Tyr Asn Val Gly Leu Asp Ile Gly Thr Asn Ser Val
1               5                   10                  15

Gly Tyr Thr Ile Val Asp Asp Asn Gly Lys Ile Leu Gln Val Lys Gly
                20                  25                  30

Lys Asn Gly Tyr Gly Val Arg Val Phe Lys Glu Gly Ala Thr Ala Ala
            35                  40                  45

Glu Arg Arg Ile Phe Arg Thr Thr His Arg Arg Leu Lys Arg Arg Lys
        50                  55                  60

Trp Arg Leu Arg Leu Leu Gln Asp Phe Phe Glu Pro Tyr Ile Leu Pro
65                  70                  75                  80

Gln Asp Asp Gly Phe Phe Ile Arg Arg Lys Glu Ser Asn Leu Val Leu
                85                  90                  95

Asn Asp Arg Asp Glu Asp Thr Ala Ser Leu Phe Asn Asp Arg Ser Asp
                100                 105                 110

Arg Asp Phe Tyr Gln Ala Tyr Pro Thr Ile Tyr His Leu Arg Gln Ala
            115                 120                 125

Leu Met Thr Glu Lys Arg Gln Phe Asp Val Arg Glu Ile Tyr Leu Ala
        130                 135                 140

Met His His Ile Ile Lys Tyr Arg Gly His Phe Leu Leu Asn Gly Thr
145                 150                 155                 160

Val Asn Asn Phe Thr Asn Asn Lys Ile Asp Leu His Ser Asp Phe Glu
                165                 170                 175

Glu Leu Asn Ala Leu Leu Leu Asn Val Ile Pro Glu Leu Lys Phe Gln
```

```
                180                 185                 190
Ile Asp Leu Asp His Ser Thr Met Phe Gln Thr Thr Leu Leu Asn Thr
                195                 200                 205
Thr Ile Ser Arg Ser Gly Arg Gln Arg Asp Leu Val Lys Ser Phe Tyr
                210                 215                 220
Asn Gly Ser Asp Asp Lys Gln Leu Ala Lys Gln Gln Lys Ser Val Ala
225                 230                 235                 240
Thr Glu Leu Leu Lys Ala Ile Leu Gly Leu Lys Ala Lys Phe His Lys
                245                 250                 255
Leu Phe Asn Leu Asp Leu Leu Glu Thr Thr Glu Trp Glu Phe Ser Phe
                260                 265                 270
Asp Ala Glu Asp Ile Asp Asp Lys Leu Ala Lys Leu Glu Pro Leu Met
                275                 280                 285
Thr Glu Asn Gln Gln Gln Val Met Asp Ile Leu Gln Arg Ile Phe Ala
                290                 295                 300
Ala Ile Thr Leu Asn Gly Ile Val Pro Glu Gly Lys Thr Leu Ser Ala
305                 310                 315                 320
Ser Lys Val Asp Ser Tyr Gln Lys His Lys Gln Asp Leu Lys Leu Leu
                325                 330                 335
Lys Ala Ile Ala Gln His Ser Asp Lys Lys Thr Ala Thr Val Leu Gln
                340                 345                 350
Thr Ala Tyr Asn Glu Tyr Ile Asn Gly Ile Ala Ser Lys Pro Leu Lys
                355                 360                 365
Gln Glu Asp Phe Tyr Lys Arg Leu Thr Asn Ala Val Lys Lys Ser Ser
                370                 375                 380
Asp Pro Gln Val Ala Asp Met Leu Ala Leu Ile Asp Gln Glu Lys Phe
385                 390                 395                 400
Leu Pro Lys Gln Arg Thr Lys Glu Asn Gly Ala Ile Pro His Gln Leu
                405                 410                 415
His Gln Leu Glu Leu Glu Arg Ile Ile Asp Asn Gln Lys Asp Tyr Tyr
                420                 425                 430
Pro Trp Leu Ala Glu Leu Asn Pro Asn Gln Ala Arg Gln Lys Val Ala
                435                 440                 445
Lys Tyr Lys Leu Ser Glu Leu Val Ala Phe Arg Val Pro Tyr Tyr Val
                450                 455                 460
Gly Pro Leu Ile Glu Pro Glu Val Gln Gln Ala Thr Ser Asn Ala His
465                 470                 475                 480
Phe Ala Trp Met Ala Arg Lys Glu Ala Gly Pro Ile Thr Pro Trp Asn
                485                 490                 495
Phe Asp Gln Lys Val Asp Arg Asn Val Ser Ala Glu Arg Phe Ile Lys
                500                 505                 510
Arg Met Thr Thr Lys Asp Thr Tyr Leu Leu Ala Glu Asp Val Leu Pro
                515                 520                 525
Leu His Ser Leu Leu Tyr Gln Arg Phe Ile Val Leu Asn Glu Leu Asn
                530                 535                 540
Asn Val Arg Val Asn Gly Gln Lys Leu Thr Lys Lys Gln Lys Gln Ala
545                 550                 555                 560
Val Tyr Gln Asp Leu Phe Lys Arg Gln Pro His Val Thr Lys Lys Gln
                565                 570                 575
Phe Lys Ser Tyr Leu Val Gln Thr Gly Glu Phe Ala Glu Ser Ser Lys
                580                 585                 590
Ile Glu Gly Leu Ala Asn Glu Thr Ser Phe Asn Ser Gly Leu Thr Thr
                595                 600                 605
```

```
Glu Asn Glu Leu Arg Lys Ile Phe Gly Ala Gln Leu Asp Glu Ala Arg
    610                 615                 620

Tyr Gln Val Asp Phe Glu Gln Ile Ile Glu Trp Ala Thr Leu Phe Glu
625                 630                 635                 640

Asp Ala Lys Ile Leu Arg Thr Lys Leu Ala Glu Ile Thr Trp Leu Thr
                645                 650                 655

Thr Glu Gln Ile Glu Lys Leu Ala Gly Ile Arg Tyr Arg Gly Trp Gly
                660                 665                 670

Arg Phe Ser Arg Lys Leu Leu Ala Gly Leu Arg Asp Gln Asn Gly Gln
            675                 680                 685

Gln Ile Ile Asp Leu Leu Trp Asp Thr Pro Asn Asn Phe Met Val Ile
        690                 695                 700

Val Ser Gln Ala Ala Phe Ser Glu Ala Ile Thr Lys Glu Asn Glu Lys
705                 710                 715                 720

Leu Ile Asp Arg Arg Gly Ala Gln Asp Val Ile Thr Asp Leu Tyr Thr
                725                 730                 735

Ser Pro Gln Asn Lys Lys Ala Leu Arg Gln Val Leu Ala Ile Val Ala
                740                 745                 750

Asp Val Gln Lys Ala Met Gly Gly Val Pro Pro Gln Arg Ile Phe Ile
            755                 760                 765

Glu Phe Ala Arg Glu Asp Glu Lys Asn Pro Arg Arg Ser Val Glu Arg
770                 775                 780

Ser Arg Gln Leu Glu Lys Leu Tyr Gln Thr Ile Ser Asn Glu Phe Leu
785                 790                 795                 800

Ile Asn Ser Glu Val Arg Gln Glu Leu Lys Glu Ala Val Asp Gln Lys
                805                 810                 815

Val Asn Phe Lys Asp Arg Leu Phe Leu Tyr Phe Leu Gln Gly Gly Val
            820                 825                 830

Asp Leu Tyr Ser Gly Lys Arg Ile Asn Ile Asp Gln Leu Ser His Tyr
            835                 840                 845

Asp Ile Asp His Ile Leu Pro Gln Ser Phe Ile Lys Asp Asp Ser Leu
        850                 855                 860

Asp Asn Arg Val Leu Val Ser Gln Lys Leu Asn Arg Ser Lys Ser Asp
865                 870                 875                 880

Ser Val Pro Leu Ser Glu Phe Ala Asn Tyr Lys Phe Gly Pro Ala Met
                885                 890                 895

Gln Ala Lys Trp Leu Gln Leu Lys Glu Ala Gly Leu Leu Ser Lys Arg
            900                 905                 910

Lys Tyr Asp Asn Leu Thr Leu Asp Pro Thr Lys Leu Ser Lys Phe Ala
        915                 920                 925

Pro Leu Gly Phe Val Asn Arg Gln Leu Val Glu Thr Arg Gln Val Ile
    930                 935                 940

Lys Leu Ala Ala Asn Leu Leu Ala Ser Glu Gly Thr Lys Val Val Thr
945                 950                 955                 960

Ile Lys Ala Asn Met Thr His Gln Val Arg Lys Glu Leu Asp Phe Pro
                965                 970                 975

Lys Asn Arg Asn Val Asn Asn Tyr His His Ala Phe Asp Ala Tyr Leu
            980                 985                 990

Thr Ala Phe Val Gly Ile Phe Leu  Ser Lys Arg Tyr Pro Lys Leu Lys
        995                 1000                1005

Pro Tyr  Phe Thr Tyr Gly Asp  Phe Gln Lys Gly Asn  Lys Leu Pro
    1010                1015                1020
```

Asp Leu Lys Asn Phe Asn Phe Leu Tyr Glu Leu Lys Asn Lys Asp
    1025                1030                1035

Arg Ser Ile Asp Ser Asn Thr Gly Glu Ile Ile Trp Asp Lys Gln
    1040                1045                1050

Arg Asp Leu Ala Tyr Met Asn Lys Ile Tyr Asn Phe Lys Lys Val
    1055                1060                1065

Thr Val Val His Glu Val Leu Thr Lys Ser Gly Ala Leu Tyr Asn
    1070                1075                1080

Gln Thr Leu Tyr Lys Ala Ser Glu Asp Lys Ala Ser Gly Arg Gly
    1085                1090                1095

Thr Lys Gln Leu Ile Arg Lys Lys Asp Asn Met Pro Thr Glu Leu
    1100                1105                1110

Tyr Gly Gly Tyr Thr Gly Ser Thr Ser Ala Phe Met Ser Ile Val
    1115                1120                1125

Arg Leu Trp Lys Lys Asp Lys Pro Tyr Tyr Lys Val Val Gly Ile
    1130                1135                1140

Pro Thr Arg Met Ala Ala Lys Leu Ala Asn Gln Ala Gln Leu Leu
    1145                1150                1155

Asp Tyr Leu Thr Lys Lys Phe Thr Thr Arg Lys Leu Val Lys Lys
    1160                1165                1170

Thr Gly Asp Tyr Lys Thr Thr Val Glu Arg Phe Glu Leu Val Val
    1175                1180                1185

Pro Lys Val Gly Phe Asn Gln Leu Val Ile Asp Gly Gly Gln Pro
    1190                1195                1200

Phe Met Leu Gly Ser Ala Thr Tyr Gln Tyr Asn Ala Arg Glu Leu
    1205                1210                1215

Phe Ile Ser Lys Glu Ala Val Lys Ala Leu Asn Lys Gln Leu Ser
    1220                1225                1230

Thr His Val Asp Leu Val Gln Val Phe Asp Glu Ile Leu Val Gln
    1235                1240                1245

Val Asn Arg Trp Phe Pro Leu Tyr Asp Thr Asn Gly Phe Arg Glu
    1250                1255                1260

Lys Leu Ser His Gly Arg Asp Arg Phe Met Lys Leu Asn Asp Ser
    1265                1270                1275

Phe Glu Glu Lys Ser Asp Thr Gln Ile Asp Val Leu Asn Arg Ile
    1280                1285                1290

Leu Ile Gly Phe His Ala Asn Ala Ala Arg Thr Asn Leu Lys Ile
    1295                1300                1305

Leu Gly Leu Gly Thr Asp Leu Gly Phe Met Thr Gln Gln Ala Gly
    1310                1315                1320

Ile Arg Leu Thr Glu Lys Ala Ile Leu Val His Gln Ser Pro Ser
    1325                1330                1335

Gly Leu Phe Glu Arg Lys Val Ala Leu Arg Asp Leu Lys Gly Leu
    1340                1345                1350

Arg

<210> SEQ ID NO 27
<211> LENGTH: 1368
<212> TYPE: PRT
<213> ORGANISM: Lactobacillus curvatus CRL 705

<400> SEQUENCE: 27

Met Ser Arg Pro Tyr Asn Ile Gly Leu Asp Ile Gly Thr Ser Ser Ile
1               5                   10                  15

```
Gly Trp Ser Val Val Asp Asp Gln Ser Lys Leu Val Ser Val Arg Gly
            20                  25                  30

Lys Tyr Gly Tyr Gly Val Arg Leu Tyr Asp Glu Gly Gln Thr Ala Ala
            35                  40                  45

Glu Arg Arg Ser Phe Arg Thr Thr Arg Arg Leu Lys Arg Arg Lys
50                  55                  60

Trp Arg Leu Gly Leu Leu Arg Glu Ile Phe Glu Pro Tyr Ile Thr Pro
65                  70                  75                  80

Ile Asp Asp Thr Phe Phe Leu Arg Gln Lys Gln Ser Asn Leu Ser Pro
                    85                  90                  95

Lys Asp Gln Arg Lys Leu Tyr Thr Gln Thr Ser Leu Phe Asn Asp Arg
                100                 105                 110

Thr Asp Arg Ala Phe Tyr Asp Asp Tyr Pro Thr Ile Tyr His Leu Arg
            115                 120                 125

Tyr Arg Leu Met Thr Glu Lys Arg Gln Phe Asp Ile Arg Glu Ile Tyr
            130                 135                 140

Leu Ala Met His His Ile Val Lys Tyr Arg Gly His Phe Leu Asn Glu
145                 150                 155                 160

Ala Pro Val Ser Ser Phe Lys Ser Ser Glu Ile Asn Leu Val Ala His
                165                 170                 175

Phe Asp Arg Leu Asn Thr Ile Phe Ala Asp Leu Phe Ser Glu Ser Gly
                180                 185                 190

Phe Gln Leu Glu Thr Asp Lys Leu Ala Glu Val Lys Ala Leu Leu Leu
            195                 200                 205

Asp Asn Gln Gln Ser Ala Ser Asn Arg Gln Arg Gln Ala Leu Ser Leu
210                 215                 220

Ile Tyr Thr Pro Ser Thr Asn Lys Ala Val Glu Lys Gln Asn Lys Ala
225                 230                 235                 240

Ile Ala Thr Glu Leu Leu Lys Ala Ile Leu Gly Leu Lys Ala Lys Phe
                245                 250                 255

Asn Val Leu Thr Gly Ile Glu Ala Glu Asp Val Lys Ala Trp Thr Leu
                260                 265                 270

Thr Phe Asn Ala Glu Asn Phe Asp Glu Glu Met Val Lys Leu Glu Ser
            275                 280                 285

Ser Leu Asp Asp Asn Ala His Gln Ile Ile Glu Ser Leu Gln Glu Leu
290                 295                 300

Tyr Ser Gly Val Leu Leu Ala Gly Ile Val Pro Glu Asn Gln Ser Leu
305                 310                 315                 320

Ser Gln Ala Met Ile Thr Lys Tyr Asp Asp His Gln Lys His Leu Lys
                325                 330                 335

Met Leu Lys Ala Val Arg Glu Ala Leu Ala Pro Gly Asp Arg Gln Arg
            340                 345                 350

Leu Lys Gln Ala Tyr Asp Gln Tyr Val Asp Gly Gln Glu Asn Thr Lys
            355                 360                 365

Ala Tyr Ser Lys Glu Asp Phe Tyr Gly Asp Ile Thr Lys Ala Leu Lys
            370                 375                 380

Asn Asn Pro Asp His Pro Ile Val Ser Glu Ile Lys Lys Leu Ile Glu
385                 390                 395                 400

Leu Asp Gln Phe Met Pro Lys Gln Arg Thr Lys Asp Asn Gly Ala Ile
                405                 410                 415

Pro His Gln Leu His Gln Glu Leu Asp Arg Ile Ile Glu Asn Gln
            420                 425                 430

Gln Gln Tyr Tyr Pro Trp Leu Ala Glu Leu Asn Pro Asn Ser Lys Arg
```

```
            435                 440                 445
Gln Thr Val Ala Lys Tyr Lys Leu Asp Glu Leu Val Ala Phe Arg Val
    450                 455                 460
Pro Tyr Tyr Val Gly Pro Leu Ile Thr Ala Glu Gln Arg Gln Ser
465                 470                 475                 480
Ser Asp Ala Lys Phe Ala Trp Leu Ile Arg Lys Ala Glu Gly Arg Ile
                485                 490                 495
Thr Pro Trp Asn Phe Asp Asp Lys Val Asp Arg Gln Ala Ser Ala Asn
            500                 505                 510
Glu Phe Ile Lys Arg Met Thr Thr Thr Asp Thr Tyr Leu Leu Ala Glu
            515                 520                 525
Asp Val Leu Pro Lys Gln Ser Leu Ile Tyr Gln Arg Phe Glu Val Leu
            530                 535                 540
Asn Glu Leu Asn Gly Leu Lys Ile Asp Asp Gln Pro Ile Thr Thr Glu
545                 550                 555                 560
Leu Lys Gln Ala Ile Phe Thr Asp Leu Phe Met Gln Lys Ile Ser Val
                565                 570                 575
Thr Val Lys Asn Ile Gln Asp Tyr Leu Val Ser Glu Lys Arg Tyr Ala
            580                 585                 590
Ser Arg Pro Ala Ile Thr Gly Leu Ser Asp Glu Asn Lys Phe Asn Ser
            595                 600                 605
Arg Leu Ser Thr Tyr His Asp Leu Lys Met Ile Val Gly Asp Ala Val
            610                 615                 620
Asp Asp Val Asp Lys Gln Ala Asp Leu Glu Lys Cys Ile Glu Trp Ser
625                 630                 635                 640
Thr Ile Phe Glu Asp Gly Lys Ile Tyr Ser Ala Lys Leu Asn Glu Ile
                645                 650                 655
Asp Trp Leu Thr Asp Gln Gln Arg Val Gln Leu Ala Ala Lys Arg Tyr
            660                 665                 670
Arg Gly Trp Gly Arg Leu Ser Ala Lys Leu Leu Thr Gln Ile Val Asn
            675                 680                 685
Ala Asn Gly Gln Arg Ile Met Asp Leu Leu Trp Asp Thr Thr Asp Asn
            690                 695                 700
Phe Met Arg Ile Val His Ser Glu Asp Phe Asp Lys Leu Ile Thr Glu
705                 710                 715                 720
Ala Asn Gln Met Met Leu Ala Glu Asn Asp Val Gln Asp Val Ile Asn
                725                 730                 735
Asp Leu Tyr Thr Ser Pro Gln Asn Lys Lys Ala Leu Arg Gln Ile Leu
            740                 745                 750
Leu Val Val Asn Asp Ile Gln Lys Ala Met Lys Gly Gln Ala Pro Glu
            755                 760                 765
Arg Ile Leu Ile Glu Phe Ala Arg Glu Asp Glu Val Asn Ser Arg Leu
            770                 775                 780
Ser Val Gln Arg Lys Arg Gln Val Glu Gln Val Tyr Gln Asn Ile Ser
785                 790                 795                 800
Asn Glu Leu Leu Asn Asn Thr Glu Ile Arg Asn Glu Leu Lys Asp Leu
                805                 810                 815
Ser Asn Ser Ala Leu Ser Asn Thr Arg Leu Phe Leu Tyr Phe Met Gln
            820                 825                 830
Gly Gly Arg Asp Met Tyr Thr Gly Asp Ser Leu Asn Ile Asp Arg Leu
            835                 840                 845
Ser Thr Tyr Asp Ile Asp His Ile Leu Pro Gln Ser Phe Ile Lys Asp
            850                 855                 860
```

```
Asn Ser Leu Asp Asn Arg Val Leu Val Ser Gln Lys Met Asn Arg Ser
865                 870                 875                 880

Lys Ala Asp Gln Val Pro Thr Asp Phe Thr Ser Val Glu Leu Gly Gln
            885                 890                 895

Lys Met Gln Ile Gln Trp Glu Gln Met Leu Arg Ala Gly Leu Ile Thr
                900                 905                 910

Lys Lys Lys Tyr Asp Asn Leu Thr Leu Asn Pro Asp His Ile Ser Lys
            915                 920                 925

Tyr Ala Met Lys Gly Phe Ile Asn Arg Gln Leu Val Glu Thr Arg Gln
            930                 935                 940

Val Ile Lys Leu Ala Thr Asn Leu Leu Met Gln Tyr Gly Glu Asp
945                 950                 955                 960

Asn Ile Glu Leu Ile Thr Val Lys Ser Gly Leu Thr His Gln Met Arg
                965                 970                 975

Thr Glu Phe Asp Phe Pro Lys Asn Arg Asn Leu Asn Asn His His His
            980                 985                 990

Ala Phe Asp Ala Tyr Leu Thr Ala Phe Val Gly Leu Tyr Leu Leu Lys
            995                 1000                1005

Arg Tyr Pro Lys Leu Lys Pro Tyr Phe Val Tyr Gly Glu Tyr Gln
    1010                1015                1020

Lys Ala Ser Gln Gln Asp Lys Trp Arg Asn Phe Asn Phe Leu Asn
    1025                1030                1035

Gly Leu Lys Lys Asp Glu Leu Val Asp Glu Asn Thr Glu Ala Val
    1040                1045                1050

Ile Trp Asp Lys Glu Ser Gly Leu Ala Tyr Leu Asn Lys Ile Tyr
    1055                1060                1065

Gln Phe Lys Lys Ile Leu Val Thr Arg Gly Val His Glu Asn Ser
    1070                1075                1080

Gly Ala Leu Phe Asn Gln Thr Leu Tyr Ala Ala Lys Asp Asp Lys
    1085                1090                1095

Ala Ser Gly Gln Gly Gly Lys Gln Leu Ile Pro Ala Lys Gln Asp
    1100                1105                1110

Arg Ser Thr Ala Leu Tyr Gly Gly Tyr Ser Gly Lys Thr Val Ala
    1115                1120                1125

Tyr Met Cys Ile Val Arg Ile Lys Asn Lys Lys Gly Asp Leu Tyr
    1130                1135                1140

Lys Val Cys Gly Val Glu Thr Ser Trp Leu Ala Gln Leu Lys Gln
    1145                1150                1155

Leu Thr Asp Glu Asp Ser Gln Lys Ala Phe Leu Glu Gln Lys Ile
    1160                1165                1170

Ser Pro Gln Phe Thr Lys Val Lys Lys Gln Lys Gly Asn Ile Ile
    1175                1180                1185

Glu Ala Val Glu Glu Phe Glu Val Ile Ala Pro His Ile Leu Ile
    1190                1195                1200

Asn Gln Arg Phe Phe Asp Asn Gly Gln Glu Leu Thr Leu Gly Ser
    1205                1210                1215

Ala Thr Tyr Lys His Asn Glu Gln Glu Leu Ile Leu Asp Lys Thr
    1220                1225                1230

Ala Val Lys Leu Leu Asn Gly Ala Leu Pro Leu Thr Gln Ser Glu
    1235                1240                1245

Glu Leu Ala Glu Gln Val Tyr Asp Glu Ile Leu Asp Gln Val Met
    1250                1255                1260
```

-continued

```
His Tyr Phe Pro Leu Tyr Asp Thr Asn Gln Phe Arg Ala Lys Leu
    1265                1270                1275

Ser Thr Gly Lys Ala Ala Phe Met Lys Leu Pro Trp Lys Ser Gln
    1280                1285                1290

Trp Asp Gly Asn Lys Met Val Gln Val Gly Gln Gln Val Ile Leu
    1295                1300                1305

Asp Arg Ile Leu Ile Gly Leu His Ala Asn Ala Ala Met Ser Asp
    1310                1315                1320

Leu Lys Val Leu Lys Met Thr Thr Pro Phe Gly Met Ile Gln Gln
    1325                1330                1335

Ser Thr Gly Ile Thr Leu Ser Ala Asp Thr Gln Ile Ile Tyr Gln
    1340                1345                1350

Ser Pro Thr Gly Leu Phe Glu Arg Arg Val Ala Leu Arg Asp Leu
    1355                1360                1365

<210> SEQ ID NO 28
<211> LENGTH: 1427
<212> TYPE: PRT
<213> ORGANISM: Lactobacillus delbrueckii subsp. Lactis CRL581

<400> SEQUENCE: 28

Met Ala Lys Pro Lys Asp Tyr Thr Ile Gly Leu Asp Ile Gly Thr Asn
1               5                   10                  15

Ser Val Gly Trp Val Val Thr Asp Asp Gln Asn Asn Ile Leu Arg Ile
            20                  25                  30

Lys Gly Lys Lys Ala Ile Gly Ala Arg Leu Phe Ala Glu Gly Lys Val
        35                  40                  45

Ala Ala Glu Arg Arg Ser Phe Arg Thr Thr Arg Arg Arg Leu Ser Arg
    50                  55                  60

Arg Arg Trp Arg Ile Lys Leu Leu Glu Glu Leu Phe Asp Lys Glu Ile
65                  70                  75                  80

Ala Lys Val Asp Pro Ser Phe Phe Ala Arg Leu His Glu Ser Trp Ile
                85                  90                  95

Ser Pro Lys Asp Lys Arg Lys Arg Tyr Ser Ala Ile Val Phe Pro Ser
            100                 105                 110

Pro Glu Glu Asp Lys Lys Phe His Glu Ser Tyr Pro Thr Ile Tyr His
        115                 120                 125

Leu Arg Asp Lys Leu Met Lys Asp Gln Lys His Asp Ile Arg Glu
    130                 135                 140

Ile Tyr Ile Ala Val His Gln Met Ile Lys Ala Arg Gly Asn Phe Leu
145                 150                 155                 160

His Asp Glu Ser Val Glu Thr Tyr Arg Ser Gly Met Ser Ser Leu Gly
                165                 170                 175

Gly Arg Ser Glu Arg Thr Ile Leu Ser Val Gln Thr Leu Glu Glu Leu
            180                 185                 190

Asn Asp Leu Phe Ala Glu Asn Glu Gly Thr Glu Glu Ala Lys Leu Asn
        195                 200                 205

Val Ala Ser Ala Glu Gln Ile Asn Asp Ile Leu Thr Gly Gly His Leu
    210                 215                 220

Asn Ala Asp Ser Gln Lys Glu Ile Gly Asn Leu Leu Leu Pro Ser Ser
225                 230                 235                 240

Phe Pro Ser Phe Asp Asp Lys Ala Lys Glu Lys Gln Val Lys Lys Leu
                245                 250                 255

Ile Lys Asn Val Ala Thr Asn Ile Ser Lys Ala Trp Leu Gly Tyr Lys
            260                 265                 270
```

-continued

```
Ala Asp Phe Ser Thr Ile Leu Asn Leu Ala Asn Val Asp Lys Asp Gln
        275                 280                 285
Lys Lys Ile Phe Ala Phe Ala Leu Gln Gly Gly Asp Glu Glu Asp Lys
    290                 295                 300
Val Gln Glu Leu Glu Ser Leu Leu Glu Gln Ser Gln Thr Asp Ile Val
305                 310                 315                 320
Asp Arg Leu Ile Glu Ile Arg His Ala Ile Val Leu Ser Glu Ile Val
                325                 330                 335
Pro Val Gly Met Thr Leu Ser Glu Ala Met Ile Asp Lys Tyr Asp Gln
                340                 345                 350
His Lys Glu Asp Leu Ile Thr Leu Lys Ala Val Ile Arg Asn Thr Lys
            355                 360                 365
Asp Lys Lys Lys Ala Ala Lys Leu Gln Ala Ile Tyr Asp Leu Tyr Val
        370                 375                 380
Asn Asn Arg His Ala Asp Leu Ala Lys Ala Met Lys Leu Thr Gly Ile
385                 390                 395                 400
Lys Lys Arg Ser Glu Leu Leu Asp Pro Glu Glu Leu Lys Lys Ala Ile
                405                 410                 415
Ser Ser Leu Leu Asp Asp Ser Pro Glu Ala Val Glu Ile Lys Gln Met
            420                 425                 430
Leu Glu Glu Lys Thr Phe Leu Pro Leu Gln Arg Ser Asn Asn Asn Gly
        435                 440                 445
Val Ile Pro Asn Gln Leu His Gln Val Glu Leu Asp Glu Ile Ile Lys
    450                 455                 460
Lys Gln Ser Lys Tyr Tyr Pro Phe Leu Ala Glu Lys Asn Pro Asp Glu
465                 470                 475                 480
Ser Glu Glu Ala Gln Lys Lys Ala Pro Thr Lys Leu Asp Ala Leu Leu
                485                 490                 495
Thr Phe Arg Val Pro Tyr Tyr Val Gly Pro Met Ile Thr Lys Glu Glu
                500                 505                 510
Gln Glu Ala Gln Asp Gly His Ser Phe Ala Trp Met Val Arg Arg Asp
            515                 520                 525
Pro Gln Asp His Glu Ala Ile Thr Pro Trp Asn Phe Glu Lys Lys Val
        530                 535                 540
Asp Lys Met Ala Ser Ala Thr Gln Phe Ile Lys Arg Met Thr Thr Lys
545                 550                 555                 560
Asp Thr Tyr Leu Leu Gly Glu Asp Val Leu Pro Ala Ser Ser Leu Lys
                565                 570                 575
Tyr Gln Leu Phe Thr Val Leu Asn Glu Leu Asn Asn Leu Arg Val Asn
                580                 585                 590
Gly Lys Lys Leu Thr Ser Asp Glu Lys Glu Gln Val Ile Glu Gly Leu
            595                 600                 605
Phe Lys Lys Gln Lys Thr Val Lys Ala Asp Lys Phe Val Lys Tyr Trp
        610                 615                 620
Gln Ala Lys His Ile Gly Ala Asp Ile Lys Val Lys Gly Leu Ser Asp
625                 630                 635                 640
Pro Ser Lys Phe Asn Ser Thr Met Ser Thr Tyr Ile Asp Phe Lys Lys
                645                 650                 655
Ile Phe Gly Asp Gln Leu Asn Asp Val Asn Arg Gln Asn Asp Phe Glu
                660                 665                 670
Lys Ile Ile Glu Tyr Ser Thr Ile Phe Glu Asp Arg Lys Ile Leu Glu
            675                 680                 685
```

```
Asp Lys Leu Arg Ala Asp Phe Ala Trp Leu Ser Glu Glu Gln Ile Lys
    690                 695                 700
Gln Leu Cys Arg Leu Arg Leu Gln Gly Trp Gly Arg Leu Ser Asp Lys
705                 710                 715                 720
Leu Leu Thr Arg Leu Thr Asp Ala Asp Gly Gln Asn Val Leu Glu Arg
                725                 730                 735
Leu Trp Asn Ser Asn Asp Asn Phe Val Gln Ile Val Ser Asp Pro Asn
            740                 745                 750
Ile Lys Ala Lys Ile Glu Gln Glu Asn Gln Lys Leu Leu Arg Asp Gly
        755                 760                 765
Gln Ser Asp Asp Ala Val Glu Ser Ile Leu Asp Asp Ala Tyr Thr Ser
770                 775                 780
Pro Gln Asn Lys Lys Ala Ile Arg Gln Val Met Arg Val Val His Asp
785                 790                 795                 800
Ile Val Lys Ala Cys Asp Gly Asn Val Pro Ala Lys Phe Ala Ile Glu
                805                 810                 815
Phe Ala Arg Ser Gln Glu Asp Asp Pro Lys Arg Thr Thr Ala Arg Val
            820                 825                 830
Asn Gln Met Gln Lys Ile Tyr Asp Gln Ile Ser Asp Glu Val Val Ser
        835                 840                 845
Gln Gly Val Lys Glu Gln Leu Ser Gly Met Lys Ser Leu Lys Asp Arg
850                 855                 860
Tyr Tyr Leu Tyr Phe Met Gln Gly Gly Arg Asp Ala Tyr Thr Gly Ala
865                 870                 875                 880
Lys Leu Asn Ile Asp Arg Leu Ser Asp Tyr Asp Ile Asp His Ile Met
                885                 890                 895
Pro Gln Ser Phe Val Lys Asp Asp Ser Leu Asp Asn Arg Val Leu Val
            900                 905                 910
Ala Arg Ala Val Asn Asn Gln Lys Ser Asp Lys Val Pro Ala Leu Leu
        915                 920                 925
Phe Gly Asn Lys Val Val Ala Asp Leu Gly Ile Thr Val Arg Glu Met
930                 935                 940
Trp Asp Lys Trp Gln Lys Leu Gly Met Ile Ser Lys Arg Lys Leu Ser
945                 950                 955                 960
Asn Leu Leu Thr Asp Pro Asp Ala Leu Thr Glu Tyr Arg Ala Gln Gly
                965                 970                 975
Phe Ile Arg Arg Gln Leu Val Glu Thr Ser Gln Val Ile Lys Leu Thr
            980                 985                 990
Ala Thr Ile Leu Gln Ser Glu Phe Pro Asp Ser Lys Ile Ile Glu Val
        995                 1000                1005
Pro Ala Lys Tyr Asn Ser Ile Val Arg Lys Gln Phe Asp Leu Tyr
1010                1015                1020
Lys Ser Arg Glu Val Asn Asp Tyr His His Ala Ile Asp Ala Tyr
1025                1030                1035
Leu Ser Thr Ile Val Gly Asn Tyr Leu Tyr Gln Val Tyr Pro Asn
1040                1045                1050
Leu Arg Arg Met Phe Val Tyr Gly Glu Phe Lys Lys Phe Ser Ser
1055                1060                1065
Asn Ala Glu Glu Ser Ala Tyr Asp Val Val Arg Val Lys Ser
1070                1075                1080
Met Asn Phe Leu Asp Asp Leu Leu Arg Gly Thr His Gly Asp Asn
1085                1090                1095
Ile Tyr Cys Arg Ser Thr Gly Glu Ile Val Phe Asn Arg Asn Asp
```

Ile Ile Ser Lys Leu Lys Gln Ala Tyr Ser Phe Lys Gln Met Leu
1115                1120                1125

Val Thr Gln Glu Val Phe Thr Lys Lys Ser Ala Leu Phe Asp Gln
        1130                1135                1140

Thr Val Tyr Pro Ser Pro Glu Arg Asp Ser Lys Lys Arg Ser Gly
1145                1150                1155

Leu Ile Pro Arg Lys Lys Gly Met Asp Thr Glu Ile Tyr Gly Gly
        1160                1165                1170

Tyr Ser Gly Asn Lys Asp Ala Tyr Phe Val Leu Ala Glu Ala Val
1175                1180                1185

Lys Glu Lys Gly His Thr Leu Gln Ile Val Gly Val Pro Ile Arg
        1190                1195                1200

Ala Leu Asn Thr Leu Lys Asn Ser Ala Asn Tyr Ser Glu Lys Leu
1205                1210                1215

Leu Glu Ile Ile Lys Pro Gln Val Met Phe Asn Lys Asp Thr Gly
        1220                1225                1230

Lys Pro Ile Lys Gly Ile Lys Asp Val Lys Ile Leu Met Asp Lys
1235                1240                1245

Ile Pro Cys Arg Gln Pro Val Leu Glu Gly Glu Ser Tyr Tyr Met
        1250                1255                1260

Leu Ala Ser Ser Lys Tyr Arg Tyr Ser Leu Lys Gln Ile Ser Leu
1265                1270                1275

Ser Gln Met Ser Met Lys Tyr Ile Leu Asp Tyr Ile Asp Asp Pro
        1280                1285                1290

Asn Phe Asn Lys His Glu Met Ile Asn Ile Asp Gln Gln Asp Glu
1295                1300                1305

Lys Glu Cys Leu Leu Ser Val Tyr Asp Glu Ile Leu Glu Lys Met
        1310                1315                1320

Asp Lys Tyr Leu Pro Leu Phe Asp Ile Arg Ser Phe Arg Lys Lys
1325                1330                1335

Leu His Asp Gly Arg Asp Ala Phe Ile Ala Leu Pro Val Ala Ser
        1340                1345                1350

Glu Glu Lys Lys Pro Gly Lys Val Asp Val Ile Arg Lys Val Leu
1355                1360                1365

Lys Gly Leu His Ala Asn Ala Asp Ile Thr Asn Leu Ala Glu Leu
        1370                1375                1380

Gly Phe Gly Thr Ala Ala Leu Gly Ala Leu Val Ser Thr Gly Gly
1385                1390                1395

Ile Lys Ile Ser Asp Asp Ala Val Phe Ile Tyr Gln Ser Pro Thr
        1400                1405                1410

Gly Leu Phe Glu Arg Arg Val Lys Val Ser Asp Leu Leu Lys
1415                1420                1425

<210> SEQ ID NO 29
<211> LENGTH: 1381
<212> TYPE: PRT
<213> ORGANISM: Lactobacillus fermentum 28-3-CHN

<400> SEQUENCE: 29

Met Asp Tyr Val Lys Glu Tyr His Ile Gly Leu Asp Ile Gly Thr Ser
1               5                   10                  15

Ser Ile Gly Trp Ala Val Thr Asp Ser Gln Phe Lys Leu Met Arg Ile
            20                  25                  30

-continued

Lys Gly Lys Thr Ala Ile Gly Val Arg Leu Phe Glu Gly Lys Thr
         35                  40                  45

Ala Ala Glu Arg Arg Thr Phe Arg Thr Thr Arg Arg Leu Lys Arg
 50                  55                  60

Arg Lys Trp Arg Leu His Tyr Leu Asp Lys Ile Phe Ala Pro His Leu
 65                  70                  75                  80

Gln Glu Val Asp Glu Asn Phe Leu Arg Arg Leu Lys Gln Ser Asn Ile
                 85                  90                  95

His Pro Glu Asp Pro Ala Lys Asn Gln Ala Phe Ile Gly Lys Leu Leu
                100                 105                 110

Phe Pro Asp Leu Leu Lys Lys Asn Glu Arg Gly Tyr Pro Thr Leu Ile
                115                 120                 125

Lys Met Arg Asp Glu Leu Pro Val Glu Gln Arg Ala His Tyr Pro Val
130                 135                 140

Thr Asn Ile Tyr Lys Leu Arg Glu Ala Met Ile Asn Glu Asp Arg Gln
145                 150                 155                 160

Phe Asp Leu Arg Glu Val Tyr Leu Ala Val His His Ile Val Lys Tyr
                165                 170                 175

Arg Gly His Phe Leu Asn Asn Ala Ser Val Asp Lys Phe Lys Val Gly
                180                 185                 190

Arg Ile Asp Phe Asp Lys Ser Phe Asn Val Leu Asn Glu Ala Tyr Glu
                195                 200                 205

Glu Leu Gln Asn Gly Glu Gly Ser Phe Thr Ile Glu Pro Ser Lys Val
                210                 215                 220

Glu Lys Ile Gly Gln Leu Leu Asp Thr Lys Met Arg Lys Leu Asp
225                 230                 235                 240

Arg Gln Lys Ala Val Ala Lys Leu Leu Glu Val Lys Val Ala Asp Lys
                245                 250                 255

Glu Glu Thr Lys Arg Asn Lys Gln Ile Ala Thr Ala Met Ser Lys Leu
                260                 265                 270

Val Leu Gly Tyr Lys Ala Asp Phe Ala Thr Val Ala Met Ala Asn Gly
                275                 280                 285

Asn Glu Trp Lys Ile Asp Leu Ser Ser Glu Thr Ser Glu Asp Glu Ile
290                 295                 300

Glu Lys Phe Arg Glu Glu Leu Ser Asp Ala Gln Asn Asp Ile Leu Thr
305                 310                 315                 320

Glu Ile Thr Ser Leu Phe Ser Gln Ile Met Leu Asn Ala Ile Val Pro
                325                 330                 335

Asn Gly Met Ser Ile Ser Glu Ser Met Met Asp Arg Tyr Trp Thr His
                340                 345                 350

Glu Arg Gln Leu Ala Glu Val Lys Glu Tyr Leu Ala Thr Gln Pro Ala
                355                 360                 365

Ser Ala Arg Lys Glu Phe Asp Gln Val Tyr Asn Lys Tyr Ile Gly Gln
                370                 375                 380

Val Pro Lys Glu Lys Gly Phe Asp Leu Glu Lys Gly Leu Lys Lys Ile
385                 390                 395                 400

Leu Ser Lys Lys Glu Asn Trp Lys Glu Ile Asp Glu Leu Leu Lys Ala
                405                 410                 415

Gly Asp Phe Leu Pro Lys Gln Arg Thr Ser Ala Asn Gly Val Ile Pro
                420                 425                 430

His Gln Met His Gln Glu Leu Asp Arg Ile Ile Glu Lys Gln Ala
                435                 440                 445

Lys Tyr Tyr Pro Trp Leu Ala Thr Glu Asn Pro Ala Thr Gly Glu Arg

-continued

```
            450                 455                 460
Asp Arg His Gln Ala Lys Tyr Glu Leu Asp Gln Leu Val Ser Phe Arg
465                 470                 475                 480

Ile Pro Tyr Tyr Val Gly Pro Leu Val Thr Pro Glu Val Gln Lys Ala
                485                 490                 495

Thr Ser Gly Ala Lys Phe Ala Trp Ala Lys Arg Lys Glu Asp Gly Glu
            500                 505                 510

Ile Thr Pro Trp Asn Leu Trp Asp Lys Ile Asp Arg Ala Glu Ser Ala
            515                 520                 525

Glu Ala Phe Ile Lys Arg Met Thr Val Lys Asp Thr Tyr Leu Leu Asn
            530                 535                 540

Glu Asp Val Leu Pro Ala Asn Ser Leu Leu Tyr Gln Lys Tyr Asn Val
545                 550                 555                 560

Leu Asn Glu Leu Asn Asn Val Arg Val Asn Gly Arg Arg Leu Ser Val
                565                 570                 575

Gly Ile Lys Gln Asp Ile Tyr Thr Glu Leu Phe Lys Lys Lys Lys Thr
            580                 585                 590

Val Lys Ala Gly Asp Val Ala Ser Leu Val Met Ala Lys Thr Arg Gly
            595                 600                 605

Val Asn Lys Pro Ser Val Glu Gly Leu Ser Asp Pro Lys Lys Phe Asn
            610                 615                 620

Ser Asn Leu Ala Thr Tyr Leu Asp Leu Lys Ser Ile Met Gly Asp Lys
625                 630                 635                 640

Val Asp Asp Asn Arg Tyr Gln Met Asp Leu Glu Asn Ile Ile Glu Trp
                645                 650                 655

Arg Ser Val Phe Glu Asp Gly Glu Ile Phe Ala Asp Lys Leu Thr Glu
                660                 665                 670

Val Glu Trp Leu Thr Asp Glu Gln Arg Ser Ala Leu Val Lys Lys Arg
            675                 680                 685

Tyr Lys Gly Trp Gly Arg Leu Ser Lys Lys Leu Leu Thr Gly Ile Val
            690                 695                 700

Asp Glu Asn Gly Gln Arg Ile Ile Asp Leu Met Trp Asn Thr Asp Gln
705                 710                 715                 720

Asn Phe Met Gln Ile Val Asn Gln Pro Val Phe Lys Glu Gln Ile Asp
                725                 730                 735

Gln Leu Asn Gln Lys Ala Ile Thr Asn Asp Gly Met Thr Leu Arg Glu
            740                 745                 750

Arg Val Glu Ser Val Leu Asp Asp Ala Tyr Thr Ser Pro Gln Asn Lys
            755                 760                 765

Lys Ala Ile Trp Gln Val Val Arg Val Val Glu Asp Ile Val Lys Ala
            770                 775                 780

Val Gly Asn Ala Pro Lys Ser Ile Ser Ile Glu Phe Ala Arg Asn Glu
785                 790                 795                 800

Gly Asn Lys Gly Glu Ile Thr Arg Ser Arg Arg Thr Gln Leu Gln Lys
                805                 810                 815

Leu Phe Glu Asp Gln Ala His Glu Leu Val Lys Asp Thr Ser Leu Thr
                820                 825                 830

Glu Glu Leu Glu Lys Ala Pro Asp Leu Ser Asp Arg Tyr Tyr Phe Tyr
            835                 840                 845

Phe Thr Gln Gly Gly Lys Asp Met Tyr Thr Gly Asp Pro Ile Asn Phe
            850                 855                 860

Asp Glu Ile Ser Thr Lys Tyr Asp Ile Asp His Ile Leu Pro Gln Ser
865                 870                 875                 880
```

```
Phe Val Lys Asp Asp Ser Leu Asp Asn Arg Val Leu Val Ser Arg Ala
            885                 890                 895

Glu Asn Asn Lys Lys Ser Asp Arg Val Pro Ala Lys Leu Tyr Ala Ala
                900                 905                 910

Lys Met Lys Pro Tyr Trp Asn Gln Leu Leu Lys Gln Gly Leu Ile Thr
        915                 920                 925

Gln Arg Lys Phe Glu Asn Leu Thr Met Asp Val Asp Gln Asn Ile Lys
    930                 935                 940

Tyr Arg Ser Leu Gly Phe Val Lys Arg Gln Leu Val Glu Thr Arg Gln
945                 950                 955                 960

Val Ile Lys Leu Thr Ala Asn Ile Leu Gly Ser Met Tyr Gln Glu Ala
                965                 970                 975

Gly Thr Asp Ile Ile Glu Thr Arg Ala Gly Leu Thr Lys Gln Leu Arg
            980                 985                 990

Glu Glu Phe Asp Leu Pro Lys Val  Arg Glu Val Asn Asp  Tyr His His
            995             1000                1005

Ala Val  Asp Ala Tyr Leu Thr  Thr Phe Ala Gly Gln  Tyr Leu Asn
    1010                1015                1020

Arg Arg  Tyr Pro Lys Leu Arg  Ser Phe Val Tyr  Gly Glu Tyr
    1025                1030                1035

Met Lys  Phe Lys His Gly Ser  Asp Leu Lys Leu Arg  Asn Phe Asn
    1040                1045                1050

Phe Phe  His Glu Leu Met Glu  Gly Asp Lys Ser Gln  Gly Lys Val
    1055                1060                1065

Val Asp  Gln Gln Thr Gly Glu  Leu Ile Thr Thr Arg  Asp Glu Val
    1070                1075                1080

Ala Lys  Ser Phe Asp Arg Leu  Leu Asn Met Lys Tyr  Met Leu Val
    1085                1090                1095

Ser Lys  Glu Val His Asp Arg  Ser Asp Gln Leu Tyr  Gly Ala Thr
    1100                1105                1110

Ile Val  Thr Ala Lys Glu Ser  Gly Lys Leu Thr Ser  Pro Ile Glu
    1115                1120                1125

Ile Lys  Lys Asn Arg Pro Val  Asp Leu Tyr Gly Ala  Tyr Thr Asn
    1130                1135                1140

Gly Thr  Ser Ala Phe Met Thr  Ile Ile Lys Phe Thr  Gly Asn Lys
    1145                1150                1155

Pro Lys  Tyr Lys Val Ile Gly  Val Pro Thr Thr Ser  Ala Val Gly
    1160                1165                1170

Leu Lys  Arg Val Gly Lys Pro  Gly Ser Glu Ser Tyr  Asn Gln Glu
    1175                1180                1185

Leu His  Arg Ile Ile Lys Ser  Asn Pro Lys Val Lys  Lys Asp Phe
    1190                1195                1200

Glu Ile  Val Val Pro His Val  Ser Tyr Ser Gln Leu  Ile Val Asp
    1205                1210                1215

Gly Asp  Cys Lys Phe Thr Leu  Ala Ser Asp Thr Tyr  Gln His Pro
    1220                1225                1230

Ala Thr  Gln Leu Val Leu Ser  Lys Glu Ser Met Glu  Ile Ile Ala
    1235                1240                1245

Asp Asp  Phe Lys Phe Val Lys  Glu Asn Pro Ala Thr  Ala Asp Glu
    1250                1255                1260

Gln Leu  Val Arg Val Phe Asp  Glu Ile Val Asn Gln  Met Asn His
    1265                1270                1275
```

```
Tyr Phe Thr Ile Phe Asp Gln Arg Ser Asn Arg Gln Lys Val Thr
    1280                1285                1290

Lys Ala Arg Asp Lys Phe Val Ser Leu Pro Thr Glu Ser Glu Tyr
1295                1300                1305

Glu Gly Ala Lys Lys Thr Gln Val Gly Lys Thr Glu Val Ile Thr
1310                1315                1320

Asn Leu Leu Met Gly Leu His Ala Asn Ala Ala Gln Gly Asp Leu
1325                1330                1335

Lys Val Leu Gly Leu Ser Thr Phe Gly Phe Phe Gln Ser Ser Gly
1340                1345                1350

Gly Leu Asn Leu Ser Glu Asp Ala Met Ile Val Tyr Gln Ser Pro
    1355                1360                1365

Thr Gly Leu Phe Glu Arg Arg Ile Cys Leu Lys Asp Ile
1370                1375                1380

<210> SEQ ID NO 30
<211> LENGTH: 1386
<212> TYPE: PRT
<213> ORGANISM: Lactobacillus gasseri K7

<400> SEQUENCE: 30

Met Thr Lys Ile Lys Asn Glu Tyr Ile Val Gly Leu Asp Ile Gly Thr
1               5                   10                  15

Asn Ser Cys Gly Trp Val Ala Met Asp Phe Gln Asn Thr Ile Leu Arg
            20                  25                  30

Met His Gly Lys Thr Ala Ile Gly Ser His Leu Phe Asp Ala Gly Asn
        35                  40                  45

Ser Ala Ala Asp Arg Arg Ala Phe Arg Thr Thr Arg Arg Ile Lys
50                  55                  60

Arg Arg Lys Trp Arg Leu Lys Leu Leu Glu Glu Ile Phe Asp Pro Tyr
65                  70                  75                  80

Met Thr Glu Val Asp Pro Tyr Phe Phe Ala Arg Leu Lys Glu Ser Gly
                85                  90                  95

Leu Ser Pro Leu Asp Lys Arg Lys Asn Ala Ser Ser Ile Val Phe Pro
            100                 105                 110

Thr Ala Leu Glu Asp Lys Lys Phe Tyr Cys Asn Tyr Pro Thr Ile Tyr
        115                 120                 125

His Leu Arg Tyr Asp Leu Met Ser Glu Asp Lys Lys Phe Asp Leu Arg
    130                 135                 140

Glu Ile Tyr Leu Ala Ile His His Ile Val Lys Tyr Arg Gly Asn Phe
145                 150                 155                 160

Leu Tyr Asn Thr Pro Val Lys Asp Phe Glu Ala Ser Lys Ile Asp Val
                165                 170                 175

Lys Asp Ser Leu Glu Lys Leu Asn Glu Leu Tyr Glu Arg Leu Asp Ser
            180                 185                 190

Glu Phe Thr Val Glu Leu Asp Ser Ser Asn Ala Leu Glu Ile Glu Lys
        195                 200                 205

Ile Ile Arg Asp Lys Asn Val Phe Lys Ile Asn Lys Val Lys Ser Ile
210                 215                 220

His Gln Leu Leu Ser Leu Lys Thr Glu Asn Lys Glu Arg Thr Lys Leu
225                 230                 235                 240

Ile Lys Asp Val Ser Lys Gln Ile Ile Asn Ala Ile Leu Gly Tyr Lys
                245                 250                 255

Thr Lys Phe Glu Thr Ile Leu Leu Lys Asn Ile Ser Lys Asp Glu Ala
            260                 265                 270
```

```
Asp Asp Trp Glu Phe Lys Leu Thr Asp Val Asp Ala Asp Asn Lys Phe
        275                 280                 285

Glu Asn Leu Ile Gly Asp Leu Asn Glu Asn Glu Gln Glu Ile Leu Leu
    290                 295                 300

Val Ile Arg Asn Leu Ala Asn Ala Ile Thr Leu Ser Asn Ile Val Glu
305                 310                 315                 320

Glu Gly Lys Thr Leu Ser Glu Ser Met Ile Asp Lys Tyr Asn Lys His
                325                 330                 335

Ser Asp Asp Leu Lys Leu Leu Lys Gln Val Ile Ser Asp His Pro Asp
                340                 345                 350

Arg Asp Lys Ala Lys Lys Leu Ala Leu Ala Tyr Asp Leu Tyr Val Asn
            355                 360                 365

Asn Arg His Gly Lys Leu Leu Gln Ala Lys Asp Val Leu Gly Ser Lys
        370                 375                 380

Lys Thr Leu Ser Lys Glu Asp Phe Tyr Lys Glu Val Lys Lys Asn Leu
385                 390                 395                 400

Asp Asp Ser Lys Ala Ser Gln Glu Ile Leu Asp Ala Ile Ala Leu Asp
                405                 410                 415

Ser Phe Met Pro Lys Gln Arg Thr Asn Glu Asn Gly Val Ile Pro Tyr
                420                 425                 430

Gln Leu His Gln Leu Glu Leu Asp Arg Ile Ile Lys Asn Gln Gly Lys
        435                 440                 445

Tyr Tyr Pro Phe Leu Lys Glu Ala Asn Pro Val Ser Ser His Leu Lys
        450                 455                 460

Gln Ala Pro Tyr Lys Leu Asp Glu Leu Ile Arg Phe Arg Val Pro Tyr
465                 470                 475                 480

Tyr Val Gly Pro Leu Ile Ser Pro Asn Glu Ser Thr Lys Asn Lys Gln
                485                 490                 495

Thr Lys Lys Asn Gln Asn Phe Ala Trp Met Ile Arg Lys Glu Gln Gly
                500                 505                 510

Gln Ile Thr Pro Trp Asn Phe Asp Gln Lys Val Asp Arg Met Ala Ser
        515                 520                 525

Ala Asn Lys Phe Ile Lys Arg Met Thr Thr Lys Asp Thr Tyr Leu Leu
        530                 535                 540

Gly Glu Asp Val Leu Pro Ala Asn Ser Leu Leu Tyr Gln Lys Phe Thr
545                 550                 555                 560

Val Leu Asn Glu Leu Asn Asn Ile Lys Ile Asn Gly Lys Arg Ile Ser
                565                 570                 575

Val Pro Leu Lys Gln Glu Leu Tyr Asn Asn Leu Phe Lys Lys Asn Ser
                580                 585                 590

Thr Val Thr Thr Asn Lys Leu Lys Ser Tyr Leu Lys Glu Asn Tyr Asn
        595                 600                 605

Leu Ile Asn Val Glu Ile Lys Gly Leu Ala Asp Glu Lys Lys Phe Asn
        610                 615                 620

Ser Gly Leu Thr Thr Tyr Asn Lys Leu Arg Asn Leu Lys Ile Phe Asp
625                 630                 635                 640

Gln Gln Ile Asp Asp Leu Asn Tyr Asp Lys Asp Phe Glu Arg Ile Ile
                645                 650                 655

Glu Trp Ser Thr Ile Phe Glu Asp Lys Ala Ile Tyr Lys Asp Lys Leu
                660                 665                 670

Lys Thr Ile Lys Trp Leu Ser Asp Arg Gln Ile Asp Lys Leu Ser Lys
        675                 680                 685
```

Ile Arg Met Gln Gly Trp Gly Gln Leu Ser Lys Lys Leu Leu Ser Gln
690                 695                 700

Leu Thr Asp Asn Gly Gln Thr Ile Ile Glu Gln Leu Trp Asp Ser
705                 710                 715                 720

Gln Asn Asn Phe Met Gln Ile Val Asn Gln Ala Asp Phe Lys Asp Ala
                725                 730                 735

Ile Ala Val Ala Asn Gln Asn Leu Leu Val Asn Thr Ser Val Glu Asp
                740                 745                 750

Ile Leu Asn Glu Ala Tyr Thr Ser Pro Ala Asn Lys Lys Ala Ile Arg
                755                 760                 765

Gln Val Val Lys Val Val Asp Asp Ile Val Lys Ala Ala Ser Gly Lys
770                 775                 780

Val Pro Lys Gln Ile Ala Ile Glu Phe Thr Arg Asp Ala Asp Asp Lys
785                 790                 795                 800

Ala Lys Ile Ser Gln Thr Arg Ala Asn Lys Leu Arg Lys Val Tyr Lys
                805                 810                 815

Glu Leu Ser Asn Glu Leu Ala Ser Glu Ala Ile Arg Asn Glu Leu Glu
                820                 825                 830

Arg Val Ala Lys Asp Gln Lys Leu Leu Lys Asp Lys Tyr Tyr Leu Tyr
                835                 840                 845

Phe Met Gln Leu Gly Arg Asp Ala Tyr Thr Gly Glu Pro Ile Asp Ile
850                 855                 860

Asp Glu Leu Glu Gln Tyr Asp Ile Asp His Ile Leu Pro Gln Ser Phe
865                 870                 875                 880

Ile Lys Asp Asp Ser Leu Glu Asn Arg Val Leu Val Lys Lys Ala Val
                885                 890                 895

Asn Asn Gly Lys Ser Asp Asn Val Pro Val Lys Leu Tyr Gly Asn His
                900                 905                 910

Met Ala Ala Asp Leu Gly Ile Thr Ile Arg His Met Trp Glu Lys Trp
                915                 920                 925

Lys Asp Gln Gly Leu Ile Thr Lys Thr Lys Tyr Asn Asn Leu Ile Ile
930                 935                 940

Asp Pro Asp Lys Ile Asn Lys Tyr Glu Ser Ser Gly Phe Ile His Arg
945                 950                 955                 960

Gln Leu Val Glu Thr Ser Gln Ile Ile Lys Leu Ala Ser Thr Ile Leu
                965                 970                 975

Gln Ser Lys Tyr Pro Asp Thr Glu Ile Ile Val Val Lys Ala Arg Tyr
                980                 985                 990

Asn His Tyr Leu Arg Lys His Leu Asn Leu Tyr Lys Ser Arg Glu Val
                995                 1000                1005

Asn Asp Tyr His His Ala Ile Asp Ala Tyr Leu Ser Ala Ile Cys
1010                1015                1020

Gly Asn Leu Leu Tyr Gln Val Tyr Pro Tyr Leu Arg Pro Phe Phe
1025                1030                1035

Val Tyr Gly Gln Tyr Lys Lys Phe Ser Ser Asp Pro Lys Lys Glu
1040                1045                1050

Lys Ile Ile Tyr Asp Lys Thr Arg Lys Tyr Asn Phe Ile Ser Gln
1055                1060                1065

Ile Phe Glu Asn Lys Gly Asn Asp Ile Ile Ser Leu Glu Thr Lys
1070                1075                1080

Lys Lys Val Phe Asp Lys Lys Asp Ile Ile Glu Lys Leu Lys His
1085                1090                1095

Ala Tyr Asp Tyr Lys Tyr Met Leu Val Ser Arg Glu Thr Glu Thr

```
                    1100                1105                1110

Arg Asp Gln Glu Met Phe Lys Met Thr Val Tyr Pro Arg Leu Ser
            1115                1120                1125

Arg Asp Thr Lys Lys Ser Arg Asn Leu Ile Pro Lys Lys Lys Asp
            1130                1135                1140

Met Pro Thr Glu Ile Tyr Gly Gly Tyr Thr Asn Asn Ser Asp Ala
            1145                1150                1155

Tyr Met Val Ile Ala Arg Ile Asn Lys Lys Lys Glu Thr Glu Tyr
            1160                1165                1170

Arg Val Phe Gly Val Pro Met Arg Glu Leu Val Asn Leu Arg Lys
            1175                1180                1185

Ala Glu Lys Lys Gly His Tyr Asn Ala Tyr Leu Lys Gln Val Leu
            1190                1195                1200

Glu Pro Glu Ile Met Tyr Asn Lys Asn Gly Lys Lys Asn Lys Thr
            1205                1210                1215

Ile Ser Ser Phe Glu Ile Val Lys Ser Lys Val Pro Tyr Lys Gln
            1220                1225                1230

Val Ile Leu Asp Gly Asp Lys Lys Phe Met Leu Gly Ser Ser Thr
            1235                1240                1245

Tyr Val Tyr Asn Ala Lys Gln Leu Thr Leu Ser Gln Asp Ala Met
            1250                1255                1260

Gln Ala Ile Thr Asp Asn Cys Glu Asn Asp Thr Asp Glu Glu Lys
            1265                1270                1275

Ala Leu Ile Glu Ala Tyr Asp Glu Ile Leu Thr Asn Ile Asp Lys
            1280                1285                1290

Tyr Leu Pro Leu Phe Asp Ile Asn Lys Phe Arg Asp Lys Leu His
            1295                1300                1305

Ala Gly Arg Glu Lys Phe Ile Asn Leu Ser Leu Asp Val Lys Lys
            1310                1315                1320

Asp Thr Ile Leu Gln Val Leu Asn Gly Leu His Asp Asn Ala Val
            1325                1330                1335

Met Pro Lys Ile Lys Ser Leu Gly Leu Ser Thr Glu Leu Gly Lys
            1340                1345                1350

Leu Gln Ile Pro Thr Gly Val Lys Leu Ser Glu Asn Ala Lys Leu
            1355                1360                1365

Ile Tyr Gln Ser Pro Thr Gly Leu Phe Glu Lys Arg Val Lys Ile
            1370                1375                1380

Ser Asp Leu
    1385

<210> SEQ ID NO 31
<211> LENGTH: 1386
<212> TYPE: PRT
<213> ORGANISM: Lactobacillus hominis CRBIP

<400> SEQUENCE: 31

Met Thr Lys Ile Thr Glu Asp Tyr Ile Val Gly Leu Asp Ile Gly Thr
1               5                   10                  15

Asn Ser Cys Gly Trp Val Ala Met Asp Ser Lys Asn Thr Ile Leu Arg
            20                  25                  30

Met His Gly Lys Thr Ala Ile Gly Ser His Leu Phe Asp Ala Gly Asn
        35                  40                  45

Ser Ala Ala Asp Arg Arg Ala Phe Arg Thr Thr Arg Arg Arg Ile Lys
    50                  55                  60
```

-continued

```
Arg Arg Lys Trp Arg Leu Lys Leu Leu Glu Glu Ile Phe Asp Ser His
 65                  70                  75                  80

Leu Ala Lys Val Asp Pro Tyr Phe Phe Ala Arg Leu Lys Glu Ser Gly
                 85                  90                  95

Leu Ser Pro Leu Asp Thr Arg Lys Asn Val Ser Ser Ile Ile Tyr Pro
            100                 105                 110

Thr Ser Leu Glu Asp Lys Lys Phe Tyr Val Asp Asn Pro Thr Ile Tyr
        115                 120                 125

His Leu Arg Tyr Lys Leu Met Thr Glu Asp Arg Lys Phe Asp Leu Arg
    130                 135                 140

Glu Val Tyr Leu Ala Ile His His Ile Val Lys Tyr Arg Gly Asn Phe
145                 150                 155                 160

Leu Tyr Asn Thr Pro Val Lys Ala Phe Glu Ala Ser Lys Ile Asp Val
                165                 170                 175

Lys Gly Ser Leu Lys Lys Leu Asn Glu Leu Tyr Glu Gly Leu Asp Ser
            180                 185                 190

Glu Phe Asn Val Glu Leu Asp Ser Asn Ala Leu Glu Ile Glu Asn
        195                 200                 205

Ile Ile Arg Asp Lys Lys Ile Phe Lys Ile Asn Lys Val Lys Glu Ile
    210                 215                 220

Asn Gln Leu Leu Ser Leu Lys Thr Glu Asp Lys Glu Arg Thr Lys Leu
225                 230                 235                 240

Met Lys Asp Val Ser Lys Gln Ile Val Asn Ala Ile Leu Gly Tyr Lys
                245                 250                 255

Thr Lys Phe Glu Thr Ile Leu Leu Lys Asp Val Ser Lys Asp Glu Ala
            260                 265                 270

Asp Asp Trp Glu Phe Lys Leu Thr Asp Val Asp Ala Asp Asn Lys Phe
        275                 280                 285

Glu Asn Leu Ile Gly Asp Leu Asn Glu Asn Glu Gln Glu Ile Leu Leu
    290                 295                 300

Val Ile Arg Lys Leu Ala Asn Ala Ile Thr Leu Ser Asn Ile Val Glu
305                 310                 315                 320

Glu Gly Lys Thr Leu Ser Glu Ser Met Lys Asp Lys Tyr Lys Lys His
                325                 330                 335

Ser Asp Asp Leu Lys Leu Leu Lys Gln Val Ile Ser Asp His Pro Asp
            340                 345                 350

Arg Asp Lys Ala Lys Lys Leu Ala Leu Ala Tyr Asp Leu Tyr Val Asn
        355                 360                 365

Asn Arg His Gly Lys Ile Leu Gln Ala Lys Asp Ile Leu Glu Lys Lys
    370                 375                 380

Lys Thr Leu Ser Lys Glu Asp Phe Tyr Lys Glu Ile Lys Lys Asn Leu
385                 390                 395                 400

Asp Asp Ser Lys Glu Ser Gln Glu Ile Leu Asp Ala Ile Ser Leu Asp
                405                 410                 415

Ser Phe Met Pro Lys Gln Arg Thr Asn Glu Asn Gly Val Ile Pro Tyr
            420                 425                 430

Gln Leu His Gln Leu Glu Leu Asp Lys Ile Ile Glu Asn Gln Gly Lys
        435                 440                 445

Tyr Tyr Pro Phe Leu Lys Glu Val Asn Pro Val Ser His Leu Lys
    450                 455                 460

Gln Ala Pro Tyr Lys Leu Asp Glu Leu Ile Arg Phe Arg Val Pro Tyr
465                 470                 475                 480

Tyr Val Gly Pro Leu Ile Ser Pro Asn Glu Ser Thr Lys Asn Lys Gln
```

```
              485                 490                 495
Thr Lys Lys Asn Gln Asn Phe Ala Trp Met Ile Arg Lys Glu Gln Gly
            500                 505                 510
Gln Ile Thr Pro Trp Asn Phe Asp Gln Lys Val Asp Arg Met Ala Ser
            515                 520                 525
Ala Asn Lys Phe Ile Lys Arg Met Thr Thr Ile Asp Thr Tyr Leu Leu
            530                 535                 540
Gly Glu Asp Val Leu Pro Ala Asn Ser Leu Leu Tyr Gln Lys Phe Thr
545                 550                 555                 560
Val Leu Asn Glu Leu Asn Asn Val Lys Ile Asn Gly Lys Arg Ile Ser
            565                 570                 575
Val Pro Leu Lys Gln Glu Leu Tyr Asn Asn Leu Phe Lys Lys Asn Ser
            580                 585                 590
Thr Val Thr Thr Asn Lys Leu Lys Ser Tyr Leu Lys Glu Asn Tyr Lys
            595                 600                 605
Leu Ile Lys Val Glu Ile Lys Gly Leu Ser Asp Glu Lys Lys Phe Asn
610                 615                 620
Ser Gly Leu Thr Thr Tyr Asn Lys Leu Lys Asn Leu Lys Ile Phe Asp
625                 630                 635                 640
Gln Gln Ile Asp Asp Pro Asn Tyr Asn Lys Asp Phe Glu Arg Ile Ile
                645                 650                 655
Glu Trp Ser Thr Ile Phe Glu Asp Lys Ala Ile Tyr Lys Glu Lys Leu
            660                 665                 670
Lys Thr Ile Asp Trp Leu Ser Asp Arg Gln Ile Asp Lys Leu Ser Lys
            675                 680                 685
Ile Arg Met Gln Gly Trp Gly Gln Leu Ser Lys Lys Leu Leu Ser Gln
            690                 695                 700
Leu Thr Asp Asn Asn Gly Gln Thr Ile Ile Glu Gln Leu Trp Asp Ser
705                 710                 715                 720
Gln Asn Asn Phe Met Gln Ile Val Asn Gln Ala Asp Phe Lys Asp Ala
            725                 730                 735
Ile Ala Val Ala Asn Gln Asn Leu Leu Val Asp Thr Ser Val Glu Asp
            740                 745                 750
Ile Leu Asn Glu Ala Tyr Thr Ser Pro Ala Asn Lys Lys Ala Ile Arg
            755                 760                 765
Gln Val Val Lys Val Val Asp Asp Ile Val Lys Ala Thr Ser Gly Lys
            770                 775                 780
Val Pro Lys Gln Ile Ala Ile Glu Phe Thr Arg Asp Ala Asp Asn
785                 790                 795                 800
Ala Lys Ile Ser Gln Ser Arg Ala Asn Lys Leu Arg Lys Val Tyr Lys
            805                 810                 815
Glu Met Ser Asn Glu Leu Ala Ser Glu Thr Ile Arg Asn Glu Leu Glu
            820                 825                 830
Arg Val Ala Lys Asp Gln Lys Leu Leu Lys Asp Lys His Tyr Leu Tyr
            835                 840                 845
Phe Met Gln Leu Gly Arg Asp Ala Tyr Thr Gly Glu Leu Ile Asp Ile
850                 855                 860
Asp Asn Leu Glu Gln Tyr Asp Ile Asp His Val Leu Pro Gln Ser Phe
865                 870                 875                 880
Ile Lys Asp Asp Ser Leu Glu Asn Arg Val Leu Val Lys Lys Ala Val
            885                 890                 895
Asn Asn Gly Lys Ser Asp Asn Val Pro Val Lys Leu Tyr Gly Asn Arg
            900                 905                 910
```

-continued

```
Met Ala Thr Asp Leu Gly Met Thr Ile Arg His Met Trp Glu Lys Trp
        915                 920                 925

Lys Glu Gln Gly Leu Ile Thr Lys Thr Lys Tyr Asn Asn Leu Ile Ile
        930                 935                 940

Asp Pro Asp Lys Ile Asn Lys Tyr Glu Ser Ser Gly Phe Ile His Arg
945                 950                 955                 960

Gln Leu Val Glu Thr Ser Gln Ile Ile Lys Leu Val Ser Thr Ile Leu
                965                 970                 975

Gln Ser Lys Tyr Pro Asp Thr Glu Ile Ile Val Val Lys Ala Arg Tyr
            980                 985                 990

Asn His Tyr Leu Arg Lys Arg Leu Asn Leu Tyr Lys Ser Arg Glu Val
            995                 1000                1005

Asn Asp Tyr His His Ala Ile Asp Ala Tyr Leu Ser Ala Ile Cys
        1010                1015                1020

Gly Asn Leu Leu Tyr Gln Val Tyr Pro Tyr Leu Arg Pro Phe Phe
        1025                1030                1035

Val Tyr Gly Gln Tyr Lys Lys Phe Ser Ser Glu Pro Glu Lys Glu
        1040                1045                1050

Lys Ile Ile Tyr Asp Lys Thr Arg Arg Tyr Asn Phe Ile Ser Gln
        1055                1060                1065

Ile Phe Glu Asn Lys Asp Asn Asp Ile Ile Ser Arg Glu Thr Lys
        1070                1075                1080

Lys Lys Val Phe Asp Lys Lys Asp Ile Ile Glu Lys Leu Lys Arg
        1085                1090                1095

Ala Tyr Asn Tyr Lys Tyr Met Leu Val Ser Arg Glu Thr Glu Thr
        1100                1105                1110

His Asp Gln Glu Met Phe Lys Met Thr Val Tyr Pro Arg Leu Ser
        1115                1120                1125

Arg Asp Thr Lys Lys Ser Arg Asn Leu Ile Pro Lys Lys Lys Asp
        1130                1135                1140

Met Pro Thr Glu Ile Tyr Gly Gly Tyr Thr Asn Asn Ser Asp Ala
        1145                1150                1155

Tyr Met Ile Ile Ala Arg Ile Asn Lys Lys Lys Gly Pro Glu Tyr
        1160                1165                1170

Arg Val Phe Gly Val Pro Met Arg Glu Leu Val Asn Leu Arg Lys
        1175                1180                1185

Ala Glu Lys Asn Gly His Tyr Lys Ala Tyr Leu Lys Gln Val Leu
        1190                1195                1200

Glu Pro Glu Ile Met Tyr Ser Lys Asn Gly Lys Lys Asn Lys Thr
        1205                1210                1215

Ile Ser Ser Phe Glu Ile Val Lys Ala Lys Val Pro Tyr Lys Gln
        1220                1225                1230

Val Ile Leu Asp Gly Asp Lys Lys Phe Met Leu Ala Ser Ser Thr
        1235                1240                1245

Tyr Val Gln Asn Ala Lys Gln Leu Thr Leu Ser Gln Tyr Ser Met
        1250                1255                1260

Gln Ala Ile Thr Asp Asn Cys Glu Asn Asp Thr Glu Glu Glu Lys
        1265                1270                1275

Ala Leu Val Glu Ala Tyr Asp Glu Ile Leu Thr Asn Ile Asp Lys
        1280                1285                1290

Tyr Leu Pro Leu Phe Asp Ile Asn Lys Phe Arg Glu Lys Leu His
        1295                1300                1305
```

-continued

```
Ala Gly Arg Glu Lys Phe Val Asp Leu Pro Leu Ala Glu Lys Lys
    1310                1315                1320

Glu Thr Ile Leu Gln Val Leu Asn Gly Leu His Asp Asn Ala Val
    1325                1330                1335

Met Pro Lys Ile Lys Ser Leu Gly Leu Ser Thr Pro Leu Gly Phe
    1340                1345                1350

Met Gln Phe His Thr Gly Val Ser Leu Ser Glu Asn Ala Lys Leu
    1355                1360                1365

Ile Tyr Gln Ser Pro Thr Gly Leu Phe Glu Lys Arg Leu Lys Ile
    1370                1375                1380

Ser Asp Leu
    1385

<210> SEQ ID NO 32
<211> LENGTH: 1395
<212> TYPE: PRT
<213> ORGANISM: Lactobacillus jensenii 115-3-CHN

<400> SEQUENCE: 32

Met Lys Glu Ile Lys Asp Tyr Ile Ile Gly Leu Asp Ile Gly Thr Asn
1               5                   10                  15

Ser Cys Gly Tyr Val Val Thr Asp Lys Gln Asn Asn Ile Leu Lys Leu
                20                  25                  30

Lys Gly Lys Thr Ala Ile Gly Ala Arg Leu Phe Lys Glu Gly Gln Ala
            35                  40                  45

Ala Ala Asp Arg Arg Ser Phe Arg Thr Thr Arg Arg Leu Ala Arg
        50                  55                  60

Arg His Trp Arg Leu Gly Leu Leu Glu Glu Ile Phe Asp Pro Glu Met
65              70                  75                  80

Glu Lys Ile Asp Pro Asn Phe Phe Arg Arg Leu Lys Glu Ser Asp Tyr
                85                  90                  95

Ser Pro Lys Asp Ser Arg Lys Gln Phe Asn Ala Ile Val Phe Lys Ser
            100                 105                 110

Ile Lys Ala Asp Lys Arg Phe Tyr Lys Lys Tyr Pro Thr Ile Tyr His
        115                 120                 125

Leu Arg Asn Ala Leu Met His Asp Asn Gln Lys His Asp Leu Arg Glu
    130                 135                 140

Ile Phe Met Ala Val His His Ile Val Lys Tyr Arg Gly Asn Phe Leu
145                 150                 155                 160

Arg Glu Asp Ser Val Asn Ala Phe Lys Ala Ala Lys Phe Ser Leu Arg
                165                 170                 175

Gly Glu Asp Gly Ile Gly Pro Val Asp Lys Leu Asn Asp Leu Leu Lys
            180                 185                 190

Glu Ile Tyr Ser Glu Tyr Ser Pro Glu Leu Ala Thr Asn Asn Leu Ser
        195                 200                 205

Lys Ile Glu Asp Ile Ile Lys Asp Lys Asn Leu Tyr Lys Gln Asp Lys
    210                 215                 220

Leu Lys Gln Val Ala Thr Leu Leu Ile Lys Glu Ala Asp Ser Lys Asp
225                 230                 235                 240

Lys Ala Lys Leu Asn Lys Asp Ile Ala Lys Gln Val Ala Asn Ser Phe
                245                 250                 255

Met Gly Tyr Met Phe Arg Leu Asp Thr Leu Phe Ser Leu Thr Asp Val
            260                 265                 270

Asp Val Lys Asp Tyr Lys Leu Lys Phe Ser Asp Ala Asn Ile Asp Glu
        275                 280                 285
```

```
Ser Leu Asp Asp Leu Thr Ser Leu Leu Thr Asp Ala Gln Ile Glu Phe
    290                 295                 300

Val Leu Glu Leu Gln Ser Ile Tyr Asn Thr Ile Val Leu Asn Glu Ile
305                 310                 315                 320

Val Pro Asp Gly Met Ser Leu Ser Glu Ser Met Ile Lys Lys Tyr Asp
                325                 330                 335

Asp His Lys Glu Asp Leu Lys Ile Phe Lys Glu Tyr Ile Asp Ser Leu
            340                 345                 350

Ser Asp Gln Lys Lys Ala Lys Lys Leu Leu Ser Ala Tyr Asn Leu Tyr
        355                 360                 365

Val Asn Tyr Arg Lys Ser Asp Leu Val Glu Ala Lys Asn Leu Phe Lys
370                 375                 380

Asn Lys Lys Val Gly Asp Lys Asn Phe Ala Asp Val Ile Ser Asn Phe
385                 390                 395                 400

Glu Val Phe Gly Lys Phe Val Ser Asp Asn Leu Asp Asp Ser Glu Leu
                405                 410                 415

Ala Asn Lys Ile Lys Ala Arg Leu Asp Leu Gly Glu Phe Leu Pro Lys
            420                 425                 430

Gln Arg Thr Asn Gln Asn Gly Val Ile Pro Tyr Gln Leu His Gln Val
        435                 440                 445

Glu Leu Thr Gln Ile Leu Glu Lys Gln Gly Lys Tyr Tyr Pro Phe Leu
450                 455                 460

Ile Thr Pro Asn Pro Val Glu Ser His Arg Asn Asn Ala Pro Tyr Glu
465                 470                 475                 480

Ile Ser Glu Leu Val Ser Phe Arg Val Pro Tyr Tyr Val Gly Pro Leu
                485                 490                 495

Ile Asp Asn Gln Ser Ile Lys Asp Lys Gln Asn Lys Asn Lys Phe Ala
            500                 505                 510

Trp Met Val Arg Gln Lys Gln Gly Gln Ile Thr Pro Trp Asn Leu Glu
        515                 520                 525

Glu Met Val Asp Thr Thr Glu Ser Ala Asn Gln Phe Ile Lys Arg Met
530                 535                 540

Thr Arg Lys Asp Thr Tyr Leu Leu Ala Glu Asp Val Leu Pro Lys Ser
545                 550                 555                 560

Ser Leu Val Tyr Gln Lys Phe Met Ile Leu Asp Glu Leu Asn Arg Ile
                565                 570                 575

Lys Ile Asp Gly Lys Lys Leu Thr Ser Glu Leu Lys His Asp Ile Phe
            580                 585                 590

Glu Lys Leu Phe Lys Gln Lys Ser Ile Asn Leu Asp Asn Leu Lys
        595                 600                 605

Asn Tyr Leu Leu Val Glu Gly Asn Ile Pro Gly Leu Ile Glu Gly Leu
610                 615                 620

Ser Asp Gly Ile Asn Phe Asn Asn Ser Phe Ser Thr Tyr Ile Asp Tyr
625                 630                 635                 640

Arg Asn Ile Phe Gly Asp Glu Ile Asp Asn Pro Asn Lys Gln Ala Asp
                645                 650                 655

Phe Glu Lys Met Ile Glu Trp Ser Thr Val Phe Glu Asp Arg Lys Ile
            660                 665                 670

Phe Lys Arg Lys Leu Lys Glu Ile Thr Trp Leu Thr Ser Glu Gln Ile
        675                 680                 685

Lys Gln Val Ser Ser Lys Arg Tyr Ser Gly Trp Gly Arg Leu Ser Lys
690                 695                 700
```

-continued

Lys Leu Leu Thr Gln Ile Thr Asp Glu Asn Gly Val Asn Ile Leu Gln
705                 710                 715                 720

Arg Leu Trp Asn Glu Pro Glu Thr Leu Thr Glu Val Leu Ala Asn Pro
            725                 730                 735

Val Ile Lys Arg Lys Ile Val Glu Ala Asn Ser Ser Phe Thr Lys Ala
            740                 745                 750

Lys Asp Met Lys Asp Ile Leu Val Glu Ala Tyr Thr Ser Pro Gln Asn
            755                 760                 765

Lys Lys Ala Ile Arg Gln Val Met Arg Val Val Asp Asp Ile Ile Ala
770                 775                 780

Ala Ala His Gly Lys Lys Pro Ser Gln Ile Ala Ile Glu Phe Ala Arg
785                 790                 795                 800

Glu Asp Gln Asp Asn Pro Gln Met Thr Lys Ser Arg Lys Ala Gln Leu
            805                 810                 815

Asp Gln Ile Tyr Ala Lys Ile Ser Asp Glu Phe Leu Asp Asp Ala Val
            820                 825                 830

Lys Asn Glu Leu Lys Asn Met Lys Asp Asn Lys Pro Leu Ala Lys Asp
            835                 840                 845

Lys Val Phe Leu Tyr Phe Lys Gln Met Gly Arg Asp Ala Tyr Ser Gly
850                 855                 860

Glu Lys Leu Ser Leu Asp Asn Leu Gln Asp Tyr Asp Ile Asp His Ile
865                 870                 875                 880

Tyr Pro Gln Ser Phe Ile Lys Asp Asp Ser Phe Asp Asn Arg Val Leu
            885                 890                 895

Val Gln Arg Ala Tyr Asn Asn Gly Lys Ser Asp Asn Val Pro Val Leu
            900                 905                 910

Leu Phe Gly Asn Lys Ile Ala Ala Gly Leu Gly Ile Thr Ile Arg Gln
            915                 920                 925

Met Trp Lys Lys Trp Leu Glu Leu Gly Leu Ile Ser Lys Arg Lys Phe
930                 935                 940

Asn Asn Leu Ile Thr Asp Pro Glu Lys Ile Ser Arg Asn Met Ala Ser
945                 950                 955                 960

Gly Phe Val Asn Arg Gln Leu Val Glu Thr Ser Gln Val Ile Lys Leu
            965                 970                 975

Val Ala Asn Ile Leu Gln Ala Lys Leu Pro Asp Thr Glu Ile Ile Glu
            980                 985                 990

Val Lys Ala Ser Tyr Asn Ser Ile Leu Arg Lys Glu Phe Asn Leu Tyr
            995                 1000                1005

Lys Ser Arg Glu Val Asn Asp Tyr His His Ala Ile Asp Ala Tyr
   1010                1015                1020

Leu Thr Thr Ile Val Gly Asn Tyr Leu Tyr Gln Val Tyr Pro Lys
   1025                1030                1035

Leu Arg Pro Tyr Phe Val Tyr Gly Gln Phe Lys Lys Phe Gly Lys
   1040                1045                1050

Ala Glu Asn Gln Glu Asp Asp Pro Val Lys Ile Lys Lys Phe
   1055                1060                1065

Asn Phe Ile Tyr Gln Leu Ile Trp Gly Lys Asp Asp Ala Ile Cys
   1070                1075                1080

Ile Ser His Thr Asn Gln Gln Val Phe Ser Lys Lys Asp Ile Ile
   1085                1090                1095

Asp Lys Leu Thr Thr Ala Tyr Asn Phe Lys Tyr Met Asn Ile Ser
   1100                1105                1110

His Ala Val Tyr Thr Arg Asn Asn Asn Met Phe Lys Gln Thr Leu

```
            1115                1120                1125
Phe Pro Ile Ile Glu Arg Thr Thr Ala Lys Thr Lys Ser Leu Ile
        1130                1135                1140
Pro Lys Lys Leu Asp Arg Pro Thr Asp Ile Tyr Gly Gly Tyr Ser
        1145                1150                1155
Asn Asn Asn Asp Ala Tyr Leu Ala Leu Val Lys Val Asp Lys Lys
        1160                1165                1170
Arg Gly Ser Glu Tyr Arg Val Val Gly Ile Pro Met Arg Ala Ala
        1175                1180                1185
Ala Met Leu Lys Ala Ser Lys Asn Tyr Asp Glu Asp Leu Arg Lys
        1190                1195                1200
Val Ile Glu Pro Met Val Met Phe Asp Lys Asn Gly Lys Ala Lys
        1205                1210                1215
Arg Gly Ile Glu Gly Phe Arg Val Leu Val Gly Lys Met Pro Phe
        1220                1225                1230
Lys Gln Ala Val Leu Asp Gly Asn Lys Lys Phe Met Leu Thr Gly
        1235                1240                1245
Thr Val Asp Thr Pro Asn Leu Lys Gln Leu Val Leu Ser Gln Gln
        1250                1255                1260
Asn Met Lys Tyr Ile Leu Asp Tyr Ile Glu Asp Val Asp Cys Arg
        1265                1270                1275
Lys His Lys Phe Gly Asp Lys Val Gln Asn Pro Asp Lys Cys Leu
        1280                1285                1290
Leu Glu Val Phe Asp Glu Ile Ile Glu Ile Val Asp Lys Tyr Phe
        1295                1300                1305
Glu Leu Phe Asp Ser Arg Asp Phe Arg Glu Lys Leu Arg Asn Ser
        1310                1315                1320
Arg Asn Lys Phe Ile Lys Leu Glu Ala Ser Lys Lys Ala Asp Thr
        1325                1330                1335
Ile Leu Ala Ile Leu Lys Gly Leu Gln Ala Lys Ser Thr Arg Ala
        1340                1345                1350
Thr Ile Lys Glu Leu Asn Ile Ser Asp Phe Gly Arg Ile Ile Thr
        1355                1360                1365
Ser Ser Ile Ser Pro Glu Ala Gln Leu Ile Tyr Gln Ser Pro Thr
        1370                1375                1380
Gly Leu Phe Glu Arg Arg Val Lys Val Lys Asp Leu
        1385                1390                1395

<210> SEQ ID NO 33
<211> LENGTH: 1375
<212> TYPE: PRT
<213> ORGANISM: Lactobacillus johnsonii DPC 6026

<400> SEQUENCE: 33

Met Thr Lys Ile Lys Asp Asp Tyr Ile Val Gly Leu Asp Ile Gly Thr
1               5                   10                  15

Asp Ser Cys Gly Trp Val Ala Met Asn Ser Asn Asn Asp Ile Leu Lys
            20                  25                  30

Leu Gln Gly Lys Thr Ala Ile Gly Ser Arg Leu Phe Glu Gly Gly Lys
        35                  40                  45

Ser Ala Ala Glu Arg Arg Leu Phe Arg Thr Thr His Arg Arg Ile Lys
    50                  55                  60

Arg Arg Arg Trp Arg Leu Lys Leu Leu Glu Glu Phe Phe Asp Pro Tyr
65                  70                  75                  80
```

```
Met Ala Glu Val Asp Pro Tyr Phe Phe Ala Arg Leu Lys Glu Ser Gly
                85                  90                  95

Leu Ser Pro Leu Asp Lys Arg Lys Thr Val Ser Ser Ile Val Phe Pro
            100                 105                 110

Thr Ser Ala Glu Asp Lys Lys Phe Tyr Asp Asp Tyr Pro Thr Ile Tyr
            115                 120                 125

His Leu Arg Tyr Lys Leu Met Thr Glu Asp Glu Lys Phe Asp Leu Arg
            130                 135                 140

Glu Val Tyr Leu Ala Ile His His Ile Ile Lys Tyr Arg Gly Asn Phe
145                 150                 155                 160

Leu Tyr Asn Thr Ser Val Lys Asp Phe Lys Ala Ser Lys Ile Asp Val
                165                 170                 175

Lys Ser Ser Ile Glu Lys Leu Asn Glu Leu Tyr Glu Asn Leu Gly Leu
                180                 185                 190

Asp Leu Asn Val Glu Phe Asn Ile Ser Asn Thr Ala Glu Ile Glu Lys
                195                 200                 205

Val Leu Lys Asp Lys Gln Ile Phe Lys Arg Asp Lys Val Lys Lys Ile
            210                 215                 220

Ala Glu Leu Phe Ala Ile Lys Thr Asp Asn Lys Glu Gln Ser Lys Arg
225                 230                 235                 240

Ile Lys Asp Ile Ser Lys Gln Val Ala Asn Ala Val Leu Gly Tyr Lys
                245                 250                 255

Thr Arg Phe Asp Thr Ile Ala Leu Lys Glu Ile Ser Lys Asp Glu Leu
                260                 265                 270

Ser Asp Trp Asn Phe Lys Leu Ser Asp Ile Asp Ala Asp Ser Lys Phe
            275                 280                 285

Glu Ala Leu Met Gly Asn Leu Asp Glu Asn Glu Gln Ala Ile Leu Leu
            290                 295                 300

Thr Ile Lys Glu Leu Phe Asn Glu Val Thr Leu Asn Gly Ile Val Glu
305                 310                 315                 320

Asp Gly Asn Thr Leu Ser Glu Ser Met Ile Asn Lys Tyr Asn Asp His
                325                 330                 335

Arg Asp Asp Leu Lys Leu Leu Lys Glu Val Ile Glu Asn His Ile Asp
            340                 345                 350

Arg Lys Lys Ala Lys Glu Leu Ala Leu Ala Tyr Asp Leu Tyr Val Asn
            355                 360                 365

Asn Arg His Gly Gln Leu Leu Gln Ala Lys Lys Leu Gly Lys Ile
            370                 375                 380

Lys Pro Arg Ser Lys Glu Asp Phe Tyr Lys Val Val Asn Lys Asn Leu
385                 390                 395                 400

Asp Asp Ser Arg Ala Ser Lys Glu Ile Lys Lys Ile Glu Leu Asp
            405                 410                 415

Ser Phe Met Pro Lys Gln Arg Thr Asn Ala Asn Gly Val Ile Pro Tyr
            420                 425                 430

Gln Leu Gln Gln Leu Glu Leu Asp Lys Ile Ile Glu Asn Gln Ser Lys
            435                 440                 445

Tyr Tyr Pro Phe Leu Lys Glu Ile Asn Pro Val Ser Ser His Leu Lys
            450                 455                 460

Glu Ala Pro Tyr Lys Leu Asp Glu Leu Ile Arg Phe Arg Val Pro Tyr
465                 470                 475                 480

Tyr Val Gly Pro Leu Ile Ser Pro Asn Glu Ser Thr Lys Asp Ile Gln
                485                 490                 495

Thr Lys Lys Asn Gln Asn Phe Ala Trp Met Ile Arg Lys Glu Glu Gly
```

```
                500            505              510
    Arg Ile Thr Pro Trp Asn Phe Asp Gln Lys Val Asp Arg Ile Glu Ser
                515            520              525

Ala Asn Lys Phe Ile Lys Arg Met Thr Thr Lys Asp Thr Tyr Leu Phe
        530            535            540

Gly Glu Asp Val Leu Pro Ala Asn Ser Leu Leu Tyr Gln Lys Phe Thr
    545            550            555                  560

Val Leu Asn Glu Leu Asn Asn Ile Arg Ile Asn Gly Lys Arg Ile Ser
                565            570            575

Val Asp Leu Lys Gln Glu Ile Tyr Glu Asn Leu Phe Lys Lys His Thr
                580            585            590

Thr Val Thr Val Lys Lys Leu Glu Asn Tyr Leu Lys Glu Asn His Asn
            595            600            605

Leu Val Lys Val Glu Ile Lys Gly Leu Ala Asp Glu Lys Lys Phe Asn
            610            615            620

Ser Gly Leu Thr Thr Tyr Asn Arg Phe Lys Asn Leu Asn Ile Phe Asp
    625            630            635            640

Asn Gln Ile Asp Asp Leu Lys Tyr Arg Asn Asp Phe Glu Lys Ile Ile
                645            650            655

Glu Trp Ser Thr Ile Phe Glu Asp Lys Ser Ile Tyr Lys Glu Lys Leu
                660            665            670

Arg Ser Ile Asp Trp Leu Asn Glu Lys Gln Ile Asn Ala Leu Ser Asn
                675            680            685

Ile Arg Leu Gln Gly Trp Gly Arg Leu Ser Lys Lys Leu Leu Ala Gln
                690            695            700

Leu His Asp His Asn Gly Gln Thr Ile Ile Glu Gln Leu Trp Asp Ser
    705            710            715            720

Gln Asn Asn Phe Met Gln Ile Val Thr Gln Ala Asp Phe Lys Asp Ala
                725            730            735

Ile Ala Lys Ala Asn Gln Asn Leu Leu Val Ala Thr Ser Val Glu Asp
                740            745            750

Ile Leu Asn Asn Ala Tyr Thr Ser Pro Ala Asn Lys Lys Ala Ile Arg
                755            760            765

Gln Val Ile Lys Val Val Asp Asp Ile Val Lys Ala Ala Ser Gly Lys
                770            775            780

Val Pro Lys Gln Ile Ala Ile Glu Phe Thr Arg Asp Ala Asp Glu Asn
    785            790            795            800

Pro Lys Arg Ser Gln Thr Arg Gly Ser Lys Leu Gln Lys Val Tyr Lys
                805            810            815

Asp Leu Ser Thr Glu Leu Ala Ser Lys Thr Ile Ala Glu Glu Leu Asn
                820            825            830

Glu Ala Ile Lys Asp Lys Lys Leu Val Gln Asp Lys Tyr Tyr Leu Tyr
                835            840            845

Phe Met Gln Leu Gly Arg Asp Ala Tyr Thr Gly Glu Pro Ile Asn Ile
                850            855            860

Asp Glu Ile Gln Lys Tyr Asp Ile Asp His Ile Leu Pro Gln Ser Phe
    865            870            875            880

Ile Lys Asp Asp Ala Leu Asp Asn Arg Val Leu Val Ser Arg Ala Val
                885            890            895

Asn Asn Gly Lys Ser Asp Asn Val Pro Val Lys Leu Phe Gly Asn Glu
                900            905            910

Met Ala Ala Asn Leu Gly Met Thr Ile Arg Lys Met Trp Glu Glu Trp
                915            920            925
```

-continued

```
Lys Asn Ile Gly Leu Ile Ser Lys Thr Lys Tyr Asn Asn Leu Leu Thr
    930                 935                 940

Asp Pro Asp His Ile Asn Lys Tyr Lys Ser Ala Gly Phe Ile Arg Arg
945                 950                 955                 960

Gln Leu Val Glu Thr Ser Gln Ile Ile Lys Leu Val Ser Thr Ile Leu
                965                 970                 975

Gln Ser Arg Tyr Pro Asn Thr Glu Ile Ile Thr Val Lys Ala Lys Tyr
            980                 985                 990

Asn His Tyr Leu Arg Glu Lys Phe Asp Leu Tyr Lys Ser Arg Glu Val
        995                 1000                1005

Asn Asp Tyr His His Ala Ile Asp Ala Tyr Leu Ser Ala Ile Cys
    1010                1015                1020

Gly Asn Leu Leu Tyr Gln Asn Tyr Pro Asn Leu Arg Pro Phe Phe
    1025                1030                1035

Val Tyr Gly Gln Tyr Lys Lys Phe Ser Ser Asp Pro Asp Lys Glu
    1040                1045                1050

Lys Ala Ile Phe Asn Lys Thr Arg Lys Phe Ser Phe Ile Ser Gln
    1055                1060                1065

Leu Leu Lys Asn Lys Ser Glu Asn Ser Lys Glu Ile Ala Lys Lys
    1070                1075                1080

Leu Lys Arg Ala Tyr Gln Phe Lys Tyr Met Leu Val Ser Arg Glu
    1085                1090                1095

Thr Glu Thr Arg Asp Gln Glu Met Phe Lys Met Thr Val Tyr Pro
    1100                1105                1110

Arg Phe Ser His Asp Thr Val Lys Ala Pro Arg Asn Leu Ile Pro
    1115                1120                1125

Lys Lys Met Gly Met Ser Pro Asp Ile Tyr Gly Gly Tyr Thr Asn
    1130                1135                1140

Asn Ser Asp Ala Tyr Met Val Ile Val Arg Ile Asp Lys Lys Lys
    1145                1150                1155

Gly Thr Glu Tyr Lys Ile Leu Gly Ile Pro Thr Arg Glu Leu Val
    1160                1165                1170

Asn Leu Lys Lys Ala Glu Lys Glu Asp His Tyr Lys Ser Tyr Leu
    1175                1180                1185

Lys Glu Ile Leu Thr Pro Arg Ile Leu Tyr Asn Lys Asn Gly Lys
    1190                1195                1200

Arg Asp Lys Lys Ile Thr Ser Phe Glu Ile Val Lys Ser Lys Ile
    1205                1210                1215

Pro Tyr Lys Gln Val Ile Gln Asp Gly Asp Lys Lys Phe Met Leu
    1220                1225                1230

Gly Ser Ser Thr Tyr Val Tyr Asn Ala Lys Gln Leu Thr Leu Ser
    1235                1240                1245

Thr Glu Ser Met Lys Ala Ile Thr Asn Asn Phe Asp Lys Asp Ser
    1250                1255                1260

Asp Glu Asn Asp Ala Leu Ile Lys Ala Tyr Asp Glu Ile Leu Asp
    1265                1270                1275

Lys Val Asp Lys Tyr Leu Pro Leu Phe Asp Ile Asn Lys Phe Arg
    1280                1285                1290

Glu Lys Leu His Ser Gly Arg Glu Lys Phe Ile Lys Leu Ser Leu
    1295                1300                1305

Glu Asp Lys Lys Asp Thr Ile Leu Lys Val Leu Glu Gly Leu His
    1310                1315                1320
```

```
Asp Asn Ala Val Met Thr Lys Ile Pro Thr Ile Gly Leu Ser Thr
1325                1330                1335

Pro Leu Gly Phe Met Gln Phe Pro Asn Gly Val Ile Leu Ser Glu
    1340                1345                1350

Asn Ala Lys Leu Ile Tyr Gln Ser Pro Thr Gly Leu Phe Lys Lys
    1355                1360                1365

Ser Val Lys Ile Ser Asp Leu
    1370            1375

<210> SEQ ID NO 34
<211> LENGTH: 1382
<212> TYPE: PRT
<213> ORGANISM: Lactobacillus mucosae LM1

<400> SEQUENCE: 34

Met Asp Ile Gly Thr Asn Ser Ile Gly Trp Thr Ala Ile Asp Asp His
1               5                   10                  15

Phe Ser Leu Leu Arg Val Lys Gly Lys Asn Ala Ile Gly Val Arg Thr
            20                  25                  30

Phe Lys Glu Gly Glu Thr Ala Ala Asp Arg Arg Gly Phe Arg Thr Ala
        35                  40                  45

Arg Arg Arg Leu Ser Arg Arg Arg Trp Arg Leu Gln Phe Leu Asp Glu
50                  55                  60

Phe Phe Ala Pro Tyr Leu Ala Glu Val Asp Pro Asn Phe Leu Ala Arg
65                  70                  75                  80

Leu Lys Gln Ser Asp Ile Ser Ala Lys Asp Pro Ala Lys Asn Gln Glu
                85                  90                  95

Tyr Met Gly Lys Leu Leu Phe Pro Asp Gln Glu Ala Ala Ser Asp Gly
            100                 105                 110

Asn Gly Tyr Pro Thr Leu Ile Gln Met Arg Lys Ala Met Pro Ala Glu
        115                 120                 125

Lys Ala Ala Asp Phe Pro Val Phe Asn Ile Tyr Gln Leu Arg Tyr Ala
130                 135                 140

Leu Met Asn Glu Lys Arg Lys Phe Asp Leu Arg Glu Ile Tyr Leu Ala
145                 150                 155                 160

Val His His Ile Val Lys Tyr Arg Gly Asn Phe Leu Asn Asn Thr Ser
                165                 170                 175

Val Asp Lys Phe Lys Ala Asp Gln Ile Asp Phe Asn Lys Ser Phe Glu
            180                 185                 190

Thr Leu Asn Asp Leu Phe Arg Gln Val Gln Pro Ile Ala Pro Phe Gln
        195                 200                 205

Ile Asp Leu Thr Lys Val Asp Glu Leu Gly Lys Leu Leu Leu Asp Thr
210                 215                 220

Lys Gln Lys Lys Leu Asp Arg Gln Lys Ala Val Ala Lys Leu Leu Pro
225                 230                 235                 240

Leu Ile Glu Asp Gly Thr Asp Lys Glu Ile Val Lys Ala His Gln Gln
                245                 250                 255

Thr Ala Arg Glu Ile Ser Lys Leu Ile Leu Gly Tyr Lys Ala Lys Val
            260                 265                 270

Gly Leu Ile Leu Gln Asn Asn Leu Asp Gln Thr Leu Asp Met Ser Thr
        275                 280                 285

Glu Asn Ser Asp Asp Gln Leu Met Gln Ile Ala Glu Glu Leu Asp Asp
290                 295                 300

Tyr Gln Met Glu Leu Ile Asn Gln Leu Ser Leu Leu Tyr Ser Gln Ile
305                 310                 315                 320
```

```
Met Leu Asn Glu Ile Val Pro Asn Gly Glu Thr Val Ser Ala Ser Met
                325                 330                 335

Leu Asn Arg Tyr Tyr Lys His Arg Cys Gln Leu Lys Glu Leu Lys Asp
            340                 345                 350

Tyr Gly Ala Ala Gln Asp Lys Lys Thr Arg Glu Gln Leu Asp His Leu
        355                 360                 365

Tyr Ala Glu Tyr Ile Gly Gln Ile Pro Lys Asp Ser Lys Phe Asp Phe
    370                 375                 380

Thr Lys Asp Leu Lys Lys Leu Met Asp Lys Ser Asp Leu Gly Gln Lys
385                 390                 395                 400

Ile Lys Asp Glu Ile Glu Ala Gly Asp Tyr Leu Pro Lys Gln Arg Thr
                405                 410                 415

Ser Ala Asn Gly Val Ile Pro His Gln Met His Gln Gln Leu Asp
            420                 425                 430

Gln Ile Ile Glu Asn Gln Lys Glu Tyr Tyr Pro Trp Leu Ala Glu Pro
        435                 440                 445

Asn Pro Val Glu Lys Asn Ile Lys Asn Ala Lys Tyr Lys Leu Asp Gln
    450                 455                 460

Leu Val Ser Phe Arg Val Pro Tyr Tyr Val Gly Pro Met Ile Thr Leu
465                 470                 475                 480

Ala Asp Gln Gln Lys Thr Ser Lys Ala Ser Phe Ala Trp Ala Val Arg
                485                 490                 495

Lys Lys Ala Gly Lys Ile Thr Pro Trp Asn Phe Tyr Asp Met Ile Asp
            500                 505                 510

Arg Glu Lys Ser Ala Asn Asn Phe Ile Lys Arg Met Thr Asn Lys Asp
        515                 520                 525

Thr Tyr Leu Leu Ser Glu Asp Val Leu Pro Ala Ser Ser Leu Leu Tyr
    530                 535                 540

Gln Lys Phe Thr Val Leu Asn Glu Leu Asn Asn Ile Arg Val Asn Gly
545                 550                 555                 560

Arg Lys Leu Gln Pro Ala Leu Lys Gln Ala Ile Tyr Thr Asp Leu Phe
                565                 570                 575

Gln Lys Arg Lys Thr Val Asn Leu Lys Thr Leu Thr Asn Phe Leu Ala
            580                 585                 590

Ile His Glu Pro Thr Leu Thr Lys Pro Lys Ile Glu Gly Leu Ser Asn
        595                 600                 605

Gly Arg Ser Phe Asn Ser Ser Leu Gly Thr Tyr Ile Asp Met Ser Lys
    610                 615                 620

Ile Leu Gly Asp Ser Leu Asp Asp Leu Asn Tyr Arg Asp Asp Ile Glu
625                 630                 635                 640

Lys Ile Ile Glu Trp Ser Thr Val Phe Glu Asp Ser Glu Ile Tyr Gly
                645                 650                 655

Val Lys Leu Gln Glu Ile Gln Trp Leu Thr Asn Glu Gln Arg Glu Lys
            660                 665                 670

Leu Val Arg Lys Arg Tyr Gln Gly Trp Gly Arg Leu Ser Lys Lys Leu
        675                 680                 685

Leu Thr Gly Ile Thr Asp Glu Asn Gly Gln Arg Ile Ile Asp Leu Met
    690                 695                 700

Trp Asp Thr Ser Lys Asn Phe Met Gln Ile Val His Gln Pro Val Phe
705                 710                 715                 720

Glu Glu Gln Ile Ala Glu Leu Asn Gln Gln Leu Leu Gln Asp Ala Asp
                725                 730                 735
```

-continued

Lys Ala Pro Leu Glu Val Val Asp Asp Ile Leu Ala Asp Ala Tyr Thr
                740                 745                 750

Ser Pro Gln Asn Lys Lys Ala Ile Arg Gln Val Val Lys Val Val Ala
            755                 760                 765

Asp Val Val Lys Ala Val Gly Asn Ala Pro Ala Ser Ile Ser Ile Glu
        770                 775                 780

Phe Ala Arg Asn Glu Asp Arg Asn Lys Glu Leu Lys Asn Ser Arg Arg
785                 790                 795                 800

His Ser Ile Glu Lys Leu Tyr His Glu Thr Ala Glu Lys Leu Val Lys
                805                 810                 815

Gln Thr Asn Leu Leu Glu Glu Leu Gly Asn Val Lys Asp Leu Asn Asp
            820                 825                 830

Arg Tyr Tyr Leu Tyr Phe Thr Gln Ala Gly Arg Asp Met Tyr Asp Gly
        835                 840                 845

Thr Pro Ile Asn Ile Asp Glu Ile Ser Thr His Tyr Glu Ile Asp His
    850                 855                 860

Ile Leu Pro Gln Ser Phe Leu Lys Asp Asn Ser Leu Asp Asn Arg Val
865                 870                 875                 880

Leu Val Lys Lys Ser Glu Asn Ala Ala Lys Ser Asp Arg Val Pro Ala
                885                 890                 895

Lys Leu Tyr Gly Ala Lys Met Arg Ala Phe Trp Lys Gln Leu Lys Glu
            900                 905                 910

Ser Gln Leu Ile Ser Asn Arg Lys Tyr Leu Asn Leu Thr Thr Asp Pro
        915                 920                 925

Glu Gln Val Asp Lys Tyr Gln Met Gln Gly Phe Val His Arg Gln Leu
    930                 935                 940

Val Glu Thr Arg Gln Ile Ile Lys Leu Ala Ala Asn Ile Phe Gly Ser
945                 950                 955                 960

Leu Tyr Pro Asp Ser Ala Val Ile Glu Thr Arg Ala Glu Leu Thr Lys
                965                 970                 975

Gln Leu Arg Glu Lys Phe Ser Leu Tyr Lys Val Arg Asp Val Asn Asp
            980                 985                 990

Tyr His His Ala Val Asp Ala Tyr Leu Thr Ala Phe Ala Gly His Tyr
        995                 1000                1005

Leu Tyr Gln Arg Tyr Pro Lys Leu Arg Pro Met Phe Val Tyr Gly
    1010                1015                1020

Asp Tyr Ala Lys Ile Tyr Ala Asp Asp Leu Lys Arg Leu Arg Ser
    1025                1030                1035

Val Asn Leu Phe His Asp Leu Glu Lys Asp Gln Tyr Asn Ser Gly
    1040                1045                1050

Thr Ala Val Asn Pro Glu Thr Lys Glu Lys Ile Val Asp Val Asp
    1055                1060                1065

Trp Leu Ser Asp Tyr Val Ser Lys Ile Gln His Phe Lys Tyr Met
    1070                1075                1080

Leu Ile Ser Lys Ala Val Tyr Thr Gln His Gly Gln Leu Tyr Gly
    1085                1090                1095

Ala Thr Ile Leu Pro Val Ala Gln Val Asp Lys Ile Ser Ala Pro
    1100                1105                1110

Ile Gly Ile Lys Asp Asp Lys Pro Val Asp Ile Tyr Gly Ala Tyr
    1115                1120                1125

Thr Asn Glu Val Ala Ala Tyr Met Ala Ile Val Arg Val Asn Gly
    1130                1135                1140

Lys Lys Pro Lys Tyr Lys Val Val Ser Val Pro Val Arg Met Leu

```
              1145                1150                1155

Gln Arg Leu Lys Met Ala Glu Gln Lys Gly His Asp Gln Tyr Met
        1160                1165                1170

Gln Thr Leu His Asp Val Leu Leu Arg Asn Phe Thr Ser Leu Lys
        1175                1180                1185

Lys Asn Arg Lys Thr Gly Leu Lys Glu Ala Val Val Lys Asp Phe
        1190                1195                1200

Asp Val Leu Val Pro Cys Val Arg Tyr Asn Gln Leu Val Ile Asp
        1205                1210                1215

Gly Asp Thr Lys Phe Thr Leu Gly Ser Ala Thr Tyr Gln His Asn
        1220                1225                1230

Ala Lys Gln Leu Val Leu Cys Asn His Ser Leu Glu Thr Leu Ala
        1235                1240                1245

Asn Asn Phe Glu Tyr Val Arg Lys His Pro Asp Glu Ala Asp Glu
        1250                1255                1260

Arg Met Ile Met Leu Tyr Asp Asp Ile Leu Asp Gln Val Asn His
        1265                1270                1275

Tyr Phe Thr Leu Tyr Asp Lys Asn Lys Phe Arg Glu Lys Leu Asn
        1280                1285                1290

Ala Gly Arg Asp Lys Tyr Leu Lys Leu Pro Thr Phe Ser Gln Phe
        1295                1300                1305

Glu Asn Asn Lys Lys Thr Ala Ile Gly Lys Ser Glu Ala Ile Ile
        1310                1315                1320

Asn Ile Leu Arg Gly Leu His Ala Asn Ala Ala Ile Thr Asn Leu
        1325                1330                1335

Lys Cys Leu Gly Val Ser Thr Pro Phe Gly Gln Leu Gln Ser Pro
        1340                1345                1350

Ser Gly Ile Glu Leu Ser Glu Asn Ala Lys Leu Val Tyr Gln Ser
        1355                1360                1365

Pro Thr Gly Leu Phe Ser Arg Glu Val Leu Leu Lys Asp Leu
        1370                1375                1380

<210> SEQ ID NO 35
<211> LENGTH: 1348
<212> TYPE: PRT
<213> ORGANISM: Lactobacillus otakiensis JCM 15040

<400> SEQUENCE: 35

Met Gly Glu Asp Gly Lys Pro Leu Arg Val Lys Gly Lys Thr Ala Ile
1               5                   10                  15

Gly Ala Arg Leu Phe Gln Glu Gly Asn Pro Ala Ala Asp Arg Arg Met
            20                  25                  30

Phe Arg Thr Thr Arg Arg Arg Leu Asn Arg Arg Lys Trp Arg Leu Lys
        35                  40                  45

Leu Leu Asp Glu Ile Phe Asp Pro Tyr Ile Thr Pro Val Asp Ser Thr
    50                  55                  60

Phe Phe Ala Arg Leu Lys Gln Ser Asn Leu Ser Pro Lys Asp Ser Arg
65                  70                  75                  80

Lys Glu Phe Lys Gly Ser Met Leu Phe Pro Asp Leu Thr Asp Lys Gln
                85                  90                  95

Tyr His Leu Asp Tyr Pro Thr Ile Tyr His Leu Arg His Ala Leu Met
            100                 105                 110

Thr Gln Asp Lys Gln Phe Asp Ile Arg Met Val Tyr Leu Ala Ile His
        115                 120                 125
```

His Ile Val Lys Tyr Arg Gly Asn Phe Leu Asn Ser Thr Pro Val Asp
130                 135                 140

Ser Phe Lys Ala Ser Lys Val Asn Phe Asp Asp Gln Phe Lys Lys Leu
145                 150                 155                 160

Asn Glu Leu Tyr Thr Ala Ile Asn Pro Glu Glu Ser Phe Gln Ile Asn
                165                 170                 175

Leu Ala Asn Ser Glu Lys Ile Gly Gln Gln Phe Leu Asp Pro Ser Ile
            180                 185                 190

Arg Lys Phe Asp Lys Lys Gln Ile Pro Lys Ile Val Pro Val Thr
        195                 200                 205

Met Asp Asp Lys Ala Val Asp Lys Leu Asn Gly Lys Ile Ala Ser Glu
210                 215                 220

Ile Ile Asn Ala Ile Leu Gly Tyr Lys Ser Lys Leu Asp Val Ala Val
225                 230                 235                 240

Gln Cys Asp Pro Glu Asp Ser Asn Pro Trp Ala Val Lys Phe Asp Asp
                245                 250                 255

Glu Asp Ile Asp Ala Lys Leu Gln Lys Ile Leu Pro Glu Met Asp Glu
            260                 265                 270

Asn Gln Gln Ser Ile Ile Gly Ile Ile Gln Asp Leu Tyr Ser Gln Val
        275                 280                 285

Thr Leu Asn Gln Ile Val Pro Asn Gly Met Ser Leu Ser Glu Ser Met
290                 295                 300

Ile Lys Lys Tyr Asn Asp His His Asp His Leu Lys Leu Tyr Lys Lys
305                 310                 315                 320

Leu Ile Gly Gln Ile Ser Asp Ser Lys Lys Thr Ala Leu Lys Lys
                325                 330                 335

Ala Tyr Asp Gln Tyr Val Gly Asn Asp Gly Lys Val Ile Glu Gln Asp
            340                 345                 350

Asp Phe Tyr Ser Ser Val Lys Lys Asn Leu Asp Asp Ser Glu Leu Ser
        355                 360                 365

Lys Gln Ile Met Asp Leu Ile Asp Ala Asp Lys Phe Met Pro Lys Gln
    370                 375                 380

Arg Thr Ser Gln Asn Gly Val Ile Pro His Gln Leu His Gln Arg Glu
385                 390                 395                 400

Leu Asp Glu Ile Ile Glu His Gln Ser Lys Tyr Tyr Pro Trp Leu Ala
                405                 410                 415

Glu Ser Asn Pro Asn Lys His Asp Leu His Leu Ala Lys Tyr Lys Ile
            420                 425                 430

Glu Glu Leu Val Ala Phe Arg Ile Pro Tyr Tyr Val Gly Pro Met Ile
        435                 440                 445

Thr Pro Glu Asp Gln Lys Lys Ser Gly Ala Ala Val Phe Ser Trp Met
    450                 455                 460

Lys Arg Lys Glu Pro Gly Gln Ile Thr Pro Trp Asn Phe Asp Glu Lys
465                 470                 475                 480

Val Asp Arg Met Glu Ser Ala Asn Lys Phe Ile Lys Arg Met Thr Thr
                485                 490                 495

Lys Asp Thr Tyr Leu Ile Gly Glu Asp Val Leu Pro Asp Glu Ser Leu
            500                 505                 510

Leu Tyr Glu Lys Phe Lys Val Leu Asn Glu Leu Asn Met Val Arg Val
        515                 520                 525

Asn Gly Asp Ser Leu Lys Val Ala Asp Lys Gln Ala Ile Tyr Gln Asp
    530                 535                 540

Leu Phe Glu Asn Tyr Lys His Ile Ser Val Lys Lys Leu Gln Asn Tyr

```
545                 550                 555                 560
Ile Lys Gly Lys Thr Gly Leu Pro Asn Asn Pro Glu Ile Ser Gly Leu
                565                 570                 575

Ser Asp Pro Asp Gln Phe Asn Asn Ser Leu Gly Thr Tyr Asn Asp Phe
                580                 585                 590

Lys Lys Leu Phe Gly Asp Lys Val Asp Asp Pro Asp Leu Gln Asn Asp
                595                 600                 605

Phe Glu Lys Ile Val Glu Trp Ser Thr Val Phe Glu Asp Lys Lys Ile
                610                 615                 620

Leu Arg Ala Lys Leu Asn Glu Ile Thr Trp Leu Thr Asp Lys Gln Lys
625                 630                 635                 640

Asp Asp Leu Glu Ser Ser Arg Tyr Gln Gly Trp Gly Arg Leu Ser Lys
                645                 650                 655

Lys Leu Leu Thr Gly Ile Val Asn Asp Gln Gly Glu Arg Ile Ile Asp
                660                 665                 670

Glu Leu Trp Asn Thr Asn Lys Asn Phe Met Gln Ile Gln Ser Asp Asp
                675                 680                 685

Asp Phe Ala Lys Arg Ile His Glu Ala Asn Ala Asp Gln Met Lys Ser
                690                 695                 700

Thr Asn Met Glu Asp Val Leu Ala Asp Ala Tyr Thr Ser Pro Gln Asn
705                 710                 715                 720

Lys Lys Ala Ile Arg Gln Val Val Lys Val Asp Asp Ile Gln Lys
                725                 730                 735

Ala Met Gly Gly Val Ala Pro Lys Phe Ile Ser Ile Glu Phe Thr Arg
                740                 745                 750

Ser Glu Asp Arg Asn Pro Arg Arg Thr Ile Ser Arg Gln Arg Gln Leu
                755                 760                 765

Glu Asn Thr Leu Lys Asp Thr Ala Lys Ser Leu Val Lys Ser Met Asn
                770                 775                 780

Pro Asn Ile Leu Ser Glu Leu Asp Asn Ala Ser Arg Ser Lys Lys Gly
785                 790                 795                 800

Leu Thr Asp Arg Leu Tyr Leu Tyr Phe Thr Gln Leu Gly Lys Asp Met
                805                 810                 815

Tyr Thr Gly Glu Pro Ile Asn Ile Asp Glu Ile Ser Asn Tyr Asp Ile
                820                 825                 830

Asp His Ile Leu Pro Gln Ala Phe Ile Lys Asp Asp Ser Leu Ser Asn
                835                 840                 845

Arg Val Leu Val Ser Lys Ala Val Asn Gly Lys Ser Ala Asn Val
850                 855                 860

Pro Leu Lys Leu Phe Gly Ala Lys Met Gly His Phe Trp Lys Gln Leu
865                 870                 875                 880

Ala Glu Ala Gly Leu Ile Asn Lys His Lys Leu Lys Asn Leu Gln Thr
                885                 890                 895

Asn Pro Asp Thr Ile Ser Lys Phe Ala Met His Gly Phe Ile Arg Arg
                900                 905                 910

Gln Leu Val Glu Thr Ser Gln Val Ile Lys Leu Val Ala Asn Ile Leu
                915                 920                 925

Gly Asp Lys Tyr Arg Asn Asp Thr Lys Ile Ile Glu Ile Thr Ala
                930                 935                 940

Arg Met Asn His Gln Met Arg Asp Glu Phe Gly Phe Ile Lys Asn Arg
945                 950                 955                 960

Glu Ile Asn Asp Tyr His His Ala Phe Asp Ala Tyr Leu Thr Ala Phe
                965                 970                 975
```

Leu Gly Arg Tyr Leu Tyr His Arg Tyr Ile Lys Leu Arg Pro Tyr Phe
            980                 985                 990

Val Tyr Gly Asp Phe Lys Lys Phe Arg Glu Asp Lys Val Thr Met Arg
        995                 1000                1005

Asn Phe Asn Phe Leu His Asp Leu Thr Asp Asp Thr Gln Ala Arg
    1010                1015                1020

Ile Ala Asp Thr Glu Thr Gly Glu Val Ile Trp Asp Arg Glu Thr
    1025                1030                1035

Ser Ile Lys Gln Leu Arg Asp Val Tyr His Tyr Lys Phe Met Leu
    1040                1045                1050

Ile Ser Gln Glu Val Tyr Thr Leu Arg Gly Ala Met Phe Asn Gln
    1055                1060                1065

Thr Ile Tyr Pro Ala Ser Gln Ala Gly Arg Lys Lys Leu Ile Pro
    1070                1075                1080

Met Lys Ala Asp Lys Pro Val Asp Val Tyr Gly Gly Tyr Ser Gly
    1085                1090                1095

Ser Thr Asp Ala Tyr Met Ala Ile Val Arg Ile His Asp Lys Lys
    1100                1105                1110

Gly Asp Lys Tyr Lys Val Val Gly Val Pro Met Arg Ala Leu Asn
    1115                1120                1125

Arg Leu Asn Thr Ala Lys Asn Val Ser Asp Ala Lys Tyr Asp Gln
    1130                1135                1140

Glu Leu Lys Glu Val Leu Thr Pro Gln Phe Thr Lys Ser Lys Lys
    1145                1150                1155

Asn Arg Lys Thr Gly Glu Ile Thr Gln Thr Val Glu Asp Phe Glu
    1160                1165                1170

Val Val Leu Gly Lys Val Met Tyr Arg Gln Leu Val Ile Asp Gly
    1175                1180                1185

Asp Lys Lys Phe Met Leu Gly Ser Ser Thr Tyr Gln Tyr Asn Ala
    1190                1195                1200

Lys Gln Leu Val Leu Ser Asp Glu Ser Ile Lys Thr Leu Ala Ser
    1205                1210                1215

Glu Gly Lys Leu Asn Glu Ala Gln Glu Ser Ala Ala Tyr Asp Lys
    1220                1225                1230

Val Tyr Asp Glu Ile Leu Asp Lys Val Asn Lys Tyr Phe Ala Leu
    1235                1240                1245

Tyr Asp Thr Asn Lys Phe Arg Gln Lys Leu Ser Leu Gly Lys Asp
    1250                1255                1260

Lys Phe Val Gly Leu Pro Asn His Asn Val Phe Asp Gly Ser Lys
    1265                1270                1275

Lys Ile Ser Ser Gly Lys Arg Glu Ile Leu Asn Glu Ile Leu Asn
    1280                1285                1290

Gly Leu His Ala Asn Ala Thr Leu Gly Thr Leu Ser Asp Ile Gly
    1295                1300                1305

Phe Ser Thr Pro Phe Gly Lys Met Gln Gln Pro Arg Gly Ile Gly
    1310                1315                1320

Leu Ser Ser Asn Thr Ser Ile Glu Tyr Glu Ser Phe Thr Gly Leu
    1325                1330                1335

Phe Lys Arg Thr Ile Phe Leu Lys Asp Leu
    1340                1345

<210> SEQ ID NO 36
<211> LENGTH: 1362

```
<212> TYPE: PRT
<213> ORGANISM: Lactobacillus paracasei subsp. Paracasei 8700:2

<400> SEQUENCE: 36
```

| | | | | | | | | | | | | | | |
|---|---|---|---|---|---|---|---|---|---|---|---|---|---|---|
| Met | Thr | Lys | Leu | Gly | Lys | Pro | Tyr | Gly | Ile | Gly | Val | Asp | Ile | Gly | Ser |
| 1 | | | | 5 | | | | | 10 | | | | | 15 | |

| Asn | Ser | Ile | Gly | Phe | Ala | Ala | Val | Asp | Glu | Asn | Ser | His | Leu | Ile | Arg |
| | | | 20 | | | | | 25 | | | | | 30 | | |

| Leu | Lys | Gly | Lys | Thr | Val | Ile | Gly | Ala | Arg | Leu | Phe | Glu | Glu | Gly | Lys |
| | | | 35 | | | | | 40 | | | | | 45 | | |

| Ala | Ala | Ala | Lys | Arg | Arg | Ala | Gly | Arg | Thr | Thr | Arg | Arg | Arg | Leu | Ser |
| | 50 | | | | | 55 | | | | | 60 | | | | |

| Arg | Asn | Arg | Trp | Arg | Leu | Ser | Phe | Leu | Arg | Asp | Phe | Phe | Glu | Ser | His |
| 65 | | | | | 70 | | | | | 75 | | | | | 80 |

| Ile | Thr | Pro | Thr | Asp | Pro | Asn | Phe | Phe | Met | Arg | Gln | Lys | Tyr | Ser | Glu |
| | | | | 85 | | | | | 90 | | | | | 95 | |

| Ile | Ser | Pro | Lys | Asp | Lys | Ala | Arg | Tyr | Lys | Tyr | Glu | Lys | Arg | Leu | Phe |
| | | | 100 | | | | | 105 | | | | | 110 | | |

| Asn | Asp | Arg | Thr | Asp | Ala | Glu | Phe | Tyr | Gln | Gln | Tyr | Ser | Thr | Met | Tyr |
| | | | 115 | | | | | 120 | | | | | 125 | | |

| His | Leu | Arg | Asn | Arg | Leu | Met | Thr | Asp | Pro | Ser | Arg | Ala | Asp | Val | Arg |
| | 130 | | | | | 135 | | | | | 140 | | | | |

| Glu | Ile | Tyr | Phe | Ala | Ile | His | His | Ile | Leu | Lys | Ser | Arg | Gly | His | Phe |
| 145 | | | | | 150 | | | | | 155 | | | | | 160 |

| Leu | Thr | Pro | Gly | Asp | Ala | Lys | Asp | Phe | Asn | Thr | Asn | Asp | Val | Ala | Leu |
| | | | | 165 | | | | | 170 | | | | | 175 | |

| Asp | Glu | Ile | Phe | Pro | Ala | Leu | Gln | Asp | Ala | Tyr | Ala | Gln | Val | Tyr | Pro |
| | | | 180 | | | | | 185 | | | | | 190 | | |

| Asp | Leu | Gly | Ile | Thr | Phe | Asp | Glu | Asp | Lys | Ala | Asn | Glu | Phe | Lys | Thr |
| | | | 195 | | | | | 200 | | | | | 205 | | |

| Ile | Leu | Leu | Asn | Glu | Ile | Ala | Thr | Ser | Ile | Asp | Thr | Gln | Arg | Ala | Leu |
| | 210 | | | | | 215 | | | | | 220 | | | | |

| Val | Lys | Leu | Leu | Leu | Ala | Glu | Glu | Asp | Lys | Asp | Ile | Leu | Lys | Gln |
| 225 | | | | | 230 | | | | | 235 | | | | | 240 |

| Gln | Lys | Gln | Val | Leu | Thr | Glu | Phe | Ala | Lys | Ala | Val | Val | Gly | Leu | Lys |
| | | | | 245 | | | | | 250 | | | | | 255 | |

| Thr | Lys | Leu | Asn | Leu | Ala | Leu | Gly | Thr | Glu | Val | Asp | Ser | Ser | Glu | Ala |
| | | | 260 | | | | | 265 | | | | | 270 | | |

| Thr | Ala | Trp | Asn | Phe | Ser | Leu | Gly | Gln | Leu | Asp | Asp | Lys | Trp | Ala | Gly |
| | | | 275 | | | | | 280 | | | | | 285 | | |

| Ile | Glu | Ser | Ala | Met | Thr | Asp | Glu | Gly | Thr | Glu | Ile | Leu | Asp | Gln | Ile |
| | 290 | | | | | 295 | | | | | 300 | | | | |

| Arg | Asp | Leu | Tyr | Arg | Ala | Arg | Leu | Leu | Asn | Gly | Ile | Val | Pro | Thr | Gly |
| 305 | | | | | 310 | | | | | 315 | | | | | 320 |

| Lys | Thr | Leu | Ser | Gln | Ala | Lys | Val | Asp | Asp | Tyr | Thr | Gln | His | His | Glu |
| | | | | 325 | | | | | 330 | | | | | 335 | |

| Asp | Leu | Gln | Leu | Phe | Lys | Ala | Tyr | Leu | Lys | Gln | Leu | Glu | Asp | Asp | Gly |
| | | | 340 | | | | | 345 | | | | | 350 | | |

| Thr | Ala | Lys | Ala | Ile | Arg | Gln | Leu | Tyr | Asp | Arg | Tyr | Ile | Asp | Gly | Asp |
| | | | 355 | | | | | 360 | | | | | 365 | | |

| Asp | Ala | Ala | Pro | Phe | Leu | Arg | Glu | Asn | Phe | Val | Lys | Ala | Leu | Thr | Lys |
| | 370 | | | | | 375 | | | | | 380 | | | | |

| Asp | Val | Thr | Ala | His | Pro | Asn | Thr | Lys | Ser | Pro | Glu | Leu | Leu | Glu | Arg |
| 385 | | | | | 390 | | | | | 395 | | | | | 400 |

```
Leu Ala Gln Pro Asp Phe Met Leu Lys Gln Arg Asn Lys Ala Asn Gly
                405                 410                 415

Ala Ile Pro Val Gln Met Gln Arg Glu Leu Asp Gln Ile Ile Lys
        420                 425                 430

Asn Gln Ala Val Tyr Tyr Asp Trp Leu Ala Ala Pro Asn Pro Val Glu
            435                 440                 445

Lys His Arg Lys Ser Met Pro Tyr Gln Leu Asp Glu Leu Leu Asn Phe
    450                 455                 460

Arg Ile Pro Tyr Tyr Val Gly Pro Leu Val Thr Ala Lys Glu Gln Lys
465                 470                 475                 480

Ala Ala Gln Gly Gly Val Phe Ala Trp Met Val Arg Lys Asp Pro Glu
                485                 490                 495

Gly Asn Ile Thr Pro Tyr Asn Phe Asp Glu Lys Val Asp Arg Glu Ala
                500                 505                 510

Ser Ala Asn Thr Phe Ile Gln Arg Met Lys Thr Thr Asp Thr Tyr Leu
            515                 520                 525

Ile Gly Glu Asp Val Leu Pro Lys Gln Ser Leu Leu Tyr Gln Arg Tyr
            530                 535                 540

Glu Val Leu Asn Glu Leu Asn Asn Val Arg Val Asn Asn Glu Lys Leu
545                 550                 555                 560

Ser Ile Glu Gln Lys Gln Gln Val Ile Arg Glu Leu Phe Glu Arg His
                565                 570                 575

Asn Ser Val Thr Ile Lys Gln Phe Ala Glu Asn Leu Arg Ala His Gly
                580                 585                 590

Asp Tyr Ala His Ile Pro Glu Ile Arg Gly Leu Ala Asp Glu Lys Arg
            595                 600                 605

Phe Leu Ser Ser Leu Ser Thr Tyr Arg Gln Leu Lys Ser Leu Leu Pro
            610                 615                 620

Glu Ala Ile Asp Asp Pro Ala Lys Gln Ala Asp Ile Glu Asn Ile Ile
625                 630                 635                 640

Ala Trp Ser Thr Val Phe Glu Asp Ala Ala Ile Phe Lys Thr Lys Leu
                645                 650                 655

Lys Glu Ile Ser Trp Leu Gly Ser Glu Ala Ile Thr Lys Leu Ser Asn
                660                 665                 670

Ile Arg Tyr Arg Gly Trp Gly Gln Phe Ser Arg Lys Phe Leu Asn Gly
            675                 680                 685

Leu Thr Leu Gly Asn Gly His Thr Ile Ile Gln Glu Leu Leu Leu Ser
    690                 695                 700

Thr Asn Asn Leu Met Gln Ile Leu Thr Asp Glu Thr Leu Gln Lys Lys
705                 710                 715                 720

Met Thr Glu Leu Asn Ala Asp Lys Leu Lys Thr Ala Asn Ile Asn Asp
                725                 730                 735

Ala Ile Asp Asn Ala Tyr Thr Ser Pro Ser Asn Lys Lys Ala Leu Arg
            740                 745                 750

Gln Val Leu Arg Val Val Asp Asp Ile Lys Arg Ala Ala Asp Gly Gln
                755                 760                 765

Asp Pro Ser Trp Leu Tyr Val Glu Thr Ala Asp Gly Gly Thr Pro
    770                 775                 780

Gly Lys Arg Thr Arg Ala Arg Gln His Gln Leu Gln Glu Ile Tyr Ala
785                 790                 795                 800

Asn Ala Ala His Glu Leu Ile Asp Thr Ala Val Arg Gly Glu Leu Glu
                805                 810                 815
```

```
Asp Lys Ile Ser Asp Lys Ala Asp Phe Asn Asp Arg Leu Val Leu Tyr
            820                 825                 830

Phe Met Gln Gly Gly Arg Asp Ile Tyr Thr Gly Ala Pro Leu Asn Ile
        835                 840                 845

Asp Gln Leu Ser Ser Tyr Asp Ile Asp His Ile Leu Pro Gln Ser Leu
        850                 855                 860

Ile Lys Asp Asn Ser Leu Asp Asn Arg Val Leu Val His Ala Ile Ile
865                 870                 875                 880

Asn Arg Glu Lys Asn Ala Thr Phe Ala Ser Thr Ile Tyr Ala Gln Lys
                885                 890                 895

Met Asn Ala Thr Trp Arg Gln Trp His Glu Ala Gly Leu Ile Ser Gly
            900                 905                 910

Arg Lys Leu Arg Asn Leu Gln Met Arg Pro Asp Gln Ile Asp Lys Tyr
        915                 920                 925

Ala Ser Gly Phe Val Ala Arg Gln Leu Val Glu Thr Arg Gln Ile Ile
        930                 935                 940

Lys Leu Thr Glu Gln Ile Val Ala Ala Gln Tyr Pro Asp Thr Lys Ile
945                 950                 955                 960

Ile Ala Val Lys Ala Gly Leu Ser His Gln Leu Arg Glu Glu Leu Glu
                965                 970                 975

Phe Pro Lys Asn Arg Asp Val Asn His Tyr His His Ala Phe Asp Ala
            980                 985                 990

Phe Leu Ala Ala Arg Ile Gly Thr Tyr Leu Leu Lys Arg Phe Pro Asn
        995                 1000                1005

Leu Gln Ala Phe Phe Thr Tyr Gly Lys Phe Thr Lys Ala Asp Val
    1010                1015                1020

Lys Lys Leu Arg Gly Phe Asn Phe Ile Arg Asp Ile Thr His Ala
    1025                1030                1035

Glu Asp Lys Ile Val Ala Lys Asp Thr Gly Glu Val Val Trp Asp
    1040                1045                1050

Lys Gln Arg Asp Val Asp Glu Leu Asp Arg Ile Tyr Asn Phe Lys
    1055                1060                1065

Arg Met Leu Ile Thr His Glu Val Arg Phe Glu Thr Ala Asp Leu
    1070                1075                1080

Phe Lys Gln Thr Val Tyr Gly Ala Arg Asp Ser Lys Glu Ala Gly
    1085                1090                1095

Gly Ser Lys Gln Leu Ile Pro Lys Lys Gly Tyr Pro Val Asp
    1100                1105                1110

Ile Tyr Gly Gly Tyr Phe Arg Glu Asn Thr Ala Tyr Leu Ala Val
    1115                1120                1125

Val Lys Val Thr Lys Lys Thr Glu Thr Ile Phe Lys Val Val Lys
    1130                1135                1140

Ile Ala Thr Ser Gln Val Ala Ala Leu Asn Lys Ala Arg Ser Arg
    1145                1150                1155

Ser Thr Ala Glu Glu Leu Ser Val Leu Thr Glu Leu Leu Lys Pro
    1160                1165                1170

Lys Phe Ser Lys Val Gly Lys Asn Gly Lys Ile Thr Asp Thr Pro
    1175                1180                1185

Phe Glu Val Val Leu Pro Arg Val Pro Arg Glu Gln Leu Phe Tyr
    1190                1195                1200

Asn Ala Lys Tyr Gly Phe Phe Met Val Asn Ser Asp Thr Met Phe
    1205                1210                1215

His Asn Phe Gln Glu Ile Trp Val Ser Arg Ser Asp Gln Lys Ile
```

```
                      1220                1225                1230
Leu Gln Gln Ile Arg Lys Ala Lys Ile Asp Tyr Pro Asn Val Asp
            1235                1240                1245

Gln Asp Leu Asp Asn Leu Phe His Asn Leu Ala Asp Gln Ile Val
            1250                1255                1260

Lys Tyr Phe Asp Leu Tyr Ser Ile Ala Gly Phe Lys Glu Lys Ile
            1265                1270                1275

Ser Gln Ser Gln Asn Thr Phe Asn Asp Leu Ala Val Asp Asp Thr
            1280                1285                1290

Asp Gln Ser Val Gly Lys Ile Thr Val Ile Asn Glu Leu Leu Lys
            1295                1300                1305

Gly Ala Gln Ala Asn Gly Met Thr Gly Ser Leu Lys Val Leu Lys
            1310                1315                1320

Ile Ser Thr Pro Phe Gly Phe Thr Gln Asp Lys Ser Gly Val Leu
            1325                1330                1335

Thr Lys Asp Ser Ser Ile Ile Tyr Gln Ser Pro Thr Gly Leu Phe
            1340                1345                1350

Glu Arg Ser Val Arg Leu Thr Asp Leu
            1355                1360

<210> SEQ ID NO 37
<211> LENGTH: 1362
<212> TYPE: PRT
<213> ORGANISM: Lactobacillus paracasei subsp. Tolerans Lpl7

<400> SEQUENCE: 37

Met Thr Lys Leu Gly Lys Pro Tyr Gly Ile Gly Val Asp Ile Gly Ser
1               5                   10                  15

Asn Ser Ile Gly Phe Ala Ala Val Asp Glu Asn Ser His Leu Ile Arg
            20                  25                  30

Leu Lys Gly Lys Thr Val Ile Gly Ala Arg Leu Phe Glu Glu Gly Lys
        35                  40                  45

Ala Ala Ala Asp Arg Arg Ala Ser Arg Thr Thr Arg Arg Arg Leu Ser
    50                  55                  60

Arg Asn Arg Trp Arg Leu Ser Phe Leu Arg Asp Phe Phe Glu Ser His
65                  70                  75                  80

Ile Thr Pro Thr Asp Pro Asn Phe Phe Met Arg Gln Lys Tyr Ser Glu
                85                  90                  95

Ile Ser Pro Lys Asp Lys Ser Arg Tyr Lys Tyr Glu Lys Arg Leu Phe
            100                 105                 110

Asn Asp Arg Thr Asp Ala Glu Phe Tyr Lys Tyr Glu Asn Cys Pro Thr
        115                 120                 125

Met Tyr His Leu Arg Asn Arg Leu Met Thr Asp Pro Ser Lys Ala Asp
    130                 135                 140

Val Arg Glu Ile Tyr Phe Ala Ile His His Ile Leu Lys Ser Arg Gly
145                 150                 155                 160

His Phe Leu Thr Pro Gly Asp Ala Lys Asp Phe Asn Thr Asn Lys Val
                165                 170                 175

Ala Val Asn Lys Ile Phe Pro Ala Leu Gln Asp Ala Tyr Ala Gln Val
            180                 185                 190

Tyr Pro Asp Leu Asp Ile Thr Phe Asp Glu Asn Lys Val Asn Glu Phe
        195                 200                 205

Lys Thr Val Leu Leu Asn Glu Lys Ala Thr Pro Ser Asp Thr Gln Arg
    210                 215                 220
```

```
Ala Leu Val Asn Leu Leu Ala Lys Glu Gly Asp Arg Asp Ile Leu
225                 230                 235                 240

Lys Gln Gln Lys Gln Ala Leu Thr Glu Phe Ala Lys Ala Val Val Gly
            245                 250                 255

Leu Lys Thr Lys Leu Asn Val Ala Leu Gly Thr Glu Val Asp Ser Ser
        260                 265                 270

Glu Ala Thr Ala Trp Asn Phe Ser Leu Gly Gln Leu Asp Asp Lys Trp
    275                 280                 285

Thr Gly Ile Glu Ser Ala Met Thr Asp Glu Gly Thr Glu Ile Leu Asp
290                 295                 300

Gln Ile Arg Asp Leu Tyr Arg Ala Arg Leu Leu Asn Gly Ile Val Pro
305                 310                 315                 320

Ala Gly Lys Thr Leu Ser Gln Ala Lys Val Asp Asp Tyr Ala Gln His
            325                 330                 335

His Glu Asp Leu Glu Leu Phe Lys Asp Tyr Leu Lys Gln Leu Glu Asp
        340                 345                 350

Asp Gly Thr Ala Lys Ala Ile Arg Gln Leu Tyr Asp Arg Tyr Ile Asp
    355                 360                 365

Gly Asp Asp Ala Lys Pro Phe Val Arg Glu Asp Phe Val Lys Ala Leu
370                 375                 380

Thr Lys Glu Val Thr Ala His Pro Asn Ala Lys Ser Pro Glu Leu Leu
385                 390                 395                 400

Glu Arg Leu Ala Gln Pro Asp Phe Met Leu Lys Gln Arg Asn Lys Ala
            405                 410                 415

Asn Gly Ala Ile Pro Val Gln Met Gln Gln Arg Glu Leu Asp Gln Ile
        420                 425                 430

Ile Lys Asn Gln Ser Val Tyr Tyr Asp Trp Leu Ala Ala Pro Asn Pro
    435                 440                 445

Val Glu Lys His Arg Lys Ser Met Pro Tyr Gln Leu Asp Glu Leu Leu
450                 455                 460

Asn Phe Arg Ile Pro Tyr Tyr Val Gly Pro Leu Val Thr Ala Lys Glu
465                 470                 475                 480

Gln Lys Ala Ala Gln Gly Gly Val Phe Ala Trp Met Val Arg Lys Asp
            485                 490                 495

Pro Asp Gly Asn Ile Thr Pro Tyr Asn Phe Asp Glu Lys Val Asp Arg
        500                 505                 510

Glu Ala Ser Ala Asn Thr Phe Ile Gln Arg Met Lys Thr Thr Asp Thr
    515                 520                 525

Tyr Leu Ile Gly Glu Asp Val Leu Pro Lys Gln Ser Leu Leu Tyr Gln
530                 535                 540

Ser Tyr Glu Val Leu Asn Glu Leu Asn Asn Val Arg Val Asn Asp Asn
545                 550                 555                 560

Lys Leu Ser Phe Asp Gln Lys Gln Val Leu Gly Glu Leu Phe Glu
            565                 570                 575

Arg His Asn Thr Val Thr Ile Lys Gln Phe Val Asp Asn Leu Leu Ala
        580                 585                 590

His Gly Asp Tyr Asp Arg Ile Pro Glu Val Arg Gly Leu Ala Asp Glu
    595                 600                 605

Lys Arg Phe Leu Ser Ser Leu Ser Thr Tyr Asn Gln Leu Lys Gly Ile
610                 615                 620

Leu His Glu Ala Ile Asp Asp Ser Asp Lys Gln Thr Asp Ile Glu Asn
625                 630                 635                 640

Ile Ile Ala Trp Ser Thr Ile Phe Glu Asp Lys Ala Ile Phe Lys Thr
```

```
                645                 650                 655
Lys Leu Asn Glu Ile Ser Trp Leu Asn Ala Gly Met Ile Asn Ser Leu
                660                 665                 670

Ala Asn Ile Arg Tyr Arg Gly Trp Gly Gln Phe Ser His Lys Leu Leu
                675                 680                 685

Asn Glu Leu Thr Leu Ser Thr Gly Arg Thr Val Phe Glu Glu Leu Leu
                690                 695                 700

Ile Ser Ser His Asn Leu Met Gln Ile Leu Thr Asp Glu Val Leu Lys
705                 710                 715                 720

Gln Lys Ile Ala Glu Leu Asn Ala His Glu Leu Lys Ala Ser Gly Ile
                725                 730                 735

Tyr Ala Ala Ile Asp Asp Ala Tyr Thr Ser Pro Ser Asn Lys Lys Ala
                740                 745                 750

Leu Arg Gln Val Leu Ser Val Ile Asp Asp Ile Thr Asn Ala Ala Gly
                755                 760                 765

Gln Ala Pro Asn Trp Leu Tyr Ile Glu Thr Ala Asp Gly Asp Gly Val
                770                 775                 780

Pro Gly Lys Arg Thr Asn Ser Arg Gln Arg Lys Ile Gln Glu Ile Tyr
785                 790                 795                 800

Ala Asn Ala Ala Gln Glu Leu Ile Thr Gly Ser Val Arg Gly Glu Leu
                805                 810                 815

Glu Asp Lys Ile Ala Ser Arg Ala Asp Phe Thr Asp Arg Leu Val Leu
                820                 825                 830

Tyr Phe Met Gln Gly Gly Arg Asp Ile Tyr Thr Gly Lys Pro Leu Asn
                835                 840                 845

Ile Asp Asn Leu Ser Ser Tyr Asp Ile Asp His Ile Leu Pro Gln Ser
850                 855                 860

Leu Ile Lys Asp Asn Ser Leu Asp Asn Arg Val Leu Val His Pro Leu
865                 870                 875                 880

Val Asn Arg Glu Lys Asp Thr Ile Phe Ala Ser Thr Arg Phe Ala Lys
                885                 890                 895

Gln Met Asn Gly Met Trp Arg Gln Trp His Ala Ala Gly Leu Ile Ser
                900                 905                 910

Ser Arg Lys Leu Arg Asn Leu Gln Met Arg Pro Asp Glu Ile Asp Lys
                915                 920                 925

Tyr Ala Ser Gly Phe Val Ala Arg Gln Leu Val Glu Thr Arg Gln Ile
                930                 935                 940

Ile Lys Leu Thr Glu Gln Ile Val Ala Asp Gln Tyr Pro Asp Thr Lys
945                 950                 955                 960

Ile Ile Ala Val Lys Ala Gly Leu Ser Ser Gln Leu Arg Lys Glu Leu
                965                 970                 975

Asp Phe Pro Lys Asn Arg Glu Val Asn His Tyr His His Ala Phe Asp
                980                 985                 990

Ala Phe Leu Ala Ala Arg Ile Gly  Thr Tyr Leu Leu Lys  Arg Tyr Pro
                995                 1000                1005

Asn Leu  Glu Pro Phe Phe Thr  Tyr Gly Lys Phe Lys  Lys Thr Glu
    1010                1015                1020

Val Lys  Lys Leu Lys Ser Phe  Asn Phe Ile Arg Asp  Met Thr His
    1025                1030                1035

Ala Lys  Asp Lys Ile Val Ala  Lys Glu Thr Gly Glu  Ile Val Trp
    1040                1045                1050

Asp Asn  Ala Ser Asp Ile Asn  Glu Leu Asp Arg Ile  Tyr Asn Phe
    1055                1060                1065
```

Lys Arg Met Leu Ile Thr His Glu Val Arg Phe Glu Thr Ala Ser
         1070                1075                1080

Leu Phe Lys Gln Thr Leu Tyr Ala Ala Lys Asn Ser Lys Asn Arg
     1085                1090                1095

Gly Gly Ser Arg Gln Leu Ile Pro Lys Lys Gly Tyr Leu Val
 1100                1105                1110

Asp Ile Tyr Gly Gly Tyr Thr Gln Glu Thr Gly Ser Tyr Leu Ser
     1115                1120                1125

Val Val Arg Leu Thr Lys Lys Ala Met Tyr Ala Val Val Lys Val
     1130                1135                1140

Ser Thr Arg Asp Ala Ala Lys Leu Ala Val Ala Lys Ser Ile Ser
     1145                1150                1155

Glu Gln Lys Glu Asn Glu Thr Leu Lys Lys Ile Asp Gly Lys
 1160                1165                1170

Leu Ser Lys Thr Ser Lys Lys Gly Lys Thr Thr His Gln Leu Phe
     1175                1180                1185

Glu Ile Val Leu Pro Arg Val Gly Gln Lys Thr Leu Phe Lys Asn
     1190                1195                1200

Ser Lys Tyr Asn Gln Phe Leu Val Asn Ser Asp Thr Tyr Met His
     1205                1210                1215

Asn Tyr Gln Glu Leu Trp Met Pro Arg Glu Tyr Gln Arg Met Trp
     1220                1225                1230

Lys Asp Ile Leu Leu Ser Asn His Gly Asp Ala Gln Leu Glu Gly
     1235                1240                1245

Gln Leu Asp Gln Ile Phe Lys Phe Ile Val Ser Gln Val Asn Ser
     1250                1255                1260

Tyr Phe Asn Leu Tyr Asp Ile Asn Gln Phe Arg Lys Lys Ile Ala
     1265                1270                1275

Asp Ala Thr Asp Lys Phe Ala Lys Leu Pro Thr His Asp Thr Asp
     1280                1285                1290

Asn Ala Arg Gly Lys Ile Ala Thr Ile Gly Gln Leu Leu Ile Gly
     1295                1300                1305

Leu Gln Ala Asn Ala Met Arg Ser Asp Leu Arg Asn Leu Asp Ile
     1310                1315                1320

Lys Thr Pro Phe Gly Leu Leu Gln Ile Gly Thr Gly Ile Thr Leu
     1325                1330                1335

Asp Leu Asp Thr Ser Ile Ile Tyr Gln Ser Pro Thr Gly Leu Phe
     1340                1345                1350

Glu Arg Glu Val Pro Leu Thr Asp Leu
     1355                1360

<210> SEQ ID NO 38
<211> LENGTH: 1382
<212> TYPE: PRT
<213> ORGANISM: Lactobacillus pentosus IG1

<400> SEQUENCE: 38

Met Lys Lys Ile Val Asn Tyr Asn Leu Gly Leu Asp Ile Gly Thr Ser
1               5                   10                  15

Ser Ile Gly Tyr Ala Ala Ile Asp Asp Gln Gly Arg Pro Val Arg His
            20                  25                  30

Gln Asn Lys Thr Val Met Gly Val Arg Leu Phe Lys Glu Gly Lys Thr
        35                  40                  45

Ala Glu Ser Thr Arg Ile Phe Arg Gly Thr Arg Arg Arg Leu Ser His

```
                50                  55                  60
Arg His Trp Arg Leu Gly Tyr Leu Asp Arg Ile Phe Asp Asn Glu Ile
 65                  70                  75                  80

Ala Lys Val Asp Glu Asn Phe Leu Pro Arg Leu Lys Ala Ser Lys Arg
                 85                  90                  95

Ala Arg Ser Asp Glu Lys Arg Ser Phe Arg Gly Ser Leu Leu Phe Pro
                100                 105                 110

Glu Thr Gly Asp Asp Ala Tyr Tyr Gln Lys Tyr Pro Thr Ile Tyr His
                115                 120                 125

Leu Arg Tyr Ala Leu Ile Thr Gln Lys Lys Gln Phe Asp Ile Arg Leu
            130                 135                 140

Ile Tyr Leu Ala Leu His His Met Ile Lys Tyr Arg Gly Asn Phe Leu
145                 150                 155                 160

Asp Thr Thr Pro Val Ser Ala Phe Asn Ile His Asp Ile Asp Leu Thr
                165                 170                 175

Asp Gln Phe Ala Ser Leu Asn Asp Cys Tyr Gln Leu Leu Asp Met Asp
                180                 185                 190

Phe Glu Phe Gln Phe Asp Leu Asn Asn Ile Glu Gln Val Gln Lys Leu
            195                 200                 205

Leu Leu Asp Glu Thr Leu Ser Lys Thr Lys Arg Gln Ala Ala Val Ser
210                 215                 220

Lys Val Leu Val Met Ser Thr Gly Asn Lys Ala Phe Asp Asp Gln Gln
225                 230                 235                 240

Asn Gly Ile Ala Ser Glu Phe Ile Lys Ala Leu Leu Gly Gly Pro Phe
                245                 250                 255

Asp Leu Ser Lys Ile Leu Asn Leu Ser Val Ala Asp Val Lys Ser Trp
                260                 265                 270

Lys Leu His Met Thr Asp Lys Asp Val Asp Asp Thr Leu Asn Ser Leu
            275                 280                 285

Val Glu Glu Leu Asp Glu Asn His Lys Gln Ile Val Asn Leu Leu Gln
                290                 295                 300

Met Ile Tyr Ser Gln Val Met Met Leu Gly Leu Leu Asn Gly Gln Gln
305                 310                 315                 320

Ser Ile Ser Ala Ser Met Ile Glu Arg Tyr Asp Asp His Ala Lys His
                325                 330                 335

Trp Ala Ala Leu Lys Lys Leu Leu Pro Ala Leu Gly Glu Gln Glu Gln
                340                 345                 350

Ser Thr Ile Ile His Ala Tyr Thr Ala Tyr Thr Gly His Ser Arg Thr
            355                 360                 365

Lys Gln Leu Ser Arg Ala Glu Phe Tyr Thr Lys Val Asn Ser Ile Leu
            370                 375                 380

Lys Lys His Glu Asn Ile Ala Glu Ala Thr Gly Leu Ile Glu Leu Ile
385                 390                 395                 400

Asp Arg Asn Glu Phe Met Pro Lys Gln Arg Asp Ala Val Asn Gly Val
                405                 410                 415

Ile Pro His Gln Leu His Gln Arg Glu Leu Gln Leu Ile Gln Asn
                420                 425                 430

Gln Gln Lys Tyr Tyr Pro Phe Leu Ala Ala Lys Ala Tyr Pro Asp Ala
            435                 440                 445

Asp Glu Thr Met Ile Glu Gln Leu Leu Ser Phe Arg Val Pro Tyr Tyr
            450                 455                 460

Ala Gly Pro Leu Val Asp Arg Asp Phe Ile Asn Glu Ser Ser Asp Gln
465                 470                 475                 480
```

```
Glu Gln Ala Met Gln Asn Thr Lys Phe Ser Trp Leu Lys Arg Arg Glu
            485                 490                 495

Ala Gly Glu Ile Thr Pro Trp Asn Phe Glu Gln Lys Val Asp Val Gln
            500                 505                 510

Glu Thr Ala Asn Arg Phe Ile Lys Arg Leu Thr Thr Lys Asp Thr Tyr
            515                 520                 525

Leu Met Thr Glu Asp Val Leu Pro Lys Glu Ser Leu Ile Tyr Gln Arg
            530                 535                 540

Phe Glu Val Leu Asn Glu Leu Asn Ala Ile Arg Ile Asn Asp Arg Arg
545                 550                 555                 560

Leu Thr Ala Glu Asn Lys Gln Leu Ala Phe Gln Gln Leu Phe Met Ala
            565                 570                 575

Gly Asn Thr Lys Asn Val Ser Ile Lys Lys Phe Arg Asn Phe Val Phe
            580                 585                 590

Asp Ser Leu Lys Phe Pro Glu Lys Val Lys Ile Thr Gly Phe Ala Gly
            595                 600                 605

Gln His Asn Phe Leu Ala Lys Leu Ser Thr Tyr His Asp Phe Lys Lys
            610                 615                 620

Ile Phe Gly Glu Arg Val Asp His Thr Asp Leu Gln Pro Asp Phe Glu
625                 630                 635                 640

Arg Ile Val Glu Trp Cys Thr Ile Phe Glu Asp Arg His Ile Tyr Arg
            645                 650                 655

Glu Lys Leu Lys Glu Ile Gln Trp Leu Ser Gln Ser Glu Ile Asp Gln
            660                 665                 670

Leu Val Leu Ile Arg Asn His Gly Trp Gly Arg Leu Ser Lys Arg Leu
            675                 680                 685

Leu Thr Gly Ile Arg Asp Ser Asp Gly Arg Thr Val Met Asp Gln Leu
            690                 695                 700

Trp Phe Gly Thr Asp Asn Phe Met Arg Ile Ile Ser Gln Ser Asp Phe
705                 710                 715                 720

Ala Ala Ala Ile Ala Asn Glu Asn Arg Thr Gln Leu Asn Gln His Gly
            725                 730                 735

Leu Glu Asp Val Leu Asp Ser Ala Phe Met Ser Pro Gln Asn Lys Lys
            740                 745                 750

Ala Ile Arg Gln Val Leu Lys Val Val Asp Asp Ile Glu Gln Thr Leu
            755                 760                 765

Gly Cys Pro Pro Lys Lys Val Met Ile Glu Phe Thr Arg Ser Pro Asp
            770                 775                 780

Lys Lys Lys Gln Arg Thr Val Thr Arg Leu Glu Lys Val Gln Gln Ala
785                 790                 795                 800

Tyr Lys Ala Val Ala Asp Gln Leu Ala Gly Gln Ser Ile Val Ser Glu
            805                 810                 815

Leu Asp Gln Tyr Ala Asn Thr His Ser Lys Leu Ser Asp Thr Tyr Tyr
            820                 825                 830

Leu Tyr Phe Met Gln Leu Gly Arg Asp Leu Tyr Ser Gly Lys Pro Ile
            835                 840                 845

Asp Ile Asp Ser Pro Met Leu Asp Asp His Ile Leu Pro Arg Ala
            850                 855                 860

Phe Met Lys Asp Asn Ser Leu Asp Asn Arg Ala Leu Thr Glu Lys Pro
865                 870                 875                 880

Ile Asn Asn Thr Lys Ala Ala Lys Phe Pro Ser Lys Val Phe Gly Gln
            885                 890                 895
```

```
Gln Lys Glu Val Thr Asp Phe Trp Lys Leu Arg Arg Cys Gly Leu
                900             905             910

Met Ser Asn Ile Lys Glu Lys His Leu Tyr Leu Asp Pro Asp Asn Val
            915             920             925

Asp Lys Trp Thr Arg Arg Gly Phe Ile His Arg Gln Leu Val Glu Thr
        930             935             940

Ser Gln Val Ile Lys Ile Val Ala Asn Ile Leu Asn Asp Arg Tyr Gln
945             950             955             960

Gln Ser Gln Thr Glu Val Leu Glu Val Pro Ala Arg Leu Gly Thr Glu
                965             970             975

Leu Arg Glu Cys Phe Gly Trp Tyr Lys Val Arg Glu Val Asn Asp Tyr
            980             985             990

His His Val Phe Asp Ala Tyr Leu Ala Ala Phe Ile Gly Asn Tyr Leu
            995             1000            1005

Tyr Arg Arg Tyr Pro Lys Leu Gln Pro Tyr Phe Val Tyr Gly Asn
        1010            1015            1020

Phe Ala Glu Leu Asn Lys Ala Gln Leu Lys Asn Ile Lys Ser Phe
        1025            1030            1035

Asn Phe Leu Tyr Asn Ile Thr Asp Asn Lys Arg Val Val Lys Asp
        1040            1045            1050

Ile Glu Thr Gly Gln Thr Leu Trp Asp Asp Gln Ile Arg Gln Gln
        1055            1060            1065

Ile Gln His Ile Tyr Glu Tyr Lys Tyr Met Leu Thr Ser His Glu
        1070            1075            1080

Ala Phe Thr Gln His Lys Glu Leu Tyr Gly Gln Thr Ile Tyr Pro
        1085            1090            1095

Arg Arg Glu Phe Lys Pro Gly Thr Leu Lys Ala Ile Lys Gln Asp
        1100            1105            1110

Gln Pro Gln Glu Leu Tyr Gly Gly Tyr Lys Asn Leu Thr Ala Ala
        1115            1120            1125

Tyr Met Cys Ile Val Lys Ile Gln Ala Arg Lys Arg Arg Ala Ala
        1130            1135            1140

Glu Tyr Arg Val Val Arg Val Ala Thr Glu Ser Leu Ser Ala Leu
        1145            1150            1155

Gln Gln Ala Lys Arg Leu Gly Val Gln Ala Tyr Glu Arg Cys Leu
        1160            1165            1170

Arg Gln Glu Leu Val Arg Asn Asn Glu Ile Leu Arg Thr Asn Ala
        1175            1180            1185

Asp Pro Asn Ser Ala Pro Arg Glu Phe Glu Val Leu Leu Asp Arg
        1190            1195            1200

Val Leu Cys His Gln Met Ile Ile Ser Asp Gly Gln Lys Tyr Leu
        1205            1210            1215

Leu Gly Ser His Ala Tyr Lys Ile Asn Cys Met Gln Leu Val Leu
        1220            1225            1230

Ser Asn Asn Ser Met Lys Ile Leu Ser Thr Ser Ile Val Lys Leu
        1235            1240            1245

Lys Gln Met Thr Asn Glu Pro Leu Val Gln Val Tyr Arg Glu Ile
        1250            1255            1260

Leu Asp Val Val Asn Lys Tyr Phe Thr Leu Tyr Asp Val Asn Ser
        1265            1270            1275

Phe Arg Glu Asn Leu Asn Gln Phe Phe Asp Lys Phe Arg Thr Leu
        1280            1285            1290

Pro Ile Thr Asn Glu Tyr Glu Ser Ser Lys Ser Gly Lys Lys Leu
```

```
            1295                1300                1305
Ile His Arg Gly Gln Leu Glu Thr Leu Thr Leu Ile Leu Arg Gly
        1310                1315                1320

Leu His Ala Asn Ser Asp Lys Val Gln Tyr Gly Asp Gln Ser Thr
    1325                1330                1335

Leu Leu Gly Gly Phe Gln Thr Lys Asp Gly Ile Lys Leu Ser Lys
    1340                1345                1350

Asp Ser Val Ile Gln Tyr Thr Ser Pro Ala Gly Leu Asn Val Arg
    1355                1360                1365

Thr Val Lys Leu Arg Asp Leu Glu Gln Lys Glu Ala Gln Lys
    1370                1375                1380

<210> SEQ ID NO 39
<211> LENGTH: 1361
<212> TYPE: PRT
<213> ORGANISM: Lactobacillus pentosus KCA1

<400> SEQUENCE: 39

Met Asn Glu Pro Tyr Gly Val Gly Leu Asp Ile Gly Thr Asn Ser Val
1               5                   10                  15

Gly Trp Thr Val Val Asp Met Asn Gly Arg Val Arg Lys Val Lys Gly
            20                  25                  30

Lys Thr Ala Leu Gly Ala Arg Leu Phe Lys Glu Gly Ala Thr Ala Glu
        35                  40                  45

Asp Arg Arg Gly Phe Arg Thr Thr Arg Arg Leu Lys Arg Val Lys
    50                  55                  60

Trp Arg Leu Arg Leu Leu Arg Glu Phe Phe Asp Gln Pro Ile Ser Lys
65                  70                  75                  80

Ile Asp Pro Asn Phe Phe Ala Arg Arg Lys Tyr Ser Asp Ile Ser Pro
                85                  90                  95

Arg Asp Pro Asn Tyr Asn Gly Leu Ala Lys Thr Leu Phe Asn Asp Arg
            100                 105                 110

Thr Asp Lys Glu Phe Tyr Asp Tyr Ala Thr Ile Tyr His Leu Arg
        115                 120                 125

Asp Lys Leu Met Thr Ser Asn Arg Lys Phe Asp Ile Arg Glu Ile Tyr
    130                 135                 140

Leu Ala Ile His His Ile Val Lys Tyr Arg Gly Asn Phe Leu Arg Thr
145                 150                 155                 160

Gly Pro Ala Ser Gln Tyr Gly Ser Ala Ser Leu His Leu Ala Thr Ser
                165                 170                 175

Phe Gln Lys Leu Asn Asp Leu Phe Ala Gln Ser Glu Glu Thr Leu Asn
            180                 185                 190

Leu Lys Leu Val Thr Asp Glu Ala Leu Leu Gln Gln Ile Gln Gln Ile
        195                 200                 205

Leu Val Arg Thr Asp Leu Ser Arg Ser Glu Gln Arg Gln Ile Trp
    210                 215                 220

Pro Leu Met Ala Val Leu Thr Gly Ala Ser Ala Ala Glu Lys Lys Arg
225                 230                 235                 240

Gln Lys Asn Val Val Val Glu Leu Ser Lys Ala Leu Val Gly Leu Lys
                245                 250                 255

Ala Lys Met Asn Val Val Thr Leu Thr Glu Val Asp Ala Ala Val Val
            260                 265                 270

Lys Asp Trp Thr Phe Thr Met Glu Glu Ser Gln Asp Lys Leu Pro Glu
        275                 280                 285
```

-continued

```
Ile Glu Glu Gln Leu Ser Glu Val Gly Gln Gln Ile Met Asp Glu Val
290                 295                 300
Ile Gln Leu Tyr Ala Ser Val Asn Leu Ala Gln Leu Ile Pro Ala Gly
305                 310                 315                 320
Lys Arg Phe Ser Gln His Met Val Glu Lys Tyr Lys His His Glu Lys
                325                 330                 335
Asn Leu Glu Leu Leu Lys Ala Tyr Ile His Ser Gln Ser Asp Ser Lys
            340                 345                 350
Arg Gly Arg Glu Ile Arg Ala Thr Tyr Asp Arg Tyr Ile Asp Gly Val
        355                 360                 365
Asp Ser Lys Pro Val Thr Gln Glu Met Phe Tyr Lys Asp Leu Met Lys
370                 375                 380
Tyr Val Glu Ala Asp Ala Thr Ser Asn His Leu Ala Ala Glu Ile Lys
385                 390                 395                 400
Asp Glu Ile Asp Ser Glu Gln Phe Met Pro Lys Leu Arg Thr Lys Gln
                405                 410                 415
Asn Gly Ser Ile Pro Tyr Gln Val Gln Gln Tyr Glu Leu Asp Gln Ile
            420                 425                 430
Ile Ser His Gln Lys Lys Tyr Tyr Pro Trp Leu Gly Glu Asn Pro
        435                 440                 445
Val Ala Glu Arg Arg Gly Lys Phe Pro Tyr Lys Leu Asp Glu Leu Val
450                 455                 460
Gly Phe Arg Val Pro Tyr Val Gly Pro Leu Ile Thr Lys Glu Asp
465                 470                 475                 480
Gln Gln Ala Thr Ser Gly Ala Gly Phe Ala Trp Met Val Arg Lys Ala
                485                 490                 495
Asp Gly Pro Ile Thr Pro Trp Asn Phe Asp Gln Lys Val Asp Arg Ile
            500                 505                 510
Ala Ser Ala Thr Ala Phe Ile Gln Arg Met Gln Thr Thr Asp Thr Tyr
        515                 520                 525
Leu Ile Gly Glu Asp Val Leu Pro Ala Arg Ser Leu Ile Tyr Gln Arg
530                 535                 540
Phe Met Val Leu Asn Glu Leu Asn Asn Met Arg Val Glu Asp Arg Lys
545                 550                 555                 560
Leu Ala Pro Gln Gln Lys Gln Arg Leu Tyr Asn Gln Val Phe Lys Gln
                565                 570                 575
His Gln His Val Ser Val Lys Asn Ile Gln Gln Asn Leu Met Asp Ala
            580                 585                 590
Gly Glu Tyr Arg Lys Thr Pro Gln Ile Thr Gly Leu Ala Asp Pro Lys
        595                 600                 605
Gly Phe Asn Ser Ser Leu Ser Thr Tyr His Asp Phe Lys Lys Ile Leu
610                 615                 620
Leu Glu Ala Ile Ala Asp Glu His Lys Arg Ala Asp Ile Glu Lys Ile
625                 630                 635                 640
Ile Leu Trp Ser Thr Thr Phe Glu Asp Ser Ala Ile Phe Lys Gln Lys
                645                 650                 655
Leu Glu Glu Val Ala Trp Leu Thr Asp Ala Gln Arg Lys Gln Leu Ser
            660                 665                 670
Gly Leu Arg Tyr Arg Gly Trp Gly Gln Leu Ser His Lys Leu Leu Thr
        675                 680                 685
Ala Phe Lys Asp Asp Lys Gly Arg Ser Ile Met Asp Gly Leu Trp Glu
690                 695                 700
Thr Ser Asp Asn Phe Met Gln Leu Arg Lys Gln Pro Ala Ile Glu Thr
```

-continued

```
            705                 710                 715                 720
        Gln Ile Lys Glu Ala Asn Gln Ala Asn Leu Thr Asp Ala Asp Ile Gln
                        725                 730                 735

Asp Thr Ile Asn Glu Leu Tyr Thr Ser Pro Gln Asn Lys Lys Ala Ile
                        740                 745                 750

Arg Glu Val Met Leu Val Leu Asp Asp Ile Lys Asn Ala Met His Gly
                        755                 760                 765

Gln Thr Pro Ser Trp Ile Phe Val Glu Ala Ala Arg Gly Gly Gly Val
                        770                 775                 780

Ala Gly Arg Arg Thr Gln Ser Arg Ser Ser Gln Ile Val Glu Ala Tyr
        785                 790                 795                 800

Lys Gly Thr Ala Lys Glu Ile Val Ser Glu Lys Val Gln His Glu Leu
                        805                 810                 815

Asn Glu Lys Ile Lys Ala Lys Ala Asp Phe Asn Thr Arg Leu Val Leu
                        820                 825                 830

Tyr Phe Leu Gln Asn Gly Arg Asp Leu Tyr Thr Asn Glu Ala Ile Asn
                        835                 840                 845

Ile Asp Arg Leu Ser Glu Tyr Asp Ile Asp His Ile Leu Pro Gln Ser
        850                 855                 860

Leu Val Lys Asp Asp Ser Leu Asp Asn Arg Val Leu Thr Ser Ala Arg
        865                 870                 875                 880

Ile Asn Arg Glu Lys Asn Asp Thr Phe Ala Ser Glu Lys Phe Gly Arg
                        885                 890                 895

Lys Met Gly Ala Gln Trp Arg Glu Leu His Arg Asn Gly Leu Met Thr
                        900                 905                 910

Gln Arg Lys Leu Lys His Leu Leu Met Arg Pro Asp Glu Ile Ser Lys
                        915                 920                 925

His Ala Thr Asp Phe Ile Asn Arg Gln Leu Val Glu Thr Arg Gln Val
                        930                 935                 940

Ile Lys Leu Val Glu Glu Leu Ile Ser Ser Glu Tyr Pro Ala Ala Ser
        945                 950                 955                 960

Ile Val Ala Val Lys Ala Asn Leu Thr His Gln Phe Arg Gln Thr Phe
                        965                 970                 975

Asn Phe Pro Lys Leu Arg Glu Val Asn Asp Tyr His His Ala Phe Asp
                        980                 985                 990

Ala Ser Leu Thr Ala Phe Ile Gly Met Tyr Leu Leu Lys Gln Tyr Pro
                        995                 1000                1005

Lys Leu Glu Arg Phe Phe Val Tyr Gly Lys Phe Ala Lys Gln Pro
                1010                1015                1020

Ile Asn Leu Thr Arg Phe Asn Ile Ile Arg Lys Leu Ala Val Ala
                1025                1030                1035

Glu Lys Pro Ile Ala Asn Ile Glu Thr Gly Glu Ile Leu Trp Asp
                1040                1045                1050

Lys Thr Ala Asp Ile Lys Tyr Phe Glu Lys Leu Tyr Asn Tyr Lys
                1055                1060                1065

Arg Leu Leu Val Thr His Glu Val Arg Glu Asn Tyr Gly Ala Met
                1070                1075                1080

Phe Lys Gln Thr Leu Phe Lys Ala Ser Tyr Asn Lys Ser Lys Thr
                1085                1090                1095

Leu Val Pro Lys Lys Asn His Met Glu Thr Ser Val Tyr Gly Gly
                1100                1105                1110

Tyr Ser Asn Gln Glu Thr Ala Tyr Leu Ala Ile Val Arg Ile Pro
                1115                1120                1125
```

Phe Lys Ser Gly Phe Lys Phe Ile Val Val Gly Ile Pro Thr Arg
    1130            1135                1140

Met Val Ala Lys Ile Lys His Tyr Gln Ser Leu Gly Ala Thr Leu
    1145            1150                1155

Asn Gln Ala Thr His Lys Val Ile Glu Pro Lys Phe Thr Lys Ile
    1160            1165                1170

Ser Arg Lys Thr Lys Gln Thr Val Ile Ser Asp Tyr Glu Val Val
    1175            1180                1185

Leu Pro Lys Val Tyr Leu Asp Gln Val Arg Asp Gln Val Lys
    1190            1195                1200

Gly Gln Met Tyr Arg Phe Ser Leu Gly Ser Asp Lys Glu Tyr His
    1205            1210                1215

Asn Val Gln Glu Leu Tyr Leu Pro Leu Ser Ile Gln Gln Ala Phe
    1220            1225                1230

Val Gly His Tyr Asp Glu Ser Asp Asp Gln Arg Ser Asn Asp Leu
    1235            1240                1245

Val Lys Val Tyr Asp Ala Ala Leu Lys Gln Leu Gln Arg Tyr Phe
    1250            1255                1260

Pro Leu His Leu Ser Arg Asn Phe Asp Gln Val Ala Ser Gln Ala
    1265            1270                1275

His Gln Ser Phe Glu Gly Leu Lys Asn Asn Val Gln Thr Ser Asp
    1280            1285                1290

Lys Gln Leu Gly Lys Lys Glu Val Leu Asn Ser Leu Phe Val Gly
    1295            1300                1305

Leu His Ala Asn Ala Thr Arg Ser Asn Leu Ser Val Leu Gly Met
    1310            1315                1320

Ser Lys Asp Phe Gly Arg Ile Lys Ser Asn Gly Ile Thr Leu Thr
    1325            1330                1335

Asp Gln Ala Glu Ile Ile Tyr Gln Ser Pro Thr Gly Leu Phe Glu
    1340            1345                1350

Arg Lys Val Ala Leu Lys Asp Leu
    1355            1360

<210> SEQ ID NO 40
<211> LENGTH: 1358
<212> TYPE: PRT
<213> ORGANISM: Lactobacillus plantarum EGD-AQ4

<400> SEQUENCE: 40

Met Lys Glu Pro Tyr Gly Val Gly Leu Asp Ile Gly Thr Asn Ser Val
1               5                   10                  15

Gly Trp Thr Val Val Asp Ala Ser Gly His Val Arg Lys Ile Lys Gly
                20                  25                  30

Gln Thr Gly Ile Gly Val Arg Leu Phe Lys Glu Gly Ala Ala Ala
            35                  40                  45

Asp Arg Arg Gly Phe Arg Thr Thr Arg Arg Leu Arg Val Lys
50                  55                  60

Trp Arg Leu Arg Leu Leu Arg Glu Phe Phe Gln Pro Ile Ser Lys
65                  70                  75                  80

Val Asp Ile Asn Phe Phe Ala Arg Arg Lys Tyr Ser Asp Val Ser Pro
                85                  90                  95

Arg Asp Pro Asn Tyr Asn Gly Leu Glu Lys Thr Leu Phe Asn Asp Arg
            100                 105                 110

Ser Asp Gln Asp Phe Tyr His Asp Tyr Pro Thr Ile Tyr His Leu Arg

```
            115                 120                 125
Glu Ala Leu Met Thr Gln His Arg Lys Phe Asp Val Arg Glu Ile Tyr
130                 135                 140

Leu Ala Ile His His Ile Val Lys Tyr Arg Gly Asn Phe Leu Arg Asn
145                 150                 155                 160

Asp Ala Ala Thr Ala Tyr Arg Ser Gly Thr Leu Asp Leu Gln Gln His
                165                 170                 175

Phe Glu Thr Leu Asn His Leu Phe Ser Gln Ala Asp Leu Glu Leu Asn
                180                 185                 190

Leu Asn Leu Thr Thr Asp Val Ala Leu Leu Asp Ser Ile Lys Gln Thr
                195                 200                 205

Leu Val Arg Thr Asp Ile Ser Arg Ser Asp Arg Gln Lys Leu Ile Met
                210                 215                 220

Pro Leu Leu Ala Val Leu Thr Gly Ala Thr Thr Ala Glu Lys Lys Arg
225                 230                 235                 240

Gln Lys Ala Val Val Thr Glu Phe Ala Lys Ala Leu Val Gly Asn Lys
                245                 250                 255

Thr Lys Ile Asp Val Leu Thr Leu Thr Asp Ile Asp Ala Thr Glu Ala
                260                 265                 270

Lys Asp Trp Ala Phe Ser Leu Glu Glu Asn Gln Asp Lys Leu Pro Gly
                275                 280                 285

Ile Glu Asp Arg Phe Ser Glu Val Gly Gln Gln Ile Ile Asp Glu Val
                290                 295                 300

Ile Arg Leu Tyr Ala Ser Val Asn Leu Ala Gln Leu Ile Pro Glu Gly
305                 310                 315                 320

Lys Arg Phe Ser Gln Ser Met Val Glu Lys Tyr Lys Arg His Gly Glu
                325                 330                 335

Asp Leu Lys Leu Leu Lys Ala Tyr Ile Arg Ser Gln Ser Asp Ala Lys
                340                 345                 350

Arg Gly Arg Ala Ile Arg Ala Thr Tyr Asp Gln Tyr Ile Asp Gly Val
                355                 360                 365

Lys Ser Lys Gln Val Thr Gln Glu Ala Phe Gln Lys Ala Leu Gly Lys
                370                 375                 380

Phe Val Asp Ala Asp Val Asp Leu Asn Ser Trp Ala Ala Gln Ile Lys
385                 390                 395                 400

Gln Ala Ile Asp Ser Glu Gln Phe Met Pro Lys Leu Arg Thr Lys Gln
                405                 410                 415

Asn Gly Ala Ile Pro Tyr Gln Val Gln Gln Asn Glu Leu Asp Gln Ile
                420                 425                 430

Ile Ser Asn Gln Lys Glu Tyr Tyr Pro Trp Leu Gly Glu Glu Asn Pro
                435                 440                 445

Val Ile Lys Arg Arg Gly Lys Phe Pro Tyr Lys Leu Asp Glu Leu Phe
                450                 455                 460

Gly Phe Arg Val Pro Tyr Tyr Val Gly Pro Leu Ile Thr Lys Glu Met
465                 470                 475                 480

Gln Ala Ala Thr Ala Asn Ala Gly Phe Ala Trp Met Val Arg Lys Ala
                485                 490                 495

Asp Gly Pro Ile Thr Pro Trp Asn Phe Asp Asp Lys Val Asp Arg Val
                500                 505                 510

Ala Ser Ala Thr Ala Phe Ile Gln Arg Met Gln Thr Thr Asp Thr Tyr
                515                 520                 525

Leu Ile Gly Glu Glu Val Leu Pro Ala Arg Ser Leu Ile Tyr Gln Arg
                530                 535                 540
```

-continued

```
Phe Met Val Leu Asn Glu Leu Asn Asn Ile Arg Val Asp Asp Gly Gln
545                 550                 555                 560

Leu Thr Pro Arg Gln Lys Gln Arg Leu Tyr Asn Gln Val Phe Lys Lys
                565                 570                 575

His Lys Arg Val Thr Ala Lys Asn Ile Gln Asp Asn Leu Val Ala Ala
                580                 585                 590

Arg Glu Phe Pro Thr Ala Pro Arg Ile Thr Gly Leu Ala Asp Pro Lys
                595                 600                 605

Val Phe Asn Ser Ser Leu Ser Thr Tyr His Asp Leu Lys Gln Val Leu
610                 615                 620

Pro Glu Ala Met Ser Asp Val Arg Lys Gln Ala Asp Ile Glu Lys Ile
625                 630                 635                 640

Ile Leu Trp Ser Thr Ile Phe Glu Asp Ser Thr Ile Phe Lys Gln Lys
                645                 650                 655

Leu Thr Glu Ile Ser Trp Leu Thr Ala Ala Gln Leu Lys Gln Leu Gly
                660                 665                 670

Gln Leu Arg Tyr Arg Gly Trp Gly Gln Leu Leu Arg Lys Leu Leu Thr
                675                 680                 685

Gly Leu Lys Asp Asp Asn Asn Arg Ser Ile Met Asp Gly Leu Trp Glu
690                 695                 700

Thr Asn Ala Asn Phe Met Gln Leu Arg Ser Gln Pro Ala Ile Glu Asn
705                 710                 715                 720

Gln Ile Lys Ser Ala Asn Gln Ala Asn Leu Thr Thr Ala Asp Leu Gln
                725                 730                 735

Asp Thr Ile Asn Glu Leu Tyr Thr Ser Pro Gln Asn Lys Lys Ala Ile
                740                 745                 750

Arg Glu Val Met Val Val Leu Ala Asp Ile Lys Asp Ala Met His Gly
                755                 760                 765

Gln Thr Pro Asn Trp Ile Phe Val Glu Ala Ala Arg Gly Gly Gly Val
                770                 775                 780

Ala Gly Arg Arg Thr Gln Ser Arg Ser Lys Gln Ile Val Ala Ala Tyr
785                 790                 795                 800

Gln Gly Thr Ala Gln Ala Ile Val Arg Asp Gln Val Gln Arg Glu Leu
                805                 810                 815

Lys Glu Lys Ile Lys Asn Lys Ala Asn Phe Asn Thr Arg Leu Val Leu
                820                 825                 830

Tyr Phe Leu Gln Asn Gly Arg Asp Leu Tyr Thr Gly Asp Ala Ile Asn
                835                 840                 845

Ile Asp Arg Leu Ser Glu Tyr Asp Ile Asp His Ile Leu Pro Gln Ser
850                 855                 860

Leu Val Lys Asp Asp Ser Leu Asp Asn Arg Val Leu Thr Asn Ala Arg
865                 870                 875                 880

Ile Asn Arg Glu Lys Asn Asp Thr Phe Ala Ser Glu Lys Phe Gly Lys
                885                 890                 895

Lys Met Gly Ala Lys Trp Lys Glu Met His Arg Met Gly Leu Met Thr
                900                 905                 910

Lys Arg Lys Leu Asp His Leu Leu Met Arg Pro Asp Glu Ile Ser Lys
                915                 920                 925

Tyr Ala Thr Gly Phe Ile Asn Arg Gln Leu Val Glu Thr Arg Gln Val
                930                 935                 940

Ile Lys Leu Val Glu Glu Leu Ile Asn Ala Glu Tyr Pro Ser Thr Ala
945                 950                 955                 960
```

-continued

```
Ile Val Ser Val Lys Ala Asn Leu Thr His Gln Phe Arg Gln Thr Phe
            965                 970                 975

Asp Phe Pro Lys Ile Arg Glu Val Asn Asp Tyr His His Ala Phe Asp
            980                 985                 990

Ala Ala Leu Thr Ala Phe Ile Gly Thr Tyr Leu Leu Lys Arg Tyr Pro
            995                1000                1005

Lys Leu Glu Arg Phe Phe Val Tyr Gly Lys Phe Ala Lys Gln Pro
        1010                1015                1020

Val Asn Leu Thr Arg Phe Asn Val Ile Arg Lys Leu Ala Lys Thr
        1025                1030                1035

Asp Thr Pro Ile Thr Asp Ile Asp Thr Gly Glu Val Leu Trp Asp
        1040                1045                1050

Lys Leu Thr Asp Ile Lys Tyr Phe Glu Thr Leu Tyr Asp Tyr Lys
        1055                1060                1065

Arg Leu Leu Val Thr Arg Glu Val Ser Glu Asn Tyr Gly Ala Met
        1070                1075                1080

Phe Asp Gln Thr Leu Leu Lys Ala Ser Asp Asn Gly Lys Arg Leu
        1085                1090                1095

Ile Arg Lys Lys Gln Ser Phe Asp Thr Ala Ile Tyr Gly Gly Tyr
        1100                1105                1110

Thr Gly Lys Thr Leu Ala Tyr Met Ala Ile Val Lys Val Ser Thr
        1115                1120                1125

Lys Lys Asp Val Gln Tyr Gln Val Val Gly Val Pro Thr Thr Met
        1130                1135                1140

Val Thr Gln Ile Glu Gln Leu Glu Gln Gln Gly Met Thr Asn Lys
        1145                1150                1155

Gln Ala Val Thr Lys Val Ile Glu Pro Leu Ile Ala Ala Asn Asn
        1160                1165                1170

Lys Lys Met Leu Thr Tyr Glu Val Leu Pro Lys Val Arg Phe
        1175                1180                1185

Glu Gln Val Val Arg Asp Arg Ile Lys Gly Gln Thr His Arg Phe
        1190                1195                1200

Ala Leu Gly Thr Asp Thr Tyr Tyr His Asn Ile Gln Glu Leu Tyr
        1205                1210                1215

Leu Pro Leu Thr Leu Gln Arg Ala Phe Leu Gly Lys Gln Asn Glu
        1220                1225                1230

Ser Glu Val Gln Leu Asn Gln Asn Leu Leu Thr Val Phe Asp Ala
        1235                1240                1245

Thr Leu Ala Gln Val Asn Arg Tyr Phe Pro Leu Tyr Glu Met Asn
        1250                1255                1260

Lys Phe Lys Lys Ile Leu Asn Ser Ala Arg Asp Gln Ile Glu Leu
        1265                1270                1275

Leu Glu Ala Lys Asn Gln Phe Val Lys Asn Lys Leu Val Leu Gly
        1280                1285                1290

Lys Gln Gly Ile Leu Thr Asn Met Phe Ile Gly Leu His Ala Asn
        1295                1300                1305

Ala Ser Tyr Gly Asp Leu Lys Val Leu Gly Val Lys Ile Asp Phe
        1310                1315                1320

Gly Lys Leu Gln Val Pro Gly Gly Ile Lys Leu Thr Gly Asp Ala
        1325                1330                1335

Glu Ile Ile Tyr Gln Ser Pro Thr Gly Leu Phe Glu Arg Lys Ile
        1340                1345                1350

Ala Leu Lys Asp Leu
```

-continued

1355

<210> SEQ ID NO 41
<211> LENGTH: 1368
<212> TYPE: PRT
<213> ORGANISM: Lactobacillus reuteri mlc3

<400> SEQUENCE: 41

Met Ile Lys Lys Asp Tyr Asn Ile Gly Leu Asp Ile Gly Ala Thr Ser
1               5                   10                  15

Val Gly Phe Ala Gly Ile Asp Glu Gln Tyr Asp Pro Ile Lys Leu Lys
            20                  25                  30

Gly Lys Thr Val Val Gly Val Asn Leu Phe Glu Glu Gly Gln Thr Ala
        35                  40                  45

Ala Asp Arg Arg Ser Phe Arg Thr Thr Arg Arg Arg Leu Asn Arg Arg
    50                  55                  60

Lys Trp Arg Leu Ser Leu Leu Glu Glu Phe Phe Asp Pro Tyr Ile Thr
65                  70                  75                  80

Pro Val Asp Pro Ala Phe Phe Ala Arg Leu Lys Glu Ser Asn Leu Ser
                85                  90                  95

Pro Lys Asp Asn Lys Asn Phe Ser Arg Ser Leu Leu Phe Pro Asp
            100                 105                 110

Ile Thr Asp Gln Lys Phe Tyr Glu Glu Tyr Pro Thr Ile Tyr His Leu
        115                 120                 125

Arg Tyr Ala Leu Met Thr Glu Asn Lys Lys Phe Asp Leu Arg Ala Ile
    130                 135                 140

Phe Leu Ala Ile His His Met Ile Lys Tyr Arg Gly Asn Phe Leu Asn
145                 150                 155                 160

Ser Thr Pro Val Ala His Phe Asp Thr Ser Lys Ile Asp Phe Ala Asn
                165                 170                 175

Asp Phe Ser Lys Leu Asn Arg Leu Tyr Leu Asn Glu Asp Pro Asn Asn
            180                 185                 190

Ile Phe Glu Ile Asn Leu Gln Asn Val Lys Glu Ile Ser Asp Ile Leu
        195                 200                 205

Leu Asp His Ser Ile Lys Lys Phe Asp Lys Gln Lys Gln Val Ala Lys
    210                 215                 220

Leu Leu Leu Thr Ser Gln Asn Asp Lys Glu Leu Asp Lys Arg Asn Lys
225                 230                 235                 240

Gln Ile Ala Thr Gln Ile Ser Lys Ala Ile Leu Gly Tyr Asn Phe Ser
                245                 250                 255

Leu Asn Glu Ile Leu Lys Leu Glu Ala Val Asn Lys Ser Lys Trp Lys
            260                 265                 270

Leu Asn Phe Ser Ser Ala Asp Ile Asp Asp Thr Leu Pro Asp Leu Ile
        275                 280                 285

Ser Glu Leu Asp Glu Ser Gln Glu Ser Ile Leu Asn Ile Ile Leu Ser
    290                 295                 300

Leu Tyr Ser Arg Leu Thr Leu Asn Gly Ile Val Pro Ser Gly Met Ser
305                 310                 315                 320

Leu Ser Glu Ser Met Ile Asp Lys Tyr Gly Thr His Lys Glu His Leu
                325                 330                 335

Asp Leu Leu Lys Lys Tyr Leu Lys Thr Leu Pro Ile Lys Asn Arg Lys
            340                 345                 350

Glu Ile Ala Glu Ala Tyr Ala Glu Tyr Val Gly Asn Ser Leu Lys Lys
        355                 360                 365

```
Ser Gly His Ile Ser Gln Glu Glu Phe Tyr Lys Ala Val Lys Lys Asn
    370             375                 380

Leu Asp Lys Ser Glu Thr Ala Gln Lys Ile Leu Ser Leu Ile Ser Glu
385             390                 395                 400

Glu Lys Phe Met Pro Lys Gln Arg Thr Asn Gln Asn Gly Val Ile Pro
                405                 410                 415

Tyr Gln Leu His Gln Lys Glu Leu Asp Gln Ile Ile Val Asn Gln Ser
            420                 425                 430

Gln Tyr Tyr Pro Trp Leu Ala Glu Leu Asn Pro Val Thr Glu His Lys
        435                 440                 445

Asp Ala Lys Tyr Lys Leu Asp Glu Leu Ile Ala Phe Arg Val Pro Tyr
450                 455                 460

Tyr Val Gly Pro Leu Ile Asp Pro Lys Thr Ile Pro Gln Thr Glu Gln
465                 470                 475                 480

Gly Asn Lys Asn Ala Ser Phe Ala Trp Met Val Arg Lys Glu Asn Gly
                485                 490                 495

Gln Ile Thr Pro Trp Asn Phe Asp Lys Lys Val Asp Arg Ile Ser Ser
                500                 505                 510

Ala Asn Asn Phe Ile Lys Arg Met Thr Thr Lys Asp Thr Tyr Leu Ile
                515                 520                 525

Gly Glu Asp Val Leu Pro Ala His Ser Leu Ile Tyr Glu Arg Phe Lys
530                 535                 540

Val Leu Asn Glu Leu Asn Met Ile Arg Val Asn Gly Lys Lys Leu Ser
545                 550                 555                 560

Val Ser Val Lys Gln Asn Leu Tyr Asn Asp Leu Phe Lys Gln Gln Lys
                565                 570                 575

Thr Ile Asn Arg Lys Lys Leu Ala Asn Tyr Leu Gln Ala Asn Leu Gly
                580                 585                 590

Ile Pro Glu Arg Pro Gln Ile Thr Gly Leu Ser Asp Pro Glu Lys Phe
                595                 600                 605

Asn Ser Gln Leu Ser Ser Tyr Ile Asp Leu Gln Lys Ile Leu Gly Ser
            610                 615                 620

Glu Ile Val Asp Asp Pro Asn Lys Gln Asp Asp Leu Glu Lys Ile Ile
625                 630                 635                 640

Glu Trp Ser Thr Val Phe Glu Asp Ser Arg Ile Tyr Lys Val Lys Leu
                645                 650                 655

Gln Glu Ile Gly Trp Phe Thr Glu Lys Gln Lys Asn Glu Leu Val Ser
                660                 665                 670

His Arg Tyr Gln Gly Trp Gly Arg Leu Ser Lys Lys Leu Leu Val Glu
            675                 680                 685

Leu Lys Asp Lys Asn Gly Arg Ser Ile Ile Asp Leu Leu Trp Asn Ser
            690                 695                 700

Gln Arg Thr Phe Met Glu Ile Gln Ser Arg Pro Glu Phe Ala Glu Gln
705                 710                 715                 720

Ile Thr Asn Glu Asn Gln Asp Lys Leu Thr Glu Asp Asn Tyr Glu Asp
                725                 730                 735

Val Leu Ala Asp Ala Tyr Thr Ser Pro Gln Asn Lys Lys Ala Ile Arg
                740                 745                 750

Gln Val Ile Lys Val Val Asp Asp Ile Val Lys Ala Thr Gly Lys Ala
                755                 760                 765

Pro Lys Phe Ile Ser Leu Glu Phe Ala Arg Ser Asp Glu Arg Ser Asp
            770                 775                 780

Arg Val Lys Ser Arg Lys Thr His Ile Gln Lys Ile Tyr Glu Thr Thr
```

-continued

```
               785                 790                 795                 800
Ala Lys Glu Leu Leu Lys Asp Asp Gln Leu Ile Lys Glu Leu Gly Ser
                805                 810                 815

Val Ser Asp Leu Ser Asp Arg Leu Tyr Leu Tyr Phe Thr Gln Leu Gly
                820                 825                 830

Arg Asp Met Tyr Thr Gly Lys Pro Ile Asn Ile Asp Glu Ile Ser Thr
                835                 840                 845

Met Tyr Asp Ile Asp His Ile Leu Pro Gln Ala Phe Leu Lys Asp Asp
    850                 855                 860

Ser Leu Asp Asn Arg Val Leu Arg Arg Gln Asp Asn Asn Ala Lys
865                 870                 875                 880

Ser Asp Thr Val Pro Ala Leu Lys Phe Gly Lys Met Lys Pro Phe Trp
                885                 890                 895

Asn Lys Leu Gln Lys His Gly Leu Ile Ser Lys Arg Lys Leu Asn Asn
                900                 905                 910

Leu Gln Thr Asn Pro Glu Ser Ile Asp Lys Phe Lys Ala Val Gly Phe
            915                 920                 925

Val Asn Arg Gln Leu Val Glu Thr Arg Gln Val Ile Lys Leu Ala Ala
    930                 935                 940

Asn Ile Leu Ala Ser Arg Tyr Pro Asp Ser Lys Ile Ile Glu Val Lys
945                 950                 955                 960

Ala Ser Leu Thr His Gln Met Arg Glu Ser Phe Asn Leu Ile Lys Asn
                965                 970                 975

Arg Asp Val Asn Asp Tyr His His Ala Val Asp Ala Tyr Leu Ser Ala
                980                 985                 990

Phe Val Gly Gln Tyr Leu Tyr Asn  Arg Tyr Pro Lys Leu  Gln Pro Tyr
            995                 1000                1005

Phe Val  Tyr Gly Gln Phe Lys  Lys Phe Asp Lys Gln  Ser Thr Arg
        1010                1015                1020

Ile Gly  Met Lys Thr Asn His  Phe Asn Phe Leu Tyr  Asp Leu Glu
        1025                1030                1035

Pro Glu  Gly Lys Asn Val Lys  Ile Lys Lys Pro Thr  Lys Ile Ile
        1040                1045                1050

Asn Lys  Glu Thr Gly Glu Ile  Ile Gly Asp Arg Asp  Glu Leu Val
        1055                1060                1065

Ala Lys  Leu Asn Arg Val Tyr  Asn Phe Lys Tyr Met  Leu Val Ser
        1070                1075                1080

Gln Glu  Val Tyr Thr Arg Ser  Gly Ala Leu Phe Asp  Gln Thr Ile
        1085                1090                1095

Tyr Pro  Ala Asn Ser Gly Lys  Lys Leu Ile Pro Leu  Lys Gln Asn
        1100                1105                1110

Lys Thr  Thr Ala Ile Tyr Gly  Gly Tyr Ser Gly Ser  Lys Ala Ala
        1115                1120                1125

Tyr Met  Ser Ile Ile Arg Leu  Arg Asp Lys Lys Gly  Gly Thr Tyr
        1130                1135                1140

Arg Ile  Val Gly Ile Pro Val  Arg Ala Val Asn Lys  Leu Asn Gln
        1145                1150                1155

Ala Lys  Lys Lys Ser Asn Glu  Lys Tyr Leu Ala Glu  Leu Lys Ala
        1160                1165                1170

Val Ile  Glu Pro Gln Ile Ala  Lys Thr Lys Lys Asp  Arg Lys Thr
        1175                1180                1185

Gly Gln  Arg Val Leu Val Pro  Gln Glu Phe Asp Val  Ile Ile Pro
        1190                1195                1200
```

```
Glu Val Met Tyr Arg Gln Leu Ile Val Asp Gly Asp Gln Lys Phe
    1205                1210                1215

Thr Leu Gly Gly Thr Ile Asp Arg Tyr Asn Ala Val Gln Leu Val
    1220                1225                1230

Leu Asn Gln Glu Ile Leu Thr Phe Leu Glu Gln Pro Thr Lys Tyr
    1235                1240                1245

Lys Asp Ala Asp Thr Lys Leu Leu Asp Ile Tyr Asp Gln Ile Val
    1250                1255                1260

Asn Leu Val Glu Lys Tyr Phe Met Leu Phe Asp Ser Lys Arg Leu
    1265                1270                1275

Ala Ala Gly Arg Val Ala Phe Glu Lys Leu Pro Thr Leu Gln Pro
    1280                1285                1290

Val Asp Lys Met Pro Ser Lys Leu Ile Ile Ile Arg Arg Ile Ile
    1295                1300                1305

Gln Gly Leu His Asp Asn Ala Ala Arg Thr Asp Leu Lys Ala Ile
    1310                1315                1320

Asn Gly Ser Ser Ser Phe Gly Arg Leu Gln Lys Arg Asn Gly Ile
    1325                1330                1335

Ile Leu Ser Pro Asn Ala Cys Leu Ile Tyr Gln Ser Pro Thr Gly
    1340                1345                1350

Leu Phe Glu Arg Lys Val Tyr Leu Asn Thr Ile Ser Pro Leu Lys
    1355                1360                1365

<210> SEQ ID NO 42
<211> LENGTH: 1361
<212> TYPE: PRT
<213> ORGANISM: Lactobacillus rhamnosus GG

<400> SEQUENCE: 42

Met Thr Lys Leu Asn Gln Pro Tyr Gly Ile Gly Leu Asp Ile Gly Ser
1               5                   10                  15

Asn Ser Ile Gly Phe Ala Val Val Asp Ala Asn Ser His Leu Leu Arg
                20                  25                  30

Leu Lys Gly Glu Thr Ala Ile Gly Ala Arg Leu Phe Arg Glu Gly Gln
            35                  40                  45

Ser Ala Ala Glu Arg Arg Glu Ser Arg Thr Thr Arg Arg Arg Leu Ser
        50                  55                  60

Arg Thr Arg Trp Arg Leu Ser Phe Leu Arg Asp Phe Phe Ala Pro His
65                  70                  75                  80

Ile Thr Lys Ile Asp Pro Asp Phe Phe Leu Arg Gln Lys Tyr Ser Glu
                85                  90                  95

Ile Ser Pro Lys Asp Lys Asp Arg Phe Lys Tyr Glu Lys Arg Leu Phe
            100                 105                 110

Asn Asp Arg Thr Asp Ala Glu Phe Tyr Glu Asp Tyr Pro Ser Met Tyr
        115                 120                 125

His Leu Arg Leu His Leu Met Thr His Thr His Lys Ala Asp Pro Arg
    130                 135                 140

Glu Ile Phe Leu Ala Ile His His Ile Leu Lys Ser Arg Gly His Phe
145                 150                 155                 160

Leu Thr Pro Gly Ala Ala Lys Asp Phe Asn Thr Asp Lys Val Asp Leu
                165                 170                 175

Glu Asp Ile Phe Pro Ala Leu Thr Glu Ala Tyr Ala Gln Val Tyr Pro
            180                 185                 190

Asp Leu Glu Leu Thr Phe Asp Leu Ala Lys Ala Asp Asp Phe Lys Ala
```

```
            195                 200                 205
Lys Leu Leu Asp Glu Gln Ala Thr Pro Ser Asp Thr Gln Lys Ala Leu
        210                 215                 220

Val Asn Leu Leu Leu Ser Ser Asp Gly Glu Lys Glu Ile Val Lys Lys
225                 230                 235                 240

Arg Lys Gln Val Leu Thr Glu Phe Ala Lys Ala Ile Thr Gly Leu Lys
            245                 250                 255

Thr Lys Phe Asn Leu Ala Leu Gly Thr Glu Val Asp Glu Ala Asp Ala
        260                 265                 270

Ser Asn Trp Gln Phe Ser Met Gly Gln Leu Asp Asp Lys Trp Ser Asn
            275                 280                 285

Ile Glu Thr Ser Met Thr Asp Gln Gly Thr Glu Ile Phe Glu Gln Ile
        290                 295                 300

Glu Glu Leu Tyr Arg Ala Arg Leu Leu Asn Gly Ile Val Pro Ala Gly
305                 310                 315                 320

Met Ser Leu Ser Gln Ala Lys Val Ala Asp Tyr Gly Gln His Lys Glu
            325                 330                 335

Asp Leu Glu Leu Phe Lys Thr Tyr Leu Lys Lys Leu Asn Asp His Glu
        340                 345                 350

Leu Ala Lys Thr Ile Arg Gly Leu Tyr Asp Arg Tyr Ile Asn Gly Asp
            355                 360                 365

Asp Ala Lys Pro Phe Leu Arg Glu Asp Phe Val Lys Ala Leu Thr Lys
        370                 375                 380

Glu Val Thr Ala His Pro Asn Glu Val Ser Glu Gln Leu Leu Asn Arg
385                 390                 395                 400

Met Gly Gln Ala Asn Phe Met Leu Lys Gln Arg Thr Lys Ala Asn Gly
            405                 410                 415

Ala Ile Pro Val Gln Leu Gln Gln Arg Glu Leu Asp Gln Ile Ile Ala
        420                 425                 430

Asn Gln Ser Lys Tyr Tyr Asp Trp Leu Ala Lys Pro Asn Pro Val Glu
            435                 440                 445

Lys His Arg Ala Ser Lys Pro Tyr Gln Leu Asp Glu Leu Leu Thr Phe
        450                 455                 460

Arg Ile Pro Tyr Tyr Val Gly Pro Leu Ile Thr Pro Lys Glu Gln Ala
465                 470                 475                 480

Glu Ser Arg Glu Asn Val Phe Ala Trp Met Ile Arg Lys Asp Pro Ser
            485                 490                 495

Gly Asn Ile Thr Pro Tyr Asn Phe Asp Glu Lys Val Asp Cys Pro Ala
        500                 505                 510

Ser Ala Asn Met Phe Ile Gln Arg Met Lys Asn Thr Asp Thr Tyr Leu
            515                 520                 525

Ile Gly Glu Asp Val Leu Pro Lys Arg Ser Leu Leu Tyr Gln Lys Tyr
        530                 535                 540

Glu Val Leu Asn Glu Leu Asn Asn Val Ser Ile Asp Gly Arg Arg Leu
545                 550                 555                 560

Gly Ala Asp Gln Lys Gln Arg Leu Ile Arg Glu Val Phe Glu Arg His
            565                 570                 575

Ser Ser Val Thr Ile Lys Gln Val Ala Glu Asn Leu Val Ala His Gly
        580                 585                 590

Asp Phe Ala Lys Arg Pro Glu Ile Arg Gly Leu Ala Asp Glu Lys Arg
            595                 600                 605

Phe Leu Ser Ser Leu Ser Thr Tyr His Gln Leu Lys Lys Ile Leu His
        610                 615                 620
```

```
Glu Ala Ile Asp Asp Pro Thr Lys Glu His Asp Ile Glu Asn Ile Ile
625                 630                 635                 640

Thr Trp Ser Thr Val Phe Glu Asp Ala Ala Ile Phe Lys Thr Glu Leu
                645                 650                 655

Ala Lys Ile Ser Trp Leu Asp Ser Asp Thr Ile Lys Ala Leu Ser Asn
            660                 665                 670

Ile Arg Tyr Arg Gly Trp Gly Gln Phe Ser Arg Lys Leu Leu Asp Gly
        675                 680                 685

Leu Lys Leu Gly Asn Gly His Thr Val Ile Gln Glu Leu Met Leu Ser
690                 695                 700

Asn His Asn Leu Met Gln Ile Leu Thr Asp Glu Thr Leu Lys Thr Thr
705                 710                 715                 720

Met Ala Glu Leu Asn Gln Asp Lys Leu Lys Ala Asp Asp Ile Glu Asp
                725                 730                 735

Val Ile Asn Asp Ala Tyr Thr Ser Pro Ser Asn Lys Lys Ala Leu Arg
            740                 745                 750

Gln Val Leu Arg Val Val Glu Asp Ile Lys His Ala Ala Asn Gly Gln
        755                 760                 765

Asp Pro Ser Trp Leu Tyr Ile Glu Thr Ala Asp Gly Pro Gly Thr Ala
770                 775                 780

Gly Lys Arg Thr Gln Ser Arg Gln Lys Gln Ile Gln Thr Val Tyr Ala
785                 790                 795                 800

Asn Ala Ala Gln Glu Leu Ile Asp Ser Ala Val Arg Gly Glu Leu Glu
                805                 810                 815

Asp Lys Ile Ala Asp Lys Ala Ser Phe Thr Asp Arg Leu Val Leu Tyr
            820                 825                 830

Phe Met Gln Gly Gly Arg Asp Ile Tyr Thr Gly Ala Pro Leu Asn Ile
        835                 840                 845

Asp Gln Leu Ser His Tyr Asp Ile Asp His Ile Leu Pro Gln Ser Leu
850                 855                 860

Ile Lys Asp Asp Ser Leu Asp Asn Arg Val Leu Val Asn Ala Thr Ile
865                 870                 875                 880

Asn Arg Glu Lys Asn Asn Val Phe Ala Ser Thr Leu Phe Ala Ser Lys
                885                 890                 895

Met Ala Ala Thr Trp Arg Lys Trp His Glu Ala Gly Leu Ile Ser Gly
            900                 905                 910

Arg Lys Leu Arg Asn Leu Met Leu Arg Pro Asp Glu Ile Asp Lys Phe
        915                 920                 925

Ala His Gly Phe Val Ala Arg Gln Leu Val Glu Thr Arg Gln Ile Ile
930                 935                 940

Lys Leu Thr Glu Gln Ile Ala Ala Gln Tyr Pro Asn Thr Lys Ile
945                 950                 955                 960

Ile Ala Val Lys Ala Gly Leu Ser His Gln Leu Arg Glu Glu Leu Asp
                965                 970                 975

Phe Pro Lys Asn Arg Asp Val Asn His Tyr His Ala Phe Asp Ala
            980                 985                 990

Phe Leu Ala Ala Arg Ile Gly Thr Tyr Leu Leu Lys Arg Tyr Pro Lys
        995                 1000                1005

Leu Ala Pro Phe Phe Thr Tyr Gly Glu Phe Ala Lys Val Asp Val
        1010                1015                1020

Lys Lys Phe Arg Glu Phe Asn Phe Ile Gly Ala Leu Thr His Ala
        1025                1030                1035
```

-continued

```
Lys Lys Asn Ile Val Ala Lys Asp Thr Gly Glu Ile Val Trp Asp
    1040                1045                1050

Lys Glu Arg Asp Ile Gln Glu Leu Asp Arg Ile Tyr Asn Phe Lys
    1055                1060                1065

Arg Met Leu Ile Thr His Glu Val Tyr Phe Glu Thr Ala Asp Leu
    1070                1075                1080

Phe Lys Gln Thr Ile Tyr Ala Ala Lys Asp Ser Lys Glu Arg Gly
    1085                1090                1095

Gly Ser Lys Gln Leu Ile Pro Lys Lys Gln Gly Tyr Pro Thr Gln
    1100                1105                1110

Val Tyr Gly Gly Tyr Thr Arg Glu Asn Thr Ala Tyr Leu Ala Val
    1115                1120                1125

Val Lys Thr Val Glu Lys Lys Ala Asp Val Tyr Arg Val Val Arg
    1130                1135                1140

Ile Ala Thr Ser Gln Val Ala Ala Leu Lys Glu Ala Arg Ala Gln
    1145                1150                1155

Ser Thr Val Lys Glu Arg Glu Leu Leu Lys Lys Phe Leu Thr Thr
    1160                1165                1170

Lys Phe Thr Lys Ile Gly Lys Asn Gly Lys Lys Ala Ile Thr Pro
    1175                1180                1185

Phe Asp Ile Val Ile Pro Arg Val Pro Arg Glu Gln Leu Phe His
    1190                1195                1200

Asn Lys Arg Tyr Gly Phe Phe Met Val Asn Ser Asp Thr Leu Met
    1205                1210                1215

His Asn Tyr Gln Glu Leu Trp Met Ser Arg Ser Asp Gln Gln Ile
    1220                1225                1230

Leu Ser Lys Leu Val Lys Ser Ala Lys Thr Val Glu Asn Gly Gln
    1235                1240                1245

Val Gly Arg Leu Phe Glu Asn Ile Val Glu Gln Ile Asn Lys Tyr
    1250                1255                1260

Phe Pro Leu Tyr Asp Ile Asn Gln Phe Arg Lys Lys Leu Asp Gln
    1265                1270                1275

Ser Lys Asp Ile Phe Ser Lys Leu Pro Leu Glu Gly Asn Gly Thr
    1280                1285                1290

Thr Ser Gly Lys Arg Glu Thr Ile Gln Asn Ile Leu Thr Gly Ala
    1295                1300                1305

Gly Thr Gly Ala Lys Asn Gly Asp Leu Lys Asn Leu Gly Ile Lys
    1310                1315                1320

Thr Pro Phe Gly Phe Leu Gln Val Pro Ser Gly Ile Val Leu Asp
    1325                1330                1335

Asp Asp Thr Thr Leu Ile Tyr Gln Ser Pro Thr Gly Met Leu Asn
    1340                1345                1350

Arg Ile Val Arg Leu Ser Glu Leu
    1355                1360

<210> SEQ ID NO 43
<211> LENGTH: 1369
<212> TYPE: PRT
<213> ORGANISM: Lactobacillus rossiae DSM 15814

<400> SEQUENCE: 43

Met Asp Lys Ser Lys Pro Tyr Gly Ile Gly Leu Asp Ile Gly Thr Asn
1               5                   10                  15

Ser Val Gly Phe Val Ala Thr Asp Ala Glu Gly His Leu Ile Arg Leu
            20                  25                  30
```

Lys Gly Lys Thr Val Ile Gly Ala Tyr Leu Phe Asn Ala Gly Ile Ser
    35                  40                  45

Ala Ala Glu Arg Arg Gly Phe Arg Thr Thr Arg Arg Leu Ser Arg
50                  55                  60

Val Lys Trp Arg Leu Gly Leu Leu Arg Glu Ile Phe Glu Thr His Phe
65                  70                  75                  80

Gln Glu Ser Met Gly Glu Asn Glu Asp Asn Asp Phe Phe Leu Arg Phe
                85                  90                  95

Lys Tyr Ser Asn Ile Ser Pro Lys Asp Pro Gln Phe Ser Thr Ala Lys
                100                 105                 110

Gly Leu Phe Asn Asp Arg Thr Asp Lys Glu Phe Tyr Asp Gln Tyr Pro
                115                 120                 125

Thr Ile Tyr His Leu Arg Arg Ala Leu Met Thr Glu Asp His Gln Phe
            130                 135                 140

Asp Ile Arg Glu Ile Tyr Ile Ala Met His His Ile Val Lys Tyr Arg
145                 150                 155                 160

Gly His Phe Leu Lys Glu Gly Arg Ala Lys Asp Phe Lys Val Gly Asp
                165                 170                 175

Leu Arg Leu Leu Asp Asn Phe Lys Met Met Asn Glu Gln Ile Glu Glu
            180                 185                 190

Ile Asn Pro Leu Trp Gln Leu Lys Leu Pro Thr Asp Asp Ala Ser Ile
                195                 200                 205

Lys Ser Ile Thr Ala Ile Leu Leu Asp Asn Thr Gln Ser Gln Asn Asp
210                 215                 220

Arg Gln Lys Ala Val Thr Lys Val Ile Leu Ala Thr Leu Val Lys Ala
225                 230                 235                 240

Ser Asp Lys Asp Ile Asn Ala Ala Arg Lys Arg Phe Val Gly Glu Leu
                245                 250                 255

Ser Lys Ala Met Val Gly Leu Lys Thr Lys Leu Trp Val Leu Ala Asp
                260                 265                 270

Val Ser Gln Asn Gly Asp Trp Glu Ile Lys Tyr Glu Asn Tyr Ala Asp
            275                 280                 285

Phe Ala Glu Thr Ile Gly Ser Gly Glu Ser Asp Thr Ile Gln Ser Leu
290                 295                 300

Phe Asn Glu Ile Asn Asp Leu Tyr Gly Val Ile Thr Leu Ala Gly Ile
305                 310                 315                 320

Ile Pro Lys Glu Ala Glu Ser Phe Ser Asp Gly Met Val Arg Lys Tyr
                325                 330                 335

Glu His His Arg Lys Asn Leu Glu Leu Leu Lys Val Tyr Cys Ala Glu
            340                 345                 350

Gln Ser Asp Gly Lys Arg Gly Arg Gln Ile Arg Gln Thr Tyr Asp Lys
            355                 360                 365

Tyr Ile Asp Gly Val Asp Ser Lys Gln Phe Thr Gln Glu Asp Phe Tyr
370                 375                 380

Lys Ala Leu Ser Lys Phe Thr Ala Lys Asp Glu Ala Thr Ser Glu Asn
385                 390                 395                 400

Ala Lys Leu Ile Ala Gln Glu Ile Ala Val Gly Thr Phe Met Pro Lys
                405                 410                 415

Leu Arg Thr Lys Ala Asn Gly Thr Ile Pro His Gln Leu His Gln Lys
            420                 425                 430

Glu Leu Asp Ala Ile Ile Glu Asn Gln Lys Lys Tyr Tyr Pro Trp Leu
            435                 440                 445

```
Gly Glu Val Asn Pro Val Glu Ser His Arg Arg Ala Leu Pro Tyr Lys
            450                 455                 460

Leu Asp Glu Leu Val Ser Phe Arg Ile Pro Tyr Tyr Val Gly Pro Met
465                 470                 475                 480

Val Thr Pro Thr Lys Gly Asp Pro Glu Lys Ser Lys Phe Ala Trp Met
                485                 490                 495

Val Arg Lys Glu Pro Gly Thr Ile Thr Pro Trp Asn Phe Asp Gln Lys
            500                 505                 510

Val Asp Arg Ser Ala Ser Gly Glu Ala Phe Ile Gln Arg Met Lys Thr
            515                 520                 525

Thr Asp Thr Phe Leu Ile Gly Glu Asp Val Leu Pro Gln Gln Ser Leu
530                 535                 540

Leu Tyr Gln Lys Phe Glu Val Leu Asn Glu Leu Asn Lys Ile Met Ile
545                 550                 555                 560

Asn Gly Lys Pro Ile Cys Arg Glu Gln Lys Gln Arg Leu Phe Lys Gln
                565                 570                 575

Leu Phe Met Gln Tyr Lys Thr Val Thr Val Lys Val Gln Gln Asn
            580                 585                 590

Leu Ile Ala Asn Gly Glu Glu Ser Glu Asn Val Pro Ile Thr Gly Leu
595                 600                 605

Ser Asp Pro Leu Arg Phe Asn Ser Ser Phe Ser Thr Tyr Ile Asp Tyr
            610                 615                 620

Lys Asp Ile Leu Gly Thr Ala Ala Val Asn Asp Asn Ala Lys Gln Ser
625                 630                 635                 640

Asp Ile Glu Gln Ile Ile Ala Trp Ser Thr Ile Phe Glu Asp Ala Ala
                645                 650                 655

Ile Phe Arg Glu Lys Leu Asn Asp Ile Thr Trp Leu Asn Asp Asp Gln
            660                 665                 670

Arg Asn Lys Leu Ser His Lys Arg Tyr Arg Gly Trp Gly Arg His Ser
            675                 680                 685

Arg Lys Leu Leu Ala Gly Leu Arg Asp Gly Glu Gly Gln Thr Ile Ile
            690                 695                 700

Glu Arg Leu Trp Asn Thr Asn Asp Asn Phe Met Gln Ile Gln Asn Asp
705                 710                 715                 720

Ser Glu Ile Ala Arg Gln Ile Thr Glu Ala Asn Ser Ser Lys Met Ala
                725                 730                 735

Thr Ala Glu Gly Thr Asp Glu Ile Ile Asp Gly Phe Tyr Thr Ser Pro
                740                 745                 750

Glu Asn Lys Lys Ala Leu Arg Glu Val Met Lys Val Lys Asp Ile
            755                 760                 765

Gln Arg Ala His His Gly Gln Ala Pro Ala Trp Val Tyr Ile Glu Ser
770                 775                 780

Pro Arg Glu Thr Pro Arg Pro Gly Gln Arg Thr Val Ser Arg Glu Gln
785                 790                 795                 800

Gln Leu Thr Asp Leu Tyr Glu Gly Ala Ala Lys Glu Ile Val Asp Asp
                805                 810                 815

Ala Val Leu Asn Glu Leu Lys Asp Lys Val Lys Ser Lys Glu Asn Phe
                820                 825                 830

Thr Asp Lys Leu Val Leu Tyr Phe Leu Gln Asn Gly His Asp Ile Tyr
            835                 840                 845

Ala Asn Asp Ser Ile Asn Ile Asp Asn Leu Asn Ala Tyr Asp Ile Asp
850                 855                 860

His Val Leu Pro Gln Ser Leu Ile Lys Asp Asp Ser Leu Asp Asn Arg
```

-continued

```
              865                 870                 875                 880
Val Leu Thr Thr His Glu Arg Asn Leu Lys Lys Ser Asn Arg Phe Ala
                    885                 890                 895
Thr Glu Leu Phe Ala Asp Gln Arg Lys Lys Trp Glu Lys Trp His Arg
                    900                 905                 910
Leu Gly Leu Ile Ser Ser Arg Lys Leu Lys His Leu Thr Met Gln Pro
                    915                 920                 925
Asn Ser Val Glu Lys Phe Ala His Gly Phe Ile Ala Arg Gln Leu Thr
                    930                 935                 940
Glu Thr Arg Gln Ile Ile His Leu Thr Ala Asn Val Leu Ser Asn Leu
945                 950                 955                 960
Tyr Gln Glu Asn Asp Thr Lys Ile Val Met Ile Lys Ala Gly Leu Asn
                    965                 970                 975
Ser Glu Phe Arg Arg Thr Phe Asp Phe Pro Lys Asn Arg Ser Val Asn
                    980                 985                 990
Asp Tyr His His Ala Phe Asp Ala Phe Leu Thr Ala Lys Ile Gly Arg
                    995                1000                1005
Tyr Leu Leu Ala Arg Tyr Pro Lys Leu Glu Pro Phe Phe Val Tyr
1010                1015                1020
Gly Asn Phe Val Lys Asn Pro Lys Ala Met Lys Arg Leu Ser Ser
1025                1030                1035
Phe Asp Phe Ile Ala Gln Leu Ala Ala Lys Thr Asp Asp Thr Ser
1040                1045                1050
His Ile Asp Gln Arg Ser Leu Lys Gln Val Pro Val Val Asn Glu
1055                1060                1065
Glu Thr Gly Glu Ile Val Trp Asp Lys Asp Ile Glu Leu Ala Glu
1070                1075                1080
Leu Asp Lys Thr Tyr Asn Tyr Lys Thr Met Leu Val Lys Arg Ala
1085                1090                1095
Gln Thr Glu Asn Asn Ala Gln Met Phe Lys Gln Thr Val Phe Lys
1100                1105                1110
Ala Arg Asp Asn Gln Asn Lys Thr Leu Ile Pro Val Lys Asn Gly
1115                1120                1125
Leu Ser Thr Asp Val Tyr Gly Gly His Ser Gln Gln Ala Ile Ser
1130                1135                1140
Tyr Leu Cys Ile Val Trp Val Gly Gln Lys Lys Tyr Arg Val
1145                1150                1155
Leu Gly Ile Ser Thr Ala His Ala Gly Ile Leu Asn Asn Phe Glu
1160                1165                1170
Lys Asn Tyr Gly Arg Phe Glu Ala Lys Lys Leu Gln Glu Ile
1175                1180                1185
Val Ser Asn Thr Leu Asp Asn Ala Asp Arg Asn Asp Phe Lys Ile
1190                1195                1200
Val Ala Pro Lys Val Leu Phe Glu Gln Val Val Glu Asp Asp Asn
1205                1210                1215
Met Lys Phe Gly Leu Gly Ser Ala Ser Asp Tyr Arg Asn Val Gln
1220                1225                1230
Gln Leu Phe Leu Ser Arg Lys Asn Gln Leu Leu Leu Ala Asn Met
1235                1240                1245
Met Thr Asp Gln Ile His Asp Gln Asp Leu Val His Leu Phe Asp
1250                1255                1260
Glu Ile Val Gly Gln Met Asn Ala His Phe Pro Ile Phe Asp Arg
1265                1270                1275
```

```
Gly Gly Tyr Arg Ser Ser Leu Thr Gln Ser Arg Asp Lys Phe Leu
        1280            1285            1290

Lys Leu Pro Phe Lys Lys Asn Glu Asp Leu Ile Thr Lys Gln Glu
    1295            1300            1305

Val Ile Arg Arg Ile Leu Asp Gly Leu His Ala Asn Ala Asn Arg
    1310            1315            1320

Lys Asp Leu Lys Ile Ile Gly Ser Lys Gly Asp Phe Gly Arg Leu
    1325            1330            1335

Gly Thr Lys Lys Ile Tyr Leu Ser Lys Asp Ala Lys Leu Ile Tyr
    1340            1345            1350

Thr Ser Pro Thr Cys Leu Phe Thr Arg Thr Val Pro Leu Ser Ser
    1355            1360            1365

Leu

<210> SEQ ID NO 44
<211> LENGTH: 1375
<212> TYPE: PRT
<213> ORGANISM: Lactobacillus ruminis ATCC 25644

<400> SEQUENCE: 44

Met Arg Lys Asn Gln Glu Pro Tyr Asn Ile Gly Leu Asp Ile Gly Thr
1               5                   10                  15

Ser Ser Ile Gly Trp Ser Ile Met Asn Asp Asn Phe Asp Leu Met Arg
            20                  25                  30

Val Lys Gly Lys Lys Gly Ile Gly Val Arg Leu Tyr Asn Glu Gly Gln
        35                  40                  45

Ser Ala Ala Glu Arg Arg Met His Arg Thr Ala Arg Arg Arg Tyr Gly
    50                  55                  60

Arg Arg Lys Trp Arg Leu Arg Leu Leu Glu Asp Phe Phe Asp Glu His
65                  70                  75                  80

Met Ala Glu Val Asp Asp Thr Phe Phe Ala Arg Leu Lys Asp Ser Asn
                85                  90                  95

Ile Ser Pro Lys Asp Asp Lys Lys Tyr Arg Lys Ser Leu Leu Phe Pro
            100                 105                 110

Lys Ser Lys Gly Val Thr Tyr Gln Asp Asp Gly Glu Phe Tyr Lys Lys
        115                 120                 125

Tyr Pro Thr Met Tyr His Leu Arg Tyr Ala Leu Met Thr Glu His Arg
    130                 135                 140

Lys Phe Asp Leu Arg Glu Ile Tyr Leu Ala Phe His His Met Val Lys
145                 150                 155                 160

Tyr Arg Gly Asn Phe Leu Tyr Asp Thr Ser Val Asp Ser Phe Glu Ala
                165                 170                 175

Lys Asn Leu Asp Ile Lys Gly Lys Phe Asp Glu Ile Asn Asp Leu Leu
            180                 185                 190

Ser Ser Tyr Thr Asp Phe Tyr Val Asp Asn Ser Asn Ala Ala Leu Val
        195                 200                 205

Glu Ser Ile Leu Leu Glu Lys Asn Thr Thr Arg Lys Asp Lys Ser Lys
    210                 215                 220

Lys Ile Ala Lys Leu Leu His Val Glu Asp Lys Glu Lys Gly Lys Asn
225                 230                 235                 240

Lys Lys Ala Lys Asp Leu Ala Thr Gln Ile Ser Asn Ala Val Leu Gly
                245                 250                 255

Leu Lys Cys Asn Phe His Leu Ile Phe Glu Leu Gln Gln Lys Tyr Ser
            260                 265                 270
```

```
Phe Asp Leu Cys Ser Glu Lys Thr Glu Glu Asn Ile Ala Lys Leu Ser
        275                 280                 285

Glu Val Leu Asp Glu Asn Gln Lys Met Leu Leu Met Ile Leu Lys Glu
    290                 295                 300

Val Gln Asp Gln Val Met Leu Asn Ala Phe Val Pro Ser Gly Met Ser
305                 310                 315                 320

Leu Ser Glu Ala Met Met Gln Lys Tyr Asp Asp Tyr Gly Glu Gln Leu
                325                 330                 335

Lys Ile Tyr His Glu Leu Glu His Ser Val Ser Asp Asp Ser Ala Ala
            340                 345                 350

Lys Leu Arg Gly Ala Tyr Arg Asp Tyr Asn Asp Asn Ile Ile Lys Arg
        355                 360                 365

Ile Asp Gly Asp Asn Lys Lys Asp Thr Phe Tyr Lys Arg Val Lys Asn
    370                 375                 380

Ile Leu Thr Lys Ile Ser Lys Glu Tyr Val Asp Gln Asp Val Leu Glu
385                 390                 395                 400

Ser Cys Gly Lys Leu Lys Lys Leu Ile Asp Glu Asn Lys Leu Phe Ile
                405                 410                 415

Arg Gln Arg Thr Ala Ala Asn Gly Val Leu Pro His Gln Leu His Gln
            420                 425                 430

Ile Glu Met Arg Lys Ile Ile Asp Asn Gln Lys Glu Tyr Tyr Pro Trp
        435                 440                 445

Leu Ala Glu Pro Asn Pro Asn Glu Lys Arg Arg Val Tyr Ser Lys Tyr
    450                 455                 460

Lys Val Glu Glu Leu Ile Ala Phe Arg Ile Pro Tyr Tyr Val Gly Pro
465                 470                 475                 480

Leu Val Asp Pro Asn Asn Ala Asp Lys Asn Lys Glu Ala Arg Phe Ser
                485                 490                 495

Trp Met Val Arg Lys Asp Gly Glu Ile Thr Pro Trp Asn Phe Tyr
            500                 505                 510

Asp Lys Val Asp Trp Ala Glu Ser Ala Asn Asn Phe Ile Glu Arg Met
        515                 520                 525

Lys Ser Lys Asp Thr Tyr Leu Leu Gly Glu Asp Val Val Pro Lys Glu
    530                 535                 540

Ser Met Leu Tyr Gln Lys Tyr Glu Val Leu Asn Glu Leu Asn Asn Leu
545                 550                 555                 560

Arg Ile Asn Asp Ser Gly Leu Ser Asp Ser Phe Glu Asp Val Lys Leu
                565                 570                 575

Lys Gln Ala Ile Tyr Asn Asp Leu Phe Lys Lys Gln Lys Ile Val Lys
            580                 585                 590

Ile Thr Asp Leu Gln Asn Tyr Leu Val Gln Asn His Lys Tyr Leu Val
        595                 600                 605

Lys Pro Lys Ile Ser Gly Leu Ala Asp Glu Asn Arg Phe Leu Ser Ser
    610                 615                 620

Leu Ser Thr Tyr Ser Asp Leu Lys Thr Ile Phe Gly Asp Lys Val Asp
625                 630                 635                 640

Asp Arg Thr Tyr Phe Asn Asp Phe Glu Lys Met Val Glu Tyr Ser Thr
                645                 650                 655

Val Phe Glu Asp Gly His Asp Tyr Asn Gln Lys Leu Asp Glu Tyr Thr
            660                 665                 670

Trp Leu Thr Lys Glu Glu Lys Tyr Lys Ile Gly Lys Lys Arg Tyr Arg
        675                 680                 685
```

```
Gly Trp Gly Lys Leu Ser Lys Lys Leu Leu Thr Gly Leu Arg Asp Lys
    690             695                 700

Asn Asn His Thr Ile Met Asp Asn Leu Trp Glu Thr Asn Arg Asn Phe
705                 710                 715                 720

Met Gln Ile Gln Thr Ala Asp Glu Phe Ser Lys Gln Ile Ala Glu Glu
                725                 730                 735

Asn Glu Arg His Leu Lys Gly Ser Val Ser Asp Ala Ile Asn Asp Met
                740                 745                 750

Tyr Thr Ser Pro Ala Asn Lys Lys Ala Ile Arg Gln Val Leu Arg Val
            755                 760                 765

Val Asp Asp Ile Gln Lys Ala Met Gly Tyr Ala Pro Ser Ser Ile Ser
770                 775                 780

Leu Glu Phe Ala Arg Glu Asp Gly Pro Ser Val Arg Thr Val Ser Arg
785                 790                 795                 800

Ala Asn Arg Met Lys Ser Ile Tyr Glu Lys Tyr Ala Ser Glu Val Ser
                805                 810                 815

Glu Glu Val Met Lys Asp Leu Asp Gly Val Ile Lys Asp Lys Lys Gly
                820                 825                 830

Leu Asn Asp Arg Leu Tyr Leu Tyr Phe Glu Gln Gln Gly Lys Asp Met
                835                 840                 845

Tyr Ser Gly His Pro Leu Asp Phe Asp Lys Val Ile Ser Gly Gln Glu
            850                 855                 860

Tyr Asp Ile Asp His Ile Leu Pro Gln Ala Val Ile Lys Asp Asp Ser
865                 870                 875                 880

Leu Asp Asn Arg Val Leu Thr Thr Lys Ala Leu Asn Asn Asp Val Lys
                885                 890                 895

Ser Lys Gly Val Pro Cys Arg Met Phe Asn Gly Met His Ser Phe Trp
                900                 905                 910

Lys Asn Leu Tyr Asp Lys Gly Phe Ile Ser Arg Arg Lys Phe Asn Asn
            915                 920                 925

Leu Thr Thr Asn Pro Glu Asn Ile Asp Lys Tyr Lys Met Lys Gly Phe
            930                 935                 940

Val Asn Arg Gln Leu Val Glu Thr Arg Gln Ile Ile Lys Leu Val Ala
945                 950                 955                 960

Asn Val Leu Asn Asp Lys Tyr Gln Asn Asp Val Asp Ile Ile Glu
                965                 970                 975

Val Arg Ala Glu Leu Thr His Asp Val Arg Lys His Phe Lys Phe Tyr
            980                 985                 990

Lys Asn Arg Asn Val Asn Asp Tyr His His Ala Phe Asp Ala Tyr Leu
            995                 1000                1005

Thr Ser Phe Ile Gly His Tyr Leu Phe Lys Lys Tyr Pro Asn Leu
    1010                1015                1020

Arg Pro Leu Phe Asp Tyr Asn Asp Phe Met Lys Val Ser Asp Asn
    1025                1030                1035

Val Phe Lys Gln Leu Arg Gly Asn Asn Phe Leu Gly Glu Phe Leu
    1040                1045                1050

Asn Lys Thr Gly Asp Ile Ile Ser Thr Asp Gly Asn Phe Val Leu
    1055                1060                1065

Asn Lys Glu Glu Met Ile Asn Lys Leu Asn Lys Ala Tyr Ala Phe
    1070                1075                1080

Lys Lys Ile Leu Val Thr Lys Glu Val Gly Gln Arg Thr Gly Ala
    1085                1090                1095

Met Phe Asn Glu Thr Arg Tyr Pro Ala Pro Asn Ser Arg Lys Ala
```

```
            1100                1105                1110
Ala Leu Lys Tyr Arg Arg Met Pro Lys Pro Asp Ser Leu Ile Ser
        1115                1120                1125
Val Lys Asp Tyr Lys Asn Thr Asp Ile Tyr Gly Gly Tyr Ser Gly
    1130                1135                1140
Lys Asn Asp Ala Tyr Met Val Ile Val Asp Met Gly Lys Gln Tyr
    1145                1150                1155
Met Val Val Gly Val Pro Val Arg Tyr Thr Glu Lys Leu Asp Lys
    1160                1165                1170
Leu Arg Ile Lys His Ser Glu Leu Tyr Arg Asp Glu Leu Arg Lys
    1175                1180                1185
Val Leu Ser Arg Asp Lys Thr Leu Leu Asp Ser Lys Gly Asn Val
    1190                1195                1200
Lys Arg Phe Asp Ile Val Leu Asp Arg Val Leu Tyr Gly Gln Leu
    1205                1210                1215
Ile Glu Asp Gly Asn Glu Leu Phe Thr Leu Gly Ser Ser Lys Tyr
    1220                1225                1230
Lys Arg Asn Phe Arg Gln Leu Phe Leu Asp Lys Gln Cys Ile Glu
    1235                1240                1245
Ile Leu Asp Ser Ser Ala Thr Pro Gln Pro Thr Asp Glu Glu Leu
    1250                1255                1260
Ile Trp Val Tyr Asp Gln Ile Leu Asp Lys Val Asp Lys Tyr Phe
    1265                1270                1275
Glu Leu Tyr Asp Ile Asn Arg Gln Arg Glu Thr Leu Arg Lys Gly
    1280                1285                1290
Arg Ala Ala Phe Cys Ser Leu Pro Asn Ile Ser Met Lys Lys Asp
    1295                1300                1305
Asp Val Thr Lys Lys Lys Ile Leu Asn Glu Ile Leu Val Ala Leu
    1310                1315                1320
His Ala Asn Glu Ser Glu Ser Asn Cys Glu Lys Ile Gly Lys Lys
    1325                1330                1335
Val Phe Gly Arg Leu Gln Val Pro Gly Gly Ile Lys Leu Ser Lys
    1340                1345                1350
Glu Ala Lys Leu Ile Tyr Gln Ser Pro Thr Gly Leu Phe Glu Arg
    1355                1360                1365
Val Val Tyr Leu Lys Asp Leu
    1370                1375

<210> SEQ ID NO 45
<211> LENGTH: 1339
<212> TYPE: PRT
<213> ORGANISM: Lactobacillus salivarius SMXD57 or UCC118

<400> SEQUENCE: 45

Met Glu Arg Tyr His Ile Gly Leu Asp Ile Gly Thr Ser Ser Ile Gly
1               5                   10                  15

Trp Ala Val Ile Gly Asp Asp Phe Lys Ile Lys Lys Lys Gly Lys
            20                  25                  30

Asn Leu Ile Gly Thr Arg Leu Phe Asn Glu Gly Ala Thr Ala Ala Glu
        35                  40                  45

Arg Arg Gly Phe Arg Thr Gln Arg Arg Leu Asn Arg Arg Lys Trp
    50                  55                  60

Arg Leu Lys Leu Leu Glu Glu Ile Phe Asp Pro Tyr Met Ala Glu Val
65                  70                  75                  80
```

```
Asp Glu Tyr Phe Phe Ala Arg Leu Lys Ser Ser Asn Leu Ser Pro Lys
                85                  90                  95

Asp Ser Asn Lys Lys Tyr Leu Gly Ser Leu Leu Phe Pro Asp Lys Ser
            100                 105                 110

Asp Ser Asn Phe Tyr Asp Lys Tyr Pro Thr Ile Tyr His Leu Arg Arg
            115                 120                 125

Asp Leu Met Glu Lys Asp Glu Lys Phe Asp Leu Arg Glu Ile Tyr Leu
        130                 135                 140

Ala Ile His His Ile Val Lys Tyr Arg Gly Asn Phe Leu Glu Lys Val
145                 150                 155                 160

Pro Ala Lys Asn Tyr Lys Asn Ser Gly Ala Ser Ile Gly Phe Leu Leu
                165                 170                 175

Glu Glu Val Asn Ser Leu Tyr Lys Asp Ile Ile Gly Asp Glu Ser Ile
            180                 185                 190

Ala Ile Leu Asn Ser Glu Lys Phe Glu Asp Val Glu Lys Ile Ile Leu
        195                 200                 205

Asp Glu Glu Thr Arg Asn Leu Asp Lys Gln Lys Ser Val Gly Lys Leu
        210                 215                 220

Leu Val Glu Asp Lys Lys Lys Asn Ile Val Thr Ala Phe Ser Lys
225                 230                 235                 240

Ala Ile Phe Gly Tyr Lys Phe Asn Ile Glu Asp Leu Leu Ile Glu
                245                 250                 255

Asn Asp Glu Lys Asn Lys Leu Thr Phe Asn Asp Glu Asn Ile Asp Asp
            260                 265                 270

Ile Phe Asn Glu Leu Ser His Ser Leu Asp Asp Lys Gln Met Asp Leu
        275                 280                 285

Leu Thr Lys Thr Arg Glu Ile Tyr Phe Lys Phe Lys Leu Asn Met Ile
        290                 295                 300

Val Pro Thr Gly Tyr Thr Leu Ser Glu Ser Met Ile Glu Lys Tyr Glu
305                 310                 315                 320

Met His Lys Ala His Leu Lys Met Tyr Lys Glu Phe Ile Asn Thr Leu
                325                 330                 335

Asn Thr Lys Asp Arg Lys Ile Leu Lys Asn Ala Tyr Ser Asp Tyr Ile
            340                 345                 350

Asn Thr Glu Lys Ala Lys Ala Ala Asn Ala Gln Glu Asn Phe Tyr Lys
        355                 360                 365

Thr Val Lys Lys Ile Ile Lys Asp Asn Asn Ser Asp Thr Ala Lys Lys
        370                 375                 380

Ile Ile Val Leu Ile Asp Glu Gly Asn Phe Met Pro Lys Gln Arg Thr
385                 390                 395                 400

Gly Glu Asn Gly Val Ile Pro His Gln Leu His Gln Ile Glu Leu Asp
                405                 410                 415

Arg Ile Ile Glu Asn Gln Ala Lys Tyr Tyr Pro Trp Leu Ala Glu Ala
            420                 425                 430

Asn Pro Val Glu Lys Asn Arg Lys Phe Ala Lys Tyr Lys Leu Asp Glu
        435                 440                 445

Leu Val Thr Phe Arg Val Pro Tyr Tyr Val Gly Pro Leu Ile Asp Lys
        450                 455                 460

Thr Glu Ser Asn Lys Asn Glu Lys Glu Thr Lys Phe Ala Trp Met Val
465                 470                 475                 480

Arg Lys Ala Lys Gly Thr Ile Thr Pro Trp Asn Phe Glu Asn Leu Val
                485                 490                 495

Asp Arg Thr Glu Ser Ala Asn Arg Phe Ile Lys Arg Met Thr Ser Lys
```

-continued

```
                500                 505                 510
Asp Thr Tyr Ile Ile Gly Glu Asp Val Leu Pro Ala Ser Ser Leu Leu
            515                 520                 525

Tyr Glu Lys Phe Lys Val Leu Asn Glu Leu Asn Asn Ile Lys Val Asn
        530                 535                 540

Glu Lys Lys Leu Asp Ile Glu Gln Lys Gln Asp Ile Tyr Leu Asn Leu
545                 550                 555                 560

Phe Thr Thr Ala Lys Asn Val Thr Lys Lys Ser Leu Ala Thr Tyr Leu
                565                 570                 575

Asn Cys Ser Ala Asp Ser Ile Ser Gly Leu Ser Asp Gly Glu Lys Phe
            580                 585                 590

Asn Ser Ser Leu Ser Ser Tyr Ile Asp Leu Lys Ala Ile Leu Gly Asn
        595                 600                 605

Ile Val Asp Asp Cys Asn Lys Asn Glu Asp Leu Glu Lys Ile Ile Glu
610                 615                 620

Tyr Ser Thr Val Phe Glu Asp Gly Asn Ile Tyr Lys Glu Lys Leu Ser
625                 630                 635                 640

Glu Ile Ser Trp Leu Thr Asp Glu Gln Ile Glu Lys Leu Ser Asn Ile
                645                 650                 655

His Phe Lys Gly Trp Gly Arg Leu Ser Lys Lys Leu Leu Thr Gln Ile
            660                 665                 670

Thr Asn Glu Asn Gly Glu Arg Ile Ile Asp Ala Leu Trp Asn Thr Ser
        675                 680                 685

Asn Asn Phe Met Gln Ile Ile Asn Asp Glu Ser Ile Gln Ala Lys Leu
        690                 695                 700

Ala Glu Ile Asn Gly Lys Tyr Ala Gly Lys Ser Asp Leu Glu Asp Ile
705                 710                 715                 720

Leu Ser Glu Ala Tyr Thr Ser Pro Gln Asn Lys Lys Ala Ile Arg Gln
                725                 730                 735

Val Met Lys Val Val Glu Asp Ile Glu Lys Ala Met Gln Cys Glu Pro
            740                 745                 750

Thr Ser Ile Ser Ile Glu Phe Thr Arg Lys Lys Gln Lys Ser Arg Leu
        755                 760                 765

Thr Asn Thr Arg Tyr Lys Lys Ile Ser Asp Val Tyr Glu Lys Ile Ala
        770                 775                 780

Asp Glu Val Ile Ser Glu Tyr Glu Leu Arg Lys Leu Gln Ser Glu Leu
785                 790                 795                 800

Asp Ser Asn Ala Asn Asn Met Arg Asp Arg Tyr Tyr Leu Tyr Phe Met
                805                 810                 815

Gln Leu Gly Arg Asp Met Tyr Thr Gly Glu Lys Ile Asn Ile Asp Glu
            820                 825                 830

Leu His Gln Arg Tyr Asp Ile Asp His Ile Leu Pro Gln Ser Phe Ile
        835                 840                 845

Lys Asp Asp Ser Ile Asn Asn Arg Val Leu Thr Arg Lys Asp Val Asn
        850                 855                 860

Asn Lys Glu Lys Ser Asp Lys Thr Ala Ala Asp Leu Tyr Ala Val Glu
865                 870                 875                 880

Met Ser Asp Phe Trp Arg Lys Leu Arg Lys Gln Gly Leu Ile Thr Glu
                885                 890                 895

Gln Lys Tyr Lys Asn Leu Leu Thr Lys Ser Asp Ser Ile Asp Lys Tyr
            900                 905                 910

Ala Lys Lys Gly Phe Ile Lys Arg Gln Leu Val Glu Thr Ser Gln Val
        915                 920                 925
```

Val Lys Leu Val Ala Asn Ile Leu Gln Asp Tyr Ser Asp Thr Lys
    930                 935                 940

Ile Ile Glu Val Arg Ala Lys Leu Asn Ser Asn Leu Arg Glu Glu Tyr
945                 950                 955                 960

Lys Leu Ile Lys Asn Arg Ala Val Asn Asp Tyr His His Ala Ile Asp
                965                 970                 975

Gly Tyr Leu Thr Thr Phe Ile Gly Gln Tyr Leu Tyr Lys Thr Tyr Pro
                980                 985                 990

Lys Leu Arg Ser Tyr Phe Val Tyr Asn Asp Phe Lys Lys Leu Asp Ser
            995                 1000                1005

Asn Tyr Leu Lys His Met Lys Lys Phe Asn Phe Leu Trp Gln Leu
    1010                1015                1020

Gln Asp Asp Lys Thr Ile Asp Ile Tyr Asp Asn Val Asn Asn Lys
    1025                1030                1035

Phe Val Leu Asn Val Pro Glu Met Lys Lys Tyr Ile Gln Lys Ile
    1040                1045                1050

Tyr Asn Tyr Lys Tyr Met Leu Val Ser Lys Glu Val Thr Thr Lys
    1055                1060                1065

Asn Gly Ala Phe Tyr Asp Gln Thr Lys Tyr Asn Ala Lys Thr Val
    1070                1075                1080

Asn Leu Ile Pro Ile Lys Lys Asn Lys Pro Thr Asn Ile Tyr Gly
    1085                1090                1095

Gly Tyr Lys Gly Lys Val Ser Ser Tyr Met Met Leu Val Lys Ile
    1100                1105                1110

Arg Lys Lys Lys Glu Val Ile Tyr Lys Phe Val Gly Val Pro Arg
    1115                1120                1125

Leu Trp Thr Asp Glu Leu Asp Arg Leu Lys Asp Thr Thr Glu Arg
    1130                1135                1140

Lys Ile Leu Leu Asn Glu Ile Ala Lys Asn Ser Leu Ser Lys Thr
    1145                1150                1155

Glu Gln Asp Phe Glu Val Ile Leu Asp Lys Val Tyr Tyr Gly Gln
    1160                1165                1170

Leu Ile Ile Asp Gly Asn Gln Lys Tyr Thr Leu Gly Ser Ser Glu
    1175                1180                1185

Tyr Lys Tyr Asn Ala Met Gln Leu His Leu Ser Lys His Ala Leu
    1190                1195                1200

Glu Val Leu Ala Lys Glu Asn Val Lys Asp Ala Glu Ile Thr Asp
    1205                1210                1215

Lys Asp Leu Val Ser Val Tyr Glu Glu Ile Leu Ser Val Val Asn
    1220                1225                1230

Lys Tyr Phe Glu Leu Tyr Asp Ile Asn Lys Phe Arg Gln Lys Leu
    1235                1240                1245

Asn Glu Gly Leu Glu Ile Phe Arg Lys Leu Pro Val Tyr Asn Val
    1250                1255                1260

Tyr Glu Ser Asn Lys Ile Lys Gln Val Gly Lys Phe Glu Val Leu
    1265                1270                1275

Asn Arg Ile Leu Met Gly Leu His Ala Asn Ala Met Ile Thr Asp
    1280                1285                1290

Leu Lys Val Leu Gly Ile Lys Thr Lys Leu Gly Gln Met Gln Val
    1295                1300                1305

Asn Gly Gly Ile Lys Leu Ser Pro Asp Ala Lys Leu Ile Tyr Gln
    1310                1315                1320

Ser Pro Thr Gly Ile Phe Ser Arg Ala Val Arg Val Lys Asp Leu
1325                1330                1335

Gly

<210> SEQ ID NO 46
<211> LENGTH: 1331
<212> TYPE: PRT
<213> ORGANISM: Lactobacillus sanfranciscensis TMW 1.1304

<400> SEQUENCE: 46

Met Asn Lys Gln Pro Tyr Asn Ile Gly Leu Asp Ile Gly Thr Ser Ser
1               5                   10                  15

Val Gly Trp Ser Ala Thr Glu Leu Asp Asn Arg Leu Leu His Ile Lys
            20                  25                  30

Gly His Asn Gly Ile Gly Val Arg Leu Phe Lys Glu Gly Glu Ser Ala
        35                  40                  45

Ala Asp Arg Arg Gly Phe Arg Thr Thr Arg Arg Arg Leu Ala Arg Arg
    50                  55                  60

Lys Trp Arg Leu Arg Leu Leu Asn Glu Ile Phe Ala Thr Glu Ile Ala
65                  70                  75                  80

Lys Val Asp Pro Ser Phe Phe Ala Arg Leu Lys Gln Ser Asn Val Ser
                85                  90                  95

Pro Lys Asp Pro Asn Lys Thr Met Phe Glu Asn Ile Leu Phe Asp Asp
            100                 105                 110

Glu Asn Leu Asp Asp Gln Lys Phe His His Asp Tyr Lys Thr Ile Tyr
        115                 120                 125

His Leu Arg Gln Ala Ile Ile Asn His Pro Glu Gln Lys Phe Asp Ile
    130                 135                 140

Arg Leu Ile Tyr Leu Ala Met His His Ile Ile Lys Tyr Arg Gly His
145                 150                 155                 160

Phe Leu Asn Gln Ala Asn Val Gln Asp Phe Lys Gly Gly Lys Ile Asp
                165                 170                 175

Leu Glu Lys Ser Phe Lys Ala Leu Asn Asp Ile Phe Glu Asn Gln Gly
            180                 185                 190

Arg Asp Leu Arg Leu Val Thr Asp Lys Ala Asn Gln Tyr Val Lys Val
        195                 200                 205

Leu Ser Asp Asn Ala Lys Thr Arg Ser Asp Arg Lys Lys Glu Leu Ser
    210                 215                 220

Lys Leu Leu Tyr Val Pro Ile Asp Lys Asp Thr Asp Lys Asn Ser Lys
225                 230                 235                 240

Lys Val Thr Gly Glu Ile Leu Lys Ala Ile Leu Gly Asn Lys Ala Lys
                245                 250                 255

Phe Asp Val Ile Phe Gly Ile Glu Val Glu Asn Pro Lys Glu Trp Val
            260                 265                 270

Leu Thr Phe Asn Ser Asp Asp Phe Asp Asp Lys Ile Glu Gly Leu Ser
        275                 280                 285

Ser Gln Met Thr Asp Glu Asp Ser Glu Ile Leu Leu Ile Leu Lys Glu
    290                 295                 300

Leu Tyr Phe Ala Leu Asn Leu Ser Asp Ile Leu Asn Asn Ser Val Thr
305                 310                 315                 320

Asp Lys Asn Ala Lys Thr Leu Ser Glu Ala Met Ile Asn Arg Tyr Asp
                325                 330                 335

Asp His Lys Asn Gln Leu Ala Met Leu Lys Lys Val Ile Asp Ser Ser
            340                 345                 350

-continued

```
Asp Lys Lys His Ala Lys Glu Leu Lys Glu Ala Tyr Ser Ala Tyr Ile
        355                 360                 365

Asp Gly Glu Asn Asn Lys Lys Ile Ser Phe Glu Asp Leu Lys Lys Arg
    370                 375                 380

Ile Gln Lys Asn Leu Val Asp Ser Glu Leu Ser Gln Lys Ile Asn Asp
385                 390                 395                 400

Leu Leu Asp His Asp Tyr Phe Leu Pro Lys Gln Arg Ser Lys Glu Asn
            405                 410                 415

Gly Ala Ile Pro His Gln Leu Gln Gln Glu Leu Asp Gln Ile Ile
        420                 425                 430

Glu Ser Gln Lys Gln Tyr Tyr Pro Phe Leu Ala Glu Leu Asn Pro Asn
    435                 440                 445

Glu Lys Arg Ser Arg Gln Ala Lys Tyr Lys Leu Asp Glu Leu Val Ala
450                 455                 460

Phe Arg Val Pro Tyr Tyr Val Gly Pro Met Val Glu Val Thr Asp Ser
465                 470                 475                 480

Asn Gln Glu Asn Asn Gly Lys Phe Ala Trp Met Ile Arg Lys Glu Gln
            485                 490                 495

Gly Glu Ile Thr Pro Trp Asn Phe Asp Glu Lys Val Asp Arg Thr Glu
        500                 505                 510

Thr Ala Thr Lys Phe Ile Thr Arg Met Thr Thr Thr Asp Thr Tyr Leu
    515                 520                 525

Ile Gly Glu Pro Val Leu Pro Lys Asn Ser Leu Leu Tyr Gln Lys Phe
530                 535                 540

Val Val Leu Asn Glu Leu Asn Asn Leu Lys Ile Asn Gln Glu Ile Ile
545                 550                 555                 560

Thr Pro Gly Gln Lys Gln Tyr Leu Tyr Glu His Val Met Lys Lys Asn
            565                 570                 575

Lys Arg Val Thr Leu Lys Lys Ile Ala Asp Ala Leu Val Ile Lys Gly
        580                 585                 590

Asp Tyr Pro Tyr Ala Pro Glu Val Lys Gly Thr Thr Asp Gln Lys Asn
    595                 600                 605

Leu Asn Asn Gly Leu Thr Thr Tyr Ile Asp Leu Ala Lys Ile Phe Gly
610                 615                 620

Asn Glu Leu Asp Asp Val Asp Arg Glu Ala Asp Phe Glu Lys Ile Ile
625                 630                 635                 640

Glu Trp Ser Thr Ile Phe Glu Asp Gln His Ile Phe Ala Leu Lys Leu
            645                 650                 655

Gln Glu Leu Lys Trp Leu Thr Glu Lys Gln Arg Asn Gln Val Val Lys
        660                 665                 670

Leu Arg Tyr Gln Gly Trp Gly Lys Leu Ser Lys Glu Leu Leu Ala Gly
    675                 680                 685

Leu Val Asp Asp Asn Gly Gln Arg Ile Ile Asp Leu Leu Trp Ser Asp
690                 695                 700

Asn Gln Asn Phe Met Gln Ile Val Asn Gln Lys Ser Phe Lys Glu Ser
705                 710                 715                 720

Ile Ala Asp His Asn Gly Ala His Leu Glu Glu Lys Asn Leu Lys Asp
            725                 730                 735

Val Ile Asn Asp Leu Tyr Thr Ser Pro Gln Asn Lys Lys Ala Ile Arg
        740                 745                 750

Gln Val Ile Leu Val Val Asp Asp Ile Ile Asn Ala Val Gly Tyr Glu
    755                 760                 765

Pro Ala Asn Ile Met Met Glu Phe Ala Arg Glu Asp Ser Asn Asp His
```

-continued

```
            770                 775                 780
Arg Leu Thr Asn Ser Arg Ser Arg Gln Leu Glu Asn Val Tyr Lys Asp
785                 790                 795                 800

Ile Thr Asn Ser Trp Phe Asp Asn Asp Ser Val Lys Asp Glu Leu Glu
                805                 810                 815

Asp Lys Ile Lys Asn Lys Asp Lys Phe Thr Asp Arg Leu Tyr Leu Tyr
                820                 825                 830

Phe Thr Gln Gly Gly Lys Asp Leu Tyr Thr Gly Glu Pro Leu Asn Ile
            835                 840                 845

Asp Asp Leu Ser Ser Tyr Asp Ile Asp His Ile Leu Pro Gln Ser Phe
850                 855                 860

Ile Leu Asp Asn Ser Leu Asp Asn Arg Val Leu Thr Ser Gln Arg Asn
865                 870                 875                 880

Asn Arg Val Ser Lys Glu Asp Gln Leu Pro Gly Glu Leu Phe Gly Thr
                885                 890                 895

Lys Met His Ala Phe Trp Lys Arg Leu Lys Ala Ala His Leu Ile Ser
                900                 905                 910

Asn Lys Lys Tyr Tyr Asn Leu Thr Leu Thr Pro Asn Ser Ile Ser Lys
                915                 920                 925

Phe Asn Asn Gln Gly Arg Phe Ile Asn Arg Gln Leu Val Glu Thr Arg
            930                 935                 940

Gln Val Ile Lys Leu Ala Ala Glu Ile Leu His Asn Arg Tyr Ser Glu
945                 950                 955                 960

Glu Lys Gly Thr Asn Ile Val Thr Ile Lys Ala Asn Leu Thr His His
                965                 970                 975

Met Arg Glu Lys Phe Asn Phe Tyr Lys Asn Arg Asn Val Asn Asp Tyr
                980                 985                 990

His His Ala Phe Asp Ala Tyr Leu Thr Ala Phe Val Gly Asn Trp Leu
                995                 1000                 1005

Leu Gln Gln Tyr Pro Lys Leu Lys Pro Tyr Phe Val Tyr Gly Asp
    1010                 1015                 1020

Phe Ala Lys Thr Glu Ile Asn Asn Leu Lys Ser Phe Asn Met Leu
    1025                 1030                 1035

Tyr Lys Phe Glu Gln Ala His Gln Leu Asn Glu Lys Asp Gly Lys
    1040                 1045                 1050

Ile Ala Lys Asp Ala Asp Ala Leu Leu Gly Tyr Met Lys Asn Val
    1055                 1060                 1065

Tyr His Phe Lys Lys Met Leu Val Thr Lys Lys Leu Glu Thr Asn
    1070                 1075                 1080

His Gly Ala Leu Phe Lys Gln Thr Leu Tyr Pro Ser Pro Ala His
    1085                 1090                 1095

Asp Ile Lys Lys Arg Gln Leu Ile Lys Pro Lys Asp Asn Arg Pro
    1100                 1105                 1110

Thr Asp Ile Tyr Gly Gly Tyr Thr His Glu Glu Arg Lys Tyr Met
    1115                 1120                 1125

Ser Leu Val Lys Val Ile Gly Lys Lys Asp Asn Glu Tyr Arg Met
    1130                 1135                 1140

Ala Asn Val Pro Leu Leu Lys Ile Asn Lys Asn Asn Asp Ile Lys
    1145                 1150                 1155

Glu Ile Leu Lys Ser Gln Phe Ser Asn Lys Lys Phe Glu Ile Val
    1160                 1165                 1170

Leu Pro Lys Val Leu Lys Asn Gln Leu Phe Ser Glu Asn Gly Ala
    1175                 1180                 1185
```

-continued

Leu Phe Val Ile Gly Ser Lys Gly Tyr Lys Tyr Asn Ala Asn Gln
    1190                1195                1200

Leu Val Leu Ser Asp Leu Asp Met Lys Leu Leu Asn Asp Leu Ser
    1205                1210                1215

Asn Asn Lys Ser Ile Asp Glu Val Thr Ile Asn Gln Leu Phe Lys
    1220                1225                1230

Asn Ile Val Asp Ser Thr Asn Lys Tyr Met Pro Leu Tyr Glu Ile
    1235                1240                1245

Lys Asn Leu Asn Glu Val Val Glu Lys Phe Asn Asn Leu Glu Phe
    1250                1255                1260

Asn Asp Lys Lys Lys Thr Ile Thr Asp Phe Leu Leu Ala Thr His
    1265                1270                1275

Ala Asn Pro Thr Met Ser Asn Leu Lys Asn Ile Gly Leu Pro Ser
    1280                1285                1290

Tyr Phe Gly Arg Phe Thr Ser Gly Asn Ala Gly Ile Lys Leu Ser
    1295                1300                1305

Glu Asn Ala Asn Val Ile Tyr Gln Ser Pro Thr Gly Leu Phe Ser
    1310                1315                1320

Arg Lys Val Lys Ile Ser Asp Phe
    1325                1330

<210> SEQ ID NO 47
<211> LENGTH: 1371
<212> TYPE: PRT
<213> ORGANISM: Lactobacillus buchneri CD034

<400> SEQUENCE: 47

Met Lys Val Asn Asn Tyr His Ile Gly Leu Asp Ile Gly Thr Ser Ser
1               5                   10                  15

Ile Gly Trp Val Ala Ile Gly Glu Asp Gly Lys Pro Leu Arg Ile Lys
                20                  25                  30

Gly Lys Thr Ala Ile Gly Ala Arg Leu Phe Gln Glu Gly Asn Pro Ala
            35                  40                  45

Ala Asp Arg Arg Met Phe Arg Thr Thr Arg Arg Leu Ser Arg Arg
        50                  55                  60

Lys Trp Arg Leu Lys Leu Leu Glu Glu Ile Phe Asp Pro Tyr Ile Thr
65                  70                  75                  80

Pro Val Asp Ser Thr Phe Phe Ala Arg Leu Lys Gln Ser Asn Leu Ser
                85                  90                  95

Pro Lys Asp Ser Arg Lys Glu Phe Lys Gly Ser Met Leu Phe Pro Asp
            100                 105                 110

Leu Thr Asp Met Gln Tyr His Lys Asp Tyr Pro Thr Ile Tyr His Leu
        115                 120                 125

Arg His Ala Leu Met Thr Gln Asp Glu Lys Phe Asp Ile Arg Met Val
    130                 135                 140

Tyr Leu Ala Ile His His Ile Val Lys Tyr Arg Gly Asn Phe Leu Asn
145                 150                 155                 160

Ser Thr Pro Val Asp Ser Phe Lys Ala Ser Lys Val Asn Phe Val Asp
                165                 170                 175

Gln Phe Lys Lys Leu Asn Glu Leu Tyr Thr Ala Ile Asn Pro Glu Glu
            180                 185                 190

Ser Phe Gln Ile Asn Leu Ala Asn Ser Glu Asp Ile Gly His Gln Phe
        195                 200                 205

Leu Asp Pro Ser Ile Arg Lys Phe Asp Lys Lys Lys Gln Ile Pro Lys

-continued

```
                210                 215                 220
Ile Val Pro Val Ser Val Asp Asp Lys Ala Thr Asp Lys Ile Asn Gly
225                 230                 235                 240

Lys Ile Ala Ser Glu Ile Ile Asn Ala Ile Leu Gly Tyr Lys Ser Lys
                245                 250                 255

Leu Asp Val Val Val Gln Cys Thr Pro Val Asp Ser Lys Ser Trp Ala
                260                 265                 270

Leu Lys Phe Asp Glu Glu Asp Ile Asp Ala Lys Leu Gln Lys Ile Leu
                275                 280                 285

Pro Glu Met Asp Glu Asn Gln Gln Ser Ile Ile Ala Ile Leu Gln Asn
290                 295                 300

Leu Tyr Ser Gln Val Thr Leu Asn Gln Ile Val Pro Asn Gly Met Ser
305                 310                 315                 320

Leu Ser Glu Ser Met Ile Glu Lys Tyr Asn Asp His His Asp His Leu
                325                 330                 335

Lys Leu Tyr Lys Lys Ile Ile Asp Gln Leu Ala Asp Pro Lys Lys Lys
                340                 345                 350

Ala Ala Leu Lys Lys Ala Tyr Ser Gln Tyr Val Gly Asp Asp Gly Lys
                355                 360                 365

Val Ile Glu Gln Ala Asp Phe Trp Ser Ser Val Lys Lys Asn Leu Asp
370                 375                 380

Asp Ser Asp Leu Ser Lys Gln Ile Met Asp Leu Ile Asp Ala Glu Lys
385                 390                 395                 400

Phe Met Pro Lys Gln Arg Thr Ser Gln Asn Gly Val Ile Pro His Gln
                405                 410                 415

Leu His Gln Arg Glu Leu Asp Glu Ile Ile Glu His Gln Ser Lys Tyr
                420                 425                 430

Tyr Pro Trp Leu Ala Glu Ile Asn Pro Asn Lys His Asp Leu His Leu
                435                 440                 445

Ala Lys Tyr Lys Ile Glu Glu Leu Val Ala Phe Arg Val Pro Tyr Tyr
450                 455                 460

Val Gly Pro Met Ile Thr Pro Asp Asp Gln Ala Lys Ser Ala Glu Thr
465                 470                 475                 480

Val Phe Ser Trp Met Glu Arg Lys Gly Lys Glu Ala Gly Gln Ile Thr
                485                 490                 495

Pro Trp Asn Phe Asp Glu Lys Val Asp Arg Asn Ala Ser Ala Asn Arg
                500                 505                 510

Phe Ile Lys Arg Met Thr Thr Lys Asp Thr Tyr Leu Ile Gly Glu Asp
                515                 520                 525

Val Leu Pro Asp Glu Ser Leu Leu Tyr Glu Lys Phe Lys Val Leu Asn
530                 535                 540

Glu Leu Asn Met Val Arg Val Asn Gly Lys Leu Leu Lys Val Ala Asp
545                 550                 555                 560

Lys Gln Ala Ile Phe Gln Asp Leu Phe Glu Asn Tyr Lys His Ile Ser
                565                 570                 575

Val Lys Lys Leu Gln Asn Tyr Ile Lys Ser Lys Thr Gly Leu Pro Ser
                580                 585                 590

Asp Pro Glu Ile Ser Gly Leu Ser Asp Pro Glu Tyr Phe Asn Asn Ser
                595                 600                 605

Leu Gly Thr Tyr Asn Asp Phe Lys Lys Leu Phe Gly Asn Lys Val Asp
                610                 615                 620

Glu Pro Asp Leu Gln Asp Asp Phe Glu Lys Ile Val Glu Trp Ser Thr
625                 630                 635                 640
```

```
Val Phe Glu Asp Lys Arg Ile Leu Arg Glu Lys Leu Asn Glu Ile Thr
                645                 650                 655

Trp Leu Ser Asp Gln Gln Lys Asp Val Leu Glu Ser Ser Arg Tyr Gln
            660                 665                 670

Gly Trp Gly Arg Leu Ser Lys Lys Leu Leu Thr Gly Ile Val Asn Asp
        675                 680                 685

Gln Gly Glu Arg Ile Ile Asp Glu Leu Trp Asn Thr Asn Lys Asn Phe
    690                 695                 700

Met Gln Ile Gln Ser Asp Asn Asp Phe Ala Lys Arg Ile His Glu Ala
705                 710                 715                 720

Asn Ala Asp Gln Met Lys Ala Val Asp Val Glu Asp Val Leu Ala Asp
                725                 730                 735

Ala Tyr Thr Ser Pro Gln Asn Lys Lys Ala Ile Arg Gln Val Val Lys
            740                 745                 750

Val Val Asp Asp Ile Gln Lys Ala Met Gly Gly Val Ala Pro Lys Tyr
        755                 760                 765

Ile Ser Ile Glu Phe Thr Arg Ser Glu Asp Arg Asn Pro Arg Arg Thr
    770                 775                 780

Ile Ser Arg Gln Arg Gln Leu Glu Asn Thr Leu Lys Asp Thr Ala Lys
785                 790                 795                 800

Ser Leu Ala Lys Ser Ile Asn Pro Glu Leu Leu Ser Glu Leu Asp Asn
                805                 810                 815

Ala Ala Lys Ser Lys Lys Gly Leu Thr Asp Arg Leu Tyr Leu Tyr Phe
            820                 825                 830

Thr Gln Leu Gly Lys Asp Ile Tyr Thr Gly Lys Pro Ile Asn Ile Asp
        835                 840                 845

Glu Ile Ser Thr Tyr Asp Ile Asp His Ile Leu Pro Gln Ala Phe Val
    850                 855                 860

Lys Asp Asp Ser Leu Asn Asn Arg Val Leu Val Ser Lys Ala Ile Asn
865                 870                 875                 880

Asn Gly Lys Ser Asp Asn Val Pro Val Gln Leu Phe Gly Ala Lys Met
                885                 890                 895

Gly His Phe Trp Lys Gln Leu Ala Glu Ala Gly Leu Ile Ser Lys Arg
            900                 905                 910

Lys Leu Lys Asn Leu Gln Thr Asp Pro Asp Thr Ile Ser Lys Tyr Ala
        915                 920                 925

Met His Gly Phe Ile Arg Arg Gln Leu Val Glu Thr Ser Gln Val Ile
    930                 935                 940

Lys Leu Val Ala Asn Ile Leu Gly Asp Lys Tyr Arg Asn Asp Asn Thr
945                 950                 955                 960

Lys Ile Ile Glu Ile Thr Ala Arg Met Asn His Gln Met Arg Asp Glu
                965                 970                 975

Phe Gly Phe Ile Lys Asn Arg Glu Ile Asn Asp Tyr His His Ala Phe
            980                 985                 990

Asp Ala Tyr Leu Thr Ala Phe Leu Gly Arg Tyr Leu Tyr His Arg Tyr
        995                 1000                1005

Ile Lys Leu Arg Pro Tyr Phe Val Tyr Gly Asp Phe Lys Lys Phe
    1010                1015                1020

Lys Glu Asp Lys Val Thr Met Arg Asn Phe Asn Phe Leu His Asp
    1025                1030                1035

Leu Thr Asp Asp Thr Gln Glu Lys Ile Ala Asp Ala Glu Thr Gly
    1040                1045                1050
```

```
Glu Val Ile Trp Asp Arg Glu Asn Ser Ile Gln Gln Leu Lys Asp
    1055                1060                1065

Val Tyr His Tyr Lys Phe Met Leu Ile Ser His Glu Val Tyr Thr
    1070                1075                1080

Leu Arg Gly Ala Met Phe Asn Gln Thr Val Tyr Pro Ala Ser Asp
    1085                1090                1095

Ala Gly Lys Arg Lys Leu Ile Pro Ile Lys Ala Asp Arg Pro Ile
    1100                1105                1110

Asn Val Tyr Gly Gly Tyr Ser Gly Ser Ala Asp Ala Tyr Met Ala
    1115                1120                1125

Ile Val Arg Ile His Asn Lys Lys Gly Asp Lys Tyr Arg Val Val
    1130                1135                1140

Gly Val Pro Met Arg Ala Arg Asp Arg Leu Asp Ala Ala Lys Lys
    1145                1150                1155

Val Ser Asp Ala Asp Cys Asp Arg Ala Leu Lys Asp Val Leu Thr
    1160                1165                1170

Pro Gln Leu Thr Lys Thr Lys Lys Ser Arg Lys Thr Gly Glu Ile
    1175                1180                1185

Thr Gln Val Val Glu Asp Phe Glu Ile Val Leu Gly Lys Val Met
    1190                1195                1200

Tyr Arg Gln Leu Met Ile Asp Gly Asp Lys Lys Phe Met Leu Gly
    1205                1210                1215

Ser Ser Thr Tyr Gln Tyr Asn Ala Lys Gln Leu Val Leu Ser Asp
    1220                1225                1230

Gln Ser Val Lys Thr Leu Ala Ser Lys Gly Arg Leu Asp Pro Leu
    1235                1240                1245

Gln Glu Ser Met Asp Tyr Asn Asn Val Tyr Thr Glu Ile Leu Asp
    1250                1255                1260

Lys Val Asn Gln Tyr Phe Ser Leu Tyr Asp Met Asn Lys Phe Arg
    1265                1270                1275

His Lys Leu Asn Leu Gly Phe Ser Lys Phe Ile Ser Phe Pro Asn
    1280                1285                1290

His Asn Val Phe Asp Gly Asn Thr Lys Ala Ser Ser Gly Lys Arg
    1295                1300                1305

Glu Ile Leu Glu Glu Val Leu Asn Gly Leu His Ala Asn Pro Thr
    1310                1315                1320

Phe Gly Asn Leu Lys Asp Ile Gly Ile Thr Thr Pro Phe Gly Gln
    1325                1330                1335

Leu Gln Gln Pro Asn Gly Ile Leu Leu Ser Asp Glu Ala Lys Ile
    1340                1345                1350

Arg Tyr Gln Ser Pro Thr Gly Leu Phe Glu Arg Thr Val Ser Leu
    1355                1360                1365

Lys Asp Leu
    1370

<210> SEQ ID NO 48
<211> LENGTH: 1314
<212> TYPE: PRT
<213> ORGANISM: Lactobacillus animalis KCTC 3501

<400> SEQUENCE: 48

Met Leu Lys Lys Asp Tyr Ser Ile Gly Leu Asp Ile Gly Thr Asn Ser
1               5                   10                  15

Val Gly His Ala Val Val Thr Asp Asp Tyr Lys Val Pro Thr Lys Lys
            20                  25                  30
```

```
Met Lys Val Phe Gly Asp Thr Ser Lys Lys Thr Ile Lys Lys Asn Met
                35                  40                  45

Leu Gly Val Leu Leu Phe Asn Glu Gly Gln Thr Ala Ala Asp Thr Arg
     50                  55                  60

Leu Lys Arg Gly Thr Arg Arg Tyr Thr Arg Arg Lys Asn Arg Leu
 65                  70                  75                  80

Arg Tyr Leu Gln Glu Ile Phe Ala Pro Glu Leu Ala Lys Val Asp Pro
                 85                  90                  95

Asn Phe Leu Tyr Arg Leu Glu Glu Ser Ser Leu Val Ala Glu Asp Lys
                100                 105                 110

Lys Tyr Asp Val Tyr Pro Ile Phe Gly Lys Arg Glu Glu Leu Leu
                115                 120                 125

Tyr His Asp Thr Tyr Lys Thr Ile Tyr His Leu Arg Ser Ala Leu Ala
                130                 135                 140

Asn Asn Asp Gln Pro Ala Asp Leu Arg Leu Val Tyr Leu Ala Leu Ala
145                 150                 155                 160

His Ile Ile Lys Tyr Arg Gly Asn Phe Leu Leu Glu Gly Glu Ile Asp
                165                 170                 175

Leu Arg Thr Thr Asp Ile Asn Lys Val Phe Ala Glu Phe Ser Glu Thr
                180                 185                 190

Leu Asn Glu Asn Ser Asp Glu Asn Leu Gly Lys Leu Asp Val Ala Asp
                195                 200                 205

Ile Phe Lys Asn Asn Thr Phe Ser Lys Thr Lys Ser Glu Glu Leu
                210                 215                 220

Leu Lys Leu Ser Gly Ala Lys Lys Asn Gln Leu Ala His Gln Leu Phe
225                 230                 235                 240

Lys Met Met Val Gly Asn Met Gly Ser Phe Lys Lys Val Leu Gly Thr
                245                 250                 255

Asp Glu Glu His Lys Leu Ser Phe Gly Lys Asp Thr Tyr Glu Asp Asp
                260                 265                 270

Leu Asn Asp Leu Leu Ala Glu Ala Gly Asp Gln Tyr Leu Asp Ile Phe
                275                 280                 285

Val Ala Ala Lys Lys Val Tyr Asp Ala Ala Ile Leu Ala Ser Ile Leu
                290                 295                 300

Asp Val Lys Asp Thr Gln Thr Lys Thr Val Phe Ser Gln Ala Met Ile
305                 310                 315                 320

Glu Arg Tyr Glu Glu His Gln Lys Asp Leu Ile Glu Leu Lys Arg Val
                325                 330                 335

Phe Lys Lys Tyr Leu Pro Glu Lys Cys His Asp Phe Phe Ser Glu Pro
                340                 345                 350

Lys Ile Ser Gly Tyr Ala Gly Tyr Ile Asp Gly Lys Val Ser Glu Glu
                355                 360                 365

Asp Phe Tyr Lys Tyr Thr Lys Lys Thr Leu Lys Gly Ile Pro Glu Thr
                370                 375                 380

Glu Glu Ile Leu Gln Lys Ile Asp Ala Asn Asn Tyr Leu Arg Lys Gln
385                 390                 395                 400

Arg Thr Phe Asp Asn Gly Ala Ile Pro His Gln Val His Leu Lys Glu
                405                 410                 415

Leu Val Ala Ile Val Glu Asn Gln Gly Lys Tyr Tyr Pro Phe Leu Arg
                420                 425                 430

Glu Asn Lys Asp Lys Phe Glu Lys Ile Leu Asn Phe Arg Ile Pro Tyr
                435                 440                 445
```

-continued

Tyr Val Gly Pro Leu Ala Arg Gly Asn Ser Lys Phe Ala Trp Leu Thr
450                 455                 460
Arg Ala Gly Glu Gly Lys Ile Thr Pro Tyr Asn Phe Asp Glu Met Ile
465                 470                 475                 480
Asp Lys Glu Thr Ser Ala Glu Asp Phe Ile Lys His Met Thr Ile Asn
            485                 490                 495
Asp Leu Tyr Leu Pro Thr Glu Pro Val Leu Pro Lys His Ser Leu Leu
                500                 505                 510
Tyr Glu Arg Tyr Thr Ile Phe Asn Glu Leu Ala Gly Val Arg Tyr Val
        515                 520                 525
Thr Glu Asn Gly Glu Ala Lys Tyr Phe Asp Ala Gln Thr Lys Arg Ser
530                 535                 540
Ile Phe Glu Leu Phe Lys Leu Asp Arg Lys Val Ser Glu Lys Met Val
545                 550                 555                 560
Ile Lys His Leu Lys Val Val Met Pro Ala Ile Arg Ile Gln Ala Leu
                565                 570                 575
Lys Gly Leu Asp Asn Gly Lys Phe Asn Ala Ser Tyr Gly Thr Tyr Lys
                580                 585                 590
Asp Leu Val Asp Met Gly Val Ala Pro Glu Leu Leu Asn Asp Glu Val
            595                 600                 605
Asn Ser Glu Lys Trp Glu Asp Ile Ile Lys Thr Leu Thr Ile Phe Glu
610                 615                 620
Gly Arg Lys Leu Ile Lys Arg Arg Leu Glu Asn Tyr Arg Asp Phe Leu
625                 630                 635                 640
Gly Glu Asp Ile Leu Arg Lys Leu Ser Arg Lys Lys Tyr Thr Gly Trp
                645                 650                 655
Gly Arg Leu Ser Ala Lys Leu Leu Asp Gly Ile Tyr Asp Lys Lys Thr
                660                 665                 670
His Lys Thr Ile Leu Asp Cys Leu Met Thr Glu Asp Tyr Ser Gln Asn
        675                 680                 685
Phe Met Gln Leu Ile Asn Asp Asp Asn Tyr Ser Phe Lys Glu Thr Ile
690                 695                 700
Lys Asn Ala Gln Val Ile Glu Lys Glu Thr Leu Ala Lys Thr Val
705                 710                 715                 720
Gln Glu Leu Pro Gly Ser Pro Ala Ile Lys Lys Gly Ile Leu Gln Ser
                725                 730                 735
Leu Glu Ile Val Asp Glu Ile Ile Lys Val Met Gly Tyr Lys Pro Lys
                740                 745                 750
Ser Ile Val Val Glu Met Ala Arg Glu Thr Gln Lys Thr His Gly Thr
        755                 760                 765
Arg Lys Arg Glu Asp Arg Val Gln Gln Ile Val Glu Asn Leu Lys Asp
770                 775                 780
Ala Asn Glu Leu Pro Glu Lys Leu Pro Ser Asn Ala Glu Leu Ser Asp
785                 790                 795                 800
Glu Arg Lys Tyr Leu Tyr Cys Leu Gln Asn Gly Arg Asp Met Tyr Thr
                805                 810                 815
Gly Ala Pro Leu Asp Tyr Asp His Leu Gln Phe Tyr Asp Val Asp His
                820                 825                 830
Ile Ile Pro Gln Ser Phe Leu Lys Asp Asp Ser Ile Glu Asn Lys Val
            835                 840                 845
Leu Thr Ile Lys Lys Glu Asn Val Arg Lys Thr Asn Gly Leu Pro Ser
850                 855                 860
Glu Ala Val Ile Gln Lys Met Gly Ser Phe Trp Lys Lys Leu Leu Asp

```
                        865                 870                 875                 880
Ala Gly Ala Met Thr Asn Lys Lys Tyr Asp Asn Leu Arg Arg Asn Leu
                            885                 890                 895
His Gly Gly Leu Asn Glu Lys Leu Lys Glu Arg Phe Ile Glu Arg Gln
                900                 905                 910
Leu Val Glu Thr Arg Gln Ile Thr Lys Tyr Val Ala Gln Leu Leu Asp
            915                 920                 925
Gln Arg Leu Asn Tyr Asp Gly Asn Gly Val Glu Leu Asp Glu Lys Ile
        930                 935                 940
Ala Ile Val Thr Leu Lys Ala Gln Leu Ala Ser Gln Phe Arg Ser Glu
945                 950                 955                 960
Phe Lys Leu Arg Lys Val Arg Ala Leu Asn Asn Leu His His Ala His
                965                 970                 975
Asp Ala Tyr Leu Asn Ala Ile Val Ala Asn Leu Ile Met Ala Lys Tyr
            980                 985                 990
Pro Glu Leu Glu Pro Glu Phe Val Tyr Gly Lys Tyr Arg Lys Ala Lys
        995                 1000                1005
Phe Lys Gly Leu Gly Lys Ala Thr Ala Lys Asn Thr Leu Tyr Ala
    1010                1015                1020
Asn Val Leu Tyr Phe Leu Lys Glu Asn Glu Val Tyr Pro Phe Trp
    1025                1030                1035
Asp Lys Ala Arg Asp Leu Pro Thr Ile Lys Arg Tyr Leu Tyr Arg
    1040                1045                1050
Ala Gln Val Asn Lys Val Arg Lys Ala Glu Arg Gln Ile Gly Gly
    1055                1060                1065
Phe Ser Asp Glu Met Leu Val Pro Lys Ser Asp Ser Gly Lys Leu
    1070                1075                1080
Leu Pro Arg Lys Glu Gly Leu Asp Pro Val Lys Tyr Gly Gly Tyr
    1085                1090                1095
Ala Lys Ala Val Glu Ser Tyr Ala Val Leu Ile Thr Ala Asp Glu
    1100                1105                1110
Val Lys Lys Gly Lys Thr Lys Lys Val Lys Thr Leu Val Asn Ile
    1115                1120                1125
Pro Ile Ile Asp Ser Lys Lys Tyr Glu Ala Asp Pro Thr Ala Tyr
    1130                1135                1140
Leu Ala Ser Arg Gly Tyr Thr Asn Val Thr Asn Ser Phe Ile Leu
    1145                1150                1155
Pro Lys Tyr Ser Leu Leu Glu Asp Pro Glu Gly Arg Arg Arg Tyr
    1160                1165                1170
Leu Ala Ser Phe Lys Glu Phe Gln Lys Ala Asn Glu Leu Ile Leu
    1175                1180                1185
Pro Gln His Leu Val Glu Leu Leu Tyr Trp Val Asn Ala Lys Asp
    1190                1195                1200
Gly Glu Gln Lys Leu Glu Asp His Lys Ala Glu Phe Lys Glu Leu
    1205                1210                1215
Phe Asp Lys Ile Met Glu Phe Ala Asp Lys Tyr Val Val Ala Pro
    1220                1225                1230
Lys Asn Ser Glu Lys Ile Arg Arg Leu Tyr Glu Glu Asn Gln Asp
    1235                1240                1245
Ala Thr Pro Met Glu Leu Gly Lys Asn Phe Val Glu Leu Leu Arg
    1250                1255                1260
Tyr Thr Ala Asp Gly Ala Ala Ser Asp Phe Lys Phe Phe Gly Glu
    1265                1270                1275
```

Asn Ile Pro Arg Lys Arg Tyr Asn Ser Ala Gly Ser Leu Leu Asn
    1280                1285                1290

Gly Thr Leu Ile Tyr Gln Ser Lys Thr Gly Leu Tyr Glu Thr Arg
    1295                1300                1305

Ile Asp Leu Gly Lys Leu
    1310

<210> SEQ ID NO 49
<211> LENGTH: 1356
<212> TYPE: PRT
<213> ORGANISM: Lactobacillus farciminis

<400> SEQUENCE: 49

Met Thr Lys Lys Glu Gln Pro Tyr Asn Ile Gly Leu Asp Ile Gly Thr
1               5                   10                  15

Ser Ser Val Gly Trp Ala Val Thr Asn Asp Asn Tyr Asp Leu Leu Asn
            20                  25                  30

Ile Lys Lys Lys Asn Leu Trp Gly Val Arg Leu Phe Glu Glu Ala Gln
        35                  40                  45

Thr Ala Lys Glu Thr Arg Leu Asn Arg Ser Thr Arg Arg Tyr Arg
    50                  55                  60

Arg Arg Lys Asn Arg Ile Asn Trp Leu Asn Glu Ile Phe Ser Glu Glu
65                  70                  75                  80

Leu Ala Lys Thr Asp Pro Ser Phe Leu Ile Arg Leu Gln Asn Ser Trp
                85                  90                  95

Val Ser Lys Lys Asp Pro Asp Arg Lys Arg Asp Lys Tyr Asn Leu Phe
            100                 105                 110

Ile Asp Gly Pro Tyr Thr Asp Lys Glu Tyr Tyr Arg Glu Phe Pro Thr
        115                 120                 125

Ile Phe His Leu Arg Lys Glu Leu Ile Leu Asn Lys Asp Lys Ala Asp
    130                 135                 140

Ile Arg Leu Ile Tyr Leu Ala Leu His Asn Ile Leu Lys Tyr Arg Gly
145                 150                 155                 160

Asn Phe Thr Tyr Glu His Gln Lys Phe Asn Ile Ser Asn Leu Asn Asn
                165                 170                 175

Asn Leu Ser Lys Glu Leu Ile Glu Leu Asn Gln Gln Leu Ile Lys Tyr
            180                 185                 190

Asp Ile Ser Phe Pro Asp Asp Cys Asp Trp Asn His Ile Ser Asp Ile
        195                 200                 205

Leu Ile Gly Arg Gly Asn Ala Thr Gln Lys Ser Ser Asn Ile Leu Lys
    210                 215                 220

Asp Phe Thr Leu Asp Lys Glu Thr Lys Lys Leu Leu Lys Glu Val Ile
225                 230                 235                 240

Asn Leu Ile Leu Gly Asn Val Ala His Leu Asn Thr Ile Phe Lys Thr
                245                 250                 255

Ser Leu Thr Lys Asp Glu Glu Lys Leu Asn Phe Ser Gly Lys Asp Ile
            260                 265                 270

Glu Ser Lys Leu Asp Asp Leu Asp Ser Ile Leu Asp Asp Gln Phe
        275                 280                 285

Thr Val Leu Asp Ala Ala Asn Arg Ile Tyr Ser Thr Ile Thr Leu Asn
    290                 295                 300

Glu Ile Leu Asn Gly Glu Ser Tyr Phe Ser Met Ala Lys Val Asn Gln
305                 310                 315                 320

Tyr Glu Asn His Ala Ile Asp Leu Cys Lys Leu Arg Asp Met Trp His

```
                    325                 330                 335
Thr Thr Lys Asn Glu Glu Ala Val Glu Gln Ser Arg Gln Ala Tyr Asp
                340                 345                 350
Asp Tyr Ile Asn Lys Pro Lys Tyr Gly Thr Lys Glu Leu Tyr Thr Ser
                355                 360                 365
Leu Lys Lys Phe Leu Lys Val Ala Leu Pro Thr Asn Leu Ala Lys Glu
                370                 375                 380
Ala Glu Lys Ile Ser Lys Gly Thr Tyr Leu Val Lys Pro Arg Asn
385                 390                 395                 400
Ser Glu Asn Gly Val Val Pro Tyr Gln Leu Asn Lys Ile Glu Met Glu
                405                 410                 415
Lys Ile Ile Asp Asn Gln Ser Gln Tyr Tyr Pro Phe Leu Lys Glu Asn
                420                 425                 430
Lys Glu Lys Leu Leu Ser Ile Leu Ser Phe Arg Ile Pro Tyr Tyr Val
                435                 440                 445
Gly Pro Leu Gln Ser Ala Glu Lys Asn Pro Phe Ala Trp Met Glu Arg
                450                 455                 460
Lys Ser Asn Gly His Ala Arg Pro Trp Asn Phe Asp Glu Ile Val Asp
465                 470                 475                 480
Arg Glu Lys Ser Ser Asn Lys Phe Ile Arg Arg Met Thr Val Thr Asp
                485                 490                 495
Ser Tyr Leu Val Gly Glu Pro Val Leu Pro Lys Asn Ser Leu Ile Tyr
                500                 505                 510
Gln Arg Tyr Glu Val Leu Asn Glu Leu Asn Asn Ile Arg Ile Thr Glu
                515                 520                 525
Asn Leu Lys Thr Asn Pro Ile Gly Ser Arg Leu Thr Val Glu Thr Lys
                530                 535                 540
Gln Arg Ile Tyr Asn Glu Leu Phe Lys Lys Tyr Lys Lys Val Thr Val
545                 550                 555                 560
Lys Lys Leu Thr Lys Trp Leu Ile Ala Gln Gly Tyr Tyr Lys Asn Pro
                565                 570                 575
Ile Leu Ile Gly Leu Ser Gln Lys Asp Glu Phe Asn Ser Thr Leu Thr
                580                 585                 590
Thr Tyr Leu Asp Met Lys Lys Ile Phe Gly Ser Ser Phe Met Glu Asp
                595                 600                 605
Asn Lys Asn Tyr Asp Gln Ile Glu Glu Leu Ile Glu Trp Leu Thr Ile
                610                 615                 620
Phe Glu Asp Lys Gln Ile Leu Asn Glu Lys Leu His Ser Ser Lys Tyr
625                 630                 635                 640
Ser Tyr Thr Pro Asp Gln Ile Lys Lys Ile Ser Asn Met Arg Tyr Lys
                645                 650                 655
Gly Trp Gly Arg Leu Ser Lys Lys Ile Leu Met Asp Ile Thr Thr Glu
                660                 665                 670
Thr Asn Thr Pro Gln Leu Leu Gln Leu Ser Asn Tyr Ser Ile Leu Asp
                675                 680                 685
Leu Met Trp Ala Thr Asn Asn Asn Phe Ile Ser Ile Met Ser Asn Asp
                690                 695                 700
Lys Tyr Asp Phe Lys Asn Tyr Ile Glu Asn His Asn Leu Asn Lys Asn
705                 710                 715                 720
Glu Asp Gln Asn Ile Ser Asp Leu Val Asn Asp Ile His Val Ser Pro
                725                 730                 735
Ala Leu Lys Arg Gly Ile Thr Gln Ser Ile Lys Ile Val Gln Glu Ile
                740                 745                 750
```

-continued

```
Val Lys Phe Met Gly His Ala Pro Lys His Ile Phe Ile Glu Val Thr
            755                 760                 765
Arg Glu Thr Lys Lys Ser Glu Ile Thr Thr Ser Arg Glu Lys Arg Ile
            770                 775                 780
Lys Arg Leu Gln Ser Lys Leu Leu Asn Lys Ala Asn Asp Phe Lys Pro
785                 790                 795                 800
Gln Leu Arg Glu Tyr Leu Val Pro Asn Lys Lys Ile Gln Glu Leu
                805                 810                 815
Lys Lys His Lys Asn Asp Leu Ser Ser Glu Arg Ile Met Leu Tyr Phe
                820                 825                 830
Leu Gln Asn Gly Lys Ser Leu Tyr Ser Glu Glu Ser Leu Asn Ile Asn
                835                 840                 845
Lys Leu Ser Asp Tyr Gln Val Asp His Ile Leu Pro Arg Thr Tyr Ile
850                 855                 860
Pro Asp Asp Ser Leu Glu Asn Lys Ala Leu Val Leu Ala Lys Glu Asn
865                 870                 875                 880
Gln Arg Lys Ala Asp Asp Leu Leu Leu Asn Ser Asn Val Ile Asp Arg
                885                 890                 895
Asn Leu Glu Arg Trp Thr Tyr Met Leu Asn Asn Asn Met Ile Gly Leu
                900                 905                 910
Lys Lys Phe Lys Asn Leu Thr Arg Arg Val Ile Thr Asp Lys Asp Lys
                915                 920                 925
Leu Gly Phe Ile His Arg Gln Leu Val Gln Thr Ser Gln Met Val Lys
930                 935                 940
Gly Val Ala Asn Ile Leu Asp Asn Met Tyr Lys Asn Gln Gly Thr Thr
945                 950                 955                 960
Cys Ile Gln Ala Arg Ala Asn Leu Ser Thr Ala Phe Arg Lys Ala Leu
                965                 970                 975
Ser Gly Gln Asp Asp Thr Tyr His Phe Lys His Pro Glu Leu Val Lys
                980                 985                 990
Asn Arg Asn Val Asn Asp Phe His His Ala Gln Asp Ala Tyr Leu Ala
                995                 1000                1005
Ser Phe Leu Gly Thr Tyr Arg Leu Arg Arg Phe Pro Thr Asn Glu
    1010                1015                1020
Met Leu Leu Met Asn Gly Glu Tyr Asn Lys Phe Tyr Gly Gln Val
    1025                1030                1035
Lys Glu Leu Tyr Ser Lys Lys Lys Lys Leu Pro Asp Ser Arg Lys
    1040                1045                1050
Asn Gly Phe Ile Ile Ser Pro Leu Val Asn Gly Thr Thr Gln Tyr
    1055                1060                1065
Asp Arg Asn Thr Gly Glu Ile Ile Trp Asn Val Gly Phe Arg Asp
    1070                1075                1080
Lys Ile Leu Lys Ile Phe Asn Tyr His Gln Cys Asn Val Thr Arg
    1085                1090                1095
Lys Thr Glu Ile Lys Thr Gly Gln Phe Tyr Asp Gln Thr Ile Tyr
    1100                1105                1110
Ser Pro Lys Asn Pro Lys Tyr Lys Lys Leu Ile Ala Gln Lys Lys
    1115                1120                1125
Asp Met Asp Pro Asn Ile Tyr Gly Gly Phe Ser Gly Asp Asn Lys
    1130                1135                1140
Ser Ser Ile Thr Ile Val Lys Ile Asp Asn Asn Lys Ile Lys Pro
    1145                1150                1155
```

```
Val Ala Ile Pro Ile Arg Leu Ile Asn Asp Leu Lys Asp Lys Lys
    1160                1165                1170

Thr Leu Gln Asn Trp Leu Glu Glu Asn Val Lys His Lys Lys Ser
    1175                1180                1185

Ile Gln Ile Ile Lys Asn Asn Val Pro Ile Gly Gln Ile Ile Tyr
    1190                1195                1200

Ser Lys Lys Val Gly Leu Leu Ser Leu Asn Ser Asp Arg Glu Val
    1205                1210                1215

Ala Asn Arg Gln Gln Leu Ile Leu Pro Pro Glu His Ser Ala Leu
    1220                1225                1230

Leu Arg Leu Leu Gln Ile Pro Asp Glu Asp Leu Asp Gln Ile Leu
    1235                1240                1245

Ala Phe Tyr Asp Lys Asn Ile Leu Val Glu Ile Leu Gln Glu Leu
    1250                1255                1260

Ile Thr Lys Met Lys Lys Phe Tyr Pro Phe Tyr Lys Gly Glu Arg
    1265                1270                1275

Glu Phe Leu Ile Ala Asn Ile Glu Asn Phe Asn Gln Ala Thr Thr
    1280                1285                1290

Ser Glu Lys Val Asn Ser Leu Glu Glu Leu Ile Thr Leu Leu His
    1295                1300                1305

Ala Asn Ser Thr Ser Ala His Leu Ile Phe Asn Asn Ile Glu Lys
    1310                1315                1320

Lys Ala Phe Gly Arg Lys Thr His Gly Leu Thr Leu Asn Asn Thr
    1325                1330                1335

Asp Phe Ile Tyr Gln Ser Val Thr Gly Leu Tyr Glu Thr Arg Ile
    1340                1345                1350

His Ile Glu
    1355

<210> SEQ ID NO 50
<211> LENGTH: 1371
<212> TYPE: PRT
<213> ORGANISM: Lactobacillus buchneri NRRL B-30929

<400> SEQUENCE: 50

Met Lys Val Asn Asn Tyr His Ile Gly Leu Asp Ile Gly Thr Ser
1               5                   10                  15

Ile Gly Trp Val Ala Ile Gly Glu Asp Gly Lys Pro Leu Arg Ile Lys
                20                  25                  30

Gly Lys Thr Ala Ile Gly Ala Arg Leu Phe Gln Glu Gly Asn Pro Ala
            35                  40                  45

Ala Asp Arg Arg Met Phe Arg Thr Thr Arg Arg Leu Ser Arg Arg
    50                  55                  60

Lys Trp Arg Leu Lys Leu Leu Glu Glu Ile Phe Asp Pro Tyr Ile Thr
65                  70                  75                  80

Pro Val Asp Ser Thr Phe Phe Ala Arg Leu Lys Gln Ser Asn Leu Ser
                85                  90                  95

Pro Lys Asp Ser Arg Lys Glu Phe Lys Gly Ser Met Leu Phe Pro Asp
            100                 105                 110

Leu Thr Asp Met Gln Tyr His Lys Asp Tyr Pro Thr Ile Tyr His Leu
        115                 120                 125

Arg His Ala Leu Met Thr Gln Asp Glu Lys Phe Asp Ile Arg Met Val
    130                 135                 140

Tyr Leu Ala Ile His His Ile Val Lys Tyr Arg Gly Asn Phe Leu Asn
145                 150                 155                 160
```

-continued

```
Ser Thr Pro Val Asp Ser Phe Lys Ala Ser Lys Val Asn Phe Val Asp
            165                 170                 175

Gln Phe Lys Lys Leu Asn Glu Leu Tyr Thr Ala Ile Asn Pro Glu Glu
        180                 185                 190

Ser Phe Gln Ile Asn Leu Ala Asn Ser Glu Asp Ile Gly His Gln Phe
    195                 200                 205

Leu Asp Pro Ser Ile Arg Lys Phe Asp Lys Lys Gln Ile Pro Lys
210                 215                 220

Ile Val Pro Val Ser Val Asp Asp Lys Ala Thr Asp Lys Ile Asn Gly
225                 230                 235                 240

Lys Ile Ala Ser Glu Ile Ile Asn Ala Ile Leu Gly Tyr Lys Ser Lys
                245                 250                 255

Leu Asp Val Val Val Gln Cys Thr Pro Val Asp Ser Lys Ser Trp Ala
            260                 265                 270

Leu Lys Phe Asp Glu Glu Asp Ile Asp Ala Lys Leu Gln Lys Ile Leu
        275                 280                 285

Pro Glu Met Asp Glu Asn Gln Gln Ser Ile Ile Ala Ile Leu Gln Asn
    290                 295                 300

Leu Tyr Ser Gln Val Thr Leu Asn Gln Ile Val Pro Asn Gly Met Ser
305                 310                 315                 320

Leu Ser Glu Ser Met Ile Glu Lys Tyr Asn Asp His His Asp His Leu
                325                 330                 335

Lys Leu Tyr Lys Lys Ile Ile Asp Gln Leu Ala Asp Pro Lys Lys Lys
            340                 345                 350

Ala Ala Leu Lys Lys Ala Tyr Ser Gln Tyr Val Gly Asp Asp Gly Lys
        355                 360                 365

Val Ile Glu Gln Ala Asp Phe Trp Ser Ser Val Lys Lys Asn Leu Asp
    370                 375                 380

Asp Ser Asp Leu Ser Lys Gln Ile Met Asp Leu Ile Asp Ala Glu Lys
385                 390                 395                 400

Phe Met Pro Lys Gln Arg Thr Ser Gln Asn Gly Val Ile Pro His Gln
                405                 410                 415

Leu His Gln Arg Glu Leu Asp Glu Ile Ile Glu His Gln Ser Lys Tyr
            420                 425                 430

Tyr Pro Trp Leu Ala Glu Ile Asn Pro Asn Lys His Asp Leu His Leu
        435                 440                 445

Ala Lys Tyr Lys Ile Glu Glu Leu Val Ala Phe Arg Val Pro Tyr Tyr
    450                 455                 460

Val Gly Pro Met Ile Thr Pro Asp Asp Gln Ala Lys Ser Ala Glu Thr
465                 470                 475                 480

Val Phe Ser Trp Met Glu Arg Lys Gly Lys Glu Ala Gly Gln Ile Thr
                485                 490                 495

Pro Trp Asn Phe Asp Glu Lys Val Asp Arg Asn Ala Ser Ala Asn Arg
            500                 505                 510

Phe Ile Lys Arg Met Thr Thr Lys Asp Thr Tyr Leu Ile Gly Glu Asp
        515                 520                 525

Val Leu Pro Asp Glu Ser Leu Leu Tyr Glu Lys Phe Lys Val Leu Asn
    530                 535                 540

Glu Leu Asn Met Val Arg Val Asn Gly Lys Leu Leu Lys Val Ala Asp
545                 550                 555                 560

Lys Gln Ala Ile Phe Gln Asp Leu Phe Glu Asn Tyr Lys His Ile Ser
                565                 570                 575
```

```
Val Lys Lys Leu Gln Asn Tyr Ile Lys Ser Lys Thr Gly Leu Pro Ser
            580                 585                 590

Asp Pro Glu Ile Ser Gly Leu Ser Asp Pro Glu Tyr Phe Asn Asn Ser
            595                 600                 605

Leu Gly Thr Tyr Asn Asp Phe Lys Lys Leu Phe Gly Asn Lys Val Asp
            610                 615                 620

Glu Pro Asp Leu Gln Asp Asp Phe Glu Lys Ile Val Glu Trp Ser Thr
625                 630                 635                 640

Val Phe Glu Asp Lys Arg Ile Leu Arg Glu Lys Leu Asn Glu Ile Thr
            645                 650                 655

Trp Leu Ser Asp Gln Gln Lys Asp Val Leu Glu Ser Ser Arg Tyr Gln
            660                 665                 670

Gly Trp Gly Arg Leu Ser Lys Lys Leu Leu Thr Gly Ile Val Asn Asp
            675                 680                 685

Gln Gly Glu Arg Ile Ile Asp Glu Leu Trp Asn Thr Asn Lys Asn Phe
            690                 695                 700

Met Gln Ile Gln Ser Asp Asn Asp Phe Ala Lys Arg Ile His Glu Ala
705                 710                 715                 720

Asn Ala Asp Gln Met Lys Ala Val Asp Val Glu Asp Val Leu Ala Asp
            725                 730                 735

Ala Tyr Thr Ser Pro Gln Asn Lys Lys Ala Ile Arg Gln Val Val Lys
            740                 745                 750

Val Val Asp Asp Ile Gln Lys Ala Met Gly Gly Val Ala Pro Lys Tyr
            755                 760                 765

Ile Ser Ile Glu Phe Thr Arg Ser Glu Asp Arg Asn Pro Arg Arg Thr
770                 775                 780

Ile Ser Arg Gln Arg Gln Leu Glu Asn Thr Leu Lys Asp Thr Ala Lys
785                 790                 795                 800

Ser Leu Ala Lys Ser Ile Asn Pro Glu Leu Leu Ser Glu Leu Asp Asn
            805                 810                 815

Ala Ala Lys Ser Lys Lys Gly Leu Thr Asp Arg Leu Tyr Leu Tyr Phe
            820                 825                 830

Thr Gln Leu Gly Lys Asp Ile Tyr Thr Gly Lys Pro Ile Asn Ile Asp
            835                 840                 845

Glu Ile Ser Thr Tyr Asp Ile Asp His Ile Leu Pro Gln Ala Phe Val
850                 855                 860

Lys Asp Asp Ser Leu Asn Asn Arg Val Leu Val Ser Lys Ala Ile Asn
865                 870                 875                 880

Asn Gly Lys Ser Asp Asn Val Pro Val Gln Leu Phe Gly Ala Lys Met
            885                 890                 895

Gly His Phe Trp Lys Gln Leu Ala Glu Ala Gly Leu Ile Ser Lys Arg
            900                 905                 910

Lys Leu Lys Asn Leu Gln Thr Asp Pro Asp Thr Ile Ser Lys Tyr Ala
            915                 920                 925

Met His Gly Phe Ile Arg Arg Gln Leu Val Glu Thr Ser Gln Val Ile
            930                 935                 940

Lys Leu Val Ala Asn Ile Leu Gly Asp Lys Tyr Arg Asn Asp Asn Thr
945                 950                 955                 960

Lys Ile Ile Glu Ile Thr Ala Arg Met Asn His Gln Met Arg Asp Glu
            965                 970                 975

Phe Gly Phe Ile Lys Asn Arg Glu Ile Asn Asp Tyr His His Ala Phe
            980                 985                 990

Asp Ala Tyr Leu Thr Ala Phe Leu  Gly Arg Tyr Leu Tyr  His Arg Tyr
```

-continued

```
           995                1000               1005
Ile Lys Leu Arg Pro Tyr Phe Val Tyr Gly Asp Phe Lys Lys Phe
    1010                1015               1020

Lys Glu Asp Lys Val Thr Met Arg Asn Phe Asn Phe Leu His Asp
    1025                1030               1035

Leu Thr Asp Asp Thr Gln Glu Lys Ile Ala Asp Ala Glu Thr Gly
    1040                1045               1050

Glu Val Ile Trp Asp Arg Glu Asn Ser Ile Gln Gln Leu Lys Asp
    1055                1060               1065

Val Tyr His Tyr Lys Phe Met Leu Ile Ser His Glu Val Tyr Thr
    1070                1075               1080

Leu Arg Gly Ala Met Phe Asn Gln Thr Val Tyr Pro Ala Ser Asp
    1085                1090               1095

Ala Gly Lys Arg Lys Leu Ile Pro Ile Lys Ala Asp Arg Pro Ile
    1100                1105               1110

Asn Val Tyr Gly Gly Tyr Ser Gly Ser Ala Asp Ala Tyr Met Ala
    1115                1120               1125

Ile Val Arg Ile His Asn Lys Lys Gly Asp Lys Tyr Arg Val Val
    1130                1135               1140

Gly Val Pro Met Arg Ala Arg Asp Arg Leu Asp Ala Ala Lys Lys
    1145                1150               1155

Val Ser Asp Ala Asp Cys Asp Arg Ala Leu Lys Asp Val Leu Thr
    1160                1165               1170

Pro Gln Leu Thr Lys Thr Lys Lys Ser Arg Lys Thr Gly Glu Ile
    1175                1180               1185

Thr Gln Val Val Glu Asp Phe Glu Ile Val Leu Gly Lys Val Met
    1190                1195               1200

Tyr Arg Gln Leu Met Ile Asp Gly Asp Lys Lys Phe Met Leu Gly
    1205                1210               1215

Ser Ser Thr Tyr Gln Tyr Asn Ala Lys Gln Leu Val Leu Ser Asp
    1220                1225               1230

Gln Ser Val Lys Thr Leu Ala Ser Lys Gly Arg Leu Asp Pro Leu
    1235                1240               1245

Gln Glu Ser Met Asp Tyr Asn Asn Val Tyr Thr Glu Ile Leu Asp
    1250                1255               1260

Lys Val Asn Gln Tyr Phe Ser Leu Tyr Asp Met Asn Lys Phe Arg
    1265                1270               1275

His Lys Leu Asn Leu Gly Phe Ser Lys Phe Ile Ser Phe Pro Asn
    1280                1285               1290

His Asn Val Phe Asp Gly Asn Thr Lys Ala Ser Ser Gly Lys Arg
    1295                1300               1305

Glu Ile Leu Glu Glu Val Leu Asn Gly Leu His Ala Asn Pro Thr
    1310                1315               1320

Phe Gly Asn Leu Lys Asp Ile Gly Ile Thr Thr Pro Phe Gly Gln
    1325                1330               1335

Leu Gln Gln Pro Asn Gly Ile Leu Leu Ser Asp Glu Ala Lys Ile
    1340                1345               1350

Arg Tyr Gln Ser Pro Thr Gly Leu Phe Glu Arg Thr Val Ser Leu
    1355                1360               1365

Lys Asp Leu
    1370
```

<210> SEQ ID NO 51

<211> LENGTH: 1125
<212> TYPE: PRT
<213> ORGANISM: Streptococcus intermedius B196

<400> SEQUENCE: 51

```
Met Asn Gly Leu Val Leu Gly Leu Asp Ile Gly Ile Ala Ser Val Gly
1               5                   10                  15

Val Gly Ile Leu Asn Lys Glu Thr Gly Glu Ile Ile His Val Asn Ser
            20                  25                  30

Arg Ile Phe Pro Ala Ala Thr Ala Asp Ser Asn Val Glu Arg Arg Gly
        35                  40                  45

Phe Arg Gln Gly Arg Arg Leu Gly Arg Arg Lys Lys His Arg Ser Ala
    50                  55                  60

Arg Leu Asn Asp Leu Phe Glu Glu Phe Gly Phe Ile Thr Asp Phe Ser
65                  70                  75                  80

Ala Val Pro Leu Asn Leu Asn Pro Tyr Ala Leu Arg Val Lys Gly Leu
                85                  90                  95

Ser Glu Glu Leu Thr Asn Glu Glu Leu Phe Ile Ala Leu Lys Asn Ile
            100                 105                 110

Ile Lys Arg Arg Gly Ile Ser Tyr Leu Asp Asp Ala Ser Glu Asp Gly
        115                 120                 125

Glu Thr Ala Ser Asn Glu Tyr Gly Lys Ala Val Glu Glu Asn Arg Lys
    130                 135                 140

Leu Leu Ala Asp Lys Thr Pro Gly Gln Ile Gln Leu Glu Arg Phe Glu
145                 150                 155                 160

Lys Tyr Gly Gln Val Arg Gly Asp Phe Thr Val Val Glu Asn Gly Glu
                165                 170                 175

Asn His Arg Leu Ile Asn Val Phe Ser Thr Ala Tyr Lys Lys Glu
            180                 185                 190

Ala Glu Arg Ile Leu Arg Arg Gln Gln Glu Phe Asn Val Arg Ile Ser
        195                 200                 205

Asp Glu Phe Ile Glu Ala Tyr Leu Thr Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Phe Arg Thr Asp Gly Thr Thr Leu Asp Asn Ile Phe Gly Ile Leu Ile
                245                 250                 255

Gly Lys Cys Thr Phe Tyr Pro Asp Glu Tyr Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Arg Pro Glu Gln Lys Arg Gln Ile
    290                 295                 300

Val Glu Tyr Ala Arg Thr Ala Lys Thr Leu Gly Thr Pro Thr Leu Leu
305                 310                 315                 320

Lys Tyr Ile Ala Lys Leu Val Asp Gly Ser Ile Asp Asp Ile Lys Gly
                325                 330                 335

Tyr Arg Ile Asp Lys Ser Asp Lys Pro Glu Met His Thr Phe Asp Ala
            340                 345                 350

Tyr Arg Lys Met Arg Thr Leu Glu Leu Val Asp Val Asp Ile Leu Ser
        355                 360                 365

Arg Glu Thr Leu Asp Asp Leu Ala Tyr Ile Leu Thr Leu Asn Thr Glu
    370                 375                 380

Ser Glu Gly Ile Leu Glu Ala Leu Asn Ser Lys Met Pro Gly Thr Phe
```

-continued

```
385                 390                 395                 400
Thr Lys Glu Gln Ile Asp Glu Leu Ile Gln Phe Arg Lys Lys Asn Ser
                405                 410                 415

Ala Val Phe Gly Lys Gly Trp His Asn Phe Ser Leu Lys Leu Met Asn
                420                 425                 430

Glu Leu Ile Pro Glu Leu Tyr Glu Thr Ser Glu Gln Met Thr Ile
                435                 440                 445

Leu Thr Arg Leu Gly Lys Gln Arg Ser Arg Glu Ile Ser Lys Arg Thr
    450                 455                 460

Lys Tyr Ile Asp Glu Lys Glu Leu Thr Asp Glu Ile Tyr Asn Pro Val
465                 470                 475                 480

Val Ala Lys Ser Val Arg Gln Ala Ile Lys Ile Ile Asn Leu Ala Thr
                485                 490                 495

Lys Lys Tyr Gly Ile Phe Asp Asn Ile Val Ile Glu Met Ala Arg Glu
                500                 505                 510

Ser Asn Glu Asp Asp Glu Lys Lys Ala Ile Gln Asn Val Gln Lys Ala
                515                 520                 525

Asn Glu Asp Glu Lys Lys Ala Ala Met Glu Lys Ala Ala Asp Leu Tyr
    530                 535                 540

Asn Gly Lys Lys Glu Leu Pro Asp Ser Ile Phe His Gly His Lys Glu
545                 550                 555                 560

Leu Ala Thr Lys Ile Arg Leu Trp His Gln Gln Gly Glu Arg Cys Leu
                565                 570                 575

Tyr Thr Gly Lys Asn Ile Ser Ile His Asp Leu Ile His Asn Pro His
                580                 585                 590

Gln Tyr Glu Ile Asp His Ile Leu Pro Leu Ser Leu Ser Phe Asp Asp
    595                 600                 605

Gly Leu Ala Asn Lys Val Leu Val Leu Ala Thr Ala Asn Gln Glu Lys
    610                 615                 620

Gly Gln Arg Thr Pro Phe Gln Ala Leu Asp Ser Met Asp Asp Ala Trp
625                 630                 635                 640

Ser Tyr Ile Glu Phe Lys Gln Tyr Val Arg Asn Ser Lys Ser Leu Ser
                645                 650                 655

Asn Lys Lys Lys Asp Tyr Leu Leu Thr Glu Glu Asp Ile Ser Lys Ile
                660                 665                 670

Glu Val Lys Gln Lys Phe Ile Glu Arg Asn Leu Val Asp Thr Arg Tyr
                675                 680                 685

Ser Ser Arg Val Val Leu Asn Thr Leu Gln Glu Phe Tyr Lys Thr Asn
    690                 695                 700

Asp Phe Asp Thr Lys Ile Ser Val Val Arg Gly Gln Phe Thr Ser Gln
705                 710                 715                 720

Leu Arg Arg Lys Trp Lys Ile Glu Lys Ser Arg Asp Thr Tyr His His
                725                 730                 735

His Ala Val Asp Ala Leu Ile Ile Ala Ala Ser Ser Gln Leu Arg Leu
                740                 745                 750

Trp Lys Lys Gln Asn Asn Pro Leu Ile Ser Tyr Arg Glu Gly Gln Leu
                755                 760                 765

Val Asp Pro Glu Thr Gly Glu Ile Leu Ser Leu Thr Asp Asp Glu Tyr
                770                 775                 780

Lys Glu Leu Val Leu Arg Pro Pro Tyr Asp Tyr Phe Val Asp Thr Leu
785                 790                 795                 800

Lys Ser Lys Ser Phe Glu Asp Ser Ile Leu Phe Ser Tyr Gln Val Asp
                805                 810                 815
```

Ser Lys Tyr Asn Arg Lys Ile Ser Asp Ala Thr Ile Tyr Gly Thr Arg
            820                 825                 830

Lys Ala Gln Leu Gly Lys Asp Lys Gln Glu Thr Tyr Val Leu Gly
            835                 840                 845

Lys Ile Lys Asp Ile Tyr Ser Gln Lys Gly Tyr Glu Asp Phe Ile Lys
            850                 855                 860

Arg Tyr Lys Lys Asp Thr Thr Gln Phe Leu Met Tyr His Lys Asp Pro
865                 870                 875                 880

Gln Thr Phe Ala Lys Val Ile Glu Glu Ile Leu Lys Thr Tyr Pro Asp
            885                 890                 895

Lys Glu Leu Asn Glu Lys Gly Lys Glu Ile Pro Cys Asn Pro Phe Glu
            900                 905                 910

Lys Tyr Arg Gln Glu Asn Gly Pro Ile Arg Lys Tyr Ser Lys Lys Gly
            915                 920                 925

Lys Gly Pro Glu Ile Lys Ser Leu Lys Tyr Tyr Asp Asn Lys Leu Gly
            930                 935                 940

Asn His Ile Asp Ile Thr Pro Val Asn Ser Gln Asn Gln Val Val Leu
945                 950                 955                 960

Gln Ser Leu Lys Pro Trp Arg Thr Asp Val Tyr Phe Asn Pro Gln Thr
            965                 970                 975

Ser Lys Tyr Glu Leu Met Gly Leu Lys Tyr Ser Asp Leu Arg Phe Glu
            980                 985                 990

Lys Gly Ser Gly Ser Tyr Gly Ile Ser Pro Glu Lys Tyr Asn Lys Val
            995                1000                1005

Lys Ala Lys Glu Gly Val Asp Glu Asp Ser Glu Phe Lys Phe Thr
            1010                1015                1020

Leu Tyr Lys Asn Asp Leu Ile Leu Ile Lys Asp Thr Glu Thr Gly
            1025                1030                1035

Glu Gln Gln Leu Phe Arg Tyr Gly Ser Arg Asn Asp Thr Ser Lys
            1040                1045                1050

His Tyr Val Glu Leu Lys Pro Tyr Glu Lys Ala Lys Phe Glu Gly
            1055                1060                1065

Asn Gln Gln Leu Met Asn Leu Leu Gly Thr Val Ala Lys Gly Gly
            1070                1075                1080

Gln Cys Leu Lys Gly Ile Asn Lys Pro Asn Leu Ser Ile Tyr Lys
            1085                1090                1095

Val Lys Thr Asp Val Leu Gly Asn Lys Tyr Phe Ile Lys Lys Glu
            1100                1105                1110

Gly Asp Gln Pro Gln Leu Asn Phe Lys Lys Lys Ile
            1115                1120                1125

<210> SEQ ID NO 52
<211> LENGTH: 866
<212> TYPE: PRT
<213> ORGANISM: Lactobacillus crispatus FB049-03

<400> SEQUENCE: 52

Met Gly Ala Thr Gln Gln Ile Asn Asn Ile Ile Ile Asp Ile Asp Val
1               5                   10                  15

Gln Gly Glu Lys Met Gly Trp Arg Asn Val Ile Ile Thr Gln His Ala
            20                  25                  30

Lys Leu Thr Tyr Ser Met Asn Met Leu Ile Val Gln Thr Lys Asp Gly
            35                  40                  45

Ile Asn Gln Ile Pro Ile Glu Asp Ile Asn Leu Val Leu Ile Ser Thr

```
            50                  55                  60
Ser Gln Ala Val Ile Thr Ser Ala Leu Ile Ser Lys Leu Ala Lys Asn
 65                  70                  75                  80

Gln Cys Lys Val Ile Phe Val Asp Asp Lys Tyr Gln Pro Val Thr Glu
                 85                  90                  95

Thr Val Asn Tyr Tyr Pro Gly Ala Arg Asp Ile Lys Lys Leu Lys Met
                100                 105                 110

Gln Phe Glu Trp Asn Glu Arg Lys Glu Asn Leu Trp Thr Lys Ile
            115                 120                 125

Val Ala Ala Lys Leu Lys Asn Gln Ile Ser Val Leu Lys Asn Tyr Arg
            130                 135                 140

Ile Asp Glu Thr Glu Val Glu Gln Glu Leu Tyr Lys Leu Glu Val Asn
145                 150                 155                 160

Asp Leu Ser Asn Arg Glu Ala Ala Ala Arg Lys Tyr Phe Met Lys
                165                 170                 175

Leu Phe Gly Lys Asp Phe Ile Arg Arg Asn Ser Gly Val Ile Asn Ala
                180                 185                 190

Ala Leu Asp Tyr Gly Tyr Ser Ile Leu Leu Ser Ser Phe Asp Arg Glu
            195                 200                 205

Ile Ala Met Asn Gly Tyr Leu Thr Tyr Leu Gly Ile His His Ser
            210                 215                 220

Val Glu Asn Gln Phe Asn Leu Ala Cys Asp Leu Met Glu Pro Phe Arg
225                 230                 235                 240

Ser Ile Val Asp Tyr Trp Val Lys Ala His Glu Asn Ile Thr Ser Phe
                245                 250                 255

Thr Pro Asp Ile Lys Tyr Gly Leu Val Glu Leu Leu Ser Leu Gln Ile
                260                 265                 270

Lys Phe Asn Gly Arg Asn Thr Ile Leu Thr Asn Ala Ile Ser Val Tyr
            275                 280                 285

Val Arg Ser Cys Leu Arg Tyr Leu Ser Gly Glu Thr Asp Asp Ile Arg
            290                 295                 300

Ile Glu Met Ser Leu Cys Asn Glu Val Pro Asn Asp Ala Ile Asn Asp
305                 310                 315                 320

Asn Val Lys Tyr Tyr Leu Tyr Phe Met Gln Leu Gly Arg Asp Ala Tyr
                325                 330                 335

Thr Gly Lys Pro Ile Asn Ile Asp Glu Val Ser Gln Tyr Tyr Asp Ile
            340                 345                 350

Asp His Ile Leu Pro Gln Ser Phe Ile Lys Asp Asp Ser Leu Asn Asn
            355                 360                 365

Arg Val Leu Val Ala Lys Pro Ile Asn Asn Gly Lys Ser Asp Gly Val
    370                 375                 380

Pro Leu Lys Leu Phe Gly Asp Asn Leu Ala Thr Gly Leu Gly Ile Thr
385                 390                 395                 400

Val Lys Gln Met Trp Asn Asn Trp Ala Asp Lys Gly Leu Ile Asn Lys
                405                 410                 415

Ala Lys Gln Asn Asn Leu Phe Leu Asp Pro Glu Asn Ile Asn Lys His
            420                 425                 430

Gln Ala Ser Gly Phe Ile Arg Lys Gln Leu Val Glu Thr Ser Gln Ile
            435                 440                 445

Ile Lys Leu Ala Thr Thr Ile Leu Gln Ala Glu Tyr Pro Lys Thr Lys
    450                 455                 460

Ile Ile Val Val Lys Ala Ser Ser Asn His Tyr Leu Arg Asn Glu Phe
465                 470                 475                 480
```

Asp Leu Tyr Lys Ser Arg Glu Val Asn Asp Tyr His His Ala Ile Asp
            485                 490                 495

Ala Tyr Leu Thr Thr Ile Cys Gly Asn Leu Leu Tyr Gln Ala Tyr Pro
        500                 505                 510

Lys Leu Arg Pro Phe Phe Val Tyr Gly Gln Phe Lys Lys Phe Ser Ser
    515                 520                 525

Asp Pro Lys Lys Glu Asn Glu Ile Leu Lys Lys Thr Lys Asn Phe Asp
530                 535                 540

Phe Val Ala Lys Leu Leu Gly Ser Lys Ala Pro Asn Glu Ile Arg Ser
545                 550                 555                 560

Gln Gln Gly Lys Val Leu Phe Glu Lys Asn Lys Ile Arg Leu Gln Leu
                565                 570                 575

Asn Lys Ala Tyr Asn Tyr Lys Tyr Met Leu Val Ser Arg Asp Thr Thr
            580                 585                 590

Thr Lys Asn Gln Glu Met Phe Gly Met Thr Ile Tyr Pro Arg Ala Glu
        595                 600                 605

Arg Asp Ile Ala Lys Ser Arg Lys Leu Ile Glu Lys Arg Lys Gly Phe
    610                 615                 620

Ser Thr Asp Ile Tyr Gly Gly Tyr Thr Gly Thr Ala Ala Ala Tyr Met
625                 630                 635                 640

Ala Ile Val Arg Ile Asn Lys Thr Lys Ser Ser Gln Tyr Lys Val Ile
                645                 650                 655

Ala Val Pro Met Thr Lys Arg Ala Ile Leu Asn Lys Ala Glu Lys Glu
            660                 665                 670

Gly Asn Tyr Glu Lys Ile Leu Lys Gln Ile Leu Ser Pro Ser Ile Leu
        675                 680                 685

Tyr Asn Asp Lys Gly Lys Arg Lys Ala Gly Val Ile Ser Phe Asp Ile
    690                 695                 700

Ile Lys Gly Lys Val Pro Tyr Asn Gln Val Val Gln Asp Gly Asn Lys
705                 710                 715                 720

Lys Phe Leu Leu Lys Ser Ala Ile Tyr Leu Cys Asn Ala Lys Gln Leu
                725                 730                 735

Val Leu Ser Glu Glu Ala Met Arg Val Ile Thr Gly His Trp Leu Asp
            740                 745                 750

Ser Asp Lys Gln Asp Gln Glu Leu Leu Asp Val Tyr Asp Glu Ile Leu
        755                 760                 765

Glu Lys Ile Asp Arg Tyr Leu Pro Leu Phe Ile Arg Asp Phe Arg
    770                 775                 780

Asn Lys Leu His Lys Gly Arg Glu Lys Phe Leu Lys Leu Asn Ala Glu
785                 790                 795                 800

Asp Lys Phe Lys Ala Ile Ile Gln Ile Leu Lys Gly Leu His Asp Asn
                805                 810                 815

Ser Asp Thr Gly Glu Leu Lys Asp Ile Gly Ile Thr Val Pro Phe Gly
            820                 825                 830

Gln Leu Gln Asn Asn Ser Gly Ile Thr Leu Ser Ser Asp Thr Ile Leu
        835                 840                 845

Val Tyr Gln Ser Pro Thr Gly Leu Phe Glu Lys Arg Val Lys Ile Ser
    850                 855                 860

Ser Leu
865

<210> SEQ ID NO 53
<211> LENGTH: 1239

```
<212> TYPE: PRT
<213> ORGANISM: Lactobacillus buchneri ATCC 11577

<400> SEQUENCE: 53

Met Thr Glu Lys Arg Lys Phe Asp Ile Arg Glu Val Tyr Leu Ala Ile
1               5                   10                  15

His His Ile Val Lys Tyr Arg Gly Asn Phe Leu Asn Ser Ala Thr Val
            20                  25                  30

Asp Ser Phe Lys Thr Ser Asn Ile Asp Phe Thr Ser Gln Phe Asp Arg
        35                  40                  45

Leu Asn Glu Leu Tyr Arg Gln Val Ile Leu Glu Glu Pro Phe Gln Ile
    50                  55                  60

Asn Met Asn Gln Val Asp Lys Met Thr Asn Lys Leu Leu Asp Asn Asp
65                  70                  75                  80

Ala Leu Lys Leu Asp Thr Gln Lys Gln Val Ala Lys Leu Leu Pro Val
                85                  90                  95

Ile Tyr Asn Asp Lys Pro Val Asp Lys Gln Tyr Thr Arg Leu Ala Thr
            100                 105                 110

Glu Phe Ser Lys Ala Ile Leu Gly Tyr Lys Thr Lys Leu Asp Val Ile
        115                 120                 125

Leu Asn Leu Asp Thr Gln Asn Ala Lys Asp Trp Ala Ile Arg Leu Asp
    130                 135                 140

Asp Glu Asp Ile Asp Asp Lys Leu Pro Ala Leu Val Glu Asn Leu Asp
145                 150                 155                 160

Glu Ser Arg Gln Glu Ile Val Thr Ile Ile Arg Asp Leu Tyr Ala Gln
                165                 170                 175

Ile Thr Leu Asn Ala Ile Val Pro Lys Gly Lys Ser Leu Ser Glu Ser
            180                 185                 190

Met Val Asp Lys Tyr Asn Asp His Lys Asp His Leu Asp Leu Leu Met
        195                 200                 205

Gly Leu Ile His Glu Leu Gly Asp Asp Ser Ala Lys Gly Ile Lys Leu
    210                 215                 220

Arg Glu Ala Tyr Thr Gln Tyr Val Gly Lys Ser Gly Asp Lys Thr Leu
225                 230                 235                 240

Asn Gln Asp Asp Phe Tyr Ala Ala Ile Lys Lys Asn Leu Asp Glu Asp
                245                 250                 255

Ser Lys Arg Ser Pro Lys Ile Gln Arg Leu Ile Glu Gln Ala Ser Phe
            260                 265                 270

Met Pro Lys Gln Arg Thr Ser Ala Asn Gly Val Ile Pro His Gln Leu
        275                 280                 285

His Gln Leu Glu Leu Asp Arg Ile Ile Glu Asn Gln Gly Arg Tyr Tyr
    290                 295                 300

Pro Phe Leu Lys Glu Pro Asn Ser Asn Thr His Lys Pro Asn Gly Gly
305                 310                 315                 320

Lys Tyr Lys Leu Asp Glu Leu Val Ala Phe Arg Ile Pro Tyr Tyr Val
                325                 330                 335

Gly Pro Leu Ile Thr Lys Gln Asp Gln Glu Lys Thr Ser Gly Ala Asp
            340                 345                 350

Phe Ala Trp Met Ile Arg Lys Pro Gly Gln Gly Gly Glu Ile Thr Pro
        355                 360                 365

Trp Asn Phe Asp Gln Glu Val Asp Arg Met Ala Ser Ala Asn Thr Phe
    370                 375                 380

Ile Arg Arg Met Thr Thr Lys Asp Ser Tyr Leu Val Ala Glu Asp Val
385                 390                 395                 400
```

```
Leu Pro Asp Ser Ser Leu Ile Tyr Glu Lys Phe Lys Val Leu Asn Glu
            405                 410                 415
Leu Asn Met Leu Lys Val Asn Asp Arg Arg Leu Ser Ile Ser Gln Lys
        420                 425                 430
Gln Asp Leu Phe Asn Asn Leu Phe Lys Lys Gln Lys Thr Ile Arg Thr
            435                 440                 445
Lys Lys Leu Gln Thr Tyr Ile Arg Thr Lys Trp Glu Leu Pro Ser Val
    450                 455                 460
Met Ile Ser Gly Leu Ser Asp Pro Asp Lys Phe Asn Ser Ser Leu Ala
465                 470                 475                 480
Thr Tyr Ile Asp Phe Arg Asp Val Phe Gly Glu Lys Val Asp Asp Pro
                485                 490                 495
Asn Arg Gln Ala Asp Tyr Glu Lys Ile Ile Glu Trp Ser Thr Val Phe
            500                 505                 510
Glu Asp Arg Lys Ile Tyr Gln Ala Lys Leu Asn Gln Leu Asp Trp Leu
        515                 520                 525
Thr Glu Ser Gln Ser Lys Ala Leu Leu Thr Lys His Tyr Thr Gly Trp
    530                 535                 540
Gly Arg Leu Ser Lys Lys Leu Leu Thr Gly Leu Lys Asp Gln Asn Gly
545                 550                 555                 560
Asp Ser Ile Leu Asp Gln Leu Trp Lys Thr Asn Asp Asn Phe Met Gln
                565                 570                 575
Ile Gln Ser Arg Asp Glu Phe Ala Lys Gln Ile His Asp Glu Asn Ala
            580                 585                 590
Lys Gln Phe His Glu Ala Asn Asn Val Asp Asp Ile Leu Asp Asp Ala
        595                 600                 605
Phe Thr Ser Pro Gln Asn Lys Lys Ala Ile Arg Gln Val Asp Lys Val
    610                 615                 620
Val Gln Asp Val Val Lys Ala Val Gly Tyr Ala Pro Asp Lys Ile Ala
625                 630                 635                 640
Ile Glu Phe Thr Arg Ser Pro Gln Asp Arg Pro Gln Arg Thr Phe Ser
                645                 650                 655
Arg Gln Arg Gln Leu Gln Ser Thr Tyr Leu Asn Val Ala Lys Ala Leu
            660                 665                 670
Met Lys Ser Asn Leu Asn Gln Glu Leu Lys Ser Val Ile Asp Ser Gln
        675                 680                 685
Gln Thr Leu Thr Asp Lys Leu Tyr Leu Tyr Phe Thr Gln Leu Gly Gln
    690                 695                 700
Asp Met Tyr Thr Gly Lys Glu Ile Asn Phe Asp Glu Leu Val Asn Tyr
705                 710                 715                 720
Gln Ile Asp His Ile Leu Pro Gln Ala Phe Ile Lys Asp Asp Ser Leu
                725                 730                 735
Asp Asn Arg Val Leu Val Ser Ala Pro Ile Asn Asn Ala Lys Ser Asp
            740                 745                 750
Asn Val Pro Val Lys Lys Phe Gly Ala Lys Met Gly Tyr Phe Trp Lys
        755                 760                 765
Gln Leu Ala Glu Asn His Leu Ile Ser Lys Arg Lys Leu Asn Asn Leu
    770                 775                 780
Thr Thr Asp Pro Asp Lys Ile Gly Lys Phe Thr Ala Gln Gly Phe Ile
785                 790                 795                 800
His Arg Gln Leu Val Glu Thr Ser Gln Val Ile Arg Leu Val Ala Asn
                805                 810                 815
```

```
Ile Leu Gly Asn Glu Tyr Gly His Asp Gly Thr Thr Ile Ile Glu Val
                820                 825                 830

Thr Ala Lys Met Asn His Gln Met Arg Lys Asp Phe Asp Leu Ile Lys
            835                 840                 845

Ile Arg Asp Val Asn Asp Tyr His His Ala Met Asp Ala Tyr Leu Thr
        850                 855                 860

Ala Tyr Val Gly Asp Tyr Leu Tyr Leu Arg Tyr Pro Lys Leu Arg Ser
865                 870                 875                 880

Tyr Phe Val Tyr Gly Asp Phe Lys Lys Leu Lys Asp Gln Ser Leu Lys
                885                 890                 895

Ile Arg Asn Phe Asn Phe Leu His Asp Leu Thr Asn Asp Glu Ala Gly
            900                 905                 910

Asp Lys Ile Val Asp Gln Glu Thr Gly Glu Ile Ile Trp Asp Lys His
        915                 920                 925

Glu Ser Val Lys Gln Leu Lys Lys Val Tyr His Tyr Lys Phe Met Leu
            930                 935                 940

Val Ser Gln Glu Val Tyr Thr Arg Gln Asp Ala Leu Phe Asn Gln Thr
945                 950                 955                 960

Ile Tyr Pro Ala Ser Asp Ala Asp Lys Arg Lys Leu Ile Pro Ile Lys
                965                 970                 975

Asn Asn Lys Pro Val Asp Val Tyr Gly Gly Tyr Ser Gly Asn Val Asp
            980                 985                 990

Ala Tyr Met Ala Ile Val Arg Ile His Gly Lys Lys Glu Asp Lys Tyr
        995                 1000                1005

Lys Val Val Gly Val Pro Met Arg Ala Val Ala Asp Leu Lys Lys
        1010                1015                1020

Ala Glu Ser Lys Gly Arg Asp Asn Tyr Leu Asn Ala Val His Glu
        1025                1030                1035

Val Leu Lys Pro Gln Phe Thr Lys Lys Lys Asp Arg Lys Thr
        1040                1045                1050

Gly Glu Ile Thr Glu Met Met Asp Asp Phe Asp Val Leu Leu Gly
        1055                1060                1065

Lys Val Tyr Tyr Arg Gln Leu Ile Val Asp Gly Asn Lys Lys Phe
        1070                1075                1080

Met Leu Gly Ser Ser Thr Tyr Gln Tyr Asn Ala Lys Gln Leu Val
        1085                1090                1095

Leu Ser Asp Lys Ala Met Gln Val Leu Ser Lys Asp Asp Lys Leu
        1100                1105                1110

Lys Asn Gln Asp Glu Asn Gln Asn Leu Ile Asp Val Tyr Asp Glu
        1115                1120                1125

Ile Leu Glu Lys Val Asp Gln Tyr Phe Glu Leu Tyr Asp Ile Asn
        1130                1135                1140

Lys Phe Arg Gln Lys Leu His Asp Gly Arg Lys Lys Phe Ile Glu
        1145                1150                1155

Leu Pro Val Asp Asn Asp Phe Asn Gly Lys Lys Leu Ile Ser Tyr
        1160                1165                1170

Gly Lys Arg Ala Thr Ile Ile Ser Ile Leu Asn Gly Leu His Ala
        1175                1180                1185

Asn Ala Thr Met Ser Asn Leu Lys Tyr Leu Gly Ile Ser Ser Pro
        1190                1195                1200

Phe Gly Met Leu Gln Val Pro Asn Gly Ile Ile Leu Ser Pro Ala
        1205                1210                1215

Ser Arg Ile Cys Tyr Gln Ser Pro Thr Gly Leu Phe Glu Arg Lys
```

Val Lys Leu Ser Asp Leu
    1235

<210> SEQ ID NO 54
<211> LENGTH: 34
<212> TYPE: DNA
<213> ORGANISM: Streptococcus thermophilus

<400> SEQUENCE: 54
guuuuagagc uguguuguuu cgaaugguuc caaa                                34

<210> SEQ ID NO 55
<211> LENGTH: 88
<212> TYPE: DNA
<213> ORGANISM: Streptococcus thermophilus

<400> SEQUENCE: 55
uuugaaacca uucgaaacaa cacagcuauc aaaaauaagg cuuagccgu acucaacuuc     60 uuuaggug gc accgauucgg uguuuuuu                                     88

<210> SEQ ID NO 56
<211> LENGTH: 36
<212> TYPE: DNA
<213> ORGANISM: Lactobacillus buchneri

<400> SEQUENCE: 56
guuuuagaag gauguuaaau caauaagguu aaaccc                              36

<210> SEQ ID NO 57
<211> LENGTH: 139
<212> TYPE: DNA
<213> ORGANISM: Lactobacillus buchneri

<400> SEQUENCE: 57
auguuugacc uuauugauuu aacauccugu guuaaaauca agcaaagcgc uuugcgcgga   60
guuucaacuu uugacccauu auagggcau uacauaagcg aaaggaacca uucuucaguu    120
ggagaauggu uccuuuuuu                                                139

<210> SEQ ID NO 58
<211> LENGTH: 31
<212> TYPE: DNA
<213> ORGANISM: Streptococcus thermophilus

<400> SEQUENCE: 58
guuuuuguac ucucaagauu uaaguaacug u                                   31

<210> SEQ ID NO 59
<211> LENGTH: 88
<212> TYPE: DNA
<213> ORGANISM: Streptococcus thermophilus

<400> SEQUENCE: 59
acaguuacuu aaaucuugca gaagcuacaa agauaaggcu ucaugccgaa aucaacaccc   60
ugucauuuua uggcagggug uuuucguu                                      88

<210> SEQ ID NO 60
<211> LENGTH: 33
<212> TYPE: DNA
<213> ORGANISM: Streptococcus pyogenes

```
<400> SEQUENCE: 60
guuuuagagc uaugcuguuu ugaauggucc caa                              33

<210> SEQ ID NO 61
<211> LENGTH: 88
<212> TYPE: DNA
<213> ORGANISM: Streptococcus pyogenes

<400> SEQUENCE: 61
uuggaaccau ucaaaacagc auagcaaagc aaaaauaagg cuaguccguu aucaacuucu    60
uuaaguggca ccgagucggu gguuuuuu                                      88

<210> SEQ ID NO 62
<211> LENGTH: 36
<212> TYPE: DNA
<213> ORGANISM: Lactobacillus rhamnosus

<400> SEQUENCE: 62
gucucaggua gaugucagau caaucaguuc aagagc                             36

<210> SEQ ID NO 63
<211> LENGTH: 110
<212> TYPE: DNA
<213> ORGANISM: Lactobacillus rhamnosus

<400> SEQUENCE: 63
caacuugaau ugauugaucu gacaucuacg aguugagauc aaacaaagcu ucagcugagu    60
uucaauuucu gagcccaugu ugggccauac auaugccacc cgagugcaaa              110

<210> SEQ ID NO 64
<211> LENGTH: 36
<212> TYPE: DNA
<213> ORGANISM: Lactobacillus animalis

<400> SEQUENCE: 64
guuuuagagc uauguuguuu uguaugacuc caaaac                             36

<210> SEQ ID NO 65
<211> LENGTH: 104
<212> TYPE: DNA
<213> ORGANISM: Lactobacillus animalis

<400> SEQUENCE: 65
cuaguggagu uauacaaaac aacauuagcg aaguuaaaau aagguuuaau ccguaaucaa    60
caaguuuuau cuugcgcgcg ccguuucggc gcuuuuuug uuuu                     104

<210> SEQ ID NO 66
<211> LENGTH: 36
<212> TYPE: DNA
<213> ORGANISM: Lactobacillus casei

<400> SEQUENCE: 66
gcucuugaac ugauugauuc gacaucuacc ugagac                             36

<210> SEQ ID NO 67
<211> LENGTH: 109
<212> TYPE: DNA
<213> ORGANISM: Lactobacillus casei

<400> SEQUENCE: 67
cguuuugaac ugauugauuc gacaucuaca cguugagauc aaacaaagcc ucggcugagu    60
```
uucaauuucu gagcccaugu ugggccauac auaccgccau ccgggaaaa        109

<210> SEQ ID NO 68
<211> LENGTH: 36
<212> TYPE: DNA
<213> ORGANISM: Lactobacillus gasseri

<400> SEQUENCE: 68
guuuuagaug guuguuagau caauaaggcu uagauc                      36

<210> SEQ ID NO 69
<211> LENGTH: 112
<212> TYPE: DNA
<213> ORGANISM: Lactobacillus gasseri

<400> SEQUENCE: 69
acacuaaacu uuauugaucu aacaaccaga uuuaaaauca agcaaugcau cuuuugaugc   60
aaaguuucaa uacuugcccc gagcuaucga gggacuuuuu uuaugcaaaa aa          112

<210> SEQ ID NO 70
<211> LENGTH: 36
<212> TYPE: DNA
<213> ORGANISM: Lactobacillus jensenii

<400> SEQUENCE: 70
guuuuagaag guuguuaaau caguaaguug aaaaac                      36

<210> SEQ ID NO 71
<211> LENGTH: 115
<212> TYPE: DNA
<213> ORGANISM: Lactobacillus jensenii

<400> SEQUENCE: 71
acauuucaau uuacugauuu aacaaccuua uuuuuaaaau caagcaaggc uuucgggccg   60
aguuuucaca uguguaccgc uuauagcggu cuuuuuuuu gcaguaaaua aaaaa         115

<210> SEQ ID NO 72
<211> LENGTH: 36
<212> TYPE: DNA
<213> ORGANISM: Lactobacillus pentosus

<400> SEQUENCE: 72
gucuugaaua guagucauau caaacagguu uagaac                      36

<210> SEQ ID NO 73
<211> LENGTH: 117
<212> TYPE: DNA
<213> ORGANISM: Lactobacillus pentosus

<400> SEQUENCE: 73
guucuaaacc uucuugauau gacuacuagc gucaagauca aacaaggcau uuugccgagu   60
uucaccuuuu gagccguau ucggaccauu acauauguau caagaugucg cccauuu      117

<210> SEQ ID NO 74
<211> LENGTH: 10
<212> TYPE: DNA
<213> ORGANISM: Artificial
<220> FEATURE:
<223> OTHER INFORMATION: Synthetic trans-encoded CRISPR sequence

<400> SEQUENCE: 74

```
gataaggctt                                                                     10

<210> SEQ ID NO 75
<211> LENGTH: 14
<212> TYPE: DNA
<213> ORGANISM: Artificial
<220> FEATURE:
<223> OTHER INFORMATION: Synthetic trans-encoded CRISPR sequence

<400> SEQUENCE: 75
gataaggcca tgcc                                                                14

<210> SEQ ID NO 76
<211> LENGTH: 12
<212> TYPE: DNA
<213> ORGANISM: Artificial
<220> FEATURE:
<223> OTHER INFORMATION: Synthetic trans-encoded CRISPR sequence

<400> SEQUENCE: 76
taaggctagt cc                                                                  12

<210> SEQ ID NO 77
<211> LENGTH: 11
<212> TYPE: DNA
<213> ORGANISM: Artificial
<220> FEATURE:
<223> OTHER INFORMATION: Synthetic trans-encoded CRISPR sequence

<400> SEQUENCE: 77
tcaagcaaag c                                                                   11

<210> SEQ ID NO 78
<211> LENGTH: 17
<212> TYPE: DNA
<213> ORGANISM: Artificial
<220> FEATURE:
<223> OTHER INFORMATION: Synthetic trans-encoded CRISPR sequence

<400> SEQUENCE: 78
tcaaacaaag cttcagc                                                             17

<210> SEQ ID NO 79
<211> LENGTH: 32
<212> TYPE: RNA
<213> ORGANISM: Lactobacillus gasseri

<400> SEQUENCE: 79
ucaagcaaug caucuuuuga ugcaaaguuu uc                                            32
```